(12) United States Patent
Stahl et al.

(10) Patent No.: US 6,927,044 B2
(45) Date of Patent: Aug. 9, 2005

(54) IL-1 RECEPTOR BASED CYTOKINE TRAPS

(75) Inventors: Neil Stahl, Carmel, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 238 days.

(21) Appl. No.: 10/282,162

(22) Filed: Oct. 28, 2002

(65) Prior Publication Data

US 2003/0143697 A1 Jul. 31, 2003

Related U.S. Application Data

(63) Continuation-in-part of application No. 09/787,835, filed as application No. PCT/US99/22045 on Sep. 22, 1999, which is a continuation of application No. 09/313,942, filed on May 19, 1999, now Pat. No. 6,472,179.
(60) Provisional application No. 60/101,858, filed on Sep. 25, 1998, now abandoned.

(51) Int. Cl.[7] .......................... C12P 21/04; C07H 21/04
(52) U.S. Cl. ................ 435/69.7; 435/320.1; 435/252.3; 435/255.1; 435/348; 435/361; 530/350; 514/12; 536/23.5
(58) Field of Search ................................ 530/351, 350; 536/23.4; 424/134.1, 192.1

(56) References Cited

U.S. PATENT DOCUMENTS 5,470,952 A 11/1995 Stahl et al.

FOREIGN PATENT DOCUMENTS

| EP | 0835939 A2 | 6/1991 |
|---|---|---|
| EP | 0533006 A1 | 9/1992 |
| WO | WO93/19163 | 9/1993 |
| WO | WO93/19777 | 10/1993 |
| WO | WO94/22914 | 10/1994 |
| WO | WO95/06737 | 3/1995 |
| WO | WO96/11213 | 4/1996 |
| WO | WO96/23881 | 8/1996 |
| WO | WO96/35783 | 11/1996 |
| WO | WO97/15669 | 5/1997 |
| WO | WO97/31946 | 9/1997 |
| WO | WO99/37772 | 7/1999 |

OTHER PUBLICATIONS

U.S. Appl. No. 60/101,858, filed Sep. 25, 1998, Stahl, N. & Yancopoulos, G.D.
U.S. Appl. No. 09/313,942, filed May 19, 1999, Stahl, N. & Yancopoulos, G.D.
J. of Biol. Chem., 1995, Greenfeeder, S.A., et. al., "Molecular Cloning and Characterization of a Second Subunit of the Interleukin 1 Receptor Complex", 270(23):13757–13765.
Biochem and Biophys Res Comm, 1997, Seipelt, I., et al., "Overexpression, Purification, and Use of a Soluble Human Interleukin–4 Receptor α–chain/Igγ1 Fusion Protein for Ligand Binding Studies," 239:534–542.
Faseb Journal, 1999, Stahl,N., et al., "Cytokine Traps: Heteromeric Receptor–Based Protein Therapeutics that Function as High–Affinity Blockers of Cytokine Action," Abstract, 1457.

Primary Examiner—Lorraine Spector
Assistant Examiner—Eileen O'Hara
(74) Attorney, Agent, or Firm—Valeta Gregg, Esq.

(57) ABSTRACT

Fusion polypeptides capable of binding interleukin-1 (IL-1) to form a nonfunctional complex are provided and nucleic acid molecules encoding the fusion polypeptides. The fusion ploypeptides form dimers to function as IL-1 antagonists.

30 Claims, 174 Drawing Sheets

Figure 4A

Amino acid sequence of human gp130-Fc-His6

Sequence Range: 1 to 861

```
            10          20          30          40          50          60
             *           *           *           *           *           *
     MVTLQTWVVQALFIFLTTES  TGELLDPCGYISPESPVVQL  HSNFTAVCVLKEKCMDYFHV 70          80          90         100         110         120
             *           *           *           *           *           *
     NANYIVWKTNHFTIPKEQYT  IINRTASSVTFTDIASLNIQ  LTCNILTFGQLEQNVYGITI 130         140         150         160         170         180
             *           *           *           *           *           *
     ISGLPPEKPKNLSCIVNEGK  KMRCEWDGGRETHLETNFTL  KSEWATHKFADCKAKRDTPT 190         200         210         220         230         240
             *           *           *           *           *           *
     SCTVDYSTVYFVNIEVWVEA  ENALGKVTSDHINFDPVYKV  KPNPPHNLSVINSEELSSIL 250         260         270         280         290         300
             *           *           *           *           *           *
     KLTWTNPSIKSVIILKYNIQ  YRTKDASTWSQIPPEDTAST  RSSFTVQDLKPFTEYVFRIR 310         320         330         340         350         360
             *           *           *           *           *           *
     CMKEDGKGYWSDWSEEASGI  TYEDRPSKAPSFWYKIDPSH  TQGYRTVQLVWKTLPPFEAN 370         380         390         400         410         420
             *           *           *           *           *           *
     GKILDYEVTLTRWKSHLQNY  TVNATKLTVNLTNDRYLATL  TVRNLVGKSDAAVLTIPACD 430         440         450         460         470         480
             *           *           *           *           *           *
     FQATHPVMDLKAFPKDNMLW  VEWTTPRESVKKYILEWCVL  SDKAPCITDWQQEDGTVHRT 490         500         510         520         530         540
             *           *           *           *           *           *
     YLRGNLAESKCYLITVTPVY  ADGPGSPESIKAYLKQAPPS  KGPTVRTKKVGKNEAVLEWD 550         560         570         580         590         600
             *           *           *           *           *           *
     QLPVDVQNGFIRNYTIFYRT  IIGNETAVNVDSSHTEYTLS  SLTSDTLYMVRMAAYTDEGG 610         620         630         640         650         660
             *           *        *  †   †      *           *           *
     KDGPEFTFTTPKFAQGEIES  GEPKSCDKTHTCPPCPAPEL  LGGPSVFLFPPKPKDTLMIS 670         680         690         700         710         720
             *           *           *           *           *           *
     RTPEVTCVVVDVSHEDPEVK  FNWYVDGVEVHNAKTKPREE  QYNSTYRVVSVLTVLHQDWL 730         740         750         760         770         780
             *           *           *           *           *           *
```

Figure 4B

NGKEYKCKVSNKALPAPIEK TISKAKGQPREPQVYTLPPS RDELTKNQVSLTCLVKGFYP

```
     790          800         810         820         830         840
      *            *           *           *           *           *
```
SDIAVEWESNGQPENNYKTT PPVLDSDGSFFLYSKLTVDK SRWQQGNVFSCSVMHEALHN

```
     850          860
      *            *
```
HYTQKSLSLSPGKHHHHHH·

Fig. 5.

The amino acid sequence of human IL-6Rα-Fc

Sequence Range: 1 to 594

```
      10           20          30          40          50          60
      *            *           *           *           *           *
```
MVAVGCALLAALLAAPGAAL APRRCPAQEVARGVLTSLPG DSVTLTCPGVEPEDNATVHW

```
      70           80          90         100         110         120
      *            *           *           *           *           *
```
VLRKPAAGSHPSRWAGMGRR LLLRSVQLHDSGNYSCYRAG RPAGTVHLLVDVPPEEPQLS

```
     130          140         150         160         170         180
      *            *           *           *           *           *
```
CFRKSPLSNVVCEWGPRSTP SLTTKAVLLVRKFQNSPAED FQEPCQYSQESQKFSCQLAV

```
     190          200         210         220         230         240
      *            *           *           *           *           *
```
PEGDSSFYIVSMCVASSVGS KFSKTQTFQGCGILQPDPPA NITVTAVARNPRWLSVTWQD

```
     250          260         270         280         290         300
      *            *           *           *           *           *
```
PHSWNSSFYRLRFELRYRAE RSKTFTTWMVKDLQHHCVIH DAWSGLRHVVQLRAQEEFGQ

```
     310          320         330         340         350         360
      *            *           *           *           *           *
```
GEWSEWSPEAMGTPWTESRS PPAENEVSTPMQALTTNKDD DNILFRDSANATSLPVQDAG

```
     370          380         390         400         410         420
      *†           †           *           *           *           *
```
EPKSCDKTHTCPPCPAPELL GGPSVFLFPPKPKDTLMISR TPEVTCVVVDVSHEDPEVKF

```
     430          440         450         460         470         480
      *            *           *           *           *           *
```
NWYVDGVEVHNAKTKPREEQ YNSTYRVVSVLTVLHQDWLN GKEYKCKVSNKALPAPIEKT

```
     490          500         510         520         530         540
      *            *           *           *           *           *
```
ISKAKGQPREPQVYTLPPSR DELTKNQVSLTCLVKGFYPS DIAVEWESNGQPENNYKTTP

```
     550          560         570         580         590
      *            *           *           *           *
```
PVLDSDGSFFLYSKLTVDKS RWQQGNVFSCSVMHEALHNH YTQKSLSLSPGK·

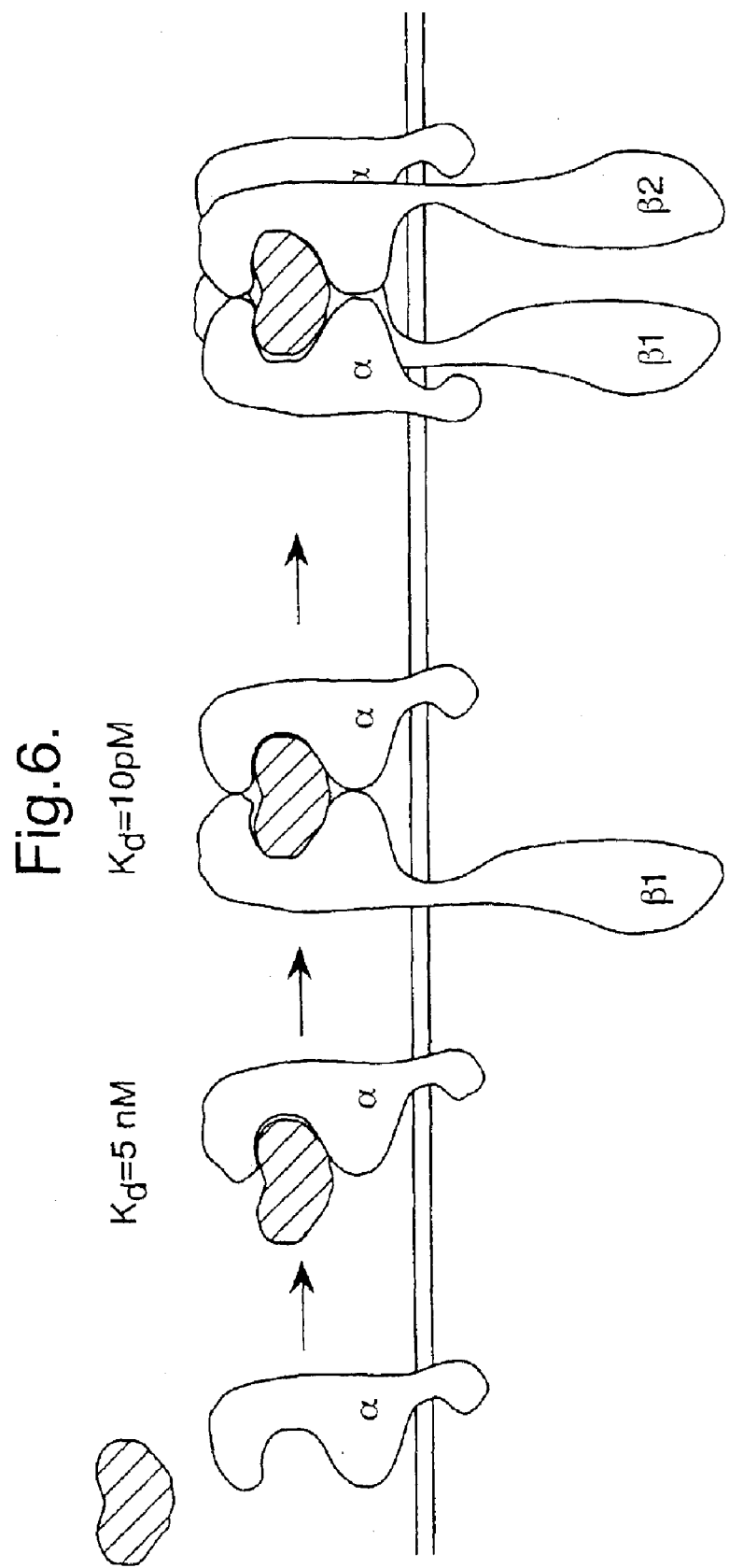

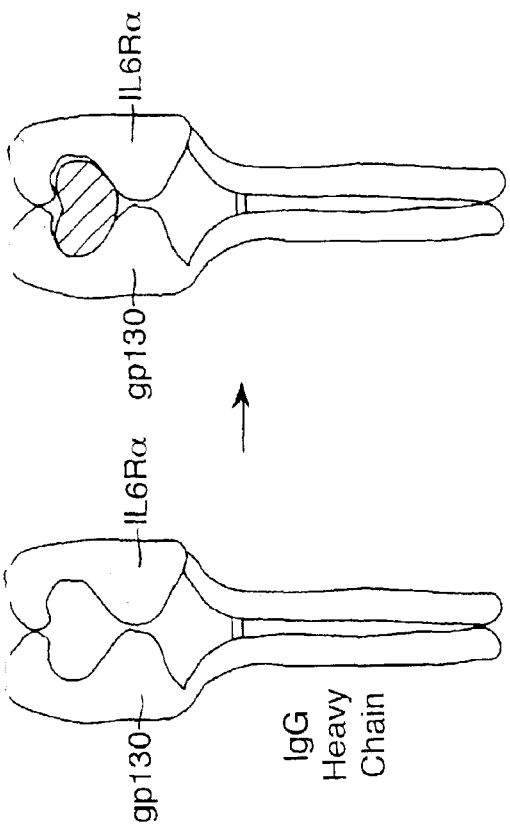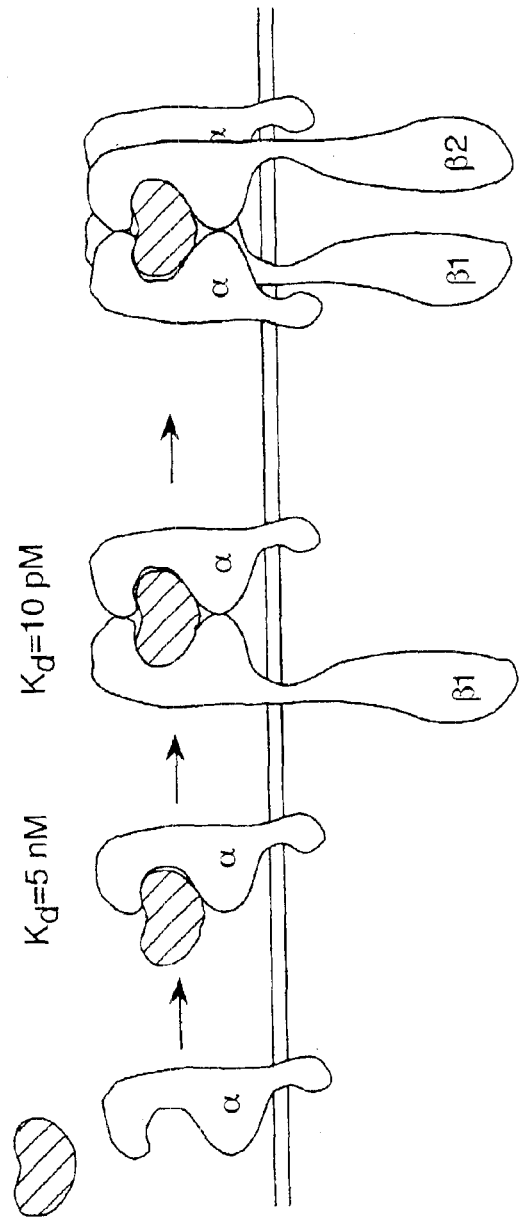
Fig. 7.

Immunoglobulin Heavy/Light Chain receptor Fusions

Figure 9A

Amino acid sequence of gp130-Cγ1

Sequence Range: 1 to 952

```
         10         20         30         40         50         60
          *          *          *          *          *          *
MVTLQTWVVQALFIFLTTES TGELLDPCGYISPESPVVQL HSNFTAVCVLKEKCMDYFHV 70         80         90        100        110        120
          *          *          *          *          *          *
NANYIVWKTNHFTIPKEQYT IINRTASSVTFTDIASLNIQ LTCNILTFGQLEQNVYGITI 130        140        150        160        170        180
          *          *          *          *          *          *
ISGLPPEKPKNLSCIVNEGK KMRCEWDGGRETHLETNFTL KSEWATHKFADCKAKRDTPT 190        200        210        220        230        240
          *          *          *          *          *          *
SCTVDYSTVYFVNIEVWVEA ENALGKVTSDHINFDPVYKV KPNPPHNLSVINSEELSSIL 250        260        270        280        290        300
          *          *          *          *          *          *
KLTWTNPSIKSVIILKYNIQ YRTKDASTWSQIPPEDTAST RSSFTVQDLKPFTEYVFRIR 310        320        330        340        350        360
          *          *          *          *          *          *
CMKEDGKGYWSDWSEEASGI TYEDRPSKAPSFWYKIDPSH TQGYRTVQLVWKTLPPFEAN 370        380        390        400        410        420
          *          *          *          *          *          *
GKILDYEVTLTRWKSHLQNY TVNATKLTVNLTNDRYLATL TVRNLVGKSDAAVLTIPACD 430        440        450        460        470        480
          *          *          *          *          *          *
FQATHPVMDLKAFPKDNMLW VEWTTPRESVKKYILEWCVL SDKAPCITDWQQEDGTVHRT 490        500        510        520        530        540
          *          *          *          *          *          *
YLRGNLAESKCYLITVTPVY ADGPGSPESIKAYLKQAPPS KGPTVRTKKVGKNEAVLEWD 550        560        570        580        590        600
          *          *          *          *          *          *
QLPVDVQNGFIRNYTIFYRT IIGNETAVNVDSSHTEYTLS SLTSDTLYMVRMAAYTDEGG 610        620        630        640        650        660
          *          *          *          *          *          *
KDGPEFTFTTPKFAQGEIES GASTKGPSVFPLAPSSKSTS GGTAALGCLVKDYFPEPVTV 670        680        690        700        710        720
          *          *          *          *          *          *
SWNSGALTSGVHTFPAVLQS SGLYSLSSVVTVPSSSLGTQ TYICNVNHKPSNTKVDKKVE 730        740        750        760        770        780
          *          *          *          *          *          *
PKSCDKTHTCPPCPAPELLG GPSVFLFPPKPKDTLMISRT PEVTCVVVDVSHEDPEVKFN
```

Figure 9B

```
        790         800         810         820         830         840
         *           *           *           *           *           *
WYVDGVEVHNAKTKPREEQY NSTYRVVSVLTVLHQDWLNG KEYKCKVSNKALPAPIEKTI 850         860         870         880         890         900
         *           *           *           *           *           *
SKAKGQPREPQVYTLPPSRD ELTKNQVSLTCLVKGFYPSD IAVEWESNGQPENNYKTTPP 910         920         930         940         950
         *           *           *           *           *
VLDSDGSFFLYSKLTVDKSR WQQGNVFSCSVMHEALHNHY TQKSLSLSPGK*
```

Fig.10.

Amino acid sequence of gp130Δ3fibro

Sequence Range: 1 to 332

```
         10          20          30          40          50          60
          *           *           *           *           *           *
MVTLQTWVVQALFIFLTTES TGELLDPCGYISPESPVVQL HSNFTAVCVLKEKCMDYFHV 70          80          90         100         110         120
          *           *           *           *           *           *
NANYIVWKTNHFTIPKEQYT IINRTASSVTFTDIASLNIQ LTCNILTFGQLEQNVYGITI 130         140         150         160         170         180
          *           *           *           *           *           *
ISGLPPEKPKNLSCIVNEGK KMRCEWDGGRETHLETNFTL KSEWATHKFADCKAKRDTPT 190         200         210         220         230         240
          *           *           *           *           *           *
SCTVDYSTVYFVNIEVWVEA ENALGKVTSDHINFDPVYKV KPNPPHNLSVINSEELSSIL 250         260         270         280         290         300
          *           *           *           *           *           *
KLTWTNPSIKSVIILKYNIQ YRTKDASTWSQIPPEDTAST RSSFTVQDLKPFTEYVFRIR 310         320         330
          *           *           *
CMKEDGKGYWSDWSEEASGI TYEDRPSKAPSG
```

Fig. 11.
Amino acid sequence of J-CH1

Sequence Range: 1 to 121

```
         10          20          30          40          50          60
          *           *           *           *           *           *
SGGQGTLVTVSSASTKGPSV FPLAPSSKSTSGGTAALGCL VKDYFPEPVTVSWNSGALTS 70          80          90         100         110         120
          *           *           *           *           *           *
GVHTFPAVLQSSGLYSLSSV VTVPSSSLGTQTYICNVNHK PSNTKVDKKVEPKSCDKTHT*
```

Fig. 12.
Amino acid sequence of Cγ4

Sequence Range: 1 to 330

```
         10          20          30          40          50          60
          *           *           *           *           *           *
SGASTKGPSVFPLAPCSRST SESTAALGCLVKDYFPEPVT VSWNSGALTSGVHTFPAVLQ 70          80          90         100         110         120
          *           *           *           *           *           *
SSGLYSLSSVVTVPSSSLGT KTYTCNVDHKPSNTKVDKRV ESKYGPPCPSCPAPEFLGGP 130         140         150         160         170         180
          *           *           *           *           *           *
SVFLFPPKPKDTLMISRTPE VTCVVVDVSQEDPEVQFNWY VDGVEVHNAKTKPREEQFNS 190         200         210         220         230         240
          *           *           *           *           *           *
TYRVVSVLTVLHQDWLNGKE YKCKVSNKGLPSSIEKTISK AKGQPREPQVYTLPPSQEEM 250         260         270         280         290         300
          *           *           *           *           *           *
TKNQVSLTCLVKGFYPSDIA VEWESNGQPENNYKTTPPVL DSDGSFFLYSRLTVDKSRWQ 310         320         330
          *           *           *
EGNVFSCSVMHEALHNHYTQ KSLSLSLGK*
```

Fig. 13.

Amino acid sequence of κ-domain

Sequence Range: 1 to 108

```
         10          20          30          40          50          60
          *           *           *           *           *           *
SCTVAAPSVFIFPPSDEQLK SGTASVVCLLNNFYPREAKV QWKVDNALQSGNSQESVTEQ 70          80          90         100
          *           *           *           *
DSKDSTYSLSSTLTLSKADY EKHKVYACEVTHQGLSSPVT KSFNRGEC*
```

Fig. 14.

Amino acid sequence of λ-domain:

Sequence Range: 1 to 107

```
         10          20          30          40          50          60
          *           *           *           *           *           *
SGPKAAPSVTLFPPSSEELQ ANKATLVCLISDFYPGAVTV AWKADSSPVKAGVETTTPSK 70          80          90         100
          *           *           *           *
QSNNKYAASSYLSLTPEQWK SHRSYSCQVTHEGSTVEKTV APTECS*
```

Fig. 15.

Amino acid sequence of the soluble IL-6Rα domain

Sequence Range: 1 to 360

```
         10          20          30          40          50          60
          *           *           *           *           *           *
MVAVGCALLAALLAAPGAAL APRRCPAQEVARGVLTSLPG DSVTLTCPGVEPEDNATVHW 70          80          90         100         110         120
          *           *           *           *           *           *
VLRKPAAGSHPSRWAGMGRR LLLRSVQLHDSGNYSCYRAG RPAGTVHLLVDVPPEEPQLS 130         140         150         160         170         180
          *           *           *           *           *           *
CFRKSPLSNVVCEWGPRSTP SLTTKAVLLVRKFQNSPAED FQEPCQYSQESQKFSCQLAV 190         200         210         220         230         240
          *           *           *           *           *           *
PEGDSSFYIVSMCVASSVGS KFSKTQTFQGCGILQPDPPA NITVTAVARNPRWLSVTWQD 250         260         270         280         290         300
          *           *           *           *           *           *
PHSWNSSFYRLRFELRYRAE RSKTFTTWMVKDLQHHCVIH DAWSGLRHVVQLRAQEEFGQ 310         320         330         340         350         360
          *           *           *           *           *           *
GEWSEWSPEAMGTPWTESRS PPAENEVSTPMQALTTNKDD DNILFRDSANATSLPVQDAG
```

Fig. 16.

Amino acid sequence of the soluble IL-6Rα313 domain

Sequence Range: 1 to 315

```
         10          20          30          40          50          60
          *           *           *           *           *           *
MVAVGCALLAALLAAPGAAL APRRCPAQEVARGVLTSLPG DSVTLTCPGVEPEDNATVHW 70          80          90         100         110         120
          *           *           *           *           *           *
VLRKPAAGSHPSRWAGMGRR LLLRSVQLHDSGNYSCYRAG RPAGTVHLLVDVPPEEPQLS 130         140         150         160         170         180
          *           *           *           *           *           *
CFRKSPLSNVVCEWGPRSTP SLTTKAVLLVRKFQNSPAED FQEPCQYSQESQKFSCQLAV 190         200         210         220         230         240
          *           *           *           *           *           *
PEGDSSFYIVSMCVASSVGS KFSKTQTFQGCGILQPDPPA NITVTAVARNPRWLSVTWQD 250         260         270         280         290         300
          *           *           *           *           *           *
PHSWNSSFYRLRFELRYRAE RSKTFTTWMVKDLQHHCVIH DAWSGLRHVVQLRAQEEFGQ

310
          *
GEWSEWSPEAMGTTG
```

IL-6 Dissociates Slowly from the Ligand Trap

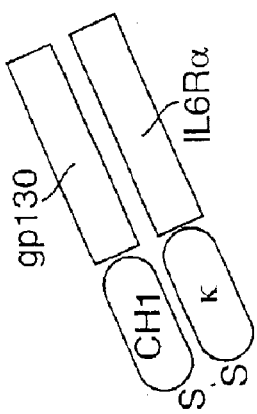
Figure 19 A
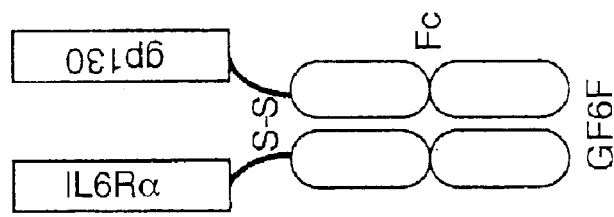
Figure 19B

Fig.21A.

```
         10          20          30          40
          *           *           *           *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50          60          70          80          90
  *           *           *           *           *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100         110         120         130         140
     *           *           *           *           *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150         160         170         180         190
     *           *           *           *           *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200         210         220         230         240
          *           *           *           *           *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250         260         270         280
          *           *           *           *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290         300         310         320         330
  *           *           *           *           *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340         350         360         370         380
     *           *           *           *           *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390         400         410         420         430
     *           *           *           *           *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440         450         460         470         480
          *           *           *           *           *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490         500         510         520
          *           *           *           *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530         540         550         560         570
  *           *           *           *           *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.21B.

```
     580              590              600            610              620
      *                *                *       *      *       *        *       *        *
TGG  GAC  CAC  AGC  TGG  ACT  GAA  CAA  TCA  GTG  GAT  TAT  AGA  CAT  AAG  TTC
Trp  Asp  His  Ser  Trp  Thr  Glu  Gln  Ser  Val  Asp  Tyr  Arg  His  Lys  Phe>

630              640              650            660              670
  *     *        *      *        *      *       *       *        *       *
TCC  TTG  CCT  AGT  GTG  GAT  GGG  CAG  AAA  CGC  TAC  ACG  TTT  CGT  GTT  CGG
Ser  Leu  Pro  Ser  Val  Asp  Gly  Gln  Lys  Arg  Tyr  Thr  Phe  Arg  Val  Arg>

680              690             700            710              720
   *       *        *       *        *       *       *        *       *       *
AGC  CGC  TTT  AAC  CCA  CTC  TGT  GGA  AGT  GCT  CAG  CAT  TGG  AGT  GAA  TGG
Ser  Arg  Phe  Asn  Pro  Leu  Cys  Gly  Ser  Ala  Gln  His  Trp  Ser  Glu  Trp>

730              740             750             760
       *      *        *       *       *       *       *        *       *
AGC  CAC  CCA  ATC  CAC  TGG  GGG  AGC  AAT  ACT  TCA  AAA  GAG  AAC  GCG  TCG
Ser  His  Pro  Ile  His  Trp  Gly  Ser  Asn  Thr  Ser  Lys  Glu  Asn  Ala  Ser>

770              780             790            800              810
 *      *        *       *       *       *       *        *       *       *
TCT  GGG  AAC  ATG  AAG  GTC  CTG  CAG  GAG  CCC  ACC  TGC  GTC  TCC  GAC  TAC
Ser  Gly  Asn  Met  Lys  Val  Leu  Gln  Glu  Pro  Thr  Cys  Val  Ser  Asp  Tyr>

820              830             840            850              860
  *     *        *       *       *       *       *        *       *       *
ATG  AGC  ATC  TCT  ACT  TGC  GAG  TGG  AAG  ATG  AAT  GGT  CCC  ACC  AAT  TGC
Met  Ser  Ile  Ser  Thr  Cys  Glu  Trp  Lys  Met  Asn  Gly  Pro  Thr  Asn  Cys>

870              880             890             900              910
   *       *        *       *       *       *       *        *       *       *
AGC  ACC  GAG  CTC  CGC  CTG  TTG  TAC  CAG  CTG  GTT  TTT  CTG  CTC  TCC  GAA
Ser  Thr  Glu  Leu  Arg  Leu  Leu  Tyr  Gln  Leu  Val  Phe  Leu  Leu  Ser  Glu>

920              930             940             950              960
       *      *        *       *       *       *       *        *       *       *
GCC  CAC  ACG  TGT  ATC  CCT  GAG  AAC  AAC  GGA  GGC  GCG  GGG  TGC  GTG  TGC
Ala  His  Thr  Cys  Ile  Pro  Glu  Asn  Asn  Gly  Gly  Ala  Gly  Cys  Val  Cys>

970              980             990            1000
   *       *        *       *       *       *       *        *       *       *
CAC  CTG  CTC  ATG  GAT  GAC  GTG  GTC  AGT  GCG  GAT  AAC  TAT  ACA  CTG  GAC
His  Leu  Leu  Met  Asp  Asp  Val  Val  Ser  Ala  Asp  Asn  Tyr  Thr  Leu  Asp>

1010             1020            1030           1040             1050
 *      *        *       *       *       *       *        *       *       *
CTG  TGG  GCT  GGG  CAG  CAG  CTG  CTG  TGG  AAG  GGC  TCC  TTC  AAG  CCC  AGC
Leu  Trp  Ala  Gly  Gln  Gln  Leu  Leu  Trp  Lys  Gly  Ser  Phe  Lys  Pro  Ser>

1060             1070            1080            1090             1100
   *     *       *        *       *       *       *        *       *       *
GAG  CAT  GTG  AAA  CCC  AGG  GCC  CCA  GGA  AAC  CTG  ACA  GTT  CAC  ACC  AAT
Glu  His  Val  Lys  Pro  Arg  Ala  Pro  Gly  Asn  Leu  Thr  Val  His  Thr  Asn>

1110            1120            1130            1140             1150
    *      *        *      *        *      *       *       *        *       *
GTC  TCC  GAC  ACT  CTG  CTG  CTG  ACC  TGG  AGC  AAC  CCG  TAT  CCC  CCT  GAC
Val  Ser  Asp  Thr  Leu  Leu  Leu  Thr  Trp  Ser  Asn  Pro  Tyr  Pro  Pro  Asp>

```
AAT TAC CTG TAT AAT CAT CTC ACC TAT GCA GTC AAC ATT TGG AGT GAA
Asn Tyr Leu Tyr Asn His Leu Thr Tyr Ala Val Asn Ile Trp Ser Glu>

1210        1220        1230        1240
          *           *           *           *           *
AAC GAC CCG GCA GAT TTC AGA ATC TAT AAC GTG ACC TAC CTA GAA CCC
Asn Asp Pro Ala Asp Phe Arg Ile Tyr Asn Val Thr Tyr Leu Glu Pro>

1250       1260        1270        1280        1290
  *          *           *           *           *           *
TCC CTC CGC ATC GCA GCC AGC ACC CTG AAG TCT GGG ATT TCC TAC AGG
Ser Leu Arg Ile Ala Ala Ser Thr Leu Lys Ser Gly Ile Ser Tyr Arg>

1300        1310        1320        1330        1340
          *           *           *           *           *
GCA CGG GTG AGG GCC TGG GCT CAG TGC TAT AAC ACC ACC TGG AGT GAG
Ala Arg Val Arg Ala Trp Ala Gln Cys Tyr Asn Thr Thr Trp Ser Glu>

1350        1360        1370        1380        1390
     *           *           *           *           *           *
TGG AGC CCC AGC ACC AAG TGG CAC AAC TCC TAC AGG GAG CCC TTC GAG
Trp Ser Pro Ser Thr Lys Trp His Asn Ser Tyr Arg Glu Pro Phe Glu>

1400        1410        1420        1430        1440
          *           *           *           *           *           *
CAG TCC GGA GAC AAA ACT CAC ACA TGC CCA CCG TGC CCA GCA CCT GAA
Gln Ser Gly Asp Lys Thr His Thr Cys Pro Pro Cys Pro Ala Pro Glu>

1450        1460        1470        1480
          *           *           *           *           *
CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>

1490       1500        1510        1520        1530
  *          *           *           *           *           *
ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>

1540        1550        1560        1570        1580
     *           *           *           *           *           *
GTG AGC CAC GAA GAC CCT GAG GTC AAG TTC AAC TGG TAC GTG GAC GGC
Val Ser His Glu Asp Pro Glu Val Lys Phe Asn Trp Tyr Val Asp Gly>

1590        1600        1610        1620        1630
          *           *           *           *           *           *
GTG GAG GTG CAT AAT GCC AAG ACA AAG CCG CGG GAG GAG CAG TAC AAC
Val Glu Val His Asn Ala Lys Thr Lys Pro Arg Glu Glu Gln Tyr Asn>

1640        1650        1660        1670        1680
          *           *           *           *           *           *
AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp>

1690        1700        1710        1720
          *           *           *           *           *
CTG AAT GGC AAG GAG TAC AAG TGC AAG GTC TCC AAC AAA GCC CTC CCA
Leu Asn Gly Lys Glu Tyr Lys Cys Lys Val Ser Asn Lys Ala Leu Pro>

1730       1740        1750        1760        1770
  *          *           *           *           *           *
GCC CCC ATC GAG AAA ACC ATC TCC AAA GCC AAA GGG CAG CCC CGA GAA
Ala Pro Ile Glu Lys Thr Ile Ser Lys Ala Lys Gly Gln Pro Arg Glu>
```

Fig.21D.

```
      1780                1790                1800                1810                1820
        *         *         *         *         *         *         *         *         *
    CCA CAG GTG TAC ACC CTG CCC CCA TCC CGG GAG GAG ATG ACC AAG AAC
    Pro Gln Val Tyr Thr Leu Pro Pro Ser Arg Glu Glu Met Thr Lys Asn>

1830                1840                1850                1860                1870
        *         *         *         *         *         *         *         *         *         *
    CAG GTC AGC CTG ACC TGC CTG GTC AAA GGC TTC TAT CCC AGC GAC ATC
    Gln Val Ser Leu Thr Cys Leu Val Lys Gly Phe Tyr Pro Ser Asp Ile>

1880                1890                1900                1910                1920
        *         *         *         *         *         *         *         *         *         *
    GCC GTG GAG TGG GAG AGC AAT GGG CAG CCG GAG AAC AAC TAC AAG ACC
    Ala Val Glu Trp Glu Ser Asn Gly Gln Pro Glu Asn Asn Tyr Lys Thr>

1930                1940                1950                1960
        *         *         *         *         *         *         *         *         *
    ACG CCT CCC GTG CTG GAC TCC GAC GGC TCC TTC TTC CTC TAT AGC AAG
    Thr Pro Pro Val Leu Asp Ser Asp Gly Ser Phe Phe Leu Tyr Ser Lys>

1970                1980                1990                2000                2010
        *         *         *         *         *         *         *         *         *         *
    CTC ACC GTG GAC AAG AGC AGG TGG CAG CAG GGG AAC GTC TTC TCA TGC
    Leu Thr Val Asp Lys Ser Arg Trp Gln Gln Gly Asn Val Phe Ser Cys>

2020                2030                2040                2050                2060
        *         *         *         *         *         *         *         *         *
    TCC GTG ATG CAT GAG GCT CTG CAC AAC CAC TAC ACG CAG AAG AGC CTC
    Ser Val Met His Glu Ala Leu His Asn His Tyr Thr Gln Lys Ser Leu>

2070                2080
        *         *         *         *         *
    TCC CTG TCT CCG GGT AAA TGA
    Ser Leu Ser Pro Gly Lys ***>
```

Fig.22A.

```
        10              20              30              40
         *       *       *       *       *       *       *       *       *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50              60              70              80              90
     *       *       *       *       *       *       *       *       *       *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100             110             120             130             140
        *       *       *       *       *       *       *       *       *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150             160             170             180             190
    *       *       *       *       *       *       *       *       *       *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200             210             220             230             240
        *       *       *       *       *       *       *       *       *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250             260             270             280
         *       *       *       *       *       *       *       *       *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290             300             310             320             330
     *       *       *       *       *       *       *       *       *       *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340             350             360             370             380
        *       *       *       *       *       *       *       *       *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390             400             410             420             430
        *       *       *       *       *       *       *       *       *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440             450             460             470             480
        *       *       *       *       *       *       *       *       *       *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490             500             510             520
            *       *       *       *       *       *       *       *       *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530             540             550             560             570
     *       *       *       *       *       *       *       *       *       *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.22B.

```
       580            590           600           610           620
        *              *             *             *             *
    *     *        *      *       *      *     *      *      *      *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630            640           650           660           670
    *     *        *      *     *      *      *      *      *      *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680           690            700           710           720
    *     *       *      *       *      *      *      *      *      *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730           740           750           760
           *      *      *      *      *      *     *      *      *
AGC CAC CCA ATC CAC TGG GGG AGC AAT ACT TCA AAA GAG AAC GGG AAC
Ser His Pro Ile His Trp Gly Ser Asn Thr Ser Lys Glu Asn Gly Asn>

770           780           790           800           810
 *      *      *      *      *      *      *      *      *      *
ATG AAG GTC CTG CAG GAG CCC ACC TGC GTC TCC GAC TAC ATG AGC ATC
Met Lys Val Leu Gln Glu Pro Thr Cys Val Ser Asp Tyr Met Ser Ile>

820           830           840           850           860
   *      *      *      *      *      *      *      *      *
TCT ACT TGC GAG TGG AAG ATG AAT GGT CCC ACC AAT TGC AGC ACC GAG
Ser Thr Cys Glu Trp Lys Met Asn Gly Pro Thr Asn Cys Ser Thr Glu>

870           880           890           900           910
      *      *      *      *      *      *      *      *      *      *
CTC CGC CTG TTG TAC CAG CTG GTT TTT CTG CTC TCC GAA GCC CAC ACG
Leu Arg Leu Leu Tyr Gln Leu Val Phe Leu Leu Ser Glu Ala His Thr>

920           930           940           950           960
       *      *      *      *      *      *      *      *      *
TGT ATC CCT GAG AAC AAC GGA GGC GCG GGG TGC GTG TGC CAC CTG CTC
Cys Ile Pro Glu Asn Asn Gly Gly Ala Gly Cys Val Cys His Leu Leu>

970           980           990           1000
           *      *      *      *      *      *      *      *      *
ATG GAT GAC GTG GTC AGT GCG GAT AAC TAT ACA CTG GAC CTG TGG GCT
Met Asp Asp Val Val Ser Ala Asp Asn Tyr Thr Leu Asp Leu Trp Ala>

1010          1020          1030          1040          1050
 *      *      *      *      *      *      *      *      *      *
GGG CAG CAG CTG CTG TGG AAG GGC TCC TTC AAG CCC AGC GAG CAT GTG
Gly Gln Gln Leu Leu Trp Lys Gly Ser Phe Lys Pro Ser Glu His Val>

1060          1070          1080          1090          1100
   *      *      *      *      *      *      *      *      *      *
AAA CCC AGG GCC CCA GGA AAC CTG ACA GTT CAC ACC AAT GTC TCC GAC
Lys Pro Arg Ala Pro Gly Asn Leu Thr Val His Thr Asn Val Ser Asp>

1110          1120          1130          1140          1150
       *      *      *      *      *      *      *      *      *      *
ACT CTG CTG CTG ACC TGG AGC AAC CCG TAT CCC CCT GAC AAT TAC CTG
Thr Leu Leu Leu Thr Trp Ser Asn Pro Tyr Pro Pro Asp Asn Tyr Leu>

```
      TAT AAT CAT CTC ACC TAT GCA GTC AAC ATT TGG AGT GAA AAC GAC CCG
      Tyr Asn His Leu Thr Tyr Ala Val Asn Ile Trp Ser Glu Asn Asp Pro>

1210        1220        1230        1240
       *    *      *    *      *    *      *    *      *
      GCA GAT TTC AGA ATC TAT AAC GTG ACC TAC CTA GAA CCC TCC CTC CGC
      Ala Asp Phe Arg Ile Tyr Asn Val Thr Tyr Leu Glu Pro Ser Leu Arg>

1250        1260        1270        1280        1290
   *    *      *    *      *    *      *    *      *    *
      ATC GCA GCC AGC ACC CTG AAG TCT GGG ATT TCC TAC AGG GCA CGG GTG
      Ile Ala Ala Ser Thr Leu Lys Ser Gly Ile Ser Tyr Arg Ala Arg Val>

1300        1310        1320        1330        1340
       *    *      *    *      *    *      *    *      *
      AGG GCC TGG GCT CAG AGC TAT AAC ACC ACC TGG AGT GAG TGG AGC CCC
      Arg Ala Trp Ala Gln Ser Tyr Asn Thr Thr Trp Ser Glu Trp Ser Pro>

1350        1360        1370        1380        1390
       *    *      *    *      *    *      *    *      *    *
      AGC ACC AAG TGG CAC AAC TCC TAC AGG GAG CCC TTC GAG CAG TCC GGA
      Ser Thr Lys Trp His Asn Ser Tyr Arg Glu Pro Phe Glu Gln Ser Gly>

1400        1410        1420        1430        1440
       *    *      *    *      *    *      *    *      *    *
      GAC AAA ACT CAC ACA TGC CCA CCG TGC CCA GCA CCT GAA CTC CTG GGG
      Asp Lys Thr His Thr Cys Pro Pro Cys Pro Ala Pro Glu Leu Leu Gly>

1450        1460        1470        1480
       *    *      *    *      *    *      *    *      *
      GGA CCG TCA GTC TTC CTC TTC CCC CCA AAA CCC AAG GAC ACC CTC ATG
      Gly Pro Ser Val Phe Leu Phe Pro Pro Lys Pro Lys Asp Thr Leu Met>

1490        1500        1510        1520        1530
   *    *      *    *      *    *      *    *      *    *
      ATC TCC CGG ACC CCT GAG GTC ACA TGC GTG GTG GTG GAC GTG AGC CAC
      Ile Ser Arg Thr Pro Glu Val Thr Cys Val Val Val Asp Val Ser His>

1540        1550        1560        1570        1580
       *    *      *    *      *    *      *    *      *
      GAA GAC CCT GAG GTC AAG TTC AAC TGG TAC GTG GAC GGC GTG GAG GTG
      Glu Asp Pro Glu Val Lys Phe Asn Trp Tyr Val Asp Gly Val Glu Val>

1590        1600        1610        1620        1630
       *    *      *    *      *    *      *    *      *    *
      CAT AAT GCC AAG ACA AAG CCG CGG GAG GAG CAG TAC AAC AGC ACG TAC
      His Asn Ala Lys Thr Lys Pro Arg Glu Glu Gln Tyr Asn Ser Thr Tyr>

1640        1650        1660        1670        1680
       *    *      *    *      *    *      *    *      *    *
      CGT GTG GTC AGC GTC CTC ACC GTC CTG CAC CAG GAC TGG CTG AAT GGC
      Arg Val Val Ser Val Leu Thr Val Leu His Gln Asp Trp Leu Asn Gly>

1690        1700        1710        1720
       *    *      *    *      *    *      *    *      *
      AAG GAG TAC AAG TGC AAG GTC TCC AAC AAA GCC CTC CCA GCC CCC ATC
      Lys Glu Tyr Lys Cys Lys Val Ser Asn Lys Ala Leu Pro Ala Pro Ile>

1730        1740        1750        1760        1770
   *    *      *    *      *    *      *    *      *    *
      GAG AAA ACC ATC TCC AAA GCC AAA GGG CAG CCC CGA GAA CCA CAG GTG
      Glu Lys Thr Ile Ser Lys Ala Lys Gly Gln Pro Arg Glu Pro Gln Val>
```

Fig.22D.

```
            1780           1790          1800         1810           1820
              *              *             *    *       *       *      *
TAC ACC CTG CCC CCA TCC CGG GAT GAG CTG ACC AAG AAC CAG GTC AGC
Tyr Thr Leu Pro Pro Ser Arg Asp Glu Leu Thr Lys Asn Gln Val Ser>

1830           1840          1850         1860           1870
  *     *     *      *      *      *     *      *      *     *
CTG ACC TGC CTG GTC AAA GGC TTC TAT CCC AGC GAC ATC GCC GTG GAG
Leu Thr Cys Leu Val Lys Gly Phe Tyr Pro Ser Asp Ile Ala Val Glu>

1880           1890          1900          1910            1920
  *      *      *       *      *      *      *      *      *      *
TGG GAG AGC AAT GGG CAG CCG GAG AAC AAC TAC AAG ACC ACG CCT CCC
Trp Glu Ser Asn Gly Gln Pro Glu Asn Asn Tyr Lys Thr Thr Pro Pro>

1930          1940         1950          1960
  *      *     *      *      *      *     *      *      *
GTG CTG GAC TCC GAC GGC TCC TTC TTC CTC TAT AGC AAG CTC ACC GTG
Val Leu Asp Ser Asp Gly Ser Phe Phe Leu Tyr Ser Lys Leu Thr Val>

1970           1980          1990          2000            2010
  *      *      *      *      *      *      *      *      *      *
GAC AAG AGC AGG TGG CAG CAG GGG AAC GTC TTC TCA TGC TCC GTG ATG
Asp Lys Ser Arg Trp Gln Gln Gly Asn Val Phe Ser Cys Ser Val Met>

2020           2030          2040         2050           2060
  *      *      *      *      *      *      *      *      *
CAT GAG GCT CTG CAC AAC CAC TAC ACG CAG AAG AGC CTC TCC CTG TCT
His Glu Ala Leu His Asn His Tyr Thr Gln Lys Ser Leu Ser Leu Ser>

2070
  *      *      *
CCG GGT AAA TGA
Pro Gly Lys ***>
```

Fig.23A.

```
          10                  20                  30                  40
     *         *         *         *         *         *         *         *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50            60                  70            80                  90
     *         *         *         *         *         *         *         *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100                 110                 120                 130                 140
     *         *         *         *         *         *         *         *         *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150                 160                 170                 180                 190
     *         *         *         *         *         *         *         *         *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200                 210                 220                 230                 240
     *         *         *         *         *         *         *         *         *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250                 260                 270                 280
     *         *         *         *         *         *         *         *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290           300                 310                 320                 330
     *         *         *         *         *         *         *         *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340                 350                 360                 370                 380
     *         *         *         *         *         *         *         *         *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390                 400                 410                 420                 430
     *         *         *         *         *         *         *         *         *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440                 450                 460                 470                 480
     *         *         *         *         *         *         *         *         *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490                 500                 510                 520
          *         *         *         *         *         *         *         *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530           540                 550                 560                 570
     *         *         *         *         *         *         *         *         *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.23B.

```
     580         590         600         610         620
      *           *           *           *           *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630         640         650         660         670
      *           *           *           *           *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680         690         700         710         720
      *           *           *           *           *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730         740         750         760
      *           *           *           *
AGC CAC CCA ATC CAC TGG GGG AGC AAT ACT TCA AAA GAG AAC GCG TCG
Ser His Pro Ile His Trp Gly Ser Asn Thr Ser Lys Glu Asn Ala Ser>

770          780         790         800         810
 *            *           *           *           *
TCT GGG AAC ATG AAG GTC CTG CAG GAG CCC ACC TGC GTC TCC GAC TAC
Ser Gly Asn Met Lys Val Leu Gln Glu Pro Thr Cys Val Ser Asp Tyr>

820         830         840         850         860
      *           *           *           *           *
ATG AGC ATC TCT ACT TGC GAG TGG AAG ATG AAT GGT CCC ACC AAT TGC
Met Ser Ile Ser Thr Cys Glu Trp Lys Met Asn Gly Pro Thr Asn Cys>

870         880         890         900         910
      *           *           *           *           *
AGC ACC GAG CTC CGC CTG TTG TAC CAG CTG GTT TTT CTG CTC TCC GAA
Ser Thr Glu Leu Arg Leu Leu Tyr Gln Leu Val Phe Leu Leu Ser Glu>

920         930         940         950         960
      *           *           *           *           *
GCC CAC ACG TGT ATC CCT GAG AAC AAC GGA GGC GCG GGG TGC GTG TGC
Ala His Thr Cys Ile Pro Glu Asn Asn Gly Gly Ala Gly Cys Val Cys>

970         980         990         1000
      *           *           *           *
CAC CTG CTC ATG GAT GAC GTG GTC AGT GCG GAT AAC TAT ACA CTG GAC
His Leu Leu Met Asp Asp Val Val Ser Ala Asp Asn Tyr Thr Leu Asp>

1010         1020        1030        1040        1050
 *            *           *           *           *
CTG TGG GCT GGG CAG CAG CTG CTG TGG AAG GGC TCC TTC AAG CCC AGC
Leu Trp Ala Gly Gln Gln Leu Leu Trp Lys Gly Ser Phe Lys Pro Ser>

1060        1070        1080        1090        1100
      *           *           *           *           *
GAG CAT GTG AAA CCC AGG GCC CCA GGA AAC CTG ACA GTT CAC ACC AAT
Glu His Val Lys Pro Arg Ala Pro Gly Asn Leu Thr Val His Thr Asn>

1110        1120        1130        1140        1150
      *           *           *           *           *
GTC TCC GAC ACT CTG CTG CTG ACC TGG AGC AAC CCG TAT CCC CCT GAC
Val Ser Asp Thr Leu Leu Leu Thr Trp Ser Asn Pro Tyr Pro Pro Asp>

```
            GAT TAC CTG TAT AAT CAT CTC ACC TAT GCA GTC AAC ATT TGG AGT GAA
            Asn Tyr Leu Tyr Asn His Leu Thr Tyr Ala Val Asn Ile Trp Ser Glu>

1210      1220      1230      1240
               *    *    *    *    *    *    *    *    *
            AAC GAC CCG GCA GAT TTC AGA ATC TAT AAC GTG ACC TAC CTA GAA CCC
            Asn Asp Pro Ala Asp Phe Arg Ile Tyr Asn Val Thr Tyr Leu Glu Pro>

1250      1260      1270      1280      1290
      *    *    *    *    *    *    *    *    *    *
            TCC CTC CGC ATC GCA GCC AGC ACC CTG AAG TCT GGG ATT TCC TAC AGG
            Ser Leu Arg Ile Ala Ala Ser Thr Leu Lys Ser Gly Ile Ser Tyr Arg>

1300      1310      1320      1330      1340
      *    *    *    *    *    *    *    *    *    *
            GCA CGG GTG AGG GCC TGG GCT CAG AGC TAT AAC ACC ACC TGG AGT GAG
            Ala Arg Val Arg Ala Trp Ala Gln Ser Tyr Asn Thr Thr Trp Ser Glu>

1350      1360      1370      1380      1390
        *    *    *    *    *    *    *    *    *    *
            TGG AGC CCC AGC ACC AAG TGG CAC AAC TCC TAC AGG GAG CCC TTC GAG
            Trp Ser Pro Ser Thr Lys Trp His Asn Ser Tyr Arg Glu Pro Phe Glu>

1400      1410      1420      1430      1440
               *    *    *    *    *    *    *    *    *    *
            CAG TCC GGA GAC AAA ACT CAC ACA TGC CCA CCG TGC CCA GCA CCT GAA
            Gln Ser Gly Asp Lys Thr His Thr Cys Pro Pro Cys Pro Ala Pro Glu>

1450      1460      1470      1480
               *    *    *    *    *    *    *    *    *
            CTC CTG GGG GGA CCG TCA GTC TTC CTC TTC CCC CCA AAA CCC AAG GAC
            Leu Leu Gly Gly Pro Ser Val Phe Leu Phe Pro Pro Lys Pro Lys Asp>

1490      1500      1510      1520      1530
      *    *    *    *    *    *    *    *    *    *
            ACC CTC ATG ATC TCC CGG ACC CCT GAG GTC ACA TGC GTG GTG GTG GAC
            Thr Leu Met Ile Ser Arg Thr Pro Glu Val Thr Cys Val Val Val Asp>

1540      1550      1560      1570      1580
        *    *    *    *    *    *    *    *    *
            GTG AGC CAC GAA GAC CCT GAG GTC AAG TTC AAC TGG TAC GTG GAC GGC
            Val Ser His Glu Asp Pro Glu Val Lys Phe Asn Trp Tyr Val Asp Gly>

1590      1600      1610      1620      1630
           *    *    *    *    *    *    *    *    *    *
            GTG GAG GTG CAT AAT GCC AAG ACA AAG CCG CGG GAG GAG CAG TAC AAC
            Val Glu Val His Asn Ala Lys Thr Lys Pro Arg Glu Glu Gln Tyr Asn>

1640      1650      1660      1670      1680
               *    *    *    *    *    *    *    *    *    *
            AGC ACG TAC CGT GTG GTC AGC GTC CTC ACC GTC CTG CAC CAG GAC TGG
            Ser Thr Tyr Arg Val Val Ser Val Leu Thr Val Leu His Gln Asp Trp>

1690      1700      1710      1720
                    *    *    *    *    *    *    *    *    *
            CTG AAT GGC AAG GAG TAC AAG TGC AAG GTC TCC AAC AAA GCC CTC CCA
            Leu Asn Gly Lys Glu Tyr Lys Cys Lys Val Ser Asn Lys Ala Leu Pro>

1730      1740      1750      1760      1770
             *    *    *    *    *    *    *    *    *    *
            GCC CCC ATC GAG AAA ACC ATC TCC AAA GCC AAA GGG CAG CCC CGA GAA
            Ala Pro Ile Glu Lys Thr Ile Ser Lys Ala Lys Gly Gln Pro Arg Glu>
```

Fig.23D.

```
       1780            1790           1800            1810           1820
         *       *       *       *       *       *       *       *       *
CCA CAG GTG TAC ACC CTG CCC CCA TCC CGG GAT GAG CTG ACC AAG AAC
Pro Gln Val Tyr Thr Leu Pro Pro Ser Arg Asp Glu Leu Thr Lys Asn>

1830            1840           1850            1860           1870
         *       *       *       *       *       *       *       *       *
CAG GTC AGC CTG ACC TGC CTG GTC AAA GGC TTC TAT CCC AGC GAC ATC
Gln Val Ser Leu Thr Cys Leu Val Lys Gly Phe Tyr Pro Ser Asp Ile>

1880            1890           1900            1910           1920
         *       *       *       *       *       *       *       *       *
GCC GTG GAG TGG GAG AGC AAT GGG CAG CCG GAG AAC AAC TAC AAG ACC
Ala Val Glu Trp Glu Ser Asn Gly Gln Pro Glu Asn Asn Tyr Lys Thr>

1930           1940           1950           1960
         *       *       *       *       *       *       *       *       *
ACG CCT CCC GTG CTG GAC TCC GAC GGC TCC TTC TTC CTC TAT AGC AAG
Thr Pro Pro Val Leu Asp Ser Asp Gly Ser Phe Phe Leu Tyr Ser Lys>

1970           1980           1990           2000           2010
    *       *       *       *       *       *       *       *       *       *
CTC ACC GTG GAC AAG AGC AGG TGG CAG CAG GGG AAC GTC TTC TCA TGC
Leu Thr Val Asp Lys Ser Arg Trp Gln Gln Gly Asn Val Phe Ser Cys>

2020           2030           2040            2050           2060
         *       *       *       *       *       *       *       *       *
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

2070           2080
         *       *       *       *       *
TCC CTG TCT CCG GGT AAA TGA
Ser Leu Ser Pro Gly Lys ***>
```

Fig.24A.

```
        10              20              30              40
         *               *               *               *
AGT GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50              60              70              80              90
    *               *               *               *               *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

100             110             120             130             140
       *               *               *               *               *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

150             160             170             180             190
          *               *               *               *               *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

200             210             220             230             240
             *               *               *               *               *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

250             260             270             280
                *               *               *               *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290             300             310             320             330
 *               *               *               *               *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

340             350             360             370             380
    *               *               *               *               *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

390             400             410             420             430
       *               *               *               *               *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

440             450             460             470             480
          *               *               *               *               *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

490             500             510             520
             *               *               *               *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530             540             550             560             570
 *               *               *               *               *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Fig.24B.

```
       580            590           600           610           620
        *       *      *       *     *      *      *      *      *
       TGC GTC GCC AGT AGT GTC GGG AGC AAG TTC AGC AAA ACT CAA ACC TTT
       Cys Val Ala Ser Ser Val Gly Ser Lys Phe Ser Lys Thr Gln Thr Phe>

630           640           650           660           670
        *     *      *      *      *      *      *      *      *      *
       CAG GGT TGT GGA ATC TTG CAG CCT GAT CCG CCT GCC AAC ATC ACA GTC
       Gln Gly Cys Gly Ile Leu Gln Pro Asp Pro Pro Ala Asn Ile Thr Val>

680           690           700           710           720
        *     *      *      *      *      *      *      *      *      *
       ACT GCC GTG GCC AGA AAC CCC CGC TGG CTC AGT GTC ACC TGG CAA GAC
       Thr Ala Val Ala Arg Asn Pro Arg Trp Leu Ser Val Thr Trp Gln Asp>

730           740           750           760
        *     *      *      *      *      *      *      *      *      *
       CCC CAC TCC TGG AAC TCA TCT TTC TAC AGA CTA CGG TTT GAG CTC AGA
       Pro His Ser Trp Asn Ser Ser Phe Tyr Arg Leu Arg Phe Glu Leu Arg>

770           780           790           800           810
        *     *      *      *      *      *      *      *      *      *
       TAT CGG GCT GAA CGG TCA AAG ACA TTC ACA ACA TGG ATG GTC AAG GAC
       Tyr Arg Ala Glu Arg Ser Lys Thr Phe Thr Thr Trp Met Val Lys Asp>

820           830           840           850           860
        *     *      *      *      *      *      *      *      *      *
       CTC CAG CAT CAC TGT GTC ATC CAC GAC GCC TGG AGC GGC CTG AGG CAC
       Leu Gln His His Cys Val Ile His Asp Ala Trp Ser Gly Leu Arg His>

870           880           890           900           910
        *     *      *      *      *      *      *      *      *      *
       GTG GTG CAG CTT CGT GCC CAG GAG GAG TTC GGG CAA GGC GAG TGG AGC
       Val Val Gln Leu Arg Ala Gln Glu Glu Phe Gly Gln Gly Glu Trp Ser>

920           930           940           950           960
        *     *      *      *      *      *      *      *      *      *
       GAG TGG AGC CCG GAG GCC ATG GGC ACG CCT TGG ACA GAA TCC AGG AGT
       Glu Trp Ser Pro Glu Ala Met Gly Thr Pro Trp Thr Glu Ser Arg Ser>

970           980           990          1000
        *     *      *      *      *      *      *      *      *      *
       CCT CCA GCT GAG AAC GAG GTG TCC ACC CCC ATG ACC GGT GGC GCG CCT
       Pro Pro Ala Glu Asn Glu Val Ser Thr Pro Met Thr Gly Gly Ala Pro>

1010          1020          1030          1040          1050
        *     *      *      *      *      *      *      *      *      *
       TCA GGT GCT CAG CTG GAA CTT CTA GAC CCA TGT GGT TAT ATC AGT CCT
       Ser Gly Ala Gln Leu Glu Leu Leu Asp Pro Cys Gly Tyr Ile Ser Pro>

1060          1070          1080          1090          1100
        *      *      *      *      *      *      *      *      *      *
       GAA TCT CCA GTT GTA CAA CTT CAT TCT AAT TTC ACT GCA GTT TGT GTG
       Glu Ser Pro Val Val Gln Leu His Ser Asn Phe Thr Ala Val Cys Val>

1110          1120          1130          1140          1150
        *      *      *      *      *      *      *      *      *      *
       CTA AAG GAA AAA TGT ATG GAT TAT TTT CAT GTA AAT GCT AAT TAC ATT
       Leu Lys Glu Lys Cys Met Asp Tyr Phe His Val Asn Ala Asn Tyr Ile>

```
  GTC TGG AAA ACA AAC CAT TTT ACT ATT CCT AAG GAG CAA TAT ACT ATC
  Val Trp Lys Thr Asn His Phe Thr Ile Pro Lys Glu Gln Tyr Thr Ile>

1210          1220          1230          1240
        *     *       *     *       *     *       *     *       *
  ATA AAC AGA ACA GCA TCC AGT GTC ACC TTT ACA GAT ATA GCT TCA TTA
  Ile Asn Arg Thr Ala Ser Ser Val Thr Phe Thr Asp Ile Ala Ser Leu>

1250         1260          1270         1280          1290
  *     *     *     *       *     *      *     *       *      *
  AAT ATT CAG CTC ACT TGC AAC ATT CTT ACA TTC GGA CAG CTT GAA CAG
  Asn Ile Gln Leu Thr Cys Asn Ile Leu Thr Phe Gly Gln Leu Glu Gln>

1300          1310          1320         1330          1340
        *     *       *     *       *     *      *     *       *
  AAT GTT TAT GGA ATC ACA ATA ATT TCA GGC TTG CCT CCA GAA AAA CCT
  Asn Val Tyr Gly Ile Thr Ile Ile Ser Gly Leu Pro Pro Glu Lys Pro>

1350          1360          1370          1380          1390
             *     *       *     *       *     *       *     *       *     *
  AAA AAT TTG AGT TGC ATT GTG AAC GAG GGG AAG AAA ATG AGG TGT GAG
  Lys Asn Leu Ser Cys Ile Val Asn Glu Gly Lys Lys Met Arg Cys Glu>

1400          1410          1420          1430          1440
        *     *       *     *       *     *       *     *       *     *
  TGG GAT GGT GGA AGG GAA ACA CAC TTG GAG ACA AAC TTC ACT TTA AAA
  Trp Asp Gly Gly Arg Glu Thr His Leu Glu Thr Asn Phe Thr Leu Lys>

1450          1460          1470          1480
             *     *       *     *       *     *       *     *      *
  TCT GAA TGG GCA ACA CAC AAG TTT GCT GAT TGC AAA GCA AAA CGT GAC
  Ser Glu Trp Ala Thr His Lys Phe Ala Asp Cys Lys Ala Lys Arg Asp>

1490          1500         1510         1520          1530
  *     *       *     *      *     *      *     *      *      *
  ACC CCC ACC TCA TGC ACT GTT GAT TAT TCT ACT GTG TAT TTT GTC AAC
  Thr Pro Thr Ser Cys Thr Val Asp Tyr Ser Thr Val Tyr Phe Val Asn>

1540          1550         1560          1570          1580
        *     *       *     *      *     *       *     *       *
  ATT GAA GTC TGG GTA GAA GCA GAG AAT GCC CTT GGG AAG GTT ACA TCA
  Ile Glu Val Trp Val Glu Ala Glu Asn Ala Leu Gly Lys Val Thr Ser>

1590          1600         1610         1620          1630
             *     *       *     *      *     *      *     *       *     *
  GAT CAT ATC AAT TTT GAT CCT GTA TAT AAA GTG AAG CCC AAT CCG CCA
  Asp His Ile Asn Phe Asp Pro Val Tyr Lys Val Lys Pro Asn Pro Pro>

1640          1650         1660          1670          1680
                  *     *       *     *      *     *       *     *       *     *
  CAT AAT TTA TCA GTG ATC AAC TCA GAG GAA CTG TCT AGT ATC TTA AAA
  His Asn Leu Ser Val Ile Asn Ser Glu Glu Leu Ser Ser Ile Leu Lys>

1690          1700          1710          1720
             *     *.      *     *       *     *       *     *      *
  TTG ACA TGG ACC AAC CCA AGT ATT AAG AGT GTT ATA ATA CTA AAA TAT
  Leu Thr Trp Thr Asn Pro Ser Ile Lys Ser Val Ile Ile Leu Lys Tyr>

1730          1740         1750          1760          1770
        *     *       *     *      *     *       *     *       *     *
  AAC ATT CAA TAT AGG ACC AAA GAT GCC TCA ACT TGG AGC CAG ATT CCT
  Asn Ile Gln Tyr Arg Thr Lys Asp Ala Ser Thr Trp Ser Gln Ile Pro>
```

Fig.24D.

```
      1780           1790           1800           1810           1820
        *      *       *      *       *      *       *      *       *      *
      CCT GAA GAC ACA GCA TCC ACC CGA TCT TCA TTC ACT GTC CAA GAC CTT
      Pro Glu Asp Thr Ala Ser Thr Arg Ser Ser Phe Thr Val Gln Asp Leu>

1830           1840           1850           1860           1870
        *      *       *      *       *      *       *      *       *      *
      AAA CCT TTT ACA GAA TAT GTG TTT AGG ATT CGC TGT ATG AAG GAA GAT
      Lys Pro Phe Thr Glu Tyr Val Phe Arg Ile Arg Cys Met Lys Glu Asp>

1880           1890           1900           1910           1920
        *      *       *      *       *      *       *      *       *      *
      GGT AAG GGA TAC TGG AGT GAC TGG AGT GAA GAA GCA AGT GGG ATC ACC
      Gly Lys Gly Tyr Trp Ser Asp Trp Ser Glu Glu Ala Ser Gly Ile Thr>

1930           1940           1950           1960
        *      *       *      *       *      *       *      *       *
      TAT GAA GAT AGA CCA TCT AAA GCA CCA AGT TTC TGG TAT AAA ATA GAT
      Tyr Glu Asp Arg Pro Ser Lys Ala Pro Ser Phe Trp Tyr Lys Ile Asp>

1970           1980           1990           2000           2010
     *      *       *      *       *      *       *      *       *      *
   CCA TCC CAT ACT CAA GGC TAC AGA ACT GTA CAA CTC GTG TGG AAG ACA
   Pro Ser His Thr Gln Gly Tyr Arg Thr Val Gln Leu Val Trp Lys Thr>

2020           2030           2040           2050           2060
     *      *       *      *       *      *       *      *       *      *
   TTG CCT CCT TTT GAA GCC AAT GGA AAA ATC TTG GAT TAT GAA GTG ACT
   Leu Pro Pro Phe Glu Ala Asn Gly Lys Ile Leu Asp Tyr Glu Val Thr>

2070           2080           2090           2100           2110
     *      *       *      *       *      *       *      *       *      *
   CTC ACA AGA TGG AAA TCA CAT TTA CAA AAT TAC ACA GTT AAT GCC ACA
   Leu Thr Arg Trp Lys Ser His Leu Gln Asn Tyr Thr Val Asn Ala Thr>

2120           2130           2140           2150           2160
            *      *       *      *       *      *       *      *       *      *
          AAA CTG ACA GTA AAT CTC ACA AAT GAT CGC TAT CTA GCA ACC CTA ACA
          Lys Leu Thr Val Asn Leu Thr Asn Asp Arg Tyr Leu Ala Thr Leu Thr>

2170           2180           2190           2200
            *      *       *      *       *      *       *      *       *
          GTA AGA AAT CTT GTT GGC AAA TCA GAT GCA GCT GTT TTA ACT ATC CCT
          Val Arg Asn Leu Val Gly Lys Ser Asp Ala Ala Val Leu Thr Ile Pro>

2210           2220           2230           2240           2250
     *      *       *      *       *      *       *      *       *      *
   GCC TGT GAC TTT CAA GCT ACT CAC CCT GTA ATG GAT CTT AAA GCA TTC
   Ala Cys Asp Phe Gln Ala Thr His Pro Val Met Asp Leu Lys Ala Phe>

2260           2270           2280           2290           2300
     *      *       *      *       *      *       *      *       *      *
   CCC AAA GAT AAC ATG CTT TGG GTG GAA TGG ACT ACT CCA AGG GAA TCT
   Pro Lys Asp Asn Met Leu Trp Val Glu Trp Thr Thr Pro Arg Glu Ser>

2310           2320           2330           2340           2350
     *      *       *      *       *      *       *      *       *      *
   GTA AAG AAA TAT ATA CTT GAG TGG TGT GTG TTA TCA GAT AAA GCA CCC
   Val Lys Lys Tyr Ile Leu Glu Trp Cys Val Leu Ser Asp Lys Ala Pro>

```
       *          *          *          *          *          *          *          *          *          *
    TGT  ATC  ACA  GAC  TGG  CAA  CAA  GAA  GAT  GGT  ACC  GTG  CAT  CGC  ACC  TAT
    Cys  Ile  Thr  Asp  Trp  Gln  Gln  Glu  Asp  Gly  Thr  Val  His  Arg  Thr  Tyr>

2410           2420           2430           2440
       *          *          *          *          *          *          *          *          *
    TTA  AGA  GGG  AAC  TTA  GCA  GAG  AGC  AAA  TGC  TAT  TTG  ATA  ACA  GTT  ACT
    Leu  Arg  Gly  Asn  Leu  Ala  Glu  Ser  Lys  Cys  Tyr  Leu  Ile  Thr  Val  Thr>

2450           2460           2470           2480           2490
       *          *          *          *          *          *          *          *          *          *
    CCA  GTA  TAT  GCT  GAT  GGA  CCA  GGA  AGC  CCT  GAA  TCC  ATA  AAG  GCA  TAC
    Pro  Val  Tyr  Ala  Asp  Gly  Pro  Gly  Ser  Pro  Glu  Ser  Ile  Lys  Ala  Tyr>

2500           2510           2520           2530           2540
       *          *          *          *          *          *          *          *          *
    CTT  AAA  CAA  GCT  CCA  CCT  TCC  AAA  GGA  CCT  ACT  GTT  CGG  ACA  AAA  AAA
    Leu  Lys  Gln  Ala  Pro  Pro  Ser  Lys  Gly  Pro  Thr  Val  Arg  Thr  Lys  Lys>

2550           2560           2570           2580           2590
       *          *          *          *          *          *          *          *          *          *
    GTA  GGG  AAA  AAC  GAA  GCT  GTC  TTA  GAG  TGG  GAC  CAA  CTT  CCT  GTT  GAT
    Val  Gly  Lys  Asn  Glu  Ala  Val  Leu  Glu  Trp  Asp  Gln  Leu  Pro  Val  Asp>

2600           2610           2620           2630           2640
       *          *          *          *          *          *          *          *          *          *
    GTT  CAG  AAT  GGA  TTT  ATC  AGA  AAT  TAT  ACT  ATA  TTT  TAT  AGA  ACC  ATC
    Val  Gln  Asn  Gly  Phe  Ile  Arg  Asn  Tyr  Thr  Ile  Phe  Tyr  Arg  Thr  Ile>

2650           2660           2670           2680
       *          *          *          *          *          *          *          *          *
    ATT  GGA  AAT  GAA  ACT  GCT  GTG  AAT  GTG  GAT  TCT  TCC  CAC  ACA  GAA  TAT
    Ile  Gly  Asn  Glu  Thr  Ala  Val  Asn  Val  Asp  Ser  Ser  His  Thr  Glu  Tyr>

2690           2700           2710           2720           2730
       *          *          *          *          *          *          *          *          *          *
    ACA  TTG  TCC  TCT  TTG  ACT  AGT  GAC  ACA  TTG  TAC  ATG  GTA  CGA  ATG  GCA
    Thr  Leu  Ser  Ser  Leu  Thr  Ser  Asp  Thr  Leu  Tyr  Met  Val  Arg  Met  Ala>

2740           2750           2760           2770           2780
       *          *          *          *          *          *          *          *          *
    GCA  TAC  ACA  GAT  GAA  GGT  GGG  AAG  GAT  GGT  CCA  GAA  TTC  ACT  TTT  ACT
    Ala  Tyr  Thr  Asp  Glu  Gly  Gly  Lys  Asp  Gly  Pro  Glu  Phe  Thr  Phe  Thr>

2790           2800           2810           2820           2830
       *          *          *          *          *          *          *          *          *          *
    ACC  CCA  AAG  TTT  GCT  CAA  GGA  GAA  ATT  GAA  TCC  GGG  GGC  GAC  AAA  ACT
    Thr  Pro  Lys  Phe  Ala  Gln  Gly  Glu  Ile  Glu  Ser  Gly  Gly  Asp  Lys  Thr>

2840           2850           2860           2870           2880
       *          *          *          *          *          *          *          *          *          *
    CAC  ACA  TGC  CCA  CCG  TGC  CCA  GCA  CCT  GAA  CTC  CTG  GGG  GGA  CCG  TCA
    His  Thr  Cys  Pro  Pro  Cys  Pro  Ala  Pro  Glu  Leu  Leu  Gly  Gly  Pro  Ser>

2890           2900           2910           2920
       *          *          *          *          *          *          *          *          *
    GTC  TTC  CTC  TTC  CCC  CCA  AAA  CCC  AAG  GAC  ACC  CTC  ATG  ATC  TCC  CGG
    Val  Phe  Leu  Phe  Pro  Pro  Lys  Pro  Lys  Asp  Thr  Leu  Met  Ile  Ser  Arg>

2930           2940           2950           2960           2970
       *          *          *          *          *          *          *          *          *
    ACC  CCT  GAG  GTC  ACA  TGC  GTG  GTG  GTG  GAC  GTG  AGC  CAC  GAA  GAC  CCT
```

Fig. 24F.

```
             Thr Pro Glu Val Thr Cys Val Val Val Asp Val Ser His Glu Asp Pro>
        2980          2990          3000          3010          3020
         *             *             *             *             *
        GAG GTC AAG TTC AAC TGG TAC GTG GAC GGC GTG GAG GTG CAT AAT GCC
        Glu Val Lys Phe Asn Trp Tyr Val Asp Gly Val Glu Val His Asn Ala>
        3030          3040          3050          3060          3070
         *             *             *             *             *
        AAG ACA AAG CCG CGG GAG GAG CAG TAC AAC AGC ACG TAC CGT GTG GTC
        Lys Thr Lys Pro Arg Glu Glu Gln Tyr Asn Ser Thr Tyr Arg Val Val>
        3080          3090          3100          3110          3120
         *             *             *             *             *
        AGC GTC CTC ACC GTC CTG CAC CAG GAC TGG CTG AAT GGC AAG GAG TAC
        Ser Val Leu Thr Val Leu His Gln Asp Trp Leu Asn Gly Lys Glu Tyr>
             3130          3140          3150          3160
              *             *             *             *
        AAG TGC AAG GTC TCC AAC AAA GCC CTC CCA GCC CCC ATC GAG AAA ACC
        Lys Cys Lys Val Ser Asn Lys Ala Leu Pro Ala Pro Ile Glu Lys Thr>
  3170          3180          3190          3200          3210
   *             *             *             *             *
  ATC TCC AAA GCC AAA GGG CAG CCC CGA GAA CCA CAG GTG TAC ACC CTG
  Ile Ser Lys Ala Lys Gly Gln Pro Arg Glu Pro Gln Val Tyr Thr Leu>
        3220          3230          3240          3250          3260
         *             *             *             *             *
        CCC CCA TCC CGG GAT GAG CTG ACC AAG AAC CAG GTC AGC CTG ACC TGC
        Pro Pro Ser Arg Asp Glu Leu Thr Lys Asn Gln Val Ser Leu Thr Cys>
        3270          3280          3290          3300          3310
         *             *             *             *             *
        CTG GTC AAA GGC TTC TAT CCC AGC GAC ATC GCC GTG GAG TGG GAG AGC
        Leu Val Lys Gly Phe Tyr Pro Ser Asp Ile Ala Val Glu Trp Glu Ser>
        3320          3330          3340          3350          3360
         *             *             *             *             *
        AAT GGG CAG CCG GAG AAC AAC TAC AAG ACC ACG CCT CCC GTG CTG GAC
        Asn Gly Gln Pro Glu Asn Asn Tyr Lys Thr Thr Pro Pro Val Leu Asp>
             3370          3380          3390          3400
              *             *             *             *
        TCC GAC GGC TCC TTC TTC CTC TAC AGC AAG CTC ACC GTG GAC AAG AGC
        Ser Asp Gly Ser Phe Phe Leu Tyr Ser Lys Leu Thr Val Asp Lys Ser>
  3410          3420          3430          3440          3450
   *             *             *             *             *
  AGG TGG CAG CAG GGG AAC GTC TTC TCA TGC TCC GTG ATG CAT GAG GCT
  Arg Trp Gln Gln Gly Asn Val Phe Ser Cys Ser Val Met His Glu Ala>
        3460          3470          3480          3490          3500
         *             *             *             *             *
        CTG CAC AAC CAC TAC ACG CAG AAG AGC CTC TCC CTG TCT CCG GGT AAA
        Leu His Asn His Tyr Thr Gln Lys Ser Leu Ser Leu Ser Pro Gly Lys>
   *
   TGA
   ***>
```

Fig.25A.

```
         10              20              30              40
         *       *       *       *       *       *       *       *       *
ATG GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50              60              70              80              90
*       *       *       *       *       *       *       *       *       *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

100             110             120             130             140
     *       *       *       *       *       *       *       *       *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

150             160             170             180             190
         *       *       *       *       *       *       *       *       *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

200             210             220             230             240
     *       *       *       *       *       *       *       *       *       *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

250             260             270             280
         *       *       *       *       *       *       *       *       *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290             300             310             320             330
*       *       *       *       *       *       *       *       *       *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

340             350             360             370             380
         *       *       *       *       *       *       *       *       *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

390             400             410             420             430
     *       *       *       *       *       *       *       *       *       *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

440             450             460             470             480
         *       *       *       *       *       *       *       *       *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

490             500             510             520
         *       *       *       *       *       *       *       *       *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530             540             550             560             570
*       *       *       *       *       *       *       *       *       *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Fig.25B.

```
       580           590           600           610           620
    *     *       *     *       *     *       *     *       *     *
TGC GTC GCC AGT AGT GTC GGG AGC AAG TTC AGC AAA ACT CAA ACC TTT
Cys Val Ala Ser Ser Val Gly Ser Lys Phe Ser Lys Thr Gln Thr Phe>

630           640           650           660           670
    *     *       *     *       *     *       *     *       *     *
CAG GGT TGT GGA ATC TTG CAG CCT GAT CCG CCT GCC AAC ATC ACA GTC
Gln Gly Cys Gly Ile Leu Gln Pro Asp Pro Pro Ala Asn Ile Thr Val>

680           690           700           710           720
    *     *       *     *       *     *       *     *       *     *
ACT GCC GTG GCC AGA AAC CCC CGC TGG CTC AGT GTC ACC TGG CAA GAC
Thr Ala Val Ala Arg Asn Pro Arg Trp Leu Ser Val Thr Trp Gln Asp>

730           740           750           760
    *     *       *     *       *     *       *     *       *     *
CCC CAC TCC TGG AAC TCA TCT TTC TAC AGA CTA CGG TTT GAG CTC AGA
Pro His Ser Trp Asn Ser Ser Phe Tyr Arg Leu Arg Phe Glu Leu Arg>

770           780           790           800           810
 *     *       *     *       *     *       *     *       *     *
TAT CGG GCT GAA CGG TCA AAG ACA TTC ACA ACA TGG ATG GTC AAG GAC
Tyr Arg Ala Glu Arg Ser Lys Thr Phe Thr Thr Trp Met Val Lys Asp>

820           830           840           850           860
 *     *       *     *       *     *       *     *       *     *
CTC CAG CAT CAC TGT GTC ATC CAC GAC GCC TGG AGC GGC CTG AGG CAC
Leu Gln His His Cys Val Ile His Asp Ala Trp Ser Gly Leu Arg His>

870           880           890           900           910
    *     *       *     *       *     *       *     *       *     *
GTG GTG CAG CTT CGT GCC CAG GAG GAG TTC GGG CAA GGC GAG TGG AGC
Val Val Gln Leu Arg Ala Gln Glu Glu Phe Gly Gln Gly Glu Trp Ser>

920           930           940           950           960
    *     *       *     *       *     *       *     *       *     *
GAG TGG AGC CCG GAG GCC ATG GGC ACG CCT TGG ACA GAA TCG CGA TCG
Glu Trp Ser Pro Glu Ala Met Gly Thr Pro Trp Thr Glu Ser Arg Ser>

970           980           990           1000
    *     *       *     *       *     *       *     *       *     *
CCT CCA GCT GAG AAC GAG GTG TCC ACC CCC ATG GAA CTT CTA GAC CCA
Pro Pro Ala Glu Asn Glu Val Ser Thr Pro Met Glu Leu Leu Asp Pro>

1010          1020          1030          1040          1050
 *     *       *     *       *     *       *     *       *     *
TGT GGT TAT ATC AGT CCT GAA TCT CCA GTT GTA CAA CTT CAT TCT AAT
Cys Gly Tyr Ile Ser Pro Glu Ser Pro Val Val Gln Leu His Ser Asn>

1060          1070          1080          1090          1100
    *     *       *     *       *     *       *     *       *     *
TTC ACT GCA GTT TGT GTG CTA AAG GAA AAA TGT ATG GAT TAT TTT CAT
Phe Thr Ala Val Cys Val Leu Lys Glu Lys Cys Met Asp Tyr Phe His>

1110          1120          1130          1140          1150
    *     *       *     *       *     *       *     *       *     *
GTA AAT GCT AAT TAC ATT GTC TGG AAA ACA AAC CAT TTT ACT ATT CCT
Val Asn Ala Asn Tyr Ile Val Trp Lys Thr Asn His Phe Thr Ile Pro>

```
AAG GAG CAA TAT ACT ATC ATA AAC AGA ACA GCA TCC AGT GTC ACC TTT
Lys Glu Gln Tyr Thr Ile Ile Asn Arg Thr Ala Ser Ser Val Thr Phe>
        1210        1220        1230        1240
         *           *           *           *          *
ACA GAT ATA GCT TCA TTA AAT ATT CAG CTC ACT TGC AAC ATT CTT ACA
Thr Asp Ile Ala Ser Leu Asn Ile Gln Leu Thr Cys Asn Ile Leu Thr>
1250        1260        1270        1280        1290
  *          *           *           *           *          *
TTC GGA CAG CTT GAA CAG AAT GTT TAT GGA ATC ACA ATA ATT TCA GGC
Phe Gly Gln Leu Glu Gln Asn Val Tyr Gly Ile Thr Ile Ile Ser Gly>
    1300        1310        1320        1330        1340
     *           *           *           *           *
TTG CCT CCA GAA AAA CCT AAA AAT TTG AGT TGC ATT GTG AAC GAG GGG
Leu Pro Pro Glu Lys Pro Lys Asn Leu Ser Cys Ile Val Asn Glu Gly>
        1350        1360        1370        1380        1390
         *           *           *           *           *
AAG AAA ATG AGG TGT GAG TGG GAT GGT GGA AGG GAA ACA CAC TTG GAG
Lys Lys Met Arg Cys Glu Trp Asp Gly Gly Arg Glu Thr His Leu Glu>
        1400        1410        1420        1430        1440
         *           *           *           *           *
ACA AAC TTC ACT TTA AAA TCT GAA TGG GCA ACA CAC AAG TTT GCT GAT
Thr Asn Phe Thr Leu Lys Ser Glu Trp Ala Thr His Lys Phe Ala Asp>
        1450        1460        1470        1480
         *           *           *           *           *
TGC AAA GCA AAA CGT GAC ACC CCC ACC TCA TGC ACT GTT GAT TAT TCT
Cys Lys Ala Lys Arg Asp Thr Pro Thr Ser Cys Thr Val Asp Tyr Ser>
1490        1500        1510        1520        1530
  *          *           *           *           *          *
ACT GTG TAT TTT GTC AAC ATT GAA GTC TGG GTA GAA GCA GAG AAT GCC
Thr Val Tyr Phe Val Asn Ile Glu Val Trp Val Glu Ala Glu Asn Ala>
    1540        1550        1560        1570        1580
     *           *           *           *           *
CTT GGG AAG GTT ACA TCA GAT CAT ATC AAT TTT GAT CCT GTA TAT AAA
Leu Gly Lys Val Thr Ser Asp His Ile Asn Phe Asp Pro Val Tyr Lys>
        1590        1600        1610        1620        1630
         *           *           *           *           *
GTG AAG CCC AAT CCG CCA CAT AAT TTA TCA GTG ATC AAC TCA GAG GAA
Val Lys Pro Asn Pro Pro His Asn Leu Ser Val Ile Asn Ser Glu Glu>
        1640        1650        1660        1670        1680
         *           *           *           *           *
CTG TCT AGT ATC TTA AAA TTG ACA TGG ACC AAC CCA AGT ATT AAG AGT
Leu Ser Ser Ile Leu Lys Leu Thr Trp Thr Asn Pro Ser Ile Lys Ser>
        1690        1700        1710        1720
         *           *           *           *           *
GTT ATA ATA CTA AAA TAT AAC ATT CAA TAT AGG ACC AAA GAT GCC TCA
Val Ile Ile Leu Lys Tyr Asn Ile Gln Tyr Arg Thr Lys Asp Ala Ser>
1730        1740        1750        1760        1770
  *          *           *           *           *          *
ACT TGG AGC CAG ATT CCT CCT GAA GAC ACA GCA TCC ACC CGA TCT TCA
Thr Trp Ser Gln Ile Pro Pro Glu Asp Thr Ala Ser Thr Arg Ser Ser>
```

Fig.25D.

```
      1780          1790          1800          1810          1820
        *             *             *             *             *
   TTC ACT GTC CAA GAC CTT AAA CCT TTT ACA GAA TAT GTG TTT AGG ATT
   Phe Thr Val Gln Asp Leu Lys Pro Phe Thr Glu Tyr Val Phe Arg Ile>

1830          1840          1850          1860          1870
        *             *             *             *             *
   CGC TGT ATG AAG GAA GAT GGT AAG GGA TAC TGG AGT GAC TGG AGT GAA
   Arg Cys Met Lys Glu Asp Gly Lys Gly Tyr Trp Ser Asp Trp Ser Glu>

1880          1890          1900          1910          1920
        *             *             *             *             *
   GAA GCA AGT GGG ATC ACC TAT GAA GAT AGA CCA TCT AAA GCA CCA AGT
   Glu Ala Ser Gly Ile Thr Tyr Glu Asp Arg Pro Ser Lys Ala Pro Ser>

1930          1940          1950          1960
              *             *             *             *
   TTC TGG TAT AAA ATA GAT CCA TCC CAT ACT CAA GGC TAC AGA ACT GTA
   Phe Trp Tyr Lys Ile Asp Pro Ser His Thr Gln Gly Tyr Arg Thr Val>

1970          1980          1990          2000          2010
   *             *             *             *             *
   CAA CTC GTG TGG AAG ACA TTG CCT CCT TTT GAA GCC AAT GGA AAA ATC
   Gln Leu Val Trp Lys Thr Leu Pro Pro Phe Glu Ala Asn Gly Lys Ile>

2020          2030          2040          2050          2060
        *             *             *             *             *
   TTG GAT TAT GAA GTG ACT CTC ACA AGA TGG AAA TCA CAT TTA CAA AAT
   Leu Asp Tyr Glu Val Thr Leu Thr Arg Trp Lys Ser His Leu Gln Asn>

2070          2080          2090          2100          2110
        *             *             *             *             *
   TAC ACA GTT AAT GCC ACA AAA CTG ACA GTA AAT CTC ACA AAT GAT CGC
   Tyr Thr Val Asn Ala Thr Lys Leu Thr Val Asn Leu Thr Asn Asp Arg>

2120          2130          2140          2150          2160
        *             *             *             *             *
   TAT CTA GCA ACC CTA ACA GTA AGA AAT CTT GTT GGC AAA TCA GAT GCA
   Tyr Leu Ala Thr Leu Thr Val Arg Asn Leu Val Gly Lys Ser Asp Ala>

2170          2180          2190          2200
              *             *             *             *
   GCT GTT TTA ACT ATC CCT GCC TGT GAC TTT CAA GCT ACT CAC CCT GTA
   Ala Val Leu Thr Ile Pro Ala Cys Asp Phe Gln Ala Thr His Pro Val>

2210          2220          2230          2240          2250
   *             *             *             *             *
   ATG GAT CTT AAA GCA TTC CCC AAA GAT AAC ATG CTT TGG GTG GAA TGG
   Met Asp Leu Lys Ala Phe Pro Lys Asp Asn Met Leu Trp Val Glu Trp>

2260          2270          2280          2290          2300
        *             *             *             *             *
   ACT ACT CCA AGG GAA TCT GTA AAG AAA TAT ATA CTT GAG TGG TGT GTG
   Thr Thr Pro Arg Glu Ser Val Lys Lys Tyr Ile Leu Glu Trp Cys Val>

2310          2320          2330          2340          2350
        *             *             *             *             *
   TTA TCA GAT AAA GCA CCC TGT ATC ACA GAC TGG CAA CAA GAA GAT GGT
   Leu Ser Asp Lys Ala Pro Cys Ile Thr Asp Trp Gln Gln Glu Asp Gly>

```
      *       *       *       *       *       *       *       *       *       *
     ACC GTG CAT CGC ACC TAT TTA AGA GGG AAC TTA GCA GAG AGC AAA TGC
     Thr Val His Arg Thr Tyr Leu Arg Gly Asn Leu Ala Glu Ser Lys Cys>

2410            2420            2430            2440
      *       *       *       *       *       *       *       *       *
     TAT TTG ATA ACA GTT ACT CCA GTA TAT GCT GAT GGA CCA GGA AGC CCT
     Tyr Leu Ile Thr Val Thr Pro Val Tyr Ala Asp Gly Pro Gly Ser Pro>

2450            2460            2470            2480            2490
      *       *       *       *       *       *       *       *       *       *
     GAA TCC ATA AAG GCA TAC CTT AAA CAA GCT CCA CCT TCC AAA GGA CCT
     Glu Ser Ile Lys Ala Tyr Leu Lys Gln Ala Pro Pro Ser Lys Gly Pro>

2500            2510            2520            2530            2540
      *       *       *       *       *       *       *       *       *
     ACT GTT CGG ACA AAA AAA GTA GGG AAA AAC GAA GCT GTC TTA GAG TGG
     Thr Val Arg Thr Lys Lys Val Gly Lys Asn Glu Ala Val Leu Glu Trp>

2550            2560            2570            2580            2590
      *       *       *       *       *       *       *       *       *       *
     GAC CAA CTT CCT GTT GAT GTT CAG AAT GGA TTT ATC AGA AAT TAT ACT
     Asp Gln Leu Pro Val Asp Val Gln Asn Gly Phe Ile Arg Asn Tyr Thr>

2600            2610            2620            2630            2640
      *       *       *       *       *       *       *       *       *       *
     ATA TTT TAT AGA ACC ATC ATT GGA AAT GAA ACT GCT GTG AAT GTG GAT
     Ile Phe Tyr Arg Thr Ile Ile Gly Asn Glu Thr Ala Val Asn Val Asp>

2650            2660            2670            2680
      *       *       *       *       *       *       *       *       *
     TCT TCC CAC ACA GAA TAT ACA TTG TCC TCT TTG ACT AGT GAC ACA TTG
     Ser Ser His Thr Glu Tyr Thr Leu Ser Ser Leu Thr Ser Asp Thr Leu>

2690            2700            2710            2720            2730
      *       *       *       *       *       *       *       *       *
     TAC ATG GTA CGA ATG GCA GCA TAC ACA GAT GAA GGT GGG AAG GAT GGT
     Tyr Met Val Arg Met Ala Ala Tyr Thr Asp Glu Gly Gly Lys Asp Gly>

2740            2750            2760            2770            2780
      *       *       *       *       *       *       *       *       *
     CCA GAA TTC ACT TTT ACT ACC CCA AAG TTT GCT CAA GGA GAA ATT GAA
     Pro Glu Phe Thr Phe Thr Thr Pro Lys Phe Ala Gln Gly Glu Ile Glu>

2790            2800            2810            2820            2830
      *       *       *       *       *       *       *       *       *       *
     TCC GGG GGC GAC AAA ACT CAC ACA TGC CCA CCG TGC CCA GCA CCT GAA
     Ser Gly Gly Asp Lys Thr His Thr Cys Pro Pro Cys Pro Ala Pro Glu>

2840            2850            2860            2870            2880
      *       *       *       *       *       *       *       *       *       *
     CTC CTG GGG GGA CCG TCA GTC TTC CTC TTC CCC CCA AAA CCC AAG GAC
     Leu Leu Gly Gly Pro Ser Val Phe Leu Phe Pro Pro Lys Pro Lys Asp>

2890            2900      .     2910            2920
      *       *       *       *       *       *       *       *       *
     ACC CTC ATG ATC TCC CGG ACC CCT GAG GTC ACA TGC GTG GTG GTG GAC
     Thr Leu Met Ile Ser Arg Thr Pro Glu Val Thr Cys Val Val Val Asp>

2930            2940            2950            2960            2970
      *       *       *       *       *       *       *       *       *
     GTG AGC CAC GAA GAC CCT GAG GTC AAG TTC AAC TGG TAC GTG GAC GGC
```

Fig.25F.

```
                        Val Ser His Glu Asp Pro Glu Val Lys Phe Asn Trp Tyr Val Asp Gly>

2980        2990        3000        3010        3020
      *           *           *           *           *
    GTG GAG GTG CAT AAT GCC AAG ACA AAG CCG CGG GAG GAG CAG TAC AAC
    Val Glu Val His Asn Ala Lys Thr Lys Pro Arg Glu Glu Gln Tyr Asn>

3030        3040        3050        3060        3070
          *           *           *           *           *
    AGC ACG TAC CGT GTG GTC AGC GTC CTC ACC GTC CTG CAC CAG GAC TGG
    Ser Thr Tyr Arg Val Val Ser Val Leu Thr Val Leu His Gln Asp Trp>

3080        3090        3100        3110        3120
            *           *           *           *           *
    CTG AAT GGC AAG GAG TAC AAG TGC AAG GTC TCC AAC AAA GCC CTC CCA
    Leu Asn Gly Lys Glu Tyr Lys Cys Lys Val Ser Asn Lys Ala Leu Pro>

3130        3140        3150        3160
              *           *           *           *
    GCC CCC ATC GAG AAA ACC ATC TCC AAA GCC AAA GGG CAG CCC CGA GAA
    Ala Pro Ile Glu Lys Thr Ile Ser Lys Ala Lys Gly Gln Pro Arg Glu>

3170        3180        3190        3200        3210
      *           *           *           *           *
    CCA CAG GTG TAC ACC CTG CCC CCA TCC CGG GAT GAG CTG ACC AAG AAC
    Pro Gln Val Tyr Thr Leu Pro Pro Ser Arg Asp Glu Leu Thr Lys Asn>

3220        3230        3240        3250        3260
      *           *           *           *           *
    CAG GTC AGC CTG ACC TGC CTG GTC AAA GGC TTC TAT CCC AGC GAC ATC
    Gln Val Ser Leu Thr Cys Leu Val Lys Gly Phe Tyr Pro Ser Asp Ile>

3270        3280        3290        3300        3310
          *           *           *           *           *
    GCC GTG GAG TGG GAG AGC AAT GGG CAG CCG GAG AAC AAC TAC AAG ACC
    Ala Val Glu Trp Glu Ser Asn Gly Gln Pro Glu Asn Asn Tyr Lys Thr>

3320        3330        3340        3350        3360
              *           *           *           *           *
    ACG CCT CCC GTG CTG GAC TCC GAC GGC TCC TTC TTC CTC TAC AGC AAG
    Thr Pro Pro Val Leu Asp Ser Asp Gly Ser Phe Phe Leu Tyr Ser Lys>

3370        3380        3390        3400
                *           *           *           *
    CTC ACC GTG GAC AAG AGC AGG TGG CAG CAG GGG AAC GTC TTC TCA TGC
    Leu Thr Val Asp Lys Ser Arg Trp Gln Gln Gly Asn Val Phe Ser Cys>

3410        3420        3430        3440        3450
      *           *           *           *           *
    TCC GTG ATG CAT GAG GCT CTG CAC AAC CAC TAC ACG CAG AAG AGC CTC
    Ser Val Met His Glu Ala Leu His Asn His Tyr Thr Gln Lys Ser Leu>

3460        3470
      *           *
    TCC CTG TCT CCG GGT AAA TGA
    Ser Leu Ser Pro Gly Lys ***>
```

Fig.26A.

```
             10              20              30              40
         *        *       *        *      *        *       *        *
ATG GTG CTT CTG TGG TGT GTA GTG AGT CTC TAC TTT TAT GGA ATC CTG
Met Val Leu Leu Trp Cys Val Val Ser Leu Tyr Phe Tyr Gly Ile Leu>

50              60              70              80              90
  *        *      *        *      *        *      *        *      *
CAA AGT GAT GCC TCA GAA CGC TGC GAT GAC TGG GGA CTA GAC ACC ATG
Gln Ser Asp Ala Ser Glu Arg Cys Asp Asp Trp Gly Leu Asp Thr Met>

100             110             120             130             140
       *       *       *       *       *       *       *       *       *
AGG CAA ATC CAA GTG TTT GAA GAT GAG CCA GCT CGC ATC AAG TGC CCA
Arg Gln Ile Gln Val Phe Glu Asp Glu Pro Ala Arg Ile Lys Cys Pro>

150             160             170             180             190
    *      *       *      *       *      *      *       *       *       *
CTC TTT GAA CAC TTC TTG AAA TTC AAC TAC AGC ACA GCC CAT TCA GCT
Leu Phe Glu His Phe Leu Lys Phe Asn Tyr Ser Thr Ala His Ser Ala>

200             210             220             230             240
        *       *       *       *       *       *       *       *       *       *
GGC CTT ACT CTG ATC TGG TAT TGG ACT AGG CAG GAC CGG GAC CTT GAG
Gly Leu Thr Leu Ile Trp Tyr Trp Thr Arg Gln Asp Arg Asp Leu Glu>

250             260             270             280
        *       *       *       *       *       *       *       *       *
GAG CCA ATT AAC TTC CGC CTC CCC GAG AAC CGC ATT AGT AAG GAG AAA
Glu Pro Ile Asn Phe Arg Leu Pro Glu Asn Arg Ile Ser Lys Glu Lys>

290             300             310             320             330
  *       *       *       *       *       *       *       *       *       *
GAT GTG CTG TGG TTC CGG CCC ACT CTC CTC AAT GAC ACT GGC AAC TAT
Asp Val Leu Trp Phe Arg Pro Thr Leu Leu Asn Asp Thr Gly Asn Tyr>

340             350             360             370             380
       *       *       *       *       *       *       *       *       *
ACC TGC ATG TTA AGG AAC ACT ACA TAT TGC AGC AAA GTT GCA TTT CCC
Thr Cys Met Leu Arg Asn Thr Thr Tyr Cys Ser Lys Val Ala Phe Pro>

390             400             410             420             430
    *       *       *       *       *       *       *       *       *       *
TTG GAA GTT GTT CAA AAA GAC AGC TGT TTC AAT TCC CCC ATG AAA CTC
Leu Glu Val Val Gln Lys Asp Ser Cys Phe Asn Ser Pro Met Lys Leu>

440             450             460             470             480
        *       *       *       *       *       *       *       *       *       *
CCA GTG CAT AAA CTG TAT ATA GAA TAT GGC ATT CAG AGG ATC ACT TGT
Pro Val His Lys Leu Tyr Ile Glu Tyr Gly Ile Gln Arg Ile Thr Cys>

490             500             510             520
            *       *       *       *       *       *       *       *       *
CCA AAT GTA GAT GGA TAT TTT CCT TCC AGT GTC AAA CCG ACT ATC ACT
Pro Asn Val Asp Gly Tyr Phe Pro Ser Ser Val Lys Pro Thr Ile Thr>

530             540             550             560             570
  *       *       *       *       *       *       *       *       *       *
TGG TAT ATG GGC TGT TAT AAA ATA CAG AAT TTT AAT AAT GTA ATA CCC
Trp Tyr Met Gly Cys Tyr Lys Ile Gln Asn Phe Asn Asn Val Ile Pro>
```

Fig.26B.

```
         580              590              600              610              620
          *       *        *       *        *       *        *       *        *
        GAA GGT ATG AAC TTG AGT TTC CTC ATT GCC TTA ATT TCA AAT AAT GGA
        Glu Gly Met Asn Leu Ser Phe Leu Ile Ala Leu Ile Ser Asn Asn Gly>

630              640              650              660              670
          *       *        *       *        *       *        *       *        *
        AAT TAC ACA TGT GTT GTT ACA TAT CCA GAA AAT GGA CGT ACG TTT CAT
        Asn Tyr Thr Cys Val Val Thr Tyr Pro Glu Asn Gly Arg Thr Phe His>

680              690              700              710              720
          *       *        *       *        *       *        *       *        *
        CTC ACC AGG ACT CTG ACT GTA AAG GTA GTA GGC TCT CCA AAA AAT GCA
        Leu Thr Arg Thr Leu Thr Val Lys Val Val Gly Ser Pro Lys Asn Ala>

730              740              750              760
                  *       *        *       *        *       *        *       *
                GTG CCC CCT GTG ATC CAT TCA CCT AAT GAT CAT GTG GTC TAT GAG AAA
                Val Pro Pro Val Ile His Ser Pro Asn Asp His Val Val Tyr Glu Lys>

770              780              790              800              810
         *       *        *       *        *       *        *       *        *       *
        GAA CCA GGA GAG GAG CTA CTC ATT CCC TGT ACG GTC TAT TTT AGT TTT
        Glu Pro Gly Glu Glu Leu Leu Ile Pro Cys Thr Val Tyr Phe Ser Phe>

820              830              840              850              860
          *       *        *       *        *       *        *       *        *
        CTG ATG GAT TCT CGC AAT GAG GTT TGG TGG ACC ATT GAT GGA AAA AAA
        Leu Met Asp Ser Arg Asn Glu Val Trp Trp Thr Ile Asp Gly Lys Lys>

870              880              890              900              910
          *       *        *       *        *       *        *       *        *
        CCT GAT GAC ATC ACT ATT GAT GTC ACC ATT AAC GAA AGT ATA AGT CAT
        Pro Asp Asp Ile Thr Ile Asp Val Thr Ile Asn Glu Ser Ile Ser His>

920              930              940              950              960
          *       *        *       *        *       *        *       *        *
        AGT AGA ACA GAA GAT GAA ACA AGA ACT CAG ATT TTG AGC ATC AAG AAA
        Ser Arg Thr Glu Asp Glu Thr Arg Thr Gln Ile Leu Ser Ile Lys Lys>

970              980              990              1000
                  *       *        *       *        *       *        *       *
                GTT ACC TCT GAG GAT CTC AAG CGC AGC TAT GTC TGT CAT GCT AGA AGT
                Val Thr Ser Glu Asp Leu Lys Arg Ser Tyr Val Cys His Ala Arg Ser>

1010             1020             1030             1040             1050
         *       *        *       *        *       *        *       *        *       *
        GCC AAA GGC GAA GTT GCC AAA GCA GCC AAG GTG AAG CAG AAA GTG CCA
        Ala Lys Gly Glu Val Ala Lys Ala Ala Lys Val Lys Gln Lys Val Pro>

1060             1070             1080             1090             1100
          *       *        *       *        *       *        *       *        *
        GCT CCA AGA TAC ACA GTG TCC GGT GGC GCG CCT ATG CTG AGC GAG GCT
        Ala Pro Arg Tyr Thr Val Ser Gly Gly Ala Pro Met Leu Ser Glu Ala>

1110             1120             1130             1140             1150
          *       *        *       *        *       *        *       *        *
        GAT AAA TGC AAG GAA CGT GAA GAA AAA ATA ATT TTA GTG TCA TCT GCA
        Asp Lys Cys Lys Glu Arg Glu Glu Lys Ile Ile Leu Val Ser Ser Ala>

```
AAT GAA ATT GAT GTT CGT CCC TGT CCT CTT AAC CCA AAT GAA CAC AAA
Asn Glu Ile Asp Val Arg Pro Cys Pro Leu Asn Pro Asn Glu His Lys>

1210        1220        1230        1240
           *           *           *           *           *
GGC ACT ATA ACT TGG TAT AAG GAT GAC AGC AAG ACA CCT GTA TCT ACA
Gly Thr Ile Thr Trp Tyr Lys Asp Asp Ser Lys Thr Pro Val Ser Thr>

1250        1260        1270        1280        1290
  *           *           *           *           *
GAA CAA GCC TCC AGG ATT CAT CAA CAC AAA GAG AAA CTT TGG TTT GTT
Glu Gln Ala Ser Arg Ile His Gln His Lys Glu Lys Leu Trp Phe Val>

1300        1310        1320        1330        1340
      *           *           *           *           *
CCT GCT AAG GTG GAG GAT TCA GGA CAT TAC TAT TGC GTG GTA AGA AAT
Pro Ala Lys Val Glu Asp Ser Gly His Tyr Tyr Cys Val Val Arg Asn>

1350        1360        1370        1380        1390
          *           *           *           *           *
TCA TCT TAC TGC CTC AGA ATT AAA ATA AGT GCA AAA TTT GTG GAG AAT
Ser Ser Tyr Cys Leu Arg Ile Lys Ile Ser Ala Lys Phe Val Glu Asn>

1400        1410        1420        1430        1440
             *           *           *           *           *
GAG CCT AAC TTA TGT TAT AAT GCA CAA GCC ATA TTT AAG CAG AAA CTA
Glu Pro Asn Leu Cys Tyr Asn Ala Gln Ala Ile Phe Lys Gln Lys Leu>

1450        1460        1470        1480
                 *           *           *           *           *
CCC GTT GCA GGA GAC GGA GGA CTT GTG TGC CCT TAT ATG GAG TTT TTT
Pro Val Ala Gly Asp Gly Gly Leu Val Cys Pro Tyr Met Glu Phe Phe>

1490        1500        1510        1520        1530
  *           *           *           *           *           *
AAA AAT GAA AAT AAT GAG TTA CCT AAA TTA CAG TGG TAT AAG GAT TGC
Lys Asn Glu Asn Asn Glu Leu Pro Lys Leu Gln Trp Tyr Lys Asp Cys>

1540        1550        1560        1570        1580
      *           *           *           *           *
AAA CCT CTA CTT CTT GAC AAT ATA CAC TTT AGT GGA GTC AAA GAT AGG
Lys Pro Leu Leu Leu Asp Asn Ile His Phe Ser Gly Val Lys Asp Arg>

1590        1600        1610        1620        1630
          *           *           *           *           *
CTC ATC GTG ATG AAT GTG GCT GAA AAG CAT AGA GGG AAC TAT ACT TGT
Leu Ile Val Met Asn Val Ala Glu Lys His Arg Gly Asn Tyr Thr Cys>

1640        1650        1660        1670        1680
             *           *           *           *           *
CAT GCA TCC TAC ACA TAC TTG GGC AAG CAA TAT CCT ATT ACC CGG GTA
His Ala Ser Tyr Thr Tyr Leu Gly Lys Gln Tyr Pro Ile Thr Arg Val>

1690        1700        1710        1720
                 *           *           *           *           *
ATA GAA TTT ATT ACT CTA GAG GAA AAC AAA CCC ACA AGG CCT GTG ATT
Ile Glu Phe Ile Thr Leu Glu Glu Asn Lys Pro Thr Arg Pro Val Ile>

1730        1740        1750        1760        1770
  *           *           *           *           *           *
GTG AGC CCA GCT AAT GAG ACA ATG GAA GTA GAC TTG GGA TCC CAG ATA
Val Ser Pro Ala Asn Glu Thr Met Glu Val Asp Leu Gly Ser Gln Ile>
```

Fig.26D.

```
      1780              1790              1800              1810              1820
        *                 *             *    *                *                 *
     CAA TTG ATC TGT AAT GTC ACC GGC CAG TTG AGT GAC ATT GCT TAC TGG
     Gln Leu Ile Cys Asn Val Thr Gly Gln Leu Ser Asp Ile Ala Tyr Trp>

1830              1840         1850              1860              1870
           *                 *        *    *                *                 *
     AAG TGG AAT GGG TCA GTA ATT GAT GAA GAT GAC CCA GTG CTA GGG GAA
     Lys Trp Asn Gly Ser Val Ile Asp Glu Asp Asp Pro Val Leu Gly Glu>

1880              1890        1900              1910              1920
                *                 *       *    *                *                 *
     GAC TAT TAC AGT GTG GAA AAT CCT GCA AAC AAA AGA AGG AGT ACC CTC
     Asp Tyr Tyr Ser Val Glu Asn Pro Ala Asn Lys Arg Arg Ser Thr Leu>

1930              1940       1950              1960
                *                 *      *    *                *                 *
     ATC ACA GTG CTT AAT ATA TCG GAA ATT GAG AGT AGA TTT TAT AAA CAT
     Ile Thr Val Leu Asn Ile Ser Glu Ile Glu Ser Arg Phe Tyr Lys His>

1970              1980         1990              2000              2010
        *                 *        *    *                *                 *
     CCA TTT ACC TGT TTT GCC AAG AAT ACA CAT GGT ATA GAT GCA GCA TAT
     Pro Phe Thr Cys Phe Ala Lys Asn Thr His Gly Ile Asp Ala Ala Tyr>

2020              2030         2040              2050              2060
           *                 *        *    *                *                 *
     ATC CAG TTA ATA TAT CCA GTC ACT AAT TCC GGA GAC AAA ACT CAC ACA
     Ile Gln Leu Ile Tyr Pro Val Thr Asn Ser Gly Asp Lys Thr His Thr>

2070              2080      2090              2100              2110
                *                 *      *    *                *                 *
     TGC CCA CCG TGC CCA GCA CCT GAA CTC CTG GGG GGA CCG TCA GTC TTC
     Cys Pro Pro Cys Pro Ala Pro Glu Leu Leu Gly Gly Pro Ser Val Phe>

2120              2130       2140              2150              2160
                    *                 *      *    *                *                 *
     CTC TTC CCC CCA AAA CCC AAG GAC ACC CTC ATG ATC TCC CGG ACC CCT
     Leu Phe Pro Pro Lys Pro Lys Asp Thr Leu Met Ile Ser Arg Thr Pro>

2170              2180       2190              2200
                    *                 *      *    *                *                 *
     GAG GTC ACA TGC GTG GTG GTG GAC GTG AGC CAC GAA GAC CCT GAG GTC
     Glu Val Thr Cys Val Val Val Asp Val Ser His Glu Asp Pro Glu Val>

2210              2220         2230              2240              2250
        *                 *        *    *                *                 *
     AAG TTC AAC TGG TAC GTG GAC GGC GTG GAG GTG CAT AAT GCC AAG ACA
     Lys Phe Asn Trp Tyr Val Asp Gly Val Glu Val His Asn Ala Lys Thr>

2260              2270         2280              2290              2300
           *                 *        *    *                *                 *
     AAG CCG CGG GAG GAG CAG TAC AAC AGC ACG TAC CGT GTG GTC AGC GTC
     Lys Pro Arg Glu Glu Gln Tyr Asn Ser Thr Tyr Arg Val Val Ser Val>

2310              2320       2330              2340              2350
                *                 *      *    *                *                 *
     CTC ACC GTC CTG CAC CAG GAC TGG CTG AAT GGC AAG GAG TAC AAG TGC
     Leu Thr Val Leu His Gln Asp Trp Leu Asn Gly Lys Glu Tyr Lys Cys>

```
AAG GTC TCC AAC AAA GCC CTC CCA GCC CCC ATC GAG AAA ACC ATC TCC
Lys Val Ser Asn Lys Ala Leu Pro Ala Pro Ile Glu Lys Thr Ile Ser>

2410          2420          2430          2440
AAA GCC AAA GGG CAG CCC CGA GAA CCA CAG GTG TAC ACC CTG CCC CCA
Lys Ala Lys Gly Gln Pro Arg Glu Pro Gln Val Tyr Thr Leu Pro Pro>

2450         2460          2470         2480         2490
TCC CGG GAG GAG ATG ACC AAG AAC CAG GTC AGC CTG ACC TGC CTG GTC
Ser Arg Glu Glu Met Thr Lys Asn Gln Val Ser Leu Thr Cys Leu Val>

2500          2510         2520          2530         2540
AAA GGC TTC TAT CCC AGC GAC ATC GCC GTG GAG TGG GAG AGC AAT GGG
Lys Gly Phe Tyr Pro Ser Asp Ile Ala Val Glu Trp Glu Ser Asn Gly>

2550         2560         2570         2580          2590
CAG CCG GAG AAC AAC TAC AAG ACC ACG CCT CCC GTG CTG GAC TCC GAC
Gln Pro Glu Asn Asn Tyr Lys Thr Thr Pro Pro Val Leu Asp Ser Asp>

2600          2610         2620         2630         2640
GGC TCC TTC TTC CTC TAT AGC AAG CTC ACC GTG GAC AAG AGC AGG TGG
Gly Ser Phe Phe Leu Tyr Ser Lys Leu Thr Val Asp Lys Ser Arg Trp>

2650          2660         2670         2680
CAG CAG GGG AAC GTC TTC TCA TGC TCC GTG ATG CAT GAG GCT CTG CAC
Gln Gln Gly Asn Val Phe Ser Cys Ser Val Met His Glu Ala Leu His>

2690         2700          2710         2720         2730
AAC CAC TAC ACG CAG AAG AGC CTC TCC CTG TCT CCG GGT AAA TGA
Asn His Tyr Thr Gln Lys Ser Leu Ser Leu Ser Pro Gly Lys ***>
```

Fig.31A.

```
         10            20            30            40
    *     *     *     *     *     *     *     *     *
ATG GTG TGG CTT TGC TCT GGG CTC CTG TTC CCT GTG AGC TGC CTG GTC
TAC CAC ACC GAA ACG AGA CCC GAG GAC AAG GGA CAC TCG ACG GAC CAG
Met Val Trp Leu Cys Ser Gly Leu Leu Phe Pro Val Ser Cys Leu Val>

50            60            70            80            90
    *     *     *     *     *     *     *     *     *     *
CTG CTG CAG GTG GCA AGC TCT GGG AAC ATG AAG GTC TTG CAG GAG CCC
GAC GAC GTC CAC CGT TCG AGA CCC TTG TAC TTC CAG AAC GTC CTC GGG
Leu Leu Gln Val Ala Ser Ser Gly Asn Met Lys Val Leu Gln Glu Pro>

100           110           120           130           140
    *     *     *     *     *     *     *     *     *
ACC TGC GTC TCC GAC TAC ATG AGC ATC TCT ACT TGC GAG TGG AAG ATG
TGG ACG CAG AGG CTG ATG TAC TCG TAG AGA TGA ACG CTC ACC TTC TAC
Thr Cys Val Ser Asp Tyr Met Ser Ile Ser Thr Cys Glu Trp Lys Met>

150           160           170           180           190
    *     *     *     *     *     *     *     *     *     *
AAT GGT CCC ACC AAT TGC AGC ACC GAG CTC CGC CTG TTG TAC CAG CTG
TTA CCA GGG TGG TTA ACG TCG TGG CTC GAG GCG GAC AAC ATG GTC GAC
Asn Gly Pro Thr Asn Cys Ser Thr Glu Leu Arg Leu Leu Tyr Gln Leu>

200           210           220           230           240
    *     *     *     *     *     *     *     *     *     *
GTT TTT CTG CTC TCC GAA GCC CAC ACG TGT ATC CCT GAG AAC AAC GGA
CAA AAA GAC GAG AGG CTT CGG GTG TGC ACA TAG GGA CTC TTG TTG CCT
Val Phe Leu Leu Ser Glu Ala His Thr Cys Ile Pro Glu Asn Asn Gly>

250           260           270           280
    *     *     *     *     *     *     *     *     *
GGC GCG GGG TGC GTG TGC CAC CTG CTC ATG GAT GAC GTG GTC AGT GCG
CCG CGC CCC ACG CAC ACG GTG GAC GAG TAC CTA CTG CAC CAG TCA CGC
Gly Ala Gly Cys Val Cys His Leu Leu Met Asp Asp Val Val Ser Ala>

290           300           310           320           330
    *     *     *     *     *     *     *     *     *     *
GAT AAC TAT ACA CTG GAC CTG TGG GCT GGG CAG CAG CTG CTG TGG AAG
CTA TTG ATA TGT GAC CTG GAC ACC CGA CCC GTC GTC GAC GAC ACC TTC
Asp Asn Tyr Thr Leu Asp Leu Trp Ala Gly Gln Gln Leu Leu Trp Lys>

340           350           360           370           380
    *     *     *     *     *     *     *     *     *
GGC TCC TTC AAG CCC AGC GAG CAT GTG AAA CCC AGG GCC CCA GGA AAC
CCG AGG AAG TTC GGG TCG CTC GTA CAC TTT GGG TCC CGG GGT CCT TTG
Gly Ser Phe Lys Pro Ser Glu His Val Lys Pro Arg Ala Pro Gly Asn>
```

Fig.31B.

```
              390           400           410           420           430
               *    *    *    *    *    *    *    *    *    *
              CTG  ACA  GTT  CAC  ACC  AAT  GTC  TCC  GAC  ACT  CTG  CTG  CTG  ACC  TGG  AGC
              GAC  TGT  CAA  GTG  TGG  TTA  CAG  AGG  CTG  TGA  GAC  GAC  GAC  TGG  ACC  TCG
              Leu  Thr  Val  His  Thr  Asn  Val  Ser  Asp  Thr  Leu  Leu  Leu  Thr  Trp  Ser>

440           450           460           470           480
               *    *    *    *    *    *    *    *    *    *
              AAC  CCG  TAT  CCC  CCT  GAC  AAT  TAC  CTG  TAT  AAT  CAT  CTC  ACC  TAT  GCA
              TTG  GGC  ATA  GGG  GGA  CTG  TTA  ATG  GAC  ATA  TTA  GTA  GAG  TGG  ATA  CGT
              Asn  Pro  Tyr  Pro  Pro  Asp  Asn  Tyr  Leu  Tyr  Asn  His  Leu  Thr  Tyr  Ala>

490           500           510           520
                       *    *    *    *    *    *    *    *    *
              GTC  AAC  ATT  TGG  AGT  GAA  AAC  GAC  CCG  GCA  GAT  TTC  AGA  ATC  TAT  AAC
              CAG  TTG  TAA  ACC  TCA  CTT  TTG  CTG  GGC  CGT  CTA  AAG  TCT  TAG  ATA  TTG
              Val  Asn  Ile  Trp  Ser  Glu  Asn  Asp  Pro  Ala  Asp  Phe  Arg  Ile  Tyr  Asn>

530           540           550           560           570
               *    *    *    *    *    *    *    *    *    *
              GTG  ACC  TAC  CTA  GAA  CCC  TCC  CTC  CGC  ATC  GCA  GCC  AGC  ACC  CTG  AAG
              CAC  TGG  ATG  GAT  CTT  GGG  AGG  GAG  GCG  TAG  CGT  CGG  TCG  TGG  GAC  TTC
              Val  Thr  Tyr  Leu  Glu  Pro  Ser  Leu  Arg  Ile  Ala  Ala  Ser  Thr  Leu  Lys>

580           590           600           610           620
               *    *    *    *    *    *    *    *    *
              TCT  GGG  ATT  TCC  TAC  AGG  GCA  CGG  GTG  AGG  GCC  TGG  GCT  CAG  AGC  TAT
              AGA  CCC  TAA  AGG  ATG  TCC  CGT  GCC  CAC  TCC  CGG  ACC  CGA  GTC  TCG  ATA
              Ser  Gly  Ile  Ser  Tyr  Arg  Ala  Arg  Val  Arg  Ala  Trp  Ala  Gln  Ser  Tyr>

630           640           650           660           670
               *    *    *    *    *    *    *    *    *    *
              AAC  ACC  ACC  TGG  AGT  GAG  TGG  AGC  CCC  AGC  ACC  AAG  TGG  CAC  AAC  TCC
              TTG  TGG  TGG  ACC  TCA  CTC  ACC  TCG  GGG  TCG  TGG  TTC  ACC  GTG  TTG  AGG
              Asn  Thr  Thr  Trp  Ser  Glu  Trp  Ser  Pro  Ser  Thr  Lys  Trp  His  Asn  Ser>

680           690           700           710           720
               *    *    *    *    *    *    *    *    *    *
              TAC  AGG  GAG  CCC  TTC  GAG  CAG  TCC  GGT  GGG  GGC  GGG  GGC  GCC  GCG  CCT
              ATG  TCC  CTC  GGG  AAG  CTC  GTC  AGG  CCA  CCC  CCG  CCC  CCG  CGG  CGC  GGA
              Tyr  Arg  Glu  Pro  Phe  Glu  Gln  Ser  Gly  Gly  Gly  Gly  Gly  Ala  Ala  Pro>

730           740           750           760
                       *    *    *    *    *    *    *    *    *
              ACG  GAA  ACT  CAG  CCA  CCT  GTG  ACA  AAT  TTG  AGT  GTC  TCT  GTT  GAA  AAC
              TGC  CTT  TGA  GTC  GGT  GGA  CAC  TGT  TTA  AAC  TCA  CAG  AGA  CAA  CTT  TTG
              Thr  Glu  Thr  Gln  Pro  Pro  Val  Thr  Asn  Leu  Ser  Val  Ser  Val  Glu  Asn>
```

Fig.31C.

```
      770           780           790           800           810
       *      *      *      *      *      *      *      *      *      *
     CTC   TGC   ACA   GTA   ATA   TGG   ACA   TGG   AAT   CCA   CCC   GAG   GGA   GCC   AGC   TCA
     GAG   ACG   TGT   CAT   TAT   ACC   TGT   ACC   TTA   GGT   GGG   CTC   CCT   CGG   TCG   AGT
     Leu   Cys   Thr   Val   Ile   Trp   Thr   Trp   Asn   Pro   Pro   Glu   Gly   Ala   Ser   Ser>

820           830           840           850           860
       *      *      *      *      *      *      *      *      *
     AAT   TGT   AGT   CTA   TGG   TAT   TTT   AGT   CAT   TTT   GGC   GAC   AAA   CAA   GAT   AAG
     TTA   ACA   TCA   GAT   ACC   ATA   AAA   TCA   GTA   AAA   CCG   CTG   TTT   GTT   CTA   TTC
     Asn   Cys   Ser   Leu   Trp   Tyr   Phe   Ser   His   Phe   Gly   Asp   Lys   Gln   Asp   Lys>

870           880           890           900           910
        *     *      *      *      *      *      *      *      *      *
     AAA   ATA   GCT   CCG   GAA   ACT   CGT   CGT   TCA   ATA   GAA   GTA   CCC   CTG   AAT   GAG
     TTT   TAT   CGA   GGC   CTT   TGA   GCA   GCA   AGT   TAT   CTT   CAT   GGG   GAC   TTA   CTC
     Lys   Ile   Ala   Pro   Glu   Thr   Arg   Arg   Ser   Ile   Glu   Val   Pro   Leu   Asn   Glu>

920           930           940           950           960
        *      *      *      *      *      *      *      *      *      *
     AGG   ATT   TGT   CTG   CAA   GTG   GGG   TCC   CAG   TGT   AGC   ACC   AAT   GAG   AGT   GAG
     TCC   TAA   ACA   GAC   GTT   CAC   CCC   AGG   GTC   ACA   TCG   TGG   TTA   CTC   TCA   CTC
     Arg   Ile   Cys   Leu   Gln   Val   Gly   Ser   Gln   Cys   Ser   Thr   Asn   Glu   Ser   Glu>

970           980           990          1000
        *      *      *      *      *      *      *      *      *
     AAG   CCT   AGC   ATT   TTG   GTT   GAA   AAA   TGC   ATC   TCA   CCC   CCA   GAA   GGT   GAT
     TTC   GGA   TCG   TAA   AAC   CAA   CTT   TTT   ACG   TAG   AGT   GGG   GGT   CTT   CCA   CTA
     Lys   Pro   Ser   Ile   Leu   Val   Glu   Lys   Cys   Ile   Ser   Pro   Pro   Glu   Gly   Asp>

1010          1020          1030          1040          1050
       *      *      *      *      *      *      *      *      *      *
     CCT   GAG   TCT   GCT   GTG   ACT   GAG   CTT   CAA   TGC   ATT   TGG   CAC   AAC   CTG   AGC
     GGA   CTC   AGA   CGA   CAC   TGA   CTC   GAA   GTT   ACG   TAA   ACC   GTG   TTG   GAC   TCG
     Pro   Glu   Ser   Ala   Val   Thr   Glu   Leu   Gln   Cys   Ile   Trp   His   Asn   Leu   Ser>

1060          1070          1080          1090          1100
       *      *      *      *      *      *      *      *      *
     TAC   ATG   AAG   TGT   TCT   TGG   CTC   CCT   GGA   AGG   AAT   ACC   AGT   CCC   GAC   ACT
     ATG   TAC   TTC   ACA   AGA   ACC   GAG   GGA   CCT   TCC   TTA   TGG   TCA   GGG   CTG   TGA
     Tyr   Met   Lys   Cys   Ser   Trp   Leu   Pro   Gly   Arg   Asn   Thr   Ser   Pro   Asp   Thr>

1110          1120          1130          1140          1150
       *      *      *      *      *      *      *      *      *      *
     AAC   TAT   ACT   CTC   TAC   TAT   TGG   CAC   AGA   AGC   CTG   GAA   AAA   ATT   CAT   CAA
     TTG   ATA   TGA   GAG   ATG   ATA   ACC   GTG   TCT   TCG   GAC   CTT   TTT   TAA   GTA   GTT
     Asn   Tyr   Thr   Leu   Tyr   Tyr   Trp   His   Arg   Ser   Leu   Glu   Lys   Ile   His   Gln>
```

Fig.31D.

```
            1160                1170                1180                1190                1200
         *        *          *        *          *        *          *        *          *        *
       TGT GAA AAC ATC TTT AGA GAA GGC CAA TAC TTT GGT TGT TCC TTT GAT
       ACA CTT TTG TAG AAA TCT CTT CCG GTT ATG AAA CCA ACA AGG AAA CTA
       Cys Glu Asn Ile Phe Arg Glu Gly Gln Tyr Phe Gly Cys Ser Phe Asp>

1210                1220                1230                1240
                *        *          *        *          *        *          *        *
       CTG ACC AAA GTG AAG GAT TCC AGT TTT GAA CAA CAC AGT GTC CAA ATA
       GAC TGG TTT CAC TTC CTA AGG TCA AAA CTT GTT GTG TCA CAG GTT TAT
       Leu Thr Lys Val Lys Asp Ser Ser Phe Glu Gln His Ser Val Gln Ile>

1250             1260                1270                1280                1290
     *        *        *          *        *          *        *          *        *
    ATG GTC AAG GAT AAT GCA GGA AAA ATT AAA CCA TCC TTC AAT ATA GTG
    TAC CAG TTC CTA TTA CGT CCT TTT TAA TTT GGT AGG AAG TTA TAT CAC
    Met Val Lys Asp Asn Ala Gly Lys Ile Lys Pro Ser Phe Asn Ile Val>

1300                1310                1320                1330                1340
      *        *          *        *          *        *          *        *          *
    CCT TTA ACT TCC CGT GTG AAA CCT GAT CCT CCA CAT ATT AAA AAC CTC
    GGA AAT TGA AGG GCA CAC TTT GGA CTA GGA GGT GTA TAA TTT TTG GAG
    Pro Leu Thr Ser Arg Val Lys Pro Asp Pro Pro His Ile Lys Asn Leu>

1350                1360                1370                1380                1390
            *        *          *        *          *        *          *        *          *        *
          TCC TTC CAC AAT GAT GAC CTA TAT GTG CAA TGG GAG AAT CCA CAG AAT
          AGG AAG GTG TTA CTA CTG GAT ATA CAC GTT ACC CTC TTA GGT GTC TTA
          Ser Phe His Asn Asp Asp Leu Tyr Val Gln Trp Glu Asn Pro Gln Asn>

1400                1410                1420                1430                1440
                *        *          *        *          *        *          *        *          *        *
          TTT ATT AGC AGA TGC CTA TTT TAT GAA GTA GAA GTC AAT AAC AGC AA
          AAA TAA TCG TCT ACG GAT AAA ATA CTT CAT CTT CAG TTA TTG TCG GTT
          Phe Ile Ser Arg Cys Leu Phe Tyr Glu Val Glu Val Asn Asn Ser Gln>

1450                1460                1470                1480
                    *        *          *        *          *        *          *        *
          ACT GAG ACA CAT AAT GTT TTC TAC GTC CAA GAG GCT AAA TGT GAG AAT
          TGA CTC TGT GTA TTA CAA AAG ATG CAG GTT CTC CGA TTT ACA CTC TTA
          Thr Glu Thr His Asn Val Phe Tyr Val Gln Glu Ala Lys Cys Glu Asn>

1490                1500                1510                1520                1530
         *        *        *          *        *          *        *          *        *          *
          CCA GAA TTT GAG AGA AAT GTG GAG AAT ACA TCT TGT TTC ATG GTC CCT
          GGT CTT AAA CTC TCT TTA CAC CTC TTA TGT AGA ACA AAG TAC CAG GGA
          Pro Glu Phe Glu Arg Asn Val Glu Asn Thr Ser Cys Phe Met Val Pro>
```

Fig.31E.

```
        1540            1550           1560             1570            1580
          *       *       *       *       *       *       *      *       *
        GGT GTT CTT CCT GAT ACT TTG AAC ACA GTC AGA ATA AGA GTC AAA ACA
        CCA CAA GAA GGA CTA TGA AAC TTG TGT CAG TCT TAT TCT CAG TTT TGT
        Gly Val Leu Pro Asp Thr Leu Asn Thr Val Arg Ile Arg Val Lys Thr>

1590             1600            1610            1620             1630
            *       *        *       *        *       *       *       *        *       *
        AAT AAG TTA TGC TAT GAG GAT GAC AAA CTC TGG AGT AAT TGG AGC CAA
        TTA TTC AAT ACG ATA CTC CTA CTG TTT GAG ACC TCA TTA ACC TCG GTT
        Asn Lys Leu Cys Tyr Glu Asp Asp Lys Leu Trp Ser Asn Trp Ser Gln>

1640            1650            1660            1670            1680
               *       *        *       *        *       *       *       *        *       *
        GAA ATG AGT ATA GGT AAG AAG CGC AAT TCC ACA ACC GGA GAC AAA ACT
        CTT TAC TCA TAT CCA TTC TTC GCG TTA AGG TGT TGG CCT CTG TTT TGA
        Glu Met Ser Ile Gly Lys Lys Arg Asn Ser Thr Thr Gly Asp Lys Thr>

1690             1700            1710            1720
                  *       *        *       *        *       *       *       *        *
        CAC ACA TGC CCA CCG TGC CCA GCA CCT GAA CTC CTG GGG GGA CCG TCA
        GTG TGT ACG GGT GGC ACG GGT CGT GGA CTT GAG GAC CCC CCT GGC AGT
        His Thr Cys Pro Pro Cys Pro Ala Pro Glu Leu Leu Gly Gly Pro Ser>

1730           1740            1750             1760            1770
          *       *       *       *       *       *       *       *       *       *
        GTC TTC CTC TTC CCC CCA AAA CCC AAG GAC ACC CTC ATG ATC TCC CGG
        CAG AAG GAG AAG GGG GGT TTT GGG TTC CTG TGG GAG TAC TAG AGG GCC
        Val Phe Leu Phe Pro Pro Lys Pro Lys Asp Thr Leu Met Ile Ser Arg>

1780             1790            1800            1810            1820
            *       *        *       *        *       *       *       *        *
        ACC CCT GAG GTC ACA TGC GTG GTG GTG GAC GTG AGC CAC GAA GAC CCT
        TGG GGA CTC CAG TGT ACG CAC CAC CAC CTG CAC TCG GTG CTT CTG GGA
        Thr Pro Glu Val Thr Cys Val Val Val Asp Val Ser His Glu Asp Pro>

1830            1840             1850            1860            1870
               *       *        *       *        *       *       *       *        *       *
        GAG GTC AAG TTC AAC TGG TAC GTG GAC GGC GTG GAG GTG CAT AAT GCC
        CTC CAG TTC AAG TTG ACC ATG CAC CTG CCG CAC CTC CAC GTA TTA CGG
        Glu Val Lys Phe Asn Trp Tyr Val Asp Gly Val Glu Val His Asn Ala>

1880             1890            1900            1910            1920
                  *       *        *       *        *       *       *       *        *       *
        AAG ACA AAG CCG CGG GAG GAG CAG TAC AAC AGC ACG TAC CGT GTG GTC
        TTC TGT TTC GGC GCC CTC CTC GTC ATG TTG TCG TGC ATG GCA CAC CAG
        Lys Thr Lys Pro Arg Glu Glu Gln Tyr Asn Ser Thr Tyr Arg Val Val>
```

Fig.31F.

```
           1930            1940            1950            1960
             *       *       *       *       *       *       *       *       *
         AGC GTC CTC ACC GTC CTG CAC CAG GAC TGG CTG AAT GGC AAG GAG TAC
         TCG CAG GAG TGG CAG GAC GTG GTC CTG ACC GAC TTA CCG TTC CTC ATG
         Ser Val Leu Thr Val Leu His Gln Asp Trp Leu Asn Gly Lys Glu Tyr>

1970            1980            1990            2000            2010
     *       *       *       *       *       *       *       *       *       *
   AAG TGC AAG GTC TCC AAC AAA GCC CTC CCA GCC CCC ATC GAG AAA ACC
   TTC ACG TTC CAG AGG TTG TTT CGG GAG GGT CGG GGG TAG CTC TTT TGG
   Lys Cys Lys Val Ser Asn Lys Ala Leu Pro Ala Pro Ile Glu Lys Thr>

2020            2030            2040            2050            2060
         *       *       *       *       *       *       *       *       *
       ATC TCC AAA GCC AAA GGG CAG CCC CGA GAA CCA CAG GTG TAC ACC CTG
       TAG AGG TTT CGG TTT CCC GTC GGG GCT CTT GGT GTC CAC ATG TGG GAC
       Ile Ser Lys Ala Lys Gly Gln Pro Arg Glu Pro Gln Val Tyr Thr Leu>

2070            2080            2090            2100            2110
             *       *       *       *       *       *       *       *       *       *
         CCC CCA TCC CGG GAG GAG ATG ACC AAG AAC CAG GTC AGC CTG ACC TGC
         GGG GGT AGG GCC CTC CTC TAC TGG TTC TTG GTC CAG TCG GAC TGG ACG
         Pro Pro Ser Arg Glu Glu Met Thr Lys Asn Gln Val Ser Leu Thr Cys>

2120            2130            2140            2150            2160
                 *       *       *       *       *       *       *       *       *       *
             CTG GTC AAA GGC TTC TAT CCC AGC GAC ATC GCC GTG GAG TGG GAG AGC
             GAC CAG TTT CCG AAG ATA GGG TCG CTG TAG CGG CAC CTC ACC CTC TCG
             Leu Val Lys Gly Phe Tyr Pro Ser Asp Ile Ala Val Glu Trp Glu Ser>

2170            2180            2190            2200
                     *       *       *       *       *       *       *       *       *
                 AAT GGG CAG CCG GAG AAC AAC TAC AAG ACC ACG CCT CCC GTG CTG GAC
                 TTA CCC GTC GGC CTC TTG TTG ATG TTC TGG TGC GGA GGG CAC GAC CTG
                 Asn Gly Gln Pro Glu Asn Asn Tyr Lys Thr Thr Pro Pro Val Leu Asp>

2210            2220            2230            2240            2250
     *       *       *       *       *       *       *       *       *       *
   TCC GAC GGC TCC TTC TTC CTC TAT AGC AAG CTC ACC GTG GAC AAG AGC
   AGG CTG CCG AGG AAG AAG GAG ATA TCG TTC GAG TGG CAC CTG TTC TCG
   Ser Asp Gly Ser Phe Phe Leu Tyr Ser Lys Leu Thr Val Asp Lys Ser>

2260            2270            2280            2290            2300
         *       *       *       *       *       *       *       *       *
       AGG TGG CAG CAG GGG AAC GTC TTC TCA TGC TCC GTG ATG CAT GAG GCT
       TCC ACC GTC GTC CCC TTG CAG AAG AGT ACG AGG CAC TAC GTA CTC CGA
       Arg Trp Gln Gln Gly Asn Val Phe Ser Cys Ser Val Met His Glu Ala>
```

Fig.31G.

```
         2310               2320              2330             2340             2350
 *         *       *          *        *         *        *         *      *         *
CTG CAC AAC CAC TAC ACG CAG AAG AGC CTC TCC CTG TCT CCG GGT AAA
GAC GTG TTG GTG ATG TGC GTC TTC TCG GAG AGG GAC AGA GGC CCA TTT
Leu His Asn His Tyr Thr Gln Lys Ser Leu Ser Leu Ser Pro Gly Lys>

*
TGA
ACT
* * *>
```

Fig.32A.

```
          10            20            30            40
           *             *             *             *       *
ATG GTG TGG CCG GCG CGG CTC TGC GGG CTG TGG GCG CTG CTG CTC TGC
TAC CAC ACC GGC CGC GCC GAG ACG CCC GAC ACC CGC GAC GAC GAG ACG
Met Val Trp Pro Ala Arg Leu Cys Gly Leu Trp Ala Leu Leu Leu Cys>

50            60            70            80            90
    *             *     *       *             *     *       *     *
GCC GGC GGC GGG GGC GGG GGC GGG GGC GCC GCG CCT ACG GAA ACT CAG
CGG CCG CCG CCC CCG CCC CCG CCC CCG CGG CGC GGA TGC CTT TGA GTC
Ala Gly Gly Gly Gly Gly Gly Gly Ala Ala Pro Thr Glu Thr Gln>

100           110           120           130           140
    *     *       *     *       *     *       *     *       *
CCA CCT GTG ACA AAT TTG AGT GTC TCT GTT GAA AAC CTC TGC ACA GTA
GGT GGA CAC TGT TTA AAC TCA CAG AGA CAA CTT TTG GAG ACG TGT CAT
Pro Pro Val Thr Asn Leu Ser Val Ser Val Glu Asn Leu Cys Thr Val>

150           160           170           180           190
 *   *     *     *     *       *       *     *       *     *
ATA TGG ACA TGG AAT CCA CCC GAG GGA GCC AGC TCA AAT TGT AGT CTA
TAT ACC TGT ACC TTA GGT GGG CTC CCT CGG TCG AGT TTA ACA TCA GAT
Ile Trp Thr Trp Asn Pro Pro Glu Gly Ala Ser Ser Asn Cys Ser Leu>

200           210           220           230           240
       *     *       *     *       *     *       *     *       *     *
TGG TAT TTT AGT CAT TTT GGC GAC AAA CAA GAT AAG AAA ATA GCT CCG
ACC ATA AAA TCA GTA AAA CCG CTG TTT GTT CTA TTC TTT TAT CGA GGC
Trp Tyr Phe Ser His Phe Gly Asp Lys Gln Asp Lys Lys Ile Ala Pro>

250           260           270           280
          *     *       *     *       *     *       *     *
GAA ACT CGT CGT TCA ATA GAA GTA CCC CTG AAT GAG AGG ATT TGT CTG
CTT TGA GCA GCA AGT TAT CTT CAT GGG GAC TTA CTC TCC TAA ACA GAC
Glu Thr Arg Arg Ser Ile Glu Val Pro Leu Asn Glu Arg Ile Cys Leu>

290           300           310           320           330
    *     *       *     *       *     *       *     *       *
CAA GTG GGG TCC CAG TGT AGC ACC AAT GAG AGT GAG AAG CCT AGC ATT
GTT CAC CCC AGG GTC ACA TCG TGG TTA CTC TCA CTC TTC GGA TCG TAA
Gln Val Gly Ser Gln Cys Ser Thr Asn Glu Ser Glu Lys Pro Ser Ile>

340           350           360           370           380
    *     *       *     *       *     *       *     *       *
TTG GTT GAA AAA TGC ATC TCA CCC CCA GAA GGT GAT CCT GAG TCT GCT
AAC CAA CTT TTT ACG TAG AGT GGG GGT CTT CCA CTA GGA CTC AGA CGA
Leu Val Glu Lys Cys Ile Ser Pro Pro Glu Gly Asp Pro Glu Ser Ala>
```

Fig.32B.

```
      390           400           410           420           430
       *     *       *     *       *     *       *     *       *     *
GTG ACT GAG CTT CAA TGC ATT TGG CAC AAC CTG AGC TAC ATG AAG TGT
CAC TGA CTC GAA GTT ACG TAA ACC GTG TTG GAC TCG ATG TAC TTC ACA
Val Thr Glu Leu Gln Cys Ile Trp His Asn Leu Ser Tyr Met Lys Cys>

440           450           460           470           480
       *     *       *     *       *     *       *     *       *     *
TCT TGG CTC CCT GGA AGG AAT ACC AGT CCC GAC ACT AAC TAT ACT CTC
AGA ACC GAG GGA CCT TCC TTA TGG TCA GGG CTG TGA TTG ATA TGA GAG
Ser Trp Leu Pro Gly Arg Asn Thr Ser Pro Asp Thr Asn Tyr Thr Leu>

490           500           510           520
           *     *       *     *       *     *       *     *       *
TAC TAT TGG CAC AGA AGC CTG GAA AAA ATT CAT CAA TGT GAA AAC ATC
ATG ATA ACC GTG TCT TCG GAC CTT TTT TAA GTA GTT ACA CTT TTG TAG
Tyr Tyr Trp His Arg Ser Leu Glu Lys Ile His Gln Cys Glu Asn Ile>

530           540           550           560           570
       *     *       *     *       *     *       *     *       *     *
TTT AGA GAA GGC CAA TAC TTT GGT TGT TCC TTT GAT CTG ACC AAA GTG
AAA TCT CTT CCG GTT ATG AAA CCA ACA AGG AAA CTA GAC TGG TTT CAC
Phe Arg Glu Gly Gln Tyr Phe Gly Cys Ser Phe Asp Leu Thr Lys Val>

580           590           600           610           620
       *     *       *     *       *     *       *     *       *     *
AAG GAT TCC AGT TTT GAA CAA CAC AGT GTC CAA ATA ATG GTC AAG GAT
TTC CTA AGG TCA AAA CTT GTT GTG TCA CAG GTT TAT TAC CAG TTC CTA
Lys Asp Ser Ser Phe Glu Gln His Ser Val Gln Ile Met Val Lys Asp>

630           640           650           660           670
       *     *       *     *       *     *       *     *       *     *
AAT GCA GGA AAA ATT AAA CCA TCC TTC AAT ATA GTG CCT TTA ACT TCC
TTA CGT CCT TTT TAA TTT GGT AGG AAG TTA TAT CAC GGA AAT TGA AGG
Asn Ala Gly Lys Ile Lys Pro Ser Phe Asn Ile Val Pro Leu Thr Ser>

680           690           700           710           720
       *     *       *     *       *     *       *     *       *     *
CGT GTG AAA CCT GAT CCT CCA CAT ATT AAA AAC CTC TCC TTC CAC AAT
GCA CAC TTT GGA CTA GGA GGT GTA TAA TTT TTG GAG AGG AAG GTG TTA
Arg Val Lys Pro Asp Pro Pro His Ile Lys Asn Leu Ser Phe His Asn>

730           740           750           760
       *     *       *     *       *     *       *     *       *
GAT GAC CTA TAT GTG CAA TGG GAG AAT CCA CAG AAT TTT ATT AGC AGA
CTA CTG GAT ATA CAC GTT ACC CTC TTA GGT GTC TTA AAA TAA TCG TCT
Asp Asp Leu Tyr Val Gln Trp Glu Asn Pro Gln Asn Phe Ile Ser Arg>
```

Fig.32C.

```
       770         780         790         800         810
        *     *     *     *     *     *     *     *     *     *
       TGC   CTA   TTT   TAT   GAA   GTA   GAA   GTC   AAT   AAC   AGC   CAA   ACT   GAG   ACA   CAT
       ACG   GAT   AAA   ATA   CTT   CAT   CTT   CAG   TTA   TTG   TCG   GTT   TGA   CTC   TGT   GTA
       Cys   Leu   Phe   Tyr   Glu   Val   Glu   Val   Asn   Asn   Ser   Gln   Thr   Glu   Thr   His>

820         830         840         850         860
        *     *     *     *     *     *     *     *     *     *
       AAT   GTT   TTC   TAC   GTC   CAA   GAG   GCT   AAA   TGT   GAG   AAT   CCA   GAA   TTT   GAG
       TTA   CAA   AAG   ATG   CAG   GTT   CTC   CGA   TTT   ACA   CTC   TTA   GGT   CTT   AAA   CTC
       Asn   Val   Phe   Tyr   Val   Gln   Glu   Ala   Lys   Cys   Glu   Asn   Pro   Glu   Phe   Glu>

870         880         890         900         910
        *     *     *     *     *     *     *     *     *     *
       AGA   AAT   GTG   GAG   AAT   ACA   TCT   TGT   TTC   ATG   GTC   CCT   GGT   GTT   CTT   CCT
       TCT   TTA   CAC   CTC   TTA   TGT   AGA   ACA   AAG   TAC   CAG   GGA   CCA   CAA   GAA   GGA
       Arg   Asn   Val   Glu   Asn   Thr   Ser   Cys   Phe   Met   Val   Pro   Gly   Val   Leu   Pro>

920         930         940         950         960
        *     *     *     *     *     *     *     *     *     *
       GAT   ACT   TTG   AAC   ACA   GTC   AGA   ATA   AGA   GTC   AAA   ACA   AAT   AAG   TTA   TGC
       CTA   TGA   AAC   TTG   TGT   CAG   TCT   TAT   TCT   CAG   TTT   TGT   TTA   TTC   AAT   ACG
       Asp   Thr   Leu   Asn   Thr   Val   Arg   Ile   Arg   Val   Lys   Thr   Asn   Lys   Leu   Cys>

970         980         990         1000
        *     *     *     *     *     *     *     *     *
       TAT   GAG   GAT   GAC   AAA   CTC   TGG   AGT   AAT   TGG   AGC   CAA   GAA   ATG   AGT   ATA
       ATA   CTC   CTA   CTG   TTT   GAG   ACC   TCA   TTA   ACC   TCG   GTT   CTT   TAC   TCA   TAT
       Tyr   Glu   Asp   Asp   Lys   Leu   Trp   Ser   Asn   Trp   Ser   Gln   Glu   Met   Ser   Ile>

1010        1020         1030         1040         1050
  *    *     *     *     *     *     *     *     *     *
 GGT  AAG   AAG   CGC   AAT   TCC   ACA   GGC   GCG   CCT   AGT   GGT   GGA   GGT   GGC   CGG
 CCA  TTC   TTC   GCG   TTA   AGG   TGT   CCG   CGC   GGA   TCA   CCA   CCT   CCA   CCG   GCC
 Gly  Lys   Lys   Arg   Asn   Ser   Thr   Gly   Ala   Pro   Ser   Gly   Gly   Gly   Gly   Arg>

1060        1070         1080         1090         1100
        *     *     *     *     *     *     *     *     *
       CCC   GCA   AGC   TCT   GGG   AAC   ATG   AAG   GTC   TTG   CAG   GAG   CCC   ACC   TGC   GTC
       GGG   CGT   TCG   AGA   CCC   TTG   TAC   TTC   CAG   AAC   GTC   CTC   GGG   TGG   ACG   CAG
       Pro   Ala   Ser   Ser   Gly   Asn   Met   Lys   Val   Leu   Gln   Glu   Pro   Thr   Cys   Val>

1110        1120         1130         1140         1150
          *     *     *     *     *     *     *     *     *     *
         TCC   GAC   TAC   ATG   AGC   ATC   TCT   ACT   TGC   GAG   TGG   AAG   ATG   AAT   GGT   CCC
         AGG   CTG   ATG   TAC   TCG   TAG   AGA   TGA   ACG   CTC   ACC   TTC   TAC   TTA   CCA   GGG
         Ser   Asp   Tyr   Met   Ser   Ile   Ser   Thr   Cys   Glu   Trp   Lys   Met   Asn   Gly   Pro>
```

Fig.32D.

```
         1160           1170           1180           1190           1200
     *      *       *      *       *      *       *      *       *      *
    ACC  AAT  TGC  AGC  ACC  GAG  CTC  CGC  CTG  TTG  TAC  CAG  CTG  GTT  TTT  CTG
    TGG  TTA  ACG  TCG  TGG  CTC  GAG  GCG  GAC  AAC  ATG  GTC  GAC  CAA  AAA  GAC
    Thr  Asn  Cys  Ser  Thr  Glu  Leu  Arg  Leu  Leu  Tyr  Gln  Leu  Val  Phe  Leu>

1210           1220           1230           1240
         *      *       *      *       *      *       *      *
        CTC  TCC  GAA  GCC  CAC  ACG  TGT  ATC  CCT  GAG  AAC  AAC  GGA  GGC  GCG  GGG
        GAG  AGG  CTT  CGG  GTG  TGC  ACA  TAG  GGA  CTC  TTG  TTG  CCT  CCG  CGC  CCC
        Leu  Ser  Glu  Ala  His  Thr  Cys  Ile  Pro  Glu  Asn  Asn  Gly  Gly  Ala  Gly>

1250           1260           1270           1280           1290
     *      *       *      *       *      *       *      *       *      *
    TGC  GTG  TGC  CAC  CTG  CTC  ATG  GAT  GAC  GTG  GTC  AGT  GCG  GAT  AAC  TAT
    ACG  CAC  ACG  GTG  GAC  GAG  TAC  CTA  CTG  CAC  CAG  TCA  CGC  CTA  TTG  ATA
    Cys  Val  Cys  His  Leu  Leu  Met  Asp  Asp  Val  Val  Ser  Ala  Asp  Asn  Tyr>

1300           1310           1320           1330           1340
         *      *       *      *       *      *       *      *       *
        ACA  CTG  GAC  CTG  TGG  GCT  GGG  CAG  CAG  CTG  CTG  TGG  AAG  GGC  TCC  TTC
        TGT  GAC  CTG  GAC  ACC  CGA  CCC  GTC  GTC  GAC  GAC  ACC  TTC  CCG  AGG  AAG
        Thr  Leu  Asp  Leu  Trp  Ala  Gly  Gln  Gln  Leu  Leu  Trp  Lys  Gly  Ser  Phe>

1350           1360           1370           1380           1390
         *      *       *      *       *      *       *      *       *      *
        AAG  CCC  AGC  GAG  CAT  GTG  AAA  CCC  AGG  GCC  CCA  GGA  AAC  CTG  ACA  GTT
        TTC  GGG  TCG  CTC  GTA  CAC  TTT  GGG  TCC  CGG  GGT  CCT  TTG  GAC  TGT  CAA
        Lys  Pro  Ser  Glu  His  Val  Lys  Pro  Arg  Ala  Pro  Gly  Asn  Leu  Thr  Val>

1400           1410           1420           1430           1440
         *      *       *      *       *      *       *      *       *      *
        CAC  ACC  AAT  GTC  TCC  GAC  ACT  CTG  CTG  CTG  ACC  TGG  AGC  AAC  CCG  TAT
        GTG  TGG  TTA  CAG  AGG  CTG  TGA  GAC  GAC  GAC  TGG  ACC  TCG  TTG  GGC  ATA
        His  Thr  Asn  Val  Ser  Asp  Thr  Leu  Leu  Leu  Thr  Trp  Ser  Asn  Pro  Tyr>

1450           1460           1470           1480
            *      *       *      *       *      *       *      *       *
           CCC  CCT  GAC  AAT  TAC  CTG  TAT  AAT  CAT  CTC  ACC  TAT  GCA  GTC  AAC  ATT
           GGG  GGA  CTG  TTA  ATG  GAC  ATA  TTA  GTA  GAG  TGG  ATA  CGT  CAG  TTG  TAA
           Pro  Pro  Asp  Asn  Tyr  Leu  Tyr  Asn  His  Leu  Thr  Tyr  Ala  Val  Asn  Ile>

1490           1500           1510           1520           1530
     *      *       *      *       *      *       *      *       *      *
    TGG  AGT  GAA  AAC  GAC  CCG  GCA  GAT  TTC  AGA  ATC  TAT  AAC  GTG  ACC  TAC
    ACC  TCA  CTT  TTG  CTG  GGC  CGT  CTA  AAG  TCT  TAG  ATA  TTG  CAC  TGG  ATG
    Trp  Ser  Glu  Asn  Asp  Pro  Ala  Asp  Phe  Arg  Ile  Tyr  Asn  Val  Thr  Tyr>
```

Fig.32E.

```
       1540        1550        1560        1570        1580
        *    *      *      *    *      *    *      *      *
CTA GAA CCC TCC CTC CGC ATC GCA GCC AGC ACC CTG AAG TCT GGG ATT
GAT CTT GGG AGG GAG GCG TAG CGT CGG TCG TGG GAC TTC AGA CCC TAA
Leu Glu Pro Ser Leu Arg Ile Ala Ala Ser Thr Leu Lys Ser Gly Ile>

1590        1600        1610        1620        1630
        *    *      *      *    *      *    *      *    *    *
TCC TAC AGG GCA CGG GTG AGG GCC TGG GCT CAG TGC TAT AAC ACC ACC
AGG ATG TCC CGT GCC CAC TCC CGG ACC CGA GTC ACG ATA TTG TGG TGG
Ser Tyr Arg Ala Arg Val Arg Ala Trp Ala Gln Cys Tyr Asn Thr Thr>

1640        1650        1660        1670        1680
            *    *      *      *    *      *    *      *    *    *
TGG AGT GAG TGG AGC CCC AGC ACC AAG TGG CAC AAC TCC TAC AGG GAG
ACC TCA CTC ACC TCG GGG TCG TGG TTC ACC GTG TTG AGG ATG TCC CTC
Trp Ser Glu Trp Ser Pro Ser Thr Lys Trp His Asn Ser Tyr Arg Glu>

1690        1700        1710        1720
                 *    *      *      *    *      *    *      *    *
CCC TTC GAG CAG TCC GGA GAC AAA ACT CAC ACA TGC CCA CCG TGC CCA
GGG AAG CTC GTC AGG CCT CTG TTT TGA GTG TGT ACG GGT GGC ACG GGT
Pro Phe Glu Gln Ser Gly Asp Lys Thr His Thr Cys Pro Pro Cys Pro>

1730        1740        1750        1760        1770
 *    *      *      *    *      *    *      *    *    *
GCA CCT GAA CTC CTG GGG GGA CCG TCA GTC TTC CTC TTC CCC CCA AAA
CGT GGA CTT GAG GAC CCC CCT GGC AGT CAG AAG GAG AAG GGG GGT TTT
Ala Pro Glu Leu Leu Gly Gly Pro Ser Val Phe Leu Phe Pro Pro Lys>

1780        1790        1800        1810        1820
        *    *      *      *    *      *    *      *    *
CCC AAG GAC ACC CTC ATG ATC TCC CGG ACC CCT GAG GTC ACA TGC GTG
GGG TTC CTG TGG GAG TAC TAG AGG GCC TGG GGA CTC CAG TGT ACG CAC
Pro Lys Asp Thr Leu Met Ile Ser Arg Thr Pro Glu Val Thr Cys Val>

1830        1840        1850        1860        1870
            *    *      *      *    *      *    *      *    *
GTG GTG GAC GTG AGC CAC GAA GAC CCT GAG GTC AAG TTC AAC TGG TAC
CAC CAC CTG CAC TCG GTG CTT CTG GGA CTC CAG TTC AAG TTG ACC ATG
Val Val Asp Val Ser His Glu Asp Pro Glu Val Lys Phe Asn Trp Tyr>

1880        1890        1900        1910        1920
        *    *      *      *    *      *    *      *    *    *
GTG GAC GGC GTG GAG GTG CAT AAT GCC AAG ACA AAG CCG CGG GAG GAG
CAC CTG CCG CAC CTC CAC GTA TTA CGG TTC TGT TTC GGC GCC CTC CTC
Val Asp Gly Val Glu Val His Asn Ala Lys Thr Lys Pro Arg Glu Glu>
```

Fig.32F.

```
          1930           1940           1950           1960
           *              *              *              *
      *        *      *       *      *       *      *       *      *       *
     CAG TAC AAC AGC ACG TAC CGT GTG GTC AGC GTC CTC ACC GTC CTG CAC
     GTC ATG TTG TCG TGC ATG GCA CAC CAG TCG CAG GAG TGG CAG GAC GTG
     Gln Tyr Asn Ser Thr Tyr Arg Val Val Ser Val Leu Thr Val Leu His>

1970           1980           1990           2000           2010
   *              *              *              *              *
  *       *      *       *      *       *      *       *      *       *
 CAG GAC TGG CTG AAT GGC AAG GAG TAC AAG TGC AAG GTC TCC AAC AAA
 GTC CTG ACC GAC TTA CCG TTC CTC ATG TTC ACG TTC CAG AGG TTG TTT
 Gln Asp Trp Leu Asn Gly Lys Glu Tyr Lys Cys Lys Val Ser Asn Lys>

2020           2030           2040           2050           2060
        *              *              *              *              *
       *      *       *      *      *       *      *       *      *
      GCC CTC CCA GCC CCC ATC GAG AAA ACC ATC TCC AAA GCC AAA GGG CAG
      CGG GAG GGT CGG GGG TAG CTC TTT TGG TAG AGG TTT CGG TTT CCC GTC
      Ala Leu Pro Ala Pro Ile Glu Lys Thr Ile Ser Lys Ala Lys Gly Gln>

2070           2080           2090           2100           2110
          *              *              *              *              *
         *      *       *      *       *      *       *      *       *      *
        CCC CGA GAA CCA CAG GTG TAC ACC CTG CCC CCA TCC CGG GAG GAG ATG
        GGG GCT CTT GGT GTC CAC ATG TGG GAC GGG GGT AGG GCC CTC CTC TAC
        Pro Arg Glu Pro Gln Val Tyr Thr Leu Pro Pro Ser Arg Glu Glu Met>

2120           2130           2140           2150           2160
           *              *              *              *              *
          *      *       *      *       *      *       *      *       *      *
         ACC AAG AAC CAG GTC AGC CTG ACC TGC CTG GTC AAA GGC TTC TAT CCC
         TGG TTC TTG GTC CAG TCG GAC TGG ACG GAC CAG TTT CCG AAG ATA GGG
         Thr Lys Asn Gln Val Ser Leu Thr Cys Leu Val Lys Gly Phe Tyr Pro>

2170           2180           2190           2200
             *              *              *              *
            *       *      *      *       *      *       *      *      *
           AGC GAC ATC GCC GTG GAG TGG GAG AGC AAT GGG CAG CCG GAG AAC AAC
           TCG CTG TAG CGG CAC CTC ACC CTC TCG TTA CCC GTC GGC CTC TTG TTG
           Ser Asp Ile Ala Val Glu Trp Glu Ser Asn Gly Gln Pro Glu Asn Asn>

2210           2220           2230           2240           2250
   *              *              *              *              *
  *       *      *      *       *      *       *      *       *      *
 TAC AAG ACC ACG CCT CCC GTG CTG GAC TCC GAC GGC TCC TTC TTC CTC
 ATG TTC TGG TGC GGA GGG CAC GAC CTG AGG CTG CCG AGG AAG AAG GAG
 Tyr Lys Thr Thr Pro Pro Val Leu Asp Ser Asp Gly Ser Phe Phe Leu>

2260           2270           2280           2290           2300
          *              *              *              *              *
         *      *       *      *       *      *       *      *       *
        TAT AGC AAG CTC ACC GTG GAC AAG AGC AGG TGG CAG CAG GGG AAC GTC
        ATA TCG TTC GAG TGG CAC CTG TTC TCG TCC ACC GTC GTC CCC TTG CAG
        Tyr Ser Lys Leu Thr Val Asp Lys Ser Arg Trp Gln Gln Gly Asn Val>
```

```
         2310                2320                2330                2340                2350
          *                   *                   *                   *                   *
  *         *         *         *         *         *         *         *         *         *
TTC TCA TGC TCC GTG ATG CAT GAG GCT CTG CAC AAC CAC TAC ACG CAG
AAG AGT ACG AGG CAC TAC GTA CTC CGA GAC GTG TTG GTG ATG TGC GTC
Phe Ser Cys Ser Val Met His Glu Ala Leu His Asn His Tyr Thr Gln>

2360                2370                2380
          *                   *                   *
  *         *         *         *         *         *
AAG AGC CTC TCC CTG TCT CCG GGT AAA TGA
TTC TCG GAG AGG GAC AGA GGC CCA TTT ACT
Lys Ser Leu Ser Leu Ser Pro Gly Lys ***>
```

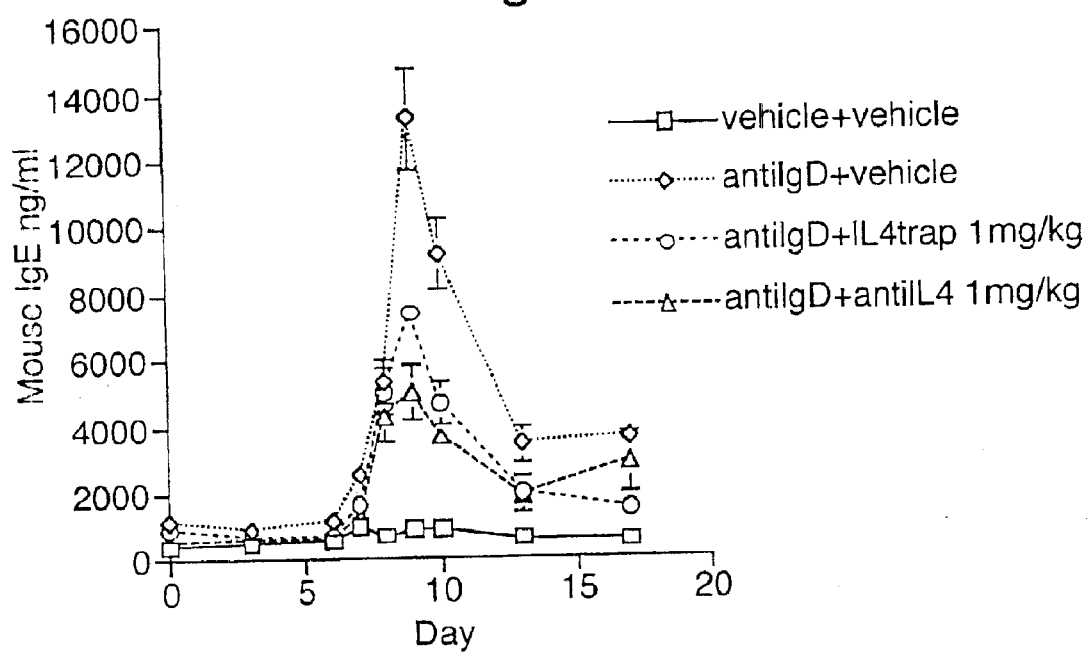

Figure 38A

```
              10                  20                  30                  40
     *         *         *         *         *         *         *         *
ATG GTG TTA CTC AGA CTT ATT TGT TTC ATA GCT CTA CTG ATT
TAC CAC AAT GAG TCT GAA TAA ACA AAG TAT CGA GAT GAC TAA
Met Val Leu Leu Arg Leu Ile Cys Phe Ile Ala Leu Leu Ile>
                        SIGNAL PEPTIDE                              >
                                IL-1RI                              >

50                  60                  70                  80
     *         *         *         *         *         *         *         *
TCT TCT CTG GAG GCT GAT AAA TGC AAG GAA CGT GAA GAA AAA
AGA AGA GAC CTC CGA CTA TTT ACG TTC CTT GCA CTT CTT TTT
Ser Ser Leu Glu Ala Asp>
    SIGNAL PEPTIDE    >
                        Lys Cys Lys Glu Arg Glu Glu Lys>
                                IL-1RI                              >

90                 100                 110                 120
     *         *         *         *         *         *         *         *
ATA ATT TTA GTG TCA TCT GCA AAT GAA ATT GAT GTT CGT CCC
TAT TAA AAT CAC AGT AGA CGT TTA CTT TAA CTA CAA GCA GGG
Ile Ile Leu Val Ser Ser Ala Asn Glu Ile Asp Val Arg Pro>
                                IL-1RI                              >

130                 140                 150                 160
     *         *         *         *         *         *         *         *
TGT CCT CTT AAC CCA AAT GAA CAC AAA GGC ACT ATA ACT TGG
ACA GGA GAA TTG GGT TTA CTT GTG TTT CCG TGA TAT TGA ACC
Cys Pro Leu Asn Pro Asn Glu His Lys Gly Thr Ile Thr Trp>
                                IL-1RI                              >

170               180                 190                 200               210
     *         *         *         *         *         *         *         *
TAT AAG GAT GAC AGC AAG ACA CCT GTA TCT ACA GAA CAA GCC
ATA TTC CTA CTG TCG TTC TGT GGA CAT AGA TGT CTT GTT CGG
Tyr Lys Asp Asp Ser Lys Thr Pro Val Ser Thr Glu Gln Ala>
                                IL-1RI                              >

220                 230                 240                 250
     *         *         *         *         *         *         *         *
TCC AGG ATT CAT CAA CAC AAA GAG AAA CTT TGG TTT GTT CCT
AGG TCC TAA GTA GTT GTG TTT CTC TTT GAA ACC AAA CAA GGA
Ser Arg Ile His Gln His Lys Glu Lys Leu Trp Phe Val Pro>
                                IL-1RI                              >

260                 270                 280                 290
     *         *         *         *         *         *         *         *
GCT AAG GTG GAG GAT TCA GGA CAT TAC TAT TGC GTG GTA AGA
CGA TTC CAC CTC CTA AGT CCT GTA ATG ATA ACG CAC CAT TCT
Ala Lys Val Glu Asp Ser Gly His Tyr Tyr Cys Val Val Arg>
                                IL-1RI                              >
```

Figure 38B

```
          300            310           320            330
        *      *       *      *    *        *     *       *      *
      AAT TCA TCT TAC TGC CTC AGA ATT AAA ATA AGT GCA AAA TTT
      TTA AGT AGA ATG ACG GAG TCT TAA TTT TAT TCA CGT TTT AAA
      Asn Ser Ser Tyr Cys Leu Arg Ile Lys Ile Ser Ala Lys Phe>
      _____IL-1RI_____>

340           350           360           370
         *     *       *     *     *      *     *      *     *
       GTG GAG AAT GAG CCT AAC TTA TGT TAT AAT GCA CAA GCC ATA
       CAC CTC TTA CTC GGA TTG AAT ACA ATA TTA CGT GTT CGG TAT
       Val Glu Asn Glu Pro Asn Leu Cys Tyr Asn Ala Gln Ala Ile>
       _____IL-1RI_____>

380           390           400           410           420
     *      *     *      *    *      *    *     *     *      *
    TTT AAG CAG AAA CTA CCC GTT GCA GGA GAC GGA GGA CTT GTG
    AAA TTC GTC TTT GAT GGG CAA CGT CCT CTG CCT CCT GAA CAC
    Phe Lys Gln Lys Leu Pro Val Ala Gly Asp Gly Gly Leu Val>
    _____IL-1RI_____>

430           440           450           460
          *      *     *      *     *      *     *  ,    *
        TGC CCT TAT ATG GAG TTT TTT AAA AAT GAA AAT AAT GAG TTA
        ACG GGA ATA TAC CTC AAA AAA TTT TTA CTT TTA TTA CTC AAT
        Cys Pro Tyr Met Glu Phe Phe Lys Asn Glu Asn Asn Glu Leu>
        _____IL-1RI_____>

470           480           490           500
         *      *      *      *     *      *     *      *
        CCT AAA TTA CAG TGG TAT AAG GAT TGC AAA CCT CTA CTT CTT
        GGA TTT AAT GTC ACC ATA TTC CTA ACG TTT GGA GAT GAA GAA
        Pro Lys Leu Gln Trp Tyr Lys Asp Cys Lys Pro Leu Leu Leu>
        _____IL-1RI_____>

510           520           530           540
         *      *     *      *     *       *     *      *      *
        GAC AAT ATA CAC TTT AGT GGA GTC AAA GAT AGG CTC ATC GTG
        CTG TTA TAT GTG AAA TCA CCT CAG TTT CTA TCC GAG TAG CAC
        Asp Asn Ile His Phe Ser Gly Val Lys Asp Arg Leu Ile Val>
        _____IL-1RI____ _____>

550           560           570           580
         *      *     *      *     *       *     *.     *
        ATG AAT GTG GCT GAA AAG CAT AGA GGG AAC TAT ACT TGT CAT
        TAC TTA CAC CGA CTT TTC GTA TCT CCC TTG ATA TGA ACA GTA
        Met Asn Val Ala Glu Lys His Arg Gly Asn Tyr Thr Cys His>
        _____IL-1RI_____>

590           600           610           620           630
         *      *     *      *     *      *     *      *      *
        GCA TCC TAC ACA TAC TTG GGC AAG CAA TAT CCT ATT ACC CGG
        CGT AGG ATG TGT ATG AAC CCG TTC GTT ATA GGA TAA TGG GCC
        Ala Ser Tyr Thr Tyr Leu Gly Lys Gln Tyr Pro Ile Thr Arg>
        _____IL-1RI_____>
```

Figure 38C

```
        640          650           660          670
         *    *       *    *        *    *       *    *
GTA ATA GAA TTT ATT ACT CTA GAG GAA AAC AAA CCC ACA AGG
CAT TAT CTT AAA TAA TGA GAT CTC CTT TTG TTT GGG TGT TCC
Val Ile Glu Phe Ile Thr Leu Glu Glu Asn Lys Pro Thr Arg>
                        IL-1RI                         >

680          690           700          710
         *    *       *    *        *    *       *    *
CCT GTG ATT GTG AGC CCA GCT AAT GAG ACA ATG GAA GTA GAC
GGA CAC TAA CAC TCG GGT CGA TTA CTC TGT TAC CTT CAT CTG
Pro Val Ile Val Ser Pro Ala Asn Glu Thr Met Glu Val Asp>
                        IL-1RI                         >

720          730           740          750
         *    *       *    *        *    *       *    *
TTG GGA TCC CAG ATA CAA TTG ATC TGT AAT GTC ACC GGC CAG
AAC CCT AGG GTC TAT GTT AAC TAG ACA TTA CAG TGG CCG GTC
Leu Gly Ser Gln Ile Gln Leu Ile Cys Asn Val Thr Gly Gln>
                        IL-1RI                         >

760          770           780          790
         *    *       *    *        *    *       *    *
TTG AGT GAC ATT GCT TAC TGG AAG TGG AAT GGG TCA GTA ATT
AAC TCA CTG TAA CGA ATG ACC TTC ACC TTA CCC AGT CAT TAA
Leu Ser Asp Ile Ala Tyr Trp Lys Trp Asn Gly Ser Val Ile>
                        IL-1RI                         >

800         810          820           830          840
   *    *      *    *       *    *        *    *       *
GAT GAA GAT GAC CCA GTG CTA GGG GAA GAC TAT TAC AGT GTG
CTA CTT CTA CTG GGT CAC GAT CCC CTT CTG ATA ATG TCA CAC
Asp Glu Asp Asp Pro Val Leu Gly Glu Asp Tyr Tyr Ser Val>
                        IL-1RI                         >

850          860           870          880
         *    *       *    *        *    *       *    *
GAA AAT CCT GCA AAC AAA AGA AGG AGT ACC CTC ATC ACA GTG
CTT TTA GGA CGT TTG TTT TCT TCC TCA TGG GAG TAG TGT CAC
Glu Asn Pro Ala Asn Lys Arg Arg Ser Thr Leu Ile Thr Val>
                        IL-1RI                         >

890          900           910          920
         *    *       *    *        *    *       *    *
CTT AAT ATA TCG GAA ATT GAG AGT AGA TTT TAT AAA CAT CCA
GAA TTA TAT AGC CTT TAA CTC TCA TCT AAA ATA TTT GTA GGT
Leu Asn Ile Ser Glu Ile Glu Ser Arg Phe Tyr Lys His Pro>
                        IL-1RI                         >

930          940           950          960
         *    *       *    *        *    *       *    *
TTT ACC TGT TTT GCC AAG AAT ACA CAT GGT ATA GAT GCA GCA
AAA TGG ACA AAA CGG TTC TTA TGT GTA CCA TAT CTA CGT CGT
Phe Thr Cys Phe Ala Lys Asn Thr His Gly Ile Asp Ala Ala>
                        IL-1RI                         >
```

Figure 38D

```
        970              980              990              1000
         *        *       *        *       *        *       *        *
       TAT ATC CAG TTA ATA TAT CCA GTC ACT AAT TCA GAA CGC TGC
       ATA TAG GTC AAT TAT ATA GGT CAG TGA TTA AGT CTT GCG ACG
       Tyr Ile Gln Leu Ile Tyr Pro Val Thr Asn>
                         IL-1RI                 >
                                                        Ser Glu Arg Cys>
                                                          IL-1RAcP      >

1010             1020             1030             1040             1050
        *       *       *        *       *        *       *        *       *
       GAT GAC TGG GGA CTA GAC ACC ATG AGG CAA ATC CAA GTG TTT
       CTA CTG ACC CCT GAT CTG TGG TAC TCC GTT TAG GTT CAC AAA
       Asp Asp Trp Gly Leu Asp Thr Met Arg Gln Ile Gln Val Phe>
                                   IL-1RAcP                         >

1060             1070             1080             1090
                *       *       *        *       *        *       *
              GAA GAT GAG CCA GCT CGC ATC AAG TGC CCA CTC TTT GAA CAC
              CTT CTA CTC GGT CGA GCG TAG TTC ACG GGT GAG AAA CTT GTG
              Glu Asp Glu Pro Ala Arg Ile Lys Cys Pro Leu Phe Glu His>
                                       IL-1RAcP                      >

1100             1110             1120             1130
             *       *       *        *       *        *       *
           TTC TTG AAA TTC AAC TAC AGC ACA GCC CAT TCA GCT GGC CTT
           AAG AAC TTT AAG TTG ATG TCG TGT CGG GTA AGT CGA CCG GAA
           Phe Leu Lys Phe Asn Tyr Ser Thr Ala His Ser Ala Gly Leu>
                                   IL-1RAcP                          >

1140             1150             1160             1170
            *       *       *       *       *       *       *       *       *
           ACT CTG ATC TGG TAT TGG ACT AGG CAG GAC CGG GAC CTT GAG
           TGA GAC TAG ACC ATA ACC TGA TCC GTC CTG GCC CTG GAA CTC
           Thr Leu Ile Trp Tyr Trp Thr Arg Gln Asp Arg Asp Leu Glu>
                                   IL-1RAcP                          >

1180             1190             1200             1210
             *       *       *        *       *        *       *       *
           GAG CCA ATT AAC TTC CGC CTC CCC GAG AAC CGC ATT AGT AAG
           CTC GGT TAA TTG AAG GCG GAG GGG CTC TTG GCG TAA TCA TTC
           Glu Pro Ile Asn Phe Arg Leu Pro Glu Asn Arg Ile Ser Lys>
                                   IL-1RAcP                          >

1220             1230             1240             1250             1260
          *       *       *       *       *       *       *       *       *
         GAG AAA GAT GTG CTG TGG TTC CGG CCC ACT CTC CTC AAT GAC
         CTC TTT CTA CAC GAC ACC AAG GCC GGG TGA GAG GAG TTA CTG
         Glu Lys Asp Val Leu Trp Phe Arg Pro Thr Leu Leu Asn Asp>
                                   IL-1RAcP                          >
```

Figure 38E

```
              1270          1280          1290          1300
                *     *       *     *       *     *       *     *
           ACT GGC AAC TAT ACC TGC ATG TTA AGG AAC ACT ACA TAT TGC
           TGA CCG TTG ATA TGG ACG TAC AAT TCC TTG TGA TGT ATA ACG
           Thr Gly Asn Tyr Thr Cys Met Leu Arg Asn Thr Thr Tyr Cys>
                                        IL-1RAcP                    >

1310          1320          1330          1340
                *     *       *     *       *     *       *     *
           AGC AAA GTT GCA TTT CCC TTG GAA GTT GTT CAA AAA GAC AGC
           TCG TTT CAA CGT AAA GGG AAC CTT CAA CAA GTT TTT CTG TCG
           Ser Lys Val Ala Phe Pro Leu Glu Val Val Gln Lys Asp Ser>
                                        IL-1RAcP                    >

1350          1360          1370          1380
                *     *       *     *       *     *       *     *
           TGT TTC AAT TCC CCC ATG AAA CTC CCA GTG CAT AAA CTG TAT
           ACA AAG TTA AGG GGG TAC TTT GAG GGT CAC GTA TTT GAC ATA
           Cys Phe Asn Ser Pro Met Lys Leu Pro Val His Lys Leu Tyr>
                                        IL-1RAcP                    >

1390          1400          1410          1420
                *     *       *     *       *     *       *     *
           ATA GAA TAT GGC ATT CAG AGG ATC ACT TGT CCA AAT GTA GAT
           TAT CTT ATA CCG TAA GTC TCC TAG TGA ACA GGT TTA CAT CTA
           Ile Glu Tyr Gly Ile Gln Arg Ile Thr Cys Pro Asn Val Asp>
                                        IL-1RAcP                    >

1430          1440          1450          1460          1470
           *     *       *     *       *     *       *     *       *
         GGA TAT TTT CCT TCC AGT GTC AAA CCG ACT ATC ACT TGG TAT
         CCT ATA AAA GGA AGG TCA CAG TTT GGC TGA TAG TGA ACC ATA
         Gly Tyr Phe Pro Ser Ser Val Lys Pro Thr Ile Thr Trp Tyr>
                                        IL-1RAcP                    >

1480          1490          1500          1510
                *     *       *     *       *     *       *     *
           ATG GGC TGT TAT AAA ATA CAG AAT TTT AAT AAT GTA ATA CCC
           TAC CCG ACA ATA TTT TAT GTC TTA AAA TTA TTA CAT TAT GGG
           Met Gly Cys Tyr Lys Ile Gln Asn Phe Asn Asn Val Ile Pro>
                                        IL-1RAcP                    >

1520          1530          1540          1550
                *     *       *     *       *     *       *     *
           GAA GGT ATG AAC TTG AGT TTC CTC ATT GCC TTA ATT TCA AAT
           CTT CCA TAC TTG AAC TCA AAG GAG TAA CGG AAT TAA AGT TTA
           Glu Gly Met Asn Leu Ser Phe Leu Ile Ala Leu Ile Ser Asn>
                                        IL-1RAcP                    >

1560          1570          1580          1590
                *     *       *     *       *     *       *     *
           AAT GGA AAT TAC ACA TGT GTT GTT ACA TAT CCA GAA AAT GGA
           TTA CCT TTA ATG TGT ACA CAA CAA TGT ATA GGT CTT TTA CCT
           Asn Gly Asn Tyr Thr Cys Val Val Thr Tyr Pro Glu Asn Gly>
                                        IL-1RAcP                    >
```

Figure 38F

```
           1600          1610          1620          1630
             *     *       *      *      *      *      *
       CGT ACG TTT CAT CTC ACC AGG ACT CTG ACT GTA AAG GTA GTA
       GCA TGC AAA GTA GAG TGG TCC TGA GAC TGA CAT TTC CAT CAT
       Arg Thr Phe His Leu Thr Arg Thr Leu Thr Val Lys Val Val>
                          _____IL-1RAcP_____>

1640          1650          1660          1670          1680
       *     *       *      *      *      *       *      *      *
       GGC TCT CCA AAA AAT GCA GTG CCC CCT GTG ATC CAT TCA CCT
       CCG AGA GGT TTT TTA CGT CAC GGG GGA CAC TAG GTA AGT GGA
       Gly Ser Pro Lys Asn Ala Val Pro Pro Val Ile His Ser Pro>
                          _____IL-1RAcP_____>

1690          1700          1710         1720
                *      *      *      *       *     *        *
       AAT GAT CAT GTG GTC TAT GAG AAA GAA CCA GGA GAG GAG CTA
       TTA CTA GTA CAC CAG ATA CTC TTT CTT GGT CCT CTC CTC GAT
       Asn Asp His Val Val Tyr Glu Lys Glu Pro Gly Glu Glu Leu>
                          _____IL-1RAcP_____>

1730          1740          1750          1760
               *      *       *      *      *      *      *      *
       CTC ATT CCC TGT ACG GTC TAT TTT AGT TTT CTG ATG GAT TCT
       GAG TAA GGG ACA TGC CAG ATA AAA TCA AAA GAC TAC CTA AGA
       Leu Ile Pro Cys Thr Val Tyr Phe Ser Phe Leu Met Asp Ser>
                          _____IL-1RAcP_____>

1770          1780          1790          1800
               *      *      *      *       *      *      *      *
       CGC AAT GAG GTT TGG TGG ACC ATT GAT GGA AAA AAA CCT GAT
       GCG TTA CTC CAA ACC ACC TGG TAA CTA CCT TTT TTT GGA CTA
       Arg Asn Glu Val Trp Trp Thr Ile Asp Gly Lys Lys Pro Asp>
                          _____IL-1RAcP_____>

1810          1820          1830          1840
             *     *       *     *       *      *      *       *
       GAC ATC ACT ATT GAT GTC ACC ATT AAC GAA AGT ATA AGT CAT
       CTG TAG TGA TAA CTA CAG TGG TAA TTG CTT TCA TAT TCA GTA
       Asp Ile Thr Ile Asp Val Thr Ile Asn Glu Ser Ile Ser His>
                          _____IL-1RAcP_____>

1850          1860          1870          1880          1890
       *      *      *      *       *      *      *      *      *
       AGT AGA ACA GAA GAT GAA ACA AGA ACT CAG ATT TTG AGC ATC
       TCA TCT TGT CTT CTA CTT TGT TCT TGA GTC TAA AAC TCG TAG
       Ser Arg Thr Glu Asp Glu Thr Arg Thr Gln Ile Leu Ser Ile>
                          _____IL-1RAcP_____>

1900          1910          1920          1930
                *      *      *      *       *      *      *      *
       AAG AAA GTT ACC TCT GAG GAT CTC AAG CGC AGC TAT GTC TGT
       TTC TTT CAA TGG AGA CTC CTA GAG TTC GCG TCG ATA CAG ACA
       Lys Lys Val Thr Ser Glu Asp Leu Lys Arg Ser Tyr Val Cys>
                          _____IL-1RAcP_____>
```

Figure 38G

```
         1940            1950            1960            1970
          *       *       *       *       *       *       *       *
CAT GCT AGA AGT GCC AAA GGC GAA GTT GCC AAA GCA GCC AAG
GTA CGA TCT TCA CGG TTT CCG CTT CAA CGG TTT CGT CGG TTC
His Ala Arg Ser Ala Lys Gly Glu Val Ala Lys Ala Ala Lys>
                        IL-1RAcP                              >

1980            1990            2000            2010
          *       *       *       *       *       *       *       *
GTG AAG CAG AAA GTG CCA GCT CCA AGA TAC ACA GTG GAA TCC
CAC TTC GTC TTT CAC GGT CGA GGT TCT ATG TGT CAC CTT AGG
Val Lys Gln Lys Val Pro Ala Pro Arg Tyr Thr Val Glu>
                        IL-1RAcP                              >
                                                   Ser>
                                                   ___>

2020            2030            2040            2050
          *       *       *       *       *       *       *       *
GGA GAC AAA ACT CAC ACA TGC CCA CCG TGC CCA GCA CCT GAA
CCT CTG TTT TGA GTG TGT ACG GGT GGC ACG GGT CGT GGA CTT
Gly Asp Lys Thr His Thr Cys Pro Pro Cys Pro Ala Pro Glu>
                        FC-IgG1                               >

2060          2070            2080            2090          2100
   *       *       *       *       *       *       *       *       *
CTC CTG GGG GGA CCG TCA GTC TTC CTC TTC CCC CCA AAA CCC
GAG GAC CCC CCT GGC AGT CAG AAG GAG AAG GGG GGT TTT GGG
Leu Leu Gly Gly Pro Ser Val Phe Leu Phe Pro Pro Lys Pro>
                        FC-IgG1                               >

2110            2120            2130            2140
          *       *       *       *       *       *       *       *
AAG GAC ACC CTC ATG ATC TCC CGG ACC CCT GAG GTC ACA TGC
TTC CTG TGG GAG TAC TAG AGG GCC TGG GGA CTC CAG TGT ACG
Lys Asp Thr Leu Met Ile Ser Arg Thr Pro Glu Val Thr Cys>
                        FC-IgG1                               >

2150            2160            2170            2180
          *       *       *       *       *       *       *
GTG GTG GTG GAC GTG AGC CAC GAA GAC CCT GAG GTC AAG TTC
CAC CAC CAC CTG CAC TCG GTG CTT CTG GGA CTC CAG TTC AAG
Val Val Val Asp Val Ser His Glu Asp Pro Glu Val Lys Phe>
                        FC-IgG1                               >

2190            2200            2210            2220
          *       *       *       *       *       *       *       *
AAC TGG TAC GTG GAC GGC GTG GAG GTG CAT AAT GCC AAG ACA
TTG ACC ATG CAC CTG CCG CAC CTC CAC GTA TTA CGG TTC TGT
Asn Trp Tyr Val Asp Gly Val Glu Val His Asn Ala Lys Thr>
                        FC-IgG1                               >
```

Figure 38H

```
          2230        2240         2250          2260
            *           *     *      *      *      *      *
        AAG CCG CGG GAG GAG CAG TAC AAC AGC ACG TAC CGT GTG GTC
        TTC GGC GCC CTC CTC GTC ATG TTG TCG TGC ATG GCA CAC CAG
        Lys Pro Arg Glu Glu Gln Tyr Asn Ser Thr Tyr Arg Val Val>
                                         FC-IgG1                       >

2270          2280         2290          2300          2310
       *      *      *     *      *      *      *     *      *
       AGC GTC CTC ACC GTC CTG CAC CAG GAC TGG CTG AAT GGC AAG
       TCG CAG GAG TGG CAG GAC GTG GTC CTG ACC GAC TTA CCG TTC
       Ser Val Leu Thr Val Leu His Gln Asp Trp Leu Asn Gly Lys>
                                         FC-IgG1                       >

2320          2330          2340           2350
         *      *      *      *     *      *      *      *
         GAG TAC AAG TGC AAG GTC TCC AAC AAA GCC CTC CCA GCC CCC
         CTC ATG TTC ACG TTC CAG AGG TTG TTT CGG GAG GGT CGG GGG
         Glu Tyr Lys Cys Lys Val Ser Asn Lys Ala Leu Pro Ala Pro>
                                         FC-IgG1                      >

2360         2370         2380          2390
         *      *      *     *      *      *      *      *
         ATC GAG AAA ACC ATC TCC AAA GCC AAA GGG CAG CCC CGA GAA
         TAG CTC TTT TGG TAG AGG TTT CGG TTT CCC GTC GGG GCT CTT
         Ile Glu Lys Thr Ile Ser Lys Ala Lys Gly Gln Pro Arg Glu>
                                         FC-IgG1                      >

2400           2410         2420          2430
         *      *      *     *      *      *     *      *      *
         CCA CAG GTG TAC ACC CTG CCC CCA TCC CGG GAG GAG ATG ACC
         GGT GTC CAC ATG TGG GAC GGG GGT AGG GCC CTC CTC TAC TGG
         Pro Gln Val Tyr Thr Leu Pro Pro Ser Arg Glu Glu Met Thr>
                                         FC-IgG1                      >

2440         2450          2460          2470
         *      *      *     *      *      *     *      *
         AAG AAC CAG GTC AGC CTG ACC TGC CTG GTC AAA GGC TTC TAT
         TTC TTG GTC CAG TCG GAC TGG ACG GAC CAG TTT CCG AAG ATA
         Lys Asn Gln Val Ser Leu Thr Cys Leu Val Lys Gly Phe Tyr>
                                         FC-IgG1                      >

2480         2490         2500          2510          2520
            *      *      *     *      *     *      *      *      *
          CCC AGC GAC ATC GCC GTG GAG TGG GAG AGC AAT GGG CAG CCG
          GGG TCG CTG TAG CGG CAC CTC ACC CTC TCG TTA CCC GTC GGC
          Pro Ser Asp Ile Ala Val Glu Trp Glu Ser Asn Gly Gln Pro>
                                         FC-IgG1                      >

2530          2540         2550          2560
          *      *      *     *      *      *     *      *
          GAG AAC AAC TAC AAG ACC ACG CCT CCC GTG CTG GAC TCC GAC
          CTC TTG TTG ATG TTC TGG TGC GGA GGG CAC GAC CTG AGG CTG
          Glu Asn Asn Tyr Lys Thr Thr Pro Pro Val Leu Asp Ser Asp>
                                         FC-IgG1                      >
```

Figure 38I

```
        2570              2580              2590              2600
    *       *        *       *        *       *        *       *
  GGC     TCC      TTC     TTC      CTC     TAT      AGC     AAG      CTC     ACC      GTG     GAC      AAG     AGC
  CCG     AGG      AAG     AAG      GAG     ATA      TCG     TTC      GAG     TGG      CAC     CTG      TTC     TCG
  Gly     Ser      Phe     Phe      Leu     Tyr      Ser     Lys      Leu     Thr      Val     Asp      Lys     Ser>
                                    _____FC-IgG1_____>

2610              2620              2630              2640
    *       *        *       *        *       *        *       *        *
  AGG     TGG      CAG     CAG      GGG     AAC      GTC     TTC      TCA     TGC      TCC     GTG      ATG     CAT
  TCC     ACC      GTC     GTC      CCC     TTG      CAG     AAG      AGT     ACG      AGG     CAC      TAC     GTA
  Arg     Trp      Gln     Gln      Gly     Asn      Val     Phe      Ser     Cys      Ser     Val      Met     His>
                                    _____FC-IgG1_____>

2650              2660              2670              2680
    *       *        *       *        *       *        *       *        *
  GAG     GCT      CTG     CAC      AAC     CAC      TAC     ACG      CAG     AAG      AGC     CTC      TCC     CTG
  CTC     CGA      GAC     GTG      TTG     GTG      ATG     TGC      GTC     TTC      TCG     GAG      AGG     GAC
  Glu     Ala      Leu     His      Asn     His      Tyr     Thr      Gln     Lys      Ser     Leu      Ser     Leu>
                                    _____FC-IgG1_____>

2690              2700
    *       *        *
  TCT     CCG      GGT     AAA      TGA
  AGA     GGC      CCA     TTT      ACT
  Ser     Pro      Gly     Lys      ***>
          _____FC-IgG1_____>
```

Figure 39A

```
              10             20             30             40
         *    *    *    *    *    *    *    *    *    *    *    *
ATG GTG TTA CTC AGA CTT ATT TGT TTC ATA GCT CTA CTG ATT
TAC CAC AAT GAG TCT GAA TAA ACA AAG TAT CGA GAT GAC TAA
Met Val Leu Leu Arg Leu Ile Cys Phe Ile Ala Leu Leu Ile>
_____SIGNAL PEPTIDE_____>
_____IL-1RI_____>

50             60             70             80
         *    *    *    *    *    *    *    *    *    *    *    *
TCT TCT CTG GAG GCT GAT AAA TGC AAG GAA CGT GAA GAA AAA
AGA AGA GAC CTC CGA CTA TTT ACG TTC CTT GCA CTT CTT TTT
Ser Ser Leu Glu Ala Asp>
____SIGNAL PEPTIDE_____>
                        Lys Cys Lys Glu Arg Glu Glu Lys>
                        _____IL-1RI_____>

90            100            110            120
         *    *    *    *    *    *    *    *    *    *    *    *
ATA ATT TTA GTG TCA TCT GCA AAT GAA ATT GAT GTT CGT CCC
TAT TAA AAT CAC AGT AGA CGT TTA CTT TAA CTA CAA GCA GGG
Ile Ile Leu Val Ser Ser Ala Asn Glu Ile Asp Val Arg Pro>
_____IL-1RI_____>

130            140            150            160
    *    *    *    *    *    *    *    *    *    *    *    *
TGT CCT CTT AAC CCA AAT GAA CAC AAA GGC ACT ATA ACT TGG
ACA GGA GAA TTG GGT TTA CTT GTG TTT CCG TGA TAT TGA ACC
Cys Pro Leu Asn Pro Asn Glu His Lys Gly Thr Ile Thr Trp>
_____IL-1RI_____>

170           180            190            200           210
    *    *    *    *    *    *    *    *    *    *    *    *
TAT AAG GAT GAC AGC AAG ACA CCT GTA TCT ACA GAA CAA GCC
ATA TTC CTA CTG TCG TTC TGT GGA CAT AGA TGT CTT GTT CGG
Tyr Lys Asp Asp Ser Lys Thr Pro Val Ser Thr Glu Gln Ala>
_____IL-1RI_____>

220            230            240           250
         *    *    *    *    *    *    *    *    *    *    *
TCC AGG ATT CAT CAA CAC AAA GAG AAA CTT TGG TTT GTT CCT
AGG TCC TAA GTA GTT GTG TTT CTC TTT GAA ACC AAA CAA GGA
Ser Arg Ile His Gln His Lys Glu Lys Leu Trp Phe Val Pro>
_____IL-1RI_____>

260            270            280           290
         *    *    *    *    *    *    *    *    *    *    *
GCT AAG GTG GAG GAT TCA GGA CAT TAC TAT TGC GTG GTA AGA
CGA TTC CAC CTC CTA AGT CCT GTA ATG ATA ACG CAC CAT TCT
Ala Lys Val Glu Asp Ser Gly His Tyr Tyr Cys Val Val Arg>
_____IL-1RI_____>
```

Figure 39B

```
         300         310         320         330
    *      *    *      *    *      *    *      *    *
   AAT TCA TCT TAC TGC CTC AGA ATT AAA ATA AGT GCA AAA TTT
   TTA AGT AGA ATG ACG GAG TCT TAA TTT TAT TCA CGT TTT AAA
   Asn Ser Ser Tyr Cys Leu Arg Ile Lys Ile Ser Ala Lys Phe>
   ─────────────────────────────IL-1RI──────────────────────>

340         350         360         370
    *      *    *      *    *      *    *      *
   GTG GAG AAT GAG CCT AAC TTA TGT TAT AAT GCA CAA GCC ATA
   CAC CTC TTA CTC GGA TTG AAT ACA ATA TTA CGT GTT CGG TAT
   Val Glu Asn Glu Pro Asn Leu Cys Tyr Asn Ala Gln Ala Ile>
   ─────────────────────────────IL-1RI──────────────────────>

380         390         400         410         420
    *    *      *    *      *    *      *    *      *    *
   TTT AAG CAG AAA CTA CCC GTT GCA GGA GAC GGA GGA CTT GTG
   AAA TTC GTC TTT GAT GGG CAA CGT CCT CTG CCT CCT GAA CAC
   Phe Lys Gln Lys Leu Pro Val Ala Gly Asp Gly Gly Leu Val>
   ─────────────────────────────IL-1RI──────────────────────>

430         440         450         460
         *      *    *      *    *      *    *      *
   TGC CCT TAT ATG GAG TTT TTT AAA AAT GAA AAT AAT GAG TTA
   ACG GGA ATA TAC CTC AAA AAA TTT TTA CTT TTA TTA CTC AAT
   Cys Pro Tyr Met Glu Phe Phe Lys Asn Glu Asn Asn Glu Leu>
   ─────────────────────────────IL-1RI──────────────────────>

470         480         490         500
         *      *    *      *    *      *    *      *
   CCT AAA TTA CAG TGG TAT AAG GAT TGC AAA CCT CTA CTT CTT
   GGA TTT AAT GTC ACC ATA TTC CTA ACG TTT GGA GAT GAA GAA
   Pro Lys Leu Gln Trp Tyr Lys Asp Cys Lys Pro Leu Leu Leu>
   ─────────────────────────────IL-1RI──────────────────────>

510         520         530         540
    *      *    *      *    *      *    *      *    *
   GAC AAT ATA CAC TTT AGT GGA GTC AAA GAT AGG CTC ATC GTG
   CTG TTA TAT GTG AAA TCA CCT CAG TTT CTA TCC GAG TAG CAC
   Asp Asn Ile His Phe Ser Gly Val Lys Asp Arg Leu Ile Val>
   ─────────────────────────────IL-1RI──────────────────────>

550         560         570         580
    *      *    *      *    *      *    *      *
   ATG AAT GTG GCT GAA AAG CAT AGA GGG AAC TAT ACT TGT CAT
   TAC TTA CAC CGA CTT TTC GTA TCT CCC TTG ATA TGA ACA GTA
   Met Asn Val Ala Glu Lys His Arg Gly Asn Tyr Thr Cys His>
   ─────────────────────────────IL-1RI──────────────────────>

590         600         610         620         630
    *    *      *    *      *    *      *    *      *    *
   GCA TCC TAC ACA TAC TTG GGC AAG CAA TAT CCT ATT ACC CGG
   CGT AGG ATG TGT ATG AAC CCG TTC GTT ATA GGA TAA TGG GCC
   Ala Ser Tyr Thr Tyr Leu Gly Lys Gln Tyr Pro Ile Thr Arg>
   ─────────────────────────────IL-1RI──────────────────────>
```

Figure 39C

```
         640              650              660              670
          *        *       *        *       *        *       *        *
     GTA ATA GAA TTT ATT ACT CTA GAG GAA AAC AAA CCC ACA AGG
     CAT TAT CTT AAA TAA TGA GAT CTC CTT TTG TTT GGG TCT TCC
     Val Ile Glu Phe Ile Thr Leu Glu Glu Asn Lys Pro Thr Arg>
                                  IL-1RI                            >

680              690              700              710
          *        *       *        *       *        *       *        *
     CCT GTG ATT GTG AGC CCA GCT AAT GAG ACA ATG GAA GTA GAC
     GGA CAC TAA CAC TCG GGT CGA TTA CTC TGT TAC CTT CAT CTG
     Pro Val Ile Val Ser Pro Ala Asn Glu Thr Met Glu Val Asp>
                                  IL-1RI                            >

720              730              740              750
          *        *       *        *       *        *       *        *
     TTG GGA TCC CAG ATA CAA TTG ATC TGT AAT GTC ACC GGC CAG
     AAC CCT AGG GTC TAT GTT AAC TAG ACA TTA CAG TGG CCG GTC
     Leu Gly Ser Gln Ile Gln Leu Ile Cys Asn Val Thr Gly Gln>
                                  IL-1RI                            >

760              770              780              790
          *        *       *        *       *        *       *        *
     TTG AGT GAC ATT GCT TAC TGG AAG TGG AAT GGG TCA GTA ATT
     AAC TCA CTG TAA CGA ATG ACC TTC ACC TTA CCC AGT CAT TAA
     Leu Ser Asp Ile Ala Tyr Trp Lys Trp Asn Gly Ser Val Ile>
                                  IL-1RI                            >

800              810              820              830              840
      *        *       *        *       *        *       *        *       *
     GAT GAA GAT GAC CCA GTG CTA GGG GAA GAC TAT TAC AGT GTG
     CTA CTT CTA CTG GGT CAC GAT CCC CTT CTG ATA ATG TCA CAC
     Asp Glu Asp Asp Pro Val Leu Gly Glu Asp Tyr Tyr Ser Val>
                                  IL-1RI                            >

850              860              870              880
           *        *       *        *       *        *       *        *
     GAA AAT CCT GCA AAC AAA AGA AGG AGT ACC CTC ATC ACA GTG
     CTT TTA GGA CGT TTG TTT TCT TCC TCA TGG GAG TAG TGT CAC
     Glu Asn Pro Ala Asn Lys Arg Arg Ser Thr Leu Ile Thr Val>
                                  IL-1RI                            >

890              900              910              920
           *        *       *        *       *        *       *        *
     CTT AAT ATA TCG GAA ATT GAG AGT AGA TTT TAT AAA CAT CCA
     GAA TTA TAT AGC CTT TAA CTC TCA TCT AAA ATA TTT GTA GGT
     Leu Asn Ile Ser Glu Ile Glu Ser Arg Phe Tyr Lys His Pro>
                                  IL-1RI                            >

930              940              950              960
          *        *       *        *       *        *       *        *
     TTT ACC TGT TTT GCC AAG AAT ACA CAT GGT ATA GAT GCA GCA
     AAA TGG ACA AAA CGG TTC TTA TGT GTA CCA TAT CTA CGT CGT
     Phe Thr Cys Phe Ala Lys Asn Thr His Gly Ile Asp Ala Ala>
                                  IL-1RI                            >
```

Figure 39D

```
        970              980              990             1000
         *        *       *        *       *        *       *        *
        TAT ATC CAG TTA ATA TAT CCA GTC ACT AAT TCA GAA CGC TGC
        ATA TAG GTC AAT TAT ATA GGT CAG TGA TTA AGT CTT GCG ACG
        Tyr Ile Gln Leu Ile Tyr Pro Val Thr Asn>
                        IL-1RI                    >
                                                  Ser Glu Arg Cys>
                                                   ___IL-1RAcP____>

1010             1020             1030             1040            1050
      *        *       *        *       *        *       *        *       *
     GAT GAC TGG GGA CTA GAC ACC ATG AGG CAA ATC CAA GTG TTT
     CTA CTG ACC CCT GAT CTG TGG TAC TCC GTT TAG GTT CAC AAA
     Asp Asp Trp Gly Leu Asp Thr Met Arg Gln Ile Gln Val Phe>
     _____IL-1RAcP_____>

1060             1070             1080             1090
                *        *       *        *       *        *       *
              GAA GAT GAG CCA GCT CGC ATC AAG TGC CCA CTC TTT GAA CAC
              CTT CTA CTC GGT CGA GCG TAG TTC ACG GGT GAG AAA CTT GTG
              Glu Asp Glu Pro Ala Arg Ile Lys Cys Pro Leu Phe Glu His>
              _____IL-1RAcP_____>

1100             1110             1120             1130
                *        *       *        *       *        *       *
              TTC TTG AAA TTC AAC TAC AGC ACA GCC CAT TCA GCT GGC CTT
              AAG AAC TTT AAG TTG ATG TCG TGT CGG GTA AGT CGA CCG GAA
              Phe Leu Lys Phe Asn Tyr Ser Thr Ala His Ser Ala Gly Leu>
              _____IL-1RAcP_____>

1140             1150             1160             1170
                *        *       *        *       *        *       *       *
              ACT CTG ATC TGG TAT TGG ACT AGG CAG GAC CGG GAC CTT GAG
              TGA GAC TAG ACC ATA ACC TGA TCC GTC CTG GCC CTG GAA CTC
              Thr Leu Ile Trp Tyr Trp Thr Arg Gln Asp Arg Asp Leu Glu>
              _____IL-1RAcP_____>

1180             1190             1200             1210
                *        *       *        *       *        *       *
              GAG CCA ATT AAC TTC CGC CTC CCC GAG AAC CGC ATT AGT AAG
              CTC GGT TAA TTG AAG GCG GAG GGG CTC TTG GCG TAA TCA TTC
              Glu Pro Ile Asn Phe Arg Leu Pro Glu Asn Arg Ile Ser Lys>
              _____IL-1RAcP_____>

1220             1230             1240             1250            1260
            *        *       *        *       *        *       *        *       *
          GAG AAA GAT GTG CTG TGG TTC CGG CCC ACT CTC CTC AAT GAC
          CTC TTT CTA CAC GAC ACC AAG GCC GGG TGA GAG GAG TTA CTG
          Glu Lys Asp Val Leu Trp Phe Arg Pro Thr Leu Leu Asn Asp>
          _____IL-1RAcP_____>
```

Figure 39E

```
            1270            1280            1290            1300
             *       *       *       *       *       *       *       *
        ACT GGC AAC TAT ACC TGC ATG TTA AGG AAC ACT ACA TAT TGC
        TGA CCG TTG ATA TGG ACG TAC AAT TCC TTG TGA TGT ATA ACG
        Thr Gly Asn Tyr Thr Cys Met Leu Arg Asn Thr Thr Tyr Cys>
                                    IL-1RAcP                        >

1310            1320            1330            1340
             *       *       *       *       *       *       *       *
        AGC AAA GTT GCA TTT CCC TTG GAA GTT GTT CAA AAA GAC AGC
        TCG TTT CAA CGT AAA GGG AAC CTT CAA CAA GTT TTT CTG TCG
        Ser Lys Val Ala Phe Pro Leu Glu Val Val Gln Lys Asp Ser>
                                    IL-1RAcP                        >

1350            1360            1370            1380
         *       *       *       *       *       *       *       *       *
        TGT TTC AAT TCC CCC ATG AAA CTC CCA GTG CAT AAA CTG TAT
        ACA AAG TTA AGG GGG TAC TTT GAG GGT CAC GTA TTT GAC ATA
        Cys Phe Asn Ser Pro Met Lys Leu Pro Val His Lys Leu Tyr>
                                    IL-1RAcP                        >

1390            1400            1410            1420
         *       *       *       *       *       *       *       *
        ATA GAA TAT GGC ATT CAG AGG ATC ACT TGT CCA AAT GTA GAT
        TAT CTT ATA CCG TAA GTC TCC TAG TGA ACA GGT TTA CAT CTA
        Ile Glu Tyr Gly Ile Gln Arg Ile Thr Cys Pro Asn Val Asp>
                                    IL-1RAcP                        >

1430            1440            1450            1460            1470
         *       *       *       *       *       *       *       *       *
        GGA TAT TTT CCT TCC AGT GTC AAA CCG ACT ATC ACT TGG TAT
        CCT ATA AAA GGA AGG TCA CAG TTT GGC TGA TAG TGA ACC ATA
        Gly Tyr Phe Pro Ser Ser Val Lys Pro Thr Ile Thr Trp Tyr>
                                    IL-1RAcP                        >

1480            1490            1500            1510
             *       *       *       *       *       *       *       *
        ATG GGC TGT TAT AAA ATA CAG AAT TTT AAT AAT GTA ATA CCC
        TAC CCG ACA ATA TTT TAT GTC TTA AAA TTA TTA CAT TAT GGG
        Met Gly Cys Tyr Lys Ile Gln Asn Phe Asn Asn Val Ile Pro>
                                    IL-1RAcP                        >

1520            1530            1540            1550
         *       *       *       *       *       *       *       *
        GAA GGT ATG AAC TTG AGT TTC CTC ATT GCC TTA ATT TCA AAT
        CTT CCA TAC TTG AAC TCA AAG GAG TAA CGG AAT TAA AGT TTA
        Glu Gly Met Asn Leu Ser Phe Leu Ile Ala Leu Ile Ser Asn>
                                    IL-1RAcP                        >

1560            1570            1580            1590
         *       *       *       *       *       *       *       *       *
        AAT GGA AAT TAC ACA TGT GTT GTT ACA TAT CCA GAA AAT GGA
        TTA CCT TTA ATG TGT ACA CAA CAA TGT ATA GGT CTT TTA CCT
        Asn Gly Asn Tyr Thr Cys Val Val Thr Tyr Pro Glu Asn Gly>
                                    IL-1RAcP                        >
```

Figure 39F

```
        1600          1610          1620          1630
         *     *      *      *      *      *      *      *
       CGT   ACG    TTT    CAT    CTC    ACC    AGG    ACT    CTG   ACT   GTA   AAG   GTA   GTA
       GCA   TGC    AAA    GTA    GAG    TGG    TCC    TGA    GAC   TGA   CAT   TTC   CAT   CAT
       Arg   Thr    Phe    His    Leu    Thr    Arg    Thr    Leu   Thr   Val   Lys   Val   Val>
       _____IL-1RAcP_____>

1640          1650          1660          1670          1680
    *     *      *      *      *      *      *      *      *
   GGC   TCT    CCA    AAA    AAT    GCA    GTG    CCC    CCT   GTG   ATC   CAT   TCA   CCT
   CCG   AGA    GGT    TTT    TTA    CGT    CAC    GGG    GGA   CAC   TAG   GTA   AGT   GGA
   Gly   Ser    Pro    Lys    Asn    Ala    Val    Pro    Pro   Val   Ile   His   Ser   Pro>
   _____IL-1RAcP_____>

1690          1700          1710          1720
               *      *      *      *      *      *      *      *
             AAT    GAT    CAT    GTG    GTC    TAT    GAG    AAA    GAA   CCA   GGA   GAG   GAG   CTA
             TTA    CTA    GTA    CAC    CAG    ATA    CTC    TTT    CTT   GGT   CCT   CTC   CTC   GAT
             Asn    Asp    His    Val    Val    Tyr    Glu    Lys    Glu   Pro   Gly   Glu   Glu   Leu>
             _____IL-1RAcP_____>

1730          1740          1750          1760
               *      *      *      *      *      *      *      *
             CTC    ATT    CCC    TGT    ACG    GTC    TAT    TTT    AGT   TTT   CTG   ATG   GAT   TCT
             GAG    TAA    GGG    ACA    TGC    CAG    ATA    AAA    TCA   AAA   GAC   TAC   CTA   AGA
             Leu    Ile    Pro    Cys    Thr    Val    Tyr    Phe    Ser   Phe   Leu   Met   Asp   Ser>
             _____IL-1RAcP_____>

1770          1780          1790          1800
               *      *      *      *      *      *      *      *      *
             CGC    AAT    GAG    GTT    TGG    TGG    ACC    ATT    GAT   GGA   AAA   AAA   CCT   GAT
             GCG    TTA    CTC    CAA    ACC    ACC    TGG    TAA    CTA   CCT   TTT   TTT   GGA   CTA
             Arg    Asn    Glu    Val    Trp    Trp    Thr    Ile    Asp   Gly   Lys   Lys   Pro   Asp>
             _____IL-1RAcP_____>

1810          1820          1830          1840
         *     *      *      *      *      *      *      *
       GAC   ATC    ACT    ATT    GAT    GTC    ACC    ATT    AAC   GAA   AGT   ATA   AGT   CAT
       CTG   TAG    TGA    TAA    CTA    CAG    TGG    TAA    TTG   CTT   TCA   TAT   TCA   GTA
       Asp   Ile    Thr    Ile    Asp    Val    Thr    Ile    Asn   Glu   Ser   Ile   Ser   His>
       _____IL-1RAcP_____>

1850          1860          1870          1880          1890
    *     *      *      *      *      *      *      *      *
   AGT   AGA    ACA    GAA    GAT    GAA    ACA    AGA    ACT   CAG   ATT   TTG   AGC   ATC
   TCA   TCT    TGT    CTT    CTA    CTT    TGT    TCT    TGA   GTC   TAA   AAC   TCG   TAG
   Ser   Arg    Thr    Glu    Asp    Glu    Thr    Arg    Thr   Gln   Ile   Leu   Ser   Ile>
   _____IL-1RAcP_____>

1900          1910          1920          1930
               *      *      *      *      *      *      *      *
             AAG    AAA    GTT    ACC    TCT    GAG    GAT    CTC    AAG   CGC   AGC   TAT   GTC   TGT
             TTC    TTT    CAA    TGG    AGA    CTC    CTA    GAG    TTC   GCG   TCG   ATA   CAG   ACA
             Lys    Lys    Val    Thr    Ser    Glu    Asp    Leu    Lys   Arg   Ser   Tyr   Val   Cys>
             _____IL-1RAcP_____>
```

Figure 39G

```
            1940           1950           1960           1970
     *        *       *      *      *      *       *       *
     CAT GCT AGA AGT GCC AAA GGC GAA GTT GCC AAA GCA GCC AAG
     GTA CGA TCT TCA CGG TTT CCG CTT CAA CGG TTT CGT CGG TTC
     His Ala Arg Ser Ala Lys Gly Glu Val Ala Lys Ala Ala Lys>
                         _____IL-1RAcP_____>

1980           1990           2000           2010
     *        *       *      *      *      *       *       *      *
     GTG AAG CAG AAA GTG CCA GCT CCA AGA TAC ACA GTG GAA TCC
     CAC TTC GTC TTT CAC GGT CGA GGT TCT ATG TGT CAC CTT AGG
     Val Lys Gln Lys Val Pro Ala Pro Arg Tyr Thr Val Glu>
                         _____IL-1RAcP_____>
                                                           Ser>
                                                           ___>

2020           2030           2040           2050
     *        *       *      *      *      *       *       *
     GGA GAG TCC AAA TAC GGT CCG CCA TGC CCA TCA TGC CCA GCA
     CCT CTC AGG TTT ATG CCA GGC GGT ACG GGT AGT ACG GGT CGT
         Glu Ser Lys Tyr Gly Pro Pro Cys Pro Ser Cys Pro Ala>
                         _____FC-IgG4_____>
     Gly>
     ___>

2060           2070           2080           2090           2100
     *       *      *      *      *       *       *      *       *
     CCT GAG TTC CTG GGG GGA CCA TCA GTC TTC CTG TTC CCC CCA
     GGA CTC AAG GAC CCC CCT GGT AGT CAG AAG GAC AAG GGG GGT
     Pro Glu Phe Leu Gly Gly Pro Ser Val Phe Leu Phe Pro Pro>
                         _____FC-IgG4_____>

2110           2120           2130           2140
     *        *       *      *      *      *       *       *
     AAA CCC AAG GAC ACT CTC ATG ATC TCC CGG ACC CCT GAG GTC
     TTT GGG TTC CTG TGA GAG TAC TAG AGG GCC TGG GGA CTC CAG
     Lys Pro Lys Asp Thr Leu Met Ile Ser Arg Thr Pro Glu Val>
                         _____FC-IgG4_____>

2150           2160           2170           2180
     *        *       *      *      *      *       *       *
     ACG TGC GTG GTG GTG GAC GTG AGC CAG GAA GAC CCC GAG GTC
     TGC ACG CAC CAC CAC CTG CAC TCG GTC CTT CTG GGG CTC CAG
     Thr Cys Val Val Val Asp Val Ser Gln Glu Asp Pro Glu Val>
                         _____FC-IgG4_____>

2190           2200           2210           2220
     *        *       *      *      *      *       *       *
     CAG TTC AAC TGG TAC GTG GAT GGC GTG GAG GTG CAT AAT GCC
     GTC AAG TTG ACC ATG CAC CTA CCG CAC CTC CAC GTA TTA CGG
     Gln Phe Asn Trp Tyr Val Asp Gly Val Glu Val His Asn Ala>
                         _____FC-IgG4_____>
```

Figure 39H

```
         2230           2240          2250            2260
           *      *       *      *      *      *       *      *
         AAG    ACA     AAG    CCG    CGG    GAG     GAG    CAG    TTC    AAC    AGC    ACG    TAC    CGT
         TTC    TGT     TTC    GGC    GCC    CTC     CTC    GTC    AAG    TTG    TCG    TGC    ATG    GCA
         Lys    Thr     Lys    Pro    Arg    Glu     Glu    Gln    Phe    Asn    Ser    Thr    Tyr    Arg>
                                              FC-IgG4                                                  >

2270            2280          2290           2300          2310
    *      *       *      *      *      *       *      *      *      *
   GTG    GTC     AGC    GTC    CTC    ACC     GTC    CTG    CAC    CAG    GAC    TGG    CTG    AAC
   CAC    CAG     TCG    CAG    GAG    TGG     CAG    GAC    GTG    GTC    CTG    ACC    GAC    TTG
   Val    Val     Ser    Val    Leu    Thr     Val    Leu    His    Gln    Asp    Trp    Leu    Asn>
                                              FC-IgG4                                                  >

2320           2330          2340          2350
           *      *       *      *      *      *       *      *
         GGC    AAG     GAG    TAC    AAG    TGC     AAG    GTC    TCC    AAC    AAA    GGC    CTC    CCG
         CCG    TTC     CTC    ATG    TTC    ACG     TTC    CAG    AGG    TTG    TTT    CCG    GAG    GGC
         Gly    Lys     Glu    Tyr    Lys    Cys     Lys    Val    Ser    Asn    Lys    Gly    Leu    Pro>
                                              FC-IgG4                                                  >

2360           2370          2380          2390
           *      *       *      *      *      *       *      *
         TCC    TCC     ATC    GAG    AAA    ACC     ATC    TCC    AAA    GCC    AAA    GGC    CAG    CCC
         AGG    AGG     TAC    CTC    TTT    TGG     TAG    AGG    TTT    CGG    TTT    CCG    GTC    GGG
         Ser    Ser     Ile    Glu    Lys    Thr     Ile    Ser    Lys    Ala    Lys    Gly    Gln    Pro>
                                              FC-IgG4                                                  >

2400           2410          2420          2430
           *      *       *      *      *      *       *      *
         CGA    GAG     CCA    CAG    GTG    TAC     ACC    CTG    CCC    CCA    TCC    CAG    GAG    GAG
         GCT    CTC     GGT    GTC    CAC    ATG     TGG    GAC    GGG    GGT    AGG    GTC    CTC    CTC
         Arg    Glu     Pro    Gln    Val    Tyr     Thr    Leu    Pro    Pro    Ser    Gln    Glu    Glu>
                                              FC-IgG4                                                  >

2440           2450          2460           2470
          *      *       *      *      *      *       *      *
        ATG    ACC     AAG    AAC    CAG    GTC     AGC    CTG    ACC    TGC    CTG    GTC    AAA    GGC
        TAC    TGG     TTC    TTG    GTC    CAG     TCG    GAC    TGG    ACG    GAC    CAG    TTT    CCG
        Met    Thr     Lys    Asn    Gln    Val     Ser    Leu    Thr    Cys    Leu    Val    Lys    Gly>
                                              FC-IgG4                                                  >

2480            2490          2500           2510           2520
    *      *       *      *      *      *       *      *      *      *
   TTC    TAC     CCC    AGC    GAC    ATC     GCC    GTG    GAG    TGG    GAG    AGC    AAT    GGG
   AAG    ATG     GGG    TCG    CTG    TAG     CGG    CAC    CTC    ACC    CTC    TCG    TTA    CCC
   Phe    Tyr     Pro    Ser    Asp    Ile     Ala    Val    Glu    Trp    Glu    Ser    Asn    Gly>
                                              FC-IgG4                                                  >

2530           2540          2550          2560
           *      *       *      *      *      *       *      *
         CAG    CCG     GAG    AAC    AAC    TAC     AAG    ACC    ACG    CCT    CCC    GTG    CTG    GAC
         GTC    GGC     CTC    TTG    TTG    ATG     TTC    TGG    TGC    GGA    GGG    CAC    GAC    CTG
         Gln    Pro     Glu    Asn    Asn    Tyr     Lys    Thr    Thr    Pro    Pro    Val    Leu    Asp>
                                              FC-IgG4                                                  >
```

Figure 39I

```
          2570              2580              2590              2600
   *        *        *        *        *        *        *        *
  TCC      GAC      GGC      TCC      TTC      TTC      CTC      TAC      AGC      AGG      CTA      ACC      GTG      GAC
  AGG      CTG      CCG      AGG      AAG      AAG      GAG      ATG      TCG      TCC      GAT      TGG      CAC      CTG
  Ser      Asp      Gly      Ser      Phe      Phe      Leu      Tyr      Ser      Arg      Leu      Thr      Val      Asp>
  _____FC-IgG4_____>

2610              2620              2630              2640
   *        *        *        *        *        *        *        *        *
  AAG      AGC      AGG      TGG      CAG      GAG      GGG      AAT      GTC      TTC      TCA      TGC      TCC      GTG
  TTC      TCG      TCC      ACC      GTC      CTC      CCC      TTA      CAG      AAG      AGT      ACG      AGG      CAC
  Lys      Ser      Arg      Trp      Gln      Glu      Gly      Asn      Val      Phe      Ser      Cys      Ser      Val>
  _____FC-IgG4_____>

2650              2660              2670              2680
   *        *        *        *        *        *        *        *
  ATG      CAT      GAG      GCT      CTG      CAC      AAC      CAC      TAC      ACA      CAG      AAG      AGC      CTC
  TAC      GTA      CTC      CGA      GAC      GTG      TTG      GTG      ATG      TGT      GTC      TTC      TCG      GAG
  Met      His      Glu      Ala      Leu      His      Asn      His      Tyr      Thr      Gln      Lys      Ser      Leu>
  _____FC-IgG4_____>

2690              2700
   *        *        *        *
  TCC      CTG      TCT      CTG      GGT      AAA      TGA
  AGG      GAC      AGA      GAC      CCA      TTT      ACT
  Ser      Leu      Ser      Leu      Gly      Lys      ***>
  _____FC-IgG4_____>
```

Figure 40A

```
              10             20              30              40
       *       *      *       *      *       *       *       *
ATG   GTG   TTA   CTC   AGA   CTT   ATT   TGT   TTC   ATA   GCT   CTA   CTG   ATT
TAC   CAC   AAT   GAG   TCT   GAA   TAA   ACA   AAG   TAT   CGA   GAT   GAC   TAA
Met   Val   Leu   Leu   Arg   Leu   Ile   Cys   Phe   Ile   Ala   Leu   Leu   Ile>
                      ____SIGNAL PEPTIDE_____>
                      _____IL-1RI_____>

50             60              70              80
       *       *      *       *       *       *       *       *
TCT   TCT   CTG   GAG   GCT   GAT   AAA   TGC   AAG   GAA   CGT   GAA   GAA   AAA
AGA   AGA   GAC   CTC   CGA   CTA   TTT   ACG   TTC   CTT   GCA   CTT   CTT   TTT
Ser   Ser   Leu   Glu   Ala   Asp>
_____SIGNAL PEPTIDE_____>
                            Lys   Cys   Lys   Glu   Arg   Glu   Glu   Lys>
                            ___IL-1RI_____>

90            100             110             120
       *       *      *       *       *       *       *       *       *
ATA   ATT   TTA   GTG   TCA   TCT   GCA   AAT   GAA   ATT   GAT   GTT   CGT   CCC
TAT   TAA   AAT   CAC   AGT   AGA   CGT   TTA   CTT   TAA   CTA   CAA   GCA   GGG
Ile   Ile   Leu   Val   Ser   Ser   Ala   Asn   Glu   Ile   Asp   Val   Arg   Pro>
                                  _____IL-1RI_____>

130            140              150              160
       *       *      *       *       *       *       *       *
TGT   CCT   CTT   AAC   CCA   AAT   GAA   CAC   AAA   GGC   ACT   ATA   ACT   TGG
ACA   GGA   GAA   TTG   GGT   TTA   CTT   GTG   TTT   CCG   TGA   TAT   TGA   ACC
Cys   Pro   Leu   Asn   Pro   Asn   Glu   His   Lys   Gly   Thr   Ile   Thr   Trp>
                             ___IL-1RI_____>

170             180            190             200             210
   *       *       *      *       *       *       *       *       *
TAT   AAG   GAT   GAC   AGC   AAG   ACA   CCT   GTA   TCT   ACA   GAA   CAA   GCC
ATA   TTC   CTA   CTG   TCG   TTC   TGT   GGA   CAT   AGA   TGT   CTT   GTT   CGG
Tyr   Lys   Asp   Asp   Ser   Lys   Thr   Pro   Val   Ser   Thr   Glu   Gln   Ala>
                              ___IL-1RI_____>

220            230              240              250
       *       *      *       *       *       *       *       *
TCC   AGG   ATT   CAT   CAA   CAC   AAA   GAG   AAA   CTT   TGG   TTT   GTT   CCT
AGG   TCC   TAA   GTA   GTT   GTG   TTT   CTC   TTT   GAA   ACC   AAA   CAA   GGA
Ser   Arg   Ile   His   Gln   His   Lys   Glu   Lys   Leu   Trp   Phe   Val   Pro>
                              ___IL-1RI_____>

260            270              280              290
       *       *      *       *       *       *       *       *
GCT   AAG   GTG   GAG   GAT   TCA   GGA   CAT   TAC   TAT   TGC   GTG   GTA   AGA
CGA   TTC   CAC   CTC   CTA   AGT   CCT   GTA   ATG   ATA   ACG   CAC   CAT   TCT
Ala   Lys   Val   Glu   Asp   Ser   Gly   His   Tyr   Tyr   Cys   Val   Val   Arg>
                              ___IL-1RI_____>
```

Figure 40B

```
          300            310           320              330
    *      *       *      *      *      *        *       *      *
   AAT TCA TCT TAC TGC CTC AGA ATT AAA ATA AGT GCA AAA TTT
   TTA AGT AGA ATG ACG GAG TCT TAA TTT TAT TCA CGT TTT AAA
   Asn Ser Ser Tyr Cys Leu Arg Ile Lys Ile Ser Ala Lys Phe>
   _____IL-1RI_____>

340            350           360           370
       *       *      *       *      *      *     *       *
      GTG GAG AAT GAG CCT AAC TTA TGT TAT AAT GCA CAA GCC ATA
      CAC CTC TTA CTC GGA TTG AAT ACA ATA TTA CGT GTT CGG TAT
      Val Glu Asn Glu Pro Asn Leu Cys Tyr Asn Ala Gln Ala Ile>
      _____IL-1RI_____>

380           390           400           410            420
    *      *      *      *       *      *      *      *      *
   TTT AAG CAG AAA CTA CCC GTT GCA GGA GAC GGA GGA CTT GTG
   AAA TTC GTC TTT GAT GGG CAA CGT CCT CTG CCT CCT GAA CAC
   Phe Lys Gln Lys Leu Pro Val Ala Gly Asp Gly Gly Leu Val>
   _____IL-1RI_____>

430           440           450           460
       *      *      *      *      *      *      *      *
      TGC CCT TAT ATG GAG TTT TTT AAA AAT GAA AAT AAT GAG TTA
      ACG GGA ATA TAC CTC AAA AAA TTT TTA CTT TTA TTA CTC AAT
      Cys Pro Tyr Met Glu Phe Phe Lys Asn Glu Asn Asn Glu Leu>
      _____IL-1RI_____>

470           480            490           500
       *      *      *      *      *      *      *      *
      CCT AAA TTA CAG TGG TAT AAG GAT TGC AAA CCT CTA CTT CTT
      GGA TTT AAT GTC ACC ATA TTC CTA ACG TTT GGA GAT GAA GAA
      Pro Lys Leu Gln Trp Tyr Lys Asp Cys Lys Pro Leu Leu Leu>
      _____IL-1RI_____>

510           520           530           540
    *      *      *      *      *      *      *      *      *
   GAC AAT ATA CAC TTT AGT GGA GTC AAA GAT AGG CTC ATC GTG
   CTG TTA TAT GTG AAA TCA CCT CAG TTT CTA TCC GAG TAG CAC
   Asp Asn Ile His Phe Ser Gly Val Lys Asp Arg Leu Ile Val>
   _____IL-1RI_____>

550           560           570           580
    *      *       *      *       *      *      *      *
   ATG AAT GTG GCT GAA AAG CAT AGA GGG AAC TAT ACT TGT CAT
   TAC TTA CAC CGA CTT TTC GTA TCT CCC TTG ATA TGA ACA GTA
   Met Asn Val Ala Glu Lys His Arg Gly Asn Tyr Thr Cys His>
   _____IL-1RI_____>

590           600           610           620            630
    *      *      *      *       *      *      *      *      *
   GCA TCC TAC ACA TAC TTG GGC AAG CAA TAT CCT ATT ACC CGG
   CGT AGG ATG TGT ATG AAC CCG TTC GTT ATA GGA TAA TGG GCC
   Ala Ser Tyr Thr Tyr Leu Gly Lys Gln Tyr Pro Ile Thr Arg>
   _____IL-1RI_____>
```

Figure 40C

```
          640           650          660          670
           *             *            *            *
    *          *             *           *           *
GTA ATA GAA TTT ATT ACT CTA GAG GAA AAC AAA CCC ACA AGG
CAT TAT CTT AAA TAA TGA GAT CTC CTT TTG TTT GGG TGT TCC
Val Ile Glu Phe Ile Thr Leu Glu Glu Asn Lys Pro Thr Arg>
                         IL-1RI                          >

680           690          700          710
           *             *            *            *
    *          *             *           *           *
CCT GTG ATT GTG AGC CCA GCT AAT GAG ACA ATG GAA GTA GAC
GGA CAC TAA CAC TCG GGT CGA TTA CTC TGT TAC CTT CAT CTG
Pro Val Ile Val Ser Pro Ala Asn Glu Thr Met Glu Val Asp>
                         IL-1RI                          >

720           730          740          750
           *             *            *            *
    *          *             *           *           *
TTG GGA TCC CAG ATA CAA TTG ATC TGT AAT GTC ACC GGC CAG
AAC CCT AGG GTC TAT GTT AAC TAG ACA TTA CAG TGG CCG GTC
Leu Gly Ser Gln Ile Gln Leu Ile Cys Asn Val Thr Gly Gln>
                         IL-1RI                          >

760          770          780          790
    *            *            *            *
         *            *            *           *
TTG AGT GAC ATT GCT TAC TGG AAG TGG AAT GGG TCA GTA ATT
AAC TCA CTG TAA CGA ATG ACC TTC ACC TTA CCC AGT CAT TAA
Leu Ser Asp Ile Ala Tyr Trp Lys Trp Asn Gly Ser Val Ile>
                         IL-1RI                          >

800          810          820          830          840
  *            *            *            *            *
       *            *            *            *
GAT GAA GAT GAC CCA GTG CTA GGG GAA GAC TAT TAC AGT GTG
CTA CTT CTA CTG GGT CAC GAT CCC CTT CTG ATA ATG TCA CAC
Asp Glu Asp Asp Pro Val Leu Gly Glu Asp Tyr Tyr Ser Val>
                         IL-1RI                          >

850          860          870          880
           *     *      *            *            *
    *                        *            *
GAA AAT CCT GCA AAC AAA AGA AGG AGT ACC CTC ATC ACA GTG
CTT TTA GGA CGT TTG TTT TCT TCC TCA TGG GAG TAG TGT CAC
Glu Asn Pro Ala Asn Lys Arg Arg Ser Thr Leu Ile Thr Val>
                         IL-1RI                          >

890          900          910          920
           *            *            *            *
    *           *            *            *
CTT AAT ATA TCG GAA ATT GAG AGT AGA TTT TAT AAA CAT CCA
GAA TTA TAT AGC CTT TAA CTC TCA TCT AAA ATA TTT GTA GGT
Leu Asn Ile Ser Glu Ile Glu Ser Arg Phe Tyr Lys His Pro>
                         IL-1RI                          >

930          940          950          960
           *            *            *            *
    *           *      *     *            *            *
TTT ACC TGT TTT GCC AAG AAT ACA CAT GGT ATA GAT GCA GCA
AAA TGG ACA AAA CGG TTC TTA TGT GTA CCA TAT CTA CGT CGT
Phe Thr Cys Phe Ala Lys Asn Thr His Gly Ile Asp Ala Ala>
                         IL-1RI                          >
```

Figure 40D

```
      970         980         990        1000
       *     *     *     *     *     *     *     *
TAT ATC CAG TTA ATA TAT CCA GTC ACT AAT TCA GAA CGC TGC
ATA TAG GTC AAT TAT ATA GGT CAG TGA TTA AGT CTT GCG ACG
Tyr Ile Gln Leu Ile Tyr Pro Val Thr Asn>
               IL-1RI                 >
                                    Ser Glu Arg Cys>
                                     IL-1RAcP    >

1010        1020        1030        1040        1050
   *     *     *     *     *     *     *     *     *
GAT GAC TGG GGA CTA GAC ACC ATG AGG CAA ATC CAA GTG TTT
CTA CTG ACC CCT GAT CTG TGG TAC TCC GTT TAG GTT CAC AAA
Asp Asp Trp Gly Leu Asp Thr Met Arg Gln Ile Gln Val Phe>
                         IL-1RAcP                      >

1060        1070        1080        1090
       *     *     *     *     *     *     *     *
GAA GAT GAG CCA GCT CGC ATC AAG TGC CCA CTC TTT GAA CAC
CTT CTA CTC GGT CGA GCG TAG TTC ACG GGT GAG AAA CTT GTG
Glu Asp Glu Pro Ala Arg Ile Lys Cys Pro Leu Phe Glu His>
                         IL-1RAcP                      >

1100        1110        1120        1130
   *     *     *     *     *     *     *     *
TTC TTG AAA TTC AAC TAC AGC ACA GCC CAT TCA GCT GGC CTT
AAG AAC TTT AAG TTG ATG TCG TGT CGG GTA AGT CGA CCG GAA
Phe Leu Lys Phe Asn Tyr Ser Thr Ala His Ser Ala Gly Leu>
                         IL-1RAcP                      >

1140        1150        1160        1170
       *     *     *     *     *     *     *     *     *
ACT CTG ATC TGG TAT TGG ACT AGG CAG GAC CGG GAC CTT GAG
TGA GAC TAG ACC ATA ACC TGA TCC GTC CTG GCC CTG GAA CTC
Thr Leu Ile Trp Tyr Trp Thr Arg Gln Asp Arg Asp Leu Glu>
                         IL-1RAcP                      >

1180        1190        1200        1210
   *     *     *     *     *     *     *     *
GAG CCA ATT AAC TTC CGC CTC CCC GAG AAC CGC ATT AGT AAG
CTC GGT TAA TTG AAG GCG GAG GGG CTC TTG GCG TAA TCA TTC
Glu Pro Ile Asn Phe Arg Leu Pro Glu Asn Arg Ile Ser Lys>
                         IL-1RAcP                      >

1220        1230        1240        1250        1260
   *     *     *     *     *     *     *     *     *
GAG AAA GAT GTG CTG TGG TTC CGG CCC ACT CTC CTC AAT GAC
CTC TTT CTA CAC GAC ACC AAG GCC GGG TGA GAG GAG TTA CTG
Glu Lys Asp Val Leu Trp Phe Arg Pro Thr Leu Leu Asn Asp>
                         IL-1RAcP                      >
```

Figure 40E

```
         1270          1280          1290          1300
          *             *             *             *
ACT  GGC  AAC  TAT  ACC  TGC  ATG  TTA  AGG  AAC  ACT  ACA  TAT  TGC
TGA  CCG  TTG  ATA  TGG  ACG  TAC  AAT  TCC  TTG  TGA  TGT  ATA  ACG
Thr  Gly  Asn  Tyr  Thr  Cys  Met  Leu  Arg  Asn  Thr  Thr  Tyr  Cys>
                         _____IL-1RAcP_____>

1310          1320          1330          1340
          *             *             *             *
AGC  AAA  GTT  GCA  TTT  CCC  TTG  GAA  GTT  GTT  CAA  AAA  GAC  AGC
TCG  TTT  CAA  CGT  AAA  GGG  AAC  CTT  CAA  CAA  GTT  TTT  CTG  TCG
Ser  Lys  Val  Ala  Phe  Pro  Leu  Glu  Val  Val  Gln  Lys  Asp  Ser>
                         _____IL-1RAcP_____>

1350          1360          1370          1380
          *             *             *             *
TGT  TTC  AAT  TCC  CCC  ATG  AAA  CTC  CCA  GTG  CAT  AAA  CTG  TAT
ACA  AAG  TTA  AGG  GGG  TAC  TTT  GAG  GGT  CAC  GTA  TTT  GAC  ATA
Cys  Phe  Asn  Ser  Pro  Met  Lys  Leu  Pro  Val  His  Lys  Leu  Tyr>
                         _____IL-1RAcP_____>

1390          1400          1410          1420
          *             *             *             *
ATA  GAA  TAT  GGC  ATT  CAG  AGG  ATC  ACT  TGT  CCA  AAT  GTA  GAT
TAT  CTT  ATA  CCG  TAA  GTC  TCC  TAG  TGA  ACA  GGT  TTA  CAT  CTA
Ile  Glu  Tyr  Gly  Ile  Gln  Arg  Ile  Thr  Cys  Pro  Asn  Val  Asp>
                         _____IL-1RAcP_____>

1430          1440          1450          1460          1470
    *             *             *             *             *
GGA  TAT  TTT  CCT  TCC  AGT  GTC  AAA  CCG  ACT  ATC  ACT  TGG  TAT
CCT  ATA  AAA  GGA  AGG  TCA  CAG  TTT  GGC  TGA  TAG  TGA  ACC  ATA
Gly  Tyr  Phe  Pro  Ser  Ser  Val  Lys  Pro  Thr  Ile  Thr  Trp  Tyr>
                         _____IL-1RAcP_____>

1480          1490          1500          1510
          *             *             *             *
ATG  GGC  TGT  TAT  AAA  ATA  CAG  AAT  TTT  AAT  AAT  GTA  ATA  CCC
TAC  CCG  ACA  ATA  TTT  TAT  GTC  TTA  AAA  TTA  TTA  CAT  TAT  GGG
Met  Gly  Cys  Tyr  Lys  Ile  Gln  Asn  Phe  Asn  Asn  Val  Ile  Pro>
                         _____IL-1RAcP_____>

1520          1530          1540          1550
          *             *             *             *
GAA  GGT  ATG  AAC  TTG  AGT  TTC  CTC  ATT  GCC  TTA  ATT  TCA  AAT
CTT  CCA  TAC  TTG  AAC  TCA  AAG  GAG  TAA  CGG  AAT  TAA  AGT  TTA
Glu  Gly  Met  Asn  Leu  Ser  Phe  Leu  Ile  Ala  Leu  Ile  Ser  Asn>
                         _____IL-1RAcP_____>

1560          1570          1580          1590
          *             *             *             *
AAT  GGA  AAT  TAC  ACA  TGT  GTT  GTT  ACA  TAT  CCA  GAA  AAT  GGA
TTA  CCT  TTA  ATG  TGT  ACA  CAA  CAA  TGT  ATA  GGT  CTT  TTA  CCT
Asn  Gly  Asn  Tyr  Thr  Cys  Val  Val  Thr  Tyr  Pro  Glu  Asn  Gly>
                         _____IL-1RAcP_____>
```

Figure 40F

```
      1600           1610          1620          1630
        *       *      *       *      *       *      *       *
      CGT ACG TTT CAT CTC ACC AGG ACT CTG ACT GTA AAG GTA GTA
      GCA TGC AAA GTA GAG TGG TCC TGA GAC TGA CAT TTC CAT CAT
      Arg Thr Phe His Leu Thr Arg Thr Leu Thr Val Lys Val Val>
      _____IL-1RAcP_____>

1640          1650          1660          1670          1680
     *       *      *       *      *       *      *       *      *
   GGC TCT CCA AAA AAT GCA GTG CCC CCT GTG ATC CAT TCA CCT
   CCG AGA GGT TTT TTA CGT CAC GGG GGA CAC TAG GTA AGT GGA
   Gly Ser Pro Lys Asn Ala Val Pro Pro Val Ile His Ser Pro>
   _____IL-1RAcP_____>

1690          1700          1710          1720
            *       *      *      *      *       *       *       *
       AAT GAT CAT GTG GTC TAT GAG AAA GAA CCA GGA GAG GAG CTA
       TTA CTA GTA CAC CAG ATA CTC TTT CTT GGT CCT CTC CTC GAT
       Asn Asp His Val Val Tyr Glu Lys Glu Pro Gly Glu Glu Leu>
       _____IL-1RAcP_____>

1730          1740          1750          1760
               *      *       *      *      *      *      *       *
         CTC ATT CCC TGT ACG GTC TAT TTT AGT TTT CTG ATG GAT TCT
         GAG TAA GGG ACA TGC CAG ATA AAA TCA AAA GAC TAC CTA AGA
         Leu Ile Pro Cys Thr Val Tyr Phe Ser Phe Leu Met Asp Ser>
         _____IL-1RAcP_____>

1770          1780          1790          1800
        *      *       *      *      *       *      *      *       *
      CGC AAT GAG GTT TGG TGG ACC ATT GAT GGA AAA AAA CCT GAT
      GCG TTA CTC CAA ACC ACC TGG TAA CTA CCT TTT TTT GGA CTA
      Arg Asn Glu Val Trp Trp Thr Ile Asp Gly Lys Lys Pro Asp>
      _____IL-1RAcP_____>

1810          1820          1830          1840
        *       *      *       *       *      *      *       *
      GAC ATC ACT ATT GAT GTC ACC ATT AAC GAA AGT ATA AGT CAT
      CTG TAG TGA TAA CTA CAG TGG TAA TTG CTT TCA TAT TCA GTA
      Asp Ile Thr Ile Asp Val Thr Ile Asn Glu Ser Ile Ser His>
      _____IL-1RAcP_____>

1850          1860          1870          1880          1890
     *       *       *      *       *       *      *       *       *
   AGT AGA ACA GAA GAT GAA ACA AGA ACT CAG ATT TTG AGC ATC
   TCA TCT TGT CTT CTA CTT TGT TCT TGA GTC TAA AAC TCG TAG
   Ser Arg Thr Glu Asp Glu Thr Arg Thr Gln Ile Leu Ser Ile>
   _____IL-1RAcP_____>

1900          1910          1920          1930
            *       *      *       *      *      *      *       *
       AAG AAA GTT ACC TCT GAG GAT CTC AAG CGC AGC TAT GTC TGT
       TTC TTT CAA TGG AGA CTC CTA GAG TTC GCG TCG ATA CAG ACA
       Lys Lys Val Thr Ser Glu Asp Leu Lys Arg Ser Tyr Val Cys>
       _____IL-1RAcP_____>
```

Figure 40G

```
          1940         1950         1960         1970
       *      *     *      *     *      *     *      *
      CAT GCT AGA AGT GCC AAA GGC GAA GTT GCC AAA GCA GCC AAG
      GTA CGA TCT TCA CGG TTT CCG CTT CAA CGG TTT CGT CGG TTC
      His Ala Arg Ser Ala Lys Gly Glu Val Ala Lys Ala Ala Lys>
                            ___IL-1RAcP_____>

1980         1990         2000         2010
       *      *     *      *     *      *     *      *     *
      GTG AAG CAG AAA GTG CCA GCT CCA AGA TAC ACA GTG GAA TCC
      CAC TTC GTC TTT CAC GGT CGA GGT TCT ATG TGT CAC CTT AGG
      Val Lys Gln Lys Val Pro Ala Pro Arg Tyr Thr Val Glu>
                            ___IL-1RAcP_____>
                                                       Ser>
                                                       ___>

>Mutation Serine to Proline
                                              |
          2020         2030         2040      |2050
       *      *     *      *     *      *     |  *      *
      GGA GAG TCC AAA TAC GGT CCG CCA TGC CCA CCA TGC CCA GCA
      CCT CTC AGG TTT ATG CCA GGC GGT ACG GGT GGT ACG GGT CGT
          Glu Ser Lys Tyr Gly Pro Pro Cys Pro Pro Cys Pro Ala>
                            ___FC-IgG4_____>
      Gly>
      ___>

2060         2070         2080         2090         2100
       *      *     *      *     *      *     *      *     *      *
      CCT GAG TTC CTG GGG GGA CCA TCA GTC TTC CTG TTC CCC CCA
      GGA CTC AAG GAC CCC CCT GGT AGT CAG AAG GAC AAG GGG GGT
      Pro Glu Phe Leu Gly Gly Pro Ser Val Phe Leu Phe Pro Pro>
                            ___FC-IgG4_____>

2110         2120         2130         2140
       *      *     *      *     *      *     *      *
      AAA CCC AAG GAC ACT CTC ATG ATC TCC CGG ACC CCT GAG GTC
      TTT GGG TTC CTG TGA GAG TAC TAG AGG GCC TGG GGA CTC CAG
      Lys Pro Lys Asp Thr Leu Met Ile Ser Arg Thr Pro Glu Val>
                            ___FC-IgG4_____>

2150         2160         2170         2180
       *      *     *      *     *      *     *      *
      ACG TGC GTG GTG GTG GAC GTG AGC CAG GAA GAC CCC GAG GTC
      TGC ACG CAC CAC CAC CTG CAC TCG GTC CTT CTG GGG CTC CAG
      Thr Cys Val Val Val Asp Val Ser Gln Glu Asp Pro Glu Val>
                            ___FC-IgG4_____>

2190         2200         2210         2220
       *      *     *      *     *      *     *      *     *
      CAG TTC AAC TGG TAC GTG GAT GGC GTG GAG GTG CAT AAT GCC
      GTC AAG TTG ACC ATG CAC CTA CCG CAC CTC CAC GTA TTA CGG
      Gln Phe Asn Trp Tyr Val Asp Gly Val Glu Val His Asn Ala>
                            ___FC-IgG4_____>
```

Figure 40H

```
      2230          2240         2250         2260
       *    *    *    *    *    *    *    *
      AAG ACA AAG CCG CGG GAG GAG CAG TTC AAC AGC ACG TAC CGT
      TTC TGT TTC GGC GCC CTC CTC GTC AAG TTG TCG TGC ATG GCA
      Lys Thr Lys Pro Arg Glu Glu Gln Phe Asn Ser Thr Tyr Arg>
                            __FC-IgG4_____>

2270         2280         2290         2300         2310
   *    *    *    *    *    *    *    *    *    *
  GTG GTC AGC GTC CTC ACC GTC CTG CAC CAG GAC TGG CTG AAC
  CAC CAG TCG CAG GAG TGG CAG GAC GTG GTC CTG ACC GAC TTG
  Val Val Ser Val Leu Thr Val Leu His Gln Asp Trp Leu Asn>
                        __FC-IgG4_____>

2320         2330         2340         2350
         *    *    *    *    *    *    *    *
        GGC AAG GAG TAC AAG TGC AAG GTC TCC AAC AAA GGC CTC CCG
        CCG TTC CTC ATG TTC ACG TTC CAG AGG TTG TTT CCG GAG GGC
        Gly Lys Glu Tyr Lys Cys Lys Val Ser Asn Lys Gly Leu Pro>
                          __FC-IgG4_____>

2360         2370         2380         2390
           *    *    *    *    *    *    *    *
         TCC TCC ATC GAG AAA ACC ATC TCC AAA GCC AAA GGG CAG CCC
         AGG AGG TAG CTC TTT TGG TAG AGG TTT CGG TTT CCC GTC GGG
         Ser Ser Ile Glu Lys Thr Ile Ser Lys Ala Lys Gly Gln Pro>
                           __FC-IgG4_____>

2400         2410         2420         2430
         *    *    *    *    *    *    *    *    *
       CGA GAG CCA CAG GTG TAC ACC CTG CCC CCA TCC CAG GAG GAG
       GCT CTC GGT GTC CAC ATG TGG GAC GGG GGT AGG GTC CTC CTC
       Arg Glu Pro Gln Val Tyr Thr Leu Pro Pro Ser Gln Glu Glu>
                         __FC-IgG4_____>

2440         2450         2460         2470
         *    *    *    *    *    *    *    *
       ATG ACC AAG AAC CAG GTC AGC CTG ACC TGC CTG GTC AAA GGC
       TAC TGG TTC TTG GTC CAG TCG GAC TGG ACG GAC CAG TTT CCG
       Met Thr Lys Asn Gln Val Ser Leu Thr Cys Leu Val Lys Gly>
                         __FC-IgG4_____>

2480         2490         2500         2510         2520
   *    *    *    *    *    *    *    *    *    *
  TTC TAC CCC AGC GAC ATC GCC GTG GAG TGG GAG AGC AAT GGG
  AAG ATG GGG TCG CTG TAG CGG CAC CTC ACC CTC TCG TTA CCC
  Phe Tyr Pro Ser Asp Ile Ala Val Glu Trp Glu Ser Asn Gly>
                        __FC-IgG4_____>

2530         2540         2550         2560
          *    *    *    *    *    *    *    *
        CAG CCG GAG AAC AAC TAC AAG ACC ACG CCT CCC GTG CTG GAC
        GTC GGC CTC TTG TTG ATG TTC TGG TGC GGA GGG CAC GAC CTG
        Gln Pro Glu Asn Asn Tyr Lys Thr Thr Pro Pro Val Leu Asp>
                          __FC-IgG4_____>
```

Figure 40I

```
            2570            2580              2590            2600
      *       *       *       *       *       *       *       *
    TCC     GAC     GGC     TCC     TTC     TTC     CTC     TAC     AGC     AGG     CTA     ACC     GTG     GAC
    AGG     CTG     CCG     AGG     AAG     AAG     GAG     ATG     TCG     TCC     GAT     TGG     CAC     CTG
    Ser     Asp     Gly     Ser     Phe     Phe     Leu     Tyr     Ser     Arg     Leu     Thr     Val     Asp>
    _____FC-IgG4_____>

2610            2620              2630            2640
      *       *       *       *       *       *       *       *       *
    AAG     AGC     AGG     TGG     CAG     GAG     GGG     AAT     GTC     TTC     TCA     TGC     TCC     GTG
    TTC     TCG     TCC     ACC     GTC     CTC     CCC     TTA     CAG     AAG     AGT     ACG     AGG     CAC
    Lys     Ser     Arg     Trp     Gln     Glu     Gly     Asn     Val     Phe     Ser     Cys     Ser     Val>
    _____FC-IgG4_____>

2650            2660              2670            2680
      *       *       *       *       *       *       *       *
    ATG     CAT     GAG     GCT     CTG     CAC     AAC     CAC     TAC     ACA     CAG     AAG     AGC     CTC
    TAC     GTA     CTC     CGA     GAC     GTG     TTG     GTG     ATG     TGT     GTC     TTC     TCG     GAG
    Met     His     Glu     Ala     Leu     His     Asn     His     Tyr     Thr     Gln     Lys     Ser     Leu>
    _____FC-IgG4_____>

2690            2700
      *       *       *       *
    TCC     CTG     TCT     CTG     GGT     AAA     TGA
    AGG     GAC     AGA     GAC     CCA     TTT     ACT
    Ser     Leu     Ser     Leu     Gly     Lys     ***>
    _____FC-IgG4_____>
```

Figure 41A

```
         10              20              30              40
         *       *       *       *       *       *       *       *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
                ___SIGNAL PEPTIDE_____>
        _____IL-1RAcP_____>

50              60              70              80
         *       *       *       *       *       *       *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
___SIGNAL PEPTIDE_____>
                        Ser Glu Arg Cys Asp Asp Trp Gly>
                        _____IL-1RAcP_____>

90             100             110             120
         *       *       *       *       *       *       *       *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
                                  IL-1RAcP_____>

130             140             150             160
     *       *       *       *       *       *       *       *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
                  _____IL-1RAcP_____>

170             180             190             200             210
 *       *       *       *       *       *       *       *       *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
                        _____IL-1RAcP_____>

220             230             240             250
         *       *       *       *       *       *       *       *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
                        _____IL-1RAcP_____>

260             270             280             290
         *       *       *       *       *       *       *       *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
                        _____IL-1RAcP_____>

300             310             320             330
         *       *       *       *       *       *       *       *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
                        _____IL-1RAcP_____>
```

Figure 41B

```
       340            350            360            370
        *       *      *       *      *       *      *       *
       ACC TGC ATG TTA AGG AAC ACT ACA TAT TGC AGC AAA GTT GCA
       TGG ACG TAC AAT TCC TTG TGA TGT ATA ACG TCG TTT CAA CGT
       Thr Cys Met Leu Arg Asn Thr Thr Tyr Cys Ser Lys Val Ala>
                                IL-1RAcP                      >

380            390            400            410            420
        *       *      *       *      *       *      *       *      *
       TTT CCC TTG GAA GTT GTT CAA AAA GAC AGC TGT TTC AAT TCC
       AAA GGG AAC CTT CAA CAA GTT TTT CTG TCG ACA AAG TTA AGG
       Phe Pro Leu Glu Val Val Gln Lys Asp Ser Cys Phe Asn Ser>
                                IL-1RAcP                      >

430            440            450            460
        *       *      *       *      *       *      *       *
       CCC ATG AAA CTC CCA GTG CAT AAA CTG TAT ATA GAA TAT GGC
       GGG TAC TTT GAG GGT CAC GTA TTT GAC ATA TAT CTT ATA CCG
       Pro Met Lys Leu Pro Val His Lys Leu Tyr Ile Glu Tyr Gly>
                                IL-1RAcP                      >

470            480            490            500
        *       *      *       *      *       *      *       *
       ATT CAG AGG ATC ACT TGT CCA AAT GTA GAT GGA TAT TTT CCT
       TAA GTC TCC TAG TGA ACA GGT TTA CAT CTA CCT ATA AAA GGA
       Ile Gln Arg Ile Thr Cys Pro Asn Val Asp Gly Tyr Phe Pro>
                                IL-1RAcP                      >

510            520            530            540
        *       *      *       *      *       *      *       *
       TCC AGT GTC AAA CCG ACT ATC ACT TGG TAT ATG GGC TGT TAT
       AGG TCA CAG TTT GGC TGA TAG TGA ACC ATA TAC CCG ACA ATA
       Ser Ser Val Lys Pro Thr Ile Thr Trp Tyr Met Gly Cys Tyr>
                                IL-1RAcP                      >

550            560            570            580
        *       *      *       *      *       *      *       *
       AAA ATA CAG AAT TTT AAT AAT GTA ATA CCC GAA GGT ATG AAC
       TTT TAT GTC TTA AAA TTA TTA CAT TAT GGG CTT CCA TAC TTG
       Lys Ile Gln Asn Phe Asn Asn Val Ile Pro Glu Gly Met Asn>
                                IL-1RAcP                      >

590            600            610            620            630
        *       *      *       *      *       *      *       *      *
       TTG AGT TTC CTC ATT GCC TTA ATT TCA AAT AAT GGA AAT TAC
       AAC TCA AAG GAG TAA CGG AAT TAA AGT TTA TTA CCT TTA ATG
       Leu Ser Phe Leu Ile Ala Leu Ile Ser Asn Asn Gly Asn Tyr>
                                IL-1RAcP                      >

640            650            660            670
        *       *      *       *      *       *      *       *
       ACA TGT GTT GTT ACA TAT CCA GAA AAT GGA CGT ACG TTT CAT
       TGT ACA CAA CAA TGT ATA GGT CTT TTA CCT GCA TGC AAA GTA
       Thr Cys Val Val Thr Tyr Pro Glu Asn Gly Arg Thr Phe His>
                                IL-1RAcP                      >
```

Figure 41C

```
          680              690              700              710
    *       *       *       *       *       *       *       *
   CTC ACC AGG ACT CTG ACT GTA AAG GTA GTA GGC TCT CCA AAA
   GAG TGG TCC TGA GAC TGA CAT TTC CAT CAT CCG AGA GGT TTT
   Leu Thr Arg Thr Leu Thr Val Lys Val Val Gly Ser Pro Lys>
   _____IL-1RAcP_____>

720              730              740              750
    *       *       *       *       *       *       *       *
   AAT GCA GTG CCC CCT GTG ATC CAT TCA CCT AAT GAT CAT GTG
   TTA CGT CAC GGG GGA CAC TAG GTA AGT GGA TTA CTA GTA CAC
   Asn Ala Val Pro Pro Val Ile His Ser Pro Asn Asp His Val>
   _____IL-1RAcP_____>

760              770              780              790
    *       *       *       *       *       *       *       *
   GTC TAT GAG AAA GAA CCA GGA GAG GAG CTA CTC ATT CCC TGT
   CAG ATA CTC TTT CTT GGT CCT CTC CTC GAT GAG TAA GGG ACA
   Val Tyr Glu Lys Glu Pro Gly Glu Glu Leu Leu Ile Pro Cys>
   _____IL-1RAcP_____>

800           810              820              830          840
    *       *       *       *       *       *       *       *       *
   ACG GTC TAT TTT AGT TTT CTG ATG GAT TCT CGC AAT GAG GTT
   TGC CAG ATA AAA TCA AAA GAC TAC CTA AGA GCG TTA CTC CAA
   Thr Val Tyr Phe Ser Phe Leu Met Asp Ser Arg Asn Glu Val>
   _____IL-1RAcP_____>

850              860              870              880
    *       *       *       *       *       *       *       *
   TGG TGG ACC ATT GAT GGA AAA AAA CCT GAT GAC ATC ACT ATT
   ACC ACC TGG TAA CTA CCT TTT TTT GGA CTA CTG TAG TGA TAA
   Trp Trp Thr Ile Asp Gly Lys Lys Pro Asp Asp Ile Thr Ile>
   _____IL-1RAcP_____>

890              900              910              920
    *       *       *       *       *       *       *       *
   GAT GTC ACC ATT AAC GAA AGT ATA AGT CAT AGT AGA ACA GAA
   CTA CAG TGG TAA TTG CTT TCA TAT TCA GTA TCA TCT TGT CTT
   Asp Val Thr Ile Asn Glu Ser Ile Ser His Ser Arg Thr Glu>
   _____IL-1RAcP_____>

930              940              950              960
    *       *       *       *       *       *       *       *
   GAT GAA ACA AGA ACT CAG ATT TTG AGC ATC AAG AAA GTT ACC
   CTA CTT TGT TCT TGA GTC TAA AAC TCG TAG TTC TTT CAA TGG
   Asp Glu Thr Arg Thr Gln Ile Leu Ser Ile Lys Lys Val Thr>
   _____IL-1RAcP_____>

970              980              990             1000
    *       *       *       *       *       *       *       *
   TCT GAG GAT CTC AAG CGC AGC TAT GTC TGT CAT GCT AGA AGT
   AGA CTC CTA GAG TTC GCG TCG ATA CAG ACA GTA CGA TCT TCA
   Ser Glu Asp Leu Lys Arg Ser Tyr Val Cys His Ala Arg Ser>
   _____IL-1RAcP_____>
```

Figure 41D

```
        1010             1020             1030             1040             1050
          *        *        *        *        *        *        *        *        *
        GCC AAA GGC GAA GTT GCC AAA GCA GCC AAG GTG AAG CAG AAA
        CGG TTT CCG CTT CAA CGG TTT CGT CGG TTC CAC TTC GTC TTT
        Ala Lys Gly Glu Val Ala Lys Ala Ala Lys Val Lys Gln Lys>
        _____IL-1RAcP_____>

1060             1070             1080             1090
             *        *        *        *        *        *        *        *
        GTG CCA GCT CCA AGA TAC ACA GTG GAA AAA TGC AAG GAA CGT
        CAC GGT CGA GGT TCT ATG TGT CAC CTT TTT ACG TTC CTT GCA
        Val Pro Ala Pro Arg Tyr Thr Val Glu>
        _____IL-1RAcP_____>
                                                  Lys Cys Lys Glu Arg>
                                                  _____IL-1RI_____>

1100             1110             1120             1130
         *        *        *        *        *        *        *        *
        GAA GAA AAA ATA ATT TTA GTG AGC TCA GCA AAT GAA ATC GAT
        CTT CTT TTT TAT TAA AAT CAC TCG AGT CGT TTA CTT TAG CTA
        Glu Glu Lys Ile Ile Leu Val Ser Ser Ala Asn Glu Ile Asp>
        _____IL-1RI_____>

1140             1150             1160             1170
         *        *        *        *        *        *        *        *
        GTT CGT CCC TGT CCT CTT AAC CCA AAT GAA CAC AAA GGC ACT
        CAA GCA GGG ACA GGA GAA TTG GGT TTA CTT GTG TTT CCG TGA
        Val Arg Pro Cys Pro Leu Asn Pro Asn Glu His Lys Gly Thr>
        _____IL-1RI_____>

1180             1190             1200             1210
         *        *        *        *        *        *        *        *
        ATA ACT TGG TAT AAG GAT GAC AGC AAG ACA CCT GTA TCT ACA
        TAT TGA ACC ATA TTC CTA CTG TCG TTC TGT GGA CAT AGA TGT
        Ile Thr Trp Tyr Lys Asp Asp Ser Lys Thr Pro Val Ser Thr>
        _____IL-1RI_____>

1220             1230             1240             1250             1260
          *        *        *        *        *        *        *        *        *
        GAA CAA GCC TCC AGG ATT CAT CAA CAC AAA GAG AAA CTT TGG
        CTT GTT CGG AGG TCC TAA GTA GTT GTG TTT CTC TTT GAA ACC
        Glu Gln Ala Ser Arg Ile His Gln His Lys Glu Lys Leu Trp>
        _____IL-1RI_____>

1270             1280             1290             1300
             *        *        *        *        *        *        *        *
        TTT GTT CCT GCT AAG GTG GAG GAT TCA GGA CAT TAC TAT TGC
        AAA CAA GGA CGA TTC CAC CTC CTA AGT CCT GTA ATG ATA ACG
        Phe Val Pro Ala Lys Val Glu Asp Ser Gly His Tyr Tyr Cys>
        _____IL-1RI_____>

1310             1320             1330             1340
         *        *        *        *        *        *        *        *
        GTG GTA AGA AAT TCA TCT TAC TGC CTC AGA ATT AAA ATA AGT
        CAC CAT TCT TTA AGT AGA ATG ACG GAG TCT TAA TTT TAT TCA
        Val Val Arg Asn Ser Ser Tyr Cys Leu Arg Ile Lys Ile Ser>
        _____IL-1RI_____>
```

Figure 41E

```
        1350            1360            1370            1380
    *        *      *        *      *        *      *        *      *
    GCA AAA TTT GTG GAG AAT GAG CCT AAC TTA TGT TAT AAT GCA
    CGT TTT AAA CAC CTC TTA CTC GGA TTG AAT ACA ATA TTA CGT
    Ala Lys Phe Val Glu Asn Glu Pro Asn Leu Cys Tyr Asn Ala>
    _____IL-1RI_____>

1390            1400            1410            1420
    *        *      *        *      *        *      *        *
    CAA GCC ATA TTT AAG CAG AAA CTA CCC GTT GCA GGA GAC GGA
    GTT CGG TAT AAA TTC GTC TTT GAT GGG CAA CGT CCT CTG CCT
    Gln Ala Ile Phe Lys Gln Lys Leu Pro Val Ala Gly Asp Gly>
    _____IL-1RI_____>

1430            1440            1450            1460            1470
  *        *      *        *      *        *      *        *      *
  GGA CTT GTG TGC CCT TAT ATG GAG TTT TTT AAA AAT GAA AAT
  CCT GAA CAC ACG GGA ATA TAC CTC AAA AAA TTT TTA CTT TTA
  Gly Leu Val Cys Pro Tyr Met Glu Phe Phe Lys Asn Glu Asn>
  _____IL-1RI_____>

1480            1490            1500            1510
    *        *      *        *      *        *      *        *
    AAT GAG TTA CCT AAA TTA CAG TGG TAT AAG GAT TGC AAA CCT
    TTA CTC AAT GGA TTT AAT GTC ACC ATA TTC CTA ACG TTT GGA
    Asn Glu Leu Pro Lys Leu Gln Trp Tyr Lys Asp Cys Lys Pro>
    _____IL-1RI_____>

1520            1530            1540            1550
    *        *      *        *      *        *      *        *
    CTA CTT CTT GAC AAT ATA CAC TTT AGT GGA GTC AAA GAT AGG
    GAT GAA GAA CTG TTA TAT GTG AAA TCA CCT CAG TTT CTA TCC
    Leu Leu Leu Asp Asn Ile His Phe Ser Gly Val Lys Asp Arg>
    _____IL-1RI_____>

1560            1570            1580            1590
    *        *      *        *      *        *      *        *      *
    CTC ATC GTG ATG AAT GTG GCT GAA AAG CAT AGA GGG AAC TAT
    GAG TAG CAC TAC TTA CAC CGA CTT TTC GTA TCT CCC TTG ATA
    Leu Ile Val Met Asn Val Ala Glu Lys His Arg Gly Asn Tyr>
    _____IL-1RI_____>

1600            1610            1620            1630
    *        *      *        *      *        *      *        *
    ACT TGT CAT GCA TCC TAC ACA TAC TTG GGC AAG CAA TAT CCT
    TGA ACA GTA CGT AGG ATG TGT ATG AAC CCG TTC GTT ATA GGA
    Thr Cys His Ala Ser Tyr Thr Tyr Leu Gly Lys Gln Tyr Pro>
    _____IL-1RI_____>

1640            1650            1660            1670            1680
  *        *      *        *      *        *      *        *      *
  ATT ACC CGG GTA ATA GAA TTT ATT ACT CTA GAG GAA AAC AAA
  TAA TGG GCC CAT TAT CTT AAA TAA TGA GAT CTC CTT TTG TTT
  Ile Thr Arg Val Ile Glu Phe Ile Thr Leu Glu Glu Asn Lys>
  _____IL-1RI_____>
```

Figure 41F

```
              1690            1700           1710            1720
               *       *       *       *       *      *        *       *
          CCC ACA AGG CCT GTG ATT GTG AGC CCA GCT AAT GAG ACA ATG
          GGG TGT TCC GGA CAC TAA CAC TCG GGT CGA TTA CTC TGT TAC
          Pro Thr Arg Pro Val Ile Val Ser Pro Ala Asn Glu Thr Met>
          _____IL-1RI_____>

1730            1740           1750            1760
               *       *       *       *       *      *        *
          GAA GTA GAC TTG GGA TCC CAG ATA CAA TTG ATC TGT AAT GTC
          CTT CAT CTG AAC CCT AGG GTC TAT GTT AAC TAG ACA TTA CAG
          Glu Val Asp Leu Gly Ser Gln Ile Gln Leu Ile Cys Asn Val>
          _____IL-1RI_____>

1770            1780           1790            1800
               *       *       *       *       *      *        *       *
          ACC GGC CAG TTG AGT GAC ATT GCT TAC TGG AAG TGG AAT GGG
          TGG CCG GTC AAC TCA CTG TAA CGA ATG ACC TTC ACC TTA CCC
          Thr Gly Gln Leu Ser Asp Ile Ala Tyr Trp Lys Trp Asn Gly>
          _____IL-1RI_____>

1810            1820           1830            1840
            *       *       *       *       *      *        *       *
          TCA GTA ATT GAT GAA GAT GAC CCA GTG CTA GGG GAA GAC TAT
          AGT CAT TAA CTA CTT CTA CTG GGT CAC GAT CCC CTT CTG ATA
          Ser Val Ile Asp Glu Asp Asp Pro Val Leu Gly Glu Asp Tyr>
          _____IL-1RI_____>

1850            1860           1870            1880          1890
            *       *       *       *       *      *        *       *       *
          TAC AGT GTG GAA AAT CCT GCA AAC AAA AGA AGG AGT ACC CTC
          ATG TCA CAC CTT TTA GGA CGT TTG TTT TCT TCC TCA TGG GAG
          Tyr Ser Val Glu Asn Pro Ala Asn Lys Arg Arg Ser Thr Leu>
          _____IL-1RI_____>

1900            1910          1920            1930
                   *       *       *       *       *      *        *       *
          ATC ACA GTG CTT AAT ATA TCG GAA ATT GAG AGT AGA TTT TAT
          TAG TGT CAC GAA TTA TAT AGC CTT TAA CTC TCA TCT AAA ATA
          Ile Thr Val Leu Asn Ile Ser Glu Ile Glu Ser Arg Phe Tyr>
          _____IL-1RI_____>

1940            1950           1960            1970
               *       *       *       *       *      *        *
          AAA CAT CCA TTT ACC TGT TTT GCC AAG AAT ACA CAT GGT ATA
          TTT GTA GGT AAA TGG ACA AAA CGG TTC TTA TGT GTA CCA TAT
          Lys His Pro Phe Thr Cys Phe Ala Lys Asn Thr His Gly Ile>
          _____IL-1RI_____>

1980            1990           2000            2010
               *       *       *       *       *      *        *       *
          GAT GCA GCA TAT ATC CAG TTA ATA TAT CCA GTC ACT AAT TCC
          CTA CGT CGT ATA TAG GTC AAT TAT ATA GGT CAG TGA TTA AGG
                                                              Ser>
                                                        _____>

Asp Ala Ala Tyr Ile Gln Leu Ile Tyr Pro Val Thr Asn>
          _____IL-1RI_____>
```

Figure 41G

```
          2020           2030          2040           2050
           *       *      *       *     *        *      *        *
         GGA  GAC  AAA  ACT  CAC  ACA  TGC  CCA  CCG  TGC  CCA  GCA  CCT  GAA
         CCT  CTG  TTT  TGA  GTG  TGT  ACG  GGT  GGC  ACG  GGT  CGT  GGA  CTT
         Gly  Asp  Lys  Thr  His  Thr  Cys  Pro  Pro  Cys  Pro  Ala  Pro  Glu>
                              _____FC-IgG1_____>

2060           2070          2080           2090            2100
    *      *      *      *      *      *       *       *       *
  CTC  CTG  GGG  GGA  CCG  TCA  GTC  TTC  CTC  TTC  CCC  CCA  AAA  CCC
  GAG  GAC  CCC  CCT  GGC  AGT  CAG  AAG  GAG  AAG  GGG  GGT  TTT  GGG
  Leu  Leu  Gly  Gly  Pro  Ser  Val  Phe  Leu  Phe  Pro  Pro  Lys  Pro>
                      _____FC-IgG1_____>

2110          2120          2130           2140
               *      *      *      *      *      *       *      *
             AAG  GAC  ACC  CTC  ATG  ATC  TCC  CGG  ACC  CCT  GAG  GTC  ACA  TGC
             TTC  CTG  TGG  GAG  TAC  TAG  AGG  GCC  TGG  GGA  CTC  CAG  TGT  ACG
             Lys  Asp  Thr  Leu  Met  Ile  Ser  Arg  Thr  Pro  Glu  Val  Thr  Cys>
                                  _____FC-IgG1_____>

2150          2160          2170          2180
             *      *      *      *      *      *      *       *
           GTG  GTG  GTG  GAC  GTG  AGC  CAC  GAA  GAC  CCT  GAG  GTC  AAG  TTC
           CAC  CAC  CAC  CTG  CAC  TCG  GTG  CTT  CTG  GGA  CTC  CAG  TTC  AAG
           Val  Val  Val  Asp  Val  Ser  His  Glu  Asp  Pro  Glu  Val  Lys  Phe>
                                _____FC-IgG1_____>

2190           2200         2210           2220
          *       *      *      *     *       *      *       *       *
         AAC  TGG  TAC  GTG  GAC  GGC  GTG  GAG  GTG  CAT  AAT  GCC  AAG  ACA
         TTG  ACC  ATG  CAC  CTG  CCG  CAC  CTC  CAC  GTA  TTA  CGG  TTC  TGT
         Asn  Trp  Tyr  Val  Asp  Gly  Val  Glu  Val  His  Asn  Ala  Lys  Thr>
                               _____FC-IgG1_____>

2230          2240          2250          2260
               *      *      *      *      *      *      *      *
             AAG  CCG  CGG  GAG  GAG  CAG  TAC  AAC  AGC  ACG  TAC  CGT  GTG  GTC
             TTC  GGC  GCC  CTC  CTC  GTC  ATG  TTG  TCG  TGC  ATG  GCA  CAC  CAG
             Lys  Pro  Arg  Glu  Glu  Gln  Tyr  Asn  Ser  Thr  Tyr  Arg  Val  Val>
                                  _____FC-IgG1_____>

2270           2280          2290          2300           2310
          *      *       *      *      *      *      *      *      *
         AGC  GTC  CTC  ACC  GTC  CTG  CAC  CAG  GAC  TGG  CTG  AAT  GGC  AAG
         TCG  CAG  GAG  TGG  CAG  GAC  GTG  GTC  CTG  ACC  GAC  TTA  CCG  TTC
         Ser  Val  Leu  Thr  Val  Leu  His  Gln  Asp  Trp  Leu  Asn  Gly  Lys>
                              _____FC-IgG1_____>

2320          2330          2340          2350
                   *      *      *      *      *      *      *      *
                 GAG  TAC  AAG  TGC  AAG  GTC  TCC  AAC  AAA  GCC  CTC  CCA  GCC  CCC
                 CTC  ATG  TTC  ACG  TTC  CAG  AGG  TTG  TTT  CGG  GAG  GGT  CGG  GGG
                 Glu  Tyr  Lys  Cys  Lys  Val  Ser  Asn  Lys  Ala  Leu  Pro  Ala  Pro>
                                      _____FC-IgG1_____>
```

Figure 41H

```
            2360              2370              2380              2390
    *    *    *         *    *         *    *         *    *
   ATC  GAG  AAA  ACC  ATC  TCC  AAA  GCC  AAA  GGG  CAG  CCC  CGA  GAA
   TAG  CTC  TTT  TGG  TAG  AGG  TTT  CGG  TTT  CCC  GTC  GGG  GCT  CTT
   Ile  Glu  Lys  Thr  Ile  Ser  Lys  Ala  Lys  Gly  Gln  Pro  Arg  Glu>
                                  FC-IgG1                                >

2400              2410              2420              2430
    *    *         *    *         *    *         *    *         *
   CCA  CAG  GTG  TAC  ACC  CTG  CCC  CCA  TCC  CGG  GAT  GAG  CTG  ACC
   GGT  GTC  CAC  ATG  TGG  GAC  GGG  GGT  AGG  GCC  CTA  CTC  GAC  TGG
   Pro  Gln  Val  Tyr  Thr  Leu  Pro  Pro  Ser  Arg  Asp  Glu  Leu  Thr>
                                  FC-IgG1                                >

2440              2450              2460              2470
         *    *         *    *         *    *         *    *
   AAG  AAC  CAG  GTC  AGC  CTG  ACC  TGC  CTG  GTC  AAA  GGC  TTC  TAT
   TTC  TTG  GTC  CAG  TCG  GAC  TGG  ACG  GAC  CAG  TTT  CCG  AAG  ATA
   Lys  Asn  Gln  Val  Ser  Leu  Thr  Cys  Leu  Val  Lys  Gly  Phe  Tyr>
                                  FC-IgG1                                >

2480           2490              2500              2510          2520
    *         *    *         *    *         *    *         *         *
   CCC  AGC  GAC  ATC  GCC  GTG  GAG  TGG  GAG  AGC  AAT  GGG  CAG  CCG
   GGG  TCG  CTG  TAG  CGG  CAC  CTC  ACC  CTC  TCG  TTA  CCC  GTC  GGC
   Pro  Ser  Asp  Ile  Ala  Val  Glu  Trp  Glu  Ser  Asn  Gly  Gln  Pro>
                                  FC-IgG1                                >

2530              2540              2550              2560
         *    *         *    *         *    *         *    *
   GAG  AAC  AAC  TAC  AAG  ACC  ACG  CCT  CCC  GTG  CTG  GAC  TCC  GAC
   CTC  TTG  TTG  ATG  TTC  TGG  TGC  GGA  GGG  CAC  GAC  CTG  AGG  CTG
   Glu  Asn  Asn  Tyr  Lys  Thr  Thr  Pro  Pro  Val  Leu  Asp  Ser  Asp>
                                  FC-IgG1                                >

2570              2580              2590              2600
         *    *         *    *         *    *         *         *
   GGC  TCC  TTC  TTC  CTC  TAC  AGC  AAG  CTC  ACC  GTG  GAC  AAG  AGC
   CCG  AGG  AAG  AAG  GAG  ATG  TCG  TTC  GAG  TGG  CAC  CTG  TTC  TCG
   Gly  Ser  Phe  Phe  Leu  Tyr  Ser  Lys  Leu  Thr  Val  Asp  Lys  Ser>
                                  FC-IgG1                                >

2610              2620              2630              2640
    *    *         *    *         *    *         *    *         *
   AGG  TGG  CAG  CAG  GGG  AAC  GTC  TTC  TCA  TGC  TCC  GTG  ATG  CAT
   TCC  ACC  GTC  GTC  CCC  TTG  CAG  AAG  AGT  ACG  AGG  CAC  TAC  GTA
   Arg  Trp  Gln  Gln  Gly  Asn  Val  Phe  Ser  Cys  Ser  Val  Met  His>
                                  FC-IgG1                                >

2650              2660              2670              2680
         *    *         *    *         *    *         *    *
   GAG  GCT  CTG  CAC  AAC  CAC  TAC  ACG  CAG  AAG  AGC  CTC  TCC  CTG
   CTC  CGA  GAC  GTG  TTG  GTG  ATG  TGC  GTC  TTC  TCG  GAG  AGG  GAC
   Glu  Ala  Leu  His  Asn  His  Tyr  Thr  Gln  Lys  Ser  Leu  Ser  Leu>
                                  FC-IgG1                                >
```

Figure 41 I

```
        2690              2700
          *       *         *
        TCT    CCG GGT AAA TGA
        AGA    GGC CCA TTT ACT
        Ser    Pro Gly Lys ***>
             __FC-IgG1_____>
```

Figure 42A

```
              10                  20                  30                  40
         *         *         *         *         *         *         *         *
    ATG GTG CTT CTG TGG TGT GTA GTG AGT CTC TAC TTT TAT GGA
    TAC CAC GAA GAC ACC ACA CAT CAC TCA GAG ATG AAA ATA CCT
    Met Val Leu Leu Trp Cys Val Val Ser Leu Tyr Phe Tyr Gly>
    _____SIGNAL PEPTIDE_____>
    _____IL-1RAcP_____>

50                  60                  70                  80
         *         *         *         *         *         *         *         *
    ATC CTG CAA AGT GAT GCC TCA GAA CGC TGC GAT GAC TGG GGA
    TAG GAC GTT TCA CTA CGG AGT CTT GCG ACG CTA CTG ACC CCT
    Ile Leu Gln Ser Asp Ala>
    ____SIGNAL PEPTIDE_____>
                            Ser Glu Arg Cys Asp Asp Trp Gly>
                            _____IL-1RAcP_____>

90                 100                 110                 120
         *         *         *         *         *         *         *         *
    CTA GAC ACC ATG AGG CAA ATC CAA GTG TTT GAA GAT GAG CCA
    GAT CTG TGG TAC TCC GTT TAG GTT CAC AAA CTT CTA CTC GGT
    Leu Asp Thr Met Arg Gln Ile Gln Val Phe Glu Asp Glu Pro>
    _____IL-1RAcP_____>

130                 140                 150                 160
         *         *         *         *         *         *         *         *
    GCT CGC ATC AAG TGC CCA CTC TTT GAA CAC TTC TTG AAA TTC
    CGA GCG TAG TTC ACG GGT GAG AAA CTT GTG AAG AAC TTT AAG
    Ala Arg Ile Lys Cys Pro Leu Phe Glu His Phe Leu Lys Phe>
    _____IL-1RAcP_____>

170                 180                 190                 200                 210
      *         *         *         *         *         *         *         *         *
    AAC TAC AGC ACA GCC CAT TCA GCT GGC CTT ACT CTG ATC TGG
    TTG ATG TCG TGT CGG GTA AGT CGA CCG GAA TGA GAC TAG ACC
    Asn Tyr Ser Thr Ala His Ser Ala Gly Leu Thr Leu Ile Trp>
    _____IL-1RAcP_____>

220                 230                 240                 250
         *         *         *         *         *         *         *         *
    TAT TGG ACT AGG CAG GAC CGG GAC CTT GAG GAG CCA ATT AAC
    ATA ACC TGA TCC GTC CTG GCC CTG GAA CTC CTC GGT TAA TTG
    Tyr Trp Thr Arg Gln Asp Arg Asp Leu Glu Glu Pro Ile Asn>
    _____IL-1RAcP_____>

260                 270                 280                 290
         *         *         *         *         *         *         *         *
    TTC CGC CTC CCC GAG AAC CGC ATT AGT AAG GAG AAA GAT GTG
    AAG GCG GAG GGG CTC TTG GCG TAA TCA TTC CTC TTT CTA CAC
    Phe Arg Leu Pro Glu Asn Arg Ile Ser Lys Glu Lys Asp Val>
    _____IL-1RAcP_____>

300                 310                 320                 330
         *         *         *         *         *         *         *         *         *
    CTG TGG TTC CGG CCC ACT CTC CTC AAT GAC ACT GGC AAC TAT
    GAC ACC AAG GCC GGG TGA GAG GAG TTA CTG TGA CCG TTG ATA
    Leu Trp Phe Arg Pro Thr Leu Leu Asn Asp Thr Gly Asn Tyr>
    _____IL-1RAcP_____>
```

Figure 42B

```
       340          350          360           370
        *    *      *    *   *    *    *   *    *
      ACC TGC ATG TTA AGG AAC ACT ACA TAT TGC AGC AAA GTT GCA
      TGG ACG TAC AAT TCC TTG TGA TGT ATA ACG TCG TTT CAA CGT
      Thr Cys Met Leu Arg Asn Thr Thr Tyr Cys Ser Lys Val Ala>
                              ____IL-1RAcP_____>

380          390          400          410          420
    *    *       *    *       *    *       *    *       *
   TTT CCC TTG GAA GTT GTT CAA AAA GAC AGC TGT TTC AAT TCC
   AAA GGG AAC CTT CAA CAA GTT TTT CTG TCG ACA AAG TTA AGG
   Phe Pro Leu Glu Val Val Gln Lys Asp Ser Cys Phe Asn Ser>
                              ____IL-1RAcP_____>

430          440          450          460
        *    *    *       *    *    *       *    *
      CCC ATG AAA CTC CCA GTG CAT AAA CTG TAT ATA GAA TAT GGC
      GGG TAC TTT GAG GGT CAC GTA TTT GAC ATA TAT CTT ATA CCG
      Pro Met Lys Leu Pro Val His Lys Leu Tyr Ile Glu Tyr Gly>
                              ____IL-1RAcP_____>

470          480          490          500
        *    *       *    *       *    *       *    *
      ATT CAG AGG ATC ACT TGT CCA AAT GTA GAT GGA TAT TTT CCT
      TAA GTC TCC TAG TGA ACA GGT TTA CAT CTA CCT ATA AAA GGA
      Ile Gln Arg Ile Thr Cys Pro Asn Val Asp Gly Tyr Phe Pro>
                              ____IL-1RAcP_____>

510          520          530          540
        *    *       *    *    *    *    *    *    *
      TCC AGT GTC AAA CCG ACT ATC ACT TGG TAT ATG GGC TGT TAT
      AGG TCA CAG TTT GGC TGA TAG TGA ACC ATA TAC CCG ACA ATA
      Ser Ser Val Lys Pro Thr Ile Thr Trp Tyr Met Gly Cys Tyr>
                              ____IL-1RAcP_____>

550          560          570          580
        *    *       *    *       *    *       *    *    *
      AAA ATA CAG AAT TTT AAT AAT GTA ATA CCC GAA GGT ATG AAC
      TTT TAT GTC TTA AAA TTA TTA CAT TAT GGG CTT CCA TAC TTG
      Lys Ile Gln Asn Phe Asn Asn Val Ile Pro Glu Gly Met Asn>
                              ____IL-1RAcP_____>

590          600          610          620          630
    *    *       *    *       *    *       *    *       *
   TTG AGT TTC CTC ATT GCC TTA ATT TCA AAT AAT GGA AAT TAC
   AAC TCA AAG GAG TAA CGG AAT TAA AGT TTA TTA CCT TTA ATG
   Leu Ser Phe Leu Ile Ala Leu Ile Ser Asn Asn Gly Asn Tyr>
                              ____IL-1RAcP_____>

640          650          660          670
        *    *    *       *    *    *       *    *
      ACA TGT GTT GTT ACA TAT CCA GAA AAT GGA CGT ACG TTT CAT
      TGT ACA CAA CAA TGT ATA GGT CTT TTA CCT GCA TGC AAA GTA
      Thr Cys Val Val Thr Tyr Pro Glu Asn Gly Arg Thr Phe His>
                              ____IL-1RAcP_____>
```

Figure 42C

```
        680             690             700             710
  *       *       *       *       *       *       *       *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
                            __IL-1RAcP_____>

720             730             740             750
  *       *       *       *       *       *       *       *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
                            __IL-1RAcP_____>

760             770             780             790
  *       *       *       *       *       *       *       *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
                            __IL-1RAcP_____>

800         810             820             830         840
   *           *       *       *       *       *       *       *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
                            __IL-1RAcP_____>

850             860             870             880
  *       *       *       *       *       *       *       *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
                            __IL-1RAcP_____>

890             900             910             920
  *       *       *       *       *       *       *       *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
                            __IL-1RAcP_____>

930             940             950             960
  *       *       *       *       *       *       *       *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
                            __IL-1RAcP_____>

970             980             990             1000
  *       *       *       *       *       *       *       *
TCT GAG GAT CTC AAG CGC AGC TAT GTC TGT CAT GCT AGA AGT
AGA CTC CTA GAG TTC GCG TCG ATA CAG ACA GTA CGA TCT TCA
Ser Glu Asp Leu Lys Arg Ser Tyr Val Cys His Ala Arg Ser>
                            __IL-1RAcP_____>
```

Figure 42D

```
     1010          1020          1030          1040          1050
       *        *     *        *     *        *     *        *     *
     GCC AAA GGC GAA GTT GCC AAA GCA GCC AAG GTG AAG CAG AAA
     CGG TTT CCG CTT CAA CGG TTT CGT CGG TTC CAC TTC GTC TTT
     Ala Lys Gly Glu Val Ala Lys Ala Ala Lys Val Lys Gln Lys>
     _____IL-1RAcP_____>

1060          1070          1080          1090
                *        *     *        *     *        *     *        *
            GTG CCA GCT CCA AGA TAC ACA GTG GAA AAA TGC AAG GAA CGT
            CAC GGT CGA GGT TCT ATG TGT CAC CTT TTT ACG TTC CTT GCA
            Val Pro Ala Pro Arg Tyr Thr Val Glu>
            _____IL-1RAcP_____>
                                              Lys Cys Lys Glu Arg>
                                              _____IL-1RI_____>

1100          1110          1120          1130
              *        *     *        *     *        *     *        *
           GAA GAA AAA ATA ATT TTA GTG AGC TCA GCA AAT GAA ATC GAT
           CTT CTT TTT TAT TAA AAT CAC TCG AGT CGT TTA CTT TAG CTA
           Glu Glu Lys Ile Ile Leu Val Ser Ser Ala Asn Glu Ile Asp>
           _____IL-1RI_____>

1140          1150          1160          1170
            *        *     *        *     *        *     *        *     *
         GTT CGT CCC TGT CCT CTT AAC CCA AAT GAA CAC AAA GGC ACT
         CAA GCA GGG ACA GGA GAA TTG GGT TTA CTT GTG TTT CCG TGA
         Val Arg Pro Cys Pro Leu Asn Pro Asn Glu His Lys Gly Thr>
         _____IL-1RI_____>

1180          1190          1200          1210
            *·       *     *        *     *        *     *        *
         ATA ACT TGG TAT AAG GAT GAC AGC AAG ACA CCT GTA TCT ACA
         TAT TGA ACC ATA TTC CTA CTG TCG TTC TGT GGA CAT AGA TGT
         Ile Thr Trp Tyr Lys Asp Asp Ser Lys Thr Pro Val Ser Thr>
         _____IL-1RI_____>

1220          1230          1240          1250          1260
         *        *     *        *     *        *     *        *     *
      GAA CAA GCC TCC AGG ATT CAT CAA CAC AAA GAG AAA CTT TGG
      CTT GTT CGG AGG TCC TAA GTA GTT GTG TTT CTC TTT GAA ACC
      Glu Gln Ala Ser Arg Ile His Gln His Lys Glu Lys Leu Trp>
      _____IL-1RI_____>

1270          1280          1290          1300
                *        *     *        *     *        *     *        *
            TTT GTT CCT GCT AAG GTG GAG GAT TCA GGA CAT TAC TAT TGC
            AAA CAA GGA CGA TTC CAC CTC CTA AGT CCT GTA ATG ATA ACG
            Phe Val Pro Ala Lys Val Glu Asp Ser Gly His Tyr Tyr Cys>
            _____IL-1RI_____>

1310          1320          1330          1340
             *        *     *        *     *        *     *        *
          GTG GTA AGA AAT TCA TCT TAC TGC CTC AGA ATT AAA ATA AGT
          CAC CAT TCT TTA AGT AGA ATG ACG GAG TCT TAA TTT TAT TCA
          Val Val Arg Asn Ser Ser Tyr Cys Leu Arg Ile Lys Ile Ser>
          _____IL-1RI_____>
```

Figure 42E

```
         1350          1360          1370          1380
      *     *     *     *     *     *     *     *     *
     GCA   AAA   TTT   GTG   GAG   AAT   GAG   CCT   AAC   TTA   TGT   TAT   AAT   GCA
     CGT   TTT   AAA   CAC   CTC   TTA   CTC   GGA   TTG   AAT   ACA   ATA   TTA   CGT
     Ala   Lys   Phe   Val   Glu   Asn   Glu   Pro   Asn   Leu   Cys   Tyr   Asn   Ala>
                                       IL-1RI                                        >

1390          1400          1410          1420
      *     *     *     *     *     *     *     *
     CAA   GCC   ATA   TTT   AAG   CAG   AAA   CTA   CCC   GTT   GCA   GGA   GAC   GGA
     GTT   CGG   TAT   AAA   TTC   GTC   TTT   GAT   GGG   CAA   CGT   CCT   CTG   CCT
     Gln   Ala   Ile   Phe   Lys   Gln   Lys   Leu   Pro   Val   Ala   Gly   Asp   Gly>
                                       IL-1RI                                        >

1430          1440          1450          1460          1470
   *     *     *     *     *     *     *     *     *
  GGA   CTT   GTG   TGC   CCT   TAT   ATG   GAG   TTT   TTT   AAA   AAT   GAA   AAT
  CCT   GAA   CAC   ACG   GGA   ATA   TAC   CTC   AAA   AAA   TTT   TTA   CTT   TTA
  Gly   Leu   Val   Cys   Pro   Tyr   Met   Glu   Phe   Phe   Lys   Asn   Glu   Asn>
                                    IL-1RI                                        >

1480          1490          1500          1510
      *     *     *     *     *     *     *     *
     AAT   GAG   TTA   CCT   AAA   TTA   CAG   TGG   TAT   AAG   GAT   TGC   AAA   CCT
     TTA   CTC   AAT   GGA   TTT   AAT   GTC   ACC   ATA   TTC   CTA   ACG   TTT   GGA
     Asn   Glu   Leu   Pro   Lys   Leu   Gln   Trp   Tyr   Lys   Asp   Cys   Lys   Pro>
                                       IL-1RI                                        >

1520          1530          1540          1550
      *     *     *     *     *     *     *     *
     CTA   CTT   CTT   GAC   AAT   ATA   CAC   TTT   AGT   GGA   GTC   AAA   GAT   AGG
     GAT   GAA   GAA   CTG   TTA   TAT   GTG   AAA   TCA   CCT   CAG   TTT   CTA   TCC
     Leu   Leu   Leu   Asp   Asn   Ile   His   Phe   Ser   Gly   Val   Lys   Asp   Arg>
                                       IL-1RI                                        >

1560          1570          1580          1590
      *     *     *     *     *     *     *     *     *
     CTC   ATC   GTG   ATG   AAT   GTG   GCT   GAA   AAG   CAT   AGA   GGG   AAC   TAT
     GAG   TAG   CAC   TAC   TTA   CAC   CGA   CTT   TTC   GTA   TCT   CCC   TTG   ATA
     Leu   Ile   Val   Met   Asn   Val   Ala   Glu   Lys   His   Arg   Gly   Asn   Tyr>
                                       IL-1RI                                        >

1600          1610          1620          1630
      *     *     *     *     *     *     *     *
     ACT   TGT   CAT   GCA   TCC   TAC   ACA   TAC   TTG   GGC   AAG   CAA   TAT   CCT
     TGA   ACA   GTA   CGT   AGG   ATG   TGT   ATG   AAC   CCG   TTC   GTT   ATA   GGA
     Thr   Cys   His   Ala   Ser   Tyr   Thr   Tyr   Leu   Gly   Lys   Gln   Tyr   Pro>
                                       IL-1RI                                        >

1640          1650          1660          1670          1680
   *     *     *     *     *     *     *     *     *
  ATT   ACC   CGG   GTA   ATA   GAA   TTT   ATT   ACT   CTA   GAG   GAA   AAC   AAA
  TAA   TGG   GCC   CAT   TAT   CTT   AAA   TAA   TGA   GAT   CTC   CTT   TTG   TTT
  Ile   Thr   Arg   Val   Ile   Glu   Phe   Ile   Thr   Leu   Glu   Glu   Asn   Lys>
                                    IL-1RI                                        >
```

Figure 42F

```
        1690          1700          1710          1720
         *       *     *       *     *       *     *       *
     CCC ACA AGG CCT GTG ATT GTG AGC CCA GCT AAT GAG ACA ATG
     GGG TGT TCC GGA CAC TAA CAC TCG GGT CGA TTA CTC TGT TAC
     Pro Thr Arg Pro Val Ile Val Ser Pro Ala Asn Glu Thr Met>
     _____IL-1RI_____>

1730          1740          1750          1760
          *       *     *       *     *       *     *
     GAA GTA GAC TTG GGA TCC CAG ATA CAA TTG ATC TGT AAT GTC
     CTT CAT CTG AAC CCT AGG GTC TAT GTT AAC TAG ACA TTA CAG
     Glu Val Asp Leu Gly Ser Gln Ile Gln Leu Ile Cys Asn Val>
     _____IL-1RI_____>

1770          1780          1790          1800
          *      *      *       *     *       *     *       *    *
     ACC GGC CAG TTG AGT GAC ATT GCT TAC TGG AAG TGG AAT GGG
     TGG CCG GTC AAC TCA CTG TAA CGA ATG ACC TTC ACC TTA CCC
     Thr Gly Gln Leu Ser Asp Ile Ala Tyr Trp Lys Trp Asn Gly>
     _____IL-1RI_____>

1810          1820          1830          1840
          *       *     *       *     *       *     *       *
     TCA GTA ATT GAT GAA GAT GAC CCA GTG CTA GGG GAA GAC TAT
     AGT CAT TAA CTA CTT CTA CTG GGT CAC GAT CCC CTT CTG ATA
     Ser Val Ile Asp Glu Asp Asp Pro Val Leu Gly Glu Asp Tyr>
     _____IL-1RI_____>

1850          1860          1870          1880          1890
    *       *     *       *     *       *     *       *     *
   TAC AGT GTG GAA AAT CCT GCA AAC AAA AGA AGG AGT ACC CTC
   ATG TCA CAC CTT TTA GGA CGT TTG TTT TCT TCC TCA TGG GAG
   Tyr Ser Val Glu Asn Pro Ala Asn Lys Arg Arg Ser Thr Leu>
   _____IL-1RI_____>

1900          1910          1920          1930
          *       *     *       *     *       *     *       *
     ATC ACA GTG CTT AAT ATA TCG GAA ATT GAG AGT AGA TTT TAT
     TAG TGT CAC GAA TTA TAT AGC CTT TAA CTC TCA TCT AAA ATA
     Ile Thr Val Leu Asn Ile Ser Glu Ile Glu Ser Arg Phe Tyr>
     _____IL-1RI_____>

1940          1950          1960          1970
          *       *     *       *     *       *     *       *
     AAA CAT CCA TTT ACC TGT TTT GCC AAG AAT ACA CAT GGT ATA
     TTT GTA GGT AAA TGG ACA AAA CGG TTC TTA TGT GTA CCA TAT
     Lys His Pro Phe Thr Cys Phe Ala Lys Asn Thr His Gly Ile>
     _____IL-1RI_____>

1980          1990          2000          2010
          *      *      *       *     *       *     *       *    *
     GAT GCA GCA TAT ATC CAG TTA ATA TAT CCA GTC ACT AAT TCC
     CTA CGT CGT ATA TAG GTC AAT TAT ATA GGT CAG TGA TTA AGG
     Asp Ala Ala Tyr Ile Gln Leu Ile Tyr Pro Val Thr Asn>
     _____IL-1RI_____>
                                                      Ser>
                                                    ____>
```

Figure 42G

```
         2020            2030            2040            2050
           *      *        *        *      *        *      *        *
         GGA GAG TCC AAA TAC GGT CCG CCA TGC CCA TCA TGC CCA GCA
         CCT CTC AGG TTT ATG CCA GGC GGT ACG GGT AGT ACG GGT CGT
         Gly>
         ___>
             Glu Ser Lys Tyr Gly Pro Pro Cys Pro Ser Cys Pro Ala>
                            FC-IgG4                              >

2060            2070            2080            2090            2100
       *      *        *      *        *      *        *      *        *
     CCT GAG TTC CTG GGG GGA CCA TCA GTC TTC CTG TTC CCC CCA
     GGA CTC AAG GAC CCC CCT GGT AGT CAG AAG GAC AAG GGG GGT
     Pro Glu Phe Leu Gly Gly Pro Ser Val Phe Leu Phe Pro Pro>
                          FC-IgG4                              >

2110            2120            2130            2140
           *        *      *        *      *        *      *        *
         AAA CCC AAG GAC ACT CTC ATG ATC TCC CGG ACC CCT GAG GTC
         TTT GGG TTC CTG TGA GAG TAC TAG AGG GCC TGG GGA CTC CAG
         Lys Pro Lys Asp Thr Leu Met Ile Ser Arg Thr Pro Glu Val>
                            FC-IgG4                              >

2150            2160            2170            2180
           *        *      *        *      *        *      *        *
         ACG TGC GTG GTG GTG GAC GTG AGC CAG GAA GAC CCC GAG GTC
         TGC ACG CAC CAC CAC CTG CAC TCG GTC CTT CTG GGG CTC CAG
         Thr Cys Val Val Val Asp Val Ser Gln Glu Asp Pro Glu Val>
                            FC-IgG4                              >

2190            2200            2210            2220
           *        *      *        *      *        *      *        *
         CAG TTC AAC TGG TAC GTG GAT GGC GTG GAG GTG CAT AAT GCC
         GTC AAG TTG ACC ATG CAC CTA CCG CAC CTC CAC GTA TTA CGG
         Gln Phe Asn Trp Tyr Val Asp Gly Val Glu Val His Asn Ala>
                            FC-IgG4                              >

2230            2240            2250            2260
           *        *      *        *      *        *      *        *
         AAG ACA AAG CCG CGG GAG GAG CAG TTC AAC AGC ACG TAC CGT
         TTC TGT TTC GGC GCC CTC CTC GTC AAG TTG TCG TGC ATG GCA
         Lys Thr Lys Pro Arg Glu Glu Gln Phe Asn Ser Thr Tyr Arg>
                            FC-IgG4                              >

2270            2280            2290            2300            2310
       *      *        *      *        *      *        *      *        *
     GTG GTC AGC GTC CTC ACC GTC CTG CAC CAG GAC TGG CTG AAC
     CAC CAG TCG CAG GAG TGG CAG GAC GTG GTC CTG ACC GAC TTG
     Val Val Ser Val Leu Thr Val Leu His Gln Asp Trp Leu Asn>
                          FC-IgG4                              >

2320            2330            2340            2350
           *        *      *        *      *        *      *        *
         GGC AAG GAG TAC AAG TGC AAG GTC TCC AAC AAA GGC CTC CCG
         CCG TTC CTC ATG TTC ACG TTC CAG AGG TTG TTT CCG GAG GGC
         Gly Lys Glu Tyr Lys Cys Lys Val Ser Asn Lys Gly Leu Pro>
                            FC-IgG4                              >
```

Figure 42H

```
          2360          2370          2380          2390
            *       *     *       *     *       *     *       *
         TCC TCC ATC GAG AAA ACC ATC TCC AAA GCC AAA GGG CAG CCC
         AGG AGG TAG CTC TTT TGG TAG AGG TTT CGG TTT CCC GTC GGG
         Ser Ser Ile Glu Lys Thr Ile Ser Lys Ala Lys Gly Gln Pro>
                              _____FC-IgG4_____>

2400          2410          2420          2430
         *   *       *     *       *     *       *     *       *
         CGA GAG CCA CAG GTG TAC ACC CTG CCC CCA TCC CAG GAG GAG
         GCT CTC GGT GTC CAC ATG TGG GAC GGG GGT AGG GTC CTC CTC
         Arg Glu Pro Gln Val Tyr Thr Leu Pro Pro Ser Gln Glu Glu>
                              _____FC-IgG4_____>

2440          2450          2460          2470
         *       *     *       *     *       *     *       *
         ATG ACC AAG AAC CAG GTC AGC CTG ACC TGC CTG GTC AAA GGC
         TAC TGG TTC TTG GTC CAG TCG GAC TGG ACG GAC CAG TTT CCG
         Met Thr Lys Asn Gln Val Ser Leu Thr Cys Leu Val Lys Gly>
                              _____FC-IgG4_____>

2480          2490          2500          2510          2520
     *       *     *       *     *       *     *       *     *
     TTC TAC CCC AGC GAC ATC GCC GTG GAG TGG GAG AGC AAT GGG
     AAG ATG GGG TCG CTG TAG CGG CAC CTC ACC CTC TCG TTA CCC
     Phe Tyr Pro Ser Asp Ile Ala Val Glu Trp Glu Ser Asn Gly>
                              _____FC-IgG4_____>

2530          2540          2550          2560
            *       *     *       *     *       *     *       *
         CAG CCG GAG AAC AAC TAC AAG ACC ACG CCT CCC GTG CTG GAC
         GTC GGC CTC TTG TTG ATG TTC TGG TGC GGA GGG CAC GAC CTG
         Gln Pro Glu Asn Asn Tyr Lys Thr Thr Pro Pro Val Leu Asp>
                              _____FC-IgG4_____>

2570          2580          2590          2600
            *       *     *       *     *       *     *       *
         TCC GAC GGC TCC TTC TTC CTC TAC AGC AGG CTA ACC GTG GAC
         AGG CTG CCG AGG AAG AAG GAG ATG TCG TCC GAT TGG CAC CTG
         Ser Asp Gly Ser Phe Phe Leu Tyr Ser Arg Leu Thr Val Asp>
                              _____FC-IgG4_____>

2610          2620          2630          2640
         *       *     *       *     *       *     *       *     *
         AAG AGC AGG TGG CAG GAG GGG AAT GTC TTC TCA TGC TCC GTG
         TTC TCG TCC ACC GTC CTC CCC TTA CAG AAG AGT ACG AGG CAC
         Lys Ser Arg Trp Gln Glu Gly Asn Val Phe Ser Cys Ser Val>
                              _____FC-IgG4_____>

2650          2660          2670          2680
            *       *     *       *     *       *     *       *
         ATG CAT GAG GCT CTG CAC AAC CAC TAC ACA CAG AAG AGC CTC
         TAC GTA CTC CGA GAC GTG TTG GTG ATG TGT GTC TTC TCG GAG
         Met His Glu Ala Leu His Asn His Tyr Thr Gln Lys Ser Leu>
                              _____FC-IgG4_____>
```

Figure 42 I

```
         2690                2700
           *         *        *         *
        TCC CTG TCT CTG GGT AAA TGA
        AGG GAC AGA GAC CCA TTT ACT
        Ser Leu Ser Leu Gly Lys ***>
                    ___FC-IgG4_____>
```

Figure 43A

```
              10              20              30              40
         *      *       *      *      *       *      *       *
        ATG GTG CTT CTG TGG TGT GTA GTG AGT CTC TAC TTT TAT GGA
        TAC CAC GAA GAC ACC ACA CAT CAC TCA GAG ATG AAA ATA CCT
        Met Val Leu Leu Trp Cys Val Val Ser Leu Tyr Phe Tyr Gly>
        _____SIGNAL PEPTIDE_____>
        _____IL-1RAcP_____>

50              60              70              80
         *      *       *      *      *       *      *       *
        ATC CTG CAA AGT GAT GCC TCA GAA CGC TGC GAT GAC TGG GGA
        TAG GAC GTT TCA CTA CGG AGT CTT GCG ACG CTA CTG ACC CCT
        Ile Leu Gln Ser Asp Ala>
        ___SIGNAL PEPTIDE ____>
                              Ser Glu Arg Cys Asp Asp Trp Gly>
                              _____IL-1RAcP_____>

90             100             110             120
         *      *       *      *      *       *      *       *
        CTA GAC ACC ATG AGG CAA ATC CAA GTG TTT GAA GAT GAG CCA
        GAT CTG TGG TAC TCC GTT TAG GTT CAC AAA CTT CTA CTC GGT
        Leu Asp Thr Met Arg Gln Ile Gln Val Phe Glu Asp Glu Pro>
        _____IL-1RAcP_____>

130             140             150             160
         *      *       *      *      *       *      *       *
        GCT CGC ATC AAG TGC CCA CTC TTT GAA CAC TTC TTG AAA TTC
        CGA GCG TAG TTC ACG GGT GAG AAA CTT GTG AAG AAC TTT AAG
        Ala Arg Ile Lys Cys Pro Leu Phe Glu His Phe Leu Lys Phe>
        _____IL-1RAcP_____>

170             180             190             200            210
         *      *       *      *      *       *      *       *      *
        AAC TAC AGC ACA GCC CAT TCA GCT GGC CTT ACT CTG ATC TGG
        TTG ATG TCG TGT CGG GTA AGT CGA CCG GAA TGA GAC TAG ACC
        Asn Tyr Ser Thr Ala His Ser Ala Gly Leu Thr Leu Ile Trp>
                              _____IL-1RAcP_____>

220             230             240             250
         *      *       *      *      *       *      *       *
        TAT TGG ACT AGG CAG GAC CGG GAC CTT GAG GAG CCA ATT AAC
        ATA ACC TGA TCC GTC CTG GCC CTG GAA CTC CTC GGT TAA TTG
        Tyr Trp Thr Arg Gln Asp Arg Asp Leu Glu Glu Pro Ile Asn>
                              _____IL-1RAcP_____>

260             270             280             290
         *      *       *      *      *       *      *       *
        TTC CGC CTC CCC GAG AAC CGC ATT AGT AAG GAG AAA GAT GTG
        AAG GCG GAG GGG CTC TTG GCG TAA TCA TTC CTC TTT CTA CAC
        Phe Arg Leu Pro Glu Asn Arg Ile Ser Lys Glu Lys Asp Val>
                              _____IL-1RAcP_____>

300             310             320             330
         *      *       *      *      *       *      *       *
        CTG TGG TTC CGG CCC ACT CTC CTC AAT GAC ACT GGC AAC TAT
        GAC ACC AAG GCC GGG TGA GAG GAG TTA CTG TGA CCG TTG ATA
        Leu Trp Phe Arg Pro Thr Leu Leu Asn Asp Thr Gly Asn Tyr>
                              _____IL-1RAcP_____>
```

Figure 43B

```
          340            350            360            370
           *      *       *      *       *      *       *      *
         ACC    TGC    ATG    TTA    AGG    AAC    ACT    ACA    TAT    TGC    AGC    AAA    GTT    GCA
         TGG    ACG    TAC    AAT    TCC    TTG    TGA    TGT    ATA    ACG    TCG    TTT    CAA    CGT
         Thr    Cys    Met    Leu    Arg    Asn    Thr    Thr    Tyr    Cys    Ser    Lys    Val    Ala>
                                         _____IL-1RAcP_____>

380            390            400            410            420
    *      *       *      *       *      *       *      *       *
  TTT    CCC    TTG    GAA    GTT    GTT    CAA    AAA    GAC    AGC    TGT    TTC    AAT    TCC
  AAA    GGG    AAC    CTT    CAA    CAA    GTT    TTT    CTG    TCG    ACA    AAG    TTA    AGG
  Phe    Pro    Leu    Glu    Val    Val    Gln    Lys    Asp    Ser    Cys    Phe    Asn    Ser>
  _____IL-1RAcP_____>

430            440            450            460
             *      *       *      *       *      *       *      *
           CCC    ATG    AAA    CTC    CCA    GTG    CAT    AAA    CTG    TAT    ATA    GAA    TAT    GGC
           GGG    TAC    TTT    GAG    GGT    CAC    GTA    TTT    GAC    ATA    TAT    CTT    ATA    CCG
           Pro    Met    Lys    Leu    Pro    Val    His    Lys    Leu    Tyr    Ile    Glu    Tyr    Gly>
           _____IL-1RAcP_____>

470            480            490            500
               *      *       *      *       *      *       *      *
             ATT    CAG    AGG    ATC    ACT    TGT    CCA    AAT    GTA    GAT    GGA    TAT    TTT    CCT
             TAA    GTC    TCC    TAG    TGA    ACA    GGT    TTA    CAT    CTA    CCT    ATA    AAA    GGA
             Ile    Gln    Arg    Ile    Thr    Cys    Pro    Asn    Val    Asp    Gly    Tyr    Phe    Pro>
             _____IL-1RAcP_____>

510            520            530            540
        *      *       *      *       *      *       *      *       *
      TCC    AGT    GTC    AAA    CCG    ACT    ATC    ACT    TGG    TAT    ATG    GGC    TGT    TAT
      AGG    TCA    CAG    TTT    GGC    TGA    TAG    TGA    ACC    ATA    TAC    CCG    ACA    ATA
      Ser    Ser    Val    Lys    Pro    Thr    Ile    Thr    Trp    Tyr    Met    Gly    Cys    Tyr>
      _____IL-1RAcP_____>

550            560            570            580
        *      *       *      *       *      *       *      *
      AAA    ATA    CAG    AAT    TTT    AAT    AAT    GTA    ATA    CCC    GAA    GGT    ATG    AAC
      TTT    TAT    GTC    TTA    AAA    TTA    TTA    CAT    TAT    GGG    CTT    CCA    TAC    TTG
      Lys    Ile    Gln    Asn    Phe    Asn    Asn    Val    Ile    Pro    Glu    Gly    Met    Asn>
      _____IL-1RAcP_____>

590            600            610            620            630
    *      *       *      *       *      *       *      *       *
  TTG    AGT    TTC    CTC    ATT    GCC    TTA    ATT    TCA    AAT    AAT    GGA    AAT    TAC
  AAC    TCA    AAG    GAG    TAA    CGG    AAT    TAA    AGT    TTA    TTA    CCT    TTA    ATG
  Leu    Ser    Phe    Leu    Ile    Ala    Leu    Ile    Ser    Asn    Asn    Gly    Asn    Tyr>
  _____IL-1RAcP_____>

640            650            660            670
             *      *       *      *       *      *       *      *
           ACA    TGT    GTT    GTT    ACA    TAT    CCA    GAA    AAT    GGA    CGT    ACG    TTT    CAT
           TGT    ACA    CAA    CAA    TGT    ATA    GGT    CTT    TTA    CCT    GCA    TGC    AAA    GTA
           Thr    Cys    Val    Val    Thr    Tyr    Pro    Glu    Asn    Gly    Arg    Thr    Phe    His>
           _____IL-1RAcP_____>
```

Figure 43C

```
           680              690              700              710
            *        *       *        *       *        *       *        *
           CTC ACC AGG ACT CTG ACT GTA AAG GTA GTA GGC TCT CCA AAA
           GAG TGG TCC TGA GAC TGA CAT TTC CAT CAT CCG AGA GGT TTT
           Leu Thr Arg Thr Leu Thr Val Lys Val Val Gly Ser Pro Lys>
           _____IL-1RAcP_____>

720              730              740              750
            *        *       *        *       *        *       *        *
           AAT GCA GTG CCC CCT GTG ATC CAT TCA CCT AAT GAT CAT GTG
           TTA CGT CAC GGG GGA CAC TAG GTA AGT GGA TTA CTA GTA CAC
           Asn Ala Val Pro Pro Val Ile His Ser Pro Asn Asp His Val>
           _____IL-1RAcP_____>

760              770              780              790
            *        *       *        *       *        *       *        *
           GTC TAT GAG AAA GAA CCA GGA GAG GAG CTA CTC ATT CCC TGT
           CAG ATA CTC TTT CTT GGT CCT CTC CTC GAT GAG TAA GGG ACA
           Val Tyr Glu Lys Glu Pro Gly Glu Glu Leu Leu Ile Pro Cys>
           _____IL-1RAcP_____>

800              810              820              830              840
           *        *       *        *       *        *       *        *
          ACG GTC TAT TTT AGT TTT CTG ATG GAT TCT CGC AAT GAG GTT
          TGC CAG ATA AAA TCA AAA GAC TAC CTA AGA GCG TTA CTC CAA
          Thr Val Tyr Phe Ser Phe Leu Met Asp Ser Arg Asn Glu Val>
          _____IL-1RAcP_____>

850              860              870              880
            *        *       *        *       *        *       *        *
           TGG TGG ACC ATT GAT GGA AAA AAA CCT GAT GAC ATC ACT ATT
           ACC ACC TGG TAA CTA CCT TTT TTT GGA CTA CTG TAG TGA TAA
           Trp Trp Thr Ile Asp Gly Lys Lys Pro Asp Asp Ile Thr Ile>
           _____IL-1RAcP_____>

890              900              910              920
            *        *       *        *       *        *       *        *
           GAT GTC ACC ATT AAC GAA AGT ATA AGT CAT AGT AGA ACA GAA
           CTA CAG TGG TAA TTG CTT TCA TAT TCA GTA TCA TCT TGT CTT
           Asp Val Thr Ile Asn Glu Ser Ile Ser His Ser Arg Thr Glu>
           _____IL-1RAcP_____>

930              940              950              960
            *        *       *        *       *        *       *        *
           GAT GAA ACA AGA ACT CAG ATT TTG AGC ATC AAG AAA GTT ACC
           CTA CTT TGT TCT TGA GTC TAA AAC TCG TAG TTC TTT CAA TGG
           Asp Glu Thr Arg Thr Gln Ile Leu Ser Ile Lys Lys Val Thr>
           _____IL-1RAcP_____>

970              980              990              1000
            *        *       *        *       *        *       *        *
           TCT GAG GAT CTC AAG CGC AGC TAT GTC TGT CAT GCT AGA AGT
           AGA CTC CTA GAG TTC GCG TCG ATA CAG ACA GTA CGA TCT TCA
           Ser Glu Asp Leu Lys Arg Ser Tyr Val Cys His Ala Arg Ser>
           _____IL-1RAcP_____>
```

Figure 43D

```
      1010          1020          1030          1040          1050
        *       *     *       *     *       *     *       *     *
       GCC AAA GGC GAA GTT GCC AAA GCA GCC AAG GTG AAG CAG AAA
       CGG TTT CCG CTT CAA CGG TTT CGT CGG TTC CAC TTC GTC TTT
       Ala Lys Gly Glu Val Ala Lys Ala Ala Lys Val Lys Gln Lys>
       _____IL-1RAcP_____>

1060          1070          1080          1090
                *       *     *       *     *       *     *       *
       GTG CCA GCT CCA AGA TAC ACA GTG GAA AAA TGC AAG GAA CGT
       CAC GGT CGA GGT TCT ATG TGT CAC CTT TTT ACG TTC CTT GCA
       Val Pro Ala Pro Arg Tyr Thr Val Glu>
       _____IL-1RAcP_____>
                                         Lys Cys Lys Glu Arg>
                                         _____IL-1RI_____>

1100          1110          1120          1130
                *       *     *       *     *       *     *       *
       GAA GAA AAA ATA ATT TTA GTG AGC TCA GCA AAT GAA ATC GAT
       CTT CTT TTT TAT TAA AAT CAC TCG AGT CGT TTA CTT TAG CTA
       Glu Glu Lys Ile Ile Leu Val Ser Ser Ala Asn Glu Ile Asp>
       _____IL-1RI_____>

1140          1150          1160          1170
          *     *       *     *       *     *       *     *       *
       GTT CGT CCC TGT CCT CTT AAC CCA AAT GAA CAC AAA GGC ACT
       CAA GCA GGG ACA GGA GAA TTG GGT TTA CTT GTG TTT CCG TGA
       Val Arg Pro Cys Pro Leu Asn Pro Asn Glu His Lys Gly Thr>
       _____IL-1RI_____>

1180          1190          1200          1210
          *     *       *     *       *     *       *     *       *
       ATA ACT TGG TAT AAG GAT GAC AGC AAG ACA CCT GTA TCT ACA
       TAT TGA ACC ATA TTC CTA CTG TCG TTC TGT GGA CAT AGA TGT
       Ile Thr Trp Tyr Lys Asp Asp Ser Lys Thr Pro Val Ser Thr>
       _____IL-1RI_____>

1220          1230          1240          1250          1260
     *       *     *       *     *       *     *       *     *
       GAA CAA GCC TCC AGG ATT CAT CAA CAC AAA GAG AAA CTT TGG
       CTT GTT CGG AGG TCC TAA GTA GTT GTG TTT CTC TTT GAA ACC
       Glu Gln Ala Ser Arg Ile His Gln His Lys Glu Lys Leu Trp>
       _____IL-1RI_____>

1270          1280          1290          1300
                *       *     *       *     *       *     *       *
       TTT GTT CCT GCT AAG GTG GAG GAT TCA GGA CAT TAC TAT TGC
       AAA CAA GGA CGA TTC CAC CTC CTA AGT CCT GTA ATG ATA ACG
       Phe Val Pro Ala Lys Val Glu Asp Ser Gly His Tyr Tyr Cys>
       _____IL-1RI_____>

1310          1320          1330          1340
                *       *     *       *     *       *     *       *
       GTG GTA AGA AAT TCA TCT TAC TGC CTC AGA ATT AAA ATA AGT
       CAC CAT TCT TTA AGT AGA ATG ACG GAG TCT TAA TTT TAT TCA
       Val Val Arg Asn Ser Ser Tyr Cys Leu Arg Ile Lys Ile Ser>
       _____IL-1RI_____>
```

Figure 43E

```
      1350           1360           1370           1380
   *     *       *      *       *      *       *      *       *
   GCA AAA TTT GTG GAG AAT GAG CCT AAC TTA TGT TAT AAT GCA
   CGT TTT AAA CAC CTC TTA CTC GGA TTG AAT ACA ATA TTA CGT
   Ala Lys Phe Val Glu Asn Glu Pro Asn Leu Cys Tyr Asn Ala>
   _____IL-1RI_____>

1390           1400           1410           1420
       *      *       *      *       *      *       *      *
       CAA GCC ATA TTT AAG CAG AAA CTA CCC GTT GCA GGA GAC GGA
       GTT CGG TAT AAA TTC GTC TTT GAT GGG CAA CGT CCT CTG CCT
       Gln Ala Ile Phe Lys Gln Lys Leu Pro Val Ala Gly Asp Gly>
       _____IL-1RI_____>

1430          1440           1450           1460           1470
    *       *      *       *      *       *      *       *      *
    GGA CTT GTG TGC CCT TAT ATG GAG TTT TTT AAA AAT GAA AAT
    CCT GAA CAC ACG GGA ATA TAC CTC AAA AAA TTT TTA CTT TTA
    Gly Leu Val Cys Pro Tyr Met Glu Phe Phe Lys Asn Glu Asn>
    _____IL-1RI_____>

1480           1490           1500           1510
        *      *       *      *       *      *       *      *
        AAT GAG TTA CCT AAA TTA CAG TGG TAT AAG GAT TGC AAA CCT
        TTA CTC AAT GGA TTT AAT GTC ACC ATA TTC CTA ACG TTT GGA
        Asn Glu Leu Pro Lys Leu Gln Trp Tyr Lys Asp Cys Lys Pro>
         |                      IL-1RI                        >

1520           1530           1540           1550
       *      *       *      *       *      *       *      *
       CTA CTT CTT GAC AAT ATA CAC TTT AGT GGA GTC AAA GAT AGG
       GAT GAA GAA CTG TTA TAT GTG AAA TCA CCT CAG TTT CTA TCC
       Leu Leu Leu Asp Asn Ile His Phe Ser Gly Val Lys Asp Arg>
       _____IL-1RI_____>

1560           1570           1580           1590
     *      *       *      *       *      *       *      *       *
     CTC ATC GTG ATG AAT GTG GCT GAA AAG CAT AGA GGG AAC TAT
     GAG TAG CAC TAC TTA CAC CGA CTT TTC GTA TCT CCC TTG ATA
     Leu Ile Val Met Asn Val Ala Glu Lys His Arg Gly Asn Tyr>
     _____IL-1RI_____>

1600           1610           1620           1630
      *      *       *      *       *      *       *      *
      ACT TGT CAT GCA TCC TAC ACA TAC TTG GGC AAG CAA TAT CCT
      TGA ACA GTA CGT AGG ATG TGT ATG AAC CCG TTC GTT ATA GGA
      Thr Cys His Ala Ser Tyr Thr Tyr Leu Gly Lys Gln Tyr Pro>
      _____IL-1RI_____>

1640          1650           1660           1670           1680
     *       *      *       *      *       *      *       *      *
     ATT ACC CGG GTA ATA GAA TTT ATT ACT CTA GAG GAA AAC AAA
     TAA TGG GCC CAT TAT CTT AAA TAA TGA GAT CTC CTT TTG TTT
     Ile Thr Arg Val Ile Glu Phe Ile Thr Leu Glu Glu Asn Lys>
     _____IL-1RI_____>
```

Figure 43F

```
         1690          1700          1710          1720
           *    *    *    *    *    *    *    *
         CCC  ACA  AGG  CCT  GTG  ATT  GTG  AGC  CCA  GCT  AAT  GAG  ACA  ATG
         GGG  TGT  TCC  GGA  CAC  TAA  CAC  TCG  GGT  CGA  TTA  CTC  TGT  TAC
         Pro  Thr  Arg  Pro  Val  Ile  Val  Ser  Pro  Ala  Asn  Glu  Thr  Met>
                                    __IL-1RI_____>

1730          1740          1750          1760
           *    *    *    *    *    *    *    *
         GAA  GTA  GAC  TTG  GGA  TCC  CAG  ATA  CAA  TTG  ATC  TGT  AAT  GTC
         CTT  CAT  CTG  AAC  CCT  AGG  GTC  TAT  GTT  AAC  TAG  ACA  TTA  CAG
         Glu  Val  Asp  Leu  Gly  Ser  Gln  Ile  Gln  Leu  Ile  Cys  Asn  Val>
                                    __IL-1RI_____>

1770          1780          1790          1800
           *    *    *    *    *    *    *    *    *
         ACC  GGC  CAG  TTG  AGT  GAC  ATT  GCT  TAC  TGG  AAG  TGG  AAT  GGG
         TGG  CCG  GTC  AAC  TCA  CTG  TAA  CGA  ATG  ACC  TTC  ACC  TTA  CCC
         Thr  Gly  Gln  Leu  Ser  Asp  Ile  Ala  Tyr  Trp  Lys  Trp  Asn  Gly>
                                    __IL-1RI_____>

1810          1820          1830          1840
           *    *    *    *    *    *    *    *
         TCA  GTA  ATT  GAT  GAA  GAT  GAC  CCA  GTG  CTA  GGG  GAA  GAC  TAT
         AGT  CAT  TAA  CTA  CTT  CTA  CTG  GGT  CAC  GAT  CCC  CTT  CTG  ATA
         Ser  Val  Ile  Asp  Glu  Asp  Asp  Pro  Val  Leu  Gly  Glu  Asp  Tyr>
                                    __IL-1RI_____>

1850          1860          1870          1880          1890
      *    *    *    *    *    *    *    *    *
    TAC  AGT  GTG  GAA  AAT  CCT  GCA  AAC  AAA  AGA  AGG  AGT  ACC  CTC
    ATG  TCA  CAC  CTT  TTA  GGA  CGT  TTG  TTT  TCT  TCC  TCA  TGG  GAG
    Tyr  Ser  Val  Glu  Asn  Pro  Ala  Asn  Lys  Arg  Arg  Ser  Thr  Leu>
                                __IL-1RI_____>

1900          1910          1920          1930
           *    *    *    *    *    *    *    *
         ATC  ACA  GTG  CTT  AAT  ATA  TCG  GAA  ATT  GAG  AGT  AGA  TTT  TAT
         TAG  TGT  CAC  GAA  TTA  TAT  AGC  CTT  TAA  CTC  TCA  TCT  AAA  ATA
         Ile  Thr  Val  Leu  Asn  Ile  Ser  Glu  Ile  Glu  Ser  Arg  Phe  Tyr>
                                    __IL-1RI_____>

1940          1950          1960          1970
           *    *    *    *    *    *    *    *
         AAA  CAT  CCA  TTT  ACC  TGT  TTT  GCC  AAG  AAT  ACA  CAT  GGT  ATA
         TTT  GTA  GGT  AAA  TGG  ACA  AAA  CGG  TTC  TTA  TGT  GTA  CCA  TAT
         Lys  His  Pro  Phe  Thr  Cys  Phe  Ala  Lys  Asn  Thr  His  Gly  Ile>
                                    __IL-1RI_____>

1980          1990          2000          2010
           *    *    *    *    *    *    *    *    *
         GAT  GCA  GCA  TAT  ATC  CAG  TTA  ATA  TAT  CCA  GTC  ACT  AAT  TCC
         CTA  CGT  CGT  ATA  TAG  GTC  AAT  TAT  ATA  GGT  CAG  TGA  TTA  AGG
         Asp  Ala  Ala  Tyr  Ile  Gln  Leu  Ile  Tyr  Pro  Val  Thr  Asn>
                                    __IL-1RI_____>
                                                                   Ser>
                                                                   ___>
```

Figure 43G

```
         2020          2030          2040          2050
           *    *        *    *        *    *        *
      GGA GAG TCC AAA TAC GGT CCG CCA TGC CCA CCA TGC CCA GCA
      CCT CTC AGG TTT ATG CCA GGC GGT ACG GGT GGT ACG GGT CGT
      Gly>
      ___>
          Glu Ser Lys Tyr Gly Pro Pro Cys Pro Pro Cys Pro Ala>
                                    FC-IgG4                  >

2060          2070          2080          2090          2100
        *    *        *    *        *    *        *    *        *
      CCT GAG TTC CTG GGG GGA CCA TCA GTC TTC CTG TTC CCC CCA
      GGA CTC AAG GAC CCC CCT GGT AGT CAG AAG GAC AAG GGG GGT
      Pro Glu Phe Leu Gly Gly Pro Ser Val Phe Leu Phe Pro Pro>
                                FC-IgG4                       >

2110          2120          2130          2140
             *    *        *    *        *    *        *    *
      AAA CCC AAG GAC ACT CTC ATG ATC TCC CGG ACC CCT GAG GTC
      TTT GGG TTC CTG TGA GAG TAC TAG AGG GCC TGG GGA CTC CAG
      Lys Pro Lys Asp Thr Leu Met Ile Ser Arg Thr Pro Glu Val>
                                FC-IgG4                       >

2150          2160          2170          2180
             *    *        *    *        *    *        *    *
      ACG TGC GTG GTG GTG GAC GTG AGC CAG GAA GAC CCC GAG GTC
      TGC ACG CAC CAC CAC CTG CAC TCG GTC CTT CTG GGG CTC CAG
      Thr Cys Val Val Val Asp Val Ser Gln Glu Asp Pro Glu Val>
                                FC-IgG4                       >

2190          2200          2210          2220
             *    *        *    *        *    *        *    *
      CAG TTC AAC TGG TAC GTG GAT GGC GTG GAG GTG CAT AAT GCC
      GTC AAG TTG ACC ATG CAC CTA CCG CAC CTC CAC GTA TTA CGG
      Gln Phe Asn Trp Tyr Val Asp Gly Val Glu Val His Asn Ala>
                                FC-IgG4                       >

2230          2240          2250          2260
             *    *        *    *        *    *        *    *
      AAG ACA AAG CCG CGG GAG GAG CAG TTC AAC AGC ACG TAC CGT
      TTC TGT TTC GGC GCC CTC CTC GTC AAG TTG TCG TGC ATG GCA
      Lys Thr Lys Pro Arg Glu Glu Gln Phe Asn Ser Thr Tyr Arg>
                                FC-IgG4                       >

2270          2280          2290          2300          2310
        *    *        *    *        *    *        *    *        *
      GTG GTC AGC GTC CTC ACC GTC CTG CAC CAG GAC TGG CTG AAC
      CAC CAG TCG CAG GAG TGG CAG GAC GTG GTC CTG ACC GAC TTG
      Val Val Ser Val Leu Thr Val Leu His Gln Asp Trp Leu Asn>
                                FC-IgG4                       >

2320          2330          2340          2350
             *    *        *    *        *    *        *    *
      GGC AAG GAG TAC AAG TGC AAG GTC TCC AAC AAA GGC CTC CCG
      CCG TTC CTC ATG TTC ACG TTC CAG AGG TTG TTT CCG GAG GGC
      Gly Lys Glu Tyr Lys Cys Lys Val Ser Asn Lys Gly Leu Pro>
                                FC-IgG4                       >
```

Figure 43H

```
          2360          2370          2380          2390
      *       *     *       *     *       *     *       *
    TCC TCC ATC GAG AAA ACC ATC TCC AAA GCC AAA GGG CAG CCC
    AGG AGG TAG CTC TTT TGG TAG AGG TTT CGG TTT CCC GTC GGG
    Ser Ser Ile Glu Lys Thr Ile Ser Lys Ala Lys Gly Gln Pro>
    _____FC-IgG4_____>

2400          2410          2420          2430
      *       *     *       *     *       *     *       *
    CGA GAG CCA CAG GTG TAC ACC CTG CCC CCA TCC CAG GAG GAG
    GCT CTC GGT GTC CAC ATG TGG GAC GGG GGT AGG GTC CTC CTC
    Arg Glu Pro Gln Val Tyr Thr Leu Pro Pro Ser Gln Glu Glu>
    _____FC-IgG4_____>

2440          2450          2460          2470
      *       *     *       *     *       *     *       *
    ATG ACC AAG AAC CAG GTC AGC CTG ACC TGC CTG GTC AAA GGC
    TAC TGG TTC TTG GTC CAG TCG GAC TGG ACG GAC CAG TTT CCG
    Met Thr Lys Asn Gln Val Ser Leu Thr Cys Leu Val Lys Gly>
    _____FC-IgG4_____>

2480          2490          2500          2510          2520
    *     *       *     *       *     *       *     *       *
    TTC TAC CCC AGC GAC ATC GCC GTG GAG TGG GAG AGC AAT GGG
    AAG ATG GGG TCG CTG TAG CGG CAC CTC ACC CTC TCG TTA CCC
    Phe Tyr Pro Ser Asp Ile Ala Val Glu Trp Glu Ser Asn Gly>
    _____FC-IgG4_____>

2530          2540          2550          2560
      *       *     *       *     *       *     *       *
    CAG CCG GAG AAC AAC TAC AAG ACC ACG CCT CCC GTG CTG GAC
    GTC GGC CTC TTG TTG ATG TTC TGG TGC GGA GGG CAC GAC CTG
    Gln Pro Glu Asn Asn Tyr Lys Thr Thr Pro Pro Val Leu Asp>
    _____FC-IgG4_____>

2570          2580          2590          2600
      *       *     *       *     *       *     *       *
    TCC GAC GGC TCC TTC TTC CTC TAC AGC AGG CTA ACC GTG GAC
    AGG CTG CCG AGG AAG AAG GAG ATG TCG TCC GAT TGG CAC CTG
    Ser Asp Gly Ser Phe Phe Leu Tyr Ser Arg Leu Thr Val Asp>
    _____FC-IgG4_____>

2610          2620          2630          2640
      *       *     *       *     *       *     *       *
    AAG AGC AGG TGG CAG GAG GGG AAT GTC TTC TCA TGC TCC GTG
    TTC TCG TCC ACC GTC CTC CCC TTA CAG AAG AGT ACG AGG CAC
    Lys Ser Arg Trp Gln Glu Gly Asn Val Phe Ser Cys Ser Val>
    _____FC-IgG4_____>

2650          2660          2670          2680
      *       *     *       *     *       *     *       *
    ATG CAT GAG GCT CTG CAC AAC CAC TAC ACA CAG AAG AGC CTC
    TAC GTA CTC CGA GAC GTG TTG GTG ATG TGT GTC TTC TCG GAG
    Met His Glu Ala Leu His Asn His Tyr Thr Gln Lys Ser Leu>
    _____FC-IgG4_____>
```

Figure 43 I

```
     2690              2700
       *         *       *        *
     TCC  CTG  TCT  CTG  GGT  AAA  TGA
     AGG  GAC  AGA  GAC  CCA  TTT  ACT
     Ser  Leu  Ser  Leu  Gly  Lys  ***>
               __FC-IgG4_____>
```

Figure 44A

```
              10             20             30             40
         *    *    *    *    *    *    *    *
    ATG GTG CGC TTG TAC GTG TTG GTA ATG GGA GTT TCT GCC TTC
    TAC CAC GCG AAC ATG CAC AAC CAT TAC CCT CAA AGA CGG AAG
    Met Val Arg Leu Tyr Val Leu Val Met Gly Val Ser Ala Phe>
    _____SIGNAL PEPTIDE_____>
    _____IL-1RII_____>

50             60             70             80
         *    *    *    *    *    *    *    *
    ACC CTT CAG CCT GCG GCA CAC ACA GGG GCT GCC AGA AGC TGC
    TGG GAA GTC GGA CGC CGT GTG TGT CCC CGA CGG TCT TCG ACG
    Thr Leu Gln Pro Ala Ala>
    ____SIGNAL PEPTIDE____>
                            His Thr Gly Ala Ala Arg Ser Cys>
    _____IL-1RII_____>

90            100            110            120
         *    *    *    *    *    *    *    *
    CGG TTT CGT GGG AGG CAT TAC AAG CGG GAG TTC AGG CTG GAA
    GCC AAA GCA CCC TCC GTA ATG TTC GCC CTC AAG TCC GAC CTT
    Arg Phe Arg Gly Arg His Tyr Lys Arg Glu Phe Arg Leu Glu>
    _____IL-1RII_____>

130            140            150            160
         *    *    *    *    *    *    *    *
    GGG GAG CCT GTA GCC CTG AGG TGC CCC CAG GTG CCC TAC TGG
    CCC CTC GGA CAT CGG GAC TCC ACG GGG GTC CAC GGG ATG ACC
    Gly Glu Pro Val Ala Leu Arg Cys Pro Gln Val Pro Tyr Trp>
    _____IL-1RII_____>

170            180            190            200            210
    *    *    *    *    *    *    *    *    *
    TTG TGG GCC TCT GTC AGC CCC CGC ATC AAC CTG ACA TGG CAT
    AAC ACC CGG AGA CAG TCG GGG GCG TAG TTG GAC TGT ACC GTA
    Leu Trp Ala Ser Val Ser Pro Arg Ile Asn Leu Thr Trp His>
    _____IL-1RII_____>

220            230            240            250
         *    *    *    *    *    *    *    *
    AAA AAT GAC TCT GCT AGG ACG GTC CCA GGA GAA GAA GAG ACA
    TTT TTA CTG AGA CGA TCC TGC CAG GGT CCT CTT CTT CTC TGT
    Lys Asn Asp Ser Ala Arg Thr Val Pro Gly Glu Glu Glu Thr>
    _____IL-1RII_____>

260            270            280            290
         *    *    *    *    *    *    *    *
    CGG ATG TGG GCC CAG GAC GGT GCT CTG TGG CTT CTG CCA GCC
    GCC TAC ACC CGG GTC CTG CCA CGA GAC ACC GAA GAC GGT CGG
    Arg Met Trp Ala Gln Asp Gly Ala Leu Trp Leu Leu Pro Ala>
    _____IL-1RII_____>
```

Figure 44B

```
          300                 310                 320                 330
  *    *         *         *         *         *         *         *         *
TTG   CAG   GAG   GAC   TCT   GGC   ACC   TAC   GTC   TGC   ACT   ACT   AGA   AAT
AAC   GTC   CTC   CTG   AGA   CCG   TGG   ATG   CAG   ACG   TGA   TGA   TCT   TTA
Leu   Gln   Glu   Asp   Ser   Gly   Thr   Tyr   Val   Cys   Thr   Thr   Arg   Asn>
_____IL-1RII_____>

340                 350                 360                 370
  *         *         *         *         *         *         *         *
GCT   TCT   TAC   TGT   GAC   AAA   ATG   TCC   ATT   GAG   CTC   AGA   GTT   TTT
CGA   AGA   ATG   ACA   CTG   TTT   TAC   AGG   TAA   CTC   GAG   TCT   CAA   AAA
Ala   Ser   Tyr   Cys   Asp   Lys   Met   Ser   Ile   Glu   Leu   Arg   Val   Phe>
_____IL-1RII_____>

380                 390                 400                 410                 420
  *         *         *         *         *         *         *         *         *
GAG   AAT   ACA   GAT   GCT   TTC   CTG   CCG   TTC   ATC   TCA   TAC   CCG   CAA
CTC   TTA   TGT   CTA   CGA   AAG   GAC   GGC   AAG   TAG   AGT   ATG   GGC   GTT
Glu   Asn   Thr   Asp   Ala   Phe   Leu   Pro   Phe   Ile   Ser   Tyr   Pro   Gln>
_____IL-1RII_____>

430                 440                 450                 460
  *         *         *         *         *         *         *         *
ATT   TTA   ACC   TTG   TCA   ACC   TCT   GGG   GTA   TTA   GTA   TGC   CCT   GAC
TAA   AAT   TGG   AAC   AGT   TGG   AGA   CCC   CAT   AAT   CAT   ACG   GGA   CTG
Ile   Leu   Thr   Leu   Ser   Thr   Ser   Gly   Val   Leu   Val   Cys   Pro   Asp>
_____IL-1RII_____>

470                 480                 490                 500
  *         *         *         *         *         *         *         *
CTG   AGT   GAA   TTC   ACC   CGT   GAC   AAA   ACT   GAC   GTG   AAG   ATT   CAA
GAC   TCA   CTT   AAG   TGG   GCA   CTG   TTT   TGA   CTG   CAC   TTC   TAA   GTT
Leu   Ser   Glu   Phe   Thr   Arg   Asp   Lys   Thr   Asp   Val   Lys   Ile   Gln>
_____IL-1RII_____>

510                 520                 530                 540
  *         *         *         *         *         *         *         *         *
TGG   TAC   AAG   GAT   TCT   CTT   CTT   TTG   GAT   AAA   GAC   AAT   GAG   AAA
ACC   ATG   TTC   CTA   AGA   GAA   GAA   AAC   CTA   TTT   CTG   TTA   CTC   TTT
Trp   Tyr   Lys   Asp   Ser   Leu   Leu   Leu   Asp   Lys   Asp   Asn   Glu   Lys>
_____IL-1RII_____>

550                 560                 570                 580
  *         *         *         *         *         *         *         *         *
TTT   CTA   AGT   GTG   AGG   GGG   ACC   ACT   CAC   TTA   CTC   GTA   CAC   GAT
AAA   GAT   TCA   CAC   TCC   CCC   TGG   TGA   GTG   AAT   GAG   CAT   GTG   CTA
Phe   Leu   Ser   Val   Arg   Gly   Thr   Thr   His   Leu   Leu   Val   His   Asp>
_____IL-1RII_____>
```

Figure 44C

```
       590           600           610           620           630
        *    *        *    *        *    *        *    *        *
       GTG GCC CTG GAA GAT GCT GGC TAT TAC CGC TGT GTC CTG ACA
       CAC CGG GAC CTT CTA CGA CCG ATA ATG GCG ACA CAG GAC TGT
       Val Ala Leu Glu Asp Ala Gly Tyr Tyr Arg Cys Val Leu Thr>
                             _____IL-1RII_____>

640           650           660           670
              *    *        *    *        *    *        *    *
             TTT GCC CAT GAA GGC CAG CAA TAC AAC ATC ACT AGG AGT ATT
             AAA CGG GTA CTT CCG GTC GTT ATG TTG TAG TGA TCC TCA TAA
             Phe Ala His Glu Gly Gln Gln Tyr Asn Ile Thr Arg Ser Ile>
                                   _____IL-1RII_____>

680           690           700           710
              *    *        *    *        *    *        *    *
             GAG CTA CGC ATC AAG AAA AAA AAA GAA GAG ACC ATT CCT GTG
             CTC GAT GCG TAG TTC TTT TTT TTT CTT CTC TGG TAA GGA CAC
             Glu Leu Arg Ile Lys Lys Lys Lys Glu Glu Thr Ile Pro Val>
                                   _____IL-1RII_____>

720           730           740           750
        *    *        *    *        *    *        *    *        *
       ATC ATT TCC CCC CTC AAG ACC ATA TCA GCT TCT CTG GGG TCA
       TAG TAA AGG GGG GAG TTC TGG TAT AGT CGA AGA GAC CCC AGT
       Ile Ile Ser Pro Leu Lys Thr Ile Ser Ala Ser Leu Gly Ser>
                             _____IL-1RII_____>

760           770           780           790
        *    *        *    *        *    *        *    *        *
       AGA CTG ACA ATC CCA TGT AAG GTG TTT CTG GGA ACC GGC ACA
       TCT GAC TGT TAG GGT ACA TTC CAC AAA GAC CCT TGG CCG TGT
       Arg Leu Thr Ile Pro Cys Lys Val Phe Leu Gly Thr Gly Thr>
                             _____IL-1RII_____>

800           810           820           830           840
        *    *        *    *        *    *        *    *        *
       CCC TTA ACC ACC ATG CTG TGG TGG ACG GCC AAT GAC ACC CAC
       GGG AAT TGG TGG TAC GAC ACC ACC TGC CGG TTA CTG TGG GTG
       Pro Leu Thr Thr Met Leu Trp Trp Thr Ala Asn Asp Thr His>
                             _____IL-1RII_____>

850           860           870           880
              *    *        *    *        *    *        *    *
             ATA GAG AGC GCC TAC CCG GGA GGC CGC GTG ACC GAG GGG CCA
             TAT CTC TCG CGG ATG GGC CCT CCG GCG CAC TGG CTC CCC GGT
             Ile Glu Ser Ala Tyr Pro Gly Gly Arg Val Thr Glu Gly Pro>
                                   _____IL-1RII_____>

890           900           910           920
              *    *        *    *        *    *        *    *
             CGC CAG GAA TAT TCA GAA AAT AAT GAG AAC TAC ATT GAA GTG
             GCG GTC CTT ATA AGT CTT TTA TTA CTC TTG ATG TAA CTT CAC
             Arg Gln Glu Tyr Ser Glu Asn Asn Glu Asn Tyr Ile Glu Val>
                                   _____IL-1RII_____>
```

Figure 44D

```
         930           940           950           960
    *      *      *      *      *      *      *      *      *
   CCA TTG ATT TTT GAT CCT GTC ACA AGA GAG GAT TTG CAC ATG
   GGT AAC TAA AAA CTA GGA CAG TGT TCT CTC CTA AAC GTG TAC
   Pro Leu Ile Phe Asp Pro Val Thr Arg Glu Asp Leu His Met>
                              IL-1RII                      >

970           980           990          1000
    *      *      *      *      *      *      *      *
   GAT TTT AAA TGT GTT GTC CAT AAT ACC CTG AGT TTT CAG ACA
   CTA AAA TTT ACA CAA CAG GTA TTA TGG GAC TCA AAA GTC TGT
   Asp Phe Lys Cys Val Val His Asn Thr Leu Ser Phe Gln Thr>
                              IL-1RII                      >

1010          1020          1030          1040          1050
    *      *      *      *      *      *      *      *      *
   CTA CGC ACC ACA GTC AAG GAA GCC TCC TCC ACG TTC TCA GAA
   GAT GCG TGG TGT CAG TTC CTT CGG AGG AGG TGC AAG AGT CTT
                                                   Ser Glu>
                                                          >

Leu Arg Thr Thr Val Lys Glu Ala Ser Ser Thr Phe>
                    IL-1RII                       >

1060          1070          1080          1090
    *      *      *      *      *      *      *      *
   CGC TGC GAT GAC TGG GGA CTA GAC ACC ATG AGG CAA ATC CAA
   GCG ACG CTA CTG ACC CCT GAT CTG TGG TAC TCC GTT TAG GTT
   Arg Cys Asp Asp Trp Gly Leu Asp Thr Met Arg Gln Ile Gln>
                             IL-1RAcP                      >

1100          1110          1120          1130
    *      *      *      *      *      *      *      *
   GTG TTT GAA GAT GAG CCA GCT CGC ATC AAG TGC CCA CTC TTT
   CAC AAA CTT CTA CTC GGT CGA GCG TAG TTC ACG GGT GAG AAA
   Val Phe Glu Asp Glu Pro Ala Arg Ile Lys Cys Pro Leu Phe>
                             IL-1RAcP                      >

1140          1150          1160          1170
    *      *      *      *      *      *      *      *      *
   GAA CAC TTC TTG AAA TTC AAC TAC AGC ACA GCC CAT TCA GCT
   CTT GTG AAG AAC TTT AAG TTG ATG TCG TGT CGG GTA AGT CGA
   Glu His Phe Leu Lys Phe Asn Tyr Ser Thr Ala His Ser Ala>
                             IL-1RAcP                      >

1180          1190          1200          1210
    *      *      *      *      *      *      *      *
   GGC CTT ACT CTG ATC TGG TAT TGG ACT AGG CAG GAC CGG GAC
   CCG GAA TGA GAC TAG ACC ATA ACC TGA TCC GTC CTG GCC CTG
   Gly Leu Thr Leu Ile Trp Tyr Trp Thr Arg Gln Asp Arg Asp>
                             IL-1RAcP                      >
```

Figure 44E

```
     1220        1230        1240        1250        1260
       *           *           *           *           *
    CTT GAG GAG CCA ATT AAC TTC CGC CTC CCC GAG AAC CGC ATT
    GAA CTC CTC GGT TAA TTG AAG GCG GAG GGG CTC TTG GCG TAA
    Leu Glu Glu Pro Ile Asn Phe Arg Leu Pro Glu Asn Arg Ile>
    _____IL-1RAcP_____>

1270        1280        1290        1300
             *           *           *           *
    AGT AAG GAG AAA GAT GTG CTG TGG TTC CGG CCC ACT CTC CTC
    TCA TTC CTC TTT CTA CAC GAC ACC AAG GCC GGG TGA GAG GAG
    Ser Lys Glu Lys Asp Val Leu Trp Phe Arg Pro Thr Leu Leu>
    _____IL-1RAcP_____>

1310        1320        1330        1340
             *           *           *           *
    AAT GAC ACT GGC AAC TAT ACC TGC ATG TTA AGG AAC ACT ACA
    TTA CTG TGA CCG TTG ATA TGG ACG TAC AAT TCC TTG TGA TGT
    Asn Asp Thr Gly Asn Tyr Thr Cys Met Leu Arg Asn Thr Thr>
    _____IL-1RAcP_____>

1350        1360        1370        1380
           *           *           *           *
    TAT TGC AGC AAA GTT GCA TTT CCC TTG GAA GTT GTT CAA AAA
    ATA ACG TCG TTT CAA CGT AAA GGG AAC CTT CAA CAA GTT TTT
    Tyr Cys Ser Lys Val Ala Phe Pro Leu Glu Val Val Gln Lys>
    _____IL-1RAcP_____>

1390        1400        1410        1420
           *           *           *           *
    GAC AGC TGT TTC AAT TCC CCC ATG AAA CTC CCA GTG CAT AAA
    CTG TCG ACA AAG TTA AGG GGG TAC TTT GAG GGT CAC GTA TTT
    Asp Ser Cys Phe Asn Ser Pro Met Lys Leu Pro Val His Lys>
    _____IL-1RAcP_____>

1430        1440        1450        1460        1470
      *           *           *           *           *
    CTG TAT ATA GAA TAT GGC ATT CAG AGG ATC ACT TGT CCA AAT
    GAC ATA TAT CTT ATA CCG TAA GTC TCC TAG TGA ACA GGT TTA
    Leu Tyr Ile Glu Tyr Gly Ile Gln Arg Ile Thr Cys Pro Asn>
    _____IL-1RAcP_____>

1480        1490        1500        1510
             *           *           *           *
    GTA GAT GGA TAT TTT CCT TCC AGT GTC AAA CCG ACT ATC ACT
    CAT CTA CCT ATA AAA GGA AGG TCA CAG TTT GGC TGA TAG TGA
    Val Asp Gly Tyr Phe Pro Ser Ser Val Lys Pro Thr Ile Thr>
    _____IL-1RAcP_____>

1520        1530        1540        1550
           *           *           *           *
    TGG TAT ATG GGC TGT TAT AAA ATA CAG AAT TTT AAT AAT GTA
    ACC ATA TAC CCG ACA ATA TTT TAT GTC TTA AAA TTA TTA CAT
    Trp Tyr Met Gly Cys Tyr Lys Ile Gln Asn Phe Asn Asn Val>
    _____IL-1RAcP_____>
```

Figure 44F

```
        1560            1570            1580            1590
     *       *       *       *       *       *       *       *       *
    ATA CCC GAA GGT ATG AAC TTG AGT TTC CTC ATT GCC TTA ATT
    TAT GGG CTT CCA TAC TTG AAC TCA AAG GAG TAA CGG AAT TAA
    Ile Pro Glu Gly Met Asn Leu Ser Phe Leu Ile Ala Leu Ile>
    _____IL-1RAcP_____>

1600            1610            1620            1630
     *       *       *       *       *       *       *       *
    TCA AAT AAT GGA AAT TAC ACA TGT GTT GTT ACA TAT CCA GAA
    AGT TTA TTA CCT TTA ATG TGT ACA CAA CAA TGT ATA GGT CTT
    Ser Asn Asn Gly Asn Tyr Thr Cys Val Val Thr Tyr Pro Glu>
    _____IL-1RAcP_____>

1640           1650            1660            1670           1680
    *       *       *       *       *       *       *       *       *
    AAT GGA CGT ACG TTT CAT CTC ACC AGG ACT CTG ACT GTA AAG
    TTA CCT GCA TGC AAA GTA GAG TGG TCC TGA GAC TGA CAT TTC
    Asn Gly Arg Thr Phe His Leu Thr Arg Thr Leu Thr Val Lys>
    _____IL-1RAcP_____>

1690            1700            1710            1720
         *       *       *       *       *       *       *       *
        GTA GTA GGC TCT CCA AAA AAT GCA GTG CCC CCT GTG ATC CAT
        CAT CAT CCG AGA GGT TTT TTA CGT CAC GGG GGA CAC TAG GTA
        Val Val Gly Ser Pro Lys Asn Ala Val Pro Pro Val Ile His>
    _____IL-1RAcP_____>

1730            1740            1750            1760
        *       *       *       *       *       *       *       *
        TCA CCT AAT GAT CAT GTG GTC TAT GAG AAA GAA CCA GGA GAG
        AGT GGA TTA CTA GTA CAC CAG ATA CTC TTT CTT GGT CCT CTC
        Ser Pro Asn Asp His Val Val Tyr Glu Lys Glu Pro Gly Glu>
    _____IL-1RAcP_____>

1770            1780            1790            1800
        *       *       *       *       *       *       *       *       *
        GAG CTA CTC ATT CCC TGT ACG GTC TAT TTT AGT TTT CTG ATG
        CTC GAT GAG TAA GGG ACA TGC CAG ATA AAA TCA AAA GAC TAC
        Glu Leu Leu Ile Pro Cys Thr Val Tyr Phe Ser Phe Leu Met>
    _____IL-1RAcP_____>

1810            1820            1830            1840
        *       *       *       *       *       *       *       *
        GAT TCT CGC AAT GAG GTT TGG TGG ACC ATT GAT GGA AAA AAA
        CTA AGA GCG TTA CTC CAA ACC ACC TGG TAA CTA CCT TTT TTT
        Asp Ser Arg Asn Glu Val Trp Trp Thr Ile Asp Gly Lys Lys>
    _____IL-1RAcP_____>

1850           1860            1870            1880           1890
    *       *       *       *       *       *       *       *       *
    CCT GAT GAC ATC ACT ATT GAT GTC ACC ATT AAC GAA AGT ATA
    GGA CTA CTG TAG TGA TAA CTA CAG TGG TAA TTG CTT TCA TAT
    Pro Asp Asp Ile Thr Ile Asp Val Thr Ile Asn Glu Ser Ile>
    _____IL-1RAcP_____>
```

Figure 44G

```
        1900           1910          1920           1930
    *     *       *      *      *      *      *      *
AGT CAT AGT AGA ACA GAA GAT GAA ACA AGA ACT CAG ATT TTG
TCA GTA TCA TCT TGT CTT CTA CTT TGT TCT TGA GTC TAA AAC
Ser His Ser Arg Thr Glu Asp Glu Thr Arg Thr Gln Ile Leu>
_____IL-1RAcP_____>

1940          1950           1960          1970
    *     *      *      *      *      *      *      *
AGC ATC AAG AAA GTT ACC TCT GAG GAT CTC AAG CGC AGC TAT
TCG TAG TTC TTT CAA TGG AGA CTC CTA GAG TTC GCG TCG ATA
Ser Ile Lys Lys Val Thr Ser Glu Asp Leu Lys Arg Ser Tyr>
_____IL-1RAcP_____>

1980           1990          2000           2010
    *     *      *      *      *      *      *      *      *
GTC TGT CAT GCT AGA AGT GCC AAA GGC GAA GTT GCC AAA GCA
CAG ACA GTA CGA TCT TCA CGG TTT CCG CTT CAA CGG TTT CGT
Val Cys His Ala Arg Ser Ala Lys Gly Glu Val Ala Lys Ala>
_____IL-1RAcP_____>

2020          2030          2040           2050
    *     *      *      *      *      *      *      *
GCC AAG GTG AAG CAG AAA GTG CCA GCT CCA AGA TAC ACA GTG
CGG TTC CAC TTC GTC TTT CAC GGT CGA GGT TCT ATG TGT CAC
Ala Lys Val Lys Gln Lys Val Pro Ala Pro Arg Tyr Thr Val>
_____IL-1RAcP_____>

2060          2070          2080          2090           2100
    *     *      *      *      *      *      *      *      *
TCC GGA GAC AAA ACT CAC ACA TGC CCA CCG TGC CCA GCA CCT
AGG CCT CTG TTT TGA GTG TGT ACG GGT GGC ACG GGT CGT GGA
Ser Gly Asp Lys Thr His Thr Cys Pro Pro Cys Pro Ala Pro>
_____FC-IgG1_____>

2110          2120          2130          2140
    *     *      *      *      *      *      *      *
GAA CTC CTG GGG GGA CCG TCA GTC TTC CTC TTC CCC CCA AAA
CTT GAG GAC CCC CCT GGC AGT CAG AAG GAG AAG GGG GGT TTT
Glu Leu Leu Gly Gly Pro Ser Val Phe Leu Phe Pro Pro Lys>
_____FC-IgG1_____>

2150          2160          2170          2180
    *     *      *      *      *      *      *      *
CCC AAG GAC ACC CTC ATG ATC TCC CGG ACC CCT GAG GTC ACA
GGG TTC CTG TGG GAG TAC TAG AGG GCC TGG GGA CTC CAG TGT
Pro Lys Asp Thr Leu Met Ile Ser Arg Thr Pro Glu Val Thr>
_____FC-IgG1_____>

2190          2200          2210          2220
    *     *      *      *      *      *      *      *
TGC GTG GTG GTG GAC GTG AGC CAC GAA GAC CCT GAG GTC AAG
ACG CAC CAC CAC CTG CAC TCG GTG CTT CTG GGA CTC CAG TTC
Cys Val Val Val Asp Val Ser His Glu Asp Pro Glu Val Lys>
_____FC-IgG1_____>
```

Figure 44H

```
         2230            2240          2250           2260
            *         *    *        *     *        *     *     *
         TTC AAC TGG TAC GTG GAC GGC GTG GAG GTG CAT AAT GCC AAG
         AAG TTG ACC ATG CAC CTG CCG CAC CTC CAC GTA TTA CGG TTC
         Phe Asn Trp Tyr Val Asp Gly Val Glu Val His Asn Ala Lys>
                              __FC-IgG1_____>

2270           2280            2290           2300           2310
      *        *     *        *     *        *     *        *     *
   ACA AAG CCG CGG GAG GAG CAG TAC AAC AGC ACG TAC CGT GTG
   TGT TTC GGC GCC CTC CTC GTC ATG TTG TCG TGC ATG GCA CAC
   Thr Lys Pro Arg Glu Glu Gln Tyr Asn Ser Thr Tyr Arg Val>
   _____FC-IgG1_____>

2320           2330          2340           2350
                 *     *        *     *        *     *        *     *
         GTC AGC GTC CTC ACC GTC CTG CAC CAG GAC TGG CTG AAT GGC
         CAG TCG CAG GAG TGG CAG GAC GTG GTC CTG ACC GAC TTA CCG
         Val Ser Val Leu Thr Val Leu His Gln Asp Trp Leu Asn Gly>
         _____FC-IgG1_____>

2360           2370          2380           2390
                 *     *        *     *        *     *        *     *
         AAG GAG TAC AAG TGC AAG GTC TCC AAC AAA GCC CTC CCA GCC
         TTC CTC ATG TTC ACG TTC CAG AGG TTG TTT CGG GAG GGT CGG
         Lys Glu Tyr Lys Cys Lys Val Ser Asn Lys Ala Leu Pro Ala>
         _____FC-IgG1_____>

2400           2410           2420           2430
           *        *     *        *     *        *     *        *     *
        CCC ATC GAG AAA ACC ATC TCC AAA GCC AAA GGG CAG CCC CGA
        GGG TAG CTC TTT TGG TAG AGG TTT CGG TTT CCC GTC GGG GCT
        Pro Ile Glu Lys Thr Ile Ser Lys Ala Lys Gly Gln Pro Arg>
        _____FC-IgG1_____>

2440           2450          2460           2470
              *        *     *        *     *        *     *        *
           GAA CCA CAG GTG TAC ACC CTG CCC CCA TCC CGG GAT GAG CTG
           CTT GGT GTC CAC ATG TGG GAC GGG GGT AGG GCC CTA CTC GAC
           Glu Pro Gln Val Tyr Thr Leu Pro Pro Ser Arg Asp Glu Leu>
           _____FC-IgG1_____>

2480           2490           2500           2510           2520
         *        *     *        *     *        *     *        *     *
      ACC AAG AAC CAG GTC AGC CTG ACC TGC CTG GTC AAA GGC TTC
      TGG TTC TTG GTC CAG TCG GAC TGG ACG GAC CAG TTT CCG AAG
      Thr Lys Asn Gln Val Ser Leu Thr Cys Leu Val Lys Gly Phe>
      _____FC-IgG1_____>

2530           2540          2550           2560
                 *     *        *     *        *     *        *     *
         TAT CCC AGC GAC ATC GCC GTG GAG TGG GAG AGC AAT GGG CAG
         ATA GGG TCG CTG TAG CGG CAC CTC ACC CTC TCG TTA CCC GTC
         Tyr Pro Ser Asp Ile Ala Val Glu Trp Glu Ser Asn Gly Gln>
         _____FC-IgG1_____>
```

Figure 44I

```
        2570            2580            2590            2600
    *       *       *       *       *       *       *       *
CCG GAG AAC AAC TAC AAG ACC ACG CCT CCC GTG CTG GAC TCC
GGC CTC TTG TTG ATG TTC TGG TGC GGA GGG CAC GAC CTG AGG
Pro Glu Asn Asn Tyr Lys Thr Thr Pro Pro Val Leu Asp Ser>
                         FC-IgG1                              >

2610            2620            2630            2640
    *       *       *       *       *       *       *       *       *
GAC GGC TCC TTC TTC CTC TAT AGC AAG CTC ACC GTG GAC AAG
CTG CCG AGG AAG AAG GAG ATA TCG TTC GAG TGG CAC CTG TTC
Asp Gly Ser Phe Phe Leu Tyr Ser Lys Leu Thr Val Asp Lys>
                         FC-IgG1                              >

2650            2660            2670            2680
    *       *       *       *       *       *       *       *
AGC AGG TGG CAG CAG GGG AAC GTC TTC TCA TGC TCC GTG ATG
TCG TCC ACC GTC GTC CCC TTG CAG AAG AGT ACG AGG CAC TAC
Ser Arg Trp Gln Gln Gly Asn Val Phe Ser Cys Ser Val Met>
                         FC-IgG1                              >

2690        2700        2710        2720        2730
    *       *       *       *       *       *       *       *       *
CAT GAG GCT CTG CAC AAC CAC TAC ACG CAG AAG AGC CTC TCC
GTA CTC CGA GAC GTG TTG GTG ATG TGC GTC TTC TCG GAG AGG
His Glu Ala Leu His Asn His Tyr Thr Gln Lys Ser Leu Ser>
                         FC-IgG1                              >

2740
    *       *       *
CTG TCT CCG GGT AAA TGA
GAC AGA GGC CCA TTT ACT
Leu Ser Pro Gly Lys ***>
         FC-IgG1         >
```

Figure 45A

```
             10           20           30           40
         *    *    *    *    *    *    *    *
ATG GTG CGC TTG TAC GTG TTG GTA ATG GGA GTT TCT GCC TTC
TAC CAC GCG AAC ATG CAC AAC CAT TAC CCT CAA AGA CGG AAG
Met Val Arg Leu Tyr Val Leu Val Met Gly Val Ser Ala Phe>
_____SIGNAL PEPTIDE_____>
_____IL-1RII_____>

50           60           70           80
         *    *    *    *    *    *    *    *
ACC CTT CAG CCT GCG GCA CAC ACA GGG GCT GCC AGA AGC TGC
TGG GAA GTC GGA CGC CGT GTG TGT CCC CGA CGG TCT TCG ACG
Thr Leu Gln Pro Ala Ala>
____SIGNAL PEPTIDE____>
                        His Thr Gly Ala Ala Arg Ser Cys>
_____IL-1RII_____>

90          100          110          120
         *    *    *    *    *    *    *    *
CGG TTT CGT GGG AGG CAT TAC AAG CGG GAG TTC AGG CTG GAA
GCC AAA GCA CCC TCC GTA ATG TTC GCC CTC AAG TCC GAC CTT
Arg Phe Arg Gly Arg His Tyr Lys Arg Glu Phe Arg Leu Glu>
_____IL-1RII_____>

130          140          150          160
         *    *    *    *    *    *    *    *
GGG GAG CCT GTA GCC CTG AGG TGC CCC CAG GTG CCC TAC TGG
CCC CTC GGA CAT CGG GAC TCC ACG GGG GTC CAC GGG ATG ACC
Gly Glu Pro Val Ala Leu Arg Cys Pro Gln Val Pro Tyr Trp>
_____IL-1RII_____>

170          180          190          200          210
    *    *    *    *    *    *    *    *    *
TTG TGG GCC TCT GTC AGC CCC CGC ATC AAC CTG ACA TGG CAT
AAC ACC CGG AGA CAG TCG GGG GCG TAG TTG GAC TGT ACC GTA
Leu Trp Ala Ser Val Ser Pro Arg Ile Asn Leu Thr Trp His>
_____IL-1RII_____>

220          230          240          250
         *    *    *    *    *    *    *    *
AAA AAT GAC TCT GCT AGG ACG GTC CCA GGA GAA GAA CAG ACA
TTT TTA CTG AGA CGA TCC TGC CAG GGT CCT CTT CTT CTC TGT
Lys Asn Asp Ser Ala Arg Thr Val Pro Gly Glu Glu Glu Thr>
_____IL-1RII_____>

260          270          280          290
         *    *    *    *    *    *    *    *
CGG ATG TGG GCC CAG GAC GGT GCT CTG TGG CTT CTG CCA GCC
GCC TAC ACC CGG GTC CTG CCA CGA GAC ACC GAA GAC GGT CGG
Arg Met Trp Ala Gln Asp Gly Ala Leu Trp Leu Leu Pro Ala>
_____IL-1RII_____>
```

Figure 45B

```
         300            310            320            330
    *     *      *      *      *      *      *      *      *
TTG  CAG  GAG  GAC  TCT  GGC  ACC  TAC  GTC  TGC  ACT  ACT  AGA  AAT
AAC  GTC  CTC  CTG  AGA  CCG  TGG  ATG  CAG  ACG  TGA  TGA  TCT  TTA
Leu  Gln  Glu  Asp  Ser  Gly  Thr  Tyr  Val  Cys  Thr  Thr  Arg  Asn>
                              ____IL-1RII_____>

340            350            360            370
      *      *      *      *      *      *      *      *
GCT  TCT  TAC  TGT  GAC  AAA  ATG  TCC  ATT  GAG  CTC  AGA  GTT  TTT
CGA  AGA  ATG  ACA  CTG  TTT  TAC  AGG  TAA  CTC  GAG  TCT  CAA  AAA
Ala  Ser  Tyr  Cys  Asp  Lys  Met  Ser  Ile  Glu  Leu  Arg  Val  Phe>
                              ____IL-1RII_____>

380            390            400            410            420
  *      *      *      *      *      *      *      *      *
GAG  AAT  ACA  GAT  GCT  TTC  CTG  CCG  TTC  ATC  TCA  TAC  CCG  CAA
CTC  TTA  TGT  CTA  CGA  AAG  GAC  GGC  AAG  TAG  AGT  ATG  GGC  GTT
Glu  Asn  Thr  Asp  Ala  Phe  Leu  Pro  Phe  Ile  Ser  Tyr  Pro  Gln>
                              ____IL-1RII_____>

430            440            450            460
      *      *      *      *      *      *      *      *
ATT  TTA  ACC  TTG  TCA  ACC  TCT  GGG  GTA  TTA  GTA  TGC  CCT  GAC
TAA  AAT  TGG  AAC  AGT  TGG  AGA  CCC  CAT  AAT  CAT  ACG  GGA  CTG
Ile  Leu  Thr  Leu  Ser  Thr  Ser  Gly  Val  Leu  Val  Cys  Pro  Asp>
                              ____IL-1RII_____>

470            480            490            500
      *      *      *      *      *      *      *      *
CTG  AGT  GAA  TTC  ACC  CGT  GAC  AAA  ACT  GAC  GTG  AAG  ATT  CAA
GAC  TCA  CTT  AAG  TGG  GCA  CTG  TTT  TGA  CTG  CAC  TTC  TAA  GTT
Leu  Ser  Glu  Phe  Thr  Arg  Asp  Lys  Thr  Asp  Val  Lys  Ile  Gln>
                              ____IL-1RII_____>

510            520            530            540
    *     *      *      *      *      *      *      *      *
TGG  TAC  AAG  GAT  TCT  CTT  CTT  TTG  GAT  AAA  GAC  AAT  GAG  AAA
ACC  ATG  TTC  CTA  AGA  GAA  GAA  AAC  CTA  TTT  CTG  TTA  CTC  TTT
Trp  Tyr  Lys  Asp  Ser  Leu  Leu  Leu  Asp  Lys  Asp  Asn  Glu  Lys>
                              ____IL-1RII_____>

550            560            570            580
    *     *      *      *      *      *      *      *
TTT  CTA  AGT  GTG  AGG  GGG  ACC  ACT  CAC  TTA  CTC  GTA  CAC  GAT
AAA  GAT  TCA  CAC  TCC  CCC  TGG  TGA  GTG  AAT  GAG  CAT  GTG  CTA
Phe  Leu  Ser  Val  Arg  Gly  Thr  Thr  His  Leu  Leu  Val  His  Asp>
                              ____IL-1RII_____>

590            600            610            620            630
  *      *      *      *      *      *      *      *      *
GTG  GCC  CTG  GAA  GAT  GCT  GGC  TAT  TAC  CGC  TGT  GTC  CTG  ACA
CAC  CGG  GAC  CTT  CTA  CGA  CCG  ATA  ATG  GCG  ACA  CAG  GAC  TGT
Val  Ala  Leu  Glu  Asp  Ala  Gly  Tyr  Tyr  Arg  Cys  Val  Leu  Thr>
                              ____IL-1RII_____>
```

Figure 45C

```
         640         650         660         670
           *           *           *           *    *           *           *           *
TTT GCC CAT GAA GGC CAG CAA TAC AAC ATC ACT AGG AGT ATT
AAA CGG GTA CTT CCG GTC GTT ATG TTG TAG TGA TCC TCA TAA
Phe Ala His Glu Gly Gln Gln Tyr Asn Ile Thr Arg Ser Ile>
                            IL-1RII                         >

680         690         700         710
           *           *           *           *    *           *           *
GAG CTA CGC ATC AAG AAA AAA AAA GAA GAG ACC ATT CCT GTG
CTC GAT GCG TAG TTC TTT TTT TTT CTT CTC TGG TAA GGA CAC
Glu Leu Arg Ile Lys Lys Lys Lys Glu Glu Thr Ile Pro Val>
                            IL-1RII                         >

720         730         740         750
 *         *           *           *           *    *           *           *           *
ATC ATT TCC CCC CTC AAG ACC ATA TCA GCT TCT CTG GGG TCA
TAG TAA AGG GGG GAG TTC TGG TAT AGT CGA AGA GAC CCC AGT
Ile Ile Ser Pro Leu Lys Thr Ile Ser Ala Ser Leu Gly Ser>
                            IL-1RII                         >

760         770         780         790
      *           *           *           *    *           *           *           *
AGA CTG ACA ATC CCA TGT AAG GTG TTT CTG GAA ACC GGC ACA
TCT GAC TGT TAG GGT ACA TTC CAC AAA GAC CCT TGG CCG TGT
Arg Leu Thr Ile Pro Cys Lys Val Phe Leu Gly Thr Gly Thr>
                            IL-1RII                         >

800         810         820         830         840
  *           *           *           *           *    *           *           *
CCC TTA ACC ACC ATG CTG TGG TGG ACG GCC AAT GAC ACC CAC
GGG AAT TGG TGG TAC GAC ACC ACC TGC CGG TTA CTG TGG GTG
Pro Leu Thr Thr Met Leu Trp Trp Thr Ala Asn Asp Thr His>
                            IL-1RII                         >

850         860         870         880
           *           *    *           *           *           *           *           *
ATA GAG AGC GCC TAC CCG GGA GGC CGC GTG ACC GAG GGG CCA
TAT CTC TCG CGG ATG GGC CCT CCG GCG CAC TGG CTC CCC GGT
Ile Glu Ser Ala Tyr Pro Gly Gly Arg Val Thr Glu Gly Pro>
                            IL-1RII                         >

890         900         910         920
           *           *           *           *    *           *           *           *
CGC CAG GAA TAT TCA GAA AAT AAT GAG AAC TAC ATT GAA GTG
GCG GTC CTT ATA AGT CTT TTA TTA CTC TTG ATG TAA CTT CAC
Arg Gln Glu Tyr Ser Glu Asn Asn Glu Asn Tyr Ile Glu Val>
                            IL-1RII                         >

930         940         950         960
        *           *           *           *    *           *           *           *
CCA TTG ATT TTT GAT CCT GTC ACA AGA GAG GAT TTG CAC ATG
GGT AAC TAA AAA CTA GGA CAG TGT TCT CTC CTA AAC GTG TAC
Pro Leu Ile Phe Asp Pro Val Thr Arg Glu Asp Leu His Met>
                            IL-1RII                         >
```

Figure 45D

```
         970          980          990         1000
          *    *       *    *       *    *       *    *
        GAT  TTT  AAA  TGT  GTT  GTC  CAT  AAT  ACC  CTG  AGT  TTT  CAG  ACA
        CTA  AAA  TTT  ACA  CAA  CAG  GTA  TTA  TGG  GAC  TCA  AAA  GTC  TGT
        Asp  Phe  Lys  Cys  Val  Val  His  Asn  Thr  Leu  Ser  Phe  Gln  Thr>
        _____IL-1RII_____>

1010         1020         1030         1040         1050
   *    *      *    *       *    *       *    *       *    *
        CTA  CGC  ACC  ACA  GTC  AAG  GAA  GCC  TCC  TCC  ACG  TTC  TCA  GAA
        GAT  GCG  TGG  TGT  CAG  TTC  CTT  CGG  AGG  AGG  TGC  AAG  AGT  CTT
                                                                  Ser  Glu>
                                                                  _____>

Leu  Arg  Thr  Thr  Val  Lys  Glu  Ala  Ser  Ser  Thr  Phe>
        _____IL-1RII_____>

1060         1070         1080         1090
               *    *       *    *       *    *       *    *
             CGC  TGC  GAT  GAC  TGG  GGA  CTA  GAC  ACC  ATG  AGG  CAA  ATC  CAA
             GCG  ACG  CTA  CTG  ACC  CCT  GAT  CTG  TGG  TAC  TCC  GTT  TAG  GTT
             Arg  Cys  Asp  Asp  Trp  Gly  Leu  Asp  Thr  Met  Arg  Gln  Ile  Gln>
             _____IL-1RAcP_____>

1100         1110         1120         1130
           *    *       *    *       *    *       *    *
        GTG  TTT  GAA  GAT  GAG  CCA  GCT  CGC  ATC  AAG  TGC  CCA  CTC  TTT
        CAC  AAA  CTT  CTA  CTC  GGT  CGA  GCG  TAG  TTC  ACG  GGT  GAG  AAA
        Val  Phe  Glu  Asp  Glu  Pro  Ala  Arg  Ile  Lys  Cys  Pro  Leu  Phe>
        _____IL-1RAcP_____>

1140         1150         1160         1170
           *    *       *    *       *    *       *    *
        GAA  CAC  TTC  TTG  AAA  TTC  AAC  TAC  AGC  ACA  GCC  CAT  TCA  GCT
        CTT  GTG  AAG  AAC  TTT  AAG  TTG  ATG  TCG  TGT  CGG  GTA  AGT  CGA
        Glu  His  Phe  Leu  Lys  Phe  Asn  Tyr  Ser  Thr  Ala  His  Ser  Ala>
        _____IL-1RAcP_____>

1180         1190         1200         1210
           *    *       *    *       *    *       *    *
        GGC  CTT  ACT  CTG  ATC  TGG  TAT  TGG  ACT  AGG  CAG  GAC  CGG  GAC
        CCG  GAA  TGA  GAC  TAG  ACC  ATA  ACC  TGA  TCC  GTC  CTG  GCC  CTG
        Gly  Leu  Thr  Leu  Ile  Trp  Tyr  Trp  Thr  Arg  Gln  Asp  Arg  Asp>
        _____IL-1RAcP_____>

1220         1230         1240         1250         1260
   *    *      *    *       *    *       *    *       *    *
        CTT  GAG  GAG  CCA  ATT  AAC  TTC  CGC  CTC  CCC  GAG  AAC  CGC  ATT
        GAA  CTC  CTC  GGT  TAA  TTG  AAG  GCG  GAG  GGG  CTC  TTG  GCG  TAA
        Leu  Glu  Glu  Pro  Ile  Asn  Phe  Arg  Leu  Pro  Glu  Asn  Arg  Ile>
        _____IL-1RAcP_____>
```

Figure 45E

```
          1270            1280            1290            1300
       *       *       *       *       *       *       *       *
      AGT AAG GAG AAA GAT GTG CTG TGG TTC CGG CCC ACT CTC CTC
      TCA TTC CTC TTT CTA CAC GAC ACC AAG GCC GGG TGA GAG GAG
      Ser Lys Glu Lys Asp Val Leu Trp Phe Arg Pro Thr Leu Leu>
      _____IL-1RAcP_____>

1310            1320            1330            1340
       *       *       *       *       *       *       *       *
      AAT GAC ACT GGC AAC TAT ACC TGC ATG TTA AGG AAC ACT ACA
      TTA CTG TGA CCG TTG ATA TGG ACG TAC AAT TCC TTG TGA TGT
      Asn Asp Thr Gly Asn Tyr Thr Cys Met Leu Arg Asn Thr Thr>
      _____IL-1RAcP_____>

1350            1360            1370            1380
       *       *       *       *       *       *       *       *
      TAT TGC AGC AAA GTT GCA TTT CCC TTG GAA GTT GTT CAA AAA
      ATA ACG TCG TTT CAA CGT AAA GGG AAC CTT CAA CAA GTT TTT
      Tyr Cys Ser Lys Val Ala Phe Pro Leu Glu Val Val Gln Lys>
      _____IL-1RAcP_____>

1390            1400            1410            1420
       *       *       *       *       *       *       *       *
      GAC AGC TGT TTC AAT TCC CCC ATG AAA CTC CCA GTG CAT AAA
      CTG TCG ACA AAG TTA AGG GGG TAC TTT GAG GGT CAC GTA TTT
      Asp Ser Cys Phe Asn Ser Pro Met Lys Leu Pro Val His Lys>
      _____IL-1RAcP_____>

1430            1440            1450            1460            1470
   *       *       *       *       *       *       *       *       *
  CTG TAT ATA GAA TAT GGC ATT CAG AGG ATC ACT TGT CCA AAT
  GAC ATA TAT CTT ATA CCG TAA GTC TCC TAG TGA ACA GGT TTA
  Leu Tyr Ile Glu Tyr Gly Ile Gln Arg Ile Thr Cys Pro Asn>
  _____IL-1RAcP_____>

1480            1490            1500            1510
       *       *       *       *       *       *       *       *
      GTA GAT GGA TAT TTT CCT TCC AGT GTC AAA CCG ACT ATC ACT
      CAT CTA CCT ATA AAA GGA AGG TCA CAG TTT GGC TGA TAG TGA
      Val Asp Gly Tyr Phe Pro Ser Ser Val Lys Pro Thr Ile Thr>
      _____IL-1RAcP_____>

1520            1530            1540            1550
       *       *       *       *       *       *       *       *
      TGG TAT ATG GGC TGT TAT AAA ATA CAG AAT TTT AAT AAT GTA
      ACC ATA TAC CCG ACA ATA TTT TAT GTC TTA AAA TTA TTA CAT
      Trp Tyr Met Gly Cys Tyr Lys Ile Gln Asn Phe Asn Asn Val>
      _____IL-1RAcP_____>

1560            1570            1580            1590
       *       *       *       *       *       *       *       *
      ATA CCC GAA GGT ATG AAC TTG AGT TTC CTC ATT GCC TTA ATT
      TAT GGG CTT CCA TAC TTG AAC TCA AAG GAG TAA CGG AAT TAA
      Ile Pro Glu Gly Met Asn Leu Ser Phe Leu Ile Ala Leu Ile>
      _____IL-1RAcP_____>
```

Figure 45F

```
           1600          1610           1620          1630
             *      *      *      *      *      *      *      *
           TCA    AAT    AAT    GGA    AAT    TAC    ACA    TGT    GTT    GTT    ACA    TAT    CCA    GAA
           AGT    TTA    TTA    CCT    TTA    ATG    TGT    ACA    CAA    CAA    TGT    ATA    GGT    CTT
           Ser    Asn    Asn    Gly    Asn    Tyr    Thr    Cys    Val    Val    Thr    Tyr    Pro    Glu>
                                              _____IL-1RAcP_____>

1640          1650          1660          1670          1680
          *      *      *      *      *      *      *      *      *      *
         AAT    GGA    CGT    ACG    TTT    CAT    CTC    ACC    AGG    ACT    CTG    ACT    GTA    AAG
         TTA    CCT    GCA    TGC    AAA    GTA    GAG    TGG    TCC    TGA    GAC    TGA    CAT    TTC
         Asn    Gly    Arg    Thr    Phe    His    Leu    Thr    Arg    Thr    Leu    Thr    Val    Lys>
                                            _____IL-1RAcP_____>

1690          1700          1710          1720
                     *      *      *      *      *      *      *      *
                   GTA    GTA    GGC    TCT    CCA    AAA    AAT    GCA    GTG    CCC    CCT    GTG    ATC    CAT
                   CAT    CAT    CCG    AGA    GGT    TTT    TTA    CGT    CAC    GGG    GGA    CAC    TAG    GTA
                   Val    Val    Gly    Ser    Pro    Lys    Asn    Ala    Val    Pro    Pro    Val    Ile    His>
                                                   _____IL-1RAcP_____>

1730          1740          1750          1760
                *      *      *      *      *      *      *      *
              TCA    CCT    AAT    GAT    CAT    GTG    GTC    TAT    GAG    AAA    GAA    CCA    GGA    GAG
              AGT    GGA    TTA    CTA    GTA    CAC    CAG    ATA    CTC    TTT    CTT    GGT    CCT    CTC
              Ser    Pro    Asn    Asp    His    Val    Val    Tyr    Glu    Lys    Glu    Pro    Gly    Glu>
                                              _____IL-1RAcP_____>

1770          1780          1790          1800
             *      *      *      *      *      *      *      *
           GAG    CTA    CTC    ATT    CCC    TGT    ACG    GTC    TAT    TTT    AGT    TTT    CTG    ATG
           CTC    GAT    GAG    TAA    GGG    ACA    TGC    CAG    ATA    AAA    TCA    AAA    GAC    TAC
           Glu    Leu    Leu    Ile    Pro    Cys    Thr    Val    Tyr    Phe    Ser    Phe    Leu    Met>
                                            _____IL-1RAcP_____>

1810          1820          1830          1840
             *      *      *      *      *      *      *      *
           GAT    TCT    CGC    AAT    GAG    GTT    TGG    TGG    ACC    ATT    GAT    GGA    AAA    AAA
           CTA    AGA    GCG    TTA    CTC    CAA    ACC    ACC    TGG    TAA    CTA    CCT    TTT    TTT
           Asp    Ser    Arg    Asn    Glu    Val    Trp    Trp    Thr    Ile    Asp    Gly    Lys    Lys>
                                            _____IL-1RAcP_____>

1850          1860          1870          1880          1890
          *      *      *      *      *      *      *      *      *      *
         CCT    GAT    GAC    ATC    ACT    ATT    GAT    GTC    ACC    ATT    AAC    GAA    AGT    ATA
         GGA    CTA    CTG    TAG    TGA    TAA    CTA    CAG    TGG    TAA    TTG    CTT    TCA    TAT
         Pro    Asp    Asp    Ile    Thr    Ile    Asp    Val    Thr    Ile    Asn    Glu    Ser    Ile>
                                            _____IL-1RAcP_____>

1900          1910          1920          1930
                   *      *      *      *      *      *      *      *
                 AGT    CAT    AGT    AGA    ACA    GAA    GAT    GAA    ACA    AGA    ACT    CAG    ATT    TTG
                 TCA    GTA    TCA    TCT    TGT    CTT    CTA    CTT    TGT    TCT    TGA    GTC    TAA    AAC
                 Ser    His    Ser    Arg    Thr    Glu    Asp    Glu    Thr    Arg    Thr    Gln    Ile    Leu>
                                                   _____IL-1RAcP_____>
```

Figure 45G

```
          1940              1950              1960              1970
     *         *         *         *         *        *        *        *
    AGC  ATC  AAG  AAA  GTT  ACC  TCT  GAG  GAT  CTC  AAG  CGC  AGC  TAT
    TCG  TAG  TTC  TTT  CAA  TGG  AGA  CTC  CTA  GAG  TTC  GCG  TCG  ATA
    Ser  Ile  Lys  Lys  Val  Thr  Ser  Glu  Asp  Leu  Lys  Arg  Ser  Tyr>
                                 __IL-1RAcP_____>

1980              1990              2000              2010
     *         *        *         *        *         *        *         *
    GTC  TGT  CAT  GCT  AGA  AGT  GCC  AAA  GGC  GAA  GTT  GCC  AAA  GCA
    CAG  ACA  GTA  CGA  TCT  TCA  CGG  TTT  CCG  CTT  CAA  CGG  TTT  CGT
    Val  Cys  His  Ala  Arg  Ser  Ala  Lys  Gly  Glu  Val  Ala  Lys  Ala>
                                 __IL-1RAcP_____>

2020              2030              2040              2050
     *        *         *        *         *        *         *        *
    GCC  AAG  GTG  AAG  CAG  AAA  GTG  CCA  GCT  CCA  AGA  TAC  ACA  GTG
    CGG  TTC  CAC  TTC  GTC  TTT  CAC  GGT  CGA  GGT  TCT  ATG  TGT  CAC
    Ala  Lys  Val  Lys  Gln  Lys  Val  Pro  Ala  Pro  Arg  Tyr  Thr  Val>
                                 __IL-1RAcP_____>

2060              2070              2080              2090              2100
     *        *        *         *        *         *        *         *        *
    TCC  GGA  GAG  TCC  AAA  TAC  GGT  CCG  CCA  TGC  CCA  TCA  TGC  CCA
    AGG  CCT  CTC  AGG  TTT  ATG  CCA  GGC  GGT  ACG  GGT  AGT  ACG  GGT
    Ser  Gly>
       ____>
             Glu  Ser  Lys  Tyr  Gly  Pro  Pro  Cys  Pro  Ser  Cys  Pro>
                                 _FC-IgG4_____>

2110              2120              2130              2140
     *        *        *         *        *         *        *        *
    GCA  CCT  GAG  TTC  CTG  GGG  GGA  CCA  TCA  GTC  TTC  CTG  TTC  CCC
    CGT  GGA  CTC  AAG  GAC  CCC  CCT  GGT  AGT  CAG  AAG  GAC  AAG  GGG
    Ala  Pro  Glu  Phe  Leu  Gly  Gly  Pro  Ser  Val  Phe  Leu  Phe  Pro>
                                 __FC-IgG4_____>

2150              2160              2170              2180
     *        *        *         *        *         *        *        *
    CCA  AAA  CCC  AAG  GAC  ACT  CTC  ATG  ATC  TCC  CGG  ACC  CCT  GAG
    GGT  TTT  GGG  TTC  CTG  TGA  GAG  TAC  TAG  AGG  GCC  TGG  GGA  CTC
    Pro  Lys  Pro  Lys  Asp  Thr  Leu  Met  Ile  Ser  Arg  Thr  Pro  Glu>
                                 __FC-IgG4_____>

2190              2200              2210              2220
     *        *        *         *        *         *        *        *
    GTC  ACG  TGC  GTG  GTG  GTG  GAC  GTG  AGC  CAG  GAA  GAC  CCC  GAG
    CAG  TGC  ACG  CAC  CAC  CAC  CTG  CAC  TCG  GTC  CTT  CTG  GGG  CTC
    Val  Thr  Cys  Val  Val  Val  Asp  Val  Ser  Gln  Glu  Asp  Pro  Glu>
                                 __FC-IgG4_____>
```

Figure 45E

```
          2230          2240           2250          2260
            *             *    *         *    *        *      *
        GTC CAG TTC AAC TGG TAC GTG GAT GGC GTG GAG GTG CAT AAT
        CAG GTC AAG TTG ACC ATG CAC CTA CCG CAC CTC CAC GTA TTA
        Val Gln Phe Asn Trp Tyr Val Asp Gly Val Glu Val His Asn>
                            ____FC-IgG4____                    >

2270          2280          2290          2300          2310
      *     *       *     *       *     *       *     *       *
    GCC AAG ACA AAG CCG CGG GAG GAG CAG TTC AAC AGC ACG TAC
    CGG TTC TGT TTC GGC GCC CTC CTC GTC AAG TTG TCG TGC ATG
    Ala Lys Thr Lys Pro Arg Glu Glu Gln Phe Asn Ser Thr Tyr>
                    ____FC-IgG4____                          >

2320          2330         2340          2350
                *     *       *     *      *     *       *     *
            CGT GTG GTC AGC GTC CTC ACC GTC CTG CAC CAG GAC TGG CTG
            GCA CAC CAG TCG CAG GAG TGG CAG GAC GTG GTC CTG ACC GAC
            Arg Val Val Ser Val Leu Thr Val Leu His Gln Asp Trp Leu>
                          ____FC-IgG4____                         >

2360          2370          2380          2390
                *     *       *     *       *     *       *     *
            AAC GGC AAG GAG TAC AAG TGC AAG GTC TCC AAC AAA GGC CTC
            TTG CCG TTC CTC ATG TTC ACG TTC CAG AGG TTG TTT CCG GAG
            Asn Gly Lys Glu Tyr Lys Cys Lys Val Ser Asn Lys Gly Leu>
                          ____FC-IgG4____                         >

2400          2410          2420          2430
            *     *       *     *       *     *       *     *
        CCG TCC TCC ATC GAG AAA ACC ATC TCC AAA GCC AAA GGG CAG
        GGC AGG AGG TAG CTC TTT TGG TAG AGG TTT CGG TTT CCC GTC
        Pro Ser Ser Ile Glu Lys Thr Ile Ser Lys Ala Lys Gly Gln>
                      ____FC-IgG4____                         >

2440          2450          2460          2470
            *     *       *     *       *     *       *     *
        CCC CGA GAG CCA CAG GTG TAC ACC CTG CCC CCA TCC CAG GAG
        GGG GCT CTC GGT GTC CAC ATG TGG GAC GGG GGT AGG GTC CTC
        Pro Arg Glu Pro Gln Val Tyr Thr Leu Pro Pro Ser Gln Glu>
                      ____FC-IgG4____                         >

2480          2490          2500          2510          2520
      *     *       *     *       *     *       *     *       *
    GAG ATG ACC AAG AAC CAG GTC AGC CTG ACC TGC CTG GTC AAA
    CTC TAC TGG TTC TTG GTC CAG TCG GAC TGG ACG GAC CAG TTT
    Glu Met Thr Lys Asn Gln Val Ser Leu Thr Cys Leu Val Lys>
                    ____FC-IgG4____                          >

2530          2540          2550          2560
                *     *       *     *       *     *       *     *
            GGC TTC TAC CCC AGC GAC ATC GCC GTG GAG TGG GAG AGC AAT
            CCG AAG ATG GGG TCG CTG TAG CGG CAC CTC ACC CTC TCG TTA
            Gly Phe Tyr Pro Ser Asp Ile Ala Val Glu Trp Glu Ser Asn>
                          ____FC-IgG4____                         >
```

Figure 45I

```
         2570              2580              2590              2600
  *        *        *        *        *        *        *        *
GGG      CAG      CCG      GAG      AAC      AAC      TAC      AAG      ACC      ACG      CCT      CCC      GTG      CTG
CCC      GTC      GGC      CTC      TTG      TTG      ATG      TTC      TGG      TGC      GGA      GGG      CAC      GAC
Gly      Gln      Pro      Glu      Asn      Asn      Tyr      Lys      Thr      Thr      Pro      Pro      Val      Leu>
                                         ___FC-IgG4_____>

2610              2620              2630              2640
  *        *        *        *        *        *        *        *        *
GAC      TCC      GAC      GGC      TCC      TTC      TTC      CTC      TAC      AGC      AGG      CTA      ACC      GTG
CTG      AGG      CTG      CCG      AGG      AAG      AAG      GAG      ATG      TCG      TCC      GAT      TGG      CAC
Asp      Ser      Asp      Gly      Ser      Phe      Phe      Leu      Tyr      Ser      Arg      Leu      Thr      Val>
                                         ___FC-IgG4_____>

2650              2660              2670              2680
  *        *        *        *        *        *        *        *
GAC      AAG      AGC      AGG      TGG      CAG      GAG      GGG      AAT      GTC      TTC      TCA      TGC      TCC
CTG      TTC      TCG      TCC      ACC      GTC      CTC      CCC      TTA      CAG      AAG      AGT      ACG      AGG
Asp      Lys      Ser      Arg      Trp      Gln      Glu      Gly      Asn      Val      Phe      Ser      Cys      Ser>
                                         ___FC-IgG4_____>

2690              2700              2710              2720              2730
  *        *        *        *        *        *        *        *        *        *
GTG      ATG      CAT      GAG      GCT      CTG      CAC      AAC      CAC      TAC      ACA      CAG      AAG      AGC
CAC      TAC      GTA      CTC      CGA      GAC      GTG      TTG      GTG      ATG      TGT      GTC      TTC      TCG
Val      Met      His      Glu      Ala      Leu      His      Asn      His      Tyr      Thr      Gln      Lys      Ser>
                                         ___FC-IgG4_____>

2740              2750
  *        *        *        *
CTC      TCC      CTG      TCT      CTG      GGT      AAA      TGA
GAG      AGG      GAC      AGA      GAC      CCA      TTT      ACT
Leu      Ser      Leu      Ser      Leu      Gly      Lys      ***>
     ___FC-IgG4_____>
```

Figure 46A

```
              10             20             30             40
          *    *         *    *         *    *         *    *
        ATG GTG CGC TTG TAC GTG TTG GTA ATG GGA GTT TCT GCC TTC
        TAC CAC GCG AAC ATG CAC AAC CAT TAC CCT CAA AGA CGG AAG
        Met Val Arg Leu Tyr Val Leu Val Met Gly Val Ser Ala Phe>
        _____SIGNAL PEPTIDE_____>
        _____IL-1RII_____>

50             60             70             80
          *    *         *    *         *    *         *    *
        ACC CTT CAG CCT GCG GCA CAC ACA GGG GCT GCC AGA AGC TGC
        TGG GAA GTC GGA CGC CGT GTG TGT CCC CGA CGG TCT TCG ACG
        Thr Leu Gln Pro Ala Ala>
        _____SIGNAL PEPTIDE_____>
                                His Thr Gly Ala Ala Arg Ser Cys>
        _____IL-1RII_____>

90            100            110            120
          *    *         *    *         *    *         *    *
        CGG TTT CGT GGG AGG CAT TAC AAG CGG GAG TTC AGG CTG GAA
        GCC AAA GCA CCC TCC GTA ATG TTC GCC CTC AAG TCC GAC CTT
        Arg Phe Arg Gly Arg His Tyr Lys Arg Glu Phe Arg Leu Glu>
        _____IL-1RII_____>

130            140            150            160
          *    *         *    *         *    *         *    *
        GGG GAG CCT GTA GCC CTG AGG TGC CCC CAG GTG CCC TAC TGG
        CCC CTC GGA CAT CGG GAC TCC ACG GGG GTC CAC GGG ATG ACC
        Gly Glu Pro Val Ala Leu Arg Cys Pro Gln Val Pro Tyr Trp>
        _____IL-1RII_____>

170            180            190            200            210
         *    *    *    *    *    *    *    *    *
        TTG TGG GCC TCT GTC AGC CCC CGC ATC AAC CTG ACA TGG CAT
        AAC ACC CGG AGA CAG TCG GGG GCG TAG TTG GAC TGT ACC GTA
        Leu Trp Ala Ser Val Ser Pro Arg Ile Asn Leu Thr Trp His>
        _____IL-1RII_____>

220            230            240            250
          *    *         *    *         *    *         *    *
        AAA AAT GAC TCT GCT AGG ACG GTC CCA GGA GAA GAA GAG ACA
        TTT TTA CTG AGA CGA TCC TGC CAG GGT CCT CTT CTT CTC TGT
        Lys Asn Asp Ser Ala Arg Thr Val Pro Gly Glu Glu Glu Thr>
        _____IL-1RII_____>

260            270            280            290
          *    *         *    *         *    *         *    *
        CGG ATG TGG GCC CAG GAC GGT GCT CTG TGG CTT CTG CCA GCC
        GCC TAC ACC CGG GTC CTG CCA CGA GAC ACC GAA GAC GGT CGG
        Arg Met Trp Ala Gln Asp Gly Ala Leu Trp Leu Leu Pro Ala>
        _____IL-1RII_____>
```

Figure 46B

```
        300             310             320             330
          *       *       *       *       *       *       *       *       *
        TTG CAG GAG GAC TCT GGC ACC TAC GTC TGC ACT ACT AGA AAT
        AAC GTC CTC CTG AGA CCG TGG ATG CAG ACG TGA TGA TCT TTA
        Leu Gln Glu Asp Ser Gly Thr Tyr Val Cys Thr Thr Arg Asn>
                              __IL-1RII__                        >

340             350             360             370
          *       *       *       *       *       *       *       *
        GCT TCT TAC TGT GAC AAA ATG TCC ATT GAG CTC AGA GTT TTT
        CGA AGA ATG ACA CTG TTT TAC AGG TAA CTC GAG TCT CAA AAA
        Ala Ser Tyr Cys Asp Lys Met Ser Ile Glu Leu Arg Val Phe>
                              __IL-1RII__                        >

380             390             400             410             420
      *       *       *       *       *       *       *       *       *
    GAG AAT ACA GAT GCT TTC CTG CCG TTC ATC TCA TAC CCG CAA
    CTC TTA TGT CTA CGA AAG GAC GGC AAG TAG AGT ATG GGC GTT
    Glu Asn Thr Asp Ala Phe Leu Pro Phe Ile Ser Tyr Pro Gln>
                          __IL-1RII__                        >

430             440             450             460
              *       *       *       *       *       *       *       *
            ATT TTA ACC TTG TCA ACC TCT GGG GTA TTA GTA TGC CCT GAC
            TAA AAT TGG AAC AGT TGG AGA CCC CAT AAT CAT ACG GGA CTG
            Ile Leu Thr Leu Ser Thr Ser Gly Val Leu Val Cys Pro Asp>
                                  __IL-1RII__                        >

470             480             490             500
              *       *       *       *       *       *       *       *
            CTG AGT GAA TTC ACC CGT GAC AAA ACT GAC GTG AAG ATT CAA
            GAC TCA CTT AAG TGG GCA CTG TTT TGA CTG CAC TTC TAA GTT
            Leu Ser Glu Phe Thr Arg Asp Lys Thr Asp Val Lys Ile Gln>
                                  __IL-1RII__                        >

510             520             530             540
          *       *       *       *       *       *       *       *       *
        TGG TAC AAG GAT TCT CTT CTT TTG GAT AAA GAC AAT GAG AAA
        ACC ATG TTC CTA AGA GAA GAA AAC CTA TTT CTG TTA CTC TTT
        Trp Tyr Lys Asp Ser Leu Leu Leu Asp Lys Asp Asn Glu Lys>
                              __IL-1RII__                        >

550             560             570             580
          *       *       *       *       *       *       *       *
        TTT CTA AGT GTG AGG GGG ACC ACT CAC TTA CTC GTA CAC GAT
        AAA GAT TCA CAC TCC CCC TGG TGA GTG AAT GAG CAT GTG CTA
        Phe Leu Ser Val Arg Gly Thr Thr His Leu Leu Val His Asp>
                              __IL-1RII__                        >

590             600             610             620             630
      *       *       *       *       *       *       *       *       *
    GTG GCC CTG GAA GAT GCT GGC TAT TAC CGC TGT GTC CTG ACA
    CAC CGG GAC CTT CTA CGA CCG ATA ATG GCG ACA CAG GAC TGT
    Val Ala Leu Glu Asp Ala Gly Tyr Tyr Arg Cys Val Leu Thr>
                          __IL-1RII__                        >
```

Figure 46C

```
         640           650           660           670
          *             *             *             *
TTT GCC CAT GAA GGC CAG CAA TAC AAC ATC ACT AGG AGT ATT
AAA CGG GTA CTT CCG GTC GTT ATG TTG TAG TGA TCC TCA TAA
Phe Ala His Glu Gly Gln Gln Tyr Asn Ile Thr Arg Ser Ile>
                         IL-1RII                         >

680           690           700           710
          *             *             *             *
GAG CTA CGC ATC AAG AAA AAA AAA GAA GAG ACC ATT CCT GTG
CTC GAT GCG TAG TTC TTT TTT TTT CTT CTC TGG TAA GGA CAC
Glu Leu Arg Ile Lys Lys Lys Lys Glu Glu Thr Ile Pro Val>
                         IL-1RII                         >

720           730           740           750
   *      *      *      *      *      *      *      *      *
ATC ATT TCC CCC CTC AAG ACC ATA TCA GCT TCT CTG GGG TCA
TAG TAA AGG GGG GAG TTC TGG TAT AGT CGA AGA GAC CCC AGT
Ile Ile Ser Pro Leu Lys Thr Ile Ser Ala Ser Leu Gly Ser>
                         IL-1RII                         >

760           770           780           790
       *             *             *             *
AGA CTG ACA ATC CCA TGT AAG GTG TTT CTG GGA ACC GGC ACA
TCT GAC TGT TAG GGT ACA TTC CAC AAA GAC CCT TGG CCG TGT
Arg Leu Thr Ile Pro Cys Lys Val Phe Leu Gly Thr Gly Thr>
                         IL-1RII                         >

800        810           820           830           840
  *      *      *      *      *      *      *      *      *
CCC TTA ACC ACC ATG CTG TGG TGG ACG GCC AAT GAC ACC CAC
GGG AAT TGG TGG TAC GAC ACC ACC TGC CGG TTA CTG TGG GTG
Pro Leu Thr Thr Met Leu Trp Trp Thr Ala Asn Asp Thr His>
                         IL-1RII                         >

850           860           870           880
          *      *      *      *      *      *      *
ATA GAG AGC GCC TAC CCG GGA GGC CGC GTG ACC GAG GGG CCA
TAT CTC TCG CGG ATG GGC CCT CCG GCG CAC TGG CTC CCC GGT
Ile Glu Ser Ala Tyr Pro Gly Gly Arg Val Thr Glu Gly Pro>
                         IL-1RII                         >

890           900           910           920
          *             *             *             *
CGC CAG GAA TAT TCA GAA AAT AAT GAG AAC TAC ATT GAA GTG
GCG GTC CTT ATA AGT CTT TTA TTA CTC TTG ATG TAA CTT CAC
Arg Gln Glu Tyr Ser Glu Asn Asn Glu Asn Tyr Ile Glu Val>
                         IL-1RII                         >

930           940           950           960
    *      *      *      *      *      *      *      *      *
CCA TTG ATT TTT GAT CCT GTC ACA AGA GAG GAT TTG CAC ATG
GGT AAC TAA AAA CTA GGA CAG TGT TCT CTC CTA AAC GTG TAC
Pro Leu Ile Phe Asp Pro Val Thr Arg Glu Asp Leu His Met>
                         IL-1RII                         >
```

Figure 46D

```
         970          980           990         1000
          *       *    *       *     *      *    *      *
        GAT TTT AAA TGT GTT GTC CAT AAT ACC CTG AGT TTT CAG ACA
        CTA AAA TTT ACA CAA CAG GTA TTA TGG GAC TCA AAA GTC TGT
        Asp Phe Lys Cys Val Val His Asn Thr Leu Ser Phe Gln Thr>
                                   IL-1RII                      >

1010         1020          1030          1040          1050
  *      *    *       *     *       *     *       *    *     *
CTA CGC ACC ACA GTC AAG GAA GCC TCC TCC ACG TTC TCA GAA
GAT GCG TGG TGT CAG TTC CTT CGG AGG AGG TGC AAG AGT CTT
                                                    Ser Glu>
                                                         ____>

Leu Arg Thr Thr Val Lys Glu Ala Ser Ser Thr Phe>
                   IL-1RII                       >

1060          1070         1080          1090
              *       *     *      *     *      *     *      *
            CGC TGC GAT GAC TGG GGA CTA GAC ACC ATG AGG CAA ATC CAA
            GCG ACG CTA CTG ACC CCT GAT CTG TGG TAC TCC GTT TAG GTT
            Arg Cys Asp Asp Trp Gly Leu Asp Thr Met Arg Gln Ile Gln>
                                       IL-1RAcP                     >

1100          1110          1120          1130
            *       *     *       *     *      *      *      *
          CTG TTT GAA GAT GAG CCA GCT CGC ATC AAG TGC CCA CTC TTT
          CAC AAA CTT CTA CTC GGT CGA GCG TAG TTC ACG GGT GAG AAA
          Val Phe Glu Asp Glu Pro Ala Arg Ile Lys Cys Pro Leu Phe>
                                     IL-1RAcP                     >

1140          1150          1160         1170
            *       *    *       *     *      *     *      *      *
          GAA CAC TTC TTG AAA TTC AAC TAC AGC ACA GCC CAT TCA GCT
          CTT GTG AAG AAC TTT AAG TTG ATG TCG TGT CGG GTA AGT CGA
          Glu His Phe Leu Lys Phe Asn Tyr Ser Thr Ala His Ser Ala>
                                     IL-1RAcP                      >

1180          1190         1200          1210
            *       *     *      *     *      *     *      *
          GGC CTT ACT CTG ATC TGG TAT TGG ACT AGG CAG GAC CGG GAC
          CCG GAA TGA GAC TAG ACC ATA ACC TGA TCC GTC CTG GCC CTG
          Gly Leu Thr Leu Ile Trp Tyr Trp Thr Arg Gln Asp Arg Asp>
                                     IL-1RAcP                      >

1220          1230          1240         1250          1260
        *       *     *      *     *       *    *      *     *      *
      CTT GAG GAG CCA ATT AAC TTC CGC CTC CCC GAG AAC CGC ATT
      GAA CTC CTC GGT TAA TTG AAG GCG GAG GGG CTC TTG GCG TAA
      Leu Glu Glu Pro Ile Asn Phe Arg Leu Pro Glu Asn Arg Ile>
                                 IL-1RAcP                     >
```

Figure 46E

```
         1270          1280          1290          1300
           *       *     *       *     *       *     *       *
       AGT AAG GAG AAA GAT GTG CTG TGG TTC CGG CCC ACT CTC CTC
       TCA TTC CTC TTT CTA CAC GAC ACC AAG GCC GGG TGA GAG GAG
       Ser Lys Glu Lys Asp Val Leu Trp Phe Arg Pro Thr Leu Leu>
                                  IL-1RAcP                        >

1310          1320          1330          1340
           *       *     *       *     *       *     *       *
       AAT GAC ACT GGC AAC TAT ACC TGC ATG TTA AGG AAC ACT ACA
       TTA CTG TGA CCG TTG ATA TGG ACG TAC AAT TCC TTG TGA TGT
       Asn Asp Thr Gly Asn Tyr Thr Cys Met Leu Arg Asn Thr Thr>
                                  IL-1RAcP                        >

1350          1360          1370          1380
           *       *     *       *     *       *     *       *     *
       TAT TGC AGC AAA GTT GCA TTT CCC TTG GAA GTT GTT CAA AAA
       ATA ACG TCG TTT CAA CGT AAA GGG AAC CTT CAA CAA GTT TTT
       Tyr Cys Ser Lys Val Ala Phe Pro Leu Glu Val Val Gln Lys>
                                  IL-1RAcP                        >

1390          1400          1410          1420
           *       *     *       *     *       *     *       *
       GAC AGC TGT TTC AAT TCC CCC ATG AAA CTC CCA GTG CAT AAA
       CTG TCG ACA AAG TTA AGG GGG TAC TTT GAG GGT CAC GTA TTT
       Asp Ser Cys Phe Asn Ser Pro Met Lys Leu Pro Val His Lys>
                                  IL-1RAcP                        >

1430          1440          1450          1460          1470
     *       *     *       *     *       *     *       *     *
   CTG TAT ATA GAA TAT GGC ATT CAG AGG ATC ACT TGT CCA AAT
   GAC ATA TAT CTT ATA CCG TAA GTC TCC TAG TGA ACA GGT TTA
   Leu Tyr Ile Glu Tyr Gly Ile Gln Arg Ile Thr Cys Pro Asn>
                                  IL-1RAcP                        >

1480          1490          1500          1510
              *       *     *       *     *       *     *       *
          GTA GAT GGA TAT TTT CCT TCC AGT GTC AAA CCG ACT ATC ACT
          CAT CTA CCT ATA AAA GGA AGG TCA CAG TTT GGC TGA TAG TGA
          Val Asp Gly Tyr Phe Pro Ser Ser Val Lys Pro Thr Ile Thr>
                                  IL-1RAcP                        >

1520          1530          1540          1550
              *       *     *       *     *       *     *       *
          TGG TAT ATG GGC TGT TAT AAA ATA CAG AAT TTT AAT AAT GTA
          ACC ATA TAC CCG ACA ATA TTT TAT GTC TTA AAA TTA TTA CAT
          Trp Tyr Met Gly Cys Tyr Lys Ile Gln Asn Phe Asn Asn Val>
                                  IL-1RAcP                        >

1560          1570          1580          1590
              *       *     *       *     *       *     *       *     *
          ATA CCC GAA GGT ATG AAC TTG AGT TTC CTC ATT GCC TTA ATT
          TAT GGG CTT CCA TAC TTG AAC TCA AAG GAG TAA CGG AAT TAA
          Ile Pro Glu Gly Met Asn Leu Ser Phe Leu Ile Ala Leu Ile>
                                  IL-1RAcP                        >
```

Figure 46F

```
       1600           1610           1620           1630
         *      *       *      *       *      *       *      *
       TCA    AAT    AAT    GGA    AAT    TAC    ACA    TGT    GTT    GTT    ACA    TAT    CCA    GAA
       AGT    TTA    TTA    CCT    TTA    ATG    TGT    ACA    CAA    CAA    TGT    ATA    GGT    CTT
       Ser    Asn    Asn    Gly    Asn    Tyr    Thr    Cys    Val    Val    Thr    Tyr    Pro    Glu>
                                              ___IL-1RAcP_____>

1640           1650           1660           1670           1680
    *      *       *      *       *      *       *      *       *      *
  AAT    GCA    CGT    ACG    TTT    CAT    CTC    ACC    AGG    ACT    CTG    ACT    GTA    AAG
  TTA    CGT    GCA    TGC    AAA    GTA    GAG    TGG    TCC    TGA    GAC    TGA    CAT    TTC
  Asn    Gly    Arg    Thr    Phe    His    Leu    Thr    Arg    Thr    Leu    Thr    Val    Lys>
                                          ___IL-1RAcP_____>

1690           1700           1710           1720
           *      *       *      *       *      *       *      *
           GTA    GTA    GGC    TCT    CCA    AAA    AAT    GCA    GTG    CCC    CCT    GTG    ATC    CAT
           CAT    CAT    CCG    AGA    GGT    TTT    TTA    CGT    CAC    GGG    GGA    CAC    TAG    GTA
           Val    Val    Gly    Ser    Pro    Lys    Asn    Ala    Val    Pro    Pro    Val    Ile    His>
                                              ___IL-1RAcP_____>

1730           1740           1750           1760
           *      *       *      *       *      *       *      *
         TCA    CCT    AAT    GAT    CAT    GTG    GTC    TAT    GAG    AAA    GAA    CCA    GGA    GAG
         AGT    GGA    TTA    CTA    GTA    CAC    CAG    ATA    CTC    TTT    CTT    GGT    CCT    CTC
         Ser    Pro    Asn    Asp    His    Val    Val    Tyr    Glu    Lys    Glu    Pro    Gly    Glu>
                                              ___IL-1RAcP_____>

1770           1780           1790           1800
         *      *       *      *       *      *       *      *
       GAG    CTA    CTC    ATT    CCC    TGT    ACG    GTC    TAT    TTT    AGT    TTT    CTG    ATG
       CTC    GAT    GAG    TAA    GGG    ACA    TGC    CAG    ATA    AAA    TCA    AAA    GAC    TAC
       Glu    Leu    Leu    Ile    Pro    Cys    Thr    Val    Tyr    Phe    Ser    Phe    Leu    Met>
                                              ___IL-1RAcP_____>

1810           1820           1830           1840
         *      *       *      *       *      *       *      *
       GAT    TCT    CGC    AAT    GAG    GTT    TGG    TGG    ACC    ATT    GAT    GGA    AAA    AAA
       CTA    AGA    GCG    TTA    CTC    CAA    ACC    ACC    TGG    TAA    CTA    CCT    TTT    TTT
       Asp    Ser    Arg    Asn    Glu    Val    Trp    Trp    Thr    Ile    Asp    Gly    Lys    Lys>
                                              ___IL-1RAcP_____>

1850           1860           1870           1880           1890
    *      *       *      *       *      *       *      *       *      *
  CCT    GAT    GAC    ATC    ACT    ATT    GAT    GTC    ACC    ATT    AAC    GAA    AGT    ATA
  GGA    CTA    CTG    TAG    TGA    TAA    CTA    CAG    TGG    TAA    TTG    CTT    TCA    TAT
  Pro    Asp    Asp    Ile    Thr    Ile    Asp    Val    Thr    Ile    Asn    Glu    Ser    Ile>
                                          ___IL-1RAcP_____>

1900           1910           1920           1930
           *      *       *      *       *      *       *      *
           AGT    CAT    AGT    AGA    ACA    GAA    GAT    GAA    ACA    AGA    ACT    CAG    ATT    TTG
           TCA    GTA    TCA    TCT    TGT    CTT    CTA    CTT    TGT    TCT    TGA    GTC    TAA    AAC
           Ser    His    Ser    Arg    Thr    Glu    Asp    Glu    Thr    Arg    Thr    Gln    Ile    Leu>
                                              ___IL-1RAcP_____>
```

Figure 46G

```
      1940            1950            1960            1970
   *       *       *       *       *       *       *       *
AGC ATC AAG AAA GTT ACC TCT GAG GAT CTC AAG CGC AGC TAT
TCG TAG TTC TTT CAA TGG AGA CTC CTA GAG TTC GCG TCG ATA
Ser Ile Lys Lys Val Thr Ser Glu Asp Leu Lys Arg Ser Tyr>
_____IL-1RAcP_____>

1980            1990            2000            2010
   *       *       *       *       *       *       *       *       *
GTC TGT CAT GCT AGA AGT GCC AAA GGC GAA GTT GCC AAA GCA
CAG ACA GTA CGA TCT TCA CGG TTT CCG CTT CAA CGG TTT CGT
Val Cys His Ala Arg Ser Ala Lys Gly Glu Val Ala Lys Ala>
_____IL-1RAcP_____>

2020            2030            2040           2050
   *       *       *       *       *       *       *       *
GCC AAG GTG AAG CAG AAA GTG CCA GCT CCA AGA TAC ACA GTG
CGG TTC CAC TTC GTC TTT CAC GGT CGA GGT TCT ATG TGT CAC
Ala Lys Val Lys Gln Lys Val Pro Ala Pro Arg Tyr Thr Val>
_____IL-1RAcP_____>

>Mutation Serine to Proline
                                                       |
   2060            2070            2080            2090 |    2100
   *       *       *       *       *       *       *   |    *       *
TCC GGA GAG TCC AAA TAC GGT CCG CCA TGC CCA CCA TGC CCA
AGG CCT CTC AGG TTT ATG CCA GGC GGT ACG GGT GGT ACG GGT
Ser Gly>
_____>
        Glu Ser Lys Tyr Gly Pro Pro Cys Pro Pro Cys Pro>
                       _____FC-IgG4_____>

2110            2120            2130            2140
   *       *       *       *       *       *       *       *
GCA CCT GAG TTC CTG GGG GGA CCA TCA GTC TTC CTG TTC CCC
CGT GGA CTC AAG GAC CCC CCT GGT AGT CAG AAG GAC AAG GGG
Ala Pro Glu Phe Leu Gly Gly Pro Ser Val Phe Leu Phe Pro>
_____FC-IgG4_____>

2150            2160            2170            2180
   *       *       *       *       *       *       *       *
CCA AAA CCC AAG GAC ACT CTC ATG ATC TCC CGG ACC CCT GAG
GGT TTT GGG TTC CTG TGA GAG TAC TAG AGG GCC TGG GGA CTC
Pro Lys Pro Lys Asp Thr Leu Met Ile Ser Arg Thr Pro Glu>
_____FC-IgG4_____>

2190            2200            2210            2220
   *       *       *       *       *       *       *       *       *
GTC ACG TGC GTG GTG GTG GAC GTG AGC CAG GAA GAC CCC GAG
CAG TGC ACG CAC CAC CAC CTG CAC TCG GTC CTT CTG GGG CTC
Val Thr Cys Val Val Val Asp Val Ser Gln Glu Asp Pro Glu>
_____FC-IgG4_____>
```

Figure 46H

```
        2230            2240           2250             2260
         *        *      *       *      *       *        *       *
        GTC CAG TTC AAC TGG TAC GTG GAT GGC GTG GAG GTG CAT AAT
        CAG GTC AAG TTG ACC ATG CAC CTA CCG CAC CTC CAC GTA TTA
        Val Gln Phe Asn Trp Tyr Val Asp Gly Val Glu Val His Asn>
                               ___FC-IgG4_____>

2270           2280            2290            2300            2310
   *       *      *       *       *       *       *       *       *
  GCC AAG ACA AAG CCG CGG GAG GAG CAG TTC AAC AGC ACG TAC
  CGG TTC TGT TTC GGC GCC CTC CTC GTC AAG TTG TCG TGC ATG
  Ala Lys Thr Lys Pro Arg Glu Glu Gln Phe Asn Ser Thr Tyr>
                          ___FC-IgG4_____>

2320            2330           2340            2350
              *       *       *       *      *       *       *
             CGT GTG GTC AGC GTC CTC ACC GTC CTG CAC CAG GAC TGG CTG
             GCA CAC CAG TCG CAG GAG TGG CAG GAC GTG GTC CTG ACC GAC
             Arg Val Val Ser Val Leu Thr Val Leu His Gln Asp Trp Leu>
                                     ___FC-IgG4_____>

2360            2370           2380            2390
           *       *       *       *      *       *       *       *
          AAC GGC AAG GAG TAC AAG TGC AAG GTC TCC AAC AAA GGC CTC
          TTG CCG TTC CTC ATG TTC ACG TTC CAG AGG TTG TTT CCG GAG
          Asn Gly Lys Glu Tyr Lys Cys Lys Val Ser Asn Lys Gly Leu>
                                 ___FC-IgG4_____>

2400           2410            2420            2430
      *       *      *       *       *       *       *       *
     CCG TCC TCC ATC GAG AAA ACC ATC TCC AAA GCC AAA GGG CAG
     GGC AGG AGG TAG CTC TTT TGG TAG AGG TTT CGG TTT CCC GTC
     Pro Ser Ser Ile Glu Lys Thr Ile Ser Lys Ala Lys Gly Gln>
                             ___FC-IgG4_____>

2440            2450           2460            2470
       *       *       *       *      *       *       *       *
      CCC CGA GAG CCA CAG GTG TAC ACC CTG CCC CCA TCC CAG GAG
      GGG GCT CTC GGT GTC CAC ATG TGG GAC GGG GGT AGG GTC CTC
      Pro Arg Glu Pro Gln Val Tyr Thr Leu Pro Pro Ser Gln Glu>
                              ___FC-IgG4_____>

2480           2490            2500            2510            2520
   *       *      *       *       *       *       *       *       *
  GAG ATG ACC AAG AAC CAG GTC AGC CTG ACC TGC CTG GTC AAA
  CTC TAC TGG TTC TTG GTC CAG TCG GAC TGG ACG GAC CAG TTT
  Glu Met Thr Lys Asn Gln Val Ser Leu Thr Cys Leu Val Lys>
                          ___FC-IgG4_____>

2530           2540           2550            2560
              *       *      *       *      *       *       *       *
             GGC TTC TAC CCC AGC GAC ATC GCC GTG GAG TGG GAG AGC AAT
             CCG AAG ATG GGG TCG CTG TAG CGG CAC CTC ACC CTC TCG TTA
             Gly Phe Tyr Pro Ser Asp Ile Ala Val Glu Trp Glu Ser Asn>
                                     ___FC-IgG4_____>
```

Figure 46I

```
            2570            2580            2590            2600
         *       *       *       *       *       *       *       *
        GGG CAG CCG GAG AAC AAC TAC AAG ACC ACG CCT CCC GTG CTG
        CCC GTC GGC CTC TTG TTG ATG TTC TGG TGC GGA GGG CAC GAC
        Gly Gln Pro Glu Asn Asn Tyr Lys Thr Thr Pro Pro Val Leu>
        _____FC-IgG4_____>

2610            2620            2630            2640
         *       *       *       *       *       *       *       *
        GAC TCC GAC GGC TCC TTC TTC CTC TAC AGC AGG CTA ACC GTG
        CTG AGG CTG CCG AGG AAG AAG GAG ATG TCG TCC GAT TGG CAC
        Asp Ser Asp Gly Ser Phe Phe Leu Tyr Ser Arg Leu Thr Val>
        _____FC-IgG4_____>

2650            2660            2670            2680
         *       *       *       *       *       *       *       *
        GAC AAG AGC AGG TGG CAG GAG GGG AAT GTC TTC TCA TGC TCC
        CTG TTC TCG TCC ACC GTC CTC CCC TTA CAG AAG AGT ACG AGG
        Asp Lys Ser Arg Trp Gln Glu Gly Asn Val Phe Ser Cys Ser>
        _____FC-IgG4_____>

2690            2700            2710            2720            2730
    *       *       *       *       *       *       *       *       *
   GTG ATG CAT GAG GCT CTG CAC AAC CAC TAC ACA CAG AAG AGC
   CAC TAC GTA CTC CGA GAC GTG TTG GTG ATG TGT GTC TTC TCG
   Val Met His Glu Ala Leu His Asn His Tyr Thr Gln Lys Ser>
   _____FC-IgG4_____>

2740            2750
         *       *       *       *
        CTC TCC CTG TCT CTG GGT AAA TGA
        GAG AGG GAC AGA GAC CCA TTT ACT
        Leu Ser Leu Ser Leu Gly Lys ***>
        _____FC-IgG4_____>
```

Figure 47A

```
           10             20             30             40
            *              *              *              *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
_____SIGNAL PEPTIDE_____>
_____IL-1RAcP_____>

50             60             70             80
            *              *              *              *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
____ SIGNAL PEPTIDE_____>
                        Ser Glu Arg Cys Asp Asp Trp Gly>
_____IL-1RAcP_____>

90            100            110            120
            *              *              *              *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_____IL-1RAcP_____>

130            140            150            160
            *              *              *              *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_____IL-1RAcP_____>

170         180            190            200         210
   *           *              *              *           *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_____IL-1RAcP_____>

220            230            240            250
            *              *              *              *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_____IL-1RAcP_____>

260            270            280            290
            *              *              *              *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_____IL-1RAcP_____>

300            310            320            330
            *              *              *              *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_____IL-1RAcP_____>
```

Figure 47B

```
         340              350              360              370
          *    *    *      *    *    *      *    *    *      *    *
         ACC  TGC  ATG    TTA  AGG  AAC    ACT  ACA  TAT    TGC  AGC  AAA  GTT  GCA
         TGG  ACG  TAC    AAT  TCC  TTG    TGA  TGT  ATA    ACG  TCG  TTT  CAA  CGT
         Thr  Cys  Met    Leu  Arg  Asn    Thr  Thr  Tyr    Cys  Ser  Lys  Val  Ala>
         _____IL-1RAcP_____>

380              390              400              410              420
     *    *    *      *    *    *      *    *    *      *    *    *      *    *
    TTT  CCC  TTG    GAA  GTT  GTT    CAA  AAA  GAC    AGC  TGT  TTC  AAT  TCC
    AAA  GGG  AAC    CTT  CAA  CAA    GTT  TTT  CTG    TCG  ACA  AAG  TTA  AGG
    Phe  Pro  Leu    Glu  Val  Val    Gln  Lys  Asp    Ser  Cys  Phe  Asn  Ser>
    _____IL-1RAcP_____>

430              440              450              460
          *    *    *      *    *    *      *    *    *      *    *
         CCC  ATG  AAA    CTC  CCA  GTG    CAT  AAA  CTG    TAT  ATA  GAA  TAT  GGC
         GGG  TAC  TTT    GAG  GGT  CAC    GTA  TTT  GAC    ATA  TAT  CTT  ATA  CCG
         Pro  Met  Lys    Leu  Pro  Val    His  Lys  Leu    Tyr  Ile  Glu  Tyr  Gly>
         _____IL-1RAcP_____>

470              480              490              500
          *    *    *      *    *    *      *    *    *      *    *
         ATT  CAG  AGG    ATC  ACT  TGT    CCA  AAT  GTA    GAT  GGA  TAT  TTT  CCT
         TAA  GTC  TCC    TAG  TGA  ACA    GGT  TTA  CAT    CTA  CCT  ATA  AAA  GGA
         Ile  Gln  Arg    Ile  Thr  Cys    Pro  Asn  Val    Asp  Gly  Tyr  Phe  Pro>
         _____IL-1RAcP_____>

510              520              530              540
     *    *    *      *    *    *      *    *    *      *    *    *      *
    TCC  AGT  GTC    AAA  CCG  ACT    ATC  ACT  TGG    TAT  ATG  GGC  TGT  TAT
    AGG  TCA  CAG    TTT  GGC  TGA    TAG  TGA  ACC    ATA  TAC  CCG  ACA  ATA
    Ser  Ser  Val    Lys  Pro  Thr    Ile  Thr  Trp    Tyr  Met  Gly  Cys  Tyr>
    _____IL-1RAcP_____>

550              560              570              580
          *    *    *      *    *    *      *    *    *      *    *
         AAA  ATA  CAG    AAT  TTT  AAT    AAT  GTA  ATA    CCC  GAA  GGT  ATG  AAC
         TTT  TAT  GTC    TTA  AAA  TTA    TTA  CAT  TAT    GGG  CTT  CCA  TAC  TTG
         Lys  Ile  Gln    Asn  Phe  Asn    Asn  Val  Ile    Pro  Glu  Gly  Met  Asn>
         _____IL-1RAcP_____>

590              600              610              620              630
     *    *    *      *    *    *      *    *    *      *    *    *      *    *
    TTG  AGT  TTC    CTC  ATT  GCC    TTA  ATT  TCA    AAT  AAT  GGA  AAT  TAC
    AAC  TCA  AAG    GAG  TAA  CGG    AAT  TAA  AGT    TTA  TTA  CCT  TTA  ATG
    Leu  Ser  Phe    Leu  Ile  Ala    Leu  Ile  Ser    Asn  Asn  Gly  Asn  Tyr>
    _____IL-1RAcP_____>

640              650              660              670
          *    *    *      *    *    *      *    *    *      *    *
         ACA  TGT  GTT    GTT  ACA  TAT    CCA  GAA  AAT    GGA  CGT  ACG  TTT  CAT
         TGT  ACA  CAA    CAA  TGT  ATA    GGT  CTT  TTA    CCT  GCA  TGC  AAA  GTA
         Thr  Cys  Val    Val  Thr  Tyr    Pro  Glu  Asn    Gly  Arg  Thr  Phe  His>
         _____IL-1RAcP_____>
```

Figure 47C

```
         680             690              700              710
    *      *      *      *       *        *       *         *
   CTC    ACC    AGG    ACT    CTG    ACT    GTA    AAG    GTA    GTA    GGC    TCT    CCA    AAA
   GAG    TGG    TCC    TGA    GAC    TGA    CAT    TTC    CAT    CAT    CCG    AGA    GGT    TTT
   Leu    Thr    Arg    Thr    Leu    Thr    Val    Lys    Val    Val    Gly    Ser    Pro    Lys>
   _____IL-1RAcP_____>

720             730              740              750
    *      *      *      *       *        *       *         *       *
   AAT    GCA    GTG    CCC    CCT    GTG    ATC    CAT    TCA    CCT    AAT    GAT    CAT    GTG
   TTA    CGT    CAC    GGG    GGA    CAC    TAG    GTA    AGT    GGA    TTA    CTA    GTA    CAC
   Asn    Ala    Val    Pro    Pro    Val    Ile    His    Ser    Pro    Asn    Asp    His    Val>
   _____IL-1RAcP_____>

760             770              780              790
    *      *      *      *       *        *       *         *       *
   GTC    TAT    GAG    AAA    GAA    CCA    GGA    GAG    GAG    CTA    CTC    ATT    CCC    TGT
   CAG    ATA    CTC    TTT    CTT    GGT    CCT    CTC    CTC    GAT    GAG    TAA    GGG    ACA
   Val    Tyr    Glu    Lys    Glu    Pro    Gly    Glu    Glu    Leu    Leu    Ile    Pro    Cys>
   _____IL-1RAcP_____>

800            810             820              830              840
   *      *       *      *       *        *       *         *       *
   ACG    GTC    TAT    TTT    AGT    TTT    CTG    ATG    GAT    TCT    CGC    AAT    GAG    GTT
   TGC    CAG    ATA    AAA    TCA    AAA    GAC    TAC    CTA    AGA    GCG    TTA    CTC    CAA
   Thr    Val    Tyr    Phe    Ser    Phe    Leu    Met    Asp    Ser    Arg    Asn    Glu    Val>
   _____IL-1RAcP_____>

850             860              870              880
      *      *      *       *       *        *       *         *
   TGG    TGG    ACC    ATT    GAT    GGA    AAA    AAA    CCT    GAT    GAC    ATC    ACT    ATT
   ACC    ACC    TGG    TAA    CTA    CCT    TTT    TTT    GGA    CTA    CTG    TAG    TGA    TAA
   Trp    Trp    Thr    Ile    Asp    Gly    Lys    Lys    Pro    Asp    Asp    Ile    Thr    Ile>
   _____IL-1RAcP_____>

890             900              910              920
    *      *      *      *       *        *       *         *
   GAT    GTC    ACC    ATT    AAC    GAA    AGT    ATA    AGT    CAT    AGT    AGA    ACA    GAA
   CTA    CAG    TGG    TAA    TTG    CTT    TCA    TAT    TCA    GTA    TCA    TCT    TGT    CTT
   Asp    Val    Thr    Ile    Asn    Glu    Ser    Ile    Ser    His    Ser    Arg    Thr    Glu>
   _____IL-1RAcP_____>

930             940              950              960
    *      *      *      *       *        *       *         *       *
   GAT    GAA    ACA    AGA    ACT    CAG    ATT    TTG    AGC    ATC    AAG    AAA    GTT    ACC
   CTA    CTT    TGT    TCT    TGA    GTC    TAA    AAC    TCG    TAG    TTC    TTT    CAA    TGG
   Asp    Glu    Thr    Arg    Thr    Gln    Ile    Leu    Ser    Ile    Lys    Lys    Val    Thr>
   _____IL-1RAcP_____>

970             980              990             1000
    *      *      *      *       *        *       *         *       *
   TCT    GAG    GAT    CTC    AAG    CGC    AGC    TAT    GTC    TGT    CAT    GCT    AGA    AGT
   AGA    CTC    CTA    GAG    TTC    GCG    TCG    ATA    CAG    ACA    GTA    CGA    TCT    TCA
   Ser    Glu    Asp    Leu    Lys    Arg    Ser    Tyr    Val    Cys    His    Ala    Arg    Ser>
   _____IL-1RAcP_____>
```

Figure 47D

```
        1010          1020         1030          1040         1050
          *        *    *        *    *        *    *        *    *
         GCC AAA GGC GAA GTT GCC AAA GCA GCC AAG GTG AAG CAG AAA
         CGG TTT CCG CTT CAA CGG TTT CGT CGG TTC CAC TTC GTC TTT
         Ala Lys Gly Glu Val Ala Lys Ala Ala Lys Val Lys Gln Lys>
         _____IL-1RAcP_____>

1060         1070          1080         1090
               *    *        *    *        *    *        *    *
              GTG CCA GCT CCA AGA TAC ACA GTG CAC ACA GGG GCT GCC AGA
              CAC GGT CGA GGT TCT ATG TGT CAC GTG TGT CCC CGA CGG TCT
              Val Pro Ala Pro Arg Tyr Thr Val>
              _____IL-1RAcP_____>
                                          His Thr Gly Ala Ala Arg>
                                          _____IL-1RII_____>

1100          1110          1120          1130
          *    *        *    *        *    *        *    *
         AGC TGC CGG TTT CGT GGG AGG CAT TAC AAG CGG GAG TTC AGG
         TCG ACG GCC AAA GCA CCC TCC GTA ATG TTC GCC CTC AAG TCC
         Ser Cys Arg Phe Arg Gly Arg His Tyr Lys Arg Glu Phe Arg>
         _____IL-1RII_____>

1140          1150         1160          1170
         *    *        *    *        *    *        *    *        *
         CTG GAA GGG GAG CCT GTA GCC CTG AGG TGC CCC CAG GTG CCC
         GAC CTT CCC CTC GGA CAT CGG GAC TCC ACG GGG GTC CAC GGG
         Leu Glu Gly Glu Pro Val Ala Leu Arg Cys Pro Gln Val Pro>
         _____IL-1RII_____>

1180         1190          1200          1210
          *    *        *    *        *    *        *    *
         TAC TGG TTG TGG GCC TCT GTC AGC CCC CGC ATC AAC CTG ACA
         ATG ACC AAC ACC CGG AGA CAG TCG GGG GCG TAG TTG GAC TGT
         Tyr Trp Leu Trp Ala Ser Val Ser Pro Arg Ile Asn Leu Thr>
         _____IL-1RII_____>

1220          1230         1240         1250          1260
       *        *    *        *    *        *    *        *    *
      TGG CAT AAA AAT GAC TCT GCT AGG ACG GTC CCA GGA GAA GAA
      ACC GTA TTT TTA CTG AGA CGA TCC TGC CAG GGT CCT CTT CTT
      Trp His Lys Asn Asp Ser Ala Arg Thr Val Pro Gly Glu Glu>
      _____IL-1RII_____>

1270         1280          1290         1300
              *    *        *    *        *    *        *    *
             GAG ACA CGG ATG TGG GCC CAG GAC GGT GCT CTG TGG CTT CTG
             CTC TGT GCC TAC ACC CGG GTC CTG CCA CGA GAC ACC GAA GAC
             Glu Thr Arg Met Trp Ala Gln Asp Gly Ala Leu Trp Leu Leu>
             _____IL-1RII_____>

1310          1320         1330          1340
            *    *        *    *        *    *        *    *
           CCA GCC TTG CAG GAG GAC TCT GGC ACC TAC GTC TGC ACT ACT
           GGT CGG AAC GTC CTC CTG AGA CCG TGG ATG CAG ACG TGA TGA
           Pro Ala Leu Gln Glu Asp Ser Gly Thr Tyr Val Cys Thr Thr>
           _____IL-1RII_____>
```

Figure 47E

```
         1350           1360           1370           1380
      *       *      *       *      *       *      *       *      *
      AGA AAT GCT TCT TAC TGT GAC AAA ATG TCC ATT GAG CTC AGA
      TCT TTA CGA AGA ATG ACA CTG TTT TAC AGG TAA CTC GAG TCT
      Arg Asn Ala Ser Tyr Cys Asp Lys Met Ser Ile Glu Leu Arg>
      _____IL-1RII_____>

1390           1400           1410           1420
      *       *      *       *      *       *      *       *
      GTT TTT GAG AAT ACA GAT GCT TTC CTG CCG TTC ATC TCA TAC
      CAA AAA CTC TTA TGT CTA CGA AAG GAC GGC AAG TAG AGT ATG
      Val Phe Glu Asn Thr Asp Ala Phe Leu Pro Phe Ile Ser Tyr>
      _____IL-1RII_____>

1430           1440           1450           1460           1470
*       *      *       *      *       *      *       *      *
CCG CAA ATT TTA ACC TTG TCA ACC TCT GGG GTA TTA GTA TGC
GGC GTT TAA AAT TGG AAC AGT TGG AGA CCC CAT AAT CAT ACG
Pro Gln Ile Leu Thr Leu Ser Thr Ser Gly Val Leu Val Cys>
_____IL-1RII_____>

1480           1490           1500           1510
      *       *      *       *      *       *      *       *
      CCT GAC CTG AGT GAA TTC ACC CGT GAC AAA ACT GAC GTG AAG
      GGA CTG GAC TCA CTT AAG TGG GCA CTG TTT TGA CTG CAC TTC
      Pro Asp Leu Ser Glu Phe Thr Arg Asp Lys Thr Asp Val Lys>
      _____IL-1RII_____>

1520           1530           1540           1550
      *       *      *       *      *       *      *       *
      ATT CAA TGG TAC AAG GAT TCT CTT CTT TTG GAT AAA GAC AAT
      TAA GTT ACC ATG TTC CTA AGA GAA GAA AAC CTA TTT CTG TTA
      Ile Gln Trp Tyr Lys Asp Ser Leu Leu Leu Asp Lys Asp Asn>
      _____IL-1RII_____>

1560           1570           1580           1590
      *       *      *       *      *       *      *       *      *
      GAG AAA TTT CTA AGT GTG AGG GGG ACC ACT CAC TTA CTC GTA
      CTC TTT AAA GAT TCA CAC TCC CCC TGG TGA GTG AAT GAG CAT
      Glu Lys Phe Leu Ser Val Arg Gly Thr Thr His Leu Leu Val>
      _____IL-1RII_____>

1600           1610           1620           1630
      *       *      *       *      *       *      *       *
      CAC GAT GTG GCC CTG GAA GAT GCT GGC TAT TAC CGC TGT GTC
      GTG CTA CAC CGG GAC CTT CTA CGA CCG ATA ATG GCG ACA CAG
      His Asp Val Ala Leu Glu Asp Ala Gly Tyr Tyr Arg Cys Val>
      _____IL-1RII_____>

1640           1650           1660           1670           1680
*       *      *       *      *       *      *       *      *
CTG ACA TTT GCC CAT GAA GGC CAG CAA TAC AAC ATC ACT AGG
GAC TGT AAA CGG GTA CTT CCG GTC GTT ATG TTG TAG TGA TCC
Leu Thr Phe Ala His Glu Gly Gln Gln Tyr Asn Ile Thr Arg>
_____IL-1RII_____>
```

Figure 47F

```
            1690            1700            1710             1720
             *       *       *       *       *       *       *       *
     AGT ATT GAG CTA CGC ATC AAG AAA AAA AAA GAA GAG ACC ATT
     TCA TAA CTC GAT GCG TAG TTC TTT TTT TTT CTT CTC TGG TAA
     Ser Ile Glu Leu Arg Ile Lys Lys Lys Lys Glu Glu Thr Ile>
     _____IL-1RII_____>

1730            1740            1750             1760
             *       *       *       *       *       *       *       *
     CCT GTG ATC ATT TCC CCC CTC AAG ACC ATA TCA GCT TCT CTG
     GGA CAC TAG TAA AGG GGG GAG TTC TGG TAT AGT CGA AGA GAC
     Pro Val Ile Ile Ser Pro Leu Lys Thr Ile Ser Ala Ser Leu>
     _____IL-1RII_____>

1770            1780            1790             1800
             *       *       *       *       *       *       *       *
     GGG TCA AGA CTG ACA ATC CCA TGT AAG GTG TTT CTG GGA ACC
     CCC AGT TCT GAC TGT TAG GGT ACA TTC CAC AAA GAC CCT TGG
     Gly Ser Arg Leu Thr Ile Pro Cys Lys Val Phe Leu Gly Thr>
     _____IL-1RII_____>

1810            1820            1830             1840
        *       *       *       *       *       *       *       *
     GGC ACA CCC TTA ACC ACC ATG CTG TGG TGG ACG GCC AAT GAC
     CCG TGT GGG AAT TGG TGG TAC GAC ACC ACC TGC CGG TTA CTG
     Gly Thr Pro Leu Thr Thr Met Leu Trp Trp Thr Ala Asn Asp>
     _____IL-1RII_____>

1850            1860            1870            1880            1890
   *       *       *       *       *       *       *       *       *
     ACC CAC ATA GAG AGC GCC TAC CCG GGA GGC CGC GTG ACC GAG
     TGG GTG TAT CTC TCG CGG ATG GGC CCT CCG GCG CAC TGG CTC
     Thr His Ile Glu Ser Ala Tyr Pro Gly Gly Arg Val Thr Glu>
     _____IL-1RII_____>

1900            1910            1920             1930
             *       *       *       *       *       *       *       *
     GGG CCA CGC CAG GAA TAT TCA GAA AAT AAT GAG AAC TAC ATT
     CCC GGT GCG GTC CTT ATA AGT CTT TTA TTA CTC TTG ATG TAA
     Gly Pro Arg Gln Glu Tyr Ser Glu Asn Asn Glu Asn Tyr Ile>
     _____IL-1RII_____>

1940            1950            1960             1970
             *       *       *       *       *       *       *       *
     GAA GTG CCA TTG ATT TTT GAT CCT GTC ACA AGA GAG GAT TTG
     CTT CAC GGT AAC TAA AAA CTA GGA CAG TGT TCT CTC CTA AAC
     Glu Val Pro Leu Ile Phe Asp Pro Val Thr Arg Glu Asp Leu>
     _____IL-1RII_____>

1980            1990            2000             2010
             *       *       *       *       *       *       *       *
     CAC ATG GAT TTT AAA TGT GTT GTC CAT AAT ACC CTG AGT TTT
     GTG TAC CTA AAA TTT ACA CAA CAG GTA TTA TGG GAC TCA AAA
     His Met Asp Phe Lys Cys Val Val His Asn Thr Leu Ser Phe>
     _____IL-1RII_____>
```

Figure 47G

```
       2020           2030         2040            2050
        *       *      *        *     *        *      *      *
      CAG ACA CTA CGC ACC ACA GTC AAG GAA GCC TCC TCC ACG TTC
      GTC TGT GAT GCG TGG TGT CAG TTC CTT CGG AGG AGG TGC AAG
      Gln Thr Leu Arg Thr Thr Val Lys Glu Ala Ser Ser Thr Phe>
                              _IL-1RII_____>

2060           2070         2080            2090           2100
   *       *      *        *     *        *      *      *     *
  TCC GGA GAC AAA ACT CAC ACA TGC CCA CCG TGC CCA GCA CCT
  AGG CCT CTG TTT TGA GTG TGT ACG GGT GGC ACG GGT CGT GGA
  Ser Gly Asp Lys Thr His Thr Cys Pro Pro Cys Pro Ala Pro>
                         _FC-IgG1_____>

2110         2120         2130         2140
           *     *      *     *      *     *      *     *
         GAA CTC CTG GGG GGA CCG TCA GTC TTC CTC TTC CCC CCA AAA
         CTT GAG GAC CCC CCT GGC AGT CAG AAG GAG AAG GGG GGT TTT
         Glu Leu Leu Gly Gly Pro Ser Val Phe Leu Phe Pro Pro Lys>
                          _FC-IgG1_____>

2150         2160         2170         2180
           *     *      *     *      *     *      *     *
         CCC AAG GAC ACC CTC ATG ATC TCC CGG ACC CCT GAG GTC ACA
         GGG TTC CTG TGG GAG TAC TAG AGG GCC TGG GGA CTC CAG TGT
         Pro Lys Asp Thr Leu Met Ile Ser Arg Thr Pro Glu Val Thr>
                          _FC-IgG1_____>

2190         2200         2210         2220
           *     *      *     *      *     *      *     *
         TGC GTG GTG GTG GAC GTG AGC CAC GAA GAC CCT GAG GTC AAG
         ACG CAC CAC CAC CTG CAC TCG GTG CTT CTG GGA CTC CAG TTC
         Cys Val Val Val Asp Val Ser His Glu Asp Pro Glu Val Lys>
                          _FC-IgG1_____>

2230         2240         2250         2260
          *     *      *     *      *     *      *     *
         TTC AAC TGG TAC GTG GAC GGC GTG GAG GTG CAT AAT GCC AAG
         AAG TTG ACC ATG CAC CTG CCG CAC CTC CAC GTA TTA CGG TTC
         Phe Asn Trp Tyr Val Asp Gly Val Glu Val His Asn Ala Lys>
                          _FC-IgG1_____>

2270           2280         2290            2300           2310
   *       *      *        *     *        *      *      *     *
  ACA AAG CCG CGG GAG GAG CAG TAC AAC AGC ACG TAC CGT GTG
  TGT TTC GGC GCC CTC CTC GTC ATG TTG TCG TGC ATG GCA CAC
  Thr Lys Pro Arg Glu Glu Gln Tyr Asn Ser Thr Tyr Arg Val>
                         _FC-IgG1_____>

2320         2330         2340         2350
           *     *      *     *      *     *      *     *
         GTC AGC GTC CTC ACC GTC CTG CAC CAG GAC TGG CTG AAT GGC
         CAG TCG CAG GAG TGG CAG GAC GTG GTC CTG ACC GAC TTA CCG
         Val Ser Val Leu Thr Val Leu His Gln Asp Trp Leu Asn Gly>
                          _FC-IgG1_____>
```

Figure 47H

```
            2360           2370           2380          2390
     *        *       *      *       *      *      *      *
    AAG   GAG   TAC   AAG   TGC   AAG   GTC   TCC   AAC   AAA   GCC   CTC   CCA   GCC
    TTC   CTC   ATG   TTC   ACG   TTC   CAG   AGG   TTG   TTT   CGG   GAG   GGT   CGG
    Lys   Glu   Tyr   Lys   Cys   Lys   Val   Ser   Asn   Lys   Ala   Leu   Pro   Ala>
                                        FC-IgG1                                      >

2400           2410           2420           2430
     *      *      *       *      *       *      *      *      *
    CCC   ATC   GAG   AAA   ACC   ATC   TCC   AAA   GCC   AAA   GGG   CAG   CCC   CGA
    GGG   TAG   CTC   TTT   TGG   TAG   AGG   TTT   CGG   TTT   CCC   GTC   GGG   GCT
    Pro   Ile   Glu   Lys   Thr   Ile   Ser   Lys   Ala   Lys   Gly   Gln   Pro   Arg>
                                        FC-IgG1                                      >

2440           2450           2460           2470
     *       *      *       *      *      *       *      *
    GAA   CCA   CAG   GTG   TAC   ACC   CTG   CCC   CCA   TCC   CGG   GAT   GAG   CTG
    CTT   GGT   GTC   CAC   ATG   TGG   GAC   GGG   GGT   AGG   GCC   CTA   CTC   GAC
    Glu   Pro   Gln   Val   Tyr   Thr   Leu   Pro   Pro   Ser   Arg   Asp   Glu   Leu>
                                        FC-IgG1                                      >

2480          2490           2500           2510          2520
     *      *       *       *      *      *       *      *      *
    ACC   AAG   AAC   CAG   GTC   AGC   CTG   ACC   TGC   CTG   GTC   AAA   GGC   TTC
    TGG   TTC   TTG   GTC   CAG   TCG   GAC   TGG   ACG   GAC   CAG   TTT   CCG   AAG
    Thr   Lys   Asn   Gln   Val   Ser   Leu   Thr   Cys   Leu   Val   Lys   Gly   Phe>
                                        FC-IgG1                                      >

2530           2540           2550           2560
      *       *      *       *      *       *      *      *
    TAT   CCC   AGC   GAC   ATC   GCC   GTG   GAG   TGG   GAG   AGC   AAT   GGG   CAG
    ATA   GGG   TCG   CTG   TAG   CGG   CAC   CTC   ACC   CTC   TCG   TTA   CCC   GTC
    Tyr   Pro   Ser   Asp   Ile   Ala   Val   Glu   Trp   Glu   Ser   Asn   Gly   Gln>
                                        FC-IgG1                                      >

2570           2580           2590          2600
      *        *      *       *      *      *       *      *
    CCG   GAG   AAC   AAC   TAC   AAG   ACC   ACG   CCT   CCC   GTG   CTG   GAC   TCC
    GGC   CTC   TTG   TTG   ATG   TTC   TGG   TGC   GGA   GGG   CAC   GAC   CTG   AGG
    Pro   Glu   Asn   Asn   Tyr   Lys   Thr   Thr   Pro   Pro   Val   Leu   Asp   Ser>
                                        FC-IgG1                                      >

2610           2620           2630           2640
      *      *      *       *       *      *      *      *      *
    GAC   GGC   TCC   TTC   TTC   CTC   TAT   AGC   AAG   CTC   ACC   GTG   GAC   AAG
    CTG   CCG   AGG   AAG   AAG   GAG   ATA   TCG   TTC   GAG   TGG   CAC   CTG   TTC
    Asp   Gly   Ser   Phe   Phe   Leu   Tyr   Ser   Lys   Leu   Thr   Val   Asp   Lys>
                                        FC-IgG1                                      >

2650           2660           2670           2680
      *      *      *       *      *       *      *       *
    AGC   AGG   TGG   CAG   CAG   GGG   AAC   GTC   TTC   TCA   TGC   TCC   GTG   ATG
    TCG   TCC   ACC   GTC   GTC   CCC   TTG   CAG   AAG   AGT   ACG   AGG   CAC   TAC
    Ser   Arg   Trp   Gln   Gln   Gly   Asn   Val   Phe   Ser   Cys   Ser   Val   Met>
                                        FC-IgG1                                      >
```

Figure 47 I

```
      2690          2700          2710          2720          2730
   *       *    *       *    *       *    *       *    *       *
CAT GAG GCT CTG CAC AAC CAC TAC ACG CAG AAG AGC CTC TCC
GTA CTC CGA GAC GTG TTG GTG ATG TGC GTC TTC TCG GAG AGG
His Glu Ala Leu His Asn His Tyr Thr Gln Lys Ser Leu Ser>
                            ____FC-IgG1_____>

2740
        *       *       *
CTG TCT CCG GGT AAA TGA
GAC AGA GGC CCA TTT ACT
Leu Ser Pro Gly Lys ***>
        _FC-IgG1_____>
```

Figure 48A

```
              10            20            30            40
         *         *    *         *    *        *     *         *
    ATG GTG CTT CTG TGG TGT GTA GTG AGT CTC TAC TTT TAT GGA
    TAC CAC GAA GAC ACC ACA CAT CAC TCA GAG ATG AAA ATA CCT
    Met Val Leu Leu Trp Cys Val Val Ser Leu Tyr Phe Tyr Gly>
    _____SIGNAL PEPTIDE_____>
    _____IL-1RAcP_____>

50            60            70            80
         *         *    *         *    *         *    *        *
    ATC CTG CAA AGT GAT GCC TCA GAA CGC TGC GAT GAC TGG GGA
    TAG GAC GTT TCA CTA CGG AGT CTT GCG ACG CTA CTG ACC CCT
    Ile Leu Gln Ser Asp Ala>
    ____SIGNAL PEPTIDE_____>
                        Ser Glu Arg Cys Asp Asp Trp Gly>
                        _____IL-1RAcP_____>

90           100           110           120
         *         *    *         *    *         *    *         *
    CTA GAC ACC ATG AGG CAA ATC CAA GTG TTT GAA GAT GAG CCA
    GAT CTG TGG TAC TCC GTT TAG GTT CAC AAA CTT CTA CTC GGT
    Leu Asp Thr Met Arg Gln Ile Gln Val Phe Glu Asp Glu Pro>
    _____IL-1RAcP_____>

130           140           150           160
         *         *    *         *    *        *     *        *
    GCT CGC ATC AAG TGC CCA CTC TTT GAA CAC TTC TTG AAA TTC
    CGA GCG TAG TTC ACG GGT GAG AAA CTT GTG AAG AAC TTT AAG
    Ala Arg Ile Lys Cys Pro Leu Phe Glu His Phe Leu Lys Phe>
    _____IL-1RAcP_____>

170           180           190           200           210
         *    *         *    *         *    *        *    *         *
    AAC TAC AGC ACA GCC CAT TCA GCT GGC CTT ACT CTG ATC TGG
    TTG ATG TCG TGT CGG GTA AGT CGA CCG GAA TGA GAC TAG ACC
    Asn Tyr Ser Thr Ala His Ser Ala Gly Leu Thr Leu Ile Trp>
    _____IL-1RAcP_____>

220           230           240           250
         *         *    *         *    *        *     *        *
    TAT TGG ACT AGG CAG GAC CGG GAC CTT GAG GAG CCA ATT AAC
    ATA ACC TGA TCC GTC CTG GCC CTG GAA CTC CTC GGT TAA TTG
    Tyr Trp Thr Arg Gln Asp Arg Asp Leu Glu Glu Pro Ile Asn>
    _____IL-1RAcP_____>

260           270           280           290
         *         *    *         *    *        *     *        *
    TTC CGC CTC CCC GAG AAC CGC ATT AGT AAG GAG AAA GAT GTG
    AAG GCG GAG GGG CTC TTG GCG TAA TCA TTC CTC TTT CTA CAC
    Phe Arg Leu Pro Glu Asn Arg Ile Ser Lys Glu Lys Asp Val>
    _____IL-1RAcP_____>

300           310           320           330
         *         *    *         *    *        *     *         *
    CTG TGG TTC CGG CCC ACT CTC CTC AAT GAC ACT GGC AAC TAT
    GAC ACC AAG GCC GGG TGA GAG GAG TTA CTG TGA CCG TTG ATA
    Leu Trp Phe Arg Pro Thr Leu Leu Asn Asp Thr Gly Asn Tyr>
    _____IL-1RAcP_____>
```

Figure 48B

```
       340            350            360            370
        *       *      *       *      *       *      *       *
       ACC TGC ATG TTA AGG AAC ACT ACA TAT TGC AGC AAA GTT GCA
       TGG ACG TAC AAT TCC TTG TGA TGT ATA ACG TCG TTT CAA CGT
       Thr Cys Met Leu Arg Asn Thr Thr Tyr Cys Ser Lys Val Ala>
                             ___IL-1RAcP_____>

380            390            400            410            420
   *       *      *       *      *       *      *       *      *
  TTT CCC TTG GAA GTT GTT CAA AAA GAC AGC TGT TTC AAT TCC
  AAA GGG AAC CTT CAA CAA GTT TTT CTG TCG ACA AAG TTA AGG
  Phe Pro Leu Glu Val Val Gln Lys Asp Ser Cys Phe Asn Ser>
                        ___IL-1RAcP___                      >

430            440            450            460
           *      *       *      *       *      *       *      *
          CCC ATG AAA CTC CCA GTG CAT AAA CTG TAT ATA GAA TAT GGC
          GGG TAC TTT GAG GGT CAC GTA TTT GAC ATA TAT CTT ATA CCG
          Pro Met Lys Leu Pro Val His Lys Leu Tyr Ile Glu Tyr Gly>
                              ___IL-1RAcP_____>

470            480            490            500
       *       *      *       *      *       *      *       *
       ATT CAG AGG ATC ACT TGT CCA AAT GTA GAT GGA TAT TTT CCT
       TAA GTC TCC TAG TGA ACA GGT TTA CAT CTA CCT ATA AAA GGA
       Ile Gln Arg Ile Thr Cys Pro Asn Val Asp Gly Tyr Phe Pro>
                              ___IL-1RAcP_____>

510            520            530            540
           *      *       *      *       *      *       *      *
          TCC AGT GTC AAA CCG ACT ATC ACT TGG TAT ATG GGC TGT TAT
          AGG TCA CAG TTT GGC TGA TAG TGA ACC ATA TAC CCG ACA ATA
          Ser Ser Val Lys Pro Thr Ile Thr Trp Tyr Met Gly Cys Tyr>
                              ___IL-1RAcP_____>

550            560            570            580
       *       *      *       *      *       *      *       *
       AAA ATA CAG AAT TTT AAT AAT GTA ATA CCC GAA GGT ATG AAC
       TTT TAT GTC TTA AAA TTA TTA CAT TAT GGG CTT CCA TAC TTG
       Lys Ile Gln Asn Phe Asn Asn Val Ile Pro Glu Gly Met Asn>
                              ___IL-1RAcP_____>

590            600            610            620            630
   *       *      *       *      *       *      *       *      *
  TTG AGT TTC CTC ATT GCC TTA ATT TCA AAT AAT GGA AAT TAC
  AAC TCA AAG GAG TAA CGG AAT TAA AGT TTA TTA CCT TTA ATG
  Leu Ser Phe Leu Ile Ala Leu Ile Ser Asn Asn Gly Asn Tyr>
                        ___IL-1RAcP___                      >

640            650            660            670
           *      *       *      *       *      *       *      *
          ACA TGT GTT GTT ACA TAT CCA GAA AAT GGA CGT ACG TTT CAT
          TGT ACA CAA CAA TGT ATA GGT CTT TTA CCT GCA TGC AAA GTA
          Thr Cys Val Val Thr Tyr Pro Glu Asn Gly Arg Thr Phe His>
                              ___IL-1RAcP_____>
```

Figure 48C

```
       680            690            700            710
   *    *         *    *         *    *         *    *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
                        _____IL-1RAcP_____>

720            730            740            750
   *    *         *    *         *    *         *    *    *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
                        _____IL-1RAcP_____>

760            770            780            790
   *    *         *    *         *    *         *    *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
                        _____IL-1RAcP_____>

800            810            820            830            840
   *    *         *    *         *    *         *    *         *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
                        _____IL-1RAcP_____>

850            860            870            880
   *    *         *    *         *    *         *    *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
                        _____IL-1RAcP_____>

890            900            910            920
   *    *         *    *         *    *         *    *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
                        _____IL-1RAcP_____>

930            940            950            960
   *    *         *    *         *    *         *    *    *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
                        _____IL-1RAcP_____>

970            980            990            1000
   *    *         *    *         *    *         *    *
TCT GAG GAT CTC AAG CGC ACC TAT GTC TGT CAT GCT AGA AGT
AGA CTC CTA GAG TTC GCG TGG ATA CAG ACA GTA CGA TCT TCA
Ser Glu Asp Leu Lys Arg Ser Tyr Val Cys His Ala Arg Ser>
                        _____IL-1RAcP_____>
```

Figure 48D

```
        1010          1020          1030          1040          1050
          *             *             *             *             *
       GCC AAA GGC GAA GTT GCC AAA GCA GCC AAG GTG AAG CAG AAA
       CGG TTT CCG CTT CAA CGG TTT CGT CGG TTC CAC TTC GTC TTT
       Ala Lys Gly Glu Val Ala Lys Ala Ala Lys Val Lys Gln Lys>
       _____IL-1RAcP_____>

1060          1070          1080          1090
                *             *             *             *
       GTG CCA GCT CCA AGA TAC ACA GTG CAC ACA GGG GCT GCC AGA
       CAC GGT CGA GGT TCT ATG TGT CAC GTG TGT CCC CGA CGG TCT
       Val Pro Ala Pro Arg Tyr Thr Val>
       _____IL-1RAcP_____>
                                        His Thr Gly Ala Ala Arg>
                                        _____IL-1RII_____>

1100          1110          1120          1130
                *             *             *             *
       AGC TGC CGG TTT CGT GGG AGG CAT TAC AAG CGG GAG TTC AGG
       TCG ACG GCC AAA GCA CCC TCC GTA ATG TTC GCC CTC AAG TCC
       Ser Cys Arg Phe Arg Gly Arg His Tyr Lys Arg Glu Phe Arg>
       _____IL-1RII_____>

1140          1150          1160          1170
                *             *             *             *
       CTG GAA GGG GAG CCT GTA GCC CTG AGG TGC CCC CAG GTG CCC
       GAC CTT CCC CTC GGA CAT CGG GAC TCC ACG GGG GTC CAC GGG
       Leu Glu Gly Glu Pro Val Ala Leu Arg Cys Pro Gln Val Pro>
       _____IL-1RII_____>

1180          1190          1200          1210
                *             *             *             *
       TAC TGG TTG TGG GCC TCT GTC AGC CCC CGC ATC AAC CTG ACA
       ATG ACC AAC ACC CGG AGA CAG TCG GGG GCG TAG TTG GAC TGT
       Tyr Trp Leu Trp Ala Ser Val Ser Pro Arg Ile Asn Leu Thr>
       _____IL-1RII_____>

1220          1230          1240          1250          1260
         *             *             *             *             *
       TGG CAT AAA AAT GAC TCT GCT AGG ACG GTC CCA GGA GAA GAA
       ACC GTA TTT TTA CTG AGA CGA TCC TGC CAG GGT CCT CTT CTT
       Trp His Lys Asn Asp Ser Ala Arg Thr Val Pro Gly Glu Glu>
       _____IL-1RII_____>

1270          1280          1290          1300
                *             *             *             *
       GAG ACA CGG ATG TGG GCC CAG GAC GGT GCT CTG TGG CTT CTG
       CTC TGT GCC TAC ACC CGG GTC CTG CCA CGA GAC ACC GAA GAC
       Glu Thr Arg Met Trp Ala Gln Asp Gly Ala Leu Trp Leu Leu>
       _____IL-1RII_____>

1310          1320          1330          1340
                *             *             *             *
       CCA GCC TTG CAG GAG GAC TCT GGC ACC TAC GTC TGC ACT ACT
       GGT CGG AAC GTC CTC CTG AGA CCG TGG ATG CAG ACG TGA TGA
       Pro Ala Leu Gln Glu Asp Ser Gly Thr Tyr Val Cys Thr Thr>
       _____IL-1RII_____>
```

Figure 48E

```
            1350            1360            1370            1380
          *       *       *       *       *       *       *       *       *
        AGA AAT GCT TCT TAC TGT GAC AAA ATG TCC ATT GAG CTC AGA
        TCT TTA CGA AGA ATG ACA CTG TTT TAC AGG TAA CTC GAG TCT
        Arg Asn Ala Ser Tyr Cys Asp Lys Met Ser Ile Glu Leu Arg>
                              ____IL-1RII_____>

1390            1400            1410            1420
          *       *       *       *       *       *       *       *
        GTT TTT GAG AAT ACA GAT GCT TTC CTG CCG TTC ATC TCA TAC
        CAA AAA CTC TTA TGT CTA CGA AAG GAC GGC AAG TAG AGT ATG
        Val Phe Glu Asn Thr Asp Ala Phe Leu Pro Phe Ile Ser Tyr>
                              ____IL-1RII_____>

1430            1440            1450            1460            1470
      *       *       *       *       *       *       *       *       *
    CCG CAA ATT TTA ACC TTG TCA ACC TCT GGG GTA TTA GTA TGC
    GGC GTT TAA AAT TGG AAC AGT TGG AGA CCC CAT AAT CAT ACG
    Pro Gln Ile Leu Thr Leu Ser Thr Ser Gly Val Leu Val Cys>
                          ____IL-1RII_____>

1480            1490            1500            1510
          *       *       *       *       *       *       *       *
        CCT GAC CTG AGT GAA TTC ACC CGT GAC AAA ACT GAC GTG AAG
        GGA CTG GAC TCA CTT AAG TGG GCA CTG TTT TGA CTG CAC TTC
        Pro Asp Leu Ser Glu Phe Thr Arg Asp Lys Thr Asp Val Lys>
                              ____IL-1RII_____>

1520            1530            1540            1550
          *       *       *       *       *       *       *       *
        ATT CAA TGG TAC AAG GAT TCT CTT CTT TTG GAT AAA GAC AAT
        TAA GTT ACC ATG TTC CTA AGA GAA GAA AAC CTA TTT CTG TTA
        Ile Gln Trp Tyr Lys Asp Ser Leu Leu Leu Asp Lys Asp Asn>
                              ____IL-1RII_____>

1560            1570            1580            1590
          *       *       *       *       *       *       *       *
        GAG AAA TTT CTA AGT GTG AGG GGG ACC ACT CAC TTA CTC GTA
        CTC TTT AAA GAT TCA CAC TCC CCC TGG TGA GTG AAT GAG CAT
        Glu Lys Phe Leu Ser Val Arg Gly Thr Thr His Leu Leu Val>
                              ____IL-1RII_____>

1600            1610            1620            1630
          *       *       *       *       *       *       *       *
        CAC GAT GTG GCC CTG GAA GAT GCT GGC TAT TAC CGC TGT GTC
        GTG CTA CAC CGG GAC CTT CTA CGA CCG ATA ATG GCG ACA CAG
        His Asp Val Ala Leu Glu Asp Ala Gly Tyr Tyr Arg Cys Val>
                              ____IL-1RII_____>

1640            1650            1660            1670            1680
      *       *       *       *       *       *       *       *       *
    CTG ACA TTT GCC CAT GAA GGC CAG CAA TAC AAC ATC ACT AGG
    GAC TGT AAA CGG GTA CTT CCG GTC GTT ATG TTG TAG TGA TCC
    Leu Thr Phe Ala His Glu Gly Gln Gln Tyr Asn Ile Thr Arg>
                          ____IL-1RII_____>
```

Figure 48F

```
            1690              1700              1710              1720
              *                 *                 *                 *
     *        *        *        *        *        *        *        *
    AGT ATT GAG CTA CGC ATC AAG AAA AAA AAA GAA GAG ACC ATT
    TCA TAA CTC GAT GCG TAG TTC TTT TTT TTT CTT CTC TGG TAA
    Ser Ile Glu Leu Arg Ile Lys Lys Lys Lys Glu Glu Thr Ile>
    _____IL-1RII_____>

1730              1740              1750              1760
              *                 *                 *                 *
     *        *        *        *        *        *        *        *
    CCT GTG ATC ATT TCC CCC CTC AAG ACC ATA TCA GCT TCT CTG
    GGA CAC TAG TAA AGG GGG GAG TTC TGG TAT AGT CGA AGA GAC
    Pro Val Ile Ile Ser Pro Leu Lys Thr Ile Ser Ala Ser Leu>
    _____IL-1RII_____>

1770              1780              1790              1800
              *                 *                 *                 *
     *        *        *        *        *        *        *        *
    GGG TCA AGA CTG ACA ATC CCA TGT AAG GTG TTT CTG GGA ACC
    CCC AGT TCT GAC TGT TAG GGT ACA TTC CAC AAA GAC CCT TGG
    Gly Ser Arg Leu Thr Ile Pro Cys Lys Val Phe Leu Gly Thr>
    _____IL-1RII_____>

1810              1820              1830              1840
              *                 *                 *                 *
     *        *        *        *        *        *        *        *
    GGC ACA CCC TTA ACC ACC ATG CTG TGG TGG ACG GCC AAT GAC
    CCG TGT GGG AAT TGG TGG TAC GAC ACC ACC TGC CGG TTA CTG
    Gly Thr Pro Leu Thr Thr Met Leu Trp Trp Thr Ala Asn Asp>
    _____IL-1RII_____>

1850      1860              1870              1880              1890
              *         *                 *                 *                 *
     *        *        *        *        *        *        *        *        *
    ACC CAC ATA GAG AGC GCC TAC CCG GGA GGC CGC GTG ACC GAG
    TGG GTG TAT CTC TCG CGG ATG GGC CCT CCG GCG CAC TGG CTC
    Thr His Ile Glu Ser Ala Tyr Pro Gly Gly Arg Val Thr Glu>
    _____IL-1RII_____>

1900              1910              1920              1930
              *                 *                 *                 *
     *        *        *        *        *        *        *        *
    GGG CCA CGC CAG GAA TAT TCA GAA AAT AAT GAG AAC TAC ATT
    CCC GGT GCG GTC CTT ATA AGT CTT TTA TTA CTC TTG ATG TAA
    Gly Pro Arg Gln Glu Tyr Ser Glu Asn Asn Glu Asn Tyr Ile>
    _____IL-1RII_____>

1940              1950              1960              1970
              *                 *                 *                 *
     *        *        *        *        *        *        *        *
    GAA GTG CCA TTG ATT TTT GAT CCT GTC ACA AGA GAG GAT TTG
    CTT CAC GGT AAC TAA AAA CTA GGA CAG TGT TCT CTC CTA AAC
    Glu Val Pro Leu Ile Phe Asp Pro Val Thr Arg Glu Asp Leu>
    _____IL-1RII_____>

1980              1990              2000              2010
              *                 *                 *                 *
     *        *        *        *        *        *        *        *
    CAC ATG GAT TTT AAA TGT GTT GTC CAT AAT ACC CTG AGT TTT
    GTG TAC CTA AAA TTT ACA CAA CAG GTA TTA TGG GAC TCA AAA
    His Met Asp Phe Lys Cys Val Val His Asn Thr Leu Ser Phe>
    _____IL-1RII_____>
```

Figure 48G

```
          2020          2030          2040          2050
           *     *       *       *     *       *     *       *
          CAG   ACA     CTA     CGC   ACC     ACA   GTC     AAG   GAA   GCC   TCC   TCC   ACG   TTC
          GTC   TGT     GAT     GCG   TGG     TGT   CAG     TTC   CTT   CGG   AGG   AGG   TGC   AAG
          Gln   Thr     Leu     Arg   Thr     Thr   Val     Lys   Glu   Ala   Ser   Ser   Thr   Phe>
          _____IL-1RII_____>

2060          2070          2080          2090          2100
     *     *       *     *       *     *       *     *       *
    TCC   GGA     GAG   TCC     AAA   TAC     GGT   CCG     CCA   TGC   CCA   TCA   TGC   CCA
    AGG   CCT     CTC   AGG     TTT   ATG     CCA   GGC     GGT   ACG   GGT   AGT   ACG   GGT
    Ser   Gly>
    _____>
                Glu   Ser     Lys   Tyr     Gly   Pro     Pro   Cys   Pro   Ser   Cys   Pro>
                _____FC-IgG4_____>

2110          2120          2130          2140
                 *     *       *     *       *     *       *     *
                GCA   CCT     GAG   TTC     CTG   GGG     GGA   CCA   TCA   GTC   TTC   CTG   TTC   CCC
                CGT   GGA     CTC   AAG     GAC   CCC     CCT   GGT   AGT   CAG   AAG   GAC   AAG   GGG
                Ala   Pro     Glu   Phe     Leu   Gly     Gly   Pro   Ser   Val   Phe   Leu   Phe   Pro>
                _____FC-IgG4_____>

2150          2160          2170          2180
                 *     *       *     *       *     *       *     *
                CCA   AAA     CCC   AAG     GAC   ACT     CTC   ATG   ATC   TCC   CGG   ACC   CCT   GAG
                GGT   TTT     GGG   TTC     CTG   TGA     GAG   TAC   TAG   AGG   GCC   TGG   GGA   CTC
                Pro   Lys     Pro   Lys     Asp   Thr     Leu   Met   Ile   Ser   Arg   Thr   Pro   Glu>
                _____FC-IgG4_____>

2190          2200          2210          2220
                 *     *       *     *       *     *       *     *
                GTC   ACG     TGC   GTG     GTG   GTG     GAC   GTG   AGC   CAG   GAA   GAC   CCC   GAG
                CAG   TGC     ACG   CAC     CAC   CAC     CTG   CAC   TCG   GTC   CTT   CTG   GGG   CTC
                Val   Thr     Cys   Val     Val   Val     Asp   Val   Ser   Gln   Glu   Asp   Pro   Glu>
                _____FC-IgG4_____>

2230          2240          2250          2260
                 *     *       *     *       *     *       *     *
                GTC   CAG     TTC   AAC     TGG   TAC     GTG   GAT   GGC   GTG   GAG   GTG   CAT   AAT
                CAG   GTC     AAG   TTG     ACC   ATG     CAC   CTA   CCG   CAC   CTC   CAC   GTA   TTA
                Val   Gln     Phe   Asn     Trp   Tyr     Val   Asp   Gly   Val   Glu   Val   His   Asn>
                _____FC-IgG4_____>

2270          2280          2290          2300          2310
         *     *       *     *       *     *       *     *       *
        GCC   AAG     ACA   AAG     CCG   CGG     GAG   GAG   CAG   TTC   AAC   AGC   ACG   TAC
        CGG   TTC     TGT   TTC     GGC   GCC     CTC   CTC   GTC   AAG   TTG   TCG   TGC   ATG
        Ala   Lys     Thr   Lys     Pro   Arg     Glu   Glu   Gln   Phe   Asn   Ser   Thr   Tyr>
        _____FC-IgG4_____>

2320          2330          2340          2350
                 *     *       *     *       *     *       *     *
                CGT   GTG     GTC   AGC     GTC   CTC     ACC   GTC   CTG   CAC   CAG   GAC   TGG   CTG
                GCA   CAC     CAG   TCG     CAG   GAG     TGG   CAG   GAC   GTG   GTC   CTG   ACC   GAC
                Arg   Val     Val   Ser     Val   Leu     Thr   Val   Leu   His   Gln   Asp   Trp   Leu>
                _____FC-IgG4_____>
```

Figure 48H

```
        2360          2370          2380          2390
    *     *      *     *      *     *      *     *
   AAC   GGC   AAG   GAG   TAC   AAG   TGC   AAG   GTC   TCC   AAC   AAA   GGC   CTC
   TTG   CCG   TTC   CTC   ATG   TTC   ACG   TTC   CAG   AGG   TTG   TTT   CCG   GAG
   Asn   Gly   Lys   Glu   Tyr   Lys   Cys   Lys   Val   Ser   Asn   Lys   Gly   Leu>
                                   __FC-IgG4_____>

2400          2410          2420          2430
    *     *      *     *      *     *      *     *     *
   CCG   TCC   TCC   ATC   GAG   AAA   ACC   ATC   TCC   AAA   GCC   AAA   GGG   CAG
   GGC   AGG   AGG   TAG   CTC   TTT   TGG   TAG   AGG   TTT   CGG   TTT   CCC   GTC
   Pro   Ser   Ser   Ile   Glu   Lys   Thr   Ile   Ser   Lys   Ala   Lys   Gly   Gln>
                                   __FC-IgG4_____>

2440          2450          2460          2470
    *     *      *     *      *     *      *     *
   CCC   CGA   GAG   CCA   CAG   GTG   TAC   ACC   CTG   CCC   CCA   TCC   CAG   GAG
   GGG   GCT   CTC   GGT   GTC   CAC   ATG   TGG   GAC   GGG   GGT   AGG   GTC   CTC
   Pro   Arg   Glu   Pro   Gln   Val   Tyr   Thr   Leu   Pro   Pro   Ser   Gln   Glu>
                                   __FC-IgG4_____>

2480          2490          2500          2510          2520
    *     *      *     *      *     *      *     *      *
   GAG   ATG   ACC   AAG   AAC   CAG   GTC   AGC   CTG   ACC   TGC   CTG   GTC   AAA
   CTC   TAC   TGG   TTC   TTG   GTC   CAG   TCG   GAC   TGG   ACG   GAC   CAG   TTT
   Glu   Met   Thr   Lys   Asn   Gln   Val   Ser   Leu   Thr   Cys   Leu   Val   Lys>
                                   __FC-IgG4_____>

2530          2540          2550          2560
    *     *      *     *      *     *      *     *
   GGC   TTC   TAC   CCC   AGC   GAC   ATC   GCC   GTG   GAG   TGG   GAG   AGC   AAT
   CCG   AAG   ATG   GGG   TCG   CTG   TAG   CGG   CAC   CTC   ACC   CTC   TCG   TTA
   Gly   Phe   Tyr   Pro   Ser   Asp   Ile   Ala   Val   Glu   Trp   Glu   Ser   Asn>
                                   __FC-IgG4_____>

2570          2580          2590          2600
    *     *      *     *      *     *      *     *
   GGG   CAG   CCG   GAG   AAC   AAC   TAC   AAG   ACC   ACG   CCT   CCC   GTG   CTG
   CCC   GTC   GGC   CTC   TTG   TTG   ATG   TTC   TGG   TGC   GGA   GGG   CAC   GAC
   Gly   Gln   Pro   Glu   Asn   Asn   Tyr   Lys   Thr   Thr   Pro   Pro   Val   Leu>
                                   __FC-IgG4_____>

2610          2620          2630          2640
    *     *      *     *      *     *      *     *     *
   GAC   TCC   GAC   GGC   TCC   TTC   TTC   CTC   TAC   AGC   AGG   CTA   ACC   GTG
   CTG   AGG   CTG   CCG   AGG   AAG   AAG   GAG   ATG   TCG   TCC   GAT   TGG   CAC
   Asp   Ser   Asp   Gly   Ser   Phe   Phe   Leu   Tyr   Ser   Arg   Leu   Thr   Val>
                                   __FC-IgG4_____>

2650          2660          2670          2680
    *     *      *     *      *     *      *     *
   GAC   AAG   AGC   AGG   TGG   CAG   GAG   GGG   AAT   GTC   TTC   TCA   TGC   TCC
   CTG   TTC   TCG   TCC   ACC   GTC   CTC   CCC   TTA   CAG   AAG   AGT   ACG   AGG
   Asp   Lys   Ser   Arg   Trp   Gln   Glu   Gly   Asn   Val   Phe   Ser   Cys   Ser>
                                   __FC-IgG4_____>
```

Figure 48 I

```
      2690            2700            2710           2720           2730
        *         *      *         *       *      *       *       *       *
       GTG ATG CAT GAG GCT CTG CAC AAC CAC TAC ACA CAG AAG AGC
       CAC TAC GTA CTC CGA GAC GTG TTG GTG ATG TGT GTC TTC TCG
       Val Met His Glu Ala Leu His Asn His Tyr Thr Gln Lys Ser>
                             _____FC-IgG4_____>

2740           2750
        *       *       *       *
       CTC TCC CTG TCT CTG GGT AAA TGA
       GAG AGG GAC AGA GAC CCA TTT ACT
       Leu Ser Leu Ser Leu Gly Lys ***>
              __FC-IgG4_____>
```

Figure 49A

```
           10              20              30              40
         *       *       *       *       *       *       *       *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
                     ____SIGNAL PEPTIDE_____>
            _____IL-1RAcP_____>

50              60              70              80
         *       *       *       *       *       *       *       *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
____SIGNAL PEPTIDE_____>
                        Ser Glu Arg Cys Asp Asp Trp Gly>
                   _____IL-1RAcP_____>

90             100             110             120
         *       *       *       *       *       *       *       *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
                     _____IL-1RAcP_____>

130             140             150             160
         *       *       *       *       *       *       *       *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
                     _____IL-1RAcP_____>

170             180             190             200             210
         *       *       *       *       *       *       *       *       *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
                     _____IL-1RAcP_____>

220             230             240             250
         *       *       *       *       *       *       *       *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
                     _____IL-1RAcP_____>

260             270             280             290
         *       *       *       *       *       *       *       *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
                     _____IL-1RAcP_____>

300             310             320             330
         *       *       *       *       *       *       *       *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
                     _____IL-1RAcP_____>
```

Figure 49B

```
          340              350              360              370
            *       *       *       *       *       *       *       *
        ACC TGC ATG TTA AGG AAC ACT ACA TAT TGC AGC AAA GTT GCA
        TGG ACG TAC AAT TCC TTG TGA TGT ATA ACG TCG TTT CAA CGT
        Thr Cys Met Leu Arg Asn Thr Thr Tyr Cys Ser Lys Val Ala>
        _____IL-1RAcP_____>

380              390              400              410              420
     *       *       *       *       *       *       *       *       *
   TTT CCC TTG GAA GTT GTT CAA AAA GAC AGC TGT TTC AAT TCC
   AAA GGG AAC CTT CAA CAA GTT TTT CTG TCG ACA AAG TTA AGG
   Phe Pro Leu Glu Val Val Gln Lys Asp Ser Cys Phe Asn Ser>
   _____IL-1RAcP_____>

430              440              450              460
        *       *       *       *       *       *       *       *
        CCC ATG AAA CTC CCA GTG CAT AAA CTG TAT ATA GAA TAT GGC
        GGG TAC TTT GAG GGT CAC GTA TTT GAC ATA TAT CTT ATA CCG
        Pro Met Lys Leu Pro Val His Lys Leu Tyr Ile Glu Tyr Gly>
        _____IL-1RAcP_____>

470              480              490              500
        *       *       *       *       *       *       *       *
        ATT CAG AGG ATC ACT TGT CCA AAT GTA GAT GGA TAT TTT CCT
        TAA GTC TCC TAG TGA ACA GGT TTA CAT CTA CCT ATA AAA GGA
        Ile Gln Arg Ile Thr Cys Pro Asn Val Asp Gly Tyr Phe Pro>
        _____IL-1RAcP_____>

510              520              530              540
     *       *       *       *       *       *       *       *       *
     TCC AGT GTC AAA CCG ACT ATC ACT TGG TAT ATG GGC TGT TAT
     AGG TCA CAG TTT GGC TGA TAG TGA ACC ATA TAC CCG ACA ATA
     Ser Ser Val Lys Pro Thr Ile Thr Trp Tyr Met Gly Cys Tyr>
     _____IL-1RAcP_____>

550              560              570              580
          *       *       *       *       *       *       *       *
        AAA ATA CAG AAT TTT AAT AAT GTA ATA CCC GAA GGT ATG AAC
        TTT TAT GTC TTA AAA TTA TTA CAT TAT GGG CTT CCA TAC TTG
        Lys Ile Gln Asn Phe Asn Asn Val Ile Pro Glu Gly Met Asn>
        _____IL-1RAcP_____>

590              600              610              620              630
     *       *       *       *       *       *       *       *       *
   TTG AGT TTC CTC ATT GCC TTA ATT TCA AAT AAT GGA AAT TAC
   AAC TCA AAG GAG TAA CGG AAT TAA AGT TTA TTA CCT TTA ATG
   Leu Ser Phe Leu Ile Ala Leu Ile Ser Asn Asn Gly Asn Tyr>
   _____IL-1RAcP_____>

640              650              660              670
        *       *       *       *       *       *       *       *
        ACA TGT GTT GTT ACA TAT CCA GAA AAT GGA CGT ACG TTT CAT
        TGT ACA CAA CAA TGT ATA GGT CTT TTA CCT GCA TGC AAA GTA
        Thr Cys Val Val Thr Tyr Pro Glu Asn Gly Arg Thr Phe His>
        _____IL-1RAcP_____>
```

Figure 49C

```
        680              690              700              710
    *    *    *    *    *    *    *    *    *    *
CTC  ACC  AGG  ACT  CTG  ACT  GTA  AAG  GTA  GTA  GGC  TCT  CCA  AAA
GAG  TGG  TCC  TGA  GAC  TGA  CAT  TTC  CAT  CAT  CCG  AGA  GGT  TTT
Leu  Thr  Arg  Thr  Leu  Thr  Val  Lys  Val  Val  Gly  Ser  Pro  Lys>
                              IL-1RAcP                                >

720              730              740              750
    *    *    *    *    *    *    *    *    *    *
AAT  GCA  GTG  CCC  CCT  GTG  ATC  CAT  TCA  CCT  AAT  GAT  CAT  GTG
TTA  CGT  CAC  GGG  GGA  CAC  TAG  GTA  AGT  GGA  TTA  CTA  GTA  CAC
Asn  Ala  Val  Pro  Pro  Val  Ile  His  Ser  Pro  Asn  Asp  His  Val>
                              IL-1RAcP                                >

760              770              780              790
    *    *    *    *    *    *    *    *    *    *
GTC  TAT  GAG  AAA  GAA  CCA  GGA  GAG  GAG  CTA  CTC  ATT  CCC  TGT
CAG  ATA  CTC  TTT  CTT  GGT  CCT  CTC  CTC  GAT  GAG  TAA  GGG  ACA
Val  Tyr  Glu  Lys  Glu  Pro  Gly  Glu  Glu  Leu  Leu  Ile  Pro  Cys>
                              IL-1RAcP                                >

800             810              820              830             840
    *    *    *    *    *    *    *    *    *    *
ACG  GTC  TAT  TTT  AGT  TTT  CTG  ATG  GAT  TCT  CGC  AAT  GAG  GTT
TGC  CAG  ATA  AAA  TCA  AAA  GAC  TAC  CTA  AGA  GCG  TTA  CTC  CAA
Thr  Val  Tyr  Phe  Ser  Phe  Leu  Met  Asp  Ser  Arg  Asn  Glu  Val>
                              IL-1RAcP                                >

850              860              870              880
    *    *    *    *    *    *    *    *    *    *
TGG  TGG  ACC  ATT  GAT  GGA  AAA  AAA  CCT  GAT  GAC  ATC  ACT  ATT
ACC  ACC  TGG  TAA  CTA  CCT  TTT  TTT  GGA  CTA  CTG  TAG  TGA  TAA
Trp  Trp  Thr  Ile  Asp  Gly  Lys  Lys  Pro  Asp  Asp  Ile  Thr  Ile>
                              IL-1RAcP                                >

890              900              910              920
    *    *    *    *    *    *    *    *    *    *
GAT  GTC  ACC  ATT  AAC  GAA  AGT  ATA  AGT  CAT  AGT  AGA  ACA  GAA
CTA  CAG  TGG  TAA  TTG  CTT  TCA  TAT  TCA  GTA  TCA  TCT  TGT  CTT
Asp  Val  Thr  Ile  Asn  Glu  Ser  Ile  Ser  His  Ser  Arg  Thr  Glu>
                              IL-1RAcP                                >

930              940              950              960
    *    *    *    *    *    *    *    *    *    *
GAT  GAA  ACA  AGA  ACT  CAG  ATT  TTG  AGC  ATC  AAG  AAA  GTT  ACC
CTA  CTT  TGT  TCT  TGA  GTC  TAA  AAC  TCG  TAG  TTC  TTT  CAA  TGG
Asp  Glu  Thr  Arg  Thr  Gln  Ile  Leu  Ser  Ile  Lys  Lys  Val  Thr>
                              IL-1RAcP                                >

970              980              990             1000
    *    *    *    *    *    *    *    *    *    *
TCT  GAG  GAT  CTC  AAG  CGC  AGC  TAT  GTC  TGT  CAT  GCT  AGA  AGT
AGA  CTC  CTA  GAG  TTC  GCG  TCG  ATA  CAG  ACA  GTA  CGA  TCT  TCA
Ser  Glu  Asp  Leu  Lys  Arg  Ser  Tyr  Val  Cys  His  Ala  Arg  Ser>
                              IL-1RAcP                                >
```

Figure 49D

```
     1010         1020         1030         1040         1050
       *    *      *    *       *    *       *    *       *    *
     GCC AAA GGC GAA GTT GCC AAA GCA GCC AAG GTG AAG CAG AAA
     CGG TTT CCG CTT CAA CGG TTT CGT CGG TTC CAC TTC GTC TTT
     Ala Lys Gly Glu Val Ala Lys Ala Ala Lys Val Lys Gln Lys>
     _____IL-1RAcP_____>

1060         1070         1080         1090
            *    *       *    *       *    *       *    *
          GTG CCA GCT CCA AGA TAC ACA GTG CAC ACA GGG GCT GCC AGA
          CAC GGT CGA GGT TCT ATG TGT CAC GTG TGT CCC CGA CGG TCT
          Val Pro Ala Pro Arg Tyr Thr Val>
          _____IL-1RAcP_____>
                                        His Thr Gly Ala Ala Arg>
                                        _____IL-1RII_____>

1100         1110         1120         1130
            *    *       *    *       *    *       *    *
          AGC TGC CGG TTT CGT GGG AGG CAT TAC AAG CGG GAG TTC AGG
          TCG ACG GCC AAA GCA CCC TCC GTA ATG TTC GCC CTC AAG TCC
          Ser Cys Arg Phe Arg Gly Arg His Tyr Lys Arg Glu Phe Arg>
          _____IL-1RII_____>

1140         1150         1160         1170
            *    *       *    *       *    *       *    *    *
          CTG GAA GGG GAG CCT GTA GCC CTG AGG TGC CCC CAG GTG CCC
          GAC CTT CCC CTC GGA CAT CGG GAC TCC ACG GGG GTC CAC GGG
          Leu Glu Gly Glu Pro Val Ala Leu Arg Cys Pro Gln Val Pro>
          _____IL-1RII_____>

1180         1190         1200         1210
            *    *       *    *       *    *       *    *
          TAC TGG TTG TGG GCC TCT GTC AGC CCC CGC ATC AAC CTG ACA
          ATG ACC AAC ACC CGG AGA CAG TCG GGG GCG TAG TTG GAC TGT
          Tyr Trp Leu Trp Ala Ser Val Ser Pro Arg Ile Asn Leu Thr>
          _____IL-1RII_____>

1220         1230         1240         1250         1260
       *    *      *    *       *    *       *    *       *    *
     TGG CAT AAA AAT GAC TCT GCT AGG ACG GTC CCA GGA GAA GAA
     ACC GTA TTT TTA CTG AGA CGA TCC TGC CAG GGT CCT CTT CTT
     Trp His Lys Asn Asp Ser Ala Arg Thr Val Pro Gly Glu Glu>
     _____IL-1RII_____>

1270         1280         1290         1300
            *    *       *    *       *    *       *    *
          CAG ACA CGG ATG TGG GCC CAG GAC GGT GCT CTG TGG CTT CTG
          GTC TGT GCC TAC ACC CGG GTC CTG CCA CGA GAC ACC GAA GAC
          Glu Thr Arg Met Trp Ala Gln Asp Gly Ala Leu Trp Leu Leu>
          _____IL-1RII_____>

1310         1320         1330         1340
            *    *       *    *       *    *       *    *
          CCA GCC TTG CAG GAG GAC TCT GGC ACC TAC GTC TGC ACT ACT
          GGT CGG AAC GTC CTC CTG AGA CCG TGG ATG CAG ACG TGA TGA
          Pro Ala Leu Gln Glu Asp Ser Gly Thr Tyr Val Cys Thr Thr>
          _____IL-1RII_____>
```

Figure 49E

```
        1350          1360          1370          1380
    *       *     *       *     *       *     *       *     *
  AGA AAT GCT TCT TAC TGT GAC AAA ATG TCC ATT GAG CTC AGA
  TCT TTA CGA AGA ATG ACA CTG TTT TAC AGG TAA CTC GAG TCT
  Arg Asn Ala Ser Tyr Cys Asp Lys Met Ser Ile Glu Leu Arg>
  _____IL-1RII_____  _____>

1390          1400          1410          1420
    *       *     *       *     *       *     *       *
  GTT TTT GAG AAT ACA GAT GCT TTC CTG CCG TTC ATC TCA TAC
  CAA AAA CTC TTA TGT CTA CGA AAG GAC GGC AAG TAG AGT ATG
  Val Phe Glu Asn Thr Asp Ala Phe Leu Pro Phe Ile Ser Tyr>
  _____IL-1RII_____>

1430          1440          1450          1460          1470
   *      *       *     *       *     *       *     *       *
  CCG CAA ATT TTA ACC TTG TCA ACC TCT GGG GTA TTA GTA TGC
  GGC GTT TAA AAT TGG AAC AGT TGG AGA CCC CAT AAT CAT ACG
  Pro Gln Ile Leu Thr Leu Ser Thr Ser Gly Val Leu Val Cys>
  _____IL-1RII_____>

1480          1490          1500          1510
    *       *     *       *     *       *     *       *
  CCT GAC CTG AGT GAA TTC ACC CGT GAC AAA ACT GAC GTG AAG
  GGA CTG GAC TCA CTT AAG TGG GCA CTG TTT TGA CTG CAC TTC
  Pro Asp Leu Ser Glu Phe Thr Arg Asp Lys Thr Asp Val Lys>
  _____IL-1RII_____>

1520          1530          1540          1550
    *       *     *       *     *       *     *       *
  ATT CAA TGG TAC AAG GAT TCT CTT CTT TTG GAT AAA GAC AAT
  TAA GTT ACC ATG TTC CTA AGA GAA GAA AAC CTA TTT CTG TTA
  Ile Gln Trp Tyr Lys Asp Ser Leu Leu Leu Asp Lys Asp Asn>
  _____IL-1RII_____>

1560          1570          1580          1590
    *       *     *       *     *       *     *       *
  GAG AAA TTT CTA AGT GTG AGG GGG ACC ACT CAC TTA CTC GTA
  CTC TTT AAA GAT TCA CAC TCC CCC TGG TGA GTG AAT GAG CAT
  Glu Lys Phe Leu Ser Val Arg Gly Thr Thr His Leu Leu Val>
  _____IL-1RII_____>

1600          1610          1620          1630
    *       *     *       *     *       *     *       *
  CAC GAT GTG GCC CTG GAA GAT GCT GGC TAT TAC CGC TGT GTC
  GTG CTA CAC CGG GAC CTT CTA CGA CCG ATA ATG GCG ACA CAG
  His Asp Val Ala Leu Glu Asp Ala Gly Tyr Tyr Arg Cys Val>
  _____IL-1RII_____>

1640          1650          1660          1670          1680
   *      *       *     *       *     *       *     *       *
  CTG ACA TTT GCC CAT GAA GGC CAG CAA TAC AAC ATC ACT AGG
  GAC TGT AAA CGG GTA CTT CCG GTC GTT ATG TTG TAG TGA TCC
  Leu Thr Phe Ala His Glu Gly Gln Gln Tyr Asn Ile Thr Arg>
  _____IL-1RII_____>
```

Figure 49F

```
              1690          1700          1710          1720
         *      *      *      *      *      *      *      *
    AGT ATT GAG CTA CGC ATC AAG AAA AAA AAA GAA GAG ACC ATT
    TCA TAA CTC GAT GCG TAG TTC TTT TTT TTT CTT CTC TGG TAA
    Ser Ile Glu Leu Arg Ile Lys Lys Lys Lys Glu Glu Thr Ile>
    _____IL-1RII_____>

1730          1740          1750          1760
         *      *      *      *      *      *      *      *
    CCT GTG ATC ATT TCC CCC CTC AAG ACC ATA TCA GCT TCT CTG
    GGA CAC TAG TAA AGG GGG GAG TTC TGG TAT AGT CGA AGA GAC
    Pro Val Ile Ile Ser Pro Leu Lys Thr Ile Ser Ala Ser Leu>
    _____IL-1RII_____>

1770          1780          1790          1800
         *      *      *      *      *      *      *      *
    GGG TCA AGA CTG ACA ATC CCA TGT AAG GTG TTT CTG GGA ACC
    CCC AGT TCT GAC TGT TAG GGT ACA TTC CAC AAA GAC CCT TGG
    Gly Ser Arg Leu Thr Ile Pro Cys Lys Val Phe Leu Gly Thr>
    _____IL-1RII_____>

1810          1820          1830          1840
         *      *      *      *      *      *      *
    GGC ACA CCC TTA ACC ACC ATG CTG TGG TGG ACG GCC AAT GAC
    CCG TGT GGG AAT TGG TGG TAC GAC ACC ACC TGC CGG TTA CTG
    Gly Thr Pro Leu Thr Thr Met Leu Trp Trp Thr Ala Asn Asp>
    _____IL-1RII_____>

1850          1860          1870          1880          1890
         *      *      *      *      *      *      *      *      *
    ACC CAC ATA GAG AGC GCC TAC CCG GGA GGC CGC GTG ACC GAG
    TGG GTG TAT CTC TCG CGG ATG GGC CCT CCG GCG CAC TGG CTC
    Thr His Ile Glu Ser Ala Tyr Pro Gly Gly Arg Val Thr Glu>
    _____IL-1RII_____>

1900          1910          1920          1930
         *      *      *      *      *      *      *      *
    GGG CCA CGC CAG GAA TAT TCA GAA AAT AAT GAG AAC TAC ATT
    CCC GGT GCG GTC CTT ATA AGT CTT TTA TTA CTC TTG ATG TAA
    Gly Pro Arg Gln Glu Tyr Ser Glu Asn Asn Glu Asn Tyr Ile>
    _____IL-1RII_____>

1940          1950          1960          1970
         *      *      *      *      *      *      *      *
    GAA GTG CCA TTG ATT TTT GAT CCT GTC ACA AGA GAG GAT TTG
    CTT CAC GGT AAC TAA AAA CTA GGA CAG TGT TCT CTC CTA AAC
    Glu Val Pro Leu Ile Phe Asp Pro Val Thr Arg Glu Asp Leu>
    _____IL-1RII_____>

1980          1990          2000          2010
         *      *      *      *      *      *      *      *
    CAC ATG GAT TTT AAA TGT GTT GTC CAT AAT ACC CTG AGT TTT
    GTG TAC CTA AAA TTT ACA CAA CAG GTA TTA TGG GAC TCA AAA
    His Met Asp Phe Lys Cys Val Val His Asn Thr Leu Ser Phe>
    _____IL-1RII_____>
```

Figure 49G

```
          2020         2030          2040          2050
            *            *             *             *
    CAG ACA CTA CGC ACC ACA GTC AAG GAA GCC TCC TCC ACG TTC
    GTC TGT GAT GCG TGG TGT CAG TTC CTT CGG AGG AGG TGC AAG
    Gln Thr Leu Arg Thr Thr Val Lys Glu Ala Ser Ser Thr Phe>
                              IL-1RII                     >

2060         2070          2080          2090         2100
    *            *             *             *            *
    TCC GGA GAG TCC AAA TAC GGT CCG CCA TGC CCA CCA TGC CCA
    AGG CCT CTC AGG TTT ATG CCA GGC GGT ACG GGT GGT ACG GGT
    Ser Gly>
    _____>
                Glu Ser Lys Tyr Gly Pro Pro Cys Pro Pro Cys Pro>
                                FC-IgG4                       >

2110          2120          2130          2140
             *             *             *             *
    GCA CCT GAG TTC CTG GGG GGA CCA TCA GTC TTC CTG TTC CCC
    CGT GGA CTC AAG GAC CCC CCT GGT AGT CAG AAG GAC AAG GGG
    Ala Pro Glu Phe Leu Gly Gly Pro Ser Val Phe Leu Phe Pro>
                               FC-IgG4                     >

2150          2160          2170          2180
             *             *             *             *
    CCA AAA CCC AAG GAC ACT CTC ATG ATC TCC CGG ACC CCT GAG
    GGT TTT GGG TTC CTG TGA GAG TAC TAG AGG GCC TGG GGA CTC
    Pro Lys Pro Lys Asp Thr Leu Met Ile Ser Arg Thr Pro Glu>
                               FC-IgG4                     >

2190          2200          2210          2220
             *             *             *             *
    GTC ACG TGC GTG GTG GTG GAC GTG AGC CAG GAA GAC CCC GAG
    CAG TGC ACG CAC CAC CAC CTG CAC TCG GTC CTT CTG GGG CTC
    Val Thr Cys Val Val Val Asp Val Ser Gln Glu Asp Pro Glu>
                               FC-IgG4                     >

2230          2240          2250          2260
             *             *             *             *
    GTC CAG TTC AAC TGG TAC GTG GAT GGC GTG GAG GTG CAT AAT
    CAG GTC AAG TTG ACC ATG CAC CTA CCG CAC CTC CAC GTA TTA
    Val Gln Phe Asn Trp Tyr Val Asp Gly Val Glu Val His Asn>
                               FC-IgG4                     >

2270         2280          2290          2300         2310
    *            *             *             *            *
    GCC AAG ACA AAG CCG CGG GAG GAG CAG TTC AAC AGC ACG TAC
    CGG TTC TGT TTC GGC GCC CTC CTC GTC AAG TTG TCG TGC ATG
    Ala Lys Thr Lys Pro Arg Glu Glu Gln Phe Asn Ser Thr Tyr>
                               FC-IgG4                     >

2320          2330          2340          2350
             *             *             *             *
    CGT GTG GTC AGC GTC CTC ACC GTC CTG CAC CAG GAC TGG CTG
    GCA CAC CAG TCG CAG GAG TGG CAG GAC GTG GTC CTG ACC GAC
    Arg Val Val Ser Val Leu Thr Val Leu His Gln Asp Trp Leu>
                               FC-IgG4                     >
```

Figure 49H

```
         2360           2370           2380           2390
    *      *      *      *      *      *      *      *
   AAC GGC AAG GAG TAC AAG TGC AAG GTC TCC AAC AAA GGC CTC
   TTG CCG TTC CTC ATG TTC ACG TTC CAG AGG TTG TTT CCG GAG
   Asn Gly Lys Glu Tyr Lys Cys Lys Val Ser Asn Lys Gly Leu>
   _____FC-IgG4_____>

2400           2410           2420           2430
    *      *      *      *      *      *      *      *      *
   CCG TCC TCC ATC GAG AAA ACC ATC TCC AAA GCC AAA GGG CAG
   GGC AGG AGG TAG CTC TTT TGG TAG AGG TTT CGG TTT CCC GTC
   Pro Ser Ser Ile Glu Lys Thr Ile Ser Lys Ala Lys Gly Gln>
   _____FC-IgG4_____>

2440           2450           2460           2470
    *      *      *      *      *      *      *      *
   CCC CGA GAG CCA CAG GTG TAC ACC CTG CCC CCA TCC CAG GAG
   GGG GCT CTC GGT GTC CAC ATG TGG GAC GGG GGT AGG GTC CTC
   Pro Arg Glu Pro Gln Val Tyr Thr Leu Pro Pro Ser Gln Glu>
   _____FC-IgG4_____>

2480           2490           2500           2510           2520
 *      *      *      *      *      *      *      *      *
GAG ATG ACC AAG AAC CAG GTC AGC CTG ACC TGC CTG GTC AAA
CTC TAC TGG TTC TTG GTC CAG TCG GAC TGG ACG GAC CAG TTT
Glu Met Thr Lys Asn Gln Val Ser Leu Thr Cys Leu Val Lys>
_____FC-IgG4_____>

2530           2540           2550           2560
    *      *      *      *      *      *      *      *
   GGC TTC TAC CCC AGC GAC ATC GCC GTG GAG TGG GAG AGC AAT
   CCG AAG ATG GGG TCG CTG TAG CGG CAC CTC ACC CTC TCG TTA
   Gly Phe Tyr Pro Ser Asp Ile Ala Val Glu Trp Glu Ser Asn>
   _____FC-IgG4_____>

2570           2580           2590           2600
    *      *      *      *      *      *      *      *
   GGG CAG CCG GAG AAC AAC TAC AAG ACC ACG CCT CCC GTG CTG
   CCC GTC GGC CTC TTG TTG ATG TTC TGG TGC GGA GGG CAC GAC
   Gly Gln Pro Glu Asn Asn Tyr Lys Thr Thr Pro Pro Val Leu>
   _____FC-IgG4_____>

2610           2620           2630           2640
    *      *      *      *      *      *      *      *      *
   GAC TCC GAC GGC TCC TTC TTC CTC TAC AGC AGG CTA ACC GTG
   CTG AGG CTG CCG AGG AAG AAG GAG ATG TCG TCC GAT TGG CAC
   Asp Ser Asp Gly Ser Phe Phe Leu Tyr Ser Arg Leu Thr Val>
   _____FC-IgG4_____>

2650           2660           2670           2680
    *      *      *      *      *      *      *      *
   GAC AAG AGC AGG TGG CAG GAG GGG AAT GTC TTC TCA TGC TCC
   CTG TTC TCG TCC ACC GTC CTC CCC TTA CAG AAG AGT ACG AGG
   Asp Lys Ser Arg Trp Gln Glu Gly Asn Val Phe Ser Cys Ser>
   _____FC-IgG4_____>
```

Figure 49 I

```
           2690              2700              2710              2720              2730
             *         *       *         *       *         *       *         *       *
           GTG ATG CAT GAG GCT CTG CAC AAC CAC TAC ACA CAG AAG AGC
           CAC TAC GTA CTC CGA GAC GTG TTG GTG ATG TGT GTC TTC TCG
           Val Met His Glu Ala Leu His Asn His Tyr Thr Gln Lys Ser>
           _____FC-IgG4_____>

2740              2750
             *         *       *         *
           CTC TCC CTG TCT CTG GGT AAA TGA
           GAG AGG GAC AGA GAC CCA TTT ACT
           Leu Ser Leu Ser Leu Gly Lys ***>
           _____FC-IgG4_____>
```

IL-1 RECEPTOR BASED CYTOKINE TRAPS

This application is a Continuation-in-Part of U.S. application Ser. No. 09/787,835, filed Mar. 22, 2001, which is a U.S. National Stage Application of International Application No. PCT/US99/22045, filed Sep. 22, 1999, which is a contiuation of U.S. application Ser. No. 09/313,942, filed May 19, 1999, now U.S. Pat. No. 6,472,179, which claims priority of U.S. Provisional Application No. 60/101,858 filed Sep. 25, 1998, now abandoned. The disclosures of these publications in their entireties are hereby incorporated by reference into this application.

BACKGROUND OF THE INVENTION

Although discovered for varying biological activities, ciliary neurotropic factor (CNTF), leukemia inhibitory factor (LIF), oncostatin M (OSM) and interleukin-6 (IL-6) comprise a defined family of cytokines (referred to herein as the "CNTF family" of cytokines). These cytokines are grouped together because of their distant structural similarities [Bazan, J. Neuron 7: 197–208 (1991); Rose and Bruce, Proc. Natl. Acad. Sci. USA 88: 8641–8645 (1991)], and, perhaps more importantly, because they share "β" signal-transducing receptor components [Baumann, et. al., J. Biol. Chem. 265:19853–19862 (1993); Davis, et al., Science 260; 1805–1808 (1993); Gearing et al., Science 255:1434–1437 (1992); Ip et al., Cell 69: 1121–1132 (1992); Stahl, et al., J. Biol. Chem. 268: 7628–7631 (1993); Stahl and Yancopoulos, Cell 74: 587–590 (1993)]. Recerter activation by this family of cytokines results from either homo- or hetero-dimerization of these β components [Davis, et al. Science 260: 1805–1808 (1993), Murakami, et al., Science 260: 1808–1810 (1993); Stahl and Yancopoulos, Cell 74: 587–590 (1993)]. IL-6 receptor activation requires homodimerization of gp130 [Murakami, et al. Science 260: 1808–1810 (1993), Hibi, et al., Cell 63: 1149–1157 (1993)], a protein initially identified as the IL-6 signal transducer [Hibi, et al., Cell 63: 1149–1157 (1990)]. CNTF, LIF and OSM receptor activation results from heterodimerazation between gp130 and a second gp130-related protein known as LIFRβ [Davis, et al., Science 260: 1805–1808 (1993)], that was initially identified by its ability to bind LIF [Gearing et al., EMBO J. 10: 2839–2848 (1991)].

In addition to the β components, some of these cytokines also require specificity-determining "α" components that are more limited in their tissue distribution than the β components, and thus determine the cellular targets of the particular cytokines [Stahl and Yancopoulos, Cell 74: 587–590 (1993)]. Thus, LIF and OSM are broadly acting factors that may only require the presence of gp130 and LIFRβ on responding cells, while CNTF requires CNTFRα [Stahl and Yancopoulos, Cell 74: 587–590 (1993)] and IL-6 requires IL-6Rα [Kishimoto, et al., Science 258: 593–597 (1992)]. Both CNTFRα (Davis et al., Science 259:1736–1739 (1993) and IL-6Rα [Hibi, et al. Cell 63:1149–1157, Murakami, et al., Science 260:1808–1810 (1990); Taga, et al., Cell 58:573–581 (1989)] can function as soluble proteins, consistent with the notion that they do not interact with intracellular signaling molecules but that they serve to help their ligands interact with the appropriate signal transducing β subunits [Stahl and Yancopoulos, Cell 74: 587–590 (1993)].

Additional evidence from other cytokine systems also supports the notion that dimerization provides a common mechanism by which all cytokine receptors initiate signal transduction. Growth hormone (GH) serves as perhaps the best example in this regard. Crystallographic studies have revealed that each GH molecule contains two distinct receptor binding sites, both of which are recognized by the same binding domain in the receptor, allowing a single molecule of GH to engage two receptor molecules [de Vos, et al., Science 255: 306–312 (1992)]. Dimerization occurs sequentially, with site 1 on the GH first binding to one receptor molecule, followed by the binding of site 2 to a second receptor molecule [Fuh, et al., Science 256: 1677–1680 (1992)]. Studies with the erythropoietin (EPO) receptor are also consistent with the importance of dimerization in receptor activation, as EPO receptors can be constitutively activated by a single amino acid change that introduces a cysteine residue and results in disulfide-linked homodimers [Watowich, et al., Proc. Natl. Acad. Sci. USA 89:2140–2144 (1992)].

In addition to homo- or hetero-dimerization of β subunits as the critical step for receptor activation, a second important feature is that formation of the final receptor complex by the CNTF family of cytokines occurs through a mechanism whereby the ligand successively binds to receptor components in an ordered manner [Davis, et al. Science 260:1805–1818 (1993); Stahl and Yancopoulos, Cell 74: 587–590 (1993)]. Thus CNTF first binds to CNTFRα, forming a complex which then binds gp130 to form an intermediate (called here the αβ1 intermediate) that is not signaling competent because it has only a single β component, before finally recruiting LIFRβ to form a heterodimer of β components which then initiates signal transduction. Although a similar intermediate containing IL-6 bound to IL-6Rα and a single molecule of gp130 has not been directly isolated, we have postulated that it does exist by analogy to its distant relative, CNTF, as well as the fact that the final active IL-6 receptor complex recruits two gp130 monomers. Altogether, these findings led to a proposal for the structure of a generic cytokine receptor complex (FIG. 1) in which each cytokine can have up to 3 receptor binding sites: a site that binds to an optional α specificity-determining component (α site), a site that binds to the first β signal-transducing component (β1 site), and a site that binds to the second β signal-transducing component (β2 site) [Stahl and Yancopoulos, Cell 74: 587–590 (1993)]. These 3 sites are used in sequential fashion, with the last step in complex formation—resulting in β component dimerization—critical for initiating signal transduction [Davis, et al. Science 260:1805–1818 (1993)]. Knowledge of the details of receptor activation and the existence of the non-functional β1 intermediate for CNTF has led to the finding that CNTF is a high affinity antagonist for IL-6 under certain circumstances, and provides the strategic basis for designing ligand or receptor-based antagonists for the CNTF family of cytokines as detailed below.

Once cytokine binding induces receptor complex formation, the dimerization of β components activates intracellular tyrosine kinase activity that results in phosphorylation of a wide variety of substrates [Ip, et al. Cell 69:121–1132 (1992)]. This activation of tyrosine kinase appears to be critical for downstream events since inhibitors that block the tyrosine phosphorylations also prevent later events such as gene inductions [Ip, et al., Cell 69:121–1132 (1992); Nakajima and Wall, Mol. Cell. Biol. 11:1409–1418 (1991)]. Recently, we have demonstrated that a newly discovered family of non-receptor tyrosine kinases that includes Jak1, Jak2, and Tyk2 (referred to as the Jak/Tyk kinases) [Firmbach-Kraft, et al., Oncogene 5:1329–1336 (1990); Wilks, et al., Mol. Cell. Biol. 11: 2057–2065 (1991] and that are involved in signal transduction with other cytokines [Argetsinger, et al., Cell 74:237–244 (1993); Silvennoinen, et al., Proc. Natl. Acad. Sci. USA 90:8429–8433 (1993); Velazquez, et al., Cell 70: 313–322 (1992); Witthuhn, et al., Cell 74:227–236 (1993)], preassociate with the cytoplasmic domains of the β subunits gp130 and LIFRβ in the absence of ligand, and become tyrosine phosphorylated and activated upon ligand addition [Stahl et al., Science 263:92–95 (1994)]. Therefore these kinases appear to be the most proximal step of intracellular signal transduction activated inside the cell as a result of ligand binding outside of the cell. Assay systems for screening collections of small molecules for specific agonist or antagonist activities based on this system are described below.

The CNTF family of cytokines play important roles in a wide variety of physiological processes that provide potential therapeutic applications for both antagonists and agonists.

SUMMARY OF THE INVENTION

An object of the present invention is the production of cytokine antagonists that are useful in the treatment of cytokine-related diseases or disorders.

Another object of the invention is the use of the disclosed cytokine antagonists for the treatment of cytokine-related diseases or disorders. For example, an IL-6 antagonist described herein may be used for the treatment of osteoporosis, the primary and second effects of cancers, including multiple myeloma, or cachexia.

Another object of the invention is the development of screening systems useful for identifying novel agonists and antagonists of cytokine receptors.

Another object of the invention is the development of screening systems useful for identifying small molecules that act as agonists or antagonists of the cytokines.

Another object of the invention is the development of screening systems useful for identifying novel agonists and antagonists of members of the CNTF family of cytokines.

Another object of the invention is the development of screening systems useful for identifying small molecules that act as agonists or antagonists of the CNTF family of cytokines.

Another object of the invention is the construction of several specific IL-1 cytokine antagonists, termed IL-1 Traps, each having different sequences but all being capable of blocking the binding of IL-1 to its receptor, thus functioning as IL-1 antagonists.

BRIEF DESCRIPTION OF THE FIGURES

FIGS. 4A–4B. The amino acid sequence of human gp130-Fc-His$_6$ (SEQ ID NO: 7). Amino acids 1 to 619 are from human gp130 (Hibi et al., Cell 63:1149–1157 (1990). Note that amino acid number 2 has been changed from a Leu to a Val in order to accommodate a Kozak sequence in the coding DNA sequence. The signal peptide of gp130-Fc-His$_6$ has been italicized (amino acids 1 to 22). The Ser-Gly bridge is shown in bold type (amino acids 620, 621). Amino acids 662 to 853 are from the Fc domain of human IgG1 (Lewis, et al., J. Immunol. 151:2829–2838 (1993). (†) mark the two cysteines (amino acids number 632 and 635) of the IgG hinge preceding the Fc that form the inter-chain disulfide bridges that link two Fc domains. The hexahistine tag is shown in bold/italic type (amino acids 854 to 859). (•) shows the position of the STOP codon.

FIG. 5: The amino acid sequence of human IL-6Rα-Fc (SEQ ID NO: 8). Key: Amino acids 1 to 358 are from human IL-6Rα (Yamasaki, et al., Science 241:825–828 (1988). Note that amino acid number 2 has been changed from a Leu to a Val in order to accommodate a Kozak sequence in the coding DNA sequence. The signal peptide of IL-6Rα-Fc has been italicized (amino acids 1 to 19). The Ala-Gly bridge is shown in bold type (amino acids 359, 360). Amino acids 361 to 592 are from the Fc domain of human IgG1 (Lewis et al., J. Immunol. 151:2829–2838 (1993). (†) mark the two cysteines (amino acids number 371 and 374) of the IgG hinge preceding the Fc that form the inter-chain disulfide bridges that link two Fc domains. (•) shows the position of the STOP codon.

FIG. 6: The CNTF/IL-6/IL-11 receptor system. The ordered formation of the hexameric signal transducing receptor complex is depicted schematically. The cytokine associates with the Rα component to form an obligatory cytokine•Rα complex (Kd is about 5 nM). This low affinity complex next associates with the first signal transducing component, marked β1, to form a high affinity cytokine•Rα•β1 complex (Kd is about 10 pM). In the case of IL-6Rα, this component is gp130. This trimeric high affinity complex subsequently associates with another such complex. Formation of this complex results in signal transduction as it involves dimerization of two signal transducing components, marked β1 and β2 respectively (adapted from (Ward et al., J. Bio. Chem. 269:23286–23289 (1994); Stahl and Yancopoulos, J. Neurobiology 25:1454–1466 (1994); Stahl and Yancopoulos, Cell 74:587–590 (1993).

FIG. 7: Design of heterodimeric receptor-based ligand Traps for IL-6. The heterodimeric ligand Trap is comprised of two interdisulfide linked proteins, gp130-Fc and IL-6Rα-Fc. The gp130-Fc•IL-6Rα-Fc complex (upper panel) is shown to mimic the high affinity cytokine•Rα•β1 complex (lower panel). The ligand Trap functions as an antagonist by sequestering IL-6 and thus rendering unavailable to interact with the native receptors on IL-6-responsive cells.

FIGS. 9A–9B. Amino acid sequence of gp130-Cγ1 (SEQ ID NO: 9). Key: Amino acids 1 to 619 are from human gp130 (Hibi, et al., Cell 63:1149–1157 (1990). Ser-Gly bridge is shown in bold type. Amino acids 662 to 651 are from the constant region of human IgG1 (Lewis et al., J. Immunol. 151:2829–2838 (1993). (*) shows the position of the STOP codon.

FIG. 10: Amino acid sequence of gp130Δ3fibro (SEQ ID NO: 10). Key: Amino acids 1 to 330 are from human gp130 (Hibi et al., Cell 63:1149–1157 (1990). Other symbols as described in FIG. 9.

FIG. 11: Amino acid sequence of J-CH1 (SEQ ID NO: 11). Key: The Ser-Gly bridge is shown in bold, the J-peptide is shown in italics, the $C_H1$ domain is underlined.

FIG. 12: Amino acid sequence of Cγ4 (SEQ ID NO: 12). Key: The Ser-Gly bridge is shown in bold type. Amino acids 2 to 239 comprise the Cγ4 sequence.

FIG. 13: Amino acid sequence of κ-domain (SEQ ID NO: 13). Key: The Ser-Gly bridge is shown in bold type. Amino acids 2 to 108 comprise the κ domain. The C-terminal cysteine (amino acid 108) is that involved in the disulfide bond of the κ domain with the $C_H1$ domain of Cγ.

FIG. 14: Amino acid sequence of λ-domain (SEQ ID NO: 14). Key: The Ser-Gly bridge is shown in bold type. Amino acids 2 to 106 comprise the λ domain (Cheung, et al., J. Virol. 66: 6714–6720 (1992). The C-terminal cysteine (amino acid 106) is that involved in the disulfide bond of the λ domain with the $C_H1$ domain of Cγ.

FIG. 15: Amino acid sequence of the soluble IL-6Rα domain (SEQ ID NO: 15). Key: Amino acids 1 to 358 comprise the soluble IL-6Rα domain (Yamasaki, et al., Science 241:825–828 (1988). The Ala-Gly bridge is shown in bold type.

FIG. 16: Amino acid sequence of the soluble IL-6Rα313 domain (SEQ ID NO: 16): Key: Amino acids 1 to 313 comprise the truncated IL-6Rα domain (IL-6Rα313). The Thr-Gly bridge is shown in bold type.

FIGS. 19A–19B: IL-6 can induce multimerization of the ligand Trap. (FIG. 19A) Two different ligand Traps are depicted schematically and listed according to their ability to bind protein A. gp130-Fc•IL-6Rα-Fc (GF6F) binds protein A via its Fc-domains, whereas gp130-$C_H$1•IL-6Rα-κ (G16K) does not bind to protein A. (FIG. 19B) Anti-kappa western blotting of proteins precipitated with Protein A-Sepharose from mixtures of GF6F±IL-6, G16K±IL-6, or GF6F plus G16K±IL-6, as marked.

FIGS. 21A–21D: Nucleotide sequence (SEQ ID NO: 17) encoding and deduced amino acid sequence (SEQ ID NO: 18) of fusion polypeptide designated 424 which is capable of binding the cytokine IL-4 to form a nonfunctional complex.

FIGS. 22A–22D: Nucleotide sequence (SEQ ID NO: 19) encoding and deduced amino acid sequence (SEQ ID NO: 20) of fusion polypeptide designated 603 which is capable of binding the cytokine IL-4 to form a nonfunctional complex.

FIGS. 23A–23D: Nucleotide sequence (SEQ ID NO: 21) encoding and deduced amino acid sequence (SEQ ID NO: 22) of fusion polypeptide designated 622 which is capable of binding the cytokine IL-4 to form a nonfunctional complex.

FIGS. 24A–24F: Nucleotide sequence (SEQ ID NO: 23) encoding and deduced amino acid sequence (SEQ ID NO: 24) of fusion polypeptide designated 412 which is capable of binding the cytokine IL-6 to form a nonfunctional complex.

FIGS. 25A–25F: Nucleotide sequence (SEQ ID NO: 25) encoding and deduced amino acid sequence (SEQ ID NO: 26) of fusion polypeptide designated 616 which is capable of binding the cytokine IL-6 to form a nonfunctional complex.

FIGS. 26A–26E: Nucleotide sequence (SEQ ID NO: 27) encoding and deduced amino acid sequence (SEQ ID NO: 28) of fusion polypeptide designated 569 which is capable of binding the cytokine IL-1 to form a nonfunctional complex.

FIGS. 31A–31G: The nucleotide (SEQ ID NO: 29) and encoded amino acid (SEQ ID NO: 30) sequence of the IL-4RαIL-13Rα1.Fc single chain Trap construct is set forth.

FIGS. 32A–32G: The nucleotide (SEQ ID NO: 31) and encoded amino acid (SEQ ID NO: 32) sequence of the IL-13Rα1.IL-4Rα.Fc single chain Trap construct is set forth.

FIG. 33: Blocking of IL-13 by IL-4Rα.IL-13Rα1.Fc and IL-13Rα1.IL-4Rα.Fc. Addition of either IL-4Rα.IL-13Rα1.Fc or IL-13Rα1.IL-4Rα.Fc Trap at a concentration of 10 nM blocks IL-13-induced growth up to ~2 nM. At an IL-13 concentration of ~4–5 nM the growth of TF1 cells is inhibited by 50%.

FIG. 36A: Cynomologus monkeys were treated in three parts as indicated. Human IL-4 (25 μg/kg) was injected subcutaneously twice daily for 4 days and human IL-4 Trap (8 mg/ml) and vehicle were given intravenously daily for 5 days, beginning 1 day prior to human IL-4 administration. Plasma was collected daily and assayed for MCP-1 levels. Results were expressed as mean+/−SEM; n=4. (ANOVA $p<0.0007$; Tukey-Kramer: Part 2 vs. Part 1, $p,0.05$; Part 2 vs. Part 3, $p,0.05$; Part 1 vs. Part 3, not significant.) FIG. 36B: Cynomologus monkeys were treated in three parts as indicated. Human IL-4 (25 μg/kg) was injected subcutaneously twice daily for 4 days and human IL-4 Trap (8 mg/ml) and vehicle were given intravenously daily for 5 days, beginning 1 day prior to human IL-4 administration. Whole blood was collected daily for flow cytometry analysis for CD16. Results were expressed as mean+/−SEM; n=4. (ANOVA $p<0.042$; Tukey-Kramer: Part 2 vs. Part 1, $p<0.05$; Part 2 vs. Part 3 and Part 1 vs. Part 3, not significant.)

FIG. 37: Murine IL-4 Trap partially prevented IL-4-mediated IgE increase in mice. BALB/C mice injected with anti-mouse IgD (100 μl/mouse, s.c.) were randomly divided into 3 groups, each received (on days 3–5) either vehicle, murine IL-4 Trap (1 mg/kg, s.c.), or a monoclonal antibody to mouse IL-4 (1 mg/kg, s.c.). Sera were collected at various time points and assayed for IgE levels. Results were expressed as mean+/−SEM (n=5 per group). (ANOVA $p=0.0002$; Tukey-Kramer: vehicle vs. IL-4 Trap, $p<0.01$; vehicle vs. IL-4 antibody, $p<0.001$; IL-4 Trap vs. IL-4 antibody, not significant).

FIGS. 38A–38I: Nucleotide (SEQ ID NO: 33) and deduced amino acid (SEQ ID NO: 34) sequence of Human IL-1 Trap 570-FE.

FIGS. 39A–39I: Nucleotide (SEQ ID NO: 35) and deduced amino acid (SEQ ID NO: 36) sequence of Human IL-1 Trap 570-FE.B.

FIGS. 40A–40I: Nucleotide (SEQ ID NO: 37) and deduced amino acid (SEQ ID NO: 38) sequence of Human IL-1 Trap 570-FE.C.

FIGS. 41A–41I: Nucleotide (SEQ ID NO: 39) and deduced amino acid (SEQ ID NO: 40) sequence of Human IL-1 Trap 823.

FIGS. 42A–42I: Nucleotide (SEQ ID NO: 41) and deduced amino acid (SEQ ID NO: 42) sequence of Human IL-1 Trap 823–1198.B.

FIGS. 43A–43I: Nucleotide (SEQ ID NO: 43) and deduced amino acid (SEQ ID NO: 44) sequence of Human IL-1 Trap 823–1267.C.

FIGS. 44A–44I: Nucleotide (SEQ ID NO: 45) and deduced amino acid (SEQ ID NO: 46) sequence of Human IL-1 Trap 1647-CtF.

FIGS. 45A–45I: Nucleotide (SEQ ID NO: 47) and deduced amino acid (SEQ ID NO: 48) sequence of Human IL-1 Trap 1647-CtF.B.

FIGS. 46A–46I: Nucleotide (SEQ ID NO: 49) and deduced amino acid (SEQ ID NO: 50) sequence of Human IL-1 Trap 1647-CtF.C.

FIGS. 47A–47I: Nucleotide (SEQ ID NO: 51) and deduced amino acid (SEQ ID NO: 52) sequence of Human IL-1 Trap 1649.

FIGS. 48A–48I: Nucleotide (SEQ ID NO: 53) and deduced amino acid (SEQ ID NO: 54) sequence of Human IL-1 Trap 1649-B.

FIGS. 49A–49I: Nucleotide (SEQ ID NO: 55) and deduced amino acid (SEQ ID NO: 56) sequence of Human IL-1 Trap 1646-C.

DETAILED DESCRIPTION OF THE INVENTION

Figure 1:
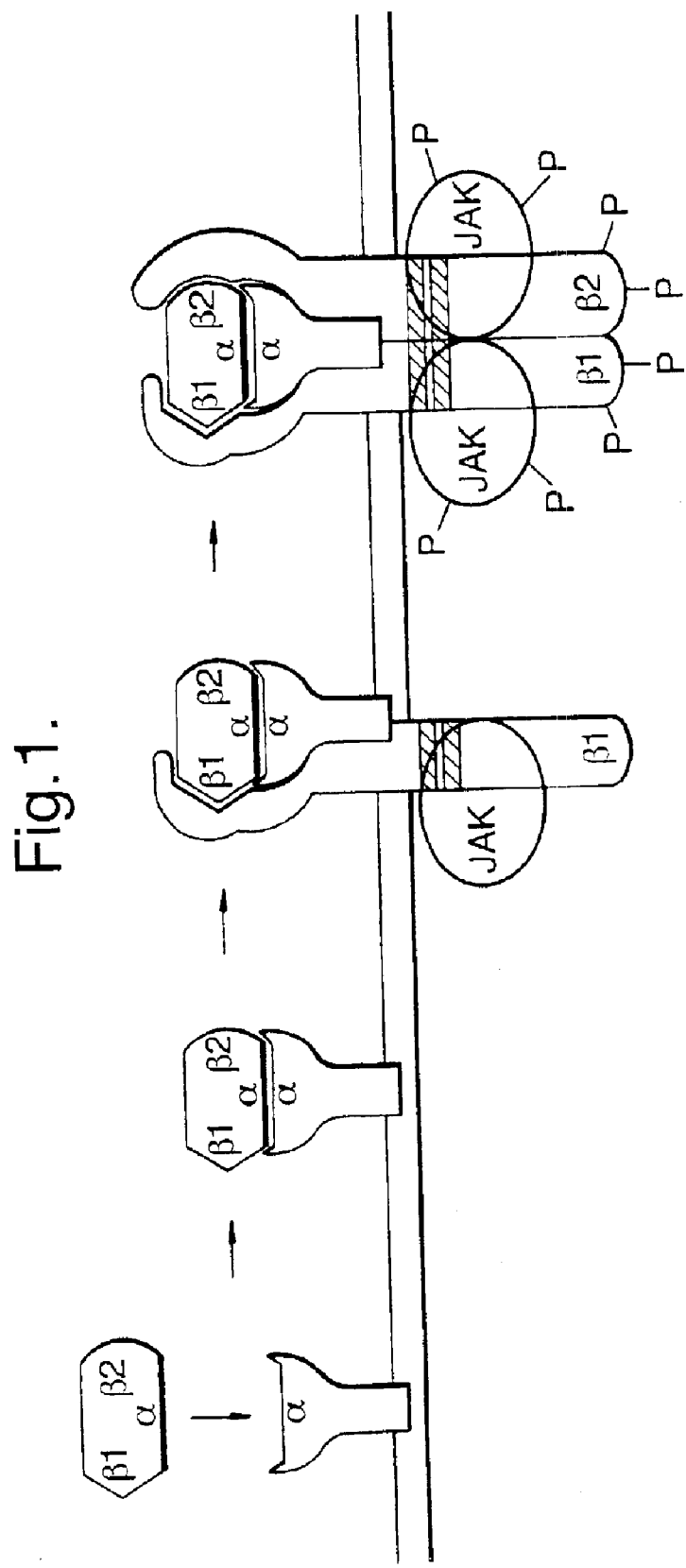
FIG. 1: Ordered binding of receptor components in a model of a generic cytokine receptor. The model indicates that cytokines contain up to 3 receptor binding sites and interact with their receptor components by binding first the optional α component, followed by binding to β1, and then β2. The β components for many cytokine receptors interact through membrane proximal regions (shaded boxes) with the Jak/Tyk family of cytoplasmic protein tyrosine kinases. Only upon dimerization of β components is signal transduction initiated, as schematized by the tyrosine phosphorylations (P) of the β components and the Jak/Tyk kinases.

The present invention provides an isolated nucleic acid molecule encoding a fusion polypeptide capable of binding a cytokine to form a nonfunctional complex comprising:

a) a nucleotide sequence encoding a first fusion polypeptide component comprising the amino acid sequence of the cytokine binding portion of the extracellular domain of the specificity determining component of a cytokine's receptor;

b) a nucleotide sequence encoding a second fusion polypeptide component comprising the amino acid sequence of the cytokine binding portion of the extracellular domain of the signal transducing component of a cytokine's receptor; and c) a nucleotide sequence encoding a third fusion polypeptide component comprising the amino acid sequence of a multimerizing component.

By "cytokine binding portion" what is meant is the minimal portion of the extracellular domain necessary to bind the cytokine. It is accepted by those of skill in the art that a defining characteristic of a cytokine receptor is the presence of the two fibronectin-like domains that contain canonical cysteines and of the WSXWS box (Bazan, J. F., 1990, PNAS 87: 6934–6938). Sequences encoding the extracellular domains of the binding component of the cytokine's receptor and of the signal transducing component of the cytokine's receptor may also be used to create the fusion polypeptide of the invention. Similarly, longer sequences encoding larger portions of the components of the cytokine's receptor may be used. However, it is contemplated that fragments smaller than the extracellular domain will function to bind the cytokine and therefore, the invention contemplates fusion polypeptides comprising the minimal portion of the extracellular domain necessary to bind the cytokine as the cytokine binding portion.

The invention comprises a "specificity determining component" of a cytokine's receptor and a "signal transducing component" of the cytokine's receptor. Regardless of the nomenclature used to designate a particular component or subunit of a cytokine receptor, one skilled in the art would recognize which component or subunit of a receptor is responsible for determining the cellular target of the cytokine, and thus would know which component constitutes the "specificity determining component."

Similarly, regardless of the nomenclature used, one of skill in the art would know which component or subunit of a receptor would constitute the "signal transducing component." As used herein, the "signal transducing component" is a component of the native receptor which is not the specificity determining component and which does not bind or weakly binds the cytokine in the absence of the specificity determining component. In the native receptor, the "signal transducing component" may participate in signaling.

For example, while some cytokine receptors have components designated α and β, the IL-4 receptor has a signal transducing component referred to as IL-2Rγ. However, regardless of what name is associated with that component, one skilled in the art would know which component of the IL-4 receptor is the signal transducing component. Thus to practice the present invention and create a high affinity Trap for IL-4, one of skill in the art would create an isolated nucleic acid comprising a nucleotide sequence encoding a first fusion polypeptide component comprising the amino acid sequence of the cytokine binding portion of the extracellular domain of the specificity determining component of the IL-4 receptor (IL-4Rα); a nucleotide sequence encoding a second fusion polypeptide component comprising the amino acid sequence of the cytokine binding portion of the extracellular domain of the signal transducing component of the IL-4 receptor (IL-2Rγ); and a nucleotide sequence encoding a third fusion polypeptide component comprising the amino acid sequence of a multimerizing component (for example, an Fc domain of IgG) to create a high affinity Trap for IL-4.

Some further examples of the receptor components that may be used to prepare cytokine antagonists according to the invention are set forth in Table 1. The Table 1 sets forth, by way of example but not by way of limitation, some of the varied nomenclature used in the scientific literature to describe those components which function as specificity determining components and those which function as signal transducing components of certain cytokine receptors.

TABLE 1

| Cytokine | Specificity determining Component | Signal transducing Component |
|---|---|---|
| Interleukin-1 (IL-1) | Type I IL-1R (ref. 8) Type II IL-1R (ref. 8) IL-1RI (ref. 11) IL-1RII (ref. 11) | IL-1R AcP (refs. 8, 11) |

TABLE 1-continued

| Cytokine | Specificity determining Component | Signal transducing Component |
|---|---|---|
| Interleukin-2 (IL-2) | α-subunit [ref. 2] <br> α-chain [ref. 3] <br> IL-2Rα [ref. 1] | β-chain [ref. 3] <br> β-subunit [ref. 2] <br> γ-chain [ref. 3] <br> IL-2Rβ [refs. 1, 10] <br> IL-2Rγ [refs. 1, 10] <br> β$_c$ [ref. 1] |
| Interleukin-3 (IL-3) | IL-3Rα [ref. 1] <br> α-subunit [ref 2] <br> α-receptor component [ref. 5] | β-subunit [ref 2] <br> β-chain [ref. 3] <br> β-receptor component [ref. 5] |
| Interleukin-4 (IL-4) | IL-4R [ref. 1] | γ-chain [ref 3] <br> IL-2Rγ [ref 1] |
| Interleukin-5 (IL-5) | IL-5Rα [ref 1] <br> α-subunit [ref 2] <br> α-receptor component [ref. 5] | β$_c$ [ref 1] <br> β-subunit [ref. 2] <br> β-chain [ref. 3] <br> β-receptor component [ref 5] |
| Granulocyte macrophage-colony stimulating factor (GM-CSF) | α-receptor component [ref. 5] <br> α-subunit [ref. 2] <br> GMRα [refs. 1, 2] | β-receptor component [ref. 5] <br> β-subunit [ref. 2] <br> β-chain [ref. 3] <br> β$_c$ [ref. 1] <br> GMRβ [refs 1, 2] |
| Leukemia inhibitory factor (LIF) | LIFBP [ref. 1] <br> α-receptor component [ref. 5] | gp130 [refs 1, 3] <br> β-receptor component [ref. 5] <br> gp130 [ref. 4] |
| Interleukin-11 (IL-11) | α-chain [ref. 4] <br> NR1 [ref. 4] | |
| Interleukin-15 (IL-15) | IL-15Rα [ref 10] | IL-2Rβ [ref. 10] <br> IL-2Rγ [ref. 10] |
| Interferon-γ (IFNγ) | IFN-γR [ref. 7] <br> IFN-γR1 [ref. 7] | AF-1 [ref. 7] <br> IFN-γR2 [ref. 7] |
| TGFβ | Type II [refs. 6, 9] | Type I [refs. 6, 9] |

Only a few of the multitude of references are cited in Table 1, and they are set forth as follows:
1. Sato and Miyajima, Current Opinions in Cell Biology 6: 174–179 (1994)—See page 176, lines 9–16;
2. Miyajima, et al., Annual Review of Immunology 10: 295–331 (1992)—See page 295, line 4 to page 296, line 1; page 305, last paragraph;
3. Kondo, et al, Science 262: 1874–1877 (1993)—See page 1874, cols. 1 & 2;
4. Hilton, et al, EMBO Journal 13: 4765–4775 (1994)—See page 4766, col. 1, lines 20 24;
5. Stahl and Yancopoulos, Cell 74: 587–590 (1993)—See page 587, column 2, lines 15–22;
6. Bassing, et al, Journal of Biological Chemistry 269: 14861–14864 (1994)—See page 14861, col. 2, lines 1–9 and 21–28;
7. Kotenko, et al, Journal of Biological Science 270: 20915–20921 (1995)—See page 20915, lines 1–5 of the abstract;
8. Greenfeder, et al., Journal of Biological Chemistry 270: 13757–13765 (1995)—See page 13757, col. 1, line 6 to col. 2, line 3 and col. 2, lines 10–12; page 13764, col. 2, last 3 lines and page 13765, col. 1, lines 1–7;
9. Lebrun and Vale, Molecular Cell Biology 17: 1682–1691 (1997)—See page 1682, Abstract lines 2–6;
10. Kennedy and Park, Journal of Clinical Immunology 16: 134–143 (1996)—See page 134, lines 1–7 of the abstract; page 136, col 2. , lines 1–5;
11. Wesche, et al., Journal of Biological Chemistry 272: 7727–7731 (1997) See page 7731, lines 20–26.

Kotenko, et al. recently identified the IL-10R2 (IL-10Rβ) chain which is reported to serve as an accessory chain that is essential for the active IL-10 receptor complex and for initiating IL-10 induced signal transduction events (S. V. Kotenko, et al., The EMBO Journal, 1997, Vol. 16: 5894–5903). Additional cytokines and their receptors are described in Appendix II, page A:9 of Immunobiology, The Immune System In Health and Disease, 2nd Edition, by Charles A. Janeway, Jr. and Paul Travers, published by Current Biology Ltd./Garland Publishing Inc., copyright 1996.

In preparing the nucleic acid sequence encoding the fusion polypeptide of the invention, the first, second, and third components of the fusion polypeptide are encoded in a single strand of nucleotides which, when expressed by a host vector system, produces a monomeric species of the fusion polypeptide. The monomers thus expressed then multimerize due to the interactions between the multimerizing components (the third fusion polypeptide components). Producing the fusion polypeptides in this manner avoids the need for purification of heterodimeric mixtures that would result if the first and second components were produced as separate molecules and then multimerized. For example, U.S. Pat. No. 5,470,952 issued Nov. 28, 1995 describes the production of heterodimeric proteins that function as CNTF or IL-6 antagonists. The heterodimers are purified from cell lines cotransfected with the appropriate alpha (α) and beta (β) components. Heterodimers are then separated from homodimers using methods such as passive elution from preparative, nondenaturing polyacrylamide gels or by using high pressure cation exchange chromatography. The need for this purification step is avoided by the methods of the present invention.

In addition, PCT International Application WO 96/11213 published Apr. 18, 1996 entitled Dimeric IL-4 Inhibitors states that the applicant has prepared homodimers in which two IL-4 receptors are bound by a polymeric spacer and has prepared heterodimers in which an IL-4 receptor is linked by a polymeric spacer to an IL-2 receptor gamma chain. The polymeric spacer described is polyethylene glycol (PEG). The two receptor components, IL-4R and IL-2Rgamma are separately expressed and purified. Pegylated homodimers and heterodimers are then produced by joining the components together using bi-functional PEG reagents. It is an advantage of the present invention that it avoids the need for such time consuming and costly purification and pegylation steps.

In one embodiment of the invention, the nucleotide sequence encoding the first component is upstream of the nucleotide sequence encoding the second component. In another embodiment of the invention, the nucleotide sequence encoding the first component is downstream of the nucleotide sequence encoding the second component. Further embodiments of the invention may be prepared in which the order of the first, second and third fusion polypeptide components are rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In further embodiments of the invention, the cytokine bound by the fusion polypeptide may be a member of the hematopoietin family of cytokines selected from the group consisting of interleukin-2, interleukin-3, interleukin-4, interleukin-5, interleukin-6, interleukin-7, interleukin-9, interleukin-11, interleukin-13, interleukin-15, granulocyte macrophage colony stimulating factor, oncostatin M, leukemia inhibitory factor, and cardiotrophin-1.

In additional embodiments of the invention, the cytokine bound by the fusion polypeptide may be a member of the interferon family of cytokines selected from the group consisting of IFN-gamma, IFN-alpha, and IFN-beta.

In additional embodiments of the invention, the cytokine bound by the fusion polypeptide may be a member of the immunoglobulin superfamily of cytokines selected from the group consisting of B7.1 (CD80) and B7.2 (B70).

In still further embodiments of the invention, the cytokine bound by the fusion polypeptide may be a member of the TNF family of cytokines selected from the group consisting of TNF-alpha, TNF-beta, LT-beta, CD40 ligand, Fas ligand, CD 27 ligand, CD 30 ligand, and 4-1BBL.

In additional embodiments of the invention, the cytokine bound by the fusion polypeptide may be a cytokine selected from the group consisting of interleukin-1, interleukin-10, interleukin-12, interleukin-14, interleukin-18, and MIF.

Because specificity determination and signal transduction occurs by a similar mechanism in the TGF-β/BMP family of cytokines (See D. Kingsley, Genes & Development, 1994, 8: 133–146; J. Wrana, Miner Electrolyte Metab, 24: 120–130 (1998); R. Derynck and X. Feng, Biochimica et Biophysica Acta 1333 (1997) F105–F150; and J. Massague and F. Weis-Garcia, "Serine/threonine Kinase Receptors: Mediators of Transforming Growth Factor Beta Family Signals" In Cancer Surveys, Vol. 27: Cell Signaling, 1996, Imperial Cancer Research Fund) the present invention may be used to produce high affinity antagonists for cytokines that are members of the TGF-β/BMP family.

Therefore, in additional embodiments of the invention, the cytokine bound by the fusion polypeptide may be a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5.

In alternative embodiments of the invention, the specificity determining component, the signal transducing component, or both, may be substituted for by a single chain Fv. A single chain Fv (scFv) is a truncated Fab having only the V region of a heavy chain linked by a stretch of synthetic peptide to a V region of a light chain. See, for example, U.S. Pat. Nos. 5,565,332; 5,733,743; 5,837,242; 5,858,657; and 5,871,907 assigned to Cambridge Antibody Technology Limited incorporated by reference herein. Thus the present invention contemplates, for example, an isolated nucleic acid molecule encoding a fusion polypeptide capable of binding a cytokine to form a nonfunctional complex comprising a nucleotide sequence encoding a first fusion polypeptide component comprising the amino acid sequence of the cytokine binding portion of the extracellular domain of the specificity determining component of the cytokine's receptor; a nucleotide sequence encoding a second fusion polypeptide component comprising the amino acid sequence of an scFv capable of binding the cytokine at a site different from the site at which the cytokine binding portion of the extracellular domain of the specificity determining component of the cytokine's receptor binds; and a nucleotide sequence encoding a third fusion polypeptide component comprising the amino acid sequence of a multimerizing component. Alternatively, the specificity determining component may be substituted for by a scFv that binds to a site on the cytokine different from the site at which the signal transducing component binds. Thus the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a scFv that binds to a site on the cytokine different from the site at which the cytokine binding portion of the extracellular domain of the signal transducing component of the cytokine's receptor binds; a nucleotide sequence encoding a second fusion polypeptide component comprising the amino acid sequence of the cytokine binding portion of the extracellular domain of the signal transducing component of the cytokine's receptor; and a nucleotide sequence encoding a third fusion polypeptide component comprising the amino acid sequence of a multimerizing component.

In another embodiment, the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a first scFv that binds to a site on the cytokine; a nucleotide sequence encoding a second fusion polypeptide component comprising the amino acid sequence a second scFv that binds to a site on the cytokine different from the site at which the first scFv binds; and a nucleotide sequence encoding a third fusion polypeptide component comprising the amino acid sequence of a multimerizing component.

In all of the above described embodiments comprising scFv's, the invention also contemplates embodiments in which the nucleotide sequence encoding the first component is upstream of the nucleotide sequence encoding the second component; embodiments in which the nucleotide sequence encoding the first component is downstream of the nucleotide sequence encoding the second component; and further embodiments of the invention in which the order of the first, second and third fusion polypeptide components is rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In preferred embodiments of the invention, the multimerizing component comprises an immunoglobulin derived domain. More specifically, the immunoglobulin derived domain may be selected from the group consisting of the Fc domain of IgG, the heavy chain of IgG, and the light chain of IgG. Even more specifically, immunoglobulin domain may be selected from the group consisting of the Fc domain of $IgG_1$ or $IgG_4$, the heavy chain of $IgG_1$ or $IgG_4$, and the light chain of $IgG_1$ or $IgG_4$. In another embodiment, the multimerizing component may be an Fc domain from which the first five amino acids (including a cysteine) have been removed to produce a multimerizing component referred to as Fc(ΔC1). Alternatively, the multimerizing component may be an Fc domain in which a cysteine within the first five amino acids has been substituted for by another amino acid such as, for example, serine or alanine.

The present invention also provides for fusion polypeptides encoded by the isolated nucleic acid molecules of the invention. Preferably, the fusion polypeptides are in multimeric form, due to the function of the third component, the multimerizing component. In a preferred embodiment, the multimer is a dimer. Suitable multimerizing components are sequences encoding an immunoglobulin heavy chain hinge region (Takahashi et al., 1982, Cell 29:671–679); immunoglobulin gene sequences, and portions thereof. In a preferred embodiment of the invention, immunoglobulin gene sequences, especially one encoding the Fc domain, are used to encode the multimerizing component.

The present invention also contemplates a vector which comprises the nucleic acid molecule of the invention as described herein.

A preferred embodiment of the invention is an isolated nucleic acid molecule having the sequence set forth in SEQ ID NO: 33 encoding a fusion polypeptide having the sequence set forth in SEQ ID NO: 34, wherein the fusion polypeptide forms a multimer that is capable of binding a cytokine to form a nonfunctional complex; an isolated nucleic acid molecule having the sequence set forth in SEQ ID NO: 35 encoding a fusion polypeptide having the sequence set forth in SEQ ID NO: 36, wherein the fusion polypeptide forms a multimer that is capable of binding a cytokine to form a nonfunctional complex; and an isolated nucleic acid molecule having the sequence set forth in SEQ ID NO: 37 encoding a fusion polypeptide having the sequence set forth in SEQ ID NO: 38, wherein the fusion polypeptide forms a multimer that is capable of binding a cytokine to form a nonfunctional complex; as well as fusion polypeptides encoded by the above-described nucleic acid molecules.

Other preferred embodiments of the invention are isolated nucleic acid molecules having the sequences set forth in SEQ ID NO: 39, 41, 43, 45, 47, 49, 51, 53, 55, 57, 59, 61, 63, 65, 67, 69, 71, 73, 75, 77, 79, 81, or 83 encoding fusion polypeptides having the sequences set forth in SEQ ID NO: 40, 42, 44, 46, 48, 50, 52, 54, 56, 58, 60, 62, 64, 66, 68, 70, 72, 74, 76, 78, 80, 82, or 84, respectively, wherein each fusion polypeptide forms a multimer that is capable of binding IL-1 to form a non-functional complex.

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

The present invention also provides for methods of producing the fusion polypeptides of the invention by growing cells of the host-vector systems described herein, under conditions permitting production of the fusion polypeptide and recovering the fusion polypeptide so produced.

The present invention provides novel antagonists which are based on receptor components that are shared by cytokines such as the CNTF family of cytokines.

The invention described herein contemplates the production of antagonists to any cytokine that utilizes an α specificity determining component which, when combined with the cytokine, binds to a first β signal transducing component to form a nonfunctional intermediate which then binds to a second β signal transducing component causing β-receptor dimerization and consequent signal transduction. According to the invention, the soluble a specificity determining component of the receptor (sRα) and the extracellular domain of the first β signal transducing component of the cytokine receptor (β1) are combined to form heterodimers (sRα:β1) that act as antagonists to the cytokine by binding the cytokine to form a nonfunctional complex.

The invention described herein also contemplates the production of antagonists to any cytokine that utilizes an α specificity determining component which, when combined with the cytokine, binds to a β signal transducing component to form a receptor complex which then initiates signal transduction. According to the invention, the soluble α specificity determining component of the receptor (sRα) and the extracellular domain of the β signal transducing component of the cytokine receptor (β) are combined to form heterodimers (sRα:β) that act as antagonists to the cytokine by binding the cytokine to form a nonfunctional complex.

As described in Example 1, CNTF and IL-6 share the β1 receptor component gp130. The fact that CNTF forms an intermediate with CNTFRα and gp130 can be demonstrated (Example 1) in cells lacking LIFRβ, where the complex of CNTF and CNTFRα binds gp130, and prevents homodimerization of gp130 by IL-6 and IL-6Rα, thereby blocking signal transduction. These studies provide the basis for the development of the IL-6 antagonists described herein, as they show that if, in the presence of a ligand, a nonfunctional intermediate complex, consisting of the ligand, its α receptor component and its β1 receptor component, can be formed, it will effectively block the action of the ligand. Other cytokines may use other β1 receptor components, such as LIFRβ, which may also be used to produce antagonists according to the present invention.

Thus for example, in one embodiment of the invention, effective antagonists of IL-6 or CNTF consist of heterodimers of the extracellular domains of the α specificity determining components of their receptors (sIL-6Rα and sCNTFRα, respectively) and the extracellular domain of gp130. The resultant heterodimers, which are referred to hereinafter as sIL-6Rα:β1 and sCNTFRα:β1, respectively, function as high-affinity Traps for IL-6 or CNTF, respectively, thus rendering the cytokine inaccessible to form a signal transducing complex with the native membrane-bound forms of their receptors.

Although soluble ligand binding domains from the extracellular portion of receptors have proven to be somewhat effective as Traps for their ligands and thus act as antagonists [Bargetzi, et al., Cancer Res. 53:4010–4013 (1993);, et al., Proc. Natl. Acad. Sci. USA 89: 8616–8620 (1992); Mohler, et al., J. Immunol. 151: 1548–1561 (1993); Narazaki, et al., Blood 82: 1120–1126 (1993)], the IL-6 and CNTF receptors are unusual in that the α receptor components constitute ligand binding domains that, in concert with their ligands, function effectively in soluble form as receptor agonists [Davis, et al. Science 259:1736–1739 (1993); Taga, et al., Cell 58: 573–581 (1989)]. The sRα:β1 heterodimers prepared according to the present invention provide effective Traps for their ligands, binding these ligands with affinities in the picomolar range (based on binding studies for CNTF to PC12D cells) without creating functional intermediates. The technology described herein may be applied to develop a cytokine Trap for any cytokine that utilizes an α-component that confers specificity, as well as a β component which, when bound to the α-specificity component, has a higher affinity for the cytokine than either component alone. Accordingly, antagonists according to the invention include antagonists of interleukins 1 through 5 [IL-1, Greenfeder, et al. J. Biol. Chem. 270:13757–13765 (1995); Guo, et al. J. Biol. Chem. 270:27562–27568 (1995)], IL-2; [Taniguchi, et al. European Patent Nos. 0386289-A and 0386304-A (1990); Takeshita, et al. Science 257:379–382 (1992)]; IL-3; [Kitamura, et al. Cell 66:1165–1174 (1991)], IL-4; [Idzerda, et al. J. Exp. Med. 171:861–873 (1990)], IL-5; [Taverneir, et al. Cell 66:1175–1184 (1991)], IL-11

[(Cherel, et al. Direct Submission to EMBL/GenBank/ DDBJ databases; accession No. Z38102)], interleukin 15 [IL-15; Hemar, et al. J. Cell Biol. 1295:55–64 (1995); Taniguchi, et al. European Patent Nos. 0386289-A and 0386304-A (1990); Takeshita, et al. Science 257:379–382 (1992)], granulocyte-macrophage colony stimulating factor [GM-CSF; Hayashida, et al. Proc. Natl. Acad. Sci. U.S.A. 97:9655–9659 (1990)], LIF, gamma interferon [IFNγ; Aguet, et al. Cell 55:273–280 (1988); Soh, et al. Cell 76:793–802 (1994)], and transforming growth factor beta [TGFβ; Inagaki, et al. Proc. Natl. Acad. Sci. USA 90:5359–5363 (1993)].

The α and β receptor extracellular domains may be prepared using methods known to those skilled in the art. The CNTFRα receptor has been cloned, sequenced and expressed [Davis, et al. (1991) Science 253:59–63 which is incorporated by reference in its entirety herein]. The cloning of LIFRβ and gp130 are described in Gearing et al. in EMBO J. 10:2839–2848 (1991), Hibi, et al. Cell 63:1149–1157 (1990) and in published PCT application WO 93/10151 published May 27, 1993, all of which are incorporated by reference in their entirety herein.

The receptor molecules useful for practicing the present invention may be prepared by cloning and expression in a prokaryotic or eukaryotic expression system. The recombinant receptor gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The sRα:β heterodimeric receptors may be engineered using known fusion regions, as described in published PCT application WO 93/10151 published May 27, 1993 entitled "Receptor for Oncostatin M and Leukemia Inhibitory Factor" which describes production of β receptor heterodimers, or they may be prepared by crosslinking of extracellular domains by chemical means. The domains utilized may consist of the entire extracellular domain of the α and β components, or they may consist of mutants or fragments thereof that maintain the ability to form a complex with its ligand and other components in the sRα:β1 complex. For example, as described below in Example 4, IL-6 antagonists have been prepared using gp130 that is lacking its three fibronectin-like domains.

In one embodiment of the invention, the extracellular domains are engineered using leucine zippers. The leucine zipper domains of the human transcription factors c-jun and c-fos have been shown to form stable heterodimers [Busch and Sassone-Corsi, Trends Genetics 6: 36–40 (1990); Gentz, et al., Science 243: 1695–1699 (1989)] with a 1:1 stoichiometry. Although jun-jun homodimers have also been shown to form, they are about 1000-fold less stable than jun-fos heterodimers. Fos-fos homodimers have not been detected.

The leucine zipper domain of either c-jun or c-fos are fused in frame at the C-terminus of the soluble or extracellular domains of the above mentioned receptor components by genetically engineering chimeric genes. The fusions may be direct or they may employ a flexible linker domain, such as the hinge region of human IgG, or polypeptide linkers consisting of small amino acids such as glycine, serine, threonine or alanine, at various lengths and combinations. Additionally, the chimeric proteins may be tagged by His-His-His-His-His-His (His6),[SEQ. ID NO. 1] to allow rapid purification by metal-chelate chromatography, and/or by epitopes to which antibodies are available, to allow for detection on western blots, immunoprecipitation, or activity depletion/blocking in bioassays.

In another embodiment, as described below in Example 3, the sRα:β1 heterodimer is prepared using a similar method, but using the Fc-domain of human IgG1 [Aruffo, et al., Cell 67:35–44 (1991)]. In contrast to the latter, formation of heterodimers must be biochemically achieved, as chimeric molecules carrying the Fc-domain will be expressed as disulfide-linked homodimers. Thus, homodimers may be reduced under conditions that favor the disruption of interchain disulfides but do not effect intra-chain disulfides. Then monomers with different extracellular portions are mixed in equimolar amounts and oxidized to form a mixture of homo- and heterodimers. The components of this mixture are separated by chromatographic techniques. Alternatively, the formation of this type of heterodimers may be biased by genetically engineering and expressing molecules that consist of the soluble or extracellular portion of the receptor components followed by the Fc-domain of hIgG, followed by either the c-jun or the c-fos leucine zippers described above [Kostelny, et al., J. Immunol. 148: 1547–1553 (1992)]. Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/blocking in bioassays.

In additional embodiments, heterodimers may be prepared using other immunoglobulin derived domains that drive the formation of dimers. Such domains include, for example, the heavy chains of IgG (Cγ1 and Cγ4), as well as the constant regions of kappa (κ) and lambda (λ) light chains of human immunoglobulins. The heterodimerization of Cγ with the light chain occurs between the CH1 domain of Cγ and the constant region of the light chain ($C_L$), and is stabilized by covalent linking of the two domains via a single disulfide bridge. Accordingly, as described in Example 4, constructs may be prepared using these immunoglobulin domains. Alternatively, the immunoglobulin domains include domains that may be derived from T cell receptor components which drive dimerization.

In another embodiment of the invention, the sRα:β1 heterodimers are prepared by expression as chimeric molecules utilizing flexible linker loops. A DNA construct encoding the chimeric protein is designed such that it expresses two soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the order of the soluble or extracellular domains fused is switched (e.g. sIL6Rα/loop/sgp130 or sgp130/loop/sIL-6Rα) and/or in which the length and composition of the loop is varied, to allow for selection of molecules with desired characteristics.

Alternatively, the heterodimers made according to the present invention may be purified from cell lines cotransfected with the appropriate α and β components. Heterodimers may be separated from homodimers using methods available to those skilled in the art. For example, limited quantities of heterodimers may be recovered by passive elution from preparative, nondenaturing polyacrylamide gels. Alternatively, heterodimers may be purified using high pressure cation exchange chromatography. Excellent purification has been obtained using a Mono S cation exchange column.

In addition to sRα:β1 heterodimers that act as antagonists by binding free CNTF or IL-6, the present invention also contemplates the use of engineered, mutated versions of IL-6 with novel properties that allow it to bind to IL-6Rα and a single gp130 molecule, but fail to engage the second gp130 to complete β component homodimerization, and thus act as an effective IL-6 antagonist on any IL-6 responsive cell. Our model for the structure of the IL-6 and CNTF receptor complexes indicates that these cytokines have distinct sites for binding the α, β1, and β2 receptor components [Stahl and Yancopoulos, Cell 74: 587–590 (1993)]. Mutations of critical amino acid residues comprising each of these sites gives rise to novel molecules which have the desired antagonistic properties. Ablation of the β1 site would give a molecule which could still bind to the α receptor component but not the β1 component, and thereby comprise an antagonist with nanomolar affinity. Mutations of critical amino acid residues comprising the β2 site of IL-6 (IL-6β2-) would give a molecule that would bind to IL-6Rα and the first gp130 monomer, but fail to engage the second gp130 and thus be functionally inactive. Similarly, mutations of the CNTF β2 site would give a molecule (CNTFβ2-) that would bind CNTFRα and gp130, but fail to engage LIFRβ, thereby antagonizing CNTF action by forming the non-functional β1 intermediate. Based on the binding results described above where CNTF forms the β1 intermediate with high affinity, both CNTFβ2- and IL-6β2- would constitute antagonists with affinity in the range of 10 pM.

A variety of means are used to generate and identify mutations of IL-6 or CNTF that have the desired properties. Random mutagenesis by standard methods of the DNA encoding IL-6 or CNTF may be used, followed by analysis of the collection of products to identify mutated cytokines having the desired novel properties as outlined below. Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis [Cunningham and Wells (1989), Science 244: 1081–1085] and homolog-scanning mutagenesis [Cunningham, et al., (1989), Science 243:1330–1336].

Targeted mutagenesis of the IL-6 or CNTF nucleic acid sequences using such methods can be used to generate CNTFβ2- or IL-6β2- candidates. The choice of regions appropriate for targeted mutagenesis is done systematically, or determined from studies whereby panels of monoclonal antibodies against each factor are used to map regions of the cytokine that might be exposed after binding of the cytokine to the α receptor component alone, or to the αβ1 heterodimeric soluble receptors described above. Similarly, chemical modification or limited proteolysis of the cytokine alone or in a complex bound to the α receptor component or the αβ1 heterodimeric soluble receptors described above, followed by analysis of the protected and exposed regions could reveal potential β2 binding sites.

Assays for identifying CNTF or IL-6 mutants with the desired properties involve the ability to block with high affinity the action of IL-6 or CNTF on appropriately responsive cell lines [Davis, et al., Science 259: 1736–1739 (1993); Murakami, et al., Proc. Natl. Acad. Sci. USA 88: 11349–11353 (1991)]. Such assays include cell proliferation, survival, or DNA synthesis driven by CNTF or IL-6, or the construction of cell lines where binding of factor induces production of reporters such as CAT or β-galactosidase [Savino, et al., Proc. Natl. Acad. Sci. USA 90: 4067–4071 (1993)].

Alternatively, the properties of various mutants may be assessed with a receptor-based assay. One such assay consists of screening mutants for their ability to bind the sRα:β1 receptor heterodimers described above using epitope-tagged [Davis et al., Science 253: 59–63 (1991)] sRα:β1 reagents. Furthermore, one can probe for the presence or absence of the β2 site by assessing whether an epitope-tagged soluble β2 reagent will bind to the cytokine in the presence of the β1 heterodimer. For example, CNTF only binds to LIFRβ (the β2 component) in the presence of both CNTFRα and gp130 [Davis, et al. Science 260: 1805–1808 (1993); Stahl, et al. J. Biol. Chem. 268: 7628–7631 (1993)]. Thus a soluble LIFRβ reagent would only bind to CNTF in the presence of the soluble sRα:β1 dimer sCNTFRα:β1. For IL-6, the sRα:β1 reagent would be IL-6Rα:β1, and the probe for the β2 site would be epitope-tagged sgp130. Thus β2-mutants of CNTF would be identified as those that bound the sRα:β1 reagent, demonstrating that the α and β1 site of the cytokine were intact, yet failed to bind the β2 reagent.

In addition, the present invention provides for methods of detecting or measuring the activity of potential β2-mutants by measuring the phosphorylation of a β-receptor component or a signal transduction component selected from the group consisting of Jak1, Jak2 and Tyk2 or any other signal transduction component, such as the CLIPs, that are determined to be phosphorylated in response to a member of the CNTF family of cytokines.

A cell that expresses the signal transduction component(s) described herein may either do so naturally or be genetically engineered to do so. For example, Jak1 and Tyk-2-encoding nucleic acid sequences obtained as described in Velazquez, et al., Cell, Vol. 70:313–322 (1992), may be introduced into a cell by transduction, transfection, microinjection, electroporation, via a transgenic animal, etc., using any known method known in the art.

According to the invention, cells are exposed to a potential antagonist and the tyrosine phosphorylation of either the β-component(s) or the signal transduction component(s) are compared to the tyrosine phosphorylation of the same component(s) in the absence of the potential antagonist.

In another embodiment of the invention, the tyrosine phosphorylation that results from contacting the above cells with the potential antagonist is compared to the tyrosine phosphorylation of the same cells exposed to the parental CNTF family member. In such assays, the cell must either express the extracellular receptor (α-component) or the cells may be exposed to the test agent in the presence of the soluble receptor component. Thus, for example, in an assay system designed to identify agonists or antagonists of CNTF, the cell may express the α-component CNTFRα, the β-components gp130 and LIFRβ and a signal transducing component such as Jak1. The cell is exposed to test agents, and the tyrosine phosphorylation of either the β-components or the signal transducing component is compared to the phosphorylation pattern produced in the presence of CNTF.

Alternatively, the tyrosine phosphorylation which results from exposure to a test agent is compared to the phosphorylation which occurs in the absence of the test agent. Alternatively, an assay system, for example, for IL-6 may involve exposing a cell that expresses the β-component gp130 and a signal transducing protein such as Jak1, Jak2 or Tyk2 to a test agent in conjunction with the soluble IL-6 receptor.

In another embodiment of the invention the above approaches are used to develop a method for screening for small molecule antagonists that act at various steps in the process of ligand binding, receptor complex formation, and subsequent signal transduction. Molecules that potentially interfere with ligand-receptor interactions are screened by assessing interference of complex formation between the soluble receptors and ligand as described above. Alternatively, cell-based assays in which IL-6 or CNTF induce response of a reporter gene are screened against libraries of small molecules or natural products to identify potential antagonists. Those molecules showing antagonist activity are rescreened on cell-based assays responding to other factors (such as GM-CSF or factors like Neurotrophin-3 that activate receptor tyrosine kinases) to evaluate their specificity against the CNTF/IL-6/OSM/LIF family of factors. Such cell-based screens are used to identify antagonists that inhibit any of numerous targets in the signal transduction process.

In one such assay system, the specific target for antagonists is the interaction of the Jak/Tyk family of kinases [Firmbach-Kraft, Oncogene 5: 1329–1336 (1990); Wilks, et al., Mol. Cell. Biol. 11:2057–2065 (1991)] with the receptor β subunits. As described above, LIFRβ and gp130 preassociate with members of the Jak/Tyk family of cytoplasmic protein tyrosine kinases, which become activated in response to ligand-induced β component dimerization Stahl, et al. Science 263:92–95 (1993). Thus small molecules that could enter the cell cytoplasm and disrupt the interaction between the β component and the Jak/Tyk kinase could potentially block all subsequent intracellular signaling. Such activity could be screened with an in vitro scheme that assessed the ability of small molecules to block the interaction between the relevant binding domains of purified β component and Jak/Tyk kinase. Alternatively, one could easily screen for molecules that could inhibit a yeast-based assay of β component binding to Jak/Tyk kinases using the two-hybrid interaction system [Chien, et al., Proc. Natl. Acad. Sci. 88: 9578–9582 (1991)]. In such a system, the interaction between two proteins (β component and Jak/Tyk kinase or relevant domains thereof in this example) induces production of a convenient marker such as β-galactosidase. Collections of small molecules are tested for their ability to disrupt the desired interaction without inhibiting the interaction between two control proteins. The advantage of this screen would be the requirement that the test compounds enter the cell before inhibiting the interaction between the β component and the Jak/Tyk kinase.

The CNTF family antagonists described herein either bind to, or compete with the cytokines CNTF and IL-6. Accordingly, they are useful for treating diseases or disorders mediated by CNTF or IL-6. For example, therapeutic uses of IL-6 antagonists would include the following:

1) In osteoporosis, which can be exacerbated by lowering of estrogen levels in post-menopausal women or through ovariectomy, IL-6 appears to be a critical mediator of osteoclastogenesis, leading to bone resorption [Horowitz, Science 260: 626–627 (1993); Jilka, et al., Science 257: 88–91 (1992)]. Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts [Jilka, et al. Science 257: 88–91 (1992)]. While estrogen replacement therapy is also used, there appear to be side effects that may include increased risk of endometrial and breast cancer. Thus, IL-6 antagonists as described herein would be more specific to reduce osteoclastogenesis to normal levels.

2) IL-6 appears to be directly involved in multiple myeloma by acting in either an autocrine or paracrine fashion to promote tumor formation [van Oers, et al., Ann Hematol. 66: 219–223 (1993)]. Furthermore, the elevated IL-6 levels create undesirable secondary effects such as bone resorption, hypercalcemia, and cachexia; in limited studies function-blocking antibodies to IL-6 or IL-6Ra have some efficacy [Klein, et al., Blood 78: 1198–1204 (1991); Suzuki, et al., Eur. J. Immunol. 22:1989–1993 (1992)]. Therefore, IL-6 antagonists as described herein would be beneficial for both the secondary effects as well as for inhibiting tumor growth.

3) IL-6 may be a mediator of tumor necrosis factor (TNF) that leads to cachexia associated with AIDS and cancer [Strassmann, et al., J. Clin. Invest. 89: 1681–1684 (1992)], perhaps by reducing lipoprotein lipase activity in adipose tissue [Greenberg, et al., Cancer Research 52: 4113–4116 (1992)]. Accordingly, antagonists described herein would be useful in alleviating or reducing cachexia in such patients.

Effective doses useful for treating these or other CNTF family related diseases or disorders may be determined using methods known to one skilled in the art [see, for example, Fingl, et al., The Pharmacological Basis of Therapeutics, Goodman and Gilman, eds. Macmillan Publishing Co., New York, pp. 1–46 ((1975)]. Pharmaceutical compositions for use according to the invention include the antagonists described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation (including antagonist expressing cells) prior to administration in vivo. For example, the pharmaceutical composition may comprise one or more of the antagonists in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, or microparticle-based implants.

EXAMPLES

Example 1

CNTF Competes with IL-6 for Binding to GP130

Materials and Methods

Materials. A clone of PC12 cells that respond to IL-6 (PC12D) was obtained from DNAX. Rat CNTF was prepared as described [Masiakowski, et al., J. Neurochem. 57:1003–10012 (1991)]. IL-6 and sIL-6Rα were purchased from R & D Systems. Antisera was raised in rabbits against a peptide derived from a region near the C-terminus of gp130 (sequence: CGTEGQVERFETVGME) [SEQ. ID. NO. 2] by the method described (Stahl, et al. J. Biol. Chem. 268:7628–7631 (1993). Anti-phosphotyrosine monoclonal 4G10 was purchased from UBI, and reagents for ECL from Amersham.

Signal Transduction Assays. Plates (10 cm) of PC12D were starved in serum-free medium (RPMI 1640+ glutamine) for 1 hour, then incubated with IL-6 (50 ng/mL)+ sIL-6R (1 mg/mL) in the presence or absence of added rat CNTF at the indicated concentrations for 5 minutes at 37° C. Samples were then subjected to anti-gp130 immunoprecipitation, SDS PAGE, and anti-phosphotyrosine immunoblotting as described (Stahl, et al. J. Biol. Chem. 268:7628–7631 (1993).

Results

Figure 2:
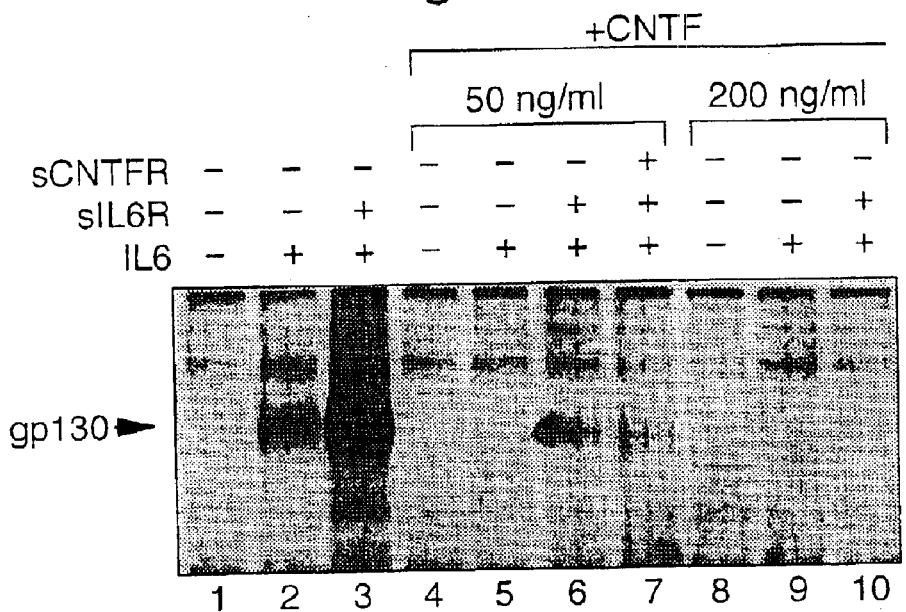
FIG. 2: CNTF inhibits IL-6 responses in a PC12 cell line (called PC12D) that expresses IL6Rα, gp130, CNTFRα, but not LIFRβ. Serum-deprived PC12D cells were incubated +IL-6 (50 ng/mL) in the presence or absence of CNTF as indicated. Some plates also received soluble IL6Rα (1 mg/mL) or soluble CNTFRα (1 mg/mL) as indicated. Cell lysates were subjected to immunoprecipitation with anti-gp130 and immunoblotted with anti-phosphotyrosine. Tyrosine phosphorylation of gp130 is indicative of IL-6 induced activation of the IL-6 receptor system, which is blocked upon coaddition of CNTF.

The ability of CNTF to block IL-6 responses was measured using a PC12 cell line (called PC12D) that expresses IL-6Rα, gp130, and CNTFRα, but not LIFRβ. As one would predict, these cells respond to IL-6, but not to CNTF (FIG. 2) since LIFRβ is a required component for CNTF signal transduction [Davis, et al., Science 260: 59–63 (1993)]. In accordance with results on other cell lines [Ip, et al., Cell 69: 1121–1132 (1992)], PC12D cells give tyrosine phosphorylation of gp130 (as well as a variety of other proteins called CLIPs) in response to 2 nM IL-6 (FIG. 2). Addition of recombinant soluble IL-6Rα (sIL-6Rα) enhances the level of gp130 tyrosine phosphorylation, as has been reported in some other systems [(Taga, et al., Cell 58: 573–581 (1989)]. However, addition of 2 nM CNTF simultaneously with IL-6 severely diminishes the tyrosine phosphorylation of gp130. Although a slight gp130 phosphorylation response remains in the presence of CNTF, IL-6, and sIL-6Rα, it is eliminated if the CNTF concentration is increased fourfold to 8 nM. Thus, in IL-6 responsive cells that contain CNTFRα but no LIFRβ, CNTF is a rather potent antagonist of IL-6 action.

Example 2

Binding of CNTF to the CNTFRα:β

Materials and Methods

Scatchard Analysis of CNTF Binding. $^{125}$I-CNTF was prepared and purified as described [Stahl et al. JBC 268: 7628–7631 (1993)]. Saturation binding studies were carried out in PC12 cells, using concentrations of $^{125}$I-CNTF ranging from 20 pM to 10 nM. Binding was performed directly on a monolayer of cells. Medium was removed from wells and cells were washed once with assay buffer consisting of phosphate buffered saline (PBS; pH 7.4), 0.1 mM bacitracin, 1 mM PMSF, 1 mg/ml leupeptin, and 1 mg/ml BSA. Cells were incubated in $^{125}$I-CNTF for 2 hours at room temperature, followed by 2 quick washes with assay buffer. Cells were lysed with PBS containing 1% SDS and counted in a Packard Gamma Counter at 90–95% efficiency. Non-specific binding was defined by the presence of 100-fold excess of unlabelled CNTF. Specific binding ranged from 70% to 95%.

Results

Figure 3:
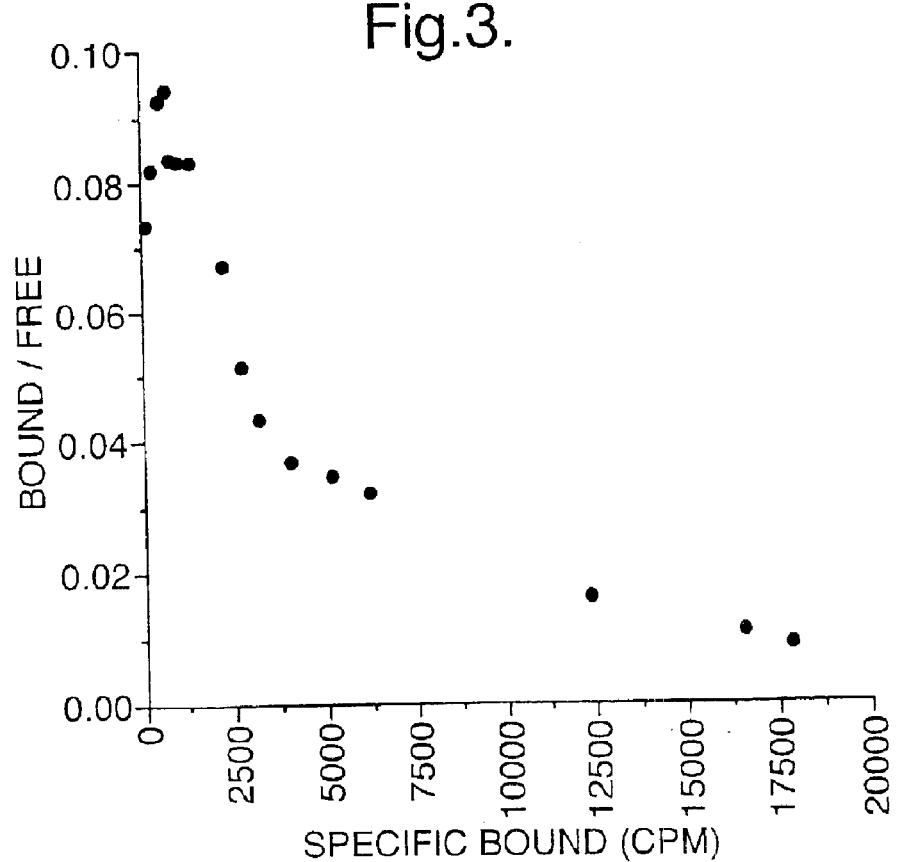
FIG. 3: Scatchard analysis of iodinated CNTF binding on PC12D cells. PC12D cells were incubated with various concentrations of iodinated CNTF in the presence or absence of excess non-radioactive competitor to determine the specific binding. The figure shows a Scatchard plot of the amount of iodinated CNTF specifically bound, and gives data consistent with two binding sites with dissociation constants of 9 pM and 3.4 nM.

The equilibrium constant for binding of CNTF to CNTFRα:β1 was estimated from Scatchard analysis of iodinated CNTF binding on PC12D cells (FIG. 3). The data is consistent with a 2 site fit having dissociation constants of 9 pM and 3.4 nM. The low affinity site corresponds to interaction of CNTF with CNTFRα, which has a Kd near 3 nM [(Panayotatos, et al., J. Biol. Chem. 268: 19000–19003 (1993)]. We interpret the high affinity complex as the intermediate containing CNTF, CNTFRα, and gp130. A Ewing sarcoma cell line (EW-1) which does contain CNTFRα, gp130, and LIFRβ, and therefore gives robust tyrosine phosphorylation in response to CNTF, displays a very similar two site fit with dissociation constants of 1 nM and 10. Thus it is apparent that CNTF binds with equally high affinity to a complex containing only CNTFRα and gp130, as it does to a complex which additionally contains LIFRβ, thus demonstrating the feasibility of creating the sRα:β antagonists described herein.

Example 3

Methods of Producing Cytokine Ligand Traps

Virus Stock Production

SF21 insect cells obtained from *Spodoptera frugiperda* were grown at 27° C. in Gibco SF900 II medium to a density of 1×10$^6$ cells/mL. The individual virus stock for either GP130-Fc-His$_6$ (FIGS. 4A–4B, SEQ ID NO: 7) or IL6Ra-Fc (FIG. 5, SEQ ID NO: 8) was added to the bioreactor to a low multiplicity 0.01–0.1 PFU/cell to begin the infection. The infection process was allowed to continue for 5–7 days allowing maximum virus replication without incurring substantial cell lysis. The cell suspension was aseptically aliquoted into sterile centrifuge bottles and the cells removed by centrifugation. The cell-free supernatant was collected in sterile bottles and stored at 4° C. until further use.

The virus titer was determined by plaque assay as described by O'Reilly, Miller and Luckow. The method is carried out in 60 mm tissue-culture dishes which are seeded with 2×10$^6$ cells. Serial dilutions of the virus stock are added to the attached cells and the mixture incubated with rocking to allow the virus to adsorb to individual cells. An agar overlay is added and plates incubated for 5–7 days at 27° C. Staining of viable cells with neutral red revealed circular plaques resulting which were counted to give the virus titer.

Coinfection of Cells for Protein Production

Uninfected SF21 Cells were grown in a 60 L ABEC bioreactor containing 40L of SF900 II medium. Temperature was controlled at 27° C. and the dissolved oxygen level was maintained at 50% of saturation by controlling the flowrate of oxygen in the inlet gas stream. When a density of 2×10$^6$ cells/mL was reached, the cells were concentrated within the bioreactor to a volume of 20 L using a low shear steam sterilizable pump with a tangential flow filtration device with Millipore Prostak 0.65 micron membranes. After concentration fresh sterile growth medium is slowly added to the bioreactor while the filtration system continues to remove the spent growth medium by diafiltration. After two volume exchanges (40 L) have been carried out an additional 20 L of fresh medium was added to the bioreactor to resuspend the cells to the original volume of 40 L. The cell density was determined once again by counting viable cells using a hemacytometer.

The required amount of each virus stock was calculated based on the cell density, virus titer and the desired multiplicity of infection (MOI). Virus stock ratios of 5:1, 5:2, 10:2 and 10:4, IL6Rα-Fc to GP130-Fc-His$_6$ all resulted in production of significant amounts of heterodimer. The ideal virus stock ratio is highly dependent on the ease of purification of the heterodimer from each of the two homodimers. The IL6Rα-Fc homodimer is relatively easy to remove downstream by immobilized metal affinity chromatography. Virus infection ratios have been chosen to minimize the formation of the GP130-Fc-His$_6$ homodimer which is more difficult to clear downstream. The relative amount of GP130-Fc-His$_6$ virus stock chosen for infection has increased with successive batches as the purification method for clearing the resultant homodimer has improved.

The virus stocks were aseptically mixed in a single vessel then transferred to the bioreactor. This results in synchronous infection of the SF21 cells. The infection is allowed to proceed for three to four days, allowing sufficient time for maximal production of the heterodimer protein.

Recovery and Protein A Chromatographic Purification

At the conclusion of the infection phase of the bioreactor process the cells were concentrated in the bioreactor using a 10 ft$^2$ Millipore Prostak filter (0.65 micron) pore size. The cell-free permeate passing through the filter was collected in a clean process vessel. At the conclusion of the filtration operation the pH of permeate stream, containing the protein product, was adjusted to 8.0 with 10N NaOH. The resultant precipitate was removed by forcing the extract through a 0.8 micron depth filter (Sartorious), followed by a 0.2 micron filter. Sufficient 0.5M EDTA stock was added to give a final concentration of 5 mM. The filtered protein solution was loaded onto a 10 cm diameter column containing 100–200 mL of Pharmacia Protein A Sepharose 4 Fast Flow, equilibrated with PBS. Protein A has a very high affinity for the Fc-Fc domain of each of the 3 recombinant protein products, allowing them to bind while other proteins in the cell-free extract flow through the column. After loading the column was washed to baseline with PBS containing an additional 350 mM NaCl. The IgG-Fc tagged proteins were eluted at low pH, either with 0.5M acetic acid or with a decreasing pH gradient of 0.1M citric acid and 0.2M disodium phosphate buffers. Tris base or disodium phosphate was added to the eluted protein to avoid prolonged exposure to low pH conditions.

The pooled protein was diafiltered into PBS or HEPES buffer and derivitized with 1 mM iodoacetamide to protect the exposed sulfhydryl group on the free cysteine near the hinge region of each Fc domain. This prevents disulfide mediated aggregation of proteins. A 6 ft$^2$ Millipore spiral wound ultrafiltration membrane with nominal 30 kiloDalton cutoff was used to perform the buffer exchange. The total protein was determined by UV absorbance at 280 nm using the diafiltration buffer as a blank. The relative amounts of heterodimer and two homodimer proteins were determined by SDS PAGE gel electrophoresis using a 6% Tris-Glycine gel (Novex). Gels were Coomassie-stained then transferred into destain solution overnight. A Shimadzu scanning densitometer was used to determine the relative intensity of the individual protein bands on the SDS PAGE gel. The peak area ratios are used to compute the fraction of heterodimer and each of the homodimers in the column pool fractions.

Immobilized Metal Affinity Chromatographic Purification

The six histidine residues on the C-terminus of the GP130-Fc-His$_6$ fusion protein provides an excellent molecular handle for separation of the heterodimeric IL6 antagonist from the two homodimers. The imidazole group on each of the C-terminal histidines of the GP130-Fc-His$_6$ moiety has a strong binding constant with several divalent metals, including copper, nickel, zinc, cobalt, iron and calcium. Since the IL6Rα-Fc homodimer has no C-terminal histidine residues, it clearly has the lowest affinity. The IL6R α-Fc-GP130-Fc-His$_6$ heterodimer has a single stand set six histidines giving it greater affinity for the metal, while the GP130-Fc-His$_6$ homodimer has two sets of six histidines each giving it the highest affinity of the three IgG tagged proteins to the metal affinity column. Selective elution of the three proteins with increasing amounts of imidazole in the elution buffer therefore elutes the proteins in the following order:

1. IL6Rα-Fc homodimer
2. IL6Rα-Fc-GP130-Fc-His heterodimer
3. GP130-Fc-His homodimer A 26 mm diameter column containing 100 mL of Pharmacia Chelating Sepharose Fast Flow was saturated with a solution of nickel sulfate until a significant green color is observed in the column eluate. The column is then washed with several column volumes of deionized water, then equilibrated with 50 mM HEPES, 40 mM imidazole, pH 8.0. The binding of imidazole to the immobilized nickel results in a green to blue color change. Imidazole was added to the protein load to a final concentration of 40 mM. Addition of imidazole to the protein load reduces the binding of IL6Rα-Fc homodimer, increasing the surface area available for the remaining two species. After loading, the column was washed with several column volumes of 50 mM HEPES, 80 mM imidazole, pH 8.0 until a steady baseline was reestablished. The heterodimer was selectively eluted with 50 mM HEPES, 150 mM imidazole, pH 8.0 over several column volumes. The protein fractions were pooled and diafiltered into PBS as described in the section above.

Example 4

Alternative Methods of Constructing Ligand Traps

As described above, receptor activation by CNTF, and analogously by IL-6 and IL-11, follows an ordered sequence of binding events (FIG. 6). The cytokine initially binds to its cognate Rα with low affinity (Kd=3 to 10 nM); this is a required step—cells which do not express the cognate Rα do not respond to the cognate cytokine. The cytokine•Rα complex associates with the first signal transducing component, gp130, to form a high affinity complex (Kd in the order of 10 pM for the CNTF•CNTFRα•gp130 complex). This complex does not transduce signal, as it is the dimerization of the signal transducing components that brings about signaling (Stahl and Yancopoulos, J. Neurobiology 25: 1454–1466 (1994); Stahl et al., Science 267:1349–1353 (1995); Davis et al., Science 260:1805–1808 (1993); Stahl et al., Science 263:92–95 (1994); Murakami, et al. Science 260:1808–1810 (1993). At least in the case of IL-6, the cytokine•Rα•signal transducer heterotrimeric complex subsequently associates with another like complex, to form a hexameric complex (FIG. 6) (Ward et al., J. Biol. Chem. 269:23286–23289 (1994). The resulting dimerization of the signal transducers—gp130 in the case of IL-6 (Murakami et al., Science 260:1808–1810 (1993) and IL-11, gp130 and LIFR in the case of CNTF (Davis et al., Science 260:1805–1808 (1993)—brings about signal transduction.

The initial heterodimeric molecules made comprised a soluble Rα-component linked to the extracellular domain of gp130. These molecules were shown to mimic the high affinity cytokine•Rα•gp130 complex and behave as a high affinity antagonist of their cognate cytokine (FIG. 7). To make these molecules, the extracellular domain of gp130 was paired with the extracellular domain of the α-receptor components for IL-6 and CNTF, IL-6Rα and CNTFRα respectively. To link the Rα with the extracellular domain of gp130, the soluble Rα-components and gp130 were fused to the Fc portion of human IgG1 to produce Rα-Fc and gp130-Fc respectively. The Fc domain was chosen primarily but not solely because it naturally forms disulfide-linked dimers. Heterodimeric molecules comprising Rα-Fc•gp130-Fc were expressed, purified and shown to behave as highly potent antagonists of their cognate ligand. Furthermore, these molecules were found to be highly specific for their cognate cytokine since it is the choice of the α-receptor component which specifies which cytokine is bound and trapped (there is no measurable binding of the cytokine to gp130 in the absence of the appropriate Rα).

Here we describe an extension of this technology which allows the engineering of different heteromeric soluble receptor ligand Traps which by virtue of their design may have additional beneficial characteristics such as stability, Fc-receptor-mediated clearance, or reduced effector functions (such as complement fixation). Furthermore, the technology described should prove suitable for the engineering of any heteromeric protein in mammalian or other suitable protein expression systems, including but not limited to heteromeric molecules which employ receptors, ligands, and catalytic components such as enzymes or catalytic antibodies.

Materials and Methods

Genetic Engineering of Heteromeric Immunoglobulin Heavy/Light Chain Soluble Receptor-based Ligand Traps for IL-6.

Figure 8:
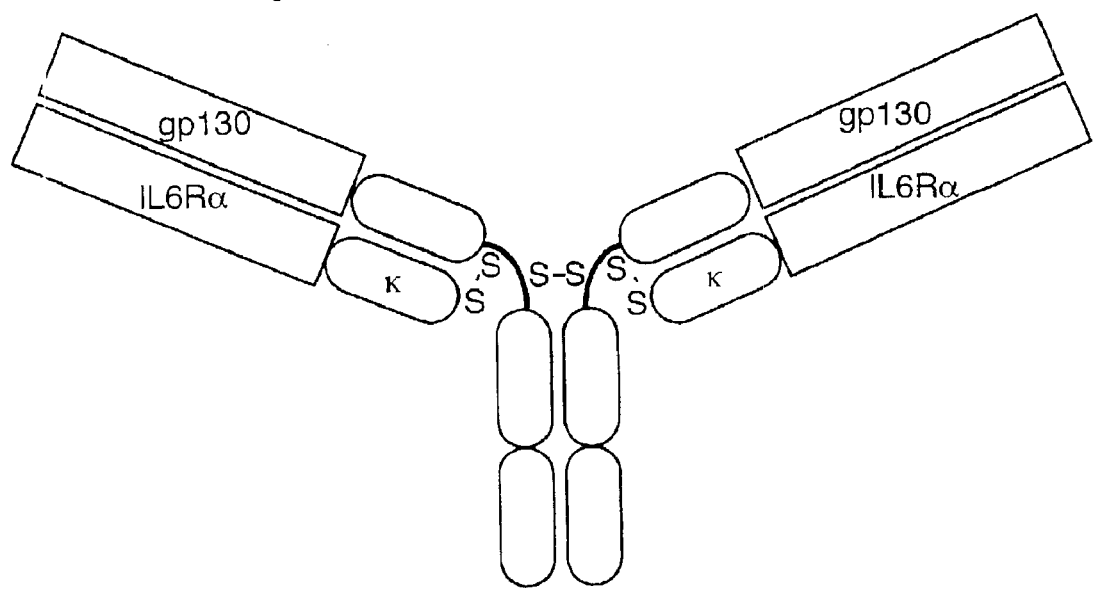
FIG. 8. Heteromeric immunoglobulin Heavy/Light Chain Receptor Fusions. An example of a heavy/light chain receptor fusion molecule is schematically depicted. The extracellular domain of gp130 is fused to Cγ, whereas the extracellular domain of IL-6Rα is fused to the constant region of the kappa chain (κ). The inter-chain disulfide bridges are also depicted (S—S).

The IL-6 Traps described here were engineered using human gp130, human IL-6 α-receptor (IL-6Rα), the constant region of the heavy chains (Cγ) of human IgG1 (Cγ1) (Lewis et al., Journal of Immunology 151:2829–2838 (1993) or IgG4 (Cγ4) with or without a join-region (J), and the constant regions of kappa (κ) and lambda (λ) (Cheung, et al., Journal of Virology 66:6714–6720 (1992) light chains of human immunoglobulin (Ig), also with or without a different j-peptide (j). This design takes advantage of the natural ability of the Cγ domain to heterodimerize with κ or λ light chains. The heterodimerization of Cγ with the light chain occurs between the CH1 domain of Cγ and the constant region of the light chain ($C_L$), and is stabilized by covalent linking of the two domains via a single disulfide bridge. We reasoned that, like the Fc domain of human IgG1, the combination of Cγ with $C_L$ could be used to produce disulfide linked heteromeric proteins comprised of the extracellular domain of gp130 on one chain and the extracellular domain of IL-6Rα on the other chain. Like their Fc-based counterparts, such proteins were postulated to be high affinity ligand Traps for IL-6 and as a result to inhibit the interaction of IL-6 with the native receptor on IL-6-responsive cells, thus functioning as IL-6 antagonists. Furthermore, constructs employing the full length Cγ region would, much like antibodies, form homodimers of the Cγ chain, giving rise to antibody-like molecules comprising of two "light chains" and two "heavy chains" (FIG. 8). The potential advantage of this design is that it may more closely mimic the IL-6•IL-6Rα•gp130 complex and may display a higher affinity for the ligand than comparable single heterodimers. An additional design is incorporated by using truncated versions of Cγ, comprised only of the $C_H1$ domain. These will form heterodimeric molecules with receptor-κ fusion proteins, and will thus resemble the Fab fragment of antibodies.

All the soluble receptor-Ig chimeric genes may be engineered in plasmid vectors including, but not limited to, vectors suitable for mammalian expression (COS monkey kidney cells, Chinese Hamster Ovary cells [CHO], and ras-transformed fibroblasts [MG-ras]) and include a Kozak sequence (CGC CGC CAC CAT GGT G) (SEQ ID NO: 3) at the beginning of each chimeric gene for efficient translation. Engineering was performed using standard genetic engineering methodology. Each construct was verified by DNA sequencing, mammalian expression followed by western blotting with suitable antibodies, biophysical assays that determine ligand binding and dissociation, and by growth inhibition assays (XG-1, as described later). Since the domains utilized to engineer these chimeric proteins are flanked by appropriate restriction sites, it is possible to use these domains to engineer other chimeric proteins, including chimeras employing the extracellular domains of the receptors for factors such as IL-1, IL-2, IL-3, IL-4, IL-5, GM-CSF, LIF, IL-11, IL-15, IFNγ, TGFβ, and others. The amino acid coordinates for each component utilized in making the IL-6 Traps are listed below (Note: numbering starts with the initiating methionine as 1; long sequences are listed using the single letter code for the twenty amino acids):

(a) Constructs Employing Human gp130:

(i) gp130-Cγ1 was engineered by fusing in frame the extracellular domain of gp130 (amino acids 1 to 619) to a Ser-Gly bridge, followed by the 330 amino acids which comprise Cγ1 and a termination codon (FIGS. 9A–9B, SEQ ID NO: 9).

(ii) gp130-J-Cγ1 was engineered in the same manner as gp130-Cγ1 except that a J-peptide (amino acid sequence: GQGTLVTVSS) (SEQ ID NO: 4) was inserted between the Ser-Gly bridge and the sequence of Cγ1 (see FIGS. 9A–9B, SEQ ID NO: 9).

(iii) gp130Δ3fibro-Cγ1 was engineered by fusing in frame the extracellular domain of gp130 without its three fibronectin-like domains (FIG. 10, SEQ ID NO: 10). The remaining part of this chimeric protein is identical to gp130-Cγ1.

(iv) gp130-J-$C_H1$ was engineered in a manner identical for that described for gp130-Cγ1, except that in place of the Cγ1 region only the $C_H1$ part of Cγ1 has been used (FIG. 11, SEQ ID NO: 11). The C-terminal domain of this construct includes the part of the hinge that contains the cysteine residue responsible for heterodimerization of the heavy chain of IgG with a light chain. The part of the hinge that contains the two cysteines involved in Cγ1 homodimerization has been deleted along with the $C_H2$ and $C_H3$ domains.

(v) gp130-Cγ4 was engineered in a manner identical to that described for gp130-Cγ1, except that Cγ4 was used in place of Cγ1 (FIG. 12, SEQ ID NO: 12). In addition, an RsrII DNA restriction site was engineered at the hinge region of the Cγ4 domain by introducing two silent base mutations. The RsrsII site allows for other desired genetic engineering manipulations, such as the construction of the $C_H1$ equivalent of gp130-Cγ4.

(vi) gp130-κ was engineered in a manner identical to that described for gp130-Cγ1, except that the constant region of the κ light chain of human Ig was used in place of Cγ1 (FIG. 13, SEQ ID NO: 13).

(vi) gp130-J-κ was engineered in a manner identical to that described for gp130-J-κ, except that a j-peptide (amino acid sequence: TFGQGTKVEIK) (SEQ ID NO: 5) was inserted between the Ser-Gly bridge and the κ-region.

(viii) gp130-λ was engineered in a manner identical to that described for gp130-Cγ1, except that the constant region of the λ light chain (Cheung, et al., Journal of Virology 66:6714–6720 (1992) of human Ig was used in place of Cγ1 (FIG. 14, SEQ ID NO: 14).

(b) Constructs Employing Human IL-6Rα:

(i) IL6RαCγ1 was engineered by fusing in frame amino acids 1 to 358 of IL-6Rα (Yamasaki et al., Science 241:825–828 (1988), which comprise the extracellular domain of IL-6Rα (FIG. 15, SEQ ID NO: 15), to an Ala-Gly bridge, followed by the 330 amino acids which comprise Cγ1 and a termination codon.

(ii) IL6Rα-κ was engineered as described for IL6Rα-Cγ1, except that the κ-domain (FIG. 13, SEQ ID NO: 13) utilized for gp130-κ was used in place of Cγ1.

(iii) IL6Rα-j -κ was engineered as described for IL6Rα-κ except that the j-peptide described for gp130-j-κ was placed between the Ala-Gly bridge and the κ-domain.

(iv) Three additional constructs, IL6Rα313-Cγ1, IL6Rα313-κ, and IL6Rα313-j-κ, were engineered as using a truncated form of IL-6Rα comprised of amino acids 1 to 313 (FIG. 16, SEQ ID NO: 16). Each of these constructs were made by fusing in frame IL6Rα313 with a Thr-Gly bridge followed by the Cγ1, κ-, and j-κ-domains described above. These constructs were engineered in order to complement the gp130Δ3fibro-derived constructs.

Expression and Purification of Ligand Traps

To produce covalently linked heterodimers of soluble gp130 and soluble IL-6Rα, gp130-Ig chimeric proteins were co-expressed with appropriate IL-6Rα-Ig chimeric proteins in complementing pairs. Co-expression was achieved by co-transfecting the corresponding expression vectors into suitable mammalian cell lines, either stably or transiently. The resulting disulfide-linked heterodimers were purified from conditioned media by several different methods, including but not limited to affinity chromatography on immobilized Protein A or Protein G, ligand-based affinity chromatography, ion exchange, and gel filtration.

Figure 17:
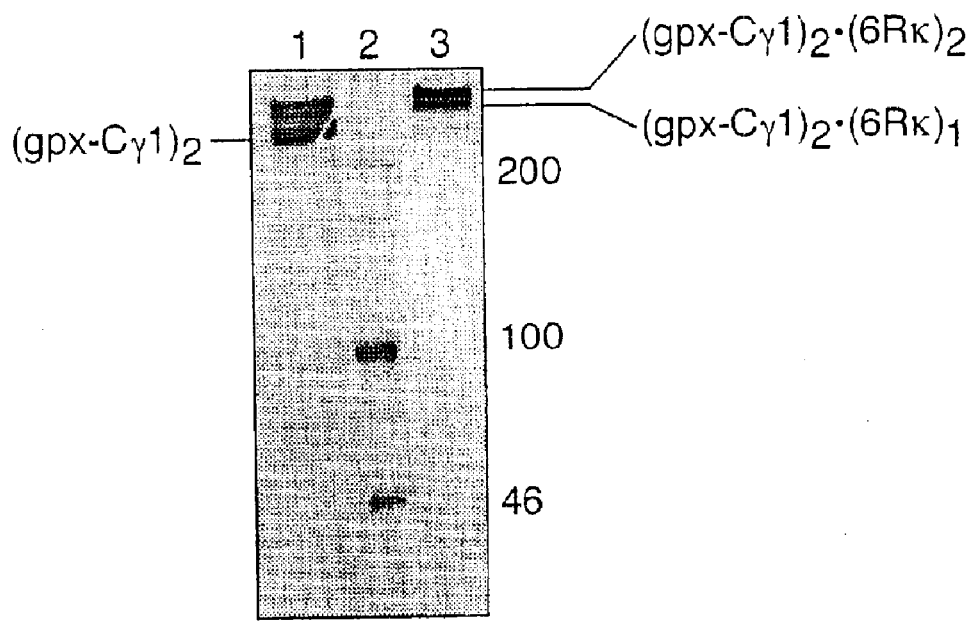
FIG. 17: Purification of gp130-Cγ1•IL-6Rα-κ. 4% to 12% SDS-PAGE gradient gel run under non-reducing conditions. Proteins were visualized by staining with silver. Lane 1: approximately 100 ng of material purified over Protein A Sepharose (Pharmacia). Lane 2: Molecular size standards (Amersham). Lane 3: The Protein A-purified material shown here after further purification over an IL-6 affinity chromatography step. The positions of the gp130-Cγ1 dimer [(gp130-Cγ1)$_2$], the gp130-Cγ1 dimer associated with one IL-6Rα-κ [(gp130-Cγ1)$_2$•(IL-6Rα-κ)$_1$], and the gp130-Cγ1 dimer associated with two IL-6Rα-κ [(gp130-Cγ1)$_2$•(IL-6Rα-κ)$_2$] are shown, as well as the sizes for the molecular size standards in kilodaltons (200, 100, and 46).

An example of the type of methods used for purification of a heavy/light receptor fusion protein is as follows: gp130-Cγ1•IL-6Rα-κ was expressed in COS cells by co-transfecting two different vectors, encoding gp130-Cγ1 and IL-6Rα-κ respectively. Serum-free conditioned media (400 ml) were collected two days post-transfection and Cγ1-bearing proteins were purified by affinity chromatography over a 1 ml Protein A Sepharose (Pharmacia). The material generated in this step was further purified by a second affinity chromatography step over a 1 ml NHS-activated Sepharose (Pharmacia) which was derivatized with recombinant human IL-6, in order to remove gp130-Cγ1 dimer from gp130-Cγ1•IL-6Rα-κ complexes (the gp130-Cγ1 dimer does not bind IL-6). Proteins generated by this method were more than 90% pure, as evidenced by SDS-PAGE followed by silver-staining (FIG. 17). Similar protocols have been employed successfully towards the purification of other heavy/light receptor heterodimers.

Results

Figure 18:
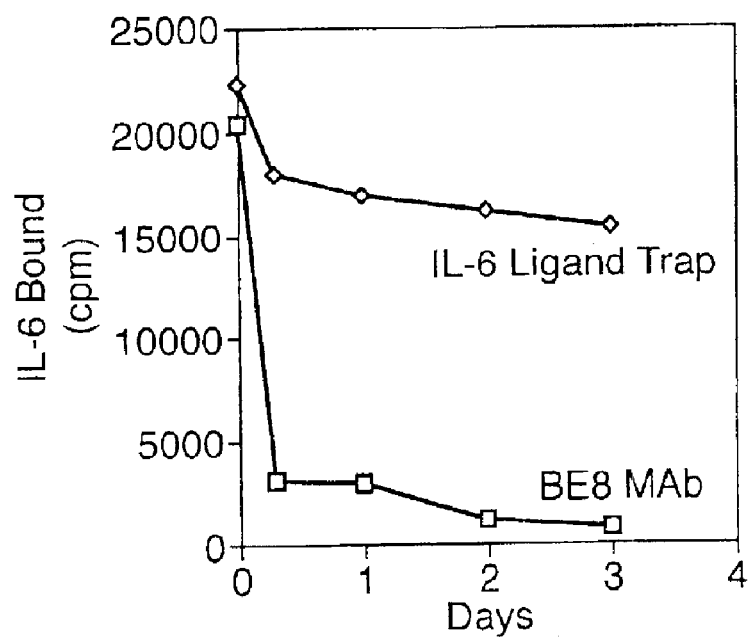
FIG. 18: IL-6 dissociates slowly from the ligand Trap. The dissociation rate of IL-6 from a heavy/light chain receptor-based ligand Trap (gp130-Cγ1•IL-6Rα-κ) was compared to that obtained with the neutralizing monoclonal antibody B-E8 (BE8 MAb).

Biological Activity of Immunoglobulin Heavy/Light Chain Receptor Fusion Antagonists The purified ligand Traps were tested for their ability to bind IL-6 in a variety of different assays. For example, the dissociation rate of IL-6 bound to the ligand Trap was measured in parallel with the dissociation rate of IL-6 from the anti-IL-6 monoclonal neutralizing antibody B-E8 [Brochier, et al., Int. J. Immunopharmacology 17:41–48 (1995), and references within]. An example of this type of experiment is shown in FIG. 18. In this experiment 20 pM $^{125}$I-IL-6 (1000 μCi/mmol; Amersham) was preincubated with 500 pM of either gp130-Cγ1•IL-6Rα-κ or mAb B-E8 for 20 hours. At this point a 1000-fold excess (20 nM) of "cold" IL-6 was added. Periodically, aliquots of the reaction were removed, the ligand Trap or B-E8 were precipitated with Protein G-Sepharose, and the number of cpm of $^{125}$I-IL-6 that remained bound was determined. Clearly, the dissociation rate of human $^{125}$I-IL6 from the ligand Trap was very slow—after three days, approximately 75% of the initial counts were still bound to the ligand Trap. In contrast, less than 5% of the counts remained associated with the antibody after three days. This result demonstrates that the dissociation rate of the ligand from these ligand Traps is very slow.

In a different set of experiments the ability of the ligand Traps to multimerize in the presence of ligand was tested. An example of this is shown in FIGS. 19A–19B. IL-6-induced association of gp130-Fc•IL-6Rα-Fc with gp130-C$_H$1•IL-6Rα-κ was determined by testing whether gp130-C$_H$1•IL-6Rα-κ, which does not by itself bind Protein A, could be precipitated by Protein A-Sepharose in the presence of gp130-Fc•IL-6Rα-Fc in an IL-6-depended manner (FIGS. 9A–9B, SEQ ID NO: 9). Precipitation of gp130-C$_H$1-IL-6Rα-κ by Protein A-Sepharose was determined by western blotting with an anti-kappa specific HRP conjugate, which does not detect gp130-Fc•IL-6Rα-Fc. gp130-C$_H$1•IL-6Rα-κ could be precipitated by Protein A-Sepharose only when both gp130-Fc•IL-6Rα-Fc and IL-6 were present. This result conclusively indicates that IL-6 can induce ligand Trap multimerization, and further indicate that the ligand Trap can mimic the hexameric cytokine•Rα•signal transducer complex (FIG. 1). Ligand-induced multimerization may play a significant role in the clearance of cytokine•ligand Trap complexes in vivo.

Figure 20:
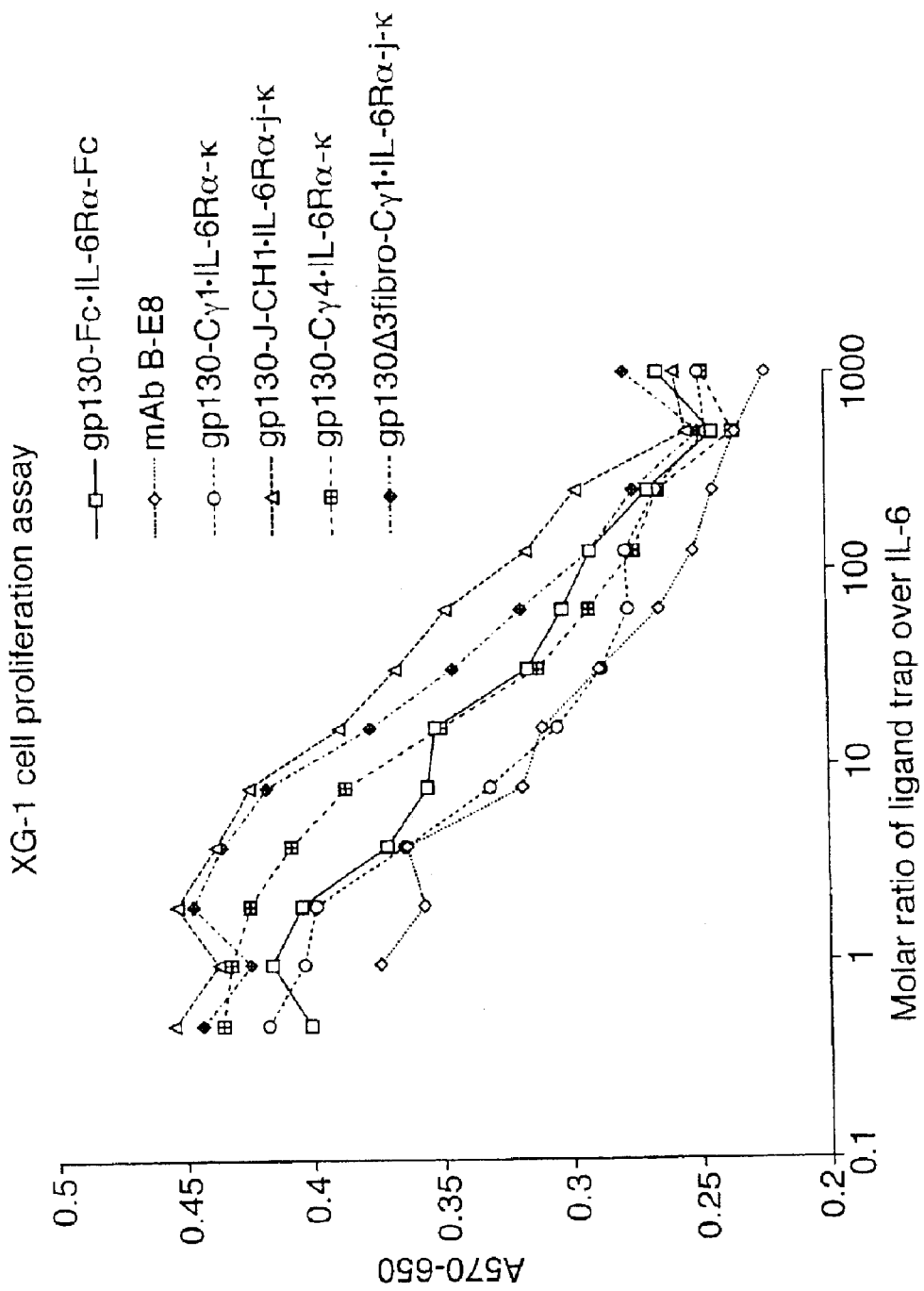
FIG. 20: Inhibition of IL-6-dependent XG-1 cell proliferation. XG-1 cells [Zhang, et al., Blood 83:3654–3663 (1994)] were prepared for a proliferation assay by starving the cells from IL-6 for 5 hours. Assays were set up in 96-well tissue culture dishes in RPMI+10% fetal calf serum+ penicillin/streptomycin+0.050 nM 2-mercaptoethanol+ glutamine. 0.1 ml of that media was used per well. Cells were suspended at a density of 250,000 per ml at the start of the assay. 72 hours post addition of IL-6±ligands Traps or antibodies, an MTT assay was performed as described (Panayotatos et al. Biochemistry 33:5813–5818 (1994). The different ligand Traps utilized are listed.

The biological activity of the different ligand Traps may be further tested in assays which measure ligand-depended cell proliferation. Several cell proliferation assays exist for IL-6 and they employ cell lines such as B9, CESS, or XG-1. An example of this type of assay using the XG-1 cell line is presented below: XG-1 is a cell line derived from a human multiple myeloma (Zhang, et al., Blood 83:3654–3663 (1994). XG-1 depends on exogenously supplied human IL-6 for survival and proliferation. The EC$_{50}$ of IL-6 for the XG-1 line is approximately 50 pmoles/ml. The ability of several different IL-6 Traps to block IL-6-depended proliferation of XG-1 cells was tested by incubating increasing amounts of purified ligand Traps with 50 pg/ml IL-6 in XG-1 cultures. The ligand Traps which were tested had been expressed and purified by methods similar to those described above. All of the ligand Traps tested were found to inhibit IL-6-dependent proliferation of XG-1 in a dose dependent manner (FIG. 20). Of the five different Traps tested gp130-Cγ1•IL-6Rα-κ was the most active and essentially display the same neutralizing activity towards IL-6 as the antibody B-E8. As little as a 10-fold molar excess of either gp130-Cγ1•IL-6Rα-κ or B-E8 completely blocked the activity of IL-6 (a reading of A570–650=0.3 AU corresponds to no proliferation of the XG-1 cells). At a 100-fold molar excess all of the ligand Traps tested completely blocked the activity of IL-6. This observed inhibition is highly selective as neither a gp130-Fc•CNTFRα-Fc ligand Trap which blocks CNTF activity, nor gp130-Fc homodimer exhibit any blocking activity towards IL-6 even when used at a 1000-fold molar excess over IL-6 (data not shown). This data demonstrates that the heteromeric immunoglobulin heavy/light chain receptor-based ligand Traps function as selective high affinity antagonists of their cognate ligand.

Example 5

Cloning of Fusion Polypeptide Components

The extracellular domains of the human cytokine receptors were obtained by standard PCR techniques using tissue cDNAs (CLONTECH), cloned into the expression vector, pMT21 (Genetics Institute, Inc.), and the sequences were sequenced by standard techniques using an ABI 373A DNA sequencer and Taq Dideoxy Terminator Cycle Sequencing Kit (Applied Biosystems, Inc., Foster City, Calif.). For the IL-4Rα, nucleotides 241 through 868 (corresponding to the amino acids 24–231) from the Genbank sequence, X52425, were cloned. For the IL-2Rγ, nucleotides 15 through 776 (corresponding to amino acids 1–233) from the Genbank sequence, D11086, were cloned. For the IL-6Rα, nucleotides 52 through 1044 (corresponding to the amino acids 1–331) from the Genbank sequence, X52425, were cloned. For gp130, nucleotides 322 through 2112 (corresponding to the amino acids 30–619) from the Genbank sequence, M57230, were cloned. For the IL-1RAcP, nucleotides 1 through 1074 (corresponding to the amino acids 1–358) from the Genbank sequence, AB006357, were cloned. For the IL-1RI, nucleotides 55 through 999 (corresponding to the amino acids 19–333) from the Genbank sequence, X16896, were cloned.

Example 6

Production of Fusion Polypeptides (Cytonine Traps)

The nucleotide sequences encoding the cytokine Traps were constructed from the individual cloned DNAs (described supra ) by standard cloning and PCR techniques. In each case, the sequences were constructed in frame such that the sequence encoding the first fusion polypeptide component was fused to the sequence encoding the second fusion polypeptide component followed by an Fc domain (hinge, CH2 and CH3 region of human IgG1) as the multimerizing component. In some cases extra nucleotides were inserted in frame between sequences encoding the first and second fusion polypeptide components to add a linker region between the two components (See FIG. 21A–FIG. 21D (SEQ ID NO: 17)—Trap 424; FIG. 24A–FIG. 24F (SEQ ID NO: 23)—Trap 412; and FIG. 26A–FIG. 26E (SEQ ID NO: 27)—Trap 569).

For the IL-4 Traps, 424 (FIG. 21A–FIG. 21D, SEQ ID NO: 17), 603 (FIG. 22A–FIG. 22D, SEQ ID NO: 19) and 622 (FIG. 23A–FIG. 23D, SEQ ID NO: 21), the IL-2Rγ component is 5', followed by the IL4Rα component and then the Fc component. For the IL-6 Traps, 412 (FIG. 24A–FIG. 24F, SEQ ID NO: 23) and 616 (FIG. 25A–FIG. 25F, SEQ ID NO: 25), the IL-6Rα component is 5' followed by the gp130 component and then the Fc domain. For the IL-1 Trap 569 (FIG. 26A–FIG. 26E, SEQ ID NO: 27), the IL-1RAcP component is 5' followed by the IL-1RI component and then the Fc domain. The final constructs were cloned into the mammalian expression vector pCDNA3.1 (STRATAGENE).

In the 569 sequence (FIG. 26A–FIG. 26E) (SEQ ID NO: 27), nucleotides 1–1074 encode the IL1RAcP component, nucleotides 1075–1098 encode a linker region, nucleotides 1099–2043 encode the IL1RI component and nucleotides 2044–2730 encode the Fc domain.

In the 412 sequence (FIG. 24A–FIG. 24F) (SEQ ID NO: 23), nucleotides 1–993 encode the IL6Rα component, nucleotides 994–1023 encode a linker region, nucleotides 1024–2814 encode the gp130 component and nucleotides 2815–3504 encode the Fc domain.

In the 616 sequence (FIG. 25A–FIG. 25F) (SEQ ID NO: 25), nucleotides 1–993 encode the IL6Rα component, nucleotides 994–2784 encode the gp130 component and nucleotides 2785–3474 encode the Fc domain.

In the 424 (FIG. 21A–FIG. 21D) (SEQ ID NO: 17) and 622 (FIG. 23A–FIG. 23D) (SEQ ID NO: 21) sequences, nucleotides 1–762 encode the IL2Rγ component, nucleotides 763–771 encode a linker region, nucleotides 772–1395 encode the IL4Rαcomponent and nucleotides 1396–2082 encode the Fc domain.

Finally, in the 603 sequence (FIG. 22A–FIG. 22D) (SEQ ID NO: 19), nucleotides 1–762 encode the IL2Rγ component, nucleotides 763–1386 encode the IL4Rα component and nucleotides 1387–2073 encode the Fc domain.

DNA constructs were either transiently transfected into COS cells or stably transfected into CHO cells by standard techniques well known to one of skill in the art. Supernatants were collected and purified by Protein A affinity chromatography and size exclusion chromatography by standard techniques. (See for example Harlow and Lane, Antibodies—A Laboratory Manual, Cold Spring Harbor Laboratory, 1988).

Example 7

IL-4 Bioassay Protocol Using TF-1 (ATCC) Cells
Reagents and Equipment Needed
MTT Dye Solution:
MTT(3-[4,5-Dimethylthiazole-2-yl]) (Sigma catalog #M2128)
Working concentration: Dissolve 5 mg of anhydrous MTT in 200 ml PBS without $Ca^{+2}$, $Mg^{+2}$.
Sterile filter and store aliquoted at −20° C.
Solubilization Solution:
For 1000 ml, combine 100 g SDS, 950 ml $dH_2O$, 50 ml Dimethyl Formamide, and 850 μl concentrated HCl.
Filter sterilize with a 0.45 μm filter unit.
Store at room temperature
TF-1 Cell Growth Medium:
RPMI 1640, 10% FBS, Pen/Strep, 2 mM L-glutamine
Other:
0.4% Trypan Blue Stain, sterile tubes for dilutions, sterile 96 well cell culture plates (Falcon #3072), hemacytometer, centrifuge, ELISA plate reader, multichannel pipet for 15, 25, 50 and 100 μl volume, sterile reagent reservoirs, sterile pipet tips, gloves.
Assay Protocol
A. Preparation of Assay Plates
1. Prepare sterile 96 well tissue culture plates to contain 5 μl of growth medium per well with various concentrations of IL-4 and 10 nM IL-4 antagonist. This can be done by preparing a working dilution of IL-4 that is 4 times the highest concentration to be assayed. In separate tubes, do a two-fold serial dilution of the IL-4. Add 25 μl of each dilution to one row across the plate (i.e. row A gets highest concentration, row G gets lowest concentration). Add 25 μl of growth medium without IL-4 to row H. Prepare the antagonists to be tested by making a stock that is 4 times the final concentration. Add 25 μl to a triplicate set of IL-4 containing wells (columns 1,2,3, A through H). Be sure to include antagonist in row H.
2. As a positive control, leave one set with no antagonist. These wells will contain IL-4 and media only.
3. Incubate the plate for 1–2 hours at 37° C. in a humidified 5% $CO_2$ incubator before preparing cells to be used for assay.
B. Preparation of Cells
4. Wash cells twice by centrifugation in assay medium free of growth factor.
5. Determine cell number and trypan blue viability and suspend cells to a final concentration of $8 \times 10^5$/ml in assay medium.

6. Dispense 50 µl of the cell suspension (40,000 cells) into all wells of the plates. Total volume should now be 100 µl/well.
7. Incubate the plate at 37° C. for 68 hours in a humidified 5% $CO_2$ incubator.

C. Color Development

8. After incubating for 68 hours, add 15 µl of the MTT dye solution to each well.
9. Incubate the plate at 37° C. for 4 hours in a humidified 5% $CO_2$ incubator.
10. After 4 hours, add 100 µl of the solubilization solution to each well. Allow the plate to stand overnight in a sealed container to completely solubilize the formazan crystals.
11. Record the absorbance at 570/650 nm.

Results

Figure 27:
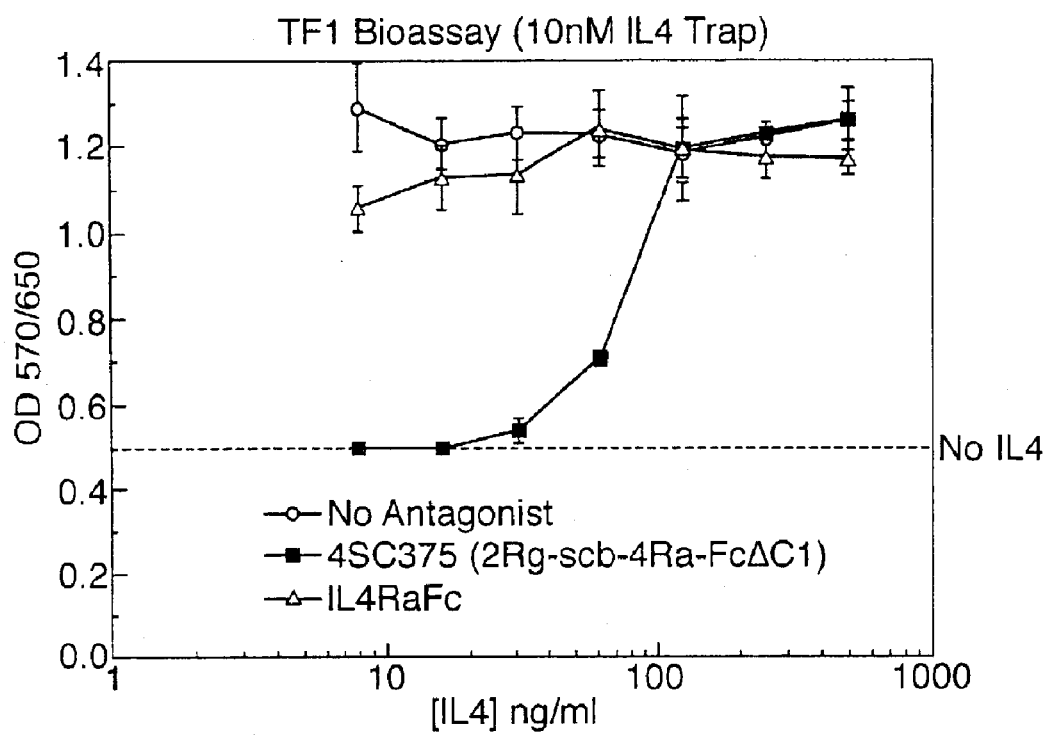
FIG. 27: Shows that an IL-4 Trap designated 4SC375, which is a fusion polypeptide of IL-2Rγ-scb-IL4Rα-FcΔC1, is several orders of magnitude better as an IL-4 antagonist than IL4RαFcΔC1 alone in the TF1 cell bioassay.

FIG. 27 shows that an IL-4 Trap designated 4SC375, which is a fusion polypeptide of IL-2Rγ-scb-IL4Rα-FcΔC1, is several orders of magnitude better as an IL-4 antagonist than IL4RαFcΔC1 alone in the TF1 cell bioassay.

Figure 28:
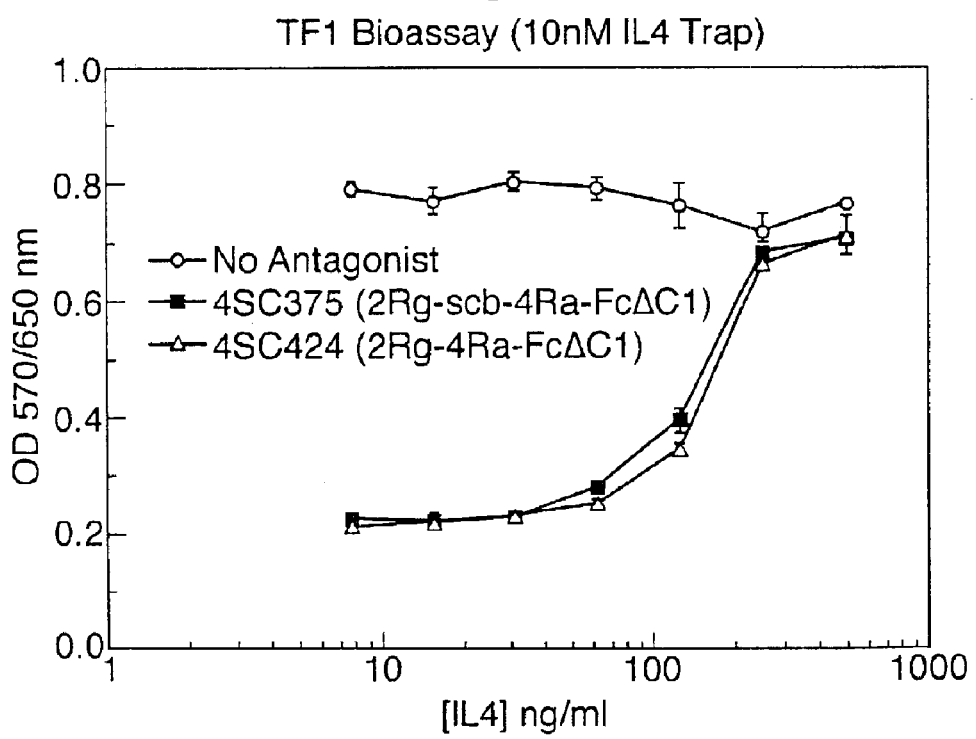
FIG. 28: Shows that an IL-4 Trap designated 4SC375 displays antagonistic activity in the TF1 cell bioassay equivalent to an IL-4 Trap designated 4SC424 (described in FIGS. 21A–21D) which is a fusion polypeptide of IL-2Rγ-IL4Rα-FcΔC1 having the IL-2Rγ component flush with the IL-4Rα component.

FIG. 28 shows that the IL-4 Trap designated 4SC375 shows antagonistic activity in the TF1 cell bioassay equivalent to an IL-4 Trap designated 4SC424 which is a fusion polypeptide of IL-2Rγ-IL4Rα-FcΔC1 having the IL-2Rγ component flush with the IL-4Rα component.

Example 8

IL-6 Bioassay Protocol Using XG-1 Cells

Reagents and Equipment Needed

MTT Dye Solution:
MTT(3-[4,5-Dimethylthiazole-2-yl]) (Sigma catalog #M2128)
Working concentration: Dissolve 5 mg of anhydrous MTT in 200 ml PBS without $Ca^{+2}$, $Mg^{+2}$.
Sterile filter and store aliquoted at −20° C.

Solubilization Solution:
For 1000 ml, combine 100 g SDS, 950 ml $dH_2O$, 50 ml Dimethyl Formamide, and 850 µl concentrated HCl.
Filter sterilize with at 0.45 µm filter unit.
Store at room temperature Assay Medium:
RPMI 1640, 10% FBS, Pen/Strep, 2 mM L-glutamine, 50 µM mercapto-ethanol.

Other:
0.4% Trypan Blue Stain, sterile tubes for dilutions, sterile 96 well cell culture plates (Falcon #3072), hemacytometer, centrifuge, ELISA plate reader, multichannel pipet for 15, 25, 50 and 100 µl volume, sterile reagent reservoirs, sterile pipet tips, gloves.

Assay Protocol

A. Preparation of Assay Plates

1. Prepare sterile 96 well tissue culture plates to contain 50 µl of growth medium per well with various concentrations of IL-6 and 10 nM IL-6 antagonist. This can be done by preparing a working dilution of IL-6 that is 4 times the highest concentration to be assayed. In separate tubes, do a two-fold serial dilution of the IL-6. Add 25 µl of each dilution to one row across the plate (i.e. row A gets highest concentration, row G gets lowest concentration). Add 25 µl of growth medium without IL-6 to row H. Prepare the antagonists to be tested by making a stock that is 4 times the final concentration. Add 25 µl to a triplicate set of IL-6 containing wells (columns 1,2,3, A through H). Be sure to include antagonist in row H. A typical IL-6 titration starts at 200 ng/ml down to 3.1 ng/ml.
2. As a positive control, leave one set with no antagonist. These wells contain IL-6 and media in place of antagonist.
3. Incubate the plate 1–2 hours at 37° C. in a humidified 5% $CO_2$ incubator before preparing cells to be used for assay.

B. Preparation of Cells

4. Wash cells twice by centrifugation (5 min at 1000 RPM) in assay medium free of growth factor.
5. Determine cell number and trypan blue viability and suspend cells to a final concentration of $8 \times 10^5$/ml in assay medium.
6. Dispense 50 µl of the cell suspension (40000 cells) into all wells of the plates. Total volume should now be 100 µl/well.
7. Incubate the plate at 37° C. for 68 hours in a humidified 5% $CO_2$ incubator.

C. Color Development

8. At 68 hours add 15 µl of the dye solution to each well.
9. Incubate the plate at 37° C. for 4 hours in a humidified 5% $CO_2$ incubator.
10. After 4 hours, add 100 µl of the solubilization solution to each well. Allow the plate to stand overnight in a sealed container to completely solubilize the formazan crystals.
11. Record the absorbance at 570/650 nm.

Results

Figure 29:
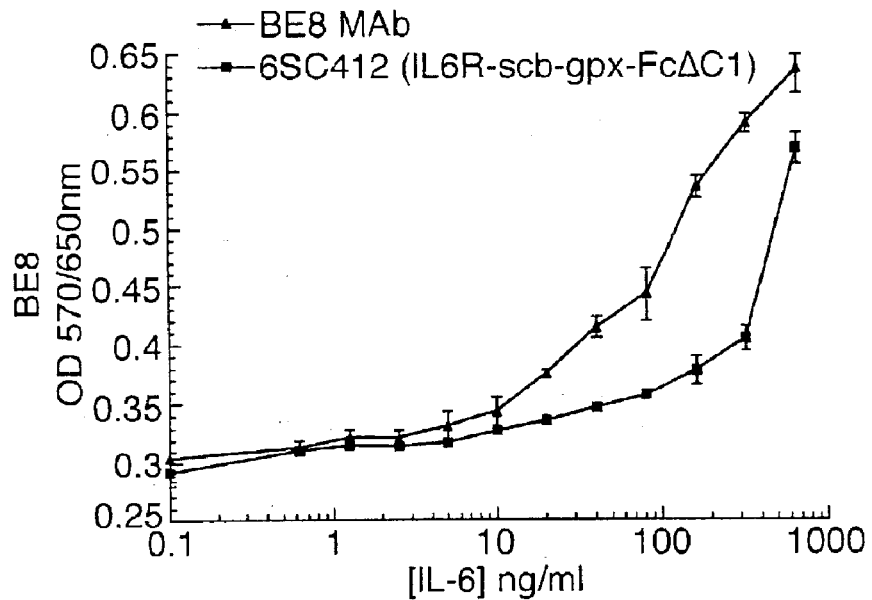
FIG. 29: Shows that the IL6 Trap (6SC412 IL6R-scb-gpx-FcΔC1) described in FIGS. 24A–24F is a better antagonist of IL-6 in the XG1 bioassay than the neutralizing monoclonal antibody to human IL-6-BE8.

FIG. 29 shows that the IL6 Trap (6SC412 IL6R-scb-gpx-FcΔC1) described in FIG. 24A–FIG. 24F (SEQ ID NO: 23 and 24) is a better antagonist of IL-6 in the XG1 bioassay than the neutralizing monoclonal antibody to human IL-6-BE8.

Example 9

MRC5 Bioassay for IL1 Traps

MRC5 human lung fibroblast cells respond to IL-1 by secreting IL-6 and thus were utilized to assay the ability of IL-1 Traps to block the IL-1-dependent production of IL-6. IL1 Trap 1SC569 (FIG. 26A–FIG. 26E) was tested against IL-1-RI.Fc which is the extracellular domain of the IL-1 Type I receptor fused to an Fc domain.

MRC5 cells are suspended at $1 \times 10^5$ cells per ml in medium and 0.1 ml of cells are plated (10,000 cells per well) into the wells of a 96 well tissue culture plate. Plates are incubated for 24 hours at 37° C. in a humidified 5% $CO_2$ incubator.

IL-1 Trap and recombinant human IL-1 at varying doses are pre-incubated in a 96 well tissue culture dish and incubated for 2 hours at 37° C. 0.1 ml of this mixture is then added to the 96 well plate containing the MRC5 cells such that the final concentration of IL-1 Trap is 10 nM and the final concentrations of the IL-1 ranges from 2.4 pM to 5 nM. Control wells contain Trap alone or nothing.

Plates are then incubated at 37° C. for 24 hours in a humidified 5% $CO_2$ incubator. Supernatant is collected and assayed for levels of IL-6 using R&D Systems Quantikine Immunoassay Kit according to the manufacturer's instructions.

Results

Figure 30:
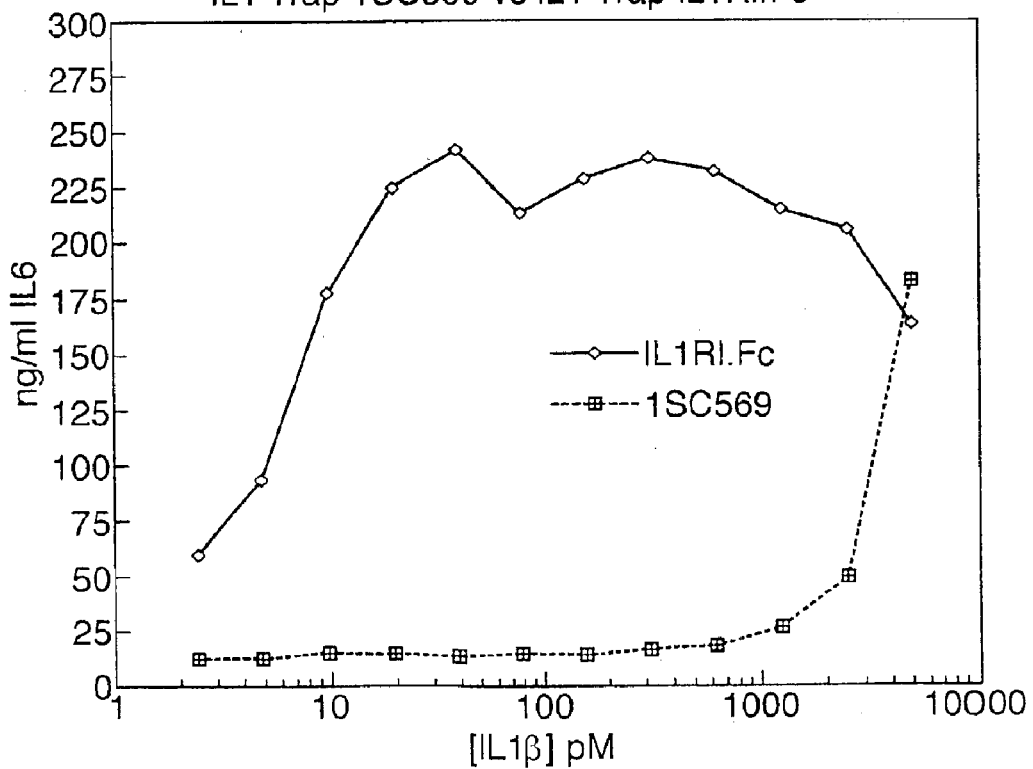
FIG. 30: Shows that the Trap 1SC569 (described in FIGS. 26A–26E) is able to antagonize the effects of IL-1 and block the IL-6 production from MRC 5 cells upon treatment with IL-1.

FIG. 30 shows that the Trap 569 (FIG. 26A–FIG. 26E) (SEQ ID NO: 27 and 28) is able to antagonize the effects of IL-1 and block the IL-6 production from MRC 5 cells upon treatment with IL-1. At a concentration of 10 nM, the Trap 569 is able to block the production of IL-6 up to an IL-1 concentration of 3 nM. In contrast, the IL-1RI.Fc is a much poorer antagonist of IL-1. It is only able to block the effects of IL-1 up to about 10–20 pM. Thus, the Trap 569 is approximately 100× better at blocking IL-1 than IL1RI.Fc.

Example 10

Construction of IL-13/IL-4 Single Chain Traps

1. To create the IL-13/IL-4 dual Trap designated IL-4Rα.IL-13Rα1.Fc, the human IL-4Rα extracellular domain (corresponding to nucleotides 1–693 of FIG. 31A–FIG. 31G) (SEQ ID NO: 29) and the human IL-13Rα1 extracellular domain (corresponding to nucleotides 700–1665 of FIG. 31A–FIG. 31G) (SEQ ID NO: 29) were amplified by standard PCR techniques and ligated into an expression vector pMT21 which contained the human Fc sequence (corresponding to nucleotides 1671–2355 of FIG. 31A–FIG. 31G) (SEQ ID NO: 29), thus creating a fusion protein consisting of the IL-4Rα, IL-13Rα1, and the hinge, CH2 and CH3 region of human IgG1 from the N to C terminus. In addition, a two amino acid linker (corresponding to nucleotides 694–699 of FIG. 31A–FIG. 31G) (SEQ ID NO: 30) with the amino acid sequence SerGly was constructed in frame between the IL-4Rα and the IL-13Rα1 and a two amino acid linker (corresponding to nucleotides 1666–1671 of FIG. 31A–FIG. 31G) (SEQ ID NO: 30) with the amino acid sequence ThrGly was constructed in frame between the IL-13Rα1 and the Fc portion. All sequences were sequence-verified by standard techniques. The IL-4Rα.IL-13Rα1.Fc coding sequence was then subcloned into the expression vector pCDNA3.1 (Stratagene) using standard molecular biology techniques.

2. To create the IL-13/IL-4 dual Trap designated IL-13Rα.1.IL-4Rα.Fc, the IL-13Rα1 extracellular domain (corresponding to nucleotides 1–1029 of FIG. 32A–FIG. 32G) (SEQ ID NO: 31) and the human IL-4Rα (corresponding to nucleotides 1060–1692 of FIG. 32A–FIG. 32G) (SEQ ID NO: 31) were amplified by standard PCR techniques and ligated into the expression vector pJFE14, which contains the human Fc sequence (corresponding to nucleotides 1699–2382 of FIG. 32A–FIG. 32G) (SEQ ID NO: 31) to create a fusion protein consisting of the IL-13Rα1, IL-4Rα, and the hinge, CH2 and CH3 region of human IgG1 from the N to C terminus. In addition, a ten amino acid linker with the amino acid sequence GlyAlaProSerGlyGlyGlyGlyArgPro (SEQ ID NO: 6) (corresponding to nucleotide 1030–1059 of FIG. 32A–FIG. 32G) (SEQ ID NO: 31) was constructed in frame between the IL-13Rα1 and the IL-4Rα and a two amino acid linker (corresponding to nucleotides 1693–1698 of FIG. 32A–FIG. 32G) (SEQ ID NO: 31) with the amino acid sequence SerGly was constructed in frame between IL-4Rα and the Fc portion. All sequences were sequence-verified using standard techniques. The coding sequence of IL-13Rα1.IL-4Rα.Fc was then subcloned into the expression vector pCDNA3.1 (Stratagene) using standard molecular biology techniques.

Example 11

Expression of IL-4Rα.IL-13Rα1.Fc and IL-13Rα1.IL-4Rα.Fc

Large scale (1 L) cultures of the pCAE801 (the DNA vector construct encoding IL-4Rα.IL-13Rα1.Fc) and pCAE802 (the DNA plasmid construct encoding IL-13Rα1.IL-4Rα.Fc) in DH10B cells were grown overnight in LB+ampicillin and the plasmid DNA was extracted using a Qiagen Endofree Mega Kit following the manufacturer's protocol. The concentration of the purified plasmid DNA was determined in a UV spectrophotometer and fluorometer. The plasmid DNA was also verified by digestion of aliquots with BbsI, XmnI and NcoI restriction enzymes. All restriction enzyme digest fragments corresponded to the predicted sizes in a 1% agarose gel.

Forty 15 cm petri plates were seeded with CHO-K1/E1A cells at a density of $4 \times 10^6$ cells/plate. Plating media was Gibco Ham's F-12 w/10% Hyclone Fetal Bovine Serum (FBS)+penicillin/streptomycin and supplemented with glutamine. The following day each plate was transfected with 6 μg of pCAE801, or pCAE802, using Gibco Optimem and Gibco Lipofectamine in 12 ml volume, following the manufacturer's protocol. Four hours after adding the transfection mix to the cells 12 ml/plate of Optimem w/10% FBS was added. Plates were incubated at 37° C. in a 5% $CO_2$ incubator overnight. The following day the media was removed from each plate and 25 ml expression media (Gibco CHO-S-SFM II w/glutamine+1 mM sodium butyrate) was added. The plates were incubated at 37° C. for 3 days.

After 3 days of incubation the media was removed from each plate and centrifuged at 400 rpm in a swinging bucket rotor to pellet cells. The supernatant was decanted into sterile 1 L bottles and expressed protein was purified as described infra.

Example 12

Purification of IL-4Rα.IL-13Rα1.Fc and IL-13Rα1.IL-4Rα.Fc Protein from Culture Media 1. Purification of IL-4Rα.IL-13Rα1.Fc.

Human IL-4Rα.IL-13Rα1.Fc was transiently expressed in CHO cells and supernatants were harvested from plate transfections as described supra. Expression of the secreted protein was determined by a sandwich ELISA using goat anti-hIgG (γ chain specific; Sigma 1–3382) and goat anti-hIgG (Fc specific)-FITC conjugate (Sigma F9512) capture and report antibodies, respectively. The yield ranged from 5.8 to 9.2 mg (average of 7.5 mg) per liter of conditioned media. Complete™ protease inhibitor tablets (Roche Diagnostics Corp.) were dissolved into the media (1 tablet/L). The conditioned media was sterile filtered (0.22 μm pore size) prior to loading onto a pre-equilibrated, 5 mL HiTrap® Protein A affinity column (Amersham Pharmacia Biotech) in Dulbecco's PBS buffer (Life Technologies), pH 7.4 at 4° C. The flow rate was ~1–2 mL/min. The column was extensively washed with PBS buffer to remove nonspecifically bound proteins from the column. IL-4Rα.IL-13Rα1.Fc-was eluted using 20 mM sodium citrate, 150 mM NaCl, pH 3.5. The eluate was immediately neutralized by titrating with 1 M Tris-OH. The fractions containing protein were pooled and immediately dialyzed in PBS buffer, pH 7.4 at 4° C. The recovery from Protein A purification was 6.8 mg (73%). IL-4Rα.IL-13Rα1.Fc was further purified by size exclusion chromatography using a superose 6 column (25 mL bed volume; Amersham Pharmacia Biotech) pre-equilibrated in PBS, 5% v/v glycerol, pH 7.4 at ambient temperature. The flow rate was 0.5 mL/min. Protein fractions were assessed from a Coomassie stained non-reduced and reduced SDS-PAGE (Novex NuPAGE 4–12% Bis-Tris gels). Fractions were conservatively pooled to reduce the amount of aggregated protein. The overall yield was 51% (4.4 mg) with a purity of 97% as judged by SDS-PAGE. Purified IL-4Rα.IL-13Rα1.Fc was analyzed by non-reduced and reduced SDS-PAGE (4–12% Bis-Tris), analytical size exclusion chromatography (Tosohaas TSKG4000SWXL), N-terminal sequencing, and immunoblotting with goat anti-hIgG-HRP conjugate (Promega W403B), and also mouse monoclonal anti-hIL-4R (R&D MAB230) followed by anti-mIgG-HRP conjugate (Promega W402B) as the secondary antibody.

2. Purification of IL-13Rα1.IL-4Rα.Fc

Human IL-13Rα1.IL-4Rα.Fc was transiently expressed in CHO cells and supernatants were harvested from plate transfections as described supra. Expression of the secreted protein was determined by a sandwich ELISA using goat anti-hIgG (γ chain specific; Sigma 1–3382) and goat anti-hIgG (Fc specific)-FITC conjugate (Sigma F9512) capture and report antibodies, respectively. The yield was 8.8 mg per liter of conditioned media. Complete™ protease inhibitor tablets (Roche Diagnostics Corp.) were dissolved into the media (1 tablet/L). The conditioned media was sterile filtered (0.22 μm pore size) prior to loading onto a pre-equilibrated, 5 mL HiTrap® Protein A affinity column (Amersham Pharmacia Biotech) in Dulbecco's PBS buffer (Life Technologies), pH 7.4 at 4° C. The flow rate was ~1–2 mL/min. The column was extensively washed with PBS buffer to remove nonspecifically bound proteins from the column. IL-13Rα1.IL-4Rα.Fc was eluted using 20 mM sodium citrate, 150 mM NaCl, pH 3.5. The eluate was immediately neutralized by titrating with 1 M Tris-OH. The fractions containing protein were pooled and immediately dialyzed in PBS buffer, pH 7.4 at 4 ° C. The recovery from Protein A purification was 3.8 mg (43%). IL-13Rα1.IL-4Rα.Fc was further purified by size exclusion chromatography using a superose 6 column (25 mL bed volume; Amersham Pharmacia Biotech) pre-equilibrated in PBS, 5% v/v glycerol, pH 7.4 at ambient temperature. The flow rate was 0.5 mL/min. Protein fractions were assessed from a Coomassie stained non-reduced and reduced SDS-PAGE (Novex NuPAGE 4–12% Bis-Tris gels). Fractions were conservatively pooled to reduce the amount of aggregated protein. The overall yield was 17% (1.5 mg) with a purity of 95% as judged by SDS-PAGE. Purified IL-13Rα1.IL-4Rα.Fc was analyzed by non-reduced and reduced SDS-PAGE (4–12% Bis-Tris), analytical size exclusion chromatography (Tosohaas TSKG4000SWXL), N-terminal sequencing, and immunoblotting with goat anti-hIgG-HRP conjugate (Promega W403B), and also mouse monoclonal anti-hIL-4Rα (R&D MAB230) followed by anti-mIgG-HRP conjugate (Promega W402B) as the secondary antibody.

Example 13

Blocking of IL-4 and IL-13 by IL-4Rα.IL-13Rα1.Fc and IL-13Rα1.IL-4Rα.Fc

Materials and Methods

TF1 Bioassay. TF1 cells were maintained in growth media (10 ng/ml GM-CSF, RPMI 1640, 10% FBS, L-glutamine, Penicillin, Streptomycin). For the bioassay, cells were washed 2 times in assay media (as above but without GM-CSF) and then plated at $2 \times 10^5$ cells in 50 μl of assay media. The purified IL-4Rα.IL-13Rα1.Fc and IL-13Rα1.IL-4Rα.Fc proteins were diluted into assay media at a concentration of 40 nM. 25 μl of each of the Traps was added to the cells. Either IL-13 or IL-4 were diluted to 40 nM in assay media and then 2-fold dilution series in assay media were made. 25 μl of either IL-13 or IL-4 was then added to the wells containing the cells and the Traps. Cells were then incubated at 37° C., 5% $CO_2$ for ~70 hrs. The extent of TF1 cell proliferation was measured by the MTS assay according to the manufacturer's protocol (Promega, Inc.).

Results

Figures 32G, 33:
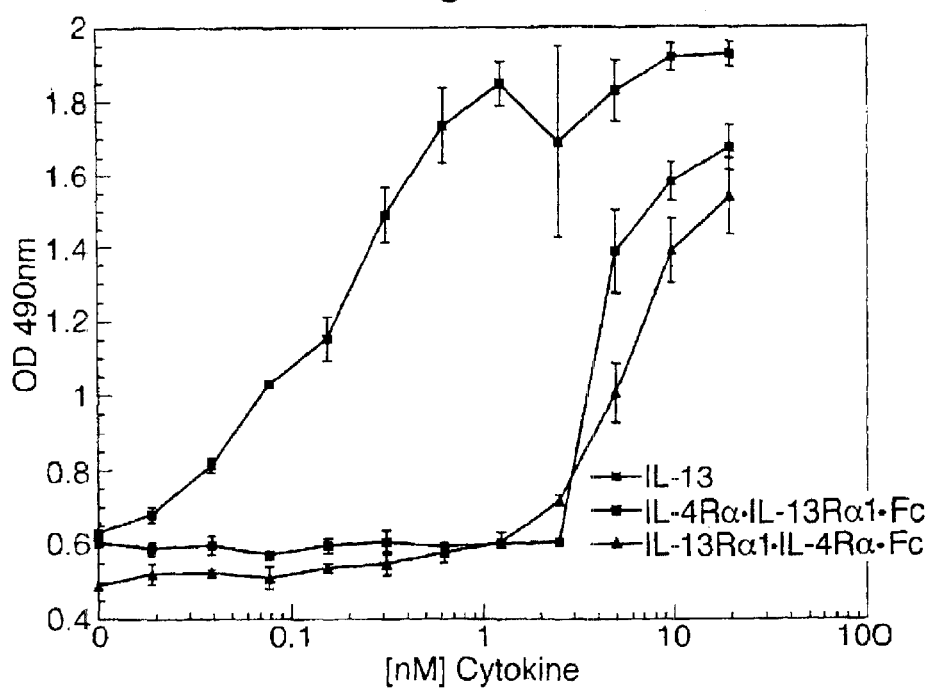
Figure 34:
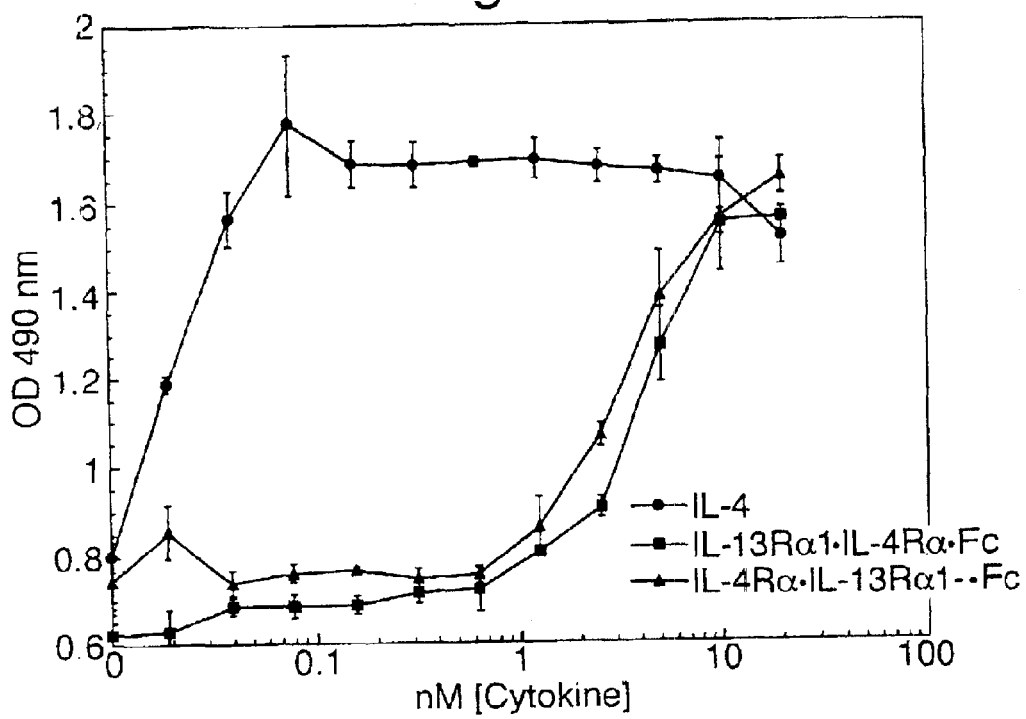
FIG. 34: Blocking of IL-4 by IL-4Rα.IL-13Rα1.Fc and IL-13Rα1.IL-4Rα.Fc. Addition of either IL-4Rα.IL-13Rα1.Fc or IL-13Rα1.IL-4Rα.Fc at a concentration of 10 nM blocks IL-4-induced growth up to ~1 nM. At an IL-4 concentration of ~3–4 nM the growth of TF1 cells is inhibited by 50%.

The ability of the IL-4Rα.IL-13Rα1.Fc and IL-13Rα1.IL-4Rα.Fc Traps to block both human IL-13 and human IL-4 activity was measured in the TF1 bioassay described supra. IL-13 stimulates proliferation of TF1 cells, with half-maximal growth at a concentration of 0.2 nM. Addition of either IL-4Rα.IL-13Rα1.Fc or IL-13Rα1.IL-4Rα.Fc Trap at a concentration of 10 nM blocks IL-13-induced growth up to ~2 nM (FIG. 33). At an IL-13 concentration of ~4–5 nM the growth of TF1 cells is inhibited by 50%. TF1 cells are more sensitive to IL-4, which stimulates their proliferation with half-maximal growth at ~0.02 nM. Addition of either IL-4Rα.IL-13Rα1.Fc or IL-13Rα1.IL-4Rα.Fc at a concentration of 10 nM blocks IL-4-induced growth up to ~1 nM (FIG. 34). At an IL-4 concentration of ~3–4 nM the growth of TF1 cells is inhibited by 50%. These results show that both IL-4Rα.IL-13Rα1.Fc and IL-13Rα1.IL-4Rα.Fc can block the ability of both IL-13 and IL-4 to stimulate cellular responses.

Example 14

Blocking of Injected IL-1 by IL-1 Trap In Vivo

IL-1 is a pro-inflammatory cytokine. Systemic administration of IL-1 has been shown to elicit acute responses in animals, including transient hyperglycemia, hypoinsulinemia, fever, anorexia, and increased serum levels of interleukin-6 (IL-6) (Reimers, 1998). Since mice are responsive to both murine and human IL-1, human IL-1 can be used and in vivo binding effects of human specific IL-1 antagonists can be evaluated. This acute mouse model was used to determine the ability of a human IL-1 Trap to antagonize the in vivo effects of exogenously administered human IL-1. This provides a rapid indication of in vivo efficacy of the human IL-1 Trap and can be used as an assay to help molecule selection.

Experimental Design:

Mice were given subcutaneous injections of human IL-1 (0.3 μg/kg). Twenty-four hours prior to human IL-1 injection, the animals were pre-treated with either vehicle or 150-fold molar excess of human IL-1 Trap (0.54 mg/kg). Two hours prior to sacrifice (26 hrs), the mice were given a second injection of human IL-1 (0.3 μg/kg). Blood samples were collected at various time points and sera were assayed for IL-6 levels.

Results

Figure 35:
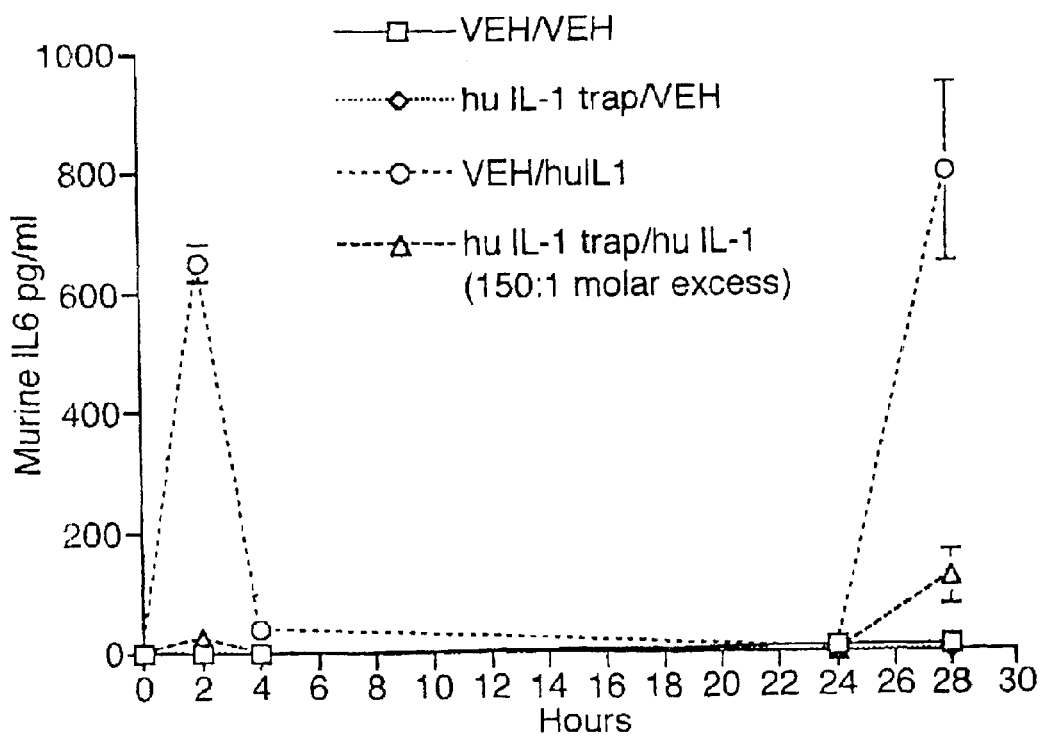
FIG. 35: Human IL-1 Trap blocks the in vivo effects of exogenously administered huIL-1. BALB/c mice were given subcutaneous injection of huIL-1 (0.3 μg/kg) at time 0. Twenty-four hours prior to huIL-1 injection, the animals were pre-treated with either vehicle or 150-fold molar excess of huIL-1 Trap. Two hours prior to sacrifice (26 hrs), the mice were re-challenged with a second injection of huIL-1 (0.3 μg/kg, s.c.). Blood samples were collected at various time points and sera were assayed for IL-1 levels (expressed as mean+/−SEM; n=5 per group).

Exogenous administration of human IL-1 resulted a dramatic induction of serum IL-6 levels. At 150-fold molar excess, the human IL-1 Trap completely blocked the IL-6 increase (FIG. 35). Furthermore, the effects of the human IL-1 Trap persisted for at least another 24 hours, preventing an IL-6 increase even when IL-1 was re-administered (FIG. 35). Such long-lasting efficacy suggests that daily injection of an IL-1 Trap may not be necessary for chronic applications.

Figure 50:
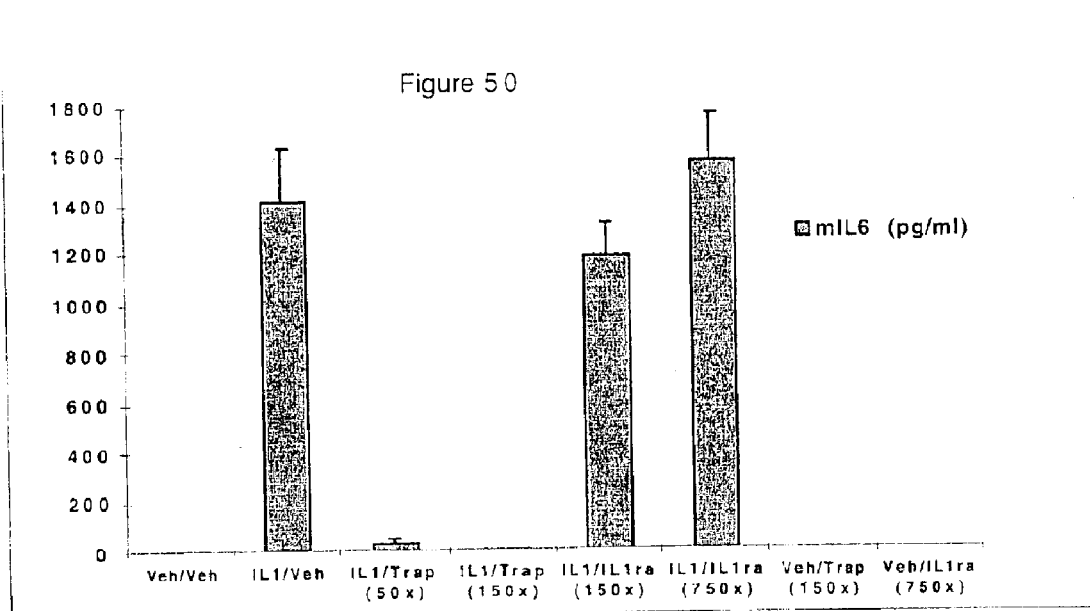
FIG. 50: Human IL-1 Trap blocks the in vivo effects of exogenously administered human IL-1. Male C57BL/6 mice were given a subcutaneous injection of recombinant human IL-1β (rhIL-1β; 0.3 mg/kg). Twenty four hours prior to rhIL-1β administration, animals were treated with either vehicle, human IL-1 Trap 569 (50 or 150-fold molar excess; 0.18 or 0.54 mg/kg, respectively), or recombinant murine IL-1 receptor antagonist (rmIL-1ra; 150 or 750-fold molar excess; 45.8 or 229 μg/kg, respectively). Blood samples were taken 2 h after administration of rhIL-1β and the sera were assayed for IL-6 levels using a mouse IL-6 ELISA. Exogenous administration of rhIL-1β significantly increased serum IL-6 levels. Pretreatment with either a 50 or 150-fold molar excess of hIL-1 Trap blocked the rhIL-1β-induction of IL-6. In contrast, injection of rmIL-1ra at either a 150 or 750-fold molar excess did not block IL-6 induction.

In a separate experiment, IL-1ra at 150-fold or 750-fold molar excess did not significantly block IL6 induction. Therefore, in this paradigm. IL-1 Trap appears to be a better blocker of IL-1 activity (see FIG. 50).

Example 15

Evaluating the Ability of an IL-4 Trap to Block the Physiological Responses to Human IL-4 in Cynomologus Monkeys Systemic administration of human IL-4 elicits systemic responses in Cynomologus monkeys (Gundel et al., 1996). Thus, the effectiveness of the IL-4 Trap in blocking human IL-4 can be demonstrated by measuring these responses.

Experimental Design:

The experiment consisted of 3 parts: human IL-4+vehicle (part 1), human IL-4+IL-4 Trap (part 2), and human IL-4+vehicle (part 3). Human IL-4 (25 μg/kg) was injected subcutaneously twice daily for 4 days and IL-4 Trap (8 mg/kg) and vehicle were given intravenously daily for 5 days, beginning 1 day prior to human IL-4 administration.

Whole blood was collected daily for flow cytometry analysis for CD16 and plasma was obtained to assay for the cytokine monocyte chemotactic protein 1 (MCP-1). CD16 and MCP-1 are markers of IL-4-mediated inflammation in both humans and monkeys.

Results

Figure 36A:
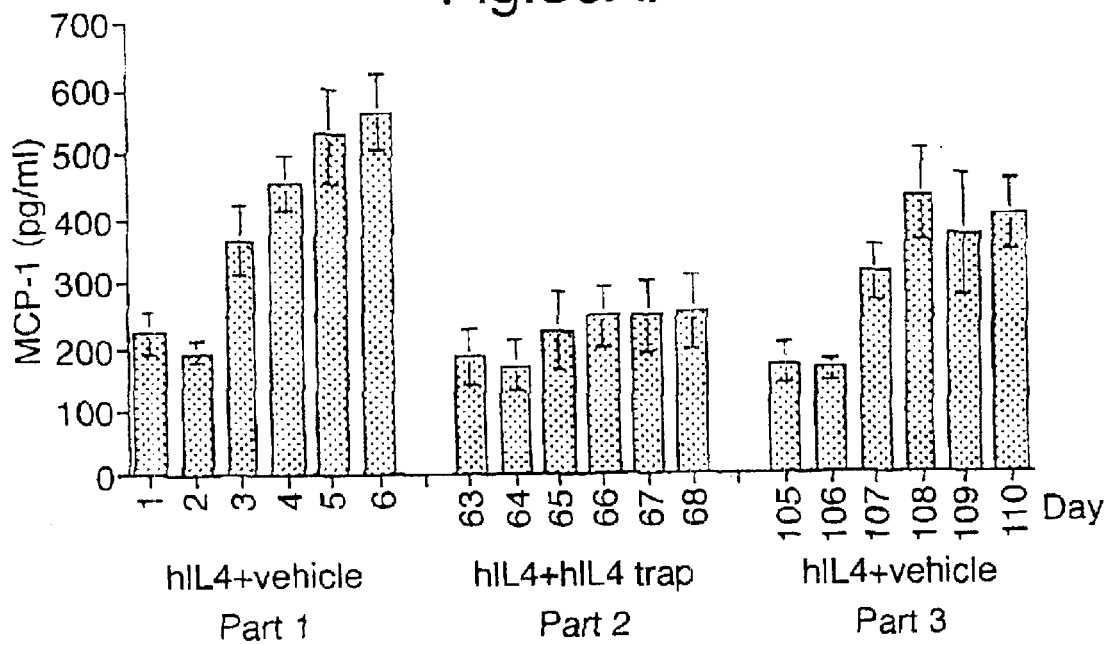
FIG. 36A & FIG. 36B: Human IL-4 Trap antagonizes the effects of human IL-4 in monkeys.
Figure 36B:
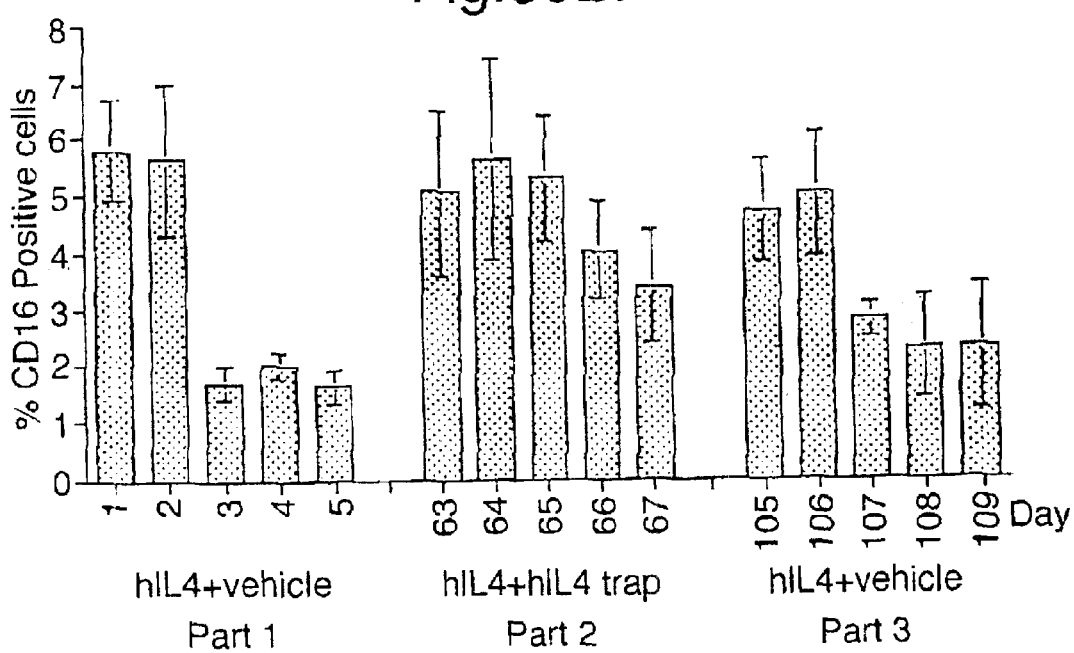

In the presence of human IL-4, MCP-1 increased 2.5-fold and was significantly blocked by the IL-4 Trap (FIG. 36A). Similarly, the decrease in the percent of CD16 positive lymphocytes in peripheral blood was attenuated by the IL-4 Trap (FIG. 36B). After a rest period, the monkeys were re-injected with human IL-4 and the responsiveness of the animals to human IL-4 was re-confirmed (FIGS. 36A and 36B), suggesting that inhibition of the MCP-1 and CD 16 responses is specifically mediated by the IL-4 Trap.

Example 16

The Effects of IL-4 Trap on 1L-4-induced IgE Secretion

It has been shown that injection of anti-mouse IgD antibody stimulates an IL-4-mediated IgE increase in normal mice. This model has been widely used to evaluate IL-4 antagonists, such as soluble IL-4 receptor and anti-IL-4 monoclonal antibodies (Sato et al., 1993). We decided to use this model to evaluate the ability if the IL-4 Trap to block IL-4-mediated increases of IgE.

Experimental Design:

BALB/C mice injected with anti-mouse IgD (100 µl/mouse, s.c.) were randomly divided into 3 groups. Each received (on days 3–5) either vehicle, murine IL-4 Trap (1 mg/kg, s.c.), or a monoclonal antibody to mouse IL-4 (1 mg/kg, s.c.). Serum was collected at various time points and assayed for IgE levels.

Results

Treatment with the murine IL-4 Trap or the mouse IL-4 antibody both significantly antagonized the IL-4-mediated IgE increase in this mouse model (FIG. 37). This suggests that the murine IL-4 Trap binds murine IL-4 and antagonizes physiological responses elicited by endogenous IL-4 in vivo.

Example 17

Construction of Additional Single Chain IL-1 Traps

The techniques used to construct the DNA vectors described herein are standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, N.Y.). All DNA sequencing is done by standard techniques using an ABI 373A DNA sequencer and Taq Dideoxy Terminator Cycle Sequencing Kit (Applied Biosystems, Inc., Foster City, Calif.).

a) IL-1 Trap 823 Sequence—The IL-1 Trap 823 sequence consists of the extracellular domain of human IL-1RAcP (corresponding to nucleotides 1–1077 of FIGS. 41A–41I, SEQ ID NO: 39) followed by the extracellular domain of human IL-1RI (corresponding to nucleotides 1078–2013 of FIGS. 41A–41I, SEQ ID NO: 39) followed by a part of the hinge region, the CH2 and CH3 domains of human IgG1 (corresponding to nucleotides 2014–2703 of FIGS. 41A–41I, SEQ ID NO: 39) containing a mutation at nucleotides 2017–2019 (TGT->GGA) to change a cysteine to a glycine. The nucleic acid sequence encodes the fusion polypeptide sequence as set forth in FIGS. 41A–41, SEQ ID NO: 40.

b) IL-1 Trap 823–1198-B Sequence—The IL-1 Trap 823–1198-B sequence consists of the extracellular domain of human IL-1RAcP (corresponding to nucleotides 1–1077 of FIGS. 42A–42I, SEQ ID NO: 41), followed by the extracellular domain of human IL-1RI (corresponding to nucleotides 1078–2013 of FIGS. 42A–42I, SEQ ID NO: 41), followed by a stretch of amino acids (corresponding to nucleotides 2014–2019 of FIGS. 42A–42I, SEQ ID NO: 41), followed by the hinge region, the CH2 and CH3 domains of human IgG4 (corresponding to nucleotides 2020–2709 of FIGS. 42A–42I, SEQ ID NO: 41). The nucleic acid sequence encodes the fusion polypeptide sequence as set forth in FIGS. 42A–42I, SEQ ID NO: 42.

c) IL-1 Trap 823–1267-C Sequence—The IL-1 Trap 823–1267-C sequence consists of the extracellular domain of human IL-1RAcP (corresponding to nucleotides 1–1077 of FIGS. 43A–43I, SEQ ID NO: 43), followed by the extracellular domain of human IL-1RI (corresponding to nucleotides 1078–2013 of FIGS. 43A–43I, SEQ ID NO: 43), followed by a stretch of amino acids (corresponding to nucleotides 2014–2019 of FIGS. 43A–43I, SEQ ID NO: 43), followed by the hinge region, the CH2 and CH3 domains of human IgG4 (corresponding to nucleotides 2020–2709 of FIGS. 43A–43I, SEQ ID NO: 43) containing a mutation at nucleotide 2047 (T>C) to change a serine to a proline. The nucleic acid sequence encodes the fusion polypeptide sequence as set forth in FIGS. 43A–43I, SEQ ID NO: 44.

d) IL-1 Trap 570-FE Sequence—The IL-1 Trap 570-FE sequence consists of the extracellular domain of human IL-1RI (corresponding to nucleotides 1 to 996 of FIGS. 38A–38I, SEQ ID NO: 33), followed by the extracellular domain of human IL-1RAcP (corresponding to nucleotides 997–2013 of FIGS. 38A–38I, SEQ ID NO: 33) followed by part of the hinge region, the CH2 and CH3 domains of human IgG1 (corresponding to nucleotides 2014–2703 of FIGS. 38A–38I, SEQ ID NO: 33) containing a mutation at nucleotides 2017–2019 (TGT->GGA) to change a cysteine to a glycine. The nucleic acid sequence encodes the fusion polypeptide sequence as set forth in FIGS. 38A–38I, SEQ ID NO: 34.

e) IL-1 Trap 570-FE-B Sequence—The IL-1 Trap 570-FE-B sequence consists of the extracellular domain of human IL-1RI (corresponding to nucleotides 1 to 996 of FIGS. 39A–39I, SEQ ID NO: 35), followed by the extracellular domain of human IL-1RAcP (corresponding to nucleotides 997–2013 of FIGS. 39A–39I, SEQ ID NO: 35) followed by a stretch of amino acids (corresponding to nucleotides 2014–2019 of FIGS. 39A–39I, SEQ ID NO: 35) followed by the hinge region, the CH2 and CH3 domains of human IgG4 (corresponding to nucleotides 2020–2709 of FIGS. 39A–39I, SEQ ID NO: 35). The nucleic acid sequence encodes the fusion polypeptide sequence as set forth in FIGS. 39A–39I, SEQ ID NO: 36.

f) IL-1 Trap 570-FE-C Sequence—The IL-1 Trap 570-FE-C sequence consists of the extracellular domain of human IL-1RI (corresponding to nucleotides 1 to 996 of FIGS. 40A–40I, SEQ ID NO: 37), followed by the extracellular domain of human IL-1RAcP (corresponding to nucleotides 997–2013 of FIGS. 40A–40I, SEQ ID NO: 37) followed by a stretch of amino acids (corresponding to nucleotides 2014–2019 of FIGS. 40A–40I, SEQ ID NO: 37) followed by the hinge region, the CH2 and CH3 domains of human IgG4 (corresponding to nucleotides 2020–2709 of FIGS. 40A–40I, SEQ ID NO: 37) containing a mutation at nucleotide 2047 (T>C) to change a serine to a proline. The nucleic acid sequence encodes the fusion polypeptide sequence as set forth in FIGS. 40A–40I, SEQ ID NO: 38.

g) IL-1 Trap 1647-CtF Sequence—The IL-1 Trap 1647-CtF sequence consists of the extracellular domain of human IL-1RII (corresponding to nucleotides 1–1044 of FIGS. 44A–44I, SEQ ID NO: 45) followed by the extracellular domain of human IL-1RAcP (corresponding to nucleotides 1045–2058 of FIGS. 44A–44I, SEQ ID NO: 45) followed by a part of the hinge region, the CH2 and CH3 domains of human IgG1 (corresponding to nucleotides 2059–2748 of FIGS. 44A–44I, SEQ ID NO: 45) containing a mutation at nucleotides 2062–2064 (TGT->GGA) to change a cysteine to a glycine. The nucleic acid sequence encodes the fusion polypeptide sequence as set forth in FIGS. 44A–44I, SEQ ID NO: 46.

h) IL-1 Trap 1647-CtF-B Sequence—The IL-1 Trap 1647-CtF-B sequence consists of the extracellular domain of human IL-1RII (corresponding to nucleotides 1–1044 of FIGS. 45A–45I, SEQ ID NO: 47) followed by the extracellular domain of human IL-1RAcP (corresponding to nucleotides 1045–2058 of FIGS. 45A–45I, SEQ ID NO: 47) followed by a stretch of amino acids (corresponding to nucleotides 2059–2064 of FIGS. 45A–45I, SEQ ID NO: 47) followed by the hinge region, the CH2 and CH3 domains of human IgG4 (corresponding to nucleotides 2065–2754 of FIGS. 45A–45I, SEQ ID NO: 47). The nucleic acid sequence encodes the fusion polypeptide sequence as set forth in FIGS. 45A–45I, SEQ ID NO: 48.

i) IL-1 Trap 1647-CtF-C Sequence—The IL-1 Trap 1647-CtF-C sequence consists of the extracellular domain of human IL-1RII (corresponding to nucleotides 1–1044 of FIGS. 46A–46I, SEQ ID NO: 49) followed by the extracellular domain of human IL-1RAcP (corresponding to nucleotides 1045–2058 of FIGS. 46A–46I, SEQ ID NO: 49) followed by a stretch of amino acids (corresponding to nucleotides 2059–2064 of FIGS. 46A–46I, SEQ ID NO: 49) followed by the hinge region, the CH2 and CH3 domains of human IgG4 (corresponding to nucleotides 2065–2754 of FIGS. 46A–46I, SEQ ID NO: 49) containing a mutation at nucleotide 2092 (T>C) to change a serine to a proline. The nucleic acid sequence encodes the fusion polypeptide sequence as set forth in FIGS. 46A–46I, SEQ ID NO: 50.

j) IL-1 Trap 1649 Sequence—The IL-1 Trap 1649 sequence consists of the extracellular domain of human IL-1RAcP (corresponding to nucleotides 1–1074 of FIGS. 47A–47I, SEQ ID NO: 51) followed by the extracellular domain of human IL-1RII (corresponding to nucleotides 1075–2058 of FIGS. 47A–47I, SEQ ID NO: 51) followed by a part of the hinge region, the CH2 and CH3 domains of human IgG1 (corresponding to nucleotides 2059–2748 of FIGS. 47A–47I, SEQ ID NO: 51) containing a mutation at nucleotides 2062–2064 (TGT->GGA) to change a cysteine to a glycine. The nucleic acid sequence encodes the fusion polypeptide sequence as set forth in FIGS. 47A–47I, SEQ ID NO: 52.

k) IL-1 Trap 1649-B Sequence—The IL-1 Trap 1649-B sequence consists of the extracellular domain of human IL-1RAcP (corresponding to nucleotides 1–1074 of FIGS. 48A–48I, SEQ ID NO:53) followed by the extracellular domain of human IL-1RII (corresponding to nucleotides 1075–2058 of FIGS. 48A–48I, SEQ ID NO:53) followed by a stretch of amino acids (corresponding to nucleotides 2059–2064) followed by the hinge region, the CH2 and CH3 domains of human IgG4 (corresponding to nucleotides 2065–2754 of FIGS. 48A–48I, SEQ ID NO:53). The nucleic acid sequence encodes the fusion polypeptide sequence as set forth in FIGS. 48A–48I, SEQ ID NO:54.

l) IL-1 Trap 1649-C Sequence—The IL-1 Trap 1649-C sequence consists of the extracellular domain of human IL-1RAcP (corresponding to nucleotides 1–1074 of FIGS. 49A–49I, SEQ ID NO: 55) followed by the extracellular domain of human IL-1RII (corresponding to nucleotides 1075–2058 of FIGS. 49A–49I, SEQ ID NO: 55) followed by a stretch of amino acids (corresponding to nucleotides 2059–2064) followed by the hinge region, the CH2 and CH3 domains of human IgG4 (corresponding to nucleotides 2065–2754 of FIGS. 49A–49I, SEQ ID NO: 55) containing a mutation at nucleotide 2092(T>C) to change a serine to a proline. The nucleic acid sequence encodes the fusion polypeptide sequence as set forth in FIGS. 49A–49I, SEQ ID NO: 56.

In addition to the sequences described supra and in the associated figures, the following modifications to those sequences are also contemplated by the subject invention For IL1 Traps 823, 823–1198. B, and 823–1267.C:

AcP alternative: A change at nucleotide 1043 from A to C to change the amino acid from Lys to Thr.

SG insertion: Between nucleotides 1077 and 1078 an insertion of the nucleotides TCC GGA would add a Ser Gly stretch of amino acids between the two receptor domains of the Trap.

For IL1 Traps 570-FE, 570-FE.B, and 570-FE.C:

AcP alternative: A change at nucleotide 1979 from A to C to change the amino acid from Lys to Thr.

SG insertion: Between nucleotides 996 and 977 an insertion of the nucleotides TCC GGA would add a Ser Gly stretch of amino acids between the two receptor domains of the Trap.

For IL1 Traps1647-CtF, 1647-CtF.B, and 1647-CtF.C:

AcP alternative: A change at nucleotide 2027 from A to C to change the amino acid from Lys to Thr.

SG insertion: Between nucleotides 1044 and 1045 an insertion of the nucleotides TCC GGA would add a Ser Gly stretch of amino acids between the two receptor domains of the Trap.

For IL1 Traps 1649, 1649-B, and 1649-C:

AcP alternative: A change at nucleotide 1043 from A to C to change the amino acid from Lys to Thr.

SG insertion: Between nucleotides 1074 and 1075 an insertion of the nucleotides TCC GGA would add a Ser Gly stretch of amino acids between the two receptor domains of the Trap.

In addition, one of skill in the art will recognize that it may be desirable to construct IL1 Traps in which the Fc domain is derived from immunoglobulins with different allotypes.

None of the modifications described supra will alter the Trap's ability to bind IL1.

Example 18

Human IL-1 Trap Blocks the Effects of IL-1 in Inflammed Joints

Background:

Zymosan is a yeast cell wall extract that when injected into the knee causes acute inflammation and upregulation of IL-1 β in the joint (Joosten L A B, Helsen M M A, van den Berg, W B (1994) Clin Exp Immunol 97:204–211.). Chondrocytes will respond to the inflammation and local IL-1β by down regulating proteoglycan synthesis, a feature of human arthritis that contributes to the gradual destruction of cartilage in the joint (van den Berg W B, Kruijsen M W M, van de Putte L B A (1982) Rheum Intl 1:165–169). Antagonists to IL-1β can be used to evaluate their ability to block the effects of zymosan-induced elevations in IL-1β.

Materials and Methods

Anesthetized male C57BL/6 mice (Taconic) were given an intra-articular (i.a.) injection of Zymosan A (Sigma; 300 µg in 10 µl) into the right knee joint through the patellar ligament. Sterile PBS was injected i.a. (10 µl) into the left knee joint through the patellar ligament. Twenty four hours prior to i.a. injections, animals were treated with either vehicle or hIL-1 Trap 569 (19 mg/kg, s.c.). The patellae were removed 24 h after injection of zymosan in order to measure proteoglycan synthesis as described by van den Berg and colleagues (1982). Briefly, each patella and associated ligament were incubated for 3 h at 37° C., 5% $CO_2$ in media (RPMI with HEPES, $HCO_3$, glutamine & penicillin/streptomycin) containing 10 µCi/ml $^{35}$S-sulfate (NEN DuPont). Following incubation, tissue was washed and fixed overnight in 10% formalin (VWR). The tissue was then placed in Decalcifing Solution (J. T. Baker) for 4 h prior to dissection of the patella from surrounding tissue. Each patella was then incubated overnight in Solvable (Packard) at 50° C. Ultima Gold liquid scintillation fluid (Packard) was added and the samples were counted in a liquid scintillation counter. Values were reported as the ratio of cpm of zymosan patella/cpm of vehicle patella for each animal.

Figure 51:
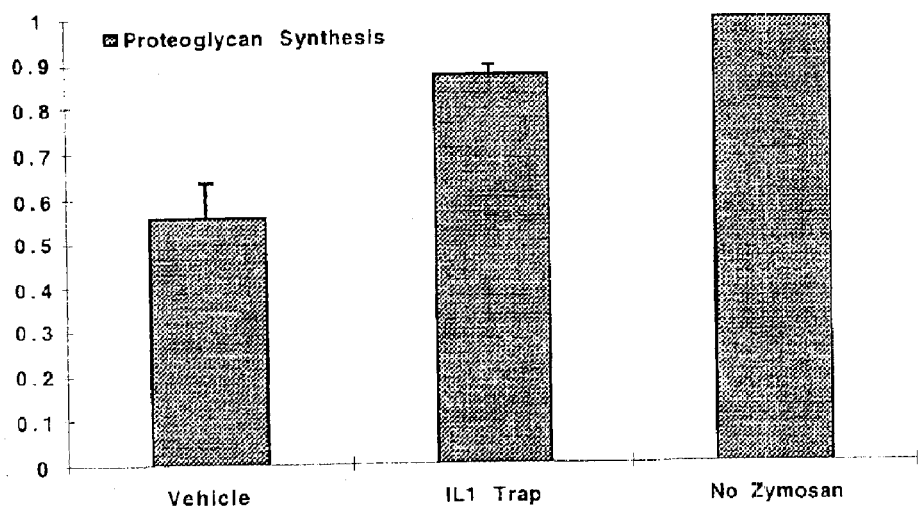
FIG. 51: Human IL-1 Trap blocks the effects of IL-1 in Inflamed Joints. Anesthetized male C57BL/6 mice were given an intra-articular (i.a.) injection of Zymosan A (300 μg in 10 μl) into the right knee joint through the patellar ligament. Sterile PBS was injected i.a. (10 μl) into the left knee joint through the patellar ligament. Twenty four hours prior to i.a. injections, animals were treated with either vehicle or hIL-1 Trap 569 (19 mg/kg, s.c.). The patellae were removed 24 h after injection of zymosan in order to measure proteoglycan synthesis, each patella and associated ligament were incubated for 3 h at 37° C., 5% $CO_2$ in media (RPMI with HEPES, $HCO_3$, glutamine & penicillin/streptomycin) containing 10 uCi/ml $^{35}$S-sulfate. Following incubation, tissue was washed and fixed overnight in 10% formalin. The tissue was then placed in Decalcifing Solution for 4 h prior to dissection of the patella from surrounding tissue. Each patella was then incubated overnight in Solvable at 50° C. Ultima Gold liquid scintillation fluid was added and the samples were counted in a liquid scintillation counter. Values were reported as the ratio of cpm of zymosan patella/cpm of vehicle patella for each animal. Intra-articular injection of zymosan reduces proteoglycan synthesis by approximately 50% relative to vehicle injection. Administration of hIL-1 Trap prior to zymosan injection blocked the local action of IL-1β and proteoglycan synthesis returned to approximately 90% of control.

Results:

Intra-articular injection of zymosan reduces proteoglycan synthesis by approximately 50% relative to vehicle injection (FIG. 51). Administration of hIL-1 Trap prior to zymosan injection blocked the local action of IL-1β and proteoglycan synthesis returned to approximately 90% of control. These data demonstrate that hIL-1 Trap 569 can penetrate the joints after subcutaneous injection to effectively neutralize the biological effect of IL-1 within these joints.

Example 19

Murine IL-1 Trap Reduces the Severity of Arthritis Symptoms in a Zymosan-accelerated Collagen-induced Arthritis (CIA) Model Background IL-1 has been implicated in the development of inflammation and cartilage destruction in rheumatoid arthritis (Dinarello C A (1996) Blood 87(6):2095–2147; Wooley P H, Whalen J D, Chapman D L, Berger A E, Richard K A, Aspar D G, Staite N D (1993) Arthritis & Rheumatism 36(9): 1305–1314). Collagen-induced arthritis (CIA) is a widely studied animal model of inflammatory polyarthritis with similarities to rheumatoid arthritis; common histopathological features include joint inflammation and erosion, synovial hyperplasia and inflammatory cell infiltration (Joe B, Wilder R L (1999) Mol Med Today 5:367–369). Since previous studies have shown that various anti-IL-1 treatments have a positive effect on reducing arthritis symptoms in CIA animals (van den Berg W B, Joosten L A B, Helsen M, van de Loo F A J (1994) Clin Exp Immunol 95:237–243; Joosten L A B, Helsen M M A, Saxne T, van de Loo F A J, Heinegard D, van de Berg W B (1999) J Immunol 163:5049–5055. ; van de Loo F A J, Arntz O J, Otterness I G, van den Berg W B (1992) J Rheumatol 19:348–356. ), Applicants examined the effect of a murine version of the IL-1 Trap (mIL-1 Trap) on the progression of arthritis symptoms in this animal model. The human version of the IL-1 Trap is poorly cross-reactive with rodent IL-1. The mIL-1 Trap consists of the extracellular domain of murine IL-1RAcP, followed by the extracellular domain of murine IL-1RI, followed by the hinge, CH2 and CH3 domain of murine IgG2a.

Materials and Methods

Male DBA-1 mice (Jackson Laboratories) were immunized intradermally at the base of the tail with 100 µg/50 µl bovine Type II collagen (CII; Chondrex) emulsified with complete and incomplete Freund's adjuvant (2:1:1 ratio; Chondrex) and boosted intradermally with CII (100 µg/50 µl) emulsified with incomplete Freund's adjuvant on day 21. Since CIA in DBA-1 mice occurs gradually over a long time period with a low incidence (Joosten L A B, Helsen M M A, van den Berg, W B (1994) Clin Exp Immunol 97:204–211. ), Applicants synchronized the onset of arthritis symptoms by injecting the animals intraperitoneally on day 30 with 3 mg zymosan (Sigma). Two hours prior to zymosan injection, the mice were randomly distributed into treatment groups and were injected with either vehicle or mIL-1 Trap (31 or 10 mg/kg, 3×/week, 8 injections, s.c.). Arthritis symptoms (ASI scores, as described by Wooley P H, Whalen J D, Chapman D L, Berger A E, Richard K A, Aspar D G, Staite N D (1993) Arthritis & Rheumatism 36(9): 1305–1314) in the paws were evaluated 3×/week by individuals who were blinded to the treatment groups. Animals were sacrificed 24 h after the 8th injection at which time paw width along with ASI scores were measured.

Results

Figure 52:
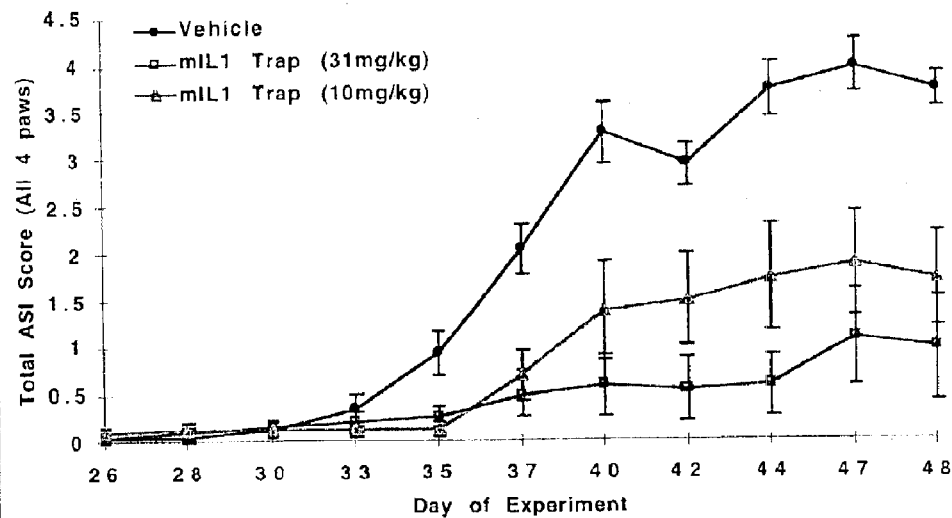
FIG. 52 AND FIG. 53: Murine IL-1 Trap Reduces the Severity of Arthritis Symptoms in a Zymosan-Accelerated Collagen-Induced Arthritis (CIA) model. Male DBA-1 mice were immunized intradermally at the base of the tail with 100 μg/50 μl bovine Type II collagen (CII) emulsified with complete and incomplete Freund's adjuvant (2:1:1 ratio) and boosted intradermally with CII (100 μg/50 μl) emulsified with incomplete Freund's adjuvant on day 21. Since CIA in DBA-1 mice occurs gradually over a long time period with a low incidence, we synchronized the onset of arthritis symptoms by injecting the animals intraperitoneally on day 30 with 3 mg zymosan. Two hours prior to zymosan injection, the mice were randomly distributed into treatment groups and were injected with either vehicle or mIL-1 Trap (31 or 10 mg/kg, 3x/week, 8 injections, s.c.). Arthritis symptoms (ASI scores) In the paws were evaluated 3x/week by individuals who were blinded to the treatment group. Animals were sacrificed 24 h after the 8th injection at which time paw width along with ASI scores were measured. Within 5 days after i.p injection of zymosan, vehicle treated animals had an significant increase in ASI score relative to those receiving mIL-1 Trap FIG. 52) with symptoms reaching a maximum 10 to 14 days after zymosan injection. Murine IL-1 Trap acted in a dose-dependent fashion such that animals receiving 10 mg/kg Trap had more arthritis symptoms (greater ASI score) than those receiving 31 mg/kg. However, both mIL-1 Trap treated groups had a significantly lower degree of arthritis symptoms than vehicle. This difference in ASI score is also reflected in the paw width at the time of sacrifice FIG. 53). Animals receiving mIL-1 Trap had paw widths that were similar to those of naive, non-collagen immunized animals
Figure 53:
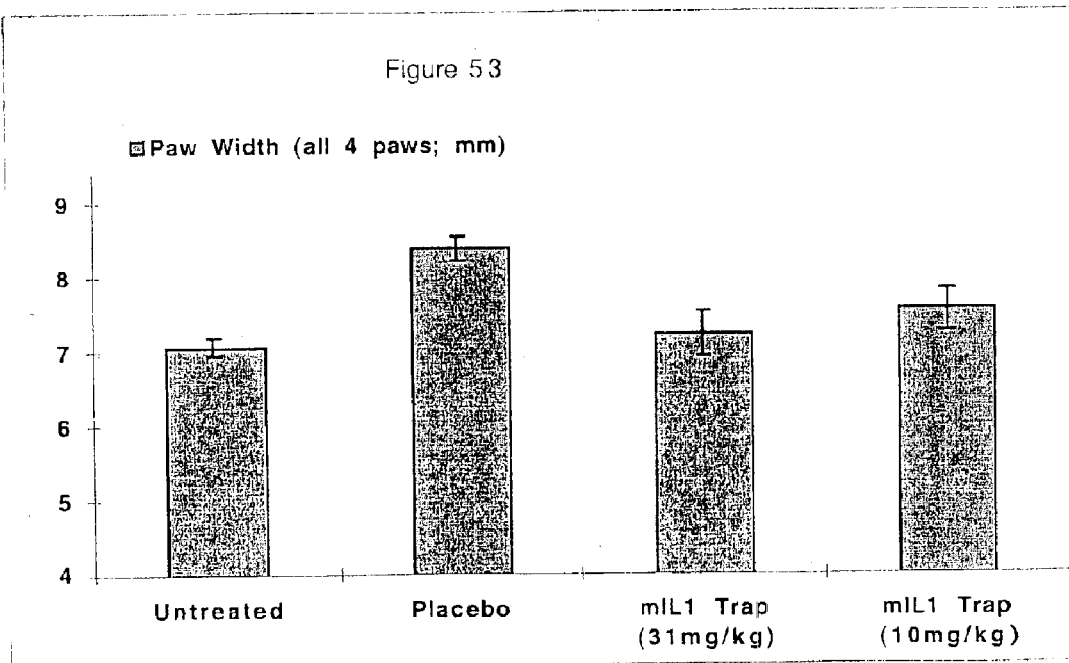

Within 5 days after i.p injection of zymosan, vehicle treated animals had an significant increase in ASI score relative to those receiving mIL-1 Trap (FIG. 52) with symptoms reaching a maximum 10 to 14 days after zymosan injection. Murine IL-1 Trap acted in a dose-dependent fashion such that animals receiving 10 mg/kg Trap had more arthritis symptoms (greater ASI score) than those receiving 31 mg/kg. However, both mIL-1 Trap-treated groups had a significantly lower degree of arthritis symptoms than vehicle. This difference in ASI score is also reflected in the paw width at the time of sacrifice (FIG. 53). Animals receiving mIL-1 Trap had paw widths that were similar to those of naive, non-collagen immunized animals. These data indicate that mIL-1 Trap can effectively neutralize IL-1 and block the development of arthritic joints.

Example 20

IL-1 Trap 1649 can Block the Activity of IL-1B

Figure 54:
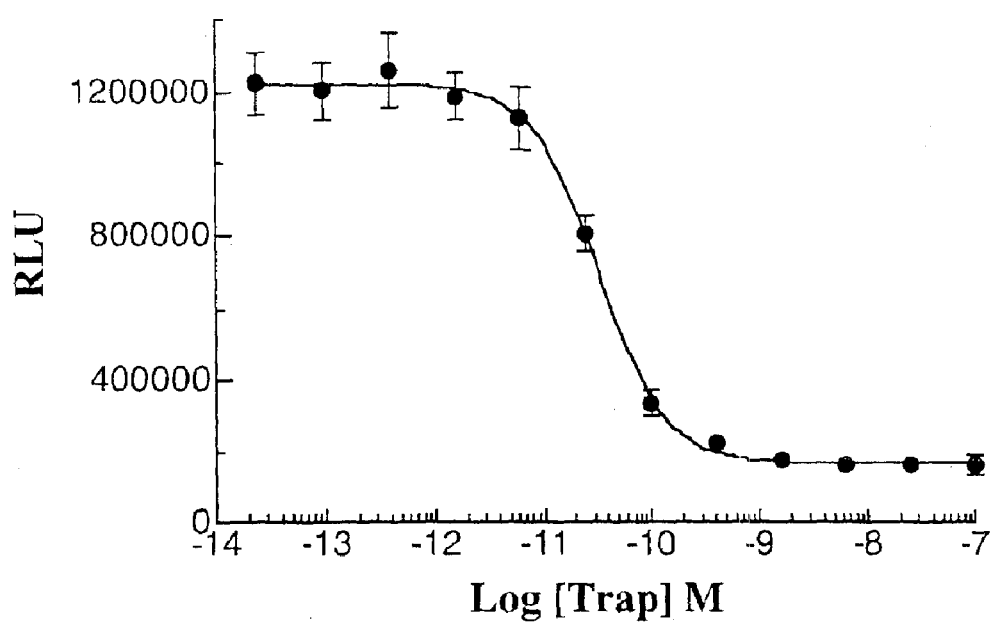
FIG. 54: Various concentrations of IL-1 Trap 1649 were incubated in the presence of 5 pM human IL-1β overnight at room temperature. The mixtures were then added to duplicate wells of 293-NFκB cells (20,000 cells/well) for 5 hrs at 37° C., 5% $CO_2$. Steady-Glo Reagent (Promega) was added to the cells for 15 min at room temperature and luciferase gene expression was quantitated as relative light units (RLU) by luminometry. IL-1 Trap 1649 displays an $IC_{50}$ of 32 pM.

Various concentrations of IL-1 Trap 1649 were incubated in the presence of 5 pM human IL-1 overnight at room temperature. The mixtures were then added to duplicate wells of 293-NFκB cells (20,000 cells/well) for 5 hrs at 37° C., 5% $CO_2$. 293-NFκB cells contain a stably integrated reporter plasmid possessing a luciferase gene driven by a promoter containing 5 NFκB sites. Addition of IL-1 results in increased luciferase gene expression. Steady-Glo Reagent (Promega) was added to the cells for 15 min at room temperature and luciferase gene expression was quantitated as relative light units (RLU) by luminometry. IL-1 Trap 1649 displays an $IC_{50}$ of 32 pM which indicates a Kd of ~30 pM (see FIG. 54). These data indicate that IL-1 Trap 1649 potently blocks IL-1.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

SEQUENCE LISTING

<160> NUMBER OF SEQ ID NOS: 56

<210> SEQ ID NO 1
<211> LENGTH: 6
<212> TYPE: PRT
<213> ORGANISM: Artificial Sequence
<220> FEATURE:
<223> OTHER INFORMATION: Tag sequence

<400> SEQUENCE: 1

His His His His His His
1               5

<210> SEQ ID NO 2
<211> LENGTH: 16
<212> TYPE: PRT
<213> ORGANISM: Artificial Sequence
<220> FEATURE:
<223> OTHER INFORMATION: peptide derived from region near C-terminus of
      gp130

<400> SEQUENCE: 2

Cys Gly Thr Glu Gly Gln Val Glu Arg Phe Glu Thr Val Gly Met Glu
1               5                   10                  15

<210> SEQ ID NO 3
<211> LENGTH: 16
<212> TYPE: DNA
<213> ORGANISM: Artificial Sequence
<220> FEATURE:
<223> OTHER INFORMATION: Kozak sequence

<400> SEQUENCE: 3
cgccgccacc atggtg                                                    16

<210> SEQ ID NO 4
<211> LENGTH: 10
<212> TYPE: PRT
<213> ORGANISM: Artificial Sequence
<220> FEATURE:
<223> OTHER INFORMATION: J peptide

<400> SEQUENCE: 4

Gly Gln Gly Thr Leu Val Thr Val Ser Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: J peptide

<400> SEQUENCE: 5

Thr Phe Gly Gln Gly Thr Lys Val Glu Ile Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: linker sequence

<400> SEQUENCE: 6

```
Gly Ala Pro Ser Gly Gly Gly Arg Pro
1               5                   10
```

<210> SEQ ID NO 7
<211> LENGTH: 859
<212> TYPE: PRT
<213> ORGANISM: Homo sapiens

<400> SEQUENCE: 7

```
Met Val Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365
```

-continued

```
Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
                500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ser Gly Glu Pro Lys
    610                 615                 620

Ser Cys Asp Lys Thr His Thr Cys Pro Pro Cys Pro Ala Pro Glu Leu
625                 630                 635                 640

Leu Gly Gly Pro Ser Val Phe Leu Phe Pro Pro Lys Pro Lys Asp Thr
                645                 650                 655

Leu Met Ile Ser Arg Thr Pro Glu Val Thr Cys Val Val Val Asp Val
            660                 665                 670

Ser His Glu Asp Pro Glu Val Lys Phe Asn Trp Tyr Val Asp Gly Val
    675                 680                 685

Glu Val His Asn Ala Lys Thr Lys Pro Arg Glu Glu Gln Tyr Asn Ser
    690                 695                 700

Thr Tyr Arg Val Val Ser Val Leu Thr Val Leu His Gln Asp Trp Leu
705                 710                 715                 720

Asn Gly Lys Glu Tyr Lys Cys Lys Val Ser Asn Lys Ala Leu Pro Ala
                725                 730                 735

Pro Ile Glu Lys Thr Ile Ser Lys Ala Lys Gly Gln Pro Arg Glu Pro
            740                 745                 750

Gln Val Tyr Thr Leu Pro Pro Ser Arg Asp Glu Leu Thr Lys Asn Gln
    755                 760                 765

Val Ser Leu Thr Cys Leu Val Lys Gly Phe Tyr Pro Ser Asp Ile Ala
770                 775                 780
```

Val Glu Trp Glu Ser Asn Gly Gln Pro Glu Asn Asn Tyr Lys Thr Thr
785                 790                 795                 800

Pro Pro Val Leu Asp Ser Asp Gly Ser Phe Phe Leu Tyr Ser Lys Leu
            805                 810                 815

Thr Val Asp Lys Ser Arg Trp Gln Gln Gly Asn Val Phe Ser Cys Ser
        820                 825                 830

Val Met His Glu Ala Leu His Asn His Tyr Thr Gln Lys Ser Leu Ser
    835                 840                 845

Leu Ser Pro Gly Lys His His His His His
    850                 855

<210> SEQ ID NO 8
<211> LENGTH: 592
<212> TYPE: PRT
<213> ORGANISM: Homo sapiens

<400> SEQUENCE: 8

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ala Gly Glu Pro Lys Ser Cys Asp Lys Thr
            355                 360                 365

His Thr Cys Pro Pro Cys Pro Ala Pro Glu Leu Leu Gly Gly Pro Ser
        370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
                420                 425                 430

Lys Thr Lys Pro Arg Glu Glu Gln Tyr Asn Ser Thr Tyr Arg Val Val
            435                 440                 445

Ser Val Leu Thr Val Leu His Gln Asp Trp Leu Asn Gly Lys Glu Tyr
        450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590

<210> SEQ ID NO 9
<211> LENGTH: 951
<212> TYPE: PRT
<213> ORGANISM: Homo sapiens

<400> SEQUENCE: 9

Met Val Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser

-continued

```
                 85                  90                  95
Leu Asn Ile Gln Leu Thr Cys Asn Ile Leu Thr Phe Gly Gln Leu Glu
            100                 105                 110
Gln Asn Val Tyr Gly Ile Thr Ile Ile Ser Gly Leu Pro Pro Glu Lys
            115                 120                 125
Pro Lys Asn Leu Ser Cys Ile Val Asn Glu Gly Lys Lys Met Arg Cys
            130                 135                 140
Glu Trp Asp Gly Gly Arg Glu Thr His Leu Glu Thr Asn Phe Thr Leu
145                 150                 155                 160
Lys Ser Glu Trp Ala Thr His Lys Phe Ala Asp Cys Lys Ala Lys Arg
            165                 170                 175
Asp Thr Pro Thr Ser Cys Thr Val Asp Tyr Ser Thr Val Tyr Phe Val
            180                 185                 190
Asn Ile Glu Val Trp Val Glu Ala Glu Asn Ala Leu Gly Lys Val Thr
            195                 200                 205
Ser Asp His Ile Asn Phe Asp Pro Val Tyr Lys Val Lys Pro Asn Pro
210                 215                 220
Pro His Asn Leu Ser Val Ile Asn Ser Glu Glu Leu Ser Ser Ile Leu
225                 230                 235                 240
Lys Leu Thr Trp Thr Asn Pro Ser Ile Lys Ser Val Ile Ile Leu Lys
            245                 250                 255
Tyr Asn Ile Gln Tyr Arg Thr Lys Asp Ala Ser Thr Trp Ser Gln Ile
            260                 265                 270
Pro Pro Glu Asp Thr Ala Ser Thr Arg Ser Ser Phe Thr Val Gln Asp
            275                 280                 285
Leu Lys Pro Phe Thr Glu Tyr Val Phe Arg Ile Arg Cys Met Lys Glu
            290                 295                 300
Asp Gly Lys Gly Tyr Trp Ser Asp Trp Ser Glu Glu Ala Ser Gly Ile
305                 310                 315                 320
Thr Tyr Glu Asp Arg Pro Ser Lys Ala Pro Ser Phe Trp Tyr Lys Ile
            325                 330                 335
Asp Pro Ser His Thr Gln Gly Tyr Arg Thr Val Gln Leu Val Trp Lys
            340                 345                 350
Thr Leu Pro Pro Phe Glu Ala Asn Gly Lys Ile Leu Asp Tyr Glu Val
            355                 360                 365
Thr Leu Thr Arg Trp Lys Ser His Leu Gln Asn Tyr Thr Val Asn Ala
            370                 375                 380
Thr Lys Leu Thr Val Asn Leu Thr Asn Asp Arg Tyr Leu Ala Thr Leu
385                 390                 395                 400
Thr Val Arg Asn Leu Val Gly Lys Ser Asp Ala Ala Val Leu Thr Ile
            405                 410                 415
Pro Ala Cys Asp Phe Gln Ala Thr His Pro Val Met Asp Leu Lys Ala
            420                 425                 430
Phe Pro Lys Asp Asn Met Leu Trp Val Glu Trp Thr Thr Pro Arg Glu
            435                 440                 445
Ser Val Lys Lys Tyr Ile Leu Glu Trp Cys Val Leu Ser Asp Lys Ala
            450                 455                 460
Pro Cys Ile Thr Asp Trp Gln Gln Glu Asp Gly Thr Val His Arg Thr
465                 470                 475                 480
Tyr Leu Arg Gly Asn Leu Ala Glu Ser Lys Cys Tyr Leu Ile Thr Val
            485                 490                 495
Thr Pro Val Tyr Ala Asp Gly Pro Gly Ser Pro Glu Ser Ile Lys Ala
            500                 505                 510
```

-continued

```
Tyr Leu Lys Gln Ala Pro Pro Ser Lys Gly Pro Thr Val Arg Thr Lys
            515                 520                 525
Lys Val Gly Lys Asn Glu Ala Val Leu Glu Trp Asp Gln Leu Pro Val
        530                 535                 540
Asp Val Gln Asn Gly Phe Ile Arg Asn Tyr Thr Ile Phe Tyr Arg Thr
545                 550                 555                 560
Ile Ile Gly Asn Glu Thr Ala Val Asn Val Asp Ser Ser His Thr Glu
                565                 570                 575
Tyr Thr Leu Ser Ser Leu Thr Ser Asp Thr Leu Tyr Met Val Arg Met
            580                 585                 590
Ala Ala Tyr Thr Asp Glu Gly Gly Lys Asp Gly Pro Glu Phe Thr Phe
        595                 600                 605
Thr Thr Pro Lys Phe Ala Gln Gly Glu Ile Glu Ser Gly Ala Ser Thr
        610                 615                 620
Lys Gly Pro Ser Val Phe Pro Leu Ala Pro Ser Ser Lys Ser Thr Ser
625                 630                 635                 640
Gly Gly Thr Ala Ala Leu Gly Cys Leu Val Lys Asp Tyr Phe Pro Glu
                645                 650                 655
Pro Val Thr Val Ser Trp Asn Ser Gly Ala Leu Thr Ser Gly Val His
            660                 665                 670
Thr Phe Pro Ala Val Leu Gln Ser Ser Gly Leu Tyr Ser Leu Ser Ser
        675                 680                 685
Val Val Thr Val Pro Ser Ser Ser Leu Gly Thr Gln Thr Tyr Ile Cys
        690                 695                 700
Asn Val Asn His Lys Pro Ser Asn Thr Lys Val Asp Lys Lys Val Glu
705                 710                 715                 720
Pro Lys Ser Cys Asp Lys Thr His Thr Cys Pro Pro Cys Pro Ala Pro
                725                 730                 735
Glu Leu Leu Gly Gly Pro Ser Val Phe Leu Phe Pro Pro Lys Pro Lys
            740                 745                 750
Asp Thr Leu Met Ile Ser Arg Thr Pro Glu Val Thr Cys Val Val Val
        755                 760                 765
Asp Val Ser His Glu Asp Pro Glu Val Lys Phe Asn Trp Tyr Val Asp
        770                 775                 780
Gly Val Glu Val His Asn Ala Lys Thr Lys Pro Arg Glu Glu Gln Tyr
785                 790                 795                 800
Asn Ser Thr Tyr Arg Val Val Ser Val Leu Thr Val Leu His Gln Asp
                805                 810                 815
Trp Leu Asn Gly Lys Glu Tyr Lys Cys Lys Val Ser Asn Lys Ala Leu
            820                 825                 830
Pro Ala Pro Ile Glu Lys Thr Ile Ser Lys Ala Lys Gly Gln Pro Arg
        835                 840                 845
Glu Pro Gln Val Tyr Thr Leu Pro Pro Ser Arg Asp Glu Leu Thr Lys
        850                 855                 860
Asn Gln Val Ser Leu Thr Cys Leu Val Lys Gly Phe Tyr Pro Ser Asp
865                 870                 875                 880
Ile Ala Val Glu Trp Glu Ser Asn Gly Gln Pro Glu Asn Asn Tyr Lys
                885                 890                 895
Thr Thr Pro Pro Val Leu Asp Ser Asp Gly Ser Phe Phe Leu Tyr Ser
            900                 905                 910
Lys Leu Thr Val Asp Lys Ser Arg Trp Gln Gln Gly Asn Val Phe Ser
        915                 920                 925
```

```
Cys Ser Val Met His Glu Ala Leu His Asn His Tyr Thr Gln Lys Ser
        930                 935                 940
Leu Ser Leu Ser Pro Gly Lys
945                 950

<210> SEQ ID NO 10
<211> LENGTH: 332
<212> TYPE: PRT
<213> ORGANISM: Homo sapiens

<400> SEQUENCE: 10

Met Val Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Gly
            325                 330

<210> SEQ ID NO 11
```

```
<211> LENGTH: 120
<212> TYPE: PRT
<213> ORGANISM: Homo sapiens

<400> SEQUENCE: 11

Ser Gly Gly Gln Gly Thr Leu Val Thr Val Ser Ser Ala Ser Thr Lys
1               5                   10                  15

Gly Pro Ser Val Phe Pro Leu Ala Pro Ser Ser Lys Ser Thr Ser Gly
            20                  25                  30

Gly Thr Ala Ala Leu Gly Cys Leu Val Lys Asp Tyr Phe Pro Glu Pro
        35                  40                  45

Val Thr Val Ser Trp Asn Ser Gly Ala Leu Thr Ser Gly Val His Thr
    50                  55                  60

Phe Pro Ala Val Leu Gln Ser Ser Gly Leu Tyr Ser Leu Ser Ser Val
65                  70                  75                  80

Val Thr Val Pro Ser Ser Leu Gly Thr Gln Thr Tyr Ile Cys Asn
    85                  90                  95

Val Asn His Lys Pro Ser Asn Thr Lys Val Asp Lys Lys Val Glu Pro
            100                 105                 110

Lys Ser Cys Asp Lys Thr His Thr
        115                 120

<210> SEQ ID NO 12
<211> LENGTH: 329
<212> TYPE: PRT
<213> ORGANISM: Homo sapiens

<400> SEQUENCE: 12

Ser Gly Ala Ser Thr Lys Gly Pro Ser Val Phe Pro Leu Ala Pro Cys
1               5                   10                  15

Ser Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Leu Gly Thr
65                  70                  75                  80

Lys Thr Tyr Thr Cys Asn Val Asp His Lys Pro Ser Asn Thr Lys Val
            85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
            165                 170                 175

Gln Phe Asn Ser Thr Tyr Arg Val Val Ser Val Leu Thr Val Leu His
        180                 185                 190

Gln Asp Trp Leu Asn Gly Lys Glu Tyr Lys Cys Lys Val Ser Asn Lys
    195                 200                 205

Gly Leu Pro Ser Ser Ile Glu Lys Thr Ile Ser Lys Ala Lys Gly Gln
210                 215                 220
```

```
Pro Arg Glu Pro Gln Val Tyr Thr Leu Pro Pro Ser Gln Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Arg Leu Thr Val Asp Lys Ser Arg Trp Gln Glu Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325

<210> SEQ ID NO 13
<211> LENGTH: 108
<212> TYPE: PRT
<213> ORGANISM: Homo sapiens

<400> SEQUENCE: 13

Ser Gly Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 14
<211> LENGTH: 106
<212> TYPE: PRT
<213> ORGANISM: Homo sapiens

<400> SEQUENCE: 14

Ser Gly Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 15
<211> LENGTH: 360
<212> TYPE: PRT
<213> ORGANISM: Homo sapiens

<400> SEQUENCE: 15

```
Met Val Ala Val Gly Cys Ala Leu Leu Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ala Gly
        355                 360
```

<210> SEQ ID NO 16
<211> LENGTH: 315
<212> TYPE: PRT
<213> ORGANISM: Homo sapiens

<400> SEQUENCE: 16

```
Met Val Ala Val Gly Cys Ala Leu Leu Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Thr Gly
305                 310                 315
```

<210> SEQ ID NO 17
<211> LENGTH: 2085
<212> TYPE: DNA
<213> ORGANISM: Homo sapiens
<220> FEATURE:
<221> NAME/KEY: CDS
<222> LOCATION: (1)...(2082)

<400> SEQUENCE: 17 atg gtg aag cca tca tta cca ttc aca tcc ctc tta ttc ctg cag ctg    48

```
        Met Val Lys Pro Ser Leu Pro Phe Thr Ser Leu Leu Phe Leu Gln Leu
        1               5                   10                  15 ccc ctg ctg gga gtg ggg ctg aac acg aca att ctg acg ccc aat ggg        96
Pro Leu Leu Gly Val Gly Leu Asn Thr Thr Ile Leu Thr Pro Asn Gly
                20                  25                  30 aat gaa gac acc aca gct gat ttc ttc ctg acc act atg ccc act gac       144
Asn Glu Asp Thr Thr Ala Asp Phe Phe Leu Thr Thr Met Pro Thr Asp
            35                  40                  45 tcc ctc agt gtt tcc act ctg ccc ctc cca gag gtt cag tgt ttt gtg       192
Ser Leu Ser Val Ser Thr Leu Pro Leu Pro Glu Val Gln Cys Phe Val
        50                  55                  60 ttc aat gtc gag tac atg aat tgc act tgg aac agc agc tct gag ccc       240
Phe Asn Val Glu Tyr Met Asn Cys Thr Trp Asn Ser Ser Ser Glu Pro
65                  70                  75                  80 cag cct acc aac ctc act ctg cat tat tgg tac aag aac tcg gat aat       288
Gln Pro Thr Asn Leu Thr Leu His Tyr Trp Tyr Lys Asn Ser Asp Asn
                85                  90                  95 gat aaa gtc cag aag tgc agc cac tat cta ttc tct gaa gaa atc act       336
Asp Lys Val Gln Lys Cys Ser His Tyr Leu Phe Ser Glu Glu Ile Thr
            100                 105                 110 tct ggc tgt cag ttg caa aaa aag gag atc cac ctc tac caa aca ttt       384
Ser Gly Cys Gln Leu Gln Lys Lys Glu Ile His Leu Tyr Gln Thr Phe
        115                 120                 125 gtt gtt cag ctc cag gac cca cgg gaa ccc agg aga cag gcc aca cag       432
Val Val Gln Leu Gln Asp Pro Arg Glu Pro Arg Arg Gln Ala Thr Gln
130                 135                 140 atg cta aaa ctg cag aat ctg gtg atc ccc tgg gct cca gag aac cta       480
Met Leu Lys Leu Gln Asn Leu Val Ile Pro Trp Ala Pro Glu Asn Leu
145                 150                 155                 160 aca ctt cac aaa ctg agt gaa tcc cag cta gaa ctg aac tgg aac aac       528
Thr Leu His Lys Leu Ser Glu Ser Gln Leu Glu Leu Asn Trp Asn Asn
                165                 170                 175 aga ttc ttg aac cac tgt ttg gag cac ttg gtg cag tac cgg act gac       576
Arg Phe Leu Asn His Cys Leu Glu His Leu Val Gln Tyr Arg Thr Asp
            180                 185                 190 tgg gac cac agc tgg act gaa caa tca gtg gat tat aga cat aag ttc       624
Trp Asp His Ser Trp Thr Glu Gln Ser Val Asp Tyr Arg His Lys Phe
        195                 200                 205 tcc ttg cct agt gtg gat ggg cag aaa cgc tac acg ttt cgt gtt cgg       672
Ser Leu Pro Ser Val Asp Gly Gln Lys Arg Tyr Thr Phe Arg Val Arg
    210                 215                 220 agc cgc ttt aac cca ctc tgt gga agt gct cag cat tgg agt gaa tgg       720
Ser Arg Phe Asn Pro Leu Cys Gly Ser Ala Gln His Trp Ser Glu Trp
225                 230                 235                 240 agc cac cca atc cac tgg ggg agc aat act tca aaa gag aac gcg tcg       768
Ser His Pro Ile His Trp Gly Ser Asn Thr Ser Lys Glu Asn Ala Ser
                245                 250                 255 tct ggg aac atg aag gtc ctg cag gag ccc acc tgc gtc tcc gac tac       816
Ser Gly Asn Met Lys Val Leu Gln Glu Pro Thr Cys Val Ser Asp Tyr
            260                 265                 270 atg agc atc tct act tgc gag tgg aag atg aat ggt ccc acc aat tgc       864
Met Ser Ile Ser Thr Cys Glu Trp Lys Met Asn Gly Pro Thr Asn Cys
        275                 280                 285 agc acc gag ctc cgc ctg ttg tac cag ctg gtt ttt ctg ctc tcc gaa       912
Ser Thr Glu Leu Arg Leu Leu Tyr Gln Leu Val Phe Leu Leu Ser Glu
290                 295                 300 gcc cac acg tgt atc cct gag aac aac gga ggc gcg ggg tgc gtg tgc       960
Ala His Thr Cys Ile Pro Glu Asn Asn Gly Gly Ala Gly Cys Val Cys
305                 310                 315                 320
```

```
cac ctg ctc atg gat gac gtg gtc agt gcg gat aac tat aca ctg gac    1008
His Leu Leu Met Asp Asp Val Val Ser Ala Asp Asn Tyr Thr Leu Asp
            325                 330                 335 ctg tgg gct ggg cag cag ctg ctg tgg aag ggc tcc ttc aag ccc agc    1056
Leu Trp Ala Gly Gln Gln Leu Leu Trp Lys Gly Ser Phe Lys Pro Ser
        340                 345                 350 gag cat gtg aaa ccc agg gcc cca gga aac ctg aca gtt cac acc aat    1104
Glu His Val Lys Pro Arg Ala Pro Gly Asn Leu Thr Val His Thr Asn
    355                 360                 365 gtc tcc gac act ctg ctg acc tgg agc aac ccg tat ccc cct gac        1152
Val Ser Asp Thr Leu Leu Thr Trp Ser Asn Pro Tyr Pro Pro Asp
370                 375                 380 aat tac ctg tat aat cat ctc acc tat gca gtc aac att tgg agt gaa    1200
Asn Tyr Leu Tyr Asn His Leu Thr Tyr Ala Val Asn Ile Trp Ser Glu
385                 390                 395                 400 aac gac ccg gca gat ttc aga atc tat aac gtg acc tac cta gaa ccc    1248
Asn Asp Pro Ala Asp Phe Arg Ile Tyr Asn Val Thr Tyr Leu Glu Pro
                405                 410                 415 tcc ctc cgc atc gca gcc agc acc ctg aag tct ggg att tcc tac agg    1296
Ser Leu Arg Ile Ala Ala Ser Thr Leu Lys Ser Gly Ile Ser Tyr Arg
            420                 425                 430 gca cgg gtg agg gcc tgg gct cag tgc tat aac acc acc tgg agt gag    1344
Ala Arg Val Arg Ala Trp Ala Gln Cys Tyr Asn Thr Thr Trp Ser Glu
        435                 440                 445 tgg agc ccc agc acc aag tgg cac aac tcc tac agg gag ccc ttc gag    1392
Trp Ser Pro Ser Thr Lys Trp His Asn Ser Tyr Arg Glu Pro Phe Glu
    450                 455                 460 cag tcc gga gac aaa act cac aca tgc cca ccg tgc cca gca cct gaa    1440
Gln Ser Gly Asp Lys Thr His Thr Cys Pro Pro Cys Pro Ala Pro Glu
465                 470                 475                 480 ctc ctg ggg gga ccg tca gtc ttc ctc ttc ccc cca aaa ccc aag gac    1488
Leu Leu Gly Gly Pro Ser Val Phe Leu Phe Pro Pro Lys Pro Lys Asp
                485                 490                 495 acc ctc atg atc tcc cgg acc cct gag gtc aca tgc gtg gtg gtg gac    1536
Thr Leu Met Ile Ser Arg Thr Pro Glu Val Thr Cys Val Val Val Asp
            500                 505                 510 gtg agc cac gaa gac cct gag gtc aag ttc aac tgg tac gtg gac ggc    1584
Val Ser His Glu Asp Pro Glu Val Lys Phe Asn Trp Tyr Val Asp Gly
        515                 520                 525 gtg gag gtg cat aat gcc aag aca aag ccg cgg gag gag cag tac aac    1632
Val Glu Val His Asn Ala Lys Thr Lys Pro Arg Glu Glu Gln Tyr Asn
    530                 535                 540 agc acg tac cgt gtg gtc agc gtc ctc acc gtc ctg cac cag gac tgg    1680
Ser Thr Tyr Arg Val Val Ser Val Leu Thr Val Leu His Gln Asp Trp
545                 550                 555                 560 ctg aat ggc aag gag tac aag tgc aag gtc tcc aac aaa gcc ctc cca    1728
Leu Asn Gly Lys Glu Tyr Lys Cys Lys Val Ser Asn Lys Ala Leu Pro
                565                 570                 575 gcc ccc atc gag aaa acc atc tcc aaa gcc aaa ggg cag ccc cga gaa    1776
Ala Pro Ile Glu Lys Thr Ile Ser Lys Ala Lys Gly Gln Pro Arg Glu
            580                 585                 590 cca cag gtg tac acc ctg ccc cca tcc cgg gag gag atg acc aag aac    1824
Pro Gln Val Tyr Thr Leu Pro Pro Ser Arg Glu Glu Met Thr Lys Asn
        595                 600                 605 cag gtc agc ctg acc tgc ctg gtc aaa ggc ttc tat ccc agc gac atc    1872
Gln Val Ser Leu Thr Cys Leu Val Lys Gly Phe Tyr Pro Ser Asp Ile
    610                 615                 620 gcc gtg gag tgg gag agc aat ggg cag ccg gag aac aac tac aag acc    1920
Ala Val Glu Trp Glu Ser Asn Gly Gln Pro Glu Asn Asn Tyr Lys Thr
625                 630                 635                 640
```

```
acg cct ccc gtg ctg gac tcc gac ggc tcc ttc ttc ctc tat agc aag      1968
Thr Pro Pro Val Leu Asp Ser Asp Gly Ser Phe Phe Leu Tyr Ser Lys
            645                 650                 655 ctc acc gtg gac aag agc agg tgg cag cag ggg aac gtc ttc tca tgc      2016
Leu Thr Val Asp Lys Ser Arg Trp Gln Gln Gly Asn Val Phe Ser Cys
            660                 665                 670 tcc gtg atg cat gag gct ctg cac aac cac tac acg cag aag agc ctc      2064
Ser Val Met His Glu Ala Leu His Asn His Tyr Thr Gln Lys Ser Leu
            675                 680                 685 tcc ctg tct ccg ggt aaa tga                                          2085
Ser Leu Ser Pro Gly Lys
        690

<210> SEQ ID NO 18
<211> LENGTH: 694
<212> TYPE: PRT
<213> ORGANISM: Homo sapiens

<400> SEQUENCE: 18

Met Val Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Ala Ser
                245                 250                 255

Ser Gly Asn Met Lys Val Leu Gln Glu Pro Thr Cys Val Ser Asp Tyr
            260                 265                 270

Met Ser Ile Ser Thr Cys Glu Trp Lys Met Asn Gly Pro Thr Asn Cys
        275                 280                 285
```

```
Ser Thr Glu Leu Arg Leu Leu Tyr Gln Leu Val Phe Leu Leu Ser Glu
    290                 295                 300
Ala His Thr Cys Ile Pro Glu Asn Asn Gly Gly Ala Gly Cys Val Cys
305                 310                 315                 320
His Leu Leu Met Asp Asp Val Val Ser Ala Asp Asn Tyr Thr Leu Asp
                325                 330                 335
Leu Trp Ala Gly Gln Gln Leu Leu Trp Lys Gly Ser Phe Lys Pro Ser
                340                 345                 350
Glu His Val Lys Pro Arg Ala Pro Gly Asn Leu Thr Val His Thr Asn
                355                 360                 365
Val Ser Asp Thr Leu Leu Thr Trp Ser Asn Pro Tyr Pro Pro Asp
    370                 375                 380
Asn Tyr Leu Tyr Asn His Leu Thr Tyr Ala Val Asn Ile Trp Ser Glu
385                 390                 395                 400
Asn Asp Pro Ala Asp Phe Arg Ile Tyr Asn Val Thr Tyr Leu Glu Pro
                405                 410                 415
Ser Leu Arg Ile Ala Ala Ser Thr Leu Lys Ser Gly Ile Ser Tyr Arg
                420                 425                 430
Ala Arg Val Arg Ala Trp Ala Gln Cys Tyr Asn Thr Thr Trp Ser Glu
                435                 440                 445
Trp Ser Pro Ser Thr Lys Trp His Asn Ser Tyr Arg Glu Pro Phe Glu
    450                 455                 460
Gln Ser Gly Asp Lys Thr His Thr Cys Pro Pro Cys Pro Ala Pro Glu
465                 470                 475                 480
Leu Leu Gly Gly Pro Ser Val Phe Leu Phe Pro Pro Lys Pro Lys Asp
                485                 490                 495
Thr Leu Met Ile Ser Arg Thr Pro Glu Val Thr Cys Val Val Val Asp
                500                 505                 510
Val Ser His Glu Asp Pro Glu Val Lys Phe Asn Trp Tyr Val Asp Gly
    515                 520                 525
Val Glu Val His Asn Ala Lys Thr Lys Pro Arg Glu Glu Gln Tyr Asn
    530                 535                 540
Ser Thr Tyr Arg Val Val Ser Val Leu Thr Val Leu His Gln Asp Trp
545                 550                 555                 560
Leu Asn Gly Lys Glu Tyr Lys Cys Lys Val Ser Asn Lys Ala Leu Pro
                565                 570                 575
Ala Pro Ile Glu Lys Thr Ile Ser Lys Ala Lys Gly Gln Pro Arg Glu
                580                 585                 590
Pro Gln Val Tyr Thr Leu Pro Pro Ser Arg Glu Glu Met Thr Lys Asn
    595                 600                 605
Gln Val Ser Leu Thr Cys Leu Val Lys Gly Phe Tyr Pro Ser Asp Ile
    610                 615                 620
Ala Val Glu Trp Glu Ser Asn Gly Gln Pro Glu Asn Asn Tyr Lys Thr
625                 630                 635                 640
Thr Pro Pro Val Leu Asp Ser Asp Gly Ser Phe Phe Leu Tyr Ser Lys
                645                 650                 655
Leu Thr Val Asp Lys Ser Arg Trp Gln Gln Gly Asn Val Phe Ser Cys
                660                 665                 670
Ser Val Met His Glu Ala Leu His Asn His Tyr Thr Gln Lys Ser Leu
                675                 680                 685
Ser Leu Ser Pro Gly Lys
    690
```

<210> SEQ ID NO 19
<211> LENGTH: 2076
<212> TYPE: DNA
<213> ORGANISM: Homo sapiens
<220> FEATURE:
<221> NAME/KEY: CDS
<222> LOCATION: (1)...(2073)

<400> SEQUENCE: 19

| | | | | | | | | | | | | | | | | |
|---|---|---|---|---|---|---|---|---|---|---|---|---|---|---|---|---|
| atg | gtg | aag | cca | tca | tta | cca | ttc | aca | tcc | ctc | tta | ttc | ctg | cag | ctg | 48 |
| Met | Val | Lys | Pro | Ser | Leu | Pro | Phe | Thr | Ser | Leu | Leu | Phe | Leu | Gln | Leu | |
| 1 | | | | 5 | | | | | 10 | | | | | 15 | | |
| ccc | ctg | ctg | gga | gtg | ggg | ctg | aac | acg | aca | att | ctg | acg | ccc | aat | ggg | 96 |
| Pro | Leu | Leu | Gly | Val | Gly | Leu | Asn | Thr | Thr | Ile | Leu | Thr | Pro | Asn | Gly | |
| | | | 20 | | | | | 25 | | | | | 30 | | | |
| aat | gaa | gac | acc | aca | gct | gat | ttc | ttc | ctg | acc | act | atg | ccc | act | gac | 144 |
| Asn | Glu | Asp | Thr | Thr | Ala | Asp | Phe | Phe | Leu | Thr | Thr | Met | Pro | Thr | Asp | |
| | | 35 | | | | | 40 | | | | | 45 | | | | |
| tcc | ctc | agt | gtt | tcc | act | ctg | ccc | ctc | cca | gag | gtt | cag | tgt | ttt | gtg | 192 |
| Ser | Leu | Ser | Val | Ser | Thr | Leu | Pro | Leu | Pro | Glu | Val | Gln | Cys | Phe | Val | |
| | 50 | | | | | 55 | | | | | 60 | | | | | |
| ttc | aat | gtc | gag | tac | atg | aat | tgc | act | tgg | aac | agc | agc | tct | gag | ccc | 240 |
| Phe | Asn | Val | Glu | Tyr | Met | Asn | Cys | Thr | Trp | Asn | Ser | Ser | Ser | Glu | Pro | |
| 65 | | | | 70 | | | | | 75 | | | | | 80 | | |
| cag | cct | acc | aac | ctc | act | ctg | cat | tat | tgg | tac | aag | aac | tcg | gat | aat | 288 |
| Gln | Pro | Thr | Asn | Leu | Thr | Leu | His | Tyr | Trp | Tyr | Lys | Asn | Ser | Asp | Asn | |
| | | | 85 | | | | | 90 | | | | | 95 | | | |
| gat | aaa | gtc | cag | aag | tgc | agc | cac | tat | cta | ttc | tct | gaa | gaa | atc | act | 336 |
| Asp | Lys | Val | Gln | Lys | Cys | Ser | His | Tyr | Leu | Phe | Ser | Glu | Glu | Ile | Thr | |
| | | 100 | | | | | 105 | | | | | 110 | | | | |
| tct | ggc | tgt | cag | ttg | caa | aaa | aag | gag | atc | cac | ctc | tac | caa | aca | ttt | 384 |
| Ser | Gly | Cys | Gln | Leu | Gln | Lys | Lys | Glu | Ile | His | Leu | Tyr | Gln | Thr | Phe | |
| | 115 | | | | | 120 | | | | | 125 | | | | | |
| gtt | gtt | cag | ctc | cag | gac | cca | cgg | gaa | ccc | agg | aga | cag | gcc | aca | cag | 432 |
| Val | Val | Gln | Leu | Gln | Asp | Pro | Arg | Glu | Pro | Arg | Arg | Gln | Ala | Thr | Gln | |
| 130 | | | | | 135 | | | | | 140 | | | | | | |
| atg | cta | aaa | ctg | cag | aat | ctg | gtg | atc | ccc | tgg | gct | cca | gag | aac | cta | 480 |
| Met | Leu | Lys | Leu | Gln | Asn | Leu | Val | Ile | Pro | Trp | Ala | Pro | Glu | Asn | Leu | |
| 145 | | | | | 150 | | | | | 155 | | | | | 160 | |
| aca | ctt | cac | aaa | ctg | agt | gaa | tcc | cag | cta | gaa | ctg | aac | tgg | aac | aac | 528 |
| Thr | Leu | His | Lys | Leu | Ser | Glu | Ser | Gln | Leu | Glu | Leu | Asn | Trp | Asn | Asn | |
| | | | 165 | | | | | 170 | | | | | 175 | | | |
| aga | ttc | ttg | aac | cac | tgt | ttg | gag | cac | ttg | gtg | cag | tac | cgg | act | gac | 576 |
| Arg | Phe | Leu | Asn | His | Cys | Leu | Glu | His | Leu | Val | Gln | Tyr | Arg | Thr | Asp | |
| | | 180 | | | | | 185 | | | | | 190 | | | | |
| tgg | gac | cac | agc | tgg | act | gaa | caa | tca | gtg | gat | tat | aga | cat | aag | ttc | 624 |
| Trp | Asp | His | Ser | Trp | Thr | Glu | Gln | Ser | Val | Asp | Tyr | Arg | His | Lys | Phe | |
| | 195 | | | | | 200 | | | | | 205 | | | | | |
| tcc | ttg | cct | agt | gtg | gat | ggg | cag | aaa | cgc | tac | acg | ttt | cgt | gtt | cgg | 672 |
| Ser | Leu | Pro | Ser | Val | Asp | Gly | Gln | Lys | Arg | Tyr | Thr | Phe | Arg | Val | Arg | |
| 210 | | | | | 215 | | | | | 220 | | | | | | |
| agc | cgc | ttt | aac | cca | ctc | tgt | gga | agt | gct | cag | cat | tgg | agt | gaa | tgg | 720 |
| Ser | Arg | Phe | Asn | Pro | Leu | Cys | Gly | Ser | Ala | Gln | His | Trp | Ser | Glu | Trp | |
| 225 | | | | | 230 | | | | | 235 | | | | | 240 | |
| agc | cac | cca | atc | cac | tgg | ggg | agc | aat | act | tca | aaa | gag | aac | ggg | aac | 768 |
| Ser | His | Pro | Ile | His | Trp | Gly | Ser | Asn | Thr | Ser | Lys | Glu | Asn | Gly | Asn | |
| | | | 245 | | | | | 250 | | | | | 255 | | | |
| atg | aag | gtc | ctg | cag | gag | ccc | acc | tgc | gtc | tcc | gac | tac | atg | agc | atc | 816 |
| Met | Lys | Val | Leu | Gln | Glu | Pro | Thr | Cys | Val | Ser | Asp | Tyr | Met | Ser | Ile | |
| | | 260 | | | | | 265 | | | | | 270 | | | | |
| tct | act | tgc | gag | tgg | aag | atg | aat | ggt | ccc | acc | aat | tgc | agc | acc | gag | 864 |

```
Ser Thr Cys Glu Trp Lys Met Asn Gly Pro Thr Asn Cys Ser Thr Glu
        275                 280                 285 ctc cgc ctg ttg tac cag ctg gtt ttt ctg ctc tcc gaa gcc cac acg      912
Leu Arg Leu Leu Tyr Gln Leu Val Phe Leu Leu Ser Glu Ala His Thr
    290                 295                 300 tgt atc cct gag aac aac gga ggc gcg ggg tgc gtg tgc cac ctg ctc      960
Cys Ile Pro Glu Asn Asn Gly Gly Ala Gly Cys Val Cys His Leu Leu
305                 310                 315                 320 atg gat gac gtg gtc agt gcg gat aac tat aca ctg gac ctg tgg gct     1008
Met Asp Asp Val Val Ser Ala Asp Asn Tyr Thr Leu Asp Leu Trp Ala
                325                 330                 335 ggg cag cag ctg ctg tgg aag ggc tcc ttc aag ccc agc gag cat gtg     1056
Gly Gln Gln Leu Leu Trp Lys Gly Ser Phe Lys Pro Ser Glu His Val
                340                 345                 350 aaa ccc agg gcc cca gga aac ctg aca gtt cac acc aat gtc tcc gac     1104
Lys Pro Arg Ala Pro Gly Asn Leu Thr Val His Thr Asn Val Ser Asp
            355                 360                 365 act ctg ctg ctg acc tgg agc aac ccg tat ccc cct gac aat tac ctg     1152
Thr Leu Leu Leu Thr Trp Ser Asn Pro Tyr Pro Pro Asp Asn Tyr Leu
    370                 375                 380 tat aat cat ctc acc tat gca gtc aac att tgg agt gaa aac gac ccg     1200
Tyr Asn His Leu Thr Tyr Ala Val Asn Ile Trp Ser Glu Asn Asp Pro
385                 390                 395                 400 gca gat ttc aga atc tat aac gtg acc tac cta gaa ccc tcc ctc cgc     1248
Ala Asp Phe Arg Ile Tyr Asn Val Thr Tyr Leu Glu Pro Ser Leu Arg
                405                 410                 415 atc gca gcc agc acc ctg aag tct ggg att tcc tac agg gca cgg gtg     1296
Ile Ala Ala Ser Thr Leu Lys Ser Gly Ile Ser Tyr Arg Ala Arg Val
                420                 425                 430 agg gcc tgg gct cag agc tat aac acc acc tgg agt gag tgg agc ccc     1344
Arg Ala Trp Ala Gln Ser Tyr Asn Thr Thr Trp Ser Glu Trp Ser Pro
            435                 440                 445 agc acc aag tgg cac aac tcc tac agg gag ccc ttc gag cag tcc gga     1392
Ser Thr Lys Trp His Asn Ser Tyr Arg Glu Pro Phe Glu Gln Ser Gly
    450                 455                 460 gac aaa act cac aca tgc cca ccg tgc cca gca cct gaa ctc ctg ggg     1440
Asp Lys Thr His Thr Cys Pro Pro Cys Pro Ala Pro Glu Leu Leu Gly
465                 470                 475                 480 gga ccg tca gtc ttc ctc ttc ccc cca aaa ccc aag gac acc ctc atg     1488
Gly Pro Ser Val Phe Leu Phe Pro Pro Lys Pro Lys Asp Thr Leu Met
                485                 490                 495 atc tcc cgg acc cct gag gtc aca tgc gtg gtg gtg gac gtg agc cac     1536
Ile Ser Arg Thr Pro Glu Val Thr Cys Val Val Val Asp Val Ser His
                500                 505                 510 gaa gac cct gag gtc aag ttc aac tgg tac gtg gac ggc gtg gag gtg     1584
Glu Asp Pro Glu Val Lys Phe Asn Trp Tyr Val Asp Gly Val Glu Val
            515                 520                 525 cat aat gcc aag aca aag ccg cgg gag gag cag tac aac agc acg tac     1632
His Asn Ala Lys Thr Lys Pro Arg Glu Glu Gln Tyr Asn Ser Thr Tyr
    530                 535                 540 cgt gtg gtc agc gtc ctc acc gtc ctg cac cag gac tgg ctg aat ggc     1680
Arg Val Val Ser Val Leu Thr Val Leu His Gln Asp Trp Leu Asn Gly
545                 550                 555                 560 aag gag tac aag tgc aag gtc tcc aac aaa gcc ctc cca gcc ccc atc     1728
Lys Glu Tyr Lys Cys Lys Val Ser Asn Lys Ala Leu Pro Ala Pro Ile
                565                 570                 575 gag aaa acc atc tcc aaa gcc aaa ggg cag ccc cga gaa cca cag gtg     1776
Glu Lys Thr Ile Ser Lys Ala Lys Gly Gln Pro Arg Glu Pro Gln Val
                580                 585                 590
```

| | | | | | | | | | | | | | | | |
|---|---|---|---|---|---|---|---|---|---|---|---|---|---|---|---|
| tac | acc | ctg | ccc | cca | tcc | cgg | gat | gag | ctg | acc | aag | aac | cag | gtc | agc | 1824 |
| Tyr | Thr | Leu | Pro | Pro | Ser | Arg | Asp | Glu | Leu | Thr | Lys | Asn | Gln | Val | Ser |
| | | 595 | | | | 600 | | | | 605 | | | | | |
| ctg | acc | tgc | ctg | gtc | aaa | ggc | ttc | tat | ccc | agc | gac | atc | gcc | gtg | gag | 1872 |
| Leu | Thr | Cys | Leu | Val | Lys | Gly | Phe | Tyr | Pro | Ser | Asp | Ile | Ala | Val | Glu |
| 610 | | | | | 615 | | | | | 620 | | | | | |
| tgg | gag | agc | aat | ggg | cag | ccg | gag | aac | aac | tac | aag | acc | acg | cct | ccc | 1920 |
| Trp | Glu | Ser | Asn | Gly | Gln | Pro | Glu | Asn | Asn | Tyr | Lys | Thr | Thr | Pro | Pro |
| 625 | | | | | 630 | | | | | 635 | | | | | 640 |
| gtg | ctg | gac | tcc | gac | ggc | tcc | ttc | ttc | ctc | tat | agc | aag | ctc | acc | gtg | 1968 |
| Val | Leu | Asp | Ser | Asp | Gly | Ser | Phe | Phe | Leu | Tyr | Ser | Lys | Leu | Thr | Val |
| | | | | 645 | | | | | 650 | | | | | 655 | |
| gac | aag | agc | agg | tgg | cag | cag | ggg | aac | gtc | ttc | tca | tgc | tcc | gtg | atg | 2016 |
| Asp | Lys | Ser | Arg | Trp | Gln | Gln | Gly | Asn | Val | Phe | Ser | Cys | Ser | Val | Met |
| | | | 660 | | | | | 665 | | | | | 670 | | |
| cat | gag | gct | ctg | cac | aac | cac | tac | acg | cag | aag | agc | ctc | tcc | ctg | tct | 2064 |
| His | Glu | Ala | Leu | His | Asn | His | Tyr | Thr | Gln | Lys | Ser | Leu | Ser | Leu | Ser |
| | | | 675 | | | | | 680 | | | | | 685 | | |
| ccg | ggt | aaa | tga | | | | | | | | | | | | | 2076 |
| Pro | Gly | Lys |
| | 690 | | |

<210> SEQ ID NO 20
<211> LENGTH: 691
<212> TYPE: PRT
<213> ORGANISM: Homo sapiens

<400> SEQUENCE: 20

```
Met Val Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
```

-continued

```
            225                 230                 235                 240
        Ser His Pro Ile His Trp Gly Ser Asn Thr Ser Lys Glu Asn Gly Asn
                        245                 250                 255

Met Lys Val Leu Gln Glu Pro Thr Cys Val Ser Asp Tyr Met Ser Ile
                        260                 265                 270

Ser Thr Cys Glu Trp Lys Met Asn Gly Pro Thr Asn Cys Ser Thr Glu
                        275                 280                 285

Leu Arg Leu Leu Tyr Gln Leu Val Phe Leu Leu Ser Glu Ala His Thr
                        290                 295                 300

Cys Ile Pro Glu Asn Asn Gly Ala Gly Cys Val Cys His Leu Leu
        305                 310                 315                 320

Met Asp Asp Val Val Ser Ala Asp Asn Tyr Thr Leu Asp Leu Trp Ala
                        325                 330                 335

Gly Gln Gln Leu Leu Trp Lys Gly Ser Phe Lys Pro Ser Glu His Val
                        340                 345                 350

Lys Pro Arg Ala Pro Gly Asn Leu Thr Val His Thr Asn Val Ser Asp
                        355                 360                 365

Thr Leu Leu Leu Thr Trp Ser Asn Pro Tyr Pro Pro Asp Asn Tyr Leu
                        370                 375                 380

Tyr Asn His Leu Thr Tyr Ala Val Asn Ile Trp Ser Glu Asn Asp Pro
        385                 390                 395                 400

Ala Asp Phe Arg Ile Tyr Asn Val Thr Tyr Leu Glu Pro Ser Leu Arg
                        405                 410                 415

Ile Ala Ala Ser Thr Leu Lys Ser Gly Ile Ser Tyr Arg Ala Arg Val
                        420                 425                 430

Arg Ala Trp Ala Gln Ser Tyr Asn Thr Thr Trp Ser Glu Trp Ser Pro
                        435                 440                 445

Ser Thr Lys Trp His Asn Ser Tyr Arg Glu Pro Phe Glu Gln Ser Gly
                        450                 455                 460

Asp Lys Thr His Thr Cys Pro Pro Cys Pro Ala Pro Glu Leu Leu Gly
        465                 470                 475                 480

Gly Pro Ser Val Phe Leu Phe Pro Pro Lys Pro Lys Asp Thr Leu Met
                        485                 490                 495

Ile Ser Arg Thr Pro Glu Val Thr Cys Val Val Val Asp Val Ser His
                        500                 505                 510

Glu Asp Pro Glu Val Lys Phe Asn Trp Tyr Val Asp Gly Val Glu Val
                        515                 520                 525

His Asn Ala Lys Thr Lys Pro Arg Glu Glu Gln Tyr Asn Ser Thr Tyr
                        530                 535                 540

Arg Val Val Ser Val Leu Thr Val Leu His Gln Asp Trp Leu Asn Gly
        545                 550                 555                 560

Lys Glu Tyr Lys Cys Lys Val Ser Asn Lys Ala Leu Pro Ala Pro Ile
                        565                 570                 575

Glu Lys Thr Ile Ser Lys Ala Lys Gly Gln Pro Arg Glu Pro Gln Val
                        580                 585                 590

Tyr Thr Leu Pro Pro Ser Arg Asp Glu Leu Thr Lys Asn Gln Val Ser
                        595                 600                 605

Leu Thr Cys Leu Val Lys Gly Phe Tyr Pro Ser Asp Ile Ala Val Glu
                        610                 615                 620

Trp Glu Ser Asn Gly Gln Pro Glu Asn Asn Tyr Lys Thr Thr Pro Pro
        625                 630                 635                 640

Val Leu Asp Ser Asp Gly Ser Phe Phe Leu Tyr Ser Lys Leu Thr Val
                        645                 650                 655
```

```
Asp Lys Ser Arg Trp Gln Gln Gly Asn Val Phe Ser Cys Ser Val Met
        660                 665                 670

His Glu Ala Leu His Asn His Tyr Thr Gln Lys Ser Leu Ser Leu Ser
            675                 680                 685

Pro Gly Lys
        690

<210> SEQ ID NO 21
<211> LENGTH: 2085
<212> TYPE: DNA
<213> ORGANISM: Homo sapiens
<220> FEATURE:
<221> NAME/KEY: CDS
<222> LOCATION: (1)...(2082)

<400> SEQUENCE: 21 atg gtg aag cca tca tta cca ttc aca tcc ctc tta ttc ctg cag ctg      48
Met Val Lys Pro Ser Leu Pro Phe Thr Ser Leu Leu Phe Leu Gln Leu
1               5                  10                  15 ccc ctg ctg gga gtg ggg ctg aac acg aca att ctg acg ccc aat ggg      96
Pro Leu Leu Gly Val Gly Leu Asn Thr Thr Ile Leu Thr Pro Asn Gly
            20                  25                  30 aat gaa gac acc aca gct gat ttc ttc ctg acc act atg ccc act gac     144
Asn Glu Asp Thr Thr Ala Asp Phe Phe Leu Thr Thr Met Pro Thr Asp
        35                  40                  45 tcc ctc agt gtt tcc act ctg ccc ctc cca gag gtt cag tgt ttt gtg     192
Ser Leu Ser Val Ser Thr Leu Pro Leu Pro Glu Val Gln Cys Phe Val
    50                  55                  60 ttc aat gtc gag tac atg aat tgc act tgg aac agc agc tct gag ccc     240
Phe Asn Val Glu Tyr Met Asn Cys Thr Trp Asn Ser Ser Ser Glu Pro
65                  70                  75                  80 cag cct acc aac ctc act ctg cat tat tgg tac aag aac tcg gat aat     288
Gln Pro Thr Asn Leu Thr Leu His Tyr Trp Tyr Lys Asn Ser Asp Asn
                85                  90                  95 gat aaa gtc cag aag tgc agc cac tat cta ttc tct gaa gaa atc act     336
Asp Lys Val Gln Lys Cys Ser His Tyr Leu Phe Ser Glu Glu Ile Thr
            100                 105                 110 tct ggc tgt cag ttg caa aaa aag gag atc cac ctc tac caa aca ttt     384
Ser Gly Cys Gln Leu Gln Lys Lys Glu Ile His Leu Tyr Gln Thr Phe
        115                 120                 125 gtt gtt cag ctc cag gac cca cgg gaa ccc agg aga cag gcc aca cag     432
Val Val Gln Leu Gln Asp Pro Arg Glu Pro Arg Arg Gln Ala Thr Gln
    130                 135                 140 atg cta aaa ctg cag aat ctg gtg atc ccc tgg gct cca gag aac cta     480
Met Leu Lys Leu Gln Asn Leu Val Ile Pro Trp Ala Pro Glu Asn Leu
145                 150                 155                 160 aca ctt cac aaa ctg agt gaa tcc cag cta gaa ctg aac tgg aac aac     528
Thr Leu His Lys Leu Ser Glu Ser Gln Leu Glu Leu Asn Trp Asn Asn
                165                 170                 175 aga ttc ttg aac cac tgt ttg gag cac ttg gtg cag tac cgg act gac     576
Arg Phe Leu Asn His Cys Leu Glu His Leu Val Gln Tyr Arg Thr Asp
            180                 185                 190 tgg gac cac agc tgg act gaa caa tca gtg gat tat aga cat aag ttc     624
Trp Asp His Ser Trp Thr Glu Gln Ser Val Asp Tyr Arg His Lys Phe
        195                 200                 205 tcc ttg cct agt gtg gat ggg cag aaa cgc tac acg ttt cgt gtt cgg     672
Ser Leu Pro Ser Val Asp Gly Gln Lys Arg Tyr Thr Phe Arg Val Arg
    210                 215                 220 agc cgc ttt aac cca ctc tgt gga agt gct cag cat tgg agt gaa tgg     720
Ser Arg Phe Asn Pro Leu Cys Gly Ser Ala Gln His Trp Ser Glu Trp
```

```
                    225                 230                 235                 240
agc cac cca atc cac tgg ggg agc aat act tca aaa gag aac gcg tcg        768
Ser His Pro Ile His Trp Gly Ser Asn Thr Ser Lys Glu Asn Ala Ser
                245                 250                 255 tct ggg aac atg aag gtc ctg cag gag ccc acc tgc gtc tcc gac tac        816
Ser Gly Asn Met Lys Val Leu Gln Glu Pro Thr Cys Val Ser Asp Tyr
            260                 265                 270 atg agc atc tct act tgc gag tgg aag atg aat ggt ccc acc aat tgc        864
Met Ser Ile Ser Thr Cys Glu Trp Lys Met Asn Gly Pro Thr Asn Cys
        275                 280                 285 agc acc gag ctc cgc ctg ttg tac cag ctg gtt ttt ctg ctc tcc gaa        912
Ser Thr Glu Leu Arg Leu Leu Tyr Gln Leu Val Phe Leu Leu Ser Glu
    290                 295                 300 gcc cac acg tgt atc cct gag aac aac gga ggc gcg ggg tgc gtg tgc        960
Ala His Thr Cys Ile Pro Glu Asn Asn Gly Gly Ala Gly Cys Val Cys
305                 310                 315                 320 cac ctg ctc atg gat gac gtg gtc agt gcg gat aac tat aca ctg gac       1008
His Leu Leu Met Asp Asp Val Val Ser Ala Asp Asn Tyr Thr Leu Asp
                325                 330                 335 ctg tgg gct ggg cag cag ctg ctg tgg aag ggc tcc ttc aag ccc agc       1056
Leu Trp Ala Gly Gln Gln Leu Leu Trp Lys Gly Ser Phe Lys Pro Ser
            340                 345                 350 gag cat gtg aaa ccc agg gcc cca gga aac ctg aca gtt cac acc aat       1104
Glu His Val Lys Pro Arg Ala Pro Gly Asn Leu Thr Val His Thr Asn
        355                 360                 365 gtc tcc gac act ctg ctg ctg acc tgg agc aac ccg tat ccc cct gac       1152
Val Ser Asp Thr Leu Leu Leu Thr Trp Ser Asn Pro Tyr Pro Pro Asp
    370                 375                 380 aat tac ctg tat aat cat ctc acc tat gca gtc aac att tgg agt gaa       1200
Asn Tyr Leu Tyr Asn His Leu Thr Tyr Ala Val Asn Ile Trp Ser Glu
385                 390                 395                 400 aac gac ccg gca gat ttc aga atc tat aac gtg acc tac cta gaa ccc       1248
Asn Asp Pro Ala Asp Phe Arg Ile Tyr Asn Val Thr Tyr Leu Glu Pro
                405                 410                 415 tcc ctc cgc atc gca gcc agc acc ctg aag tct ggg att tcc tac agg       1296
Ser Leu Arg Ile Ala Ala Ser Thr Leu Lys Ser Gly Ile Ser Tyr Arg
            420                 425                 430 gca cgg gtg agg gcc tgg gct cag agc tat aac acc acc tgg agt gag       1344
Ala Arg Val Arg Ala Trp Ala Gln Ser Tyr Asn Thr Thr Trp Ser Glu
        435                 440                 445 tgg agc ccc agc acc aag tgg cac aac tcc tac agg gag ccc ttc gag       1392
Trp Ser Pro Ser Thr Lys Trp His Asn Ser Tyr Arg Glu Pro Phe Glu
    450                 455                 460 cag tcc gga gac aaa act cac aca tgc cca ccg tgc cca gca cct gaa       1440
Gln Ser Gly Asp Lys Thr His Thr Cys Pro Pro Cys Pro Ala Pro Glu
465                 470                 475                 480 ctc ctg ggg gga ccg tca gtc ttc ctc ttc ccc cca aaa ccc aag gac       1488
Leu Leu Gly Gly Pro Ser Val Phe Leu Phe Pro Pro Lys Pro Lys Asp
                485                 490                 495 acc ctc atg atc tcc cgg acc cct gag gtc aca tgc gtg gtg gtg gac       1536
Thr Leu Met Ile Ser Arg Thr Pro Glu Val Thr Cys Val Val Val Asp
            500                 505                 510 gtg agc cac gaa gac cct gag gtc aag ttc aac tgg tac gtg gac ggc       1584
Val Ser His Glu Asp Pro Glu Val Lys Phe Asn Trp Tyr Val Asp Gly
        515                 520                 525 gtg gag gtg cat aat gcc aag aca aag ccg cgg gag gag cag tac aac       1632
Val Glu Val His Asn Ala Lys Thr Lys Pro Arg Glu Glu Gln Tyr Asn
    530                 535                 540 agc acg tac cgt gtg gtc agc gtc ctc acc gtc ctg cac cag gac tgg       1680
```

```
Ser Thr Tyr Arg Val Val Ser Val Leu Thr Val Leu His Gln Asp Trp
545                 550                 555                 560 ctg aat ggc aag gag tac aag tgc aag gtc tcc aac aaa gcc ctc cca      1728
Leu Asn Gly Lys Glu Tyr Lys Cys Lys Val Ser Asn Lys Ala Leu Pro
                565                 570                 575 gcc ccc atc gag aaa acc atc tcc aaa gcc aaa ggg cag ccc cga gaa      1776
Ala Pro Ile Glu Lys Thr Ile Ser Lys Ala Lys Gly Gln Pro Arg Glu
            580                 585                 590 cca cag gtg tac acc ctg ccc cca tcc cgg gat gag ctg acc aag aac      1824
Pro Gln Val Tyr Thr Leu Pro Pro Ser Arg Asp Glu Leu Thr Lys Asn
        595                 600                 605 cag gtc agc ctg acc tgc ctg gtc aaa ggc ttc tat ccc agc gac atc      1872
Gln Val Ser Leu Thr Cys Leu Val Lys Gly Phe Tyr Pro Ser Asp Ile
    610                 615                 620 gcc gtg gag tgg gag agc aat ggg cag ccg gag aac aac tac aag acc      1920
Ala Val Glu Trp Glu Ser Asn Gly Gln Pro Glu Asn Asn Tyr Lys Thr
625                 630                 635                 640 acg cct ccc gtg ctg gac tcc gac ggc tcc ttc ttc ctc tat agc aag      1968
Thr Pro Pro Val Leu Asp Ser Asp Gly Ser Phe Phe Leu Tyr Ser Lys
                645                 650                 655 ctc acc gtg gac aag agc agg tgg cag cag ggg aac gtc ttc tca tgc      2016
Leu Thr Val Asp Lys Ser Arg Trp Gln Gln Gly Asn Val Phe Ser Cys
            660                 665                 670 tcc gtg atg cat gag gct ctg cac aac cac tac acg cag aag agc ctc      2064
Ser Val Met His Glu Ala Leu His Asn His Tyr Thr Gln Lys Ser Leu
        675                 680                 685 tcc ctg tct ccg ggt aaa tga                                          2085
Ser Leu Ser Pro Gly Lys
    690

<210> SEQ ID NO 22
<211> LENGTH: 694
<212> TYPE: PRT
<213> ORGANISM: Homo sapiens

<400> SEQUENCE: 22

Met Val Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175
```

-continued

```
Arg Phe Leu Asn His Cys Leu Glu His Leu Val Gln Tyr Arg Thr Asp
            180                 185                 190
Trp Asp His Ser Trp Thr Glu Gln Ser Val Asp Tyr Arg His Lys Phe
            195                 200                 205
Ser Leu Pro Ser Val Asp Gly Gln Lys Arg Tyr Thr Phe Arg Val Arg
            210                 215                 220
Ser Arg Phe Asn Pro Leu Cys Gly Ser Ala Gln His Trp Ser Glu Trp
225                 230                 235                 240
Ser His Pro Ile His Trp Gly Ser Asn Thr Ser Lys Glu Asn Ala Ser
                245                 250                 255
Ser Gly Asn Met Lys Val Leu Gln Glu Pro Thr Cys Val Ser Asp Tyr
            260                 265                 270
Met Ser Ile Ser Thr Cys Glu Trp Lys Met Asn Gly Pro Thr Asn Cys
            275                 280                 285
Ser Thr Glu Leu Arg Leu Leu Tyr Gln Leu Val Phe Leu Leu Ser Glu
            290                 295                 300
Ala His Thr Cys Ile Pro Glu Asn Asn Gly Ala Gly Cys Val Cys
305                 310                 315                 320
His Leu Leu Met Asp Asp Val Val Ser Ala Asp Asn Tyr Thr Leu Asp
                325                 330                 335
Leu Trp Ala Gly Gln Gln Leu Leu Trp Lys Gly Ser Phe Lys Pro Ser
            340                 345                 350
Glu His Val Lys Pro Arg Ala Pro Gly Asn Leu Thr Val His Thr Asn
            355                 360                 365
Val Ser Asp Thr Leu Leu Leu Thr Trp Ser Asn Pro Tyr Pro Pro Asp
            370                 375                 380
Asn Tyr Leu Tyr Asn His Leu Thr Tyr Ala Val Asn Ile Trp Ser Glu
385                 390                 395                 400
Asn Asp Pro Ala Asp Phe Arg Ile Tyr Asn Val Thr Tyr Leu Glu Pro
                405                 410                 415
Ser Leu Arg Ile Ala Ala Ser Thr Leu Lys Ser Gly Ile Ser Tyr Arg
            420                 425                 430
Ala Arg Val Arg Ala Trp Ala Gln Ser Tyr Asn Thr Thr Trp Ser Glu
            435                 440                 445
Trp Ser Pro Ser Thr Lys Trp His Asn Ser Tyr Arg Glu Pro Phe Glu
            450                 455                 460
Gln Ser Gly Asp Lys Thr His Thr Cys Pro Pro Cys Pro Ala Pro Glu
465                 470                 475                 480
Leu Leu Gly Gly Pro Ser Val Phe Leu Phe Pro Pro Lys Pro Lys Asp
                485                 490                 495
Thr Leu Met Ile Ser Arg Thr Pro Glu Val Thr Cys Val Val Val Asp
            500                 505                 510
Val Ser His Glu Asp Pro Glu Val Lys Phe Asn Trp Tyr Val Asp Gly
            515                 520                 525
Val Glu Val His Asn Ala Lys Thr Lys Pro Arg Glu Glu Gln Tyr Asn
            530                 535                 540
Ser Thr Tyr Arg Val Val Ser Val Leu Thr Val Leu His Gln Asp Trp
545                 550                 555                 560
Leu Asn Gly Lys Glu Tyr Lys Cys Lys Val Ser Asn Lys Ala Leu Pro
                565                 570                 575
Ala Pro Ile Glu Lys Thr Ile Ser Lys Ala Lys Gly Gln Pro Arg Glu
            580                 585                 590
```

```
Pro Gln Val Tyr Thr Leu Pro Pro Ser Arg Asp Glu Leu Thr Lys Asn
            595                 600                 605

Gln Val Ser Leu Thr Cys Leu Val Lys Gly Phe Tyr Pro Ser Asp Ile
        610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
                660                 665                 670

Ser Val Met His Glu Ala Leu His Asn His Tyr Thr Gln Lys Ser Leu
            675                 680                 685

Ser Leu Ser Pro Gly Lys
        690

<210> SEQ ID NO 23
<211> LENGTH: 3507
<212> TYPE: DNA
<213> ORGANISM: Homo sapiens
<220> FEATURE:
<221> NAME/KEY: CDS
<222> LOCATION: (1)...(3504)

<400> SEQUENCE: 23 atg gtg gcc gtc ggc tgc gcg ctg ctg gct gcc ctg ctg gcc gcg ccg       48
Met Val Ala Val Gly Cys Ala Leu Leu Ala Ala Leu Leu Ala Ala Pro
1               5                   10                  15 gga gcg gcg ctg gcc cca agg cgc tgc cct gcg cag gag gtg gca aga       96
Gly Ala Ala Leu Ala Pro Arg Arg Cys Pro Ala Gln Glu Val Ala Arg
            20                  25                  30 ggc gtg ctg acc agt ctg cca gga gac agc gtg act ctg acc tgc ccg      144
Gly Val Leu Thr Ser Leu Pro Gly Asp Ser Val Thr Leu Thr Cys Pro
        35                  40                  45 ggg gta gag ccg gaa gac aat gcc act gtt cac tgg gtg ctc agg aag      192
Gly Val Glu Pro Glu Asp Asn Ala Thr Val His Trp Val Leu Arg Lys
    50                  55                  60 ccg gct gca ggc tcc cac ccc agc aga tgg gct ggc atg gga agg agg      240
Pro Ala Ala Gly Ser His Pro Ser Arg Trp Ala Gly Met Gly Arg Arg
65                  70                  75                  80 ctg ctg ctg agg tcg gtg cag ctc cac gac tct gga aac tat tca tgc      288
Leu Leu Leu Arg Ser Val Gln Leu His Asp Ser Gly Asn Tyr Ser Cys
                85                  90                  95 tac cgg gcc ggc cgc cca gct ggg act gtg cac ttg ctg gtg gat gtt      336
Tyr Arg Ala Gly Arg Pro Ala Gly Thr Val His Leu Leu Val Asp Val
            100                 105                 110 ccc ccc gag gag ccc cag ctc tcc tgc ttc cgg aag agc ccc ctc agc      384
Pro Pro Glu Glu Pro Gln Leu Ser Cys Phe Arg Lys Ser Pro Leu Ser
        115                 120                 125 aat gtt gtt tgt gag tgg ggt cct cgg agc acc cca tcc ctg acg aca      432
Asn Val Val Cys Glu Trp Gly Pro Arg Ser Thr Pro Ser Leu Thr Thr
    130                 135                 140 aag gct gtg ctc ttg gtg agg aag ttt cag aac agt ccg gcc gaa gac      480
Lys Ala Val Leu Leu Val Arg Lys Phe Gln Asn Ser Pro Ala Glu Asp
145                 150                 155                 160 ttc cag gag ccg tgc cag tat tcc cag gag tcc cag aag ttc tcc tgc      528
Phe Gln Glu Pro Cys Gln Tyr Ser Gln Glu Ser Gln Lys Phe Ser Cys
                165                 170                 175 cag tta gca gtc ccg gag gga gac agc tct ttc tac ata gtg tcc atg      576
Gln Leu Ala Val Pro Glu Gly Asp Ser Ser Phe Tyr Ile Val Ser Met
            180                 185                 190
```

-continued

| | | |
|---|---|---|
| tgc gtc gcc agt agt gtc ggg agc aag ttc agc aaa act caa acc ttt<br>Cys Val Ala Ser Ser Val Gly Ser Lys Phe Ser Lys Thr Gln Thr Phe<br>195 200 205 | | 624 |
| cag ggt tgt gga atc ttg cag cct gat ccg cct gcc aac atc aca gtc<br>Gln Gly Cys Gly Ile Leu Gln Pro Asp Pro Pro Ala Asn Ile Thr Val<br>210 215 220 | | 672 |
| act gcc gtg gcc aga aac ccc cgc tgg ctc agt gtc acc tgg caa gac<br>Thr Ala Val Ala Arg Asn Pro Arg Trp Leu Ser Val Thr Trp Gln Asp<br>225 230 235 240 | | 720 |
| ccc cac tcc tgg aac tca tct ttc tac aga cta cgg ttt gag ctc aga<br>Pro His Ser Trp Asn Ser Ser Phe Tyr Arg Leu Arg Phe Glu Leu Arg<br>245 250 255 | | 768 |
| tat cgg gct gaa cgg tca aag aca ttc aca aca tgg atg gtc aag gac<br>Tyr Arg Ala Glu Arg Ser Lys Thr Phe Thr Thr Trp Met Val Lys Asp<br>260 265 270 | | 816 |
| ctc cag cat cac tgt gtc atc cac gac gcc tgg agc ggc ctg agg cac<br>Leu Gln His His Cys Val Ile His Asp Ala Trp Ser Gly Leu Arg His<br>275 280 285 | | 864 |
| gtg gtg cag ctt cgt gcc cag gag gag ttc ggg caa ggc gag tgg agc<br>Val Val Gln Leu Arg Ala Gln Glu Glu Phe Gly Gln Gly Glu Trp Ser<br>290 295 300 | | 912 |
| gag tgg agc ccg gag gcc atg ggc acg cct tgg aca gaa tcc agg agt<br>Glu Trp Ser Pro Glu Ala Met Gly Thr Pro Trp Thr Glu Ser Arg Ser<br>305 310 315 320 | | 960 |
| cct cca gct gag aac gag gtg tcc acc ccc atg acc ggt ggc gcg cct<br>Pro Pro Ala Glu Asn Glu Val Ser Thr Pro Met Thr Gly Gly Ala Pro<br>325 330 335 | | 1008 |
| tca ggt gct cag ctg gaa ctt cta gac cca tgt ggt tat atc agt cct<br>Ser Gly Ala Gln Leu Glu Leu Leu Asp Pro Cys Gly Tyr Ile Ser Pro<br>340 345 350 | | 1056 |
| gaa tct cca gtt gta caa ctt cat tct aat ttc act gca gtt tgt gtg<br>Glu Ser Pro Val Val Gln Leu His Ser Asn Phe Thr Ala Val Cys Val<br>355 360 365 | | 1104 |
| cta aag gaa aaa tgt atg gat tat ttt cat gta aat gct aat tac att<br>Leu Lys Glu Lys Cys Met Asp Tyr Phe His Val Asn Ala Asn Tyr Ile<br>370 375 380 | | 1152 |
| gtc tgg aaa aca aac cat ttt act att cct aag gag caa tat act atc<br>Val Trp Lys Thr Asn His Phe Thr Ile Pro Lys Glu Gln Tyr Thr Ile<br>385 390 395 400 | | 1200 |
| ata aac aga aca gca tcc agt gtc acc ttt aca gat ata gct tca tta<br>Ile Asn Arg Thr Ala Ser Ser Val Thr Phe Thr Asp Ile Ala Ser Leu<br>405 410 415 | | 1248 |
| aat att cag ctc act tgc aac att ctt aca ttc gga cag ctt gaa cag<br>Asn Ile Gln Leu Thr Cys Asn Ile Leu Thr Phe Gly Gln Leu Glu Gln<br>420 425 430 | | 1296 |
| aat gtt tat gga atc aca ata att tca ggc ttg cct cca gaa aaa cct<br>Asn Val Tyr Gly Ile Thr Ile Ile Ser Gly Leu Pro Pro Glu Lys Pro<br>435 440 445 | | 1344 |
| aaa aat ttg agt tgc att gtg aac gag ggg aag aaa atg agg tgt gag<br>Lys Asn Leu Ser Cys Ile Val Asn Glu Gly Lys Lys Met Arg Cys Glu<br>450 455 460 | | 1392 |
| tgg gat ggt gga agg gaa aca cac ttg gag aca aac ttc act tta aaa<br>Trp Asp Gly Gly Arg Glu Thr His Leu Glu Thr Asn Phe Thr Leu Lys<br>465 470 475 480 | | 1440 |
| tct gaa tgg gca aca cac aag ttt gct gat tgc aaa gca aaa cgt gac<br>Ser Glu Trp Ala Thr His Lys Phe Ala Asp Cys Lys Ala Lys Arg Asp<br>485 490 495 | | 1488 |
| acc ccc acc tca tgc act gtt gat tat tct act gtg tat ttt gtc aac<br>Thr Pro Thr Ser Cys Thr Val Asp Tyr Ser Thr Val Tyr Phe Val Asn | | 1536 |

-continued

```
                  500                 505                 510
att gaa gtc tgg gta gaa gca gag aat gcc ctt ggg aag gtt aca tca    1584
Ile Glu Val Trp Val Glu Ala Glu Asn Ala Leu Gly Lys Val Thr Ser
            515                 520                 525 gat cat atc aat ttt gat cct gta tat aaa gtg aag ccc aat ccg cca    1632
Asp His Ile Asn Phe Asp Pro Val Tyr Lys Val Lys Pro Asn Pro Pro
        530                 535                 540 cat aat tta tca gtg atc aac tca gag gaa ctg tct agt atc tta aaa    1680
His Asn Leu Ser Val Ile Asn Ser Glu Glu Leu Ser Ser Ile Leu Lys
545                 550                 555                 560 ttg aca tgg acc aac cca agt att aag agt gtt ata ata cta aaa tat    1728
Leu Thr Trp Thr Asn Pro Ser Ile Lys Ser Val Ile Ile Leu Lys Tyr
                565                 570                 575 aac att caa tat agg acc aaa gat gcc tca act tgg agc cag att cct    1776
Asn Ile Gln Tyr Arg Thr Lys Asp Ala Ser Thr Trp Ser Gln Ile Pro
            580                 585                 590 cct gaa gac aca gca tcc acc cga tct tca ttc act gtc caa gac ctt    1824
Pro Glu Asp Thr Ala Ser Thr Arg Ser Ser Phe Thr Val Gln Asp Leu
        595                 600                 605 aaa cct ttt aca gaa tat gtg ttt agg att cgc tgt atg aag gaa gat    1872
Lys Pro Phe Thr Glu Tyr Val Phe Arg Ile Arg Cys Met Lys Glu Asp
610                 615                 620 ggt aag gga tac tgg agt gac tgg agt gaa gaa gca agt ggg atc acc    1920
Gly Lys Gly Tyr Trp Ser Asp Trp Ser Glu Glu Ala Ser Gly Ile Thr
625                 630                 635                 640 tat gaa gat aga cca tct aaa gca cca agt ttc tgg tat aaa ata gat    1968
Tyr Glu Asp Arg Pro Ser Lys Ala Pro Ser Phe Trp Tyr Lys Ile Asp
                645                 650                 655 cca tcc cat act caa ggc tac aga act gta caa ctc gtg tgg aag aca    2016
Pro Ser His Thr Gln Gly Tyr Arg Thr Val Gln Leu Val Trp Lys Thr
            660                 665                 670 ttg cct cct ttt gaa gcc aat gga aaa atc ttg gat tat gaa gtg act    2064
Leu Pro Pro Phe Glu Ala Asn Gly Lys Ile Leu Asp Tyr Glu Val Thr
        675                 680                 685 ctc aca aga tgg aaa tca cat tta caa aat tac aca gtt aat gcc aca    2112
Leu Thr Arg Trp Lys Ser His Leu Gln Asn Tyr Thr Val Asn Ala Thr
690                 695                 700 aaa ctg aca gta aat ctc aca aat gat cgc tat cta gca acc cta aca    2160
Lys Leu Thr Val Asn Leu Thr Asn Asp Arg Tyr Leu Ala Thr Leu Thr
705                 710                 715                 720 gta aga aat ctt gtt ggc aaa tca gat gca gct gtt tta act atc cct    2208
Val Arg Asn Leu Val Gly Lys Ser Asp Ala Ala Val Leu Thr Ile Pro
                725                 730                 735 gcc tgt gac ttt caa gct act cac cct gta atg gat ctt aaa gca ttc    2256
Ala Cys Asp Phe Gln Ala Thr His Pro Val Met Asp Leu Lys Ala Phe
            740                 745                 750 ccc aaa gat aac atg ctt tgg gtg gaa tgg act act cca agg gaa tct    2304
Pro Lys Asp Asn Met Leu Trp Val Glu Trp Thr Thr Pro Arg Glu Ser
        755                 760                 765 gta aag aaa tat ata ctt gag tgg tgt gtg tta tca gat aaa gca ccc    2352
Val Lys Lys Tyr Ile Leu Glu Trp Cys Val Leu Ser Asp Lys Ala Pro
770                 775                 780 tgt atc aca gac tgg caa caa gaa gat ggt acc gtg cat cgc acc tat    2400
Cys Ile Thr Asp Trp Gln Gln Glu Asp Gly Thr Val His Arg Thr Tyr
785                 790                 795                 800 tta aga ggg aac tta gca gag agc aaa tgc tat ttg ata aca gtt act    2448
Leu Arg Gly Asn Leu Ala Glu Ser Lys Cys Tyr Leu Ile Thr Val Thr
                805                 810                 815 cca gta tat gct gat gga cca gga agc cct gaa tcc ata aag gca tac    2496
```

-continued

```
                Pro Val Tyr Ala Asp Gly Pro Gly Ser Pro Glu Ser Ile Lys Ala Tyr
                            820                 825                 830 ctt aaa caa gct cca cct tcc aaa gga cct act gtt cgg aca aaa aaa              2544
Leu Lys Gln Ala Pro Pro Ser Lys Gly Pro Thr Val Arg Thr Lys Lys
            835                 840                 845 gta ggg aaa aac gaa gct gtc tta gag tgg gac caa ctt cct gtt gat              2592
Val Gly Lys Asn Glu Ala Val Leu Glu Trp Asp Gln Leu Pro Val Asp
850                 855                 860 gtt cag aat gga ttt atc aga aat tat act ata ttt tat aga acc atc              2640
Val Gln Asn Gly Phe Ile Arg Asn Tyr Thr Ile Phe Tyr Arg Thr Ile
865                 870                 875                 880 att gga aat gaa act gct gtg aat gtg gat tct tcc cac aca gaa tat              2688
Ile Gly Asn Glu Thr Ala Val Asn Val Asp Ser Ser His Thr Glu Tyr
                885                 890                 895 aca ttg tcc tct ttg act agt gac aca ttg tac atg gta cga atg gca              2736
Thr Leu Ser Ser Leu Thr Ser Asp Thr Leu Tyr Met Val Arg Met Ala
            900                 905                 910 gca tac aca gat gaa ggt ggg aag gat ggt cca gaa ttc act ttt act              2784
Ala Tyr Thr Asp Glu Gly Gly Lys Asp Gly Pro Glu Phe Thr Phe Thr
        915                 920                 925 acc cca aag ttt gct caa gga gaa att gaa tcc ggg ggc gac aaa act              2832
Thr Pro Lys Phe Ala Gln Gly Glu Ile Glu Ser Gly Gly Asp Lys Thr
930                 935                 940 cac aca tgc cca ccg tgc cca gca cct gaa ctc ctg ggg gga ccg tca              2880
His Thr Cys Pro Pro Cys Pro Ala Pro Glu Leu Leu Gly Gly Pro Ser
945                 950                 955                 960 gtc ttc ctc ttc ccc cca aaa ccc aag gac acc ctc atg atc tcc cgg              2928
Val Phe Leu Phe Pro Pro Lys Pro Lys Asp Thr Leu Met Ile Ser Arg
                965                 970                 975 acc cct gag gtc aca tgc gtg gtg gtg gac gtg agc cac gaa gac cct              2976
Thr Pro Glu Val Thr Cys Val Val Val Asp Val Ser His Glu Asp Pro
            980                 985                 990 gag gtc aag ttc aac tgg tac gtg gac ggc gtg gag gtg cat aat gcc              3024
Glu Val Lys Phe Asn Trp Tyr Val Asp Gly Val Glu Val His Asn Ala
        995                 1000                1005 aag aca aag ccg cgg gag gag cag tac aac agc acg tac cgt gtg gtc              3072
Lys Thr Lys Pro Arg Glu Glu Gln Tyr Asn Ser Thr Tyr Arg Val Val
    1010                1015                1020 agc gtc ctc acc gtc ctg cac cag gac tgg ctg aat ggc aag gag tac              3120
Ser Val Leu Thr Val Leu His Gln Asp Trp Leu Asn Gly Lys Glu Tyr
1025                1030                1035                1040 aag tgc aag gtc tcc aac aaa gcc ctc cca gcc ccc atc gag aaa acc              3168
Lys Cys Lys Val Ser Asn Lys Ala Leu Pro Ala Pro Ile Glu Lys Thr
                1045                1050                1055 atc tcc aaa gcc aaa ggg cag ccc cga gaa cca cag gtg tac acc ctg              3216
Ile Ser Lys Ala Lys Gly Gln Pro Arg Glu Pro Gln Val Tyr Thr Leu
            1060                1065                1070 ccc cca tcc cgg gat gag ctg acc aag aac cag gtc agc ctg acc tgc              3264
Pro Pro Ser Arg Asp Glu Leu Thr Lys Asn Gln Val Ser Leu Thr Cys
        1075                1080                1085 ctg gtc aaa ggc ttc tat ccc agc gac atc gcc gtg gag tgg gag agc              3312
Leu Val Lys Gly Phe Tyr Pro Ser Asp Ile Ala Val Glu Trp Glu Ser
1090                1095                1100 aat ggg cag ccg gag aac aac tac aag acc acg cct ccc gtg ctg gac              3360
Asn Gly Gln Pro Glu Asn Asn Tyr Lys Thr Thr Pro Pro Val Leu Asp
1105                1110                1115                1120 tcc gac ggc tcc ttc ttc ctc tac agc aag ctc acc gtg gac aag agc              3408
Ser Asp Gly Ser Phe Phe Leu Tyr Ser Lys Leu Thr Val Asp Lys Ser
                1125                1130                1135
```

|  |  |  |  |  |  |  |  |  |  |  |  |
|---|---|---|---|---|---|---|---|---|---|---|---|
| agg | tgg | cag | cag | ggg | aac | gtc | ttc | tca | tgc | tcc | gtg | atg | cat | gag | gct | 3456 |
| Arg | Trp | Gln | Gln | Gly | Asn | Val | Phe | Ser | Cys | Ser | Val | Met | His | Glu | Ala |  |
|  |  | 1140 |  |  |  | 1145 |  |  |  | 1150 |  |  |  |  |  |  |
| ctg | cac | aac | cac | tac | acg | cag | aag | agc | ctc | tcc | ctg | tct | ccg | ggt | aaa | 3504 |
| Leu | His | Asn | His | Tyr | Thr | Gln | Lys | Ser | Leu | Ser | Leu | Ser | Pro | Gly | Lys |  |
|  |  | 1155 |  |  |  | 1160 |  |  |  | 1165 |  |  |  |  |  |  |
| tga |  |  |  |  |  |  |  |  |  |  |  |  |  |  |  | 3507 |

<210> SEQ ID NO 24
<211> LENGTH: 1168
<212> TYPE: PRT
<213> ORGANISM: Homo sapiens

<400> SEQUENCE: 24

```
Met Val Ala Val Gly Cys Ala Leu Leu Ala Leu Leu Ala Ala Pro
 1               5                  10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Thr Gly Gly Ala Pro
```

-continued

```
                325                 330                 335
Ser Gly Ala Gln Leu Glu Leu Leu Asp Pro Cys Gly Tyr Ile Ser Pro
                340                 345                 350

Glu Ser Pro Val Val Gln Leu His Ser Asn Phe Thr Ala Val Cys Val
                355                 360                 365

Leu Lys Glu Lys Cys Met Asp Tyr Phe His Val Asn Ala Asn Tyr Ile
                370                 375             380

Val Trp Lys Thr Asn His Phe Thr Ile Pro Lys Glu Gln Tyr Thr Ile
385                     390                 395                 400

Ile Asn Arg Thr Ala Ser Ser Val Thr Phe Thr Asp Ile Ala Ser Leu
                405                 410                 415

Asn Ile Gln Leu Thr Cys Asn Ile Leu Thr Phe Gly Gln Leu Glu Gln
                420                 425                 430

Asn Val Tyr Gly Ile Thr Ile Ile Ser Gly Leu Pro Pro Glu Lys Pro
                435                 440                 445

Lys Asn Leu Ser Cys Ile Val Asn Glu Gly Lys Lys Met Arg Cys Glu
450                     455                 460

Trp Asp Gly Gly Arg Glu Thr His Leu Glu Thr Asn Phe Thr Leu Lys
465                     470                 475                 480

Ser Glu Trp Ala Thr His Lys Phe Ala Asp Cys Lys Ala Lys Arg Asp
                485                 490                 495

Thr Pro Thr Ser Cys Thr Val Asp Tyr Ser Thr Val Tyr Phe Val Asn
                500                 505                 510

Ile Glu Val Trp Val Glu Ala Glu Asn Ala Leu Gly Lys Val Thr Ser
                515                 520                 525

Asp His Ile Asn Phe Asp Pro Val Tyr Lys Val Lys Pro Asn Pro Pro
530                     535                 540

His Asn Leu Ser Val Ile Asn Ser Glu Glu Leu Ser Ser Ile Leu Lys
545                     550                 555                 560

Leu Thr Trp Thr Asn Pro Ser Ile Lys Ser Val Ile Ile Leu Lys Tyr
                565                 570                 575

Asn Ile Gln Tyr Arg Thr Lys Asp Ala Ser Thr Trp Ser Gln Ile Pro
                580                 585                 590

Pro Glu Asp Thr Ala Ser Thr Arg Ser Ser Phe Thr Val Gln Asp Leu
                595                 600                 605

Lys Pro Phe Thr Glu Tyr Val Phe Arg Ile Arg Cys Met Lys Glu Asp
                610                 615                 620

Gly Lys Gly Tyr Trp Ser Asp Trp Ser Glu Glu Ala Ser Gly Ile Thr
625                     630                 635                 640

Tyr Glu Asp Arg Pro Ser Lys Ala Pro Ser Phe Trp Tyr Lys Ile Asp
                645                 650                 655

Pro Ser His Thr Gln Gly Tyr Arg Thr Val Gln Leu Val Trp Lys Thr
                660                 665                 670

Leu Pro Pro Phe Glu Ala Asn Gly Lys Ile Leu Asp Tyr Glu Val Thr
                675                 680                 685

Leu Thr Arg Trp Lys Ser His Leu Gln Asn Tyr Thr Val Asn Ala Thr
                690                 695                 700

Lys Leu Thr Val Asn Leu Thr Asn Asp Arg Tyr Leu Ala Thr Leu Thr
705                     710                 715                 720

Val Arg Asn Leu Val Gly Lys Ser Asp Ala Ala Val Leu Thr Ile Pro
                725                 730                 735

Ala Cys Asp Phe Gln Ala Thr His Pro Val Met Asp Leu Lys Ala Phe
                740                 745                 750
```

-continued

```
Pro Lys Asp Asn Met Leu Trp Val Glu Trp Thr Thr Pro Arg Glu Ser
        755                 760                 765
Val Lys Lys Tyr Ile Leu Glu Trp Cys Val Leu Ser Asp Lys Ala Pro
        770                 775                 780
Cys Ile Thr Asp Trp Gln Gln Glu Asp Gly Thr Val His Arg Thr Tyr
785                 790                 795                 800
Leu Arg Gly Asn Leu Ala Glu Ser Lys Cys Tyr Leu Ile Thr Val Thr
                805                 810                 815
Pro Val Tyr Ala Asp Gly Pro Gly Ser Pro Glu Ser Ile Lys Ala Tyr
                820                 825                 830
Leu Lys Gln Ala Pro Pro Ser Lys Gly Pro Thr Val Arg Thr Lys Lys
                835                 840                 845
Val Gly Lys Asn Glu Ala Val Leu Glu Trp Asp Gln Leu Pro Val Asp
                850                 855                 860
Val Gln Asn Gly Phe Ile Arg Asn Tyr Thr Ile Phe Tyr Arg Thr Ile
865                 870                 875                 880
Ile Gly Asn Glu Thr Ala Val Asn Val Asp Ser Ser His Thr Glu Tyr
                885                 890                 895
Thr Leu Ser Ser Leu Thr Ser Asp Thr Leu Tyr Met Val Arg Met Ala
                900                 905                 910
Ala Tyr Thr Asp Glu Gly Gly Lys Asp Gly Pro Glu Phe Thr Phe Thr
        915                 920                 925
Thr Pro Lys Phe Ala Gln Gly Glu Ile Glu Ser Gly Gly Asp Lys Thr
        930                 935                 940
His Thr Cys Pro Pro Cys Pro Ala Pro Glu Leu Leu Gly Gly Pro Ser
945                 950                 955                 960
Val Phe Leu Phe Pro Lys Pro Lys Asp Thr Leu Met Ile Ser Arg
                965                 970                 975
Thr Pro Glu Val Thr Cys Val Val Asp Val Ser His Glu Asp Pro
                980                 985                 990
Glu Val Lys Phe Asn Trp Tyr Val Asp Gly Val Glu Val His Asn Ala
        995                 1000                1005
Lys Thr Lys Pro Arg Glu Glu Gln Tyr Asn Ser Thr Tyr Arg Val Val
        1010                1015                1020
Ser Val Leu Thr Val Leu His Gln Asp Trp Leu Asn Gly Lys Glu Tyr
1025                1030                1035                1040
Lys Cys Lys Val Ser Asn Lys Ala Leu Pro Ala Pro Ile Glu Lys Thr
                1045                1050                1055
Ile Ser Lys Ala Lys Gly Gln Pro Arg Glu Pro Gln Val Tyr Thr Leu
                1060                1065                1070
Pro Pro Ser Arg Asp Glu Leu Thr Lys Asn Gln Val Ser Leu Thr Cys
        1075                1080                1085
Leu Val Lys Gly Phe Tyr Pro Ser Asp Ile Ala Val Glu Trp Glu Ser
        1090                1095                1100
Asn Gly Gln Pro Glu Asn Asn Tyr Lys Thr Thr Pro Pro Val Leu Asp
1105                1110                1115                1120
Ser Asp Gly Ser Phe Phe Leu Tyr Ser Lys Leu Thr Val Asp Lys Ser
                1125                1130                1135
Arg Trp Gln Gln Gly Asn Val Phe Ser Cys Ser Val Met His Glu Ala
                1140                1145                1150
Leu His Asn His Tyr Thr Gln Lys Ser Leu Ser Leu Ser Pro Gly Lys
                1155                1160                1165
```

-continued

```
<210> SEQ ID NO 25
<211> LENGTH: 3477
<212> TYPE: DNA
<213> ORGANISM: Homo sapiens
<220> FEATURE:
<221> NAME/KEY: CDS
<222> LOCATION: (1)...(3474)

<400> SEQUENCE: 25 atg gtg gcc gtc ggc tgc gcg ctg ctg gct gcc ctg ctg gcc gcg ccg      48
Met Val Ala Val Gly Cys Ala Leu Leu Ala Ala Leu Leu Ala Ala Pro
1               5                  10                  15 gga gcg gcg ctg gcc cca agg cgc tgc cct gcg cag gag gtg gca aga      96
Gly Ala Ala Leu Ala Pro Arg Arg Cys Pro Ala Gln Glu Val Ala Arg
            20                  25                  30 ggc gtg ctg acc agt ctg cca gga gac agc gtg act ctg acc tgc ccg     144
Gly Val Leu Thr Ser Leu Pro Gly Asp Ser Val Thr Leu Thr Cys Pro
        35                  40                  45 ggg gta gag ccg gaa gac aat gcc act gtt cac tgg gtg ctc agg aag     192
Gly Val Glu Pro Glu Asp Asn Ala Thr Val His Trp Val Leu Arg Lys
    50                  55                  60 ccg gct gca ggc tcc cac ccc agc aga tgg gct ggc atg gga agg agg     240
Pro Ala Ala Gly Ser His Pro Ser Arg Trp Ala Gly Met Gly Arg Arg
65                  70                  75                  80 ctg ctg ctg agg tcg gtg cag ctc cac gac tct gga aac tat tca tgc     288
Leu Leu Leu Arg Ser Val Gln Leu His Asp Ser Gly Asn Tyr Ser Cys
                85                  90                  95 tac cgg gcc ggc cgc cca gct ggg act gtg cac ttg ctg gtg gat gtt     336
Tyr Arg Ala Gly Arg Pro Ala Gly Thr Val His Leu Leu Val Asp Val
            100                 105                 110 ccc ccc gag gag ccc cag ctc tcc tgc ttc cgg aag agc ccc ctc agc     384
Pro Pro Glu Glu Pro Gln Leu Ser Cys Phe Arg Lys Ser Pro Leu Ser
        115                 120                 125 aat gtt gtt tgt gag tgg ggt cct cgg agc acc cca tcc ctg acg aca     432
Asn Val Val Cys Glu Trp Gly Pro Arg Ser Thr Pro Ser Leu Thr Thr
    130                 135                 140 aag gct gtg ctc ttg gtg agg aag ttt cag aac agt ccg gcc gaa gac     480
Lys Ala Val Leu Leu Val Arg Lys Phe Gln Asn Ser Pro Ala Glu Asp
145                 150                 155                 160 ttc cag gag ccg tgc cag tat tcc cag gag tcc cag aag ttc tcc tgc     528
Phe Gln Glu Pro Cys Gln Tyr Ser Gln Glu Ser Gln Lys Phe Ser Cys
                165                 170                 175 cag tta gca gtc ccg gag gga gac agc tct ttc tac ata gtg tcc atg     576
Gln Leu Ala Val Pro Glu Gly Asp Ser Ser Phe Tyr Ile Val Ser Met
            180                 185                 190 tgc gtc gcc agt agt gtc ggg agc aag ttc agc aaa act caa acc ttt     624
Cys Val Ala Ser Ser Val Gly Ser Lys Phe Ser Lys Thr Gln Thr Phe
        195                 200                 205 cag ggt tgt gga atc ttg cag cct gat ccg cct gcc aac atc aca gtc     672
Gln Gly Cys Gly Ile Leu Gln Pro Asp Pro Pro Ala Asn Ile Thr Val
    210                 215                 220 act gcc gtg gcc aga aac ccc cgc tgg ctc agt gtc acc tgg caa gac     720
Thr Ala Val Ala Arg Asn Pro Arg Trp Leu Ser Val Thr Trp Gln Asp
225                 230                 235                 240 ccc cac tcc tgg aac tca tct ttc tac aga cta cgg ttt gag ctc aga     768
Pro His Ser Trp Asn Ser Ser Phe Tyr Arg Leu Arg Phe Glu Leu Arg
                245                 250                 255 tat cgg gct gaa cgg tca aag aca ttc aca aca tgg atg gtc aag gac     816
Tyr Arg Ala Glu Arg Ser Lys Thr Phe Thr Thr Trp Met Val Lys Asp
            260                 265                 270
```

```
ctc cag cat cac tgt gtc atc cac gac gcc tgg agc ggc ctg agg cac       864
Leu Gln His His Cys Val Ile His Asp Ala Trp Ser Gly Leu Arg His
        275                 280                 285 gtg gtg cag ctt cgt gcc cag gag gag ttc ggg caa ggc gag tgg agc       912
Val Val Gln Leu Arg Ala Gln Glu Glu Phe Gly Gln Gly Glu Trp Ser
    290                 295                 300 gag tgg agc ccg gag gcc atg ggc acg cct tgg aca gaa tcg cga tcg       960
Glu Trp Ser Pro Glu Ala Met Gly Thr Pro Trp Thr Glu Ser Arg Ser
305                 310                 315                 320 cct cca gct gag aac gag gtg tcc acc ccc atg gaa ctt cta gac cca      1008
Pro Pro Ala Glu Asn Glu Val Ser Thr Pro Met Glu Leu Leu Asp Pro
                325                 330                 335 tgt ggt tat atc agt cct gaa tct cca gtt gta caa ctt cat tct aat      1056
Cys Gly Tyr Ile Ser Pro Glu Ser Pro Val Val Gln Leu His Ser Asn
            340                 345                 350 ttc act gca gtt tgt gtg cta aag gaa aaa tgt atg gat tat ttt cat      1104
Phe Thr Ala Val Cys Val Leu Lys Glu Lys Cys Met Asp Tyr Phe His
        355                 360                 365 gta aat gct aat tac att gtc tgg aaa aca aac cat ttt act att cct      1152
Val Asn Ala Asn Tyr Ile Val Trp Lys Thr Asn His Phe Thr Ile Pro
370                 375                 380 aag gag caa tat act atc ata aac aga aca gca tcc agt gtc acc ttt      1200
Lys Glu Gln Tyr Thr Ile Ile Asn Arg Thr Ala Ser Ser Val Thr Phe
385                 390                 395                 400 aca gat ata gct tca tta aat att cag ctc act tgc aac att ctt aca      1248
Thr Asp Ile Ala Ser Leu Asn Ile Gln Leu Thr Cys Asn Ile Leu Thr
                405                 410                 415 ttc gga cag ctt gaa cag aat gtt tat gga atc aca ata att tca ggc      1296
Phe Gly Gln Leu Glu Gln Asn Val Tyr Gly Ile Thr Ile Ile Ser Gly
            420                 425                 430 ttg cct cca gaa aaa cct aaa aat ttg agt tgc att gtg aac gag ggg      1344
Leu Pro Pro Glu Lys Pro Lys Asn Leu Ser Cys Ile Val Asn Glu Gly
        435                 440                 445 aag aaa atg agg tgt gag tgg gat ggt gga agg gaa aca cac ttg gag      1392
Lys Lys Met Arg Cys Glu Trp Asp Gly Gly Arg Glu Thr His Leu Glu
450                 455                 460 aca aac ttc act tta aaa tct gaa tgg gca aca cac aag ttt gct gat      1440
Thr Asn Phe Thr Leu Lys Ser Glu Trp Ala Thr His Lys Phe Ala Asp
465                 470                 475                 480 tgc aaa gca aaa cgt gac acc ccc acc tca tgc act gtt gat tat tct      1488
Cys Lys Ala Lys Arg Asp Thr Pro Thr Ser Cys Thr Val Asp Tyr Ser
                485                 490                 495 act gtg tat ttt gtc aac att gaa gtc tgg gta gaa gca gag aat gcc      1536
Thr Val Tyr Phe Val Asn Ile Glu Val Trp Val Glu Ala Glu Asn Ala
            500                 505                 510 ctt ggg aag gtt aca tca gat cat atc aat ttt gat cct gta tat aaa      1584
Leu Gly Lys Val Thr Ser Asp His Ile Asn Phe Asp Pro Val Tyr Lys
        515                 520                 525 gtg aag ccc aat ccg cca cat aat tta tca gtg atc aac tca gag gaa      1632
Val Lys Pro Asn Pro Pro His Asn Leu Ser Val Ile Asn Ser Glu Glu
530                 535                 540 ctg tct agt atc tta aaa ttg aca tgg acc aac cca agt att aag agt      1680
Leu Ser Ser Ile Leu Lys Leu Thr Trp Thr Asn Pro Ser Ile Lys Ser
545                 550                 555                 560 gtt ata ata cta aaa tat aac att caa tat agg acc aaa gat gcc tca      1728
Val Ile Ile Leu Lys Tyr Asn Ile Gln Tyr Arg Thr Lys Asp Ala Ser
                565                 570                 575 act tgg agc cag att cct cct gaa gac aca gca tcc acc cga tct tca      1776
Thr Trp Ser Gln Ile Pro Pro Glu Asp Thr Ala Ser Thr Arg Ser Ser
            580                 585                 590
```

-continued

| | | |
|---|---|---|
| ttc act gtc caa gac ctt aaa cct ttt aca gaa tat gtg ttt agg att<br>Phe Thr Val Gln Asp Leu Lys Pro Phe Thr Glu Tyr Val Phe Arg Ile<br>               595                    600               605 | 1824 |
| cgc tgt atg aag gaa gat ggt aag gga tac tgg agt gac tgg agt gaa<br>Arg Cys Met Lys Glu Asp Gly Lys Gly Tyr Trp Ser Asp Trp Ser Glu<br>610                    615                    620 | 1872 |
| gaa gca agt ggg atc acc tat gaa gat aga cca tct aaa gca cca agt<br>Glu Ala Ser Gly Ile Thr Tyr Glu Asp Arg Pro Ser Lys Ala Pro Ser<br>625                   630                    635               640 | 1920 |
| ttc tgg tat aaa ata gat cca tcc cat act caa ggc tac aga act gta<br>Phe Trp Tyr Lys Ile Asp Pro Ser His Thr Gln Gly Tyr Arg Thr Val<br>               645                    650               655 | 1968 |
| caa ctc gtg tgg aag aca ttg cct cct ttt gaa gcc aat gga aaa atc<br>Gln Leu Val Trp Lys Thr Leu Pro Pro Phe Glu Ala Asn Gly Lys Ile<br>                   660                    665               670 | 2016 |
| ttg gat tat gaa gtg act ctc aca aga tgg aaa tca cat tta caa aat<br>Leu Asp Tyr Glu Val Thr Leu Thr Arg Trp Lys Ser His Leu Gln Asn<br>             675                    680               685 | 2064 |
| tac aca gtt aat gcc aca aaa ctg aca gta aat ctc aca aat gat cgc<br>Tyr Thr Val Asn Ala Thr Lys Leu Thr Val Asn Leu Thr Asn Asp Arg<br>690                      695                    700 | 2112 |
| tat cta gca acc cta aca gta aga aat ctt gtt ggc aaa tca gat gca<br>Tyr Leu Ala Thr Leu Thr Val Arg Asn Leu Val Gly Lys Ser Asp Ala<br>705                   710                   715               720 | 2160 |
| gct gtt tta act atc cct gcc tgt gac ttt caa gct act cac cct gta<br>Ala Val Leu Thr Ile Pro Ala Cys Asp Phe Gln Ala Thr His Pro Val<br>                   725        &ni730             735 | 2208 |
| atg gat ctt aaa gca ttc ccc aaa gat aac atg ctt tgg gtg gaa tgg<br>Met Asp Leu Lys Ala Phe Pro Lys Asp Asn Met Leu Trp Val Glu Trp<br>             740                    745               750 | 2256 |
| act act cca agg gaa tct gta aag aaa tat ata ctt gag tgg tgt gtg<br>Thr Thr Pro Arg Glu Ser Val Lys Lys Tyr Ile Leu Glu Trp Cys Val<br>             755                   760               765 | 2304 |
| tta tca gat aaa gca ccc tgt atc aca gac tgg caa caa gaa gat ggt<br>Leu Ser Asp Lys Ala Pro Cys Ile Thr Asp Trp Gln Gln Glu Asp Gly<br>770                    775                    780 | 2352 |
| acc gtg cat cgc acc tat tta aga ggg aac tta gca gag agc aaa tgc<br>Thr Val His Arg Thr Tyr Leu Arg Gly Asn Leu Ala Glu Ser Lys Cys<br>785                   790                   795              800 | 2400 |
| tat ttg ata aca gtt act cca gta tat gct gat gga cca gga agc cct<br>Tyr Leu Ile Thr Val Thr Pro Val Tyr Ala Asp Gly Pro Gly Ser Pro<br>                   805                    810               815 | 2448 |
| gaa tcc ata aag gca tac ctt aaa caa gct cca cct tcc aaa gga cct<br>Glu Ser Ile Lys Ala Tyr Leu Lys Gln Ala Pro Pro Ser Lys Gly Pro<br>820                      825                    830 | 2496 |
| act gtt cgg aca aaa aaa gta ggg aaa aac gaa gct gtc tta gag tgg<br>Thr Val Arg Thr Lys Lys Val Gly Lys Asn Glu Ala Val Leu Glu Trp<br>             835                    840               845 | 2544 |
| gac caa ctt cct gtt gat gtt cag aat gga ttt atc aga aat tat act<br>Asp Gln Leu Pro Val Asp Val Gln Asn Gly Phe Ile Arg Asn Tyr Thr<br>850                      855                    860 | 2592 |
| ata ttt tat aga acc atc att gga aat gaa act gct gtg aat gtg gat<br>Ile Phe Tyr Arg Thr Ile Ile Gly Asn Glu Thr Ala Val Asn Val Asp<br>865                   870                   875               880 | 2640 |
| tct tcc cac aca gaa tat aca ttg tcc tct ttg act agt gac aca ttg<br>Ser Ser His Thr Glu Tyr Thr Leu Ser Ser Leu Thr Ser Asp Thr Leu<br>                   885                    890               895 | 2688 |
| tac atg gta cga atg gca gca tac aca gat gaa ggt ggg aag gat ggt<br>Tyr Met Val Arg Met Ala Ala Tyr Thr Asp Glu Gly Gly Lys Asp Gly | 2736 |

```
                900             905             910
cca gaa ttc act ttt act acc cca aag ttt gct caa gga gaa att gaa        2784
Pro Glu Phe Thr Phe Thr Thr Pro Lys Phe Ala Gln Gly Glu Ile Glu
        915             920             925 tcc ggg ggc gac aaa act cac aca tgc cca ccg tgc cca gca cct gaa        2832
Ser Gly Gly Asp Lys Thr His Thr Cys Pro Pro Cys Pro Ala Pro Glu
930             935             940 ctc ctg ggg gga ccg tca gtc ttc ctc ttc ccc cca aaa ccc aag gac        2880
Leu Leu Gly Gly Pro Ser Val Phe Leu Phe Pro Pro Lys Pro Lys Asp
945             950             955             960 acc ctc atg atc tcc cgg acc cct gag gtc aca tgc gtg gtg gtg gac        2928
Thr Leu Met Ile Ser Arg Thr Pro Glu Val Thr Cys Val Val Val Asp
            965             970             975 gtg agc cac gaa gac cct gag gtc aag ttc aac tgg tac gtg gac ggc        2976
Val Ser His Glu Asp Pro Glu Val Lys Phe Asn Trp Tyr Val Asp Gly
        980             985             990 gtg gag gtg cat aat gcc aag aca aag ccg cgg gag gag cag tac aac        3024
Val Glu Val His Asn Ala Lys Thr Lys Pro Arg Glu Glu Gln Tyr Asn
        995             1000            1005 agc acg tac cgt gtg gtc agc gtc ctc acc gtc ctg cac cag gac tgg        3072
Ser Thr Tyr Arg Val Val Ser Val Leu Thr Val Leu His Gln Asp Trp
    1010            1015            1020 ctg aat ggc aag gag tac aag tgc aag gtc tcc aac aaa gcc ctc cca        3120
Leu Asn Gly Lys Glu Tyr Lys Cys Lys Val Ser Asn Lys Ala Leu Pro
1025            1030            1035            1040 gcc ccc atc gag aaa acc atc tcc aaa gcc aaa ggg cag ccc cga gaa        3168
Ala Pro Ile Glu Lys Thr Ile Ser Lys Ala Lys Gly Gln Pro Arg Glu
            1045            1050            1055 cca cag gtg tac acc ctg ccc cca tcc cgg gat gag ctg acc aag aac        3216
Pro Gln Val Tyr Thr Leu Pro Pro Ser Arg Asp Glu Leu Thr Lys Asn
        1060            1065            1070 cag gtc agc ctg acc tgc ctg gtc aaa ggc ttc tat ccc agc gac atc        3264
Gln Val Ser Leu Thr Cys Leu Val Lys Gly Phe Tyr Pro Ser Asp Ile
        1075            1080            1085 gcc gtg gag tgg gag agc aat ggg cag ccg gag aac aac tac aag acc        3312
Ala Val Glu Trp Glu Ser Asn Gly Gln Pro Glu Asn Asn Tyr Lys Thr
    1090            1095            1100 acg cct ccc gtg ctg gac tcc gac ggc tcc ttc ttc ctc tac agc aag        3360
Thr Pro Pro Val Leu Asp Ser Asp Gly Ser Phe Phe Leu Tyr Ser Lys
1105            1110            1115            1120 ctc acc gtg gac aag agc agg tgg cag cag ggg aac gtc ttc tca tgc        3408
Leu Thr Val Asp Lys Ser Arg Trp Gln Gln Gly Asn Val Phe Ser Cys
            1125            1130            1135 tcc gtg atg cat gag gct ctg cac aac cac tac acg cag aag agc ctc        3456
Ser Val Met His Glu Ala Leu His Asn His Tyr Thr Gln Lys Ser Leu
        1140            1145            1150 tcc ctg tct ccg ggt aaa tga                                            3477
Ser Leu Ser Pro Gly Lys
        1155

<210> SEQ ID NO 26
<211> LENGTH: 1158
<212> TYPE: PRT
<213> ORGANISM: Homo sapiens

<400> SEQUENCE: 26

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30
```

-continued

```
Gly Val Leu Thr Ser Leu Pro Gly Asp Ser Val Thr Leu Thr Cys Pro
         35                  40                  45

Gly Val Glu Pro Glu Asp Asn Ala Thr Val His Trp Val Leu Arg Lys
 50                  55                  60

Pro Ala Gly Ser His Pro Ser Arg Trp Ala Gly Met Gly Arg Arg
 65                  70                  75                  80

Leu Leu Leu Arg Ser Val Gln Leu His Asp Ser Gly Asn Tyr Ser Cys
                 85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
             115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
                195                 200                 205

Gln Gly Cys Gly Ile Leu Gln Pro Asp Pro Pro Ala Asn Ile Thr Val
                210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
                275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Glu Leu Leu Asp Pro
                325                 330                 335

Cys Gly Tyr Ile Ser Pro Glu Ser Pro Val Val Gln Leu His Ser Asn
                340                 345                 350

Phe Thr Ala Val Cys Val Leu Lys Glu Lys Cys Met Asp Tyr Phe His
                355                 360                 365

Val Asn Ala Asn Tyr Ile Val Trp Lys Thr Asn His Phe Thr Ile Pro
                370                 375                 380

Lys Glu Gln Tyr Thr Ile Ile Asn Arg Thr Ala Ser Ser Val Thr Phe
385                 390                 395                 400

Thr Asp Ile Ala Ser Leu Asn Ile Gln Leu Thr Cys Asn Ile Leu Thr
                405                 410                 415

Phe Gly Gln Leu Glu Gln Asn Val Tyr Gly Ile Thr Ile Ile Ser Gly
                420                 425                 430

Leu Pro Pro Glu Lys Pro Lys Asn Leu Ser Cys Ile Val Asn Glu Gly
                435                 440                 445
```

-continued

```
Lys Lys Met Arg Cys Glu Trp Asp Gly Gly Arg Glu Thr His Leu Glu
    450                 455                 460
Thr Asn Phe Thr Leu Lys Ser Glu Trp Ala Thr His Lys Phe Ala Asp
465                 470                 475                 480
Cys Lys Ala Lys Arg Asp Thr Pro Thr Ser Cys Thr Val Asp Tyr Ser
                485                 490                 495
Thr Val Tyr Phe Val Asn Ile Glu Val Trp Val Glu Ala Glu Asn Ala
            500                 505                 510
Leu Gly Lys Val Thr Ser Asp His Ile Asn Phe Asp Pro Val Tyr Lys
        515                 520                 525
Val Lys Pro Asn Pro His Asn Leu Ser Val Ile Asn Ser Glu Glu
    530                 535                 540
Leu Ser Ser Ile Leu Lys Leu Thr Trp Thr Asn Pro Ser Ile Lys Ser
545                 550                 555                 560
Val Ile Ile Leu Lys Tyr Asn Ile Gln Tyr Arg Thr Lys Asp Ala Ser
                565                 570                 575
Thr Trp Ser Gln Ile Pro Pro Glu Asp Thr Ala Ser Thr Arg Ser Ser
            580                 585                 590
Phe Thr Val Gln Asp Leu Lys Pro Phe Thr Glu Tyr Val Phe Arg Ile
        595                 600                 605
Arg Cys Met Lys Glu Asp Gly Lys Gly Tyr Trp Ser Asp Trp Ser Glu
    610                 615                 620
Glu Ala Ser Gly Ile Thr Tyr Glu Asp Arg Pro Ser Lys Ala Pro Ser
625                 630                 635                 640
Phe Trp Tyr Lys Ile Asp Pro Ser His Thr Gln Gly Tyr Arg Thr Val
                645                 650                 655
Gln Leu Val Trp Lys Thr Leu Pro Pro Phe Glu Ala Asn Gly Lys Ile
            660                 665                 670
Leu Asp Tyr Glu Val Thr Leu Thr Arg Trp Lys Ser His Leu Gln Asn
        675                 680                 685
Tyr Thr Val Asn Ala Thr Lys Leu Thr Val Asn Leu Thr Asn Asp Arg
    690                 695                 700
Tyr Leu Ala Thr Leu Thr Val Arg Asn Leu Val Gly Lys Ser Asp Ala
705                 710                 715                 720
Ala Val Leu Thr Ile Pro Ala Cys Asp Phe Gln Ala Thr His Pro Val
                725                 730                 735
Met Asp Leu Lys Ala Phe Pro Lys Asp Asn Met Leu Trp Val Glu Trp
            740                 745                 750
Thr Thr Pro Arg Glu Ser Val Lys Lys Tyr Ile Leu Glu Trp Cys Val
        755                 760                 765
Leu Ser Asp Lys Ala Pro Cys Ile Thr Asp Trp Gln Gln Glu Asp Gly
    770                 775                 780
Thr Val His Arg Thr Tyr Leu Arg Gly Asn Leu Ala Glu Ser Lys Cys
785                 790                 795                 800
Tyr Leu Ile Thr Val Thr Pro Val Tyr Ala Asp Gly Pro Gly Ser Pro
                805                 810                 815
Glu Ser Ile Lys Ala Tyr Leu Lys Gln Ala Pro Ser Lys Gly Pro
            820                 825                 830
Thr Val Arg Thr Lys Lys Val Gly Lys Asn Glu Ala Val Leu Glu Trp
        835                 840                 845
Asp Gln Leu Pro Val Asp Val Gln Asn Gly Phe Ile Arg Asn Tyr Thr
    850                 855                 860
Ile Phe Tyr Arg Thr Ile Ile Gly Asn Glu Thr Ala Val Asn Val Asp
```

-continued

```
                865                 870                 875                 880
Ser Ser His Thr Glu Tyr Thr Leu Ser Ser Leu Thr Ser Asp Thr Leu
                    885                 890                 895

Tyr Met Val Arg Met Ala Ala Tyr Thr Asp Glu Gly Gly Lys Asp Gly
                900                 905                 910

Pro Glu Phe Thr Phe Thr Thr Pro Lys Phe Ala Gln Gly Glu Ile Glu
            915                 920                 925

Ser Gly Gly Asp Lys Thr His Thr Cys Pro Pro Cys Pro Ala Pro Glu
    930                 935                 940

Leu Leu Gly Gly Pro Ser Val Phe Leu Phe Pro Pro Lys Pro Lys Asp
945                 950                 955                 960

Thr Leu Met Ile Ser Arg Thr Pro Glu Val Thr Cys Val Val Val Asp
                965                 970                 975

Val Ser His Glu Asp Pro Glu Val Lys Phe Asn Trp Tyr Val Asp Gly
            980                 985                 990

Val Glu Val His Asn Ala Lys Thr Lys Pro Arg Glu Gln Tyr Asn
        995                 1000                1005

Ser Thr Tyr Arg Val Val Ser Val Leu Thr Val Leu His Gln Asp Trp
    1010                1015                1020

Leu Asn Gly Lys Glu Tyr Lys Cys Lys Val Ser Asn Lys Ala Leu Pro
1025                1030                1035                1040

Ala Pro Ile Glu Lys Thr Ile Ser Lys Ala Lys Gly Gln Pro Arg Glu
                1045                1050                1055

Pro Gln Val Tyr Thr Leu Pro Pro Ser Arg Asp Glu Leu Thr Lys Asn
            1060                1065                1070

Gln Val Ser Leu Thr Cys Leu Val Lys Gly Phe Tyr Pro Ser Asp Ile
    1075                1080                1085

Ala Val Glu Trp Glu Ser Asn Gly Gln Pro Glu Asn Asn Tyr Lys Thr
    1090                1095                1100

Thr Pro Pro Val Leu Asp Ser Asp Gly Ser Phe Phe Leu Tyr Ser Lys
1105                1110                1115                1120

Leu Thr Val Asp Lys Ser Arg Trp Gln Gln Gly Asn Val Phe Ser Cys
                1125                1130                1135

Ser Val Met His Glu Ala Leu His Asn His Tyr Thr Gln Lys Ser Leu
            1140                1145                1150

Ser Leu Ser Pro Gly Lys
        1155

<210> SEQ ID NO 27
<211> LENGTH: 2733
<212> TYPE: DNA
<213> ORGANISM: Homo sapiens
<220> FEATURE:
<221> NAME/KEY: CDS
<222> LOCATION: (1)...(2730)

<400> SEQUENCE: 27 atg gtg ctt ctg tgg tgt gta gtg agt ctc tac ttt tat gga atc ctg     48
Met Val Leu Leu Trp Cys Val Val Ser Leu Tyr Phe Tyr Gly Ile Leu
1               5                   10                  15 caa agt gat gcc tca gaa cgc tgc gat gac tgg gga cta gac acc atg     96
Gln Ser Asp Ala Ser Glu Arg Cys Asp Asp Trp Gly Leu Asp Thr Met
            20                  25                  30 agg caa atc caa gtg ttt gaa gat gag cca gct cgc atc aag tgc cca    144
Arg Gln Ile Gln Val Phe Glu Asp Glu Pro Ala Arg Ile Lys Cys Pro
        35                  40                  45
```

| | |
|---|---|
| ctc ttt gaa cac ttc ttg aaa ttc aac tac agc aca gcc cat tca gct<br>Leu Phe Glu His Phe Leu Lys Phe Asn Tyr Ser Thr Ala His Ser Ala<br>50                         55                     60 | 192 |
| ggc ctt act ctg atc tgg tat tgg act agg cag gac cgg gac ctt gag<br>Gly Leu Thr Leu Ile Trp Tyr Trp Thr Arg Gln Asp Arg Asp Leu Glu<br>65                       70                    75                     80 | 240 |
| gag cca att aac ttc cgc ctc ccc gag aac cgc att agt aag gag aaa<br>Glu Pro Ile Asn Phe Arg Leu Pro Glu Asn Arg Ile Ser Lys Glu Lys<br>                       85                    90                    95 | 288 |
| gat gtg ctg tgg ttc cgg ccc act ctc ctc aat gac act ggc aac tat<br>Asp Val Leu Trp Phe Arg Pro Thr Leu Leu Asn Asp Thr Gly Asn Tyr<br>            100                    105                    110 | 336 |
| acc tgc atg tta agg aac act aca tat tgc agc aaa gtt gca ttt ccc<br>Thr Cys Met Leu Arg Asn Thr Thr Tyr Cys Ser Lys Val Ala Phe Pro<br>        115                    120                    125 | 384 |
| ttg gaa gtt gtt caa aaa gac agc tgt ttc aat tcc ccc atg aaa ctc<br>Leu Glu Val Val Gln Lys Asp Ser Cys Phe Asn Ser Pro Met Lys Leu<br>130                      135                    140 | 432 |
| cca gtg cat aaa ctg tat ata gaa tat ggc att cag agg atc act tgt<br>Pro Val His Lys Leu Tyr Ile Glu Tyr Gly Ile Gln Arg Ile Thr Cys<br>145                    150                    155                    160 | 480 |
| cca aat gta gat gga tat ttt cct tcc agt gtc aaa ccg act atc act<br>Pro Asn Val Asp Gly Tyr Phe Pro Ser Ser Val Lys Pro Thr Ile Thr<br>                      165                    170                    175 | 528 |
| tgg tat atg ggc tgt tat aaa ata cag aat ttt aat aat gta ata ccc<br>Trp Tyr Met Gly Cys Tyr Lys Ile Gln Asn Phe Asn Asn Val Ile Pro<br>                    180                    185                    190 | 576 |
| gaa ggt atg aac ttg agt ttc ctc att gcc tta att tca aat aat gga<br>Glu Gly Met Asn Leu Ser Phe Leu Ile Ala Leu Ile Ser Asn Asn Gly<br>        195                    200                    205 | 624 |
| aat tac aca tgt gtt gtt aca tat cca gaa aat gga cgt acg ttt cat<br>Asn Tyr Thr Cys Val Val Thr Tyr Pro Glu Asn Gly Arg Thr Phe His<br>210                      215                    220 | 672 |
| ctc acc agg act ctg act gta aag gta gta ggc tct cca aaa aat gca<br>Leu Thr Arg Thr Leu Thr Val Lys Val Val Gly Ser Pro Lys Asn Ala<br>225                      230                    235                    240 | 720 |
| gtg ccc cct gtg atc cat tca cct aat gat cat gtg gtc tat gag aaa<br>Val Pro Pro Val Ile His Ser Pro Asn Asp His Val Val Tyr Glu Lys<br>                    245                    250                    255 | 768 |
| gaa cca gga gag gag cta ctc att ccc tgt acg gtc tat ttt agt ttt<br>Glu Pro Gly Glu Glu Leu Leu Ile Pro Cys Thr Val Tyr Phe Ser Phe<br>        260                    265                    270 | 816 |
| ctg atg gat tct cgc aat gag gtt tgg tgg acc att gat gga aaa aaa<br>Leu Met Asp Ser Arg Asn Glu Val Trp Trp Thr Ile Asp Gly Lys Lys<br>275                      280                    285 | 864 |
| cct gat gac atc act att gat gtc acc att aac gaa agt ata agt cat<br>Pro Asp Asp Ile Thr Ile Asp Val Thr Ile Asn Glu Ser Ile Ser His<br>290                      295                    300 | 912 |
| agt aga aca gaa gat gaa aca aga act cag att ttg agc atc aag aaa<br>Ser Arg Thr Glu Asp Glu Thr Arg Thr Gln Ile Leu Ser Ile Lys Lys<br>305                      310                    315                    320 | 960 |
| gtt acc tct gag gat ctc aag cgc agc tat gtc tgt cat gct aga agt<br>Val Thr Ser Glu Asp Leu Lys Arg Ser Tyr Val Cys His Ala Arg Ser<br>                    325                    330                    335 | 1008 |
| gcc aaa ggc gaa gtt gcc aaa gca gcc aag gtg aag cag aaa gtg cca<br>Ala Lys Gly Glu Val Ala Lys Ala Ala Lys Val Lys Gln Lys Val Pro<br>        340                    345                    350 | 1056 |
| gct cca aga tac aca gtg tcc ggt ggc gcg cct atg ctg agc gag gct<br>Ala Pro Arg Tyr Thr Val Ser Gly Gly Ala Pro Met Leu Ser Glu Ala<br>        355                    360                    365 | 1104 |

```
gat aaa tgc aag gaa cgt gaa gaa aaa ata att tta gtg tca tct gca    1152
Asp Lys Cys Lys Glu Arg Glu Glu Lys Ile Ile Leu Val Ser Ser Ala
    370                 375                 380 aat gaa att gat gtt cgt ccc tgt cct ctt aac cca aat gaa cac aaa    1200
Asn Glu Ile Asp Val Arg Pro Cys Pro Leu Asn Pro Asn Glu His Lys
385                 390                 395                 400 ggc act ata act tgg tat aag gat gac agc aag aca cct gta tct aca    1248
Gly Thr Ile Thr Trp Tyr Lys Asp Asp Ser Lys Thr Pro Val Ser Thr
                405                 410                 415 gaa caa gcc tcc agg att cat caa cac aaa gag aaa ctt tgg ttt gtt    1296
Glu Gln Ala Ser Arg Ile His Gln His Lys Glu Lys Leu Trp Phe Val
            420                 425                 430 cct gct aag gtg gag gat tca gga cat tac tat tgc gtg gta aga aat    1344
Pro Ala Lys Val Glu Asp Ser Gly His Tyr Tyr Cys Val Val Arg Asn
        435                 440                 445 tca tct tac tgc ctc aga att aaa ata agt gca aaa ttt gtg gag aat    1392
Ser Ser Tyr Cys Leu Arg Ile Lys Ile Ser Ala Lys Phe Val Glu Asn
    450                 455                 460 gag cct aac tta tgt tat aat gca caa gcc ata ttt aag cag aaa cta    1440
Glu Pro Asn Leu Cys Tyr Asn Ala Gln Ala Ile Phe Lys Gln Lys Leu
465                 470                 475                 480 ccc gtt gca gga gac gga gga ctt gtg tgc cct tat atg gag ttt ttt    1488
Pro Val Ala Gly Asp Gly Gly Leu Val Cys Pro Tyr Met Glu Phe Phe
                485                 490                 495 aaa aat gaa aat aat gag tta cct aaa tta cag tgg tat aag gat tgc    1536
Lys Asn Glu Asn Asn Glu Leu Pro Lys Leu Gln Trp Tyr Lys Asp Cys
            500                 505                 510 aaa cct cta ctt ctt gac aat ata cac ttt agt gga gtc aaa gat agg    1584
Lys Pro Leu Leu Leu Asp Asn Ile His Phe Ser Gly Val Lys Asp Arg
        515                 520                 525 ctc atc gtg atg aat gtg gct gaa aag cat aga ggg aac tat act tgt    1632
Leu Ile Val Met Asn Val Ala Glu Lys His Arg Gly Asn Tyr Thr Cys
    530                 535                 540 cat gca tcc tac aca tac ttg ggc aag caa tat cct att acc cgg gta    1680
His Ala Ser Tyr Thr Tyr Leu Gly Lys Gln Tyr Pro Ile Thr Arg Val
545                 550                 555                 560 ata gaa ttt att act cta gag gaa aac aaa ccc aca agg cct gtg att    1728
Ile Glu Phe Ile Thr Leu Glu Glu Asn Lys Pro Thr Arg Pro Val Ile
                565                 570                 575 gtg agc cca gct aat gag aca atg gaa gta gac ttg gga tcc cag ata    1776
Val Ser Pro Ala Asn Glu Thr Met Glu Val Asp Leu Gly Ser Gln Ile
            580                 585                 590 caa ttg atc tgt aat gtc acc ggc cag ttg agt gac att gct tac tgg    1824
Gln Leu Ile Cys Asn Val Thr Gly Gln Leu Ser Asp Ile Ala Tyr Trp
        595                 600                 605 aag tgg aat ggg tca gta att gat gaa gat gac cca gtg cta ggg gaa    1872
Lys Trp Asn Gly Ser Val Ile Asp Glu Asp Asp Pro Val Leu Gly Glu
    610                 615                 620 gac tat tac agt gtg gaa aat cct gca aac aaa aga agg agt acc ctc    1920
Asp Tyr Tyr Ser Val Glu Asn Pro Ala Asn Lys Arg Arg Ser Thr Leu
625                 630                 635                 640 atc aca gtg ctt aat ata tcg gaa att gag agt aga ttt tat aaa cat    1968
Ile Thr Val Leu Asn Ile Ser Glu Ile Glu Ser Arg Phe Tyr Lys His
                645                 650                 655 cca ttt acc tgt ttt gcc aag aat aca cat ggt ata gat gca gca tat    2016
Pro Phe Thr Cys Phe Ala Lys Asn Thr His Gly Ile Asp Ala Ala Tyr
            660                 665                 670 atc cag tta ata tat cca gtc act aat tcc gga gac aaa act cac aca    2064
Ile Gln Leu Ile Tyr Pro Val Thr Asn Ser Gly Asp Lys Thr His Thr
```

-continued

```
                    675                 680                 685
tgc cca ccg tgc cca gca cct gaa ctc ctg ggg gga ccg tca gtc ttc         2112
Cys Pro Pro Cys Pro Ala Pro Glu Leu Leu Gly Gly Pro Ser Val Phe
        690                 695                 700 ctc ttc ccc cca aaa ccc aag gac acc ctc atg atc tcc cgg acc cct         2160
Leu Phe Pro Pro Lys Pro Lys Asp Thr Leu Met Ile Ser Arg Thr Pro
705                 710                 715                 720 gag gtc aca tgc gtg gtg gtg gac gtg agc cac gaa gac cct gag gtc         2208
Glu Val Thr Cys Val Val Val Asp Val Ser His Glu Asp Pro Glu Val
                725                 730                 735 aag ttc aac tgg tac gtg gac ggc gtg gag gtg cat aat gcc aag aca         2256
Lys Phe Asn Trp Tyr Val Asp Gly Val Glu Val His Asn Ala Lys Thr
            740                 745                 750 aag ccg cgg gag gag cag tac aac agc acg tac cgt gtg gtc agc gtc         2304
Lys Pro Arg Glu Glu Gln Tyr Asn Ser Thr Tyr Arg Val Val Ser Val
        755                 760                 765 ctc acc gtc ctg cac cag gac tgg ctg aat ggc aag gag tac aag tgc         2352
Leu Thr Val Leu His Gln Asp Trp Leu Asn Gly Lys Glu Tyr Lys Cys
    770                 775                 780 aag gtc tcc aac aaa gcc ctc cca gcc ccc atc gag aaa acc atc tcc         2400
Lys Val Ser Asn Lys Ala Leu Pro Ala Pro Ile Glu Lys Thr Ile Ser
785                 790                 795                 800 aaa gcc aaa ggg cag ccc cga gaa cca cag gtg tac acc ctg ccc cca         2448
Lys Ala Lys Gly Gln Pro Arg Glu Pro Gln Val Tyr Thr Leu Pro Pro
                805                 810                 815 tcc cgg gag gag atg acc aag aac cag gtc agc ctg acc tgc ctg gtc         2496
Ser Arg Glu Glu Met Thr Lys Asn Gln Val Ser Leu Thr Cys Leu Val
            820                 825                 830 aaa ggc ttc tat ccc agc gac atc gcc gtg gag tgg gag agc aat ggg         2544
Lys Gly Phe Tyr Pro Ser Asp Ile Ala Val Glu Trp Glu Ser Asn Gly
        835                 840                 845 cag ccg gag aac aac tac aag acc acg cct ccc gtg ctg gac tcc gac         2592
Gln Pro Glu Asn Asn Tyr Lys Thr Thr Pro Pro Val Leu Asp Ser Asp
    850                 855                 860 ggc tcc ttc ttc ctc tat agc aag ctc acc gtg gac aag agc agg tgg         2640
Gly Ser Phe Phe Leu Tyr Ser Lys Leu Thr Val Asp Lys Ser Arg Trp
865                 870                 875                 880 cag cag ggg aac gtc ttc tca tgc tcc gtg atg cat gag gct ctg cac         2688
Gln Gln Gly Asn Val Phe Ser Cys Ser Val Met His Glu Ala Leu His
                885                 890                 895 aac cac tac acg cag aag agc ctc tcc ctg tct ccg ggt aaa                 2730
Asn His Tyr Thr Gln Lys Ser Leu Ser Leu Ser Pro Gly Lys
            900                 905                 910 tga                                                                      2733
```

<210> SEQ ID NO 28
<211> LENGTH: 910
<212> TYPE: PRT
<213> ORGANISM: Homo sapiens

<400> SEQUENCE: 28

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60
```

```
Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Pro Met Lys Leu
        130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
        210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
            275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Ser Gly Gly Ala Pro Met Leu Ser Glu Ala
            355                 360                 365

Asp Lys Cys Lys Glu Arg Glu Glu Lys Ile Ile Leu Val Ser Ser Ala
        370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
                405                 410                 415

Glu Gln Ala Ser Arg Ile His Gln His Lys Glu Lys Leu Trp Phe Val
            420                 425                 430

Pro Ala Lys Val Glu Asp Ser Gly His Tyr Tyr Cys Val Val Arg Asn
            435                 440                 445

Ser Ser Tyr Cys Leu Arg Ile Lys Ile Ser Ala Lys Phe Val Glu Asn
        450                 455                 460

Glu Pro Asn Leu Cys Tyr Asn Ala Gln Ala Ile Phe Lys Gln Lys Leu
465                 470                 475                 480
```

```
Pro Val Ala Gly Asp Gly Gly Leu Val Cys Pro Tyr Met Glu Phe Phe
                485                 490                 495

Lys Asn Glu Asn Asn Glu Leu Pro Lys Leu Gln Trp Tyr Lys Asp Cys
            500                 505                 510

Lys Pro Leu Leu Leu Asp Asn Ile His Phe Ser Gly Val Lys Asp Arg
        515                 520                 525

Leu Ile Val Met Asn Val Ala Glu Lys His Arg Gly Asn Tyr Thr Cys
    530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
                565                 570                 575

Val Ser Pro Ala Asn Glu Thr Met Glu Val Asp Leu Gly Ser Gln Ile
            580                 585                 590

Gln Leu Ile Cys Asn Val Thr Gly Gln Leu Ser Asp Ile Ala Tyr Trp
        595                 600                 605

Lys Trp Asn Gly Ser Val Ile Asp Glu Asp Asp Pro Val Leu Gly Glu
    610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
                645                 650                 655

Pro Phe Thr Cys Phe Ala Lys Asn Thr His Gly Ile Asp Ala Ala Tyr
            660                 665                 670

Ile Gln Leu Ile Tyr Pro Val Thr Asn Ser Gly Asp Lys Thr His Thr
        675                 680                 685

Cys Pro Pro Cys Pro Ala Pro Glu Leu Leu Gly Gly Pro Ser Val Phe
    690                 695                 700

Leu Phe Pro Pro Lys Pro Lys Asp Thr Leu Met Ile Ser Arg Thr Pro
705                 710                 715                 720

Glu Val Thr Cys Val Val Val Asp Val Ser His Glu Asp Pro Glu Val
                725                 730                 735

Lys Phe Asn Trp Tyr Val Asp Gly Val Glu Val His Asn Ala Lys Thr
            740                 745                 750

Lys Pro Arg Glu Glu Gln Tyr Asn Ser Thr Tyr Arg Val Val Ser Val
        755                 760                 765

Leu Thr Val Leu His Gln Asp Trp Leu Asn Gly Lys Glu Tyr Lys Cys
    770                 775                 780

Lys Val Ser Asn Lys Ala Leu Pro Ala Pro Ile Glu Lys Thr Ile Ser
785                 790                 795                 800

Lys Ala Lys Gly Gln Pro Arg Glu Pro Gln Val Tyr Thr Leu Pro Pro
                805                 810                 815

Ser Arg Glu Glu Met Thr Lys Asn Gln Val Ser Leu Thr Cys Leu Val
            820                 825                 830

Lys Gly Phe Tyr Pro Ser Asp Ile Ala Val Glu Trp Glu Ser Asn Gly
        835                 840                 845

Gln Pro Glu Asn Asn Tyr Lys Thr Thr Pro Pro Val Leu Asp Ser Asp
    850                 855                 860

Gly Ser Phe Phe Leu Tyr Ser Lys Leu Thr Val Asp Lys Ser Arg Trp
865                 870                 875                 880

Gln Gln Gly Asn Val Phe Ser Cys Ser Val Met His Glu Ala Leu His
                885                 890                 895

Asn His Tyr Thr Gln Lys Ser Leu Ser Leu Ser Pro Gly Lys
```

<210> SEQ ID NO 29
<211> LENGTH: 2355
<212> TYPE: DNA
<213> ORGANISM: Homo sapiens
<220> FEATURE:
<221> NAME/KEY: CDS
<222> LOCATION: (1)...(2352)

<400> SEQUENCE: 29

| | | |
|---|---|---|
| atg gtg tgg ctt tgc tct ggg ctc ctg ttc cct gtg agc tgc ctg gtc<br>Met Val Trp Leu Cys Ser Gly Leu Leu Phe Pro Val Ser Cys Leu Val<br>1                   5                       10                     15 | | 48 |
| ctg ctg cag gtg gca agc tct ggg aac atg aag gtc ttg cag gag ccc<br>Leu Leu Gln Val Ala Ser Ser Gly Asn Met Lys Val Leu Gln Glu Pro<br>                    20                            25                       30 | | 96 |
| acc tgc gtc tcc gac tac atg agc atc tct act tgc gag tgg aag atg<br>Thr Cys Val Ser Asp Tyr Met Ser Ile Ser Thr Cys Glu Trp Lys Met<br>                    35                            40                       45 | | 144 |
| aat ggt ccc acc aat tgc agc acc gag ctc cgc ctg ttg tac cag ctg<br>Asn Gly Pro Thr Asn Cys Ser Thr Glu Leu Arg Leu Leu Tyr Gln Leu<br>     50                            55                            60 | | 192 |
| gtt ttt ctg ctc tcc gaa gcc cac acg tgt atc cct gag aac aac gga<br>Val Phe Leu Leu Ser Glu Ala His Thr Cys Ile Pro Glu Asn Asn Gly<br>65                   70                       75                            80 | | 240 |
| ggc gcg ggg tgc gtg tgc cac ctg ctc atg gat gac gtg gtc agt gcg<br>Gly Ala Gly Cys Val Cys His Leu Leu Met Asp Asp Val Val Ser Ala<br>                                 85                            90                       95 | | 288 |
| gat aac tat aca ctg gac ctg tgg gct ggg cag cag ctg ctg tgg aag<br>Asp Asn Tyr Thr Leu Asp Leu Trp Ala Gly Gln Gln Leu Leu Trp Lys<br>                         100                             105                      110 | | 336 |
| ggc tcc ttc aag ccc agc gag cat gtg aaa ccc agg gcc cca gga aac<br>Gly Ser Phe Lys Pro Ser Glu His Val Lys Pro Arg Ala Pro Gly Asn<br>               115                            120                          125 | | 384 |
| ctg aca gtt cac acc aat gtc tcc gac act ctg ctg ctg acc tgg agc<br>Leu Thr Val His Thr Asn Val Ser Asp Thr Leu Leu Leu Thr Trp Ser<br>         130                          135                            140 | | 432 |
| aac ccg tat ccc cct gac aat tac ctg tat aat cat ctc acc tat gca<br>Asn Pro Tyr Pro Pro Asp Asn Tyr Leu Tyr Asn His Leu Thr Tyr Ala<br>145                    150                       155                           160 | | 480 |
| gtc aac att tgg agt gaa aac gac ccg gca gat ttc aga atc tat aac<br>Val Asn Ile Trp Ser Glu Asn Asp Pro Ala Asp Phe Arg Ile Tyr Asn<br>                                      165                            170                      175 | | 528 |
| gtg acc tac cta gaa ccc tcc ctc cgc atc gca gcc agc acc ctg aag<br>Val Thr Tyr Leu Glu Pro Ser Leu Arg Ile Ala Ala Ser Thr Leu Lys<br>                       180                             185                      190 | | 576 |
| tct ggg att tcc tac agg gca cgg gtg agg gcc tgg gct cag agc tat<br>Ser Gly Ile Ser Tyr Arg Ala Arg Val Arg Ala Trp Ala Gln Ser Tyr<br>               195                            200                          205 | | 624 |
| aac acc acc tgg agt gag tgg agc ccc agc acc aag tgg cac aac tcc<br>Asn Thr Thr Trp Ser Glu Trp Ser Pro Ser Thr Lys Trp His Asn Ser<br>         210                          215                            220 | | 672 |
| tac agg gag ccc ttc gag cag tcc ggt ggg ggc ggg ggc gcc gcg cct<br>Tyr Arg Glu Pro Phe Glu Gln Ser Gly Gly Gly Gly Gly Ala Ala Pro<br>225                    230                       235                           240 | | 720 |
| acg gaa act cag cca cct gtg aca aat ttg agt gtc tct gtt gaa aac<br>Thr Glu Thr Gln Pro Pro Val Thr Asn Leu Ser Val Ser Val Glu Asn<br>                                      245                            250                      255 | | 768 |
| ctc tgc aca gta ata tgg aca tgg aat cca ccc gag gga gcc agc tca<br>Leu Cys Thr Val Ile Trp Thr Trp Asn Pro Pro Glu Gly Ala Ser Ser | | 816 |

-continued

```
            260                 265                 270
aat tgt agt cta tgg tat ttt agt cat ttt ggc gac aaa caa gat aag      864
Asn Cys Ser Leu Trp Tyr Phe Ser His Phe Gly Asp Lys Gln Asp Lys
        275                 280                 285 aaa ata gct ccg gaa act cgt cgt tca ata gaa gta ccc ctg aat gag      912
Lys Ile Ala Pro Glu Thr Arg Arg Ser Ile Glu Val Pro Leu Asn Glu
    290                 295                 300 agg att tgt ctg caa gtg ggg tcc cag tgt agc acc aat gag agt gag      960
Arg Ile Cys Leu Gln Val Gly Ser Gln Cys Ser Thr Asn Glu Ser Glu
305                 310                 315                 320 aag cct agc att ttg gtt gaa aaa tgc atc tca ccc cca gaa ggt gat     1008
Lys Pro Ser Ile Leu Val Glu Lys Cys Ile Ser Pro Pro Glu Gly Asp
            325                 330                 335 cct gag tct gct gtg act gag ctt caa tgc att tgg cac aac ctg agc     1056
Pro Glu Ser Ala Val Thr Glu Leu Gln Cys Ile Trp His Asn Leu Ser
        340                 345                 350 tac atg aag tgt tct tgg ctc cct gga agg aat acc agt ccc gac act     1104
Tyr Met Lys Cys Ser Trp Leu Pro Gly Arg Asn Thr Ser Pro Asp Thr
    355                 360                 365 aac tat act ctc tac tat tgg cac aga agc ctg gaa aaa att cat caa     1152
Asn Tyr Thr Leu Tyr Tyr Trp His Arg Ser Leu Glu Lys Ile His Gln
370                 375                 380 tgt gaa aac atc ttt aga gaa ggc caa tac ttt ggt tgt tcc ttt gat     1200
Cys Glu Asn Ile Phe Arg Glu Gly Gln Tyr Phe Gly Cys Ser Phe Asp
385                 390                 395                 400 ctg acc aaa gtg aag gat tcc agt ttt gaa caa cac agt gtc caa ata     1248
Leu Thr Lys Val Lys Asp Ser Ser Phe Glu Gln His Ser Val Gln Ile
            405                 410                 415 atg gtc aag gat aat gca gga aaa att aaa cca tcc ttc aat ata gtg     1296
Met Val Lys Asp Asn Ala Gly Lys Ile Lys Pro Ser Phe Asn Ile Val
        420                 425                 430 cct tta act tcc cgt gtg aaa cct gat cct cca cat att aaa aac ctc     1344
Pro Leu Thr Ser Arg Val Lys Pro Asp Pro Pro His Ile Lys Asn Leu
    435                 440                 445 tcc ttc cac aat gat gac cta tat gtg caa tgg gag aat cca cag aat     1392
Ser Phe His Asn Asp Asp Leu Tyr Val Gln Trp Glu Asn Pro Gln Asn
450                 455                 460 ttt att agc aga tgc cta ttt tat gaa gta gaa gtc aat aac agc caa     1440
Phe Ile Ser Arg Cys Leu Phe Tyr Glu Val Glu Val Asn Asn Ser Gln
465                 470                 475                 480 act gag aca cat aat gtt ttc tac gtc caa gag gct aaa tgt gag aat     1488
Thr Glu Thr His Asn Val Phe Tyr Val Gln Glu Ala Lys Cys Glu Asn
            485                 490                 495 cca gaa ttt gag aga aat gtg gag aat aca tct tgt ttc atg gtc cct     1536
Pro Glu Phe Glu Arg Asn Val Glu Asn Thr Ser Cys Phe Met Val Pro
        500                 505                 510 ggt gtt ctt cct gat act ttg aac aca gtc aga ata aga gtc aaa aca     1584
Gly Val Leu Pro Asp Thr Leu Asn Thr Val Arg Ile Arg Val Lys Thr
    515                 520                 525 aat aag tta tgc tat gag gat gac aaa ctc tgg agt aat tgg agc caa     1632
Asn Lys Leu Cys Tyr Glu Asp Asp Lys Leu Trp Ser Asn Trp Ser Gln
530                 535                 540 gaa atg agt ata ggt aag aag cgc aat tcc aca acc gga gac aaa act     1680
Glu Met Ser Ile Gly Lys Lys Arg Asn Ser Thr Thr Gly Asp Lys Thr
545                 550                 555                 560 cac aca tgc cca ccg tgc cca gca cct gaa ctc ctg ggg gga ccg tca     1728
His Thr Cys Pro Pro Cys Pro Ala Pro Glu Leu Leu Gly Gly Pro Ser
            565                 570                 575 gtc ttc ctc ttc ccc cca aaa ccc aag gac acc ctc atg atc tcc cgg     1776
```

-continued

```
Val Phe Leu Phe Pro Pro Lys Pro Lys Asp Thr Leu Met Ile Ser Arg
            580                 585                 590 acc cct gag gtc aca tgc gtg gtg gtg gac gtg agc cac gaa gac cct      1824
Thr Pro Glu Val Thr Cys Val Val Val Asp Val Ser His Glu Asp Pro
        595                 600                 605 gag gtc aag ttc aac tgg tac gtg gac ggc gtg gag gtg cat aat gcc      1872
Glu Val Lys Phe Asn Trp Tyr Val Asp Gly Val Glu Val His Asn Ala
    610                 615                 620 aag aca aag ccg cgg gag gag cag tac aac agc acg tac cgt gtg gtc      1920
Lys Thr Lys Pro Arg Glu Glu Gln Tyr Asn Ser Thr Tyr Arg Val Val
625                 630                 635                 640 agc gtc ctc acc gtc ctg cac cag gac tgg ctg aat ggc aag gag tac      1968
Ser Val Leu Thr Val Leu His Gln Asp Trp Leu Asn Gly Lys Glu Tyr
            645                 650                 655 aag tgc aag gtc tcc aac aaa gcc ctc cca gcc ccc atc gag aaa acc      2016
Lys Cys Lys Val Ser Asn Lys Ala Leu Pro Ala Pro Ile Glu Lys Thr
        660                 665                 670 atc tcc aaa gcc aaa ggg cag ccc cga gaa cca cag gtg tac acc ctg      2064
Ile Ser Lys Ala Lys Gly Gln Pro Arg Glu Pro Gln Val Tyr Thr Leu
    675                 680                 685 ccc cca tcc cgg gag gag atg acc aag aac cag gtc agc ctg acc tgc      2112
Pro Pro Ser Arg Glu Glu Met Thr Lys Asn Gln Val Ser Leu Thr Cys
690                 695                 700 ctg gtc aaa ggc ttc tat ccc agc gac atc gcc gtg gag tgg gag agc      2160
Leu Val Lys Gly Phe Tyr Pro Ser Asp Ile Ala Val Glu Trp Glu Ser
705                 710                 715                 720 aat ggg cag ccg gag aac aac tac aag acc acg cct ccc gtg ctg gac      2208
Asn Gly Gln Pro Glu Asn Asn Tyr Lys Thr Thr Pro Pro Val Leu Asp
            725                 730                 735 tcc gac ggc tcc ttc ttc ctc tat agc aag ctc acc gtg gac aag agc      2256
Ser Asp Gly Ser Phe Phe Leu Tyr Ser Lys Leu Thr Val Asp Lys Ser
        740                 745                 750 agg tgg cag cag ggg aac gtc ttc tca tgc tcc gtg atg cat gag gct      2304
Arg Trp Gln Gln Gly Asn Val Phe Ser Cys Ser Val Met His Glu Ala
    755                 760                 765 ctg cac aac cac tac acg cag aag agc ctc tcc ctg tct ccg ggt aaa      2352
Leu His Asn His Tyr Thr Gln Lys Ser Leu Ser Leu Ser Pro Gly Lys
770                 775                 780 tga                                                                   2355
```

<210> SEQ ID NO 30
<211> LENGTH: 784
<212> TYPE: PRT
<213> ORGANISM: Homo sapiens

<400> SEQUENCE: 30

```
Met Val Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
            85                  90                  95
```

-continued

```
Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
                180                 185                 190

Ser Gly Ile Ser Tyr Arg Ala Arg Val Arg Ala Trp Ala Gln Ser Tyr
            195                 200                 205

Asn Thr Thr Trp Ser Glu Trp Ser Pro Ser Thr Lys Trp His Asn Ser
    210                 215                 220

Tyr Arg Glu Pro Phe Glu Gln Ser Gly Gly Gly Gly Ala Ala Pro
225                 230                 235                 240

Thr Glu Thr Gln Pro Pro Val Thr Asn Leu Ser Val Ser Val Glu Asn
                245                 250                 255

Leu Cys Thr Val Ile Trp Thr Trp Asn Pro Pro Glu Gly Ala Ser Ser
            260                 265                 270

Asn Cys Ser Leu Trp Tyr Phe Ser His Phe Gly Asp Lys Gln Asp Lys
        275                 280                 285

Lys Ile Ala Pro Glu Thr Arg Arg Ser Ile Glu Val Pro Leu Asn Glu
    290                 295                 300

Arg Ile Cys Leu Gln Val Gly Ser Gln Cys Ser Thr Asn Glu Ser Glu
305                 310                 315                 320

Lys Pro Ser Ile Leu Val Glu Lys Cys Ile Ser Pro Pro Glu Gly Asp
                325                 330                 335

Pro Glu Ser Ala Val Thr Glu Leu Gln Cys Ile Trp His Asn Leu Ser
            340                 345                 350

Tyr Met Lys Cys Ser Trp Leu Pro Gly Arg Asn Thr Ser Pro Asp Thr
        355                 360                 365

Asn Tyr Thr Leu Tyr Tyr Trp His Arg Ser Leu Glu Lys Ile His Gln
    370                 375                 380

Cys Glu Asn Ile Phe Arg Glu Gly Gln Tyr Phe Gly Cys Ser Phe Asp
385                 390                 395                 400

Leu Thr Lys Val Lys Asp Ser Ser Phe Glu Gln His Ser Val Gln Ile
                405                 410                 415

Met Val Lys Asp Asn Ala Gly Lys Ile Lys Pro Ser Phe Asn Ile Val
            420                 425                 430

Pro Leu Thr Ser Arg Val Lys Pro Asp Pro Pro His Ile Lys Asn Leu
        435                 440                 445

Ser Phe His Asn Asp Asp Leu Tyr Val Gln Trp Glu Asn Pro Gln Asn
    450                 455                 460

Phe Ile Ser Arg Cys Leu Phe Tyr Glu Val Glu Val Asn Asn Ser Gln
465                 470                 475                 480

Thr Glu Thr His Asn Val Phe Tyr Val Gln Glu Ala Lys Cys Glu Asn
                485                 490                 495

Pro Glu Phe Glu Arg Asn Val Glu Asn Thr Ser Cys Phe Met Val Pro
            500                 505                 510

Gly Val Leu Pro Asp Thr Leu Asn Thr Val Arg Ile Arg Val Lys Thr
```

-continued

```
                515                 520                 525
Asn Lys Leu Cys Tyr Glu Asp Asp Lys Leu Trp Ser Asn Trp Ser Gln
            530                 535                 540

Glu Met Ser Ile Gly Lys Lys Arg Asn Ser Thr Thr Gly Asp Lys Thr
545                 550                 555                 560

His Thr Cys Pro Pro Cys Pro Ala Pro Glu Leu Leu Gly Gly Pro Ser
                565                 570                 575

Val Phe Leu Phe Pro Pro Lys Pro Lys Asp Thr Leu Met Ile Ser Arg
            580                 585                 590

Thr Pro Glu Val Thr Cys Val Val Val Asp Val Ser His Glu Asp Pro
        595                 600                 605

Glu Val Lys Phe Asn Trp Tyr Val Asp Gly Val Glu Val His Asn Ala
610                 615                 620

Lys Thr Lys Pro Arg Glu Glu Gln Tyr Asn Ser Thr Tyr Arg Val Val
625                 630                 635                 640

Ser Val Leu Thr Val Leu His Gln Asp Trp Leu Asn Gly Lys Glu Tyr
                645                 650                 655

Lys Cys Lys Val Ser Asn Lys Ala Leu Pro Ala Pro Ile Glu Lys Thr
            660                 665                 670

Ile Ser Lys Ala Lys Gly Gln Pro Arg Glu Pro Gln Val Tyr Thr Leu
        675                 680                 685

Pro Pro Ser Arg Glu Glu Met Thr Lys Asn Gln Val Ser Leu Thr Cys
690                 695                 700

Leu Val Lys Gly Phe Tyr Pro Ser Asp Ile Ala Val Glu Trp Glu Ser
705                 710                 715                 720

Asn Gly Gln Pro Glu Asn Asn Tyr Lys Thr Thr Pro Pro Val Leu Asp
                725                 730                 735

Ser Asp Gly Ser Phe Phe Leu Tyr Ser Lys Leu Thr Val Asp Lys Ser
            740                 745                 750

Arg Trp Gln Gln Gly Asn Val Phe Ser Cys Ser Val Met His Glu Ala
        755                 760                 765

Leu His Asn His Tyr Thr Gln Lys Ser Leu Ser Leu Ser Pro Gly Lys
    770                 775                 780

<210> SEQ ID NO 31
<211> LENGTH: 2382
<212> TYPE: DNA
<213> ORGANISM: Homo sapiens
<220> FEATURE:
<221> NAME/KEY: CDS
<222> LOCATION: (1)...(2379)

<400> SEQUENCE: 31 atg gtg tgg ccg gcg cgg ctc tgc ggg ctg tgg gcg ctg ctg ctc tgc      48
Met Val Trp Pro Ala Arg Leu Cys Gly Leu Trp Ala Leu Leu Leu Cys
1               5                  10                  15 gcc ggc ggc ggg ggc ggg ggc ggg ggc gcc gcg cct acg gaa act cag      96
Ala Gly Gly Gly Gly Gly Gly Gly Gly Ala Ala Pro Thr Glu Thr Gln
                20                  25                  30 cca cct gtg aca aat ttg agt gtc tct gtt gaa aac ctc tgc aca gta     144
Pro Pro Val Thr Asn Leu Ser Val Ser Val Glu Asn Leu Cys Thr Val
            35                  40                  45 ata tgg aca tgg aat cca ccc gag gga gcc agc tca aat tgt agt cta     192
Ile Trp Thr Trp Asn Pro Pro Glu Gly Ala Ser Ser Asn Cys Ser Leu
        50                  55                  60 tgg tat ttt agt cat ttt ggc gac aaa caa gat aag aaa ata gct ccg     240
Trp Tyr Phe Ser His Phe Gly Asp Lys Gln Asp Lys Lys Ile Ala Pro
```

-continued

```
                65                  70                  75                  80 gaa act cgt cgt tca ata gaa gta ccc ctg aat gag agg att tgt ctg         288
Glu Thr Arg Arg Ser Ile Glu Val Pro Leu Asn Glu Arg Ile Cys Leu
                    85                  90                  95 caa gtg ggg tcc cag tgt agc acc aat gag agt gag aag cct agc att         336
Gln Val Gly Ser Gln Cys Ser Thr Asn Glu Ser Glu Lys Pro Ser Ile
            100                 105                 110 ttg gtt gaa aaa tgc atc tca ccc cca gaa ggt gat cct gag tct gct         384
Leu Val Glu Lys Cys Ile Ser Pro Pro Glu Gly Asp Pro Glu Ser Ala
        115                 120                 125 gtg act gag ctt caa tgc att tgg cac aac ctg agc tac atg aag tgt         432
Val Thr Glu Leu Gln Cys Ile Trp His Asn Leu Ser Tyr Met Lys Cys
    130                 135                 140 tct tgg ctc cct gga agg aat acc agt ccc gac act aac tat act ctc         480
Ser Trp Leu Pro Gly Arg Asn Thr Ser Pro Asp Thr Asn Tyr Thr Leu
145                 150                 155                 160 tac tat tgg cac aga agc ctg gaa aaa att cat caa tgt gaa aac atc         528
Tyr Tyr Trp His Arg Ser Leu Glu Lys Ile His Gln Cys Glu Asn Ile
                    165                 170                 175 ttt aga gaa ggc caa tac ttt ggt tgt tcc ttt gat ctg acc aaa gtg         576
Phe Arg Glu Gly Gln Tyr Phe Gly Cys Ser Phe Asp Leu Thr Lys Val
            180                 185                 190 aag gat tcc agt ttt gaa caa cac agt gtc caa ata atg gtc aag gat         624
Lys Asp Ser Ser Phe Glu Gln His Ser Val Gln Ile Met Val Lys Asp
        195                 200                 205 aat gca gga aaa att aaa cca tcc ttc aat ata gtg cct tta act tcc         672
Asn Ala Gly Lys Ile Lys Pro Ser Phe Asn Ile Val Pro Leu Thr Ser
    210                 215                 220 cgt gtg aaa cct gat cct cca cat att aaa aac ctc tcc ttc cac aat         720
Arg Val Lys Pro Asp Pro Pro His Ile Lys Asn Leu Ser Phe His Asn
225                 230                 235                 240 gat gac cta tat gtg caa tgg gag aat cca cag aat ttt att agc aga         768
Asp Asp Leu Tyr Val Gln Trp Glu Asn Pro Gln Asn Phe Ile Ser Arg
                    245                 250                 255 tgc cta ttt tat gaa gta gaa gtc aat aac agc caa act gag aca cat         816
Cys Leu Phe Tyr Glu Val Glu Val Asn Asn Ser Gln Thr Glu Thr His
            260                 265                 270 aat gtt ttc tac gtc caa gag gct aaa tgt gag aat cca gaa ttt gag         864
Asn Val Phe Tyr Val Gln Glu Ala Lys Cys Glu Asn Pro Glu Phe Glu
        275                 280                 285 aga aat gtg gag aat aca tct tgt ttc atg gtc cct ggt gtt ctt cct         912
Arg Asn Val Glu Asn Thr Ser Cys Phe Met Val Pro Gly Val Leu Pro
    290                 295                 300 gat act ttg aac aca gtc aga ata aga gtc aaa aca aat aag tta tgc         960
Asp Thr Leu Asn Thr Val Arg Ile Arg Val Lys Thr Asn Lys Leu Cys
305                 310                 315                 320 tat gag gat gac aaa ctc tgg agt aat tgg agc caa gaa atg agt ata        1008
Tyr Glu Asp Asp Lys Leu Trp Ser Asn Trp Ser Gln Glu Met Ser Ile
                    325                 330                 335 ggt aag aag cgc aat tcc aca ggc gcg cct agt ggt gga ggt ggc cgg        1056
Gly Lys Lys Arg Asn Ser Thr Gly Ala Pro Ser Gly Gly Gly Gly Arg
            340                 345                 350 ccc gca agc tct ggg aac atg aag gtc ttg cag gag ccc acc tgc gtc        1104
Pro Ala Ser Ser Gly Asn Met Lys Val Leu Gln Glu Pro Thr Cys Val
        355                 360                 365 tcc gac tac atg agc atc tct act tgc gag tgg aag atg aat ggt ccc        1152
Ser Asp Tyr Met Ser Ile Ser Thr Cys Glu Trp Lys Met Asn Gly Pro
    370                 375                 380 acc aat tgc agc acc gag ctc cgc ctg ttg tac cag ctg gtt ttt ctg        1200
```

```
                                                        -continued

Thr Asn Cys Ser Thr Glu Leu Arg Leu Leu Tyr Gln Leu Val Phe Leu
385                 390                 395                 400 ctc tcc gaa gcc cac acg tgt atc cct gag aac aac gga ggc gcg ggg    1248
Leu Ser Glu Ala His Thr Cys Ile Pro Glu Asn Asn Gly Gly Ala Gly
                405                 410                 415 tgc gtg tgc cac ctg ctc atg gat gac gtg gtc agt gcg gat aac tat    1296
Cys Val Cys His Leu Leu Met Asp Asp Val Val Ser Ala Asp Asn Tyr
            420                 425                 430 aca ctg gac ctg tgg gct ggg cag cag ctg ctg tgg aag ggc tcc ttc    1344
Thr Leu Asp Leu Trp Ala Gly Gln Gln Leu Leu Trp Lys Gly Ser Phe
        435                 440                 445 aag ccc agc gag cat gtg aaa ccc agg gcc cca gga aac ctg aca gtt    1392
Lys Pro Ser Glu His Val Lys Pro Arg Ala Pro Gly Asn Leu Thr Val
    450                 455                 460 cac acc aat gtc tcc gac act ctg ctg ctg acc tgg agc aac ccg tat    1440
His Thr Asn Val Ser Asp Thr Leu Leu Leu Thr Trp Ser Asn Pro Tyr
465                 470                 475                 480 ccc cct gac aat tac ctg tat aat cat ctc acc tat gca gtc aac att    1488
Pro Pro Asp Asn Tyr Leu Tyr Asn His Leu Thr Tyr Ala Val Asn Ile
                485                 490                 495 tgg agt gaa aac gac ccg gca gat ttc aga atc tat aac gtg acc tac    1536
Trp Ser Glu Asn Asp Pro Ala Asp Phe Arg Ile Tyr Asn Val Thr Tyr
                500                 505                 510 cta gaa ccc tcc ctc cgc atc gca gcc agc acc ctg aag tct ggg att    1584
Leu Glu Pro Ser Leu Arg Ile Ala Ala Ser Thr Leu Lys Ser Gly Ile
        515                 520                 525 tcc tac agg gca cgg gtg agg gcc tgg gct cag tgc tat aac acc acc    1632
Ser Tyr Arg Ala Arg Val Arg Ala Trp Ala Gln Cys Tyr Asn Thr Thr
    530                 535                 540 tgg agt gag tgg agc ccc agc acc aag tgg cac aac tcc tac agg gag    1680
Trp Ser Glu Trp Ser Pro Ser Thr Lys Trp His Asn Ser Tyr Arg Glu
545                 550                 555                 560 ccc ttc gag cag tcc gga gac aaa act cac aca tgc cca ccg tgc cca    1728
Pro Phe Glu Gln Ser Gly Asp Lys Thr His Thr Cys Pro Pro Cys Pro
                565                 570                 575 gca cct gaa ctc ctg ggg gga ccg tca gtc ttc ctc ttc ccc cca aaa    1776
Ala Pro Glu Leu Leu Gly Gly Pro Ser Val Phe Leu Phe Pro Pro Lys
                580                 585                 590 ccc aag gac acc ctc atg atc tcc cgg acc cct gag gtc aca tgc gtg    1824
Pro Lys Asp Thr Leu Met Ile Ser Arg Thr Pro Glu Val Thr Cys Val
        595                 600                 605 gtg gtg gac gtg agc cac gaa gac cct gag gtc aag ttc aac tgg tac    1872
Val Val Asp Val Ser His Glu Asp Pro Glu Val Lys Phe Asn Trp Tyr
    610                 615                 620 gtg gac ggc gtg gag gtg cat aat gcc aag aca aag ccg cgg gag gag    1920
Val Asp Gly Val Glu Val His Asn Ala Lys Thr Lys Pro Arg Glu Glu
625                 630                 635                 640 cag tac aac agc acg tac cgt gtg gtc agc gtc ctc acc gtc ctg cac    1968
Gln Tyr Asn Ser Thr Tyr Arg Val Val Ser Val Leu Thr Val Leu His
                645                 650                 655 cag gac tgg ctg aat ggc aag gag tac aag tgc aag gtc tcc aac aaa    2016
Gln Asp Trp Leu Asn Gly Lys Glu Tyr Lys Cys Lys Val Ser Asn Lys
                660                 665                 670 gcc ctc cca gcc ccc atc gag aaa acc atc tcc aaa gcc aaa ggg cag    2064
Ala Leu Pro Ala Pro Ile Glu Lys Thr Ile Ser Lys Ala Lys Gly Gln
        675                 680                 685 ccc cga gaa cca cag gtg tac acc ctg ccc cca tcc cgg gag gag atg    2112
Pro Arg Glu Pro Gln Val Tyr Thr Leu Pro Pro Ser Arg Glu Glu Met
    690                 695                 700
```

-continued

| | | | | | | | | | | | | | | | |
|---|---|---|---|---|---|---|---|---|---|---|---|---|---|---|---|
| acc | aag | aac | cag | gtc | agc | ctg | acc | tgc | ctg | gtc | aaa | ggc | ttc | tat | ccc | 2160 |
| Thr | Lys | Asn | Gln | Val | Ser | Leu | Thr | Cys | Leu | Val | Lys | Gly | Phe | Tyr | Pro |
| 705 | | | | 710 | | | | | 715 | | | | | 720 | agc gac atc gcc gtg gag tgg gag agc aat ggg cag ccg gag aac aac    2208
Ser Asp Ile Ala Val Glu Trp Glu Ser Asn Gly Gln Pro Glu Asn Asn
            725                 730                 735 tac aag acc acg cct ccc gtg ctg gac tcc gac ggc tcc ttc ttc ctc    2256
Tyr Lys Thr Thr Pro Pro Val Leu Asp Ser Asp Gly Ser Phe Phe Leu
        740                 745                 750 tat agc aag ctc acc gtg gac aag agc agg tgg cag cag ggg aac gtc    2304
Tyr Ser Lys Leu Thr Val Asp Lys Ser Arg Trp Gln Gln Gly Asn Val
    755                 760                 765 ttc tca tgc tcc gtg atg cat gag gct ctg cac aac cac tac acg cag    2352
Phe Ser Cys Ser Val Met His Glu Ala Leu His Asn His Tyr Thr Gln
770                 775                 780 aag agc ctc tcc ctg tct ccg ggt aaa tga                            2382
Lys Ser Leu Ser Leu Ser Pro Gly Lys
785                 790

<210> SEQ ID NO 32
<211> LENGTH: 793
<212> TYPE: PRT
<213> ORGANISM: Homo sapiens

<400> SEQUENCE: 32

Met Val Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val
        35                  40                  45

Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

-continued

```
Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
            275                 280                 285

Arg Asn Val Glu Asn Thr Ser Cys Phe Met Val Pro Gly Val Leu Pro
            290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Gly Ala Pro Ser Gly Gly Gly Gly Arg
                340                 345                 350

Pro Ala Ser Ser Gly Asn Met Lys Val Leu Gln Glu Pro Thr Cys Val
            355                 360                 365

Ser Asp Tyr Met Ser Ile Ser Thr Cys Glu Trp Lys Met Asn Gly Pro
            370                 375                 380

Thr Asn Cys Ser Thr Glu Leu Arg Leu Leu Tyr Gln Leu Val Phe Leu
385                 390                 395                 400

Leu Ser Glu Ala His Thr Cys Ile Pro Glu Asn Asn Gly Gly Ala Gly
                405                 410                 415

Cys Val Cys His Leu Leu Met Asp Asp Val Val Ser Ala Asp Asn Tyr
            420                 425                 430

Thr Leu Asp Leu Trp Ala Gly Gln Gln Leu Leu Trp Lys Gly Ser Phe
            435                 440                 445

Lys Pro Ser Glu His Val Lys Pro Arg Ala Pro Gly Asn Leu Thr Val
            450                 455                 460

His Thr Asn Val Ser Asp Thr Leu Leu Leu Thr Trp Ser Asn Pro Tyr
465                 470                 475                 480

Pro Pro Asp Asn Tyr Leu Tyr Asn His Leu Thr Tyr Ala Val Asn Ile
                485                 490                 495

Trp Ser Glu Asn Asp Pro Ala Asp Phe Arg Ile Tyr Asn Val Thr Tyr
            500                 505                 510

Leu Glu Pro Ser Leu Arg Ile Ala Ala Ser Thr Leu Lys Ser Gly Ile
            515                 520                 525

Ser Tyr Arg Ala Arg Val Arg Ala Trp Ala Gln Cys Tyr Asn Thr Thr
            530                 535                 540

Trp Ser Glu Trp Ser Pro Ser Thr Lys Trp His Asn Ser Tyr Arg Glu
545                 550                 555                 560

Pro Phe Glu Gln Ser Gly Asp Lys Thr His Thr Cys Pro Pro Cys Pro
                565                 570                 575

Ala Pro Glu Leu Leu Gly Gly Pro Ser Val Phe Leu Phe Pro Pro Lys
            580                 585                 590

Pro Lys Asp Thr Leu Met Ile Ser Arg Thr Pro Glu Val Thr Cys Val
            595                 600                 605

Val Val Asp Val Ser His Glu Asp Pro Glu Val Lys Phe Asn Trp Tyr
            610                 615                 620

Val Asp Gly Val Glu Val His Asn Ala Lys Thr Lys Pro Arg Glu Glu
625                 630                 635                 640

Gln Tyr Asn Ser Thr Tyr Arg Val Val Ser Val Leu Thr Val Leu His
                645                 650                 655

Gln Asp Trp Leu Asn Gly Lys Glu Tyr Lys Cys Lys Val Ser Asn Lys
            660                 665                 670
```

-continued

| | | | | | | | | | | | |
|---|---|---|---|---|---|---|---|---|---|---|---|
|Ala|Leu|Pro|Ala|Pro|Ile|Glu|Lys|Thr|Ile|Ser|Lys|Ala|Lys|Gly|Gln
| | |675| | | |680| | | |685| |

Pro Arg Glu Pro Gln Val Tyr Thr Leu Pro Pro Ser Arg Glu Glu Met
690 695 700

Thr Lys Asn Gln Val Ser Leu Thr Cys Leu Val Lys Gly Phe Tyr Pro
705 710 715 720

Ser Asp Ile Ala Val Glu Trp Glu Ser Asn Gly Gln Pro Glu Asn Asn
725 730 735

Tyr Lys Thr Thr Pro Pro Val Leu Asp Ser Asp Gly Ser Phe Phe Leu
740 745 750

Tyr Ser Lys Leu Thr Val Asp Lys Ser Arg Trp Gln Gln Gly Asn Val
755 760 765

Phe Ser Cys Ser Val Met His Glu Ala Leu His Asn His Tyr Thr Gln
770 775 780

Lys Ser Leu Ser Leu Ser Pro Gly Lys
785 790

<210> SEQ ID NO 33
<211> LENGTH: 2703
<212> TYPE: DNA
<213> ORGANISM: Homo sapiens

<400> SEQUENCE: 33

```
atggtgttac tcagacttat ttgtttcata gctctactga tttcttctct ggaggctgat      60
aaatgcaagg aacgtgaaga aaaaataatt ttagtgtcat ctgcaaatga aattgatgtt     120
cgtccctgtc ctcttaaccc aaatgaacac aaaggcacta aacttggta taaggatgac     180
agcaagacac ctgtatctac agaacaagcc tccaggattc atcaaacaaa agagaaactt     240
tggtttgttc ctgctaaggt ggaggattca ggacattact attgcgtggt aagaaattca     300
tcttactgcc tcagaattaa aataagtgca aaatttgtgg agaatgagcc taacttatgt     360
tataatgcac aagccatatt taagcagaaa ctacccgttg caggagacgg aggacttgtg     420
tgcccttata tggagttttt taaaaatgaa aataatgagt acctaaaatt acagtggtat     480
aaggattgca aacctctact tcttgacaat atacacttta gtggagtcaa agataggctc     540
atcgtgatga atgtggctga aaagcataga gggaactata cttgtcatgc atcctacaca     600
tacttgggca agcaatatcc tattacccgg gtaatagaat ttattactct agaggaaaac     660
aaacccacaa ggcctgtgat tgtgagccca gctaatgaga caatggaagt agactttgga     720
tcccagatac aattgatctg taatgtcacc ggccagttga gtgacattgc ttactggaag     780
tggaatgggt cagtaattga tgaagatgac ccagtgctag ggaagactat tacagtgtg     840
gaaaatcctg caaacaaaag aaggagtacc ctcatcacag tgcttaatat atcggaaatt     900
gagagtagat tttataaaca tccatttacc tgttttgcca agaatacaca tggtatagat     960
gcagcatata tccagttaat atatccagtc actaattcag aacgctgcga tgactgggga    1020
ctagacacca tgaggcaaat ccaagtgttt gaagatgagc cagctcgcat caagtgccca    1080
ctctttgaac acttcttgaa attcaactac agcacagccc attcagctgg ccttactctg    1140
atctggtatt ggactaggca ggaccgggac cttgaggagc caattaactt ccgcctcccc    1200
gagaaccgca ttagtaagga aaagatgtg ctgtggttcc ggcccactct cctcaatgac    1260
actggcaact atacctgcat gttaaggaac actacatatt gcagcaaagt tgcatttccc    1320
ttggaagttg ttcaaaaaga cagctgtttc aattccccca tgaaactccc agtgcataaa    1380
ctgtatatag aatatggcat tcagaggatc acttgtccaa atgtagatgg atatttcct    1440
```

```
tccagtgtca aaccgactat cacttggtat atgggctgtt ataaaataca gaattttaat      1500
aatgtaatac ccgaaggtat gaacttgagt ttcctcattg ccttaatttc aaataatgga      1560
aattacacat gtgttgttac atatccagaa aatggacgta cgtttcatct caccaggact      1620
ctgactgtaa aggtagtagg ctctccaaaa aatgcagtgc ccctgtgat ccattcacct       1680
aatgatcatg tggtctatga gaagaaacca ggagaggagc tactcattcc ctgtacggtc      1740
tattttagtt ttctgatgga ttctcgcaat gaggtttggt ggaccattga tggaaaaaaa      1800
cctgatgaca tcactattga tgtcaccatt aacgaaagta taagtcatag tagaacagaa      1860
gatgaaacaa gaactcagat tttgagcatc aagaaagtta cctctgagga tctcaagcgc      1920
agctatgtct gtcatgctag aagtgccaaa ggcgaagttg ccaaagcagc caaggtgaag      1980
cagaaagtgc cagctccaag atacacagtg gaatccggag acaaaactca cacatgccca      2040
ccgtgcccag cacctgaact cctgggggga ccgtcagtct tcctcttccc cccaaaaccc      2100
aaggacaccc tcatgatctc ccggacccct gaggtcacat gcgtggtggt ggacgtgagc      2160
cacgaagacc ctgaggtcaa gttcaactgg tacgtggacg gcgtggaggt gcataatgcc      2220
aagacaaagc cgcgggagga gcagtacaac agcacgtacc gtgtggtcag cgtcctcacc      2280
gtcctgcacc aggactggct gaatggcaag gagtacaagt gcaaggtctc caacaaagcc      2340
ctcccagccc ccatcgagaa aaccatctcc aaagccaaag ggcagccccg agaaccacag      2400
gtgtacaccc tgcccccatc ccgggaggag atgaccaaga accaggtcag cctgacctgc      2460
ctggtcaaag gcttctatcc cagcgacatc gccgtggagt gggagagcaa tgggcagccg      2520
gagaacaact acaagaccac gcctcccgtg ctggactccg acggctcctt cttcctctat      2580
agcaagctca ccgtggacaa gagcaggtgg cagcagggga acgtcttctc atgctccgtg      2640
atgcatgagg ctctgcacaa ccactacacg cagaagagcc tctccctgtc tccgggtaaa      2700
tga                                                                   2703
```

<210> SEQ ID NO 34
<211> LENGTH: 900
<212> TYPE: PRT
<213> ORGANISM: Homo sapiens

<400> SEQUENCE: 34

```
Met Val Leu Leu Arg Leu Ile Cys Phe Ile Ala Leu Ile Ser Ser
1               5                   10                  15

Leu Glu Ala Asp Lys Cys Lys Glu Arg Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140
```

```
Glu Phe Phe Lys Asn Glu Asn Glu Leu Pro Lys Leu Gln Trp Tyr
145                 150                 155                 160

Lys Asp Cys Lys Pro Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
            195                 200                 205

Thr Arg Val Ile Glu Phe Ile Thr Leu Glu Glu Asn Lys Pro Thr Arg
            210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Pro Val
            260                 265                 270

Leu Gly Glu Asp Tyr Tyr Ser Val Glu Asn Pro Ala Asn Lys Arg Arg
    275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
            355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
    435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
    515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560
```

-continued

```
Asn Asp His Val Val Tyr Glu Lys Glu Pro Gly Glu Leu Leu Ile
            565                 570                 575
Pro Cys Thr Val Tyr Phe Ser Phe Leu Met Asp Ser Arg Asn Glu Val
            580                 585                 590
Trp Trp Thr Ile Asp Gly Lys Lys Pro Asp Asp Ile Thr Ile Asp Val
            595                 600                 605
Thr Ile Asn Glu Ser Ile Ser His Ser Arg Thr Glu Asp Thr Arg
            610                 615                 620
Thr Gln Ile Leu Ser Ile Lys Lys Val Thr Ser Glu Asp Leu Lys Arg
625                 630                 635                 640
Ser Tyr Val Cys His Ala Arg Ser Ala Lys Gly Glu Val Ala Lys Ala
                    645                 650                 655
Ala Lys Val Lys Gln Lys Val Pro Ala Pro Arg Tyr Thr Val Glu Ser
                    660                 665                 670
Gly Asp Lys Thr His Thr Cys Pro Pro Cys Pro Ala Pro Glu Leu Leu
                675                 680                 685
Gly Gly Pro Ser Val Phe Leu Phe Pro Pro Lys Pro Lys Asp Thr Leu
            690                 695                 700
Met Ile Ser Arg Thr Pro Glu Val Thr Cys Val Val Val Asp Val Ser
705                 710                 715                 720
His Glu Asp Pro Glu Val Lys Phe Asn Trp Tyr Val Asp Gly Val Glu
                    725                 730                 735
Val His Asn Ala Lys Thr Lys Pro Arg Glu Glu Gln Tyr Asn Ser Thr
                    740                 745                 750
Tyr Arg Val Val Ser Val Leu Thr Val Leu His Gln Asp Trp Leu Asn
                755                 760                 765
Gly Lys Glu Tyr Lys Cys Lys Val Ser Asn Lys Ala Leu Pro Ala Pro
            770                 775                 780
Ile Glu Lys Thr Ile Ser Lys Ala Lys Gly Gln Pro Arg Glu Pro Gln
785                 790                 795                 800
Val Tyr Thr Leu Pro Pro Ser Arg Glu Glu Met Thr Lys Asn Gln Val
                    805                 810                 815
Ser Leu Thr Cys Leu Val Lys Gly Phe Tyr Pro Ser Asp Ile Ala Val
                    820                 825                 830
Glu Trp Glu Ser Asn Gly Gln Pro Glu Asn Asn Tyr Lys Thr Thr Pro
                835                 840                 845
Pro Val Leu Asp Ser Asp Gly Ser Phe Phe Leu Tyr Ser Lys Leu Thr
            850                 855                 860
Val Asp Lys Ser Arg Trp Gln Gln Gly Asn Val Phe Ser Cys Ser Val
865                 870                 875                 880
Met His Glu Ala Leu His Asn His Tyr Thr Gln Lys Ser Leu Ser Leu
                    885                 890                 895
Ser Pro Gly Lys
            900
```

<210> SEQ ID NO 35
<211> LENGTH: 2709
<212> TYPE: DNA
<213> ORGANISM: Homo sapiens

<400> SEQUENCE: 35

```
atggtgttac tcagacttat ttgtttcata gctctactga tttcttctct ggaggctgat      60
aaatgcaagg aacgtgaaga aaaataatt ttagtgtcat ctgcaaatga aattgatgtt     120
cgtccctgtc ctcttaaccc aaatgaacac aaaggcacta aacttggta taaggatgac    180
```

-continued

```
agcaagacac ctgtatctac agaacaagcc tccaggattc atcaacacaa agagaaactt    240
tggtttgttc ctgctaaggt ggaggattca ggacattact attgcgtggt aagaaattca    300
tcttactgcc tcagaattaa aataagtgca aaatttgtgg agaatgagcc taacttatgt    360
tataatgcac aagccatatt taagcagaaa ctacccgttg caggagacgg aggacttgtg    420
tgcccttata tggagttttt taaaaatgaa aataatgagt tacctaaatt acagtggtat    480
aaggattgca aacctctact tcttgacaat atacacttta gtggagtcaa agataggctc    540
atcgtgatga atgtggctga aaagcataga gggaactata cttgtcatgc atcctacaca    600
tacttgggca agcaatatcc tattacccgg gtaatagaat ttattactct agaggaaaac    660
aaacccacaa ggcctgtgat tgtgagccca gctaatgaga caatggaagt agacttggga    720
tcccagatac aattgatctg taatgtcacc ggccagttga gtgacattgc ttactggaag    780
tggaatgggt cagtaattga tgaagatgac ccagtgctag gggaagacta ttacagtgtg    840
gaaaatcctg caaacaaaag aaggagtacc ctcatcacag tgcttaatat atcggaaatt    900
gagagtagat tttataaaca tccatttacc tgttttgcca agaatacaca tggtatagat    960
gcagcatata tccagttaat atatccagtc actaattcag aacgctgcga tgactgggga   1020
ctagacacca tgaggcaaat ccaagtgttt gaagatgagc cagctcgcat caagtgccca   1080
ctctttgaac acttcttgaa attcaactac agcacagccc attcagctgg ccttactctg   1140
atctggtatt ggactaggca ggaccgggac cttgaggagc caattaactt ccgcctcccc   1200
gagaaccgca ttagtaagga gaaagatgtg ctgtggttcc ggcccactct cctcaatgac   1260
actggcaact ataaacctgcat gttaaggaac actacatatt gcagcaaagt tgcatttccc   1320
ttggaagttg ttcaaaaaga cagctgtttc aattccccca tgaaactccc agtgcataaa   1380
ctgtatatag aatatggcat tcagaggatc acttgtccaa atgtagatgg atattttcct   1440
tccagtgtca aaccgactat cacttggtat atgggctgtt ataaaataca gaattttaat   1500
aatgtaatac ccgaaggtat gaacttgagt ttcctcattg ccttaatttc aaataatgga   1560
aattacacat gtgttgttac atatccagaa aatggacgta cgtttcatct caccaggact   1620
ctgactgtaa aggtagtagg ctctccaaaa aatgcagtgc cccctgtgat ccattcacct   1680
aatgatcatg tggtctatga aaagaacca ggagaggagc tactcattcc ctgtacggtc   1740 tatttagtt ttctgatgga ttctcgcaat gaggtttggt ggaccattga tggaaaaaaa   1800
cctgatgaca tcactattga tgtcaccatt aacgaaagta taagtcatag tagaacagaa   1860
gatgaaacaa gaactcagat tttgagcatc aagaaagtta cctctgagga tctcaagcgc   1920
agctatgtct gtcatgctag aagtgccaaa ggcgaagttg ccaaagcagc caaggtgaag   1980
cagaaagtgc cagctccaag atacacagtg gaatccggag agtccaaata cggtccgcca   2040
tgcccatcat gcccagcacc tgagttcctg gggggaccat cagtcttcct gttccccca   2100 aaacccaagg acactctcat gatctcccgg acccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaaagggca gccccgagag   2400
ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
```

|  |  |
|---|---|
| cagccggaga acaactacaa gaccacgcct cccgtgctgg actccgacgg ctccttcttc | 2580 |
| ctctacagca ggctaaccgt ggacaagagc aggtggcagg agggaatgt cttctcatgc | 2640 |
| tccgtgatgc atgaggctct gcacaaccac tacacacaga agagcctctc cctgtctctg | 2700 |
| ggtaaatga | 2709 |

<210> SEQ ID NO 36
<211> LENGTH: 902
<212> TYPE: PRT
<213> ORGANISM: Homo sapiens

<400> SEQUENCE: 36

```
Met Val Leu Leu Arg Leu Ile Cys Phe Ile Ala Leu Leu Ile Ser Ser
1               5                   10                  15

Leu Glu Ala Asp Lys Cys Lys Glu Arg Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335
```

-continued

```
Asp Asp Trp Gly Leu Asp Thr Met Arg Gln Ile Gln Val Phe Glu Asp
            340                 345                 350
Glu Pro Ala Arg Ile Lys Cys Pro Leu Phe Glu His Phe Leu Lys Phe
        355                 360                 365
Asn Tyr Ser Thr Ala His Ser Ala Gly Leu Thr Leu Ile Trp Tyr Trp
    370                 375                 380
Thr Arg Gln Asp Arg Asp Leu Glu Glu Pro Ile Asn Phe Arg Leu Pro
385                 390                 395                 400
Glu Asn Arg Ile Ser Lys Glu Lys Asp Val Leu Trp Phe Arg Pro Thr
                405                 410                 415
Leu Leu Asn Asp Thr Gly Asn Tyr Thr Cys Met Leu Arg Asn Thr Thr
            420                 425                 430
Tyr Cys Ser Lys Val Ala Phe Pro Leu Glu Val Val Gln Lys Asp Ser
        435                 440                 445
Cys Phe Asn Ser Pro Met Lys Leu Pro Val His Lys Leu Tyr Ile Glu
    450                 455                 460
Tyr Gly Ile Gln Arg Ile Thr Cys Pro Asn Val Asp Gly Tyr Phe Pro
465                 470                 475                 480
Ser Ser Val Lys Pro Thr Ile Thr Trp Tyr Met Gly Cys Tyr Lys Ile
                485                 490                 495
Gln Asn Phe Asn Asn Val Ile Pro Glu Gly Met Asn Leu Ser Phe Leu
            500                 505                 510
Ile Ala Leu Ile Ser Asn Asn Gly Asn Tyr Thr Cys Val Val Thr Tyr
        515                 520                 525
Pro Glu Asn Gly Arg Thr Phe His Leu Thr Arg Thr Leu Thr Val Lys
    530                 535                 540
Val Val Gly Ser Pro Lys Asn Ala Val Pro Pro Val Ile His Ser Pro
545                 550                 555                 560
Asn Asp His Val Val Tyr Glu Lys Glu Pro Gly Glu Glu Leu Leu Ile
                565                 570                 575
Pro Cys Thr Val Tyr Phe Ser Phe Leu Met Asp Ser Arg Asn Glu Val
            580                 585                 590
Trp Trp Thr Ile Asp Gly Lys Lys Pro Asp Asp Ile Thr Ile Asp Val
        595                 600                 605
Thr Ile Asn Glu Ser Ile Ser His Ser Arg Thr Glu Asp Glu Thr Arg
    610                 615                 620
Thr Gln Ile Leu Ser Ile Lys Lys Val Thr Ser Glu Asp Leu Lys Arg
625                 630                 635                 640
Ser Tyr Val Cys His Ala Arg Ser Ala Lys Gly Glu Val Ala Lys Ala
                645                 650                 655
Ala Lys Val Lys Gln Lys Val Pro Ala Pro Arg Tyr Thr Val Glu Ser
            660                 665                 670
Gly Glu Ser Lys Tyr Gly Pro Pro Cys Pro Ser Cys Pro Ala Pro Glu
        675                 680                 685
Phe Leu Gly Gly Pro Ser Val Phe Leu Phe Pro Pro Lys Pro Lys Asp
    690                 695                 700
Thr Leu Met Ile Ser Arg Thr Pro Glu Val Thr Cys Val Val Val Asp
705                 710                 715                 720
Val Ser Gln Glu Asp Pro Glu Val Gln Phe Asn Trp Tyr Val Asp Gly
                725                 730                 735
Val Glu Val His Asn Ala Lys Thr Lys Pro Arg Glu Glu Gln Phe Asn
            740                 745                 750
Ser Thr Tyr Arg Val Val Ser Val Leu Thr Val Leu His Gln Asp Trp
```

```
                    755                 760                 765
Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Met Thr Lys Asn
                805                 810                 815

Gln Val Ser Leu Thr Cys Leu Val Lys Gly Phe Tyr Pro Ser Asp Ile
                820                 825                 830

Ala Val Glu Trp Glu Ser Asn Gly Gln Pro Glu Asn Asn Tyr Lys Thr
            835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 37
<211> LENGTH: 2709
<212> TYPE: DNA
<213> ORGANISM: Homo sapiens

<400> SEQUENCE: 37
atggtgttac tcagacttat ttgtttcata gctctactga tttcttctct ggaggctgat      60
aaatgcaagg aacgtgaaga aaaataatt ttagtgtcat ctgcaaatga aattgatgtt     120
cgtccctgtc ctcttaaccc aaatgaacac aaaggcacta aacttggta taaggatgac     180 agcaagacac ctgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aaatttgtgg agaatgagcc taacttatgt     360
tataatgcac aagccatatt taagcagaaa ctacccgttg caggagacgg aggacttgtg     420
tgcccttata tggagttttt taaaaatgaa aataatgagt acctaaaatt acagtggtat     480
aaggattgca aacctctact tcttgacaat atacacttta gtggagtcaa agataggctc     540
atcgtgatga atgtggctga aaagcataga gggaactata cttgtcatgc atcctacaca     600
tacttgggca agcaatatcc tattacccgg gtaatagaat ttattactct agaggaaaac     660
aaacccacaa ggcctgtgat tgtgagccca gctaatgaga caatggaagt agacttggga     720
tcccagatac aattgatctg taatgtcacc ggccagttga gtgacattgc ttactggaag     780
tggaatgggt cagtaattga tgaagatgac ccagtgctag ggaagactta ttacagtgtg     840
gaaaatcctg caaacaaaag aaggagtacc ctcatcacag tgcttaatat atcggaaatt     900
gagagtagat tttataaaca tccatttacc tgttttgcca agaatacaca tggtatagat     960
gcagcatata tccagttaat atatccagtc actaattcag aacgctgcga tgactgggga    1020
ctagacacca tgaggcaaat ccaagtgttt gaagatgagc cagctcgcat caagtgccca    1080
ctctttgaac acttcttgaa attcaactac agcacagccc attcagctgg ccttactctg    1140
atctggtatt ggactaggca ggaccgggac cttgaggagc caattaactt ccgcctcccc    1200
gagaaccgca ttagtaagga aaagatgtg ctgtggttcc ggcccactct cctcaatgac    1260
```

-continued

```
actggcaact atacctgcat gttaaggaac actacatatt gcagcaaagt tgcatttccc      1320
ttggaagttg ttcaaaaaga cagctgtttc aattccccca tgaaactccc agtgcataaa      1380
ctgtatatag aatatggcat tcagaggatc acttgtccaa atgtagatgg atattttcct      1440
tccagtgtca aaccgactat cacttggtat atgggctgtt ataaaataca gaattttaat      1500
aatgtaatac ccgaaggtat gaacttgagt ttcctcattg ccttaatttc aaataatgga      1560
aattacacat gtgttgttac atatccagaa aatggacgta cgtttcatct caccaggact      1620
ctgactgtaa aggtagtagg ctctccaaaa aatgcagtgc ccctgtgat ccattcacct       1680 aatgatcatg tggtctatga gaaagaacca ggagaggagc tactcattcc ctgtacggtc      1740
tattttagtt ttctgatgga ttctcgcaat gaggtttggt ggaccattga tggaaaaaaa      1800
cctgatgaca tcactattga tgtcaccatt aacgaaagta taagtcatag tagaacagaa      1860
gatgaaacaa gaactcagat tttgagcatc aagaaagtta cctctgagga tctcaagcgc      1920
agctatgtct gtcatgctag aagtgccaaa ggcgaagttg ccaaagcagc caaggtgaag      1980
cagaaagtgc cagctccaag atacacagtg aatccggag agtccaaata cggtccgcca       2040
tgcccaccat gcccagcacc tgagttcctg gggggaccat cagtcttcct gttcccccca      2100
aaacccaagg acactctcat gatctcccgg acccctgagg tcacgtgcgt ggtggtggac      2160
gtgagccagg aagaccccga ggtccagttc aactggtacg tggatggcgt ggaggtgcat      2220
aatgccaaga caaagccgcg ggaggagcag ttcaacagca cgtaccgtgt ggtcagcgtc      2280
ctcaccgtcc tgcaccagga ctggctgaac ggcaaggagt acaagtgcaa ggtctccaac      2340
aaaggcctcc cgtcctccat cgagaaaacc atctccaaag ccaaagggca gccccgagag      2400
ccacaggtgt acaccctgcc cccatcccag gaggagatga ccaagaacca ggtcagcctg      2460
acctgcctgg tcaaaggctt ctaccccagc gacatcgccg tggagtggga gagcaatggg      2520
cagccggaga acaactacaa gaccacgcct cccgtgctgg actccgacgg ctccttcttc      2580
ctctacagca ggctaaccgt ggacaagagc aggtggcagg aggggaatgt cttctcatgc      2640
tccgtgatgc atgaggctct gcacaaccac tacacacaga gagcctctc cctgtctctg       2700 ggtaaatga                                                              2709
```

<210> SEQ ID NO 38
<211> LENGTH: 902
<212> TYPE: PRT
<213> ORGANISM: Homo sapiens

<400> SEQUENCE: 38

```
Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
                20                  25                  30

Ser Ser Ala Asn Glu Ile Asp Val Arg Pro Cys Pro Leu Asn Pro Asn
            35                  40                  45

Glu His Lys Gly Thr Ile Thr Trp Tyr Lys Asp Asp Ser Lys Thr Pro
        50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
                100                 105                 110
```

```
Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
        130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
                180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
        210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
                260                 265                 270

Leu Gly Glu Asp Tyr Tyr Ser Val Glu Asn Pro Ala Asn Lys Arg Arg
                275                 280                 285

Ser Thr Leu Ile Thr Val Leu Asn Ile Ser Glu Ile Glu Ser Arg Phe
        290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
                340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
        370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
                420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
        450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
                500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
```

```
                530                 535                 540
Val Val Gly Ser Pro Lys Asn Ala Val Pro Val Ile His Ser Pro
545                 550                 555                 560

Asn Asp His Val Val Tyr Glu Lys Glu Pro Gly Glu Leu Leu Ile
                565                 570                 575

Pro Cys Thr Val Tyr Phe Ser Phe Leu Met Asp Ser Arg Asn Glu Val
                580                 585                 590

Trp Trp Thr Ile Asp Gly Lys Lys Pro Asp Asp Ile Thr Ile Asp Val
                595                 600                 605

Thr Ile Asn Glu Ser Ile Ser His Ser Arg Thr Glu Asp Glu Thr Arg
610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
                660                 665                 670

Gly Glu Ser Lys Tyr Gly Pro Pro Cys Pro Pro Cys Pro Ala Pro Glu
                675                 680                 685

Phe Leu Gly Gly Pro Ser Val Phe Leu Phe Pro Pro Lys Pro Lys Asp
690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
                740                 745                 750

Ser Thr Tyr Arg Val Val Ser Val Leu Thr Val Leu His Gln Asp Trp
                755                 760                 765

Leu Asn Gly Lys Glu Tyr Lys Cys Lys Val Ser Asn Lys Gly Leu Pro
770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
                820                 825                 830

Ala Val Glu Trp Glu Ser Asn Gly Gln Pro Glu Asn Asn Tyr Lys Thr
                835                 840                 845

Thr Pro Pro Val Leu Asp Ser Asp Gly Ser Phe Phe Leu Tyr Ser Arg
850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
                900

<210> SEQ ID NO 39
<211> LENGTH: 2703
<212> TYPE: DNA
<213> ORGANISM: Homo sapiens

<400> SEQUENCE: 39
```

-continued

| | |
|---|---|
| atggtgcttc tgtggtgtgt agtgagtctc tacttttatg gaatcctgca aagtgatgcc | 60 |
| tcagaacgct gcgatgactg gggactagac accatgaggc aaatccaagt gtttgaagat | 120 |
| gagccagctc gcatcaagtg cccactcttt gaacacttct tgaaattcaa ctacagcaca | 180 |
| gcccattcag ctggccttac tctgatctgg tattggacta ggcaggaccg ggaccttgag | 240 |
| gagccaatta acttccgcct ccccgagaac cgcattagta aggagaaaga tgtgctgtgg | 300 |
| ttccggccca ctctcctcaa tgacactggc aactatacct gcatgttaag gaacactaca | 360 |
| tattgcagca aagttgcatt tcccttggaa gttgttcaaa agacagctg tttcaattcc | 420 |
| cccatgaaac tcccagtgca taaactgtat atagaatatg gcattcagag gatcacttgt | 480 |
| ccaaatgtag atggatattt tccttccagt gtcaaaccga ctatcacttg gtatatgggc | 540 |
| tgttataaaa tacagaattt taataatgta atacccgaag gtatgaactt gagtttcctc | 600 |
| attgccttaa tttcaaataa tggaaattac acatgtgttg ttacatatcc agaaaatgga | 660 |
| cgtacgtttc atctcaccag gactctgact gtaaaggtag taggctctcc aaaaaatgca | 720 |
| gtgcccctg tgatccattc acctaatgat catgtggtct atgagaaaga accaggagag | 780 |
| gagctactca ttccctgtac ggtctatttt agttttctga tggattctcg caatgaggtt | 840 |
| tggtggacca ttgatggaaa aaaacctgat gacatcacta ttgatgtcac cattaacgaa | 900 |
| agtataagtc atagtagaac agaagatgaa acaagaactc agattttgag catcaagaaa | 960 |
| gttacctctg aggatctcaa gcgcagctat gtctgtcatg ctagaagtgc caaaggcgaa | 1020 |
| gttgccaaag cagccaaggt gaagcagaaa gtgccagctc aagatacac agtggaaaaa | 1080 |
| tgcaaggaac gtgaagaaaa ataaatttta gtgagctcag caaatgaaat cgatgttcgt | 1140 |
| ccctgtcctc ttaacccaaa tgaacacaaa ggcactataa cttggtataa ggatgacagc | 1200 |
| aagacacctg tatctacaga acaagcctcc aggattcatc aacacaaaga gaaactttgg | 1260 |
| tttgttcctg ctaaggtgga ggattcagga cattactatt gcgtggtaag aaattcatct | 1320 |
| tactgcctca gaattaaaat aagtgcaaaa tttgtggaga atgagcctaa cttatgttat | 1380 |
| aatgcacaag ccatatttaa gcagaaacta cccgttgcag gagacggagg acttgtgtgc | 1440 |
| ccttatatgg agttttttaa aaatgaaaat aatgagttac ctaaattaca gtggtataag | 1500 |
| gattgcaaac tctacttct tgacaatata cactttagtg gagtcaaaga taggctcatc | 1560 |
| gtgatgaatg tggctgaaaa gcatagaggg aactatactt gtcatgcatc ctacacatac | 1620 |
| ttgggcaagc aatatcctat tacccgggta atagaattta ttactctaga ggaaaacaaa | 1680 |
| cccacaaggc ctgtgattgt gagcccagct aatgagacaa tggaagtaga cttgggatcc | 1740 |
| cagatacaat tgatctgtaa tgtcaccggc cagttgagtg acattgctta ctggaagtgg | 1800 |
| aatgggtcag taattgatga agatgaccca gtgctagggg aagactatta cagtgtggaa | 1860 |
| aatcctgcaa acaaaagaag gagtaccctc atcacagtgc ttaatatatc ggaaattgag | 1920 |
| agtagatttt ataaacatcc atttacctgt tttgccaaga atacacatgg tatagatgca | 1980 |
| gcatatatcc agttaatata tccagtcact aattccggag acaaaactca cacatgccca | 2040 |
| ccgtgcccag cacctgaact cctgggggga ccgtcagtct tcctcttccc cccaaaaccc | 2100 |
| aaggacaccc tcatgatctc ccggacccct gaggtcacat gcgtggtggt ggacgtgagc | 2160 |
| cacgaagacc ctgaggtcaa gttcaactgg tacgtggacg gcgtggaggt gcataatgcc | 2220 |
| aagacaaagc cgcgggagga gcagtacaac agcacgtacc gtgtggtcag cgtcctcacc | 2280 |
| gtcctgcacc aggactggct gaatggcaag gagtacaagt gcaaggtctc caacaaagcc | 2340 |
| ctcccagccc ccatcgagaa aaccatctcc aaagccaaag ggcagccccg agaaccacag | 2400 |

-continued

```
gtgtacaccc tgcccccatc ccgggatgag ctgaccaaga accaggtcag cctgacctgc      2460
ctggtcaaag gcttctatcc cagcgacatc gccgtggagt gggagagcaa tgggcagccg      2520
gagaacaact acaagaccac gcctcccgtg ctggactccg acggctcctt cttcctctac      2580
agcaagctca ccgtggacaa gagcaggtgg cagcagggga acgtcttctc atgctccgtg      2640
atgcatgagg ctctgcacaa ccactacacg cagaagagcc tctccctgtc tccgggtaaa      2700
tga                                                                    2703
```

<210> SEQ ID NO 40
<211> LENGTH: 900
<212> TYPE: PRT
<213> ORGANISM: Homo sapiens

<400> SEQUENCE: 40

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
```

```
                  305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
                340                 345                 350
Ala Pro Arg Tyr Thr Val Glu Lys Cys Lys Glu Arg Glu Glu Lys Ile
                355                 360                 365
Ile Leu Val Ser Ser Ala Asn Glu Ile Asp Val Arg Pro Cys Pro Leu
            370                 375                 380
Asn Pro Asn Glu His Lys Gly Thr Ile Thr Trp Tyr Lys Asp Asp Ser
385                 390                 395                 400
Lys Thr Pro Val Ser Thr Glu Gln Ala Ser Arg Ile His Gln His Lys
                405                 410                 415
Glu Lys Leu Trp Phe Val Pro Ala Lys Val Glu Asp Ser Gly His Tyr
                420                 425                 430
Tyr Cys Val Val Arg Asn Ser Ser Tyr Cys Leu Arg Ile Lys Ile Ser
            435                 440                 445
Ala Lys Phe Val Glu Asn Glu Pro Asn Leu Cys Tyr Asn Ala Gln Ala
450                 455                 460
Ile Phe Lys Gln Lys Leu Pro Val Ala Gly Asp Gly Leu Val Cys
465                 470                 475                 480
Pro Tyr Met Glu Phe Phe Lys Asn Glu Asn Asn Glu Leu Pro Lys Leu
                485                 490                 495
Gln Trp Tyr Lys Asp Cys Lys Pro Leu Leu Asp Asn Ile His Phe
            500                 505                 510
Ser Gly Val Lys Asp Arg Leu Ile Val Met Asn Val Ala Glu Lys His
            515                 520                 525
Arg Gly Asn Tyr Thr Cys His Ala Ser Tyr Thr Tyr Leu Gly Lys Gln
            530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
                565                 570                 575
Asp Leu Gly Ser Gln Ile Gln Leu Ile Cys Asn Val Thr Gly Gln Leu
            580                 585                 590
Ser Asp Ile Ala Tyr Trp Lys Trp Asn Gly Ser Val Ile Asp Glu Asp
            595                 600                 605
Asp Pro Val Leu Gly Glu Asp Tyr Tyr Ser Val Glu Asn Pro Ala Asn
            610                 615                 620
Lys Arg Arg Ser Thr Leu Ile Thr Val Leu Asn Ile Ser Glu Ile Glu
625                 630                 635                 640
Ser Arg Phe Tyr Lys His Pro Phe Thr Cys Phe Ala Lys Asn Thr His
                645                 650                 655
Gly Ile Asp Ala Ala Tyr Ile Gln Leu Ile Tyr Pro Val Thr Asn Ser
                660                 665                 670
Gly Asp Lys Thr His Thr Cys Pro Pro Cys Pro Ala Pro Glu Leu Leu
            675                 680                 685
Gly Gly Pro Ser Val Phe Leu Phe Pro Pro Lys Pro Lys Asp Thr Leu
            690                 695                 700
Met Ile Ser Arg Thr Pro Glu Val Thr Cys Val Val Val Asp Val Ser
705                 710                 715                 720
His Glu Asp Pro Glu Val Lys Phe Asn Trp Tyr Val Asp Gly Val Glu
                725                 730                 735
```

```
Val His Asn Ala Lys Thr Lys Pro Arg Glu Glu Gln Tyr Asn Ser Thr
            740                 745                 750

Tyr Arg Val Val Ser Val Leu Thr Val Leu His Gln Asp Trp Leu Asn
        755                 760                 765

Gly Lys Glu Tyr Lys Cys Lys Val Ser Asn Lys Ala Leu Pro Ala Pro
    770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
        835                 840                 845

Pro Val Leu Asp Ser Asp Gly Ser Phe Phe Leu Tyr Ser Lys Leu Thr
    850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900

<210> SEQ ID NO 41
<211> LENGTH: 2709
<212> TYPE: DNA
<213> ORGANISM: Homo sapiens

<400> SEQUENCE: 41
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta acttccgcct ccccgagaac cgcattagta aggagaaaga tgtgctgtgg     300
ttccggccca ctctcctcaa tgacactggc aactatacct gcatgttaag gaacactaca     360
tattgcagca aagttgcatt tcccttggaa gttgttcaaa agacagctg tttcaattcc     420 cccatgaaac tcccagtgca taaactgtat atagaatatg gcattcagag gatcacttgt     480
ccaaatgtag atggatattt tccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaatgca     720 gtgccccctg tgatccattc acctaatgat catgtggtct atgagaaaga accaggagag     780
gagctactca ttcctgtac ggtctatttt agttttctga tggattctcg caatgaggtt     840
tggtggacca ttgatggaaa aaacctgat gacatcacta ttgatgtcac cattaacgaa     900
agtataagtc atagtagaac agaagatgaa acaagaactc agattttgag catcaagaaa     960
gttacctctg aggatctcaa gcgcagctat gtctgtcatg ctagaagtgc caaaggcgaa    1020
gttgccaaag cagccaaggt gaagcagaaa gtgccagctc aagatacac agtggaaaaa    1080 tgcaaggaac gtgaagaaaa ataaattta gtgagctcag caaatgaaat cgatgttcgt    1140
```

-continued

```
ccctgtcctc ttaacccaaa tgaacacaaa ggcactataa cttggtataa ggatgacagc    1200
aagacacctg tatctacaga acaagcctcc aggattcatc aacacaaaga gaaactttgg    1260
tttgttcctg ctaaggtgga ggattcagga cattactatt gcgtggtaag aaattcatct    1320
tactgcctca gaattaaaat aagtgcaaaa tttgtggaga atgagcctaa cttatgttat    1380
aatgcacaag ccatatttaa gcagaaacta cccgttgcag gagacggagg acttgtgtgc    1440
ccttatatgg agttttttaa aaatgaaaat aatgagttac ctaaattaca gtggtataag    1500
gattgcaaac ctctacttct tgacaatata cactttagtg gagtcaaaga taggctcatc    1560
gtgatgaatg tggctgaaaa gcatagaggg aactatactt gtcatgcatc ctacacatac    1620
ttgggcaagc aatatcctat tacccgggta atagaattta ttactctaga ggaaaacaaa    1680
cccacaaggc ctgtgattgt gagcccagct aatgagacaa tggaagtaga cttgggatcc    1740
cagatacaat tgatctgtaa tgtcaccggc cagttgagtg acattgctta ctggaagtgg    1800
aatgggtcag taattgatga agatgaccca gtgctagggg aagactatta cagtgtggaa    1860
aatcctgcaa acaaaagaag gagtaccctc atcacagtgc ttaatatatc ggaaattgag    1920
agtagatttt ataaacatcc atttacctgt tttgccaaga atacacatgg tatagatgca    1980
gcatatatcc agttaatata tccagtcact aattccggag agtccaaata cggtccgcca    2040
tgcccatcat gcccagcacc tgagttcctg gggggaccat cagtcttcct gttcccccca    2100
aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga acaactacaa gaccacgcct cccgtgctgg actccgacgg ctccttcttc    2580
ctctacagca ggctaaccgt ggacaagagc aggtggcagg aggggaatgt cttctcatgc    2640
tccgtgatgc atgaggctct gcacaaccac tacacacaga gagcctctc cctgtctctg    2700 ggtaaatga                                                            2709
```

<210> SEQ ID NO 42
<211> LENGTH: 902
<212> TYPE: PRT
<213> ORGANISM: Homo sapiens

<400> SEQUENCE: 42

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
```

-continued

```
                85                  90                  95
Asp Val Leu Trp Phe Arg Pro Thr Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510
```

-continued

```
Ser Gly Val Lys Asp Arg Leu Ile Val Met Asn Val Ala Glu Lys His
            515                 520                 525
Arg Gly Asn Tyr Thr Cys His Ala Ser Tyr Thr Tyr Leu Gly Lys Gln
        530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
                565                 570                 575
Asp Leu Gly Ser Gln Ile Gln Leu Ile Cys Asn Val Thr Gly Gln Leu
            580                 585                 590
Ser Asp Ile Ala Tyr Trp Lys Trp Asn Gly Ser Val Ile Asp Glu Asp
        595                 600                 605
Asp Pro Val Leu Gly Glu Asp Tyr Tyr Ser Val Glu Asn Pro Ala Asn
    610                 615                 620
Lys Arg Arg Ser Thr Leu Ile Thr Val Leu Asn Ile Ser Glu Ile Glu
625                 630                 635                 640
Ser Arg Phe Tyr Lys His Pro Phe Thr Cys Phe Ala Lys Asn Thr His
                645                 650                 655
Gly Ile Asp Ala Ala Tyr Ile Gln Leu Ile Tyr Pro Val Thr Asn Ser
            660                 665                 670
Gly Glu Ser Lys Tyr Gly Pro Pro Cys Pro Ser Cys Pro Ala Pro Glu
        675                 680                 685
Phe Leu Gly Gly Pro Ser Val Phe Leu Phe Pro Pro Lys Pro Lys Asp
    690                 695                 700
Thr Leu Met Ile Ser Arg Thr Pro Glu Val Thr Cys Val Val Val Asp
705                 710                 715                 720
Val Ser Gln Glu Asp Pro Glu Val Gln Phe Asn Trp Tyr Val Asp Gly
                725                 730                 735
Val Glu Val His Asn Ala Lys Thr Lys Pro Arg Glu Glu Gln Phe Asn
            740                 745                 750
Ser Thr Tyr Arg Val Val Ser Val Leu Thr Val Leu His Gln Asp Trp
        755                 760                 765
Leu Asn Gly Lys Glu Tyr Lys Cys Lys Val Ser Asn Lys Gly Leu Pro
    770                 775                 780
Ser Ser Ile Glu Lys Thr Ile Ser Lys Ala Lys Gly Gln Pro Arg Glu
785                 790                 795                 800
Pro Gln Val Tyr Thr Leu Pro Pro Ser Gln Glu Glu Met Thr Lys Asn
                805                 810                 815
Gln Val Ser Leu Thr Cys Leu Val Lys Gly Phe Tyr Pro Ser Asp Ile
            820                 825                 830
Ala Val Glu Trp Glu Ser Asn Gly Gln Pro Glu Asn Asn Tyr Lys Thr
        835                 840                 845
Thr Pro Pro Val Leu Asp Ser Asp Gly Ser Phe Phe Leu Tyr Ser Arg
    850                 855                 860
Leu Thr Val Asp Lys Ser Arg Trp Gln Glu Gly Asn Val Phe Ser Cys
865                 870                 875                 880
Ser Val Met His Glu Ala Leu His Asn His Tyr Thr Gln Lys Ser Leu
                885                 890                 895
Ser Leu Ser Leu Gly Lys
            900

<210> SEQ ID NO 43
<211> LENGTH: 2709
```

-continued

<212> TYPE: DNA
<213> ORGANISM: Homo sapiens

<400> SEQUENCE: 43

| | | | | | |
|---|---|---|---|---|---|
| atggtgcttc | tgtggtgtgt | agtgagtctc | tacttttatg | gaatcctgca | aagtgatgcc | 60 |
| tcagaacgct | gcgatgactg | gggactagac | accatgaggc | aaatccaagt | gtttgaagat | 120 |
| gagccagctc | gcatcaagtg | cccactcttt | gaacacttct | tgaaattcaa | ctacagcaca | 180 |
| gcccattcag | ctggccttac | tctgatctgg | tattggacta | ggcaggaccg | ggaccttgag | 240 |
| gagccaatta | acttccgcct | ccccgagaac | cgcattagta | aggagaaaga | tgtgctgtgg | 300 |
| ttccggccca | ctctcctcaa | tgacactggc | aactatacct | gcatgttaag | gaacactaca | 360 |
| tattgcagca | aagttgcatt | tcccttggaa | gttgttcaaa | aagacagctg | tttcaattcc | 420 |
| cccatgaaac | tcccagtgca | taaactgtat | atagaatatg | gcattcagag | gatcacttgt | 480 |
| ccaaatgtag | atggatattt | tccttccagt | gtcaaaccga | ctatcacttg | gtatatgggc | 540 |
| tgttataaaa | tacagaattt | taataatgta | atacccgaag | gtatgaactt | gagtttcctc | 600 |
| attgccttaa | tttcaaataa | tggaaattac | acatgtgttg | ttacatatcc | agaaaatgga | 660 |
| cgtacgtttc | atctcaccag | gactctgact | gtaaaggtag | taggctctcc | aaaaaatgca | 720 |
| gtgcccctg | tgatccattc | acctaatgat | catgtggtct | atgagaaaga | accaggagag | 780 |
| gagctactca | ttccctgtac | ggtctatttt | agttttctga | tggattctcg | caatgaggtt | 840 |
| tggtggacca | ttgatggaaa | aaacctgat | gacatcacta | ttgatgtcac | cattaacgaa | 900 |
| agtataagtc | atagtagaac | agaagatgaa | acaagaactc | agattttgag | catcaagaaa | 960 |
| gttacctctg | aggatctcaa | gcgcagctat | gtctgtcatg | ctagaagtgc | aaaggcgaa | 1020 |
| gttgccaaag | cagccaaggt | gaagcagaaa | gtgccagctc | caagatacac | agtggaaaaa | 1080 |
| tgcaaggaac | gtgaagaaaa | aataattta | gtgagctcag | caaatgaaat | cgatgttcgt | 1140 |
| ccctgtcctc | ttaacccaaa | tgaacacaaa | ggcactataa | cttggtataa | ggatgacagc | 1200 |
| aagacacctg | tatctacaga | acaagcctcc | aggattcatc | aacacaaaga | gaaactttgg | 1260 |
| tttgttcctg | ctaaggtgga | ggattcagga | cattactatt | gcgtggtaag | aaattcatct | 1320 |
| tactgcctca | gaattaaaat | aagtgcaaaa | tttgtggaga | atgagcctaa | cttatgttat | 1380 |
| aatgcacaag | ccatatttaa | gcagaaacta | cccgttgcag | gagacggagg | acttgtgtgc | 1440 |
| ccttatatgg | agtttttaa | aaatgaaaat | aatgagttac | ctaaattaca | gtggtataag | 1500 |
| gattgcaaac | tctacttct | tgacaatata | cactttagtg | gagtcaaaga | taggctcatc | 1560 |
| gtgatgaatg | tggctgaaaa | gcatagaggg | aactatactt | gtcatgcatc | ctacacatac | 1620 |
| ttgggcaagc | aatatcctat | tacccgggta | atagaattta | ttactctaga | ggaaaacaaa | 1680 |
| cccacaaggc | ctgtgattgt | gagcccagct | aatgagacaa | tggaagtaga | cttgggatcc | 1740 |
| cagatacaat | tgatctgtaa | tgtcaccggc | cagttgagtg | acattgctta | ctggaagtgg | 1800 |
| aatgggtcag | taattgatga | agatgaccca | gtgctagggg | aagactatta | cagtgtggaa | 1860 |
| aatcctgcaa | acaaaagaag | gagtaccctc | atcacagtgc | ttaatatatc | ggaaattgag | 1920 |
| agtagatttt | ataaacatcc | atttacctgt | tttgccaaga | atacacatgg | tatagatgca | 1980 |
| gcatatatcc | agttaatata | tccagtcact | aattccggag | agtccaaata | cggtccgcca | 2040 |
| tgcccaccat | gcccagcacc | tgagttcctg | gggggaccat | cagtcttcct | gttccccca | 2100 |
| aaacccaagg | acactctcat | gatctcccgg | acccctgagg | tcacgtgcgt | ggtggtggac | 2160 |
| gtgagccagg | aagacccga | ggtccagttc | aactggtacg | tggatggcgt | ggaggtgcat | 2220 |

```
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga caactacaa gaccacgcct cccgtgctgg actccgacgg ctccttcttc    2580
ctctacagca ggctaaccgt ggacaagagc aggtggcagg aggggaatgt cttctcatgc    2640
tccgtgatgc atgaggctct gcacaaccac tacacacaga gagcctctc cctgtctctg    2700 ggtaaatga                                                           2709
```

<210> SEQ ID NO 44
<211> LENGTH: 902
<212> TYPE: PRT
<213> ORGANISM: Homo sapiens

<400> SEQUENCE: 44

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285
```

-continued

```
Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Lys Val Lys Gln Lys Val Pro
            340                 345                 350

Ala Pro Arg Tyr Thr Val Glu Lys Cys Lys Glu Arg Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Glu Ser Lys Tyr Gly Pro Pro Cys Pro Cys Pro Ala Pro Glu
        675                 680                 685

Phe Leu Gly Gly Pro Ser Val Phe Leu Phe Pro Pro Lys Pro Lys Asp
690                 695                 700
```

```
Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
            725                 730                 735

Val Glu Val His Asn Ala Lys Thr Lys Pro Arg Glu Glu Gln Phe Asn
        740                 745                 750

Ser Thr Tyr Arg Val Val Ser Val Leu Thr Val Leu His Gln Asp Trp
    755                 760                 765

Leu Asn Gly Lys Glu Tyr Lys Cys Lys Val Ser Asn Lys Gly Leu Pro
770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
            805                 810                 815

Gln Val Ser Leu Thr Cys Leu Val Lys Gly Phe Tyr Pro Ser Asp Ile
        820                 825                 830

Ala Val Glu Trp Glu Ser Asn Gly Gln Pro Glu Asn Asn Tyr Lys Thr
    835                 840                 845

Thr Pro Pro Val Leu Asp Ser Asp Gly Ser Phe Phe Leu Tyr Ser Arg
850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
            885                 890                 895

Ser Leu Ser Leu Gly Lys
            900

<210> SEQ ID NO 45
<211> LENGTH: 2748
<212> TYPE: DNA
<213> ORGANISM: Homo sapiens

<400> SEQUENCE: 45
atggtgcgct tgtacgtgtt ggtaatggga gtttctgcct tcacccttca gcctgcggca      60
cacacagggg ctgccagaag ctgccggttt cgtgggaggc attacaagcg ggagttcagg     120
ctggaagggg agcctgtagc cctgaggtgc ccccaggtgc cctactggtt gtgggccttct    180 gtcagccccc gcatcaacct gacatggcat aaaaatgact ctgctaggac ggtcccagga     240
gaagaagaga cacggatgtg ggcccaggac ggtgctctgt ggcttctgcc agccttgcag     300
gaggactctg gcacctacgt ctgcactact agaaatgctt cttactgtga caaaatgtcc     360
attgagctca gagttttga gaatacagat gctttcctgc cgttcatctc atacccgcaa     420 atttttaacct tgtcaacctc tggggtatta gtatgccctg acctgagtga attcacccgt     480
gacaaaactg acgtgaagat tcaatggtac aaggattctc ttcttttgga taaagacaat     540
gagaaatttc taagtgtgag ggggaccact cacttactcg tacacgatgt ggccctggaa     600
gatgctggct attaccgctg tgtcctgaca tttgcccatg aaggccagca atacaacatc     660
actaggagta ttgagctacg catcaagaaa aaaaagaag agaccattcc tgtgatcatt     720
tcccccctca agaccatatc agcttctctg gggtcaagac tgacaatccc atgtaaggtg     780
tttctgggaa ccggcacacc cttaaccacc atgctgtggt ggacggccaa tgacacccac     840
atagagagcg cctacccggg aggccgcgtg accgaggggc acgccagga atattcagaa     900 aataatgaga actacattga agtgccattg attttttgatc ctgtcacaag agaggatttg     960
```

```
cacatggatt ttaaatgtgt tgtccataat accctgagtt ttcagacact acgcaccaca    1020
gtcaaggaag cctcctccac gttctcagaa cgctgcgatg actggggact agacaccatg    1080
aggcaaatcc aagtgtttga agatgagcca gctcgcatca agtgcccact ctttgaacac    1140
ttcttgaaat tcaactacag cacagcccat tcagctggcc ttactctgat ctggtattgg    1200
actaggcagg accgggacct tgaggagcca attaacttcc gcctccccga gaaccgcatt    1260
agtaaggaga aagatgtgct gtggttccgg cccactctcc tcaatgacac tggcaactat    1320
acctgcatgt taaggaacac tacatattgc agcaaagttg catttccctt ggaagttgtt    1380
caaaagaca gctgtttcaa ttcccccatg aaactcccag tgcataaact gtatatagaa    1440
tatggcattc agaggatcac ttgtccaaat gtagatggat attttccttc cagtgtcaaa    1500
ccgactatca cttggtatat gggctgttat aaaatacaga attttaataa tgtaataccc    1560
gaaggtatga acttgagttt cctcattgcc ttaatttcaa ataatggaaa ttacacatgt    1620
gttgttacat atccagaaaa tggacgtacg tttcatctca ccaggactct gactgtaaag    1680
gtagtaggct ctccaaaaaa tgcagtgccc cctgtgatcc attcacctaa tgatcatgtg    1740
gtctatgaga agaaccagg agaggagcta ctcattccct gtacggtcta ttttagtttt    1800
ctgatggatt ctcgcaatga ggtttggtgg accattgatg gaaaaaaacc tgatgacatc    1860
actattgatg tcaccattaa cgaaagtata agtcatagta aacagaaga tgaaacaaga    1920
actcagattt tgagcatcaa gaaagttacc tctgaggatc tcaagcgcag ctatgtctgt    1980
catgctagaa gtgccaaagg cgaagttgcc aaagcagcca aggtgaagca gaaagtgcca    2040
gctccaagat acacagtgtc cggagacaaa actcacacat gcccaccgtg cccagcacct    2100
gaactcctgg gggaccgtc agtcttcctc ttccccccaa aacccaagga caccctcatg    2160
atctcccgga cccctgaggt cacatgcgtg gtggtggacg tgagccacga agaccctgag    2220
gtcaagttca actggtacgt ggacggcgtg gaggtgcata atgccaagac aaagccgcgg    2280
gaggagcagt acaacagcac gtaccgtgtg gtcagcgtcc tcaccgtcct gcaccaggac    2340
tggctgaatg gcaaggagta caagtgcaag gtctccaaca aagccctccc agcccccatc    2400
gagaaaacca tctccaaagc caaagggcag ccccgagaac acaggtgta caccctgccc    2460
ccatcccggg atgagctgac caagaaccag gtcagcctga cctgcctggt caaaggcttc    2520
tatcccagcg acatcgccgt ggagtgggag agcaatgggc agccggagaa caactacaag    2580
accacgcctc ccgtgctgga ctccgacggc tccttcttcc tctatagcaa gctcaccgtg    2640
gacaagagca ggtggcagca ggggaacgtc ttctcatgct ccgtgatgca tgaggctctg    2700
cacaaccact acacgcagaa gagcctctcc ctgtctccgg gtaaatga              2748
```

<210> SEQ ID NO 46
<211> LENGTH: 915
<212> TYPE: PRT
<213> ORGANISM: Homo sapiens

<400> SEQUENCE: 46

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60
```

-continued

```
Ile Asn Leu Thr Trp His Lys Asn Asp Ser Ala Arg Thr Val Pro Gly
 65                  70                  75                  80

Glu Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480
```

-continued

```
Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
```

```
                900            905            910
Pro Gly Lys
        915

<210> SEQ ID NO 47
<211> LENGTH: 2754
<212> TYPE: DNA
<213> ORGANISM: Homo sapiens

<400> SEQUENCE: 47
atggtgcgct tgtacgtgtt ggtaatggga gtttctgcct tcacccttca gcctgcggca        60
cacacagggg ctgccagaag ctgccggttt cgtgggaggc attacaagcg ggagttcagg       120
ctggaagggg agcctgtagc cctgaggtgc cccaggtgc cctactggtt gtgggcctct        180
gtcagccccc gcatcaacct gacatggcat aaaaatgact ctgctaggac ggtcccagga       240
gaagaagaga cacggatgtg ggcccaggac ggtgctctgt ggcttctgcc agccttgcag       300
gaggactctg gcacctacgt ctgcactact agaaatgctt cttactgtga caaaatgtcc       360
attgagctca gagttttga gaatacagat gctttcctgc cgttcatctc ataccccgcaa       420 attttaacct tgtcaacctc tggggtatta gtatgccctg acctgagtga attcacccgt       480
gacaaaactg acgtgaagat caatggtac aaggattctc ttcttttgga taaagacaat       540
gagaaatttc taagtgtgag ggggaccact cacttactcg tacacgatgt ggccctggaa       600
gatgctggct attaccgctg tgtcctgaca tttgcccatg aaggccagca atacaacatc       660
actaggagta ttgagctacg catcaagaaa aaaaagaag agaccattcc tgtgatcatt       720 tccccctca agaccatatc agcttctctg gggtcaagac tgacaatccc atgtaaggtg       780
tttctgggaa ccggcacacc cttaaccacc atgctgtggt ggacggccaa tgacacccac       840
atagagagcg cctacccggg aggccgcgtg accgagggc acgccagga atattcagaa        900 aataatgaga actacattga agtgccattg attttgatc ctgtcacaag agaggattg        960 cacatggatt ttaaatgtgt tgtccataat accctgagtt tcagacact acgcaccaca       1020 gtcaaggaag cctcctccac gttctcagaa cgctgcgatg actggggact agacaccatg       1080
aggcaaatcc aagtgtttga agatgagcca gctcgcatca agtgcccact ctttgaacac       1140
ttcttgaaat tcaactacag cacagcccat tcagctggcc ttactctgat ctggtattgg       1200
actaggcagg accgggacct tgaggagcca attaacttcc gcctccccga gaaccgcatt       1260
agtaaggaga aagatgtgct gtggttccgg cccactctcc tcaatgacac tggcaactat       1320
acctgcatgt taggaacac tacatattgc agcaaagttg catttcccct tggaagttgt       1380
caaaaagaca gctgtttcaa ttcccccatg aaactcccag tgcataaact gtatatagaa       1440
tatggcattc agaggatcac ttgtccaaat gtagatggat attttccttc cagtgtcaaa       1500
ccgactatca cttggtatat gggctgttat aaaatacaga atttaataa tgtaataccc       1560 gaaggtatga acttgagttt cctcattgcc ttaattcaa ataatggaaa ttacacatgt       1620
gttgttacat atcagaaaa tggacgtacg tttcatctca ccaggactct gactgtaaag       1680
gtagtaggct ctccaaaaaa tgcagtgccc cctgtgatcc attcacctaa tgatcatgtg       1740
gtctatgaga aagaaccagg agaggagcta ctcattccct gtacggtcta ttttagtttt       1800
ctgatggatt ctcgcaatga ggtttggtgg accattgatg aaaaaaacc tgatgacatc       1860 actattgatg tcaccattaa cgaaagtata agtcatagta gaacagaaga tgaaacaaga       1920
actcagattt tgagcatcaa gaaagttacc tctgaggatc tcaagcgcag ctatgtctgt       1980
```

-continued

```
catgctagaa gtgccaaagg cgaagttgcc aaagcagcca aggtgaagca gaaagtgcca    2040
gctccaagat acacagtgtc cggagagtcc aaatacggtc cgccatgccc atcatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga gatgaccaag aaccaggtca gcctgacctg cctggtcaaa    2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga          2754
```

<210> SEQ ID NO 48
<211> LENGTH: 917
<212> TYPE: PRT
<213> ORGANISM: Homo sapiens

<400> SEQUENCE: 48

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
                20                  25                  30

Arg His Tyr Lys Arg Glu Phe Arg Leu Glu Gly Glu Pro Val Ala Leu
            35                  40                  45

Arg Cys Pro Gln Val Pro Tyr Trp Leu Trp Ala Ser Val Ser Pro Arg
        50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
                100                 105                 110

Ala Ser Tyr Cys Asp Lys Met Ser Ile Glu Leu Arg Val Phe Glu Asn
            115                 120                 125

Thr Asp Ala Phe Leu Pro Phe Ile Ser Tyr Pro Gln Ile Leu Thr Leu
        130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
                180                 185                 190

Leu Val His Asp Val Ala Leu Glu Asp Ala Gly Tyr Tyr Arg Cys Val
            195                 200                 205

Leu Thr Phe Ala His Glu Gly Gln Gln Tyr Asn Ile Thr Arg Ser Ile
        210                 215                 220

Glu Leu Arg Ile Lys Lys Lys Glu Glu Thr Ile Pro Val Ile Ile
225                 230                 235                 240
```

-continued

```
Ser Pro Leu Lys Thr Ile Ser Ala Ser Leu Gly Ser Arg Leu Thr Ile
            245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
            275                 280                 285

Arg Val Thr Glu Gly Pro Arg Gln Glu Tyr Ser Glu Asn Asn Glu Asn
            290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
            355                 360                 365

Glu Pro Ala Arg Ile Lys Cys Pro Leu Phe Glu His Phe Leu Lys Phe
            370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
            435                 440                 445

Tyr Cys Ser Lys Val Ala Phe Pro Leu Glu Val Val Gln Lys Asp Ser
            450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
            515                 520                 525

Ile Ala Leu Ile Ser Asn Asn Gly Asn Tyr Thr Cys Val Val Thr Tyr
            530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
            595                 600                 605

Trp Trp Thr Ile Asp Gly Lys Lys Pro Asp Asp Ile Thr Ile Asp Val
            610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
```

```
                660                  665                  670
Ala Lys Val Lys Gln Lys Val Pro Ala Pro Arg Tyr Thr Val Ser Gly
            675                  680                  685

Glu Ser Lys Tyr Gly Pro Pro Cys Pro Ser Cys Pro Ala Pro Glu Phe
        690                  695                  700

Leu Gly Gly Pro Ser Val Phe Leu Phe Pro Pro Lys Pro Lys Asp Thr
705                  710                  715                  720

Leu Met Ile Ser Arg Thr Pro Glu Val Thr Cys Val Val Val Asp Val
                725                  730                  735

Ser Gln Glu Asp Pro Glu Val Gln Phe Asn Trp Tyr Val Asp Gly Val
            740                  745                  750

Glu Val His Asn Ala Lys Thr Lys Pro Arg Glu Glu Gln Phe Asn Ser
        755                  760                  765

Thr Tyr Arg Val Val Ser Val Leu Thr Val Leu His Gln Asp Trp Leu
770                  775                  780

Asn Gly Lys Glu Tyr Lys Cys Lys Val Ser Asn Lys Gly Leu Pro Ser
785                  790                  795                  800

Ser Ile Glu Lys Thr Ile Ser Lys Ala Lys Gly Gln Pro Arg Glu Pro
                805                  810                  815

Gln Val Tyr Thr Leu Pro Pro Ser Gln Glu Glu Met Thr Lys Asn Gln
            820                  825                  830

Val Ser Leu Thr Cys Leu Val Lys Gly Phe Tyr Pro Ser Asp Ile Ala
        835                  840                  845

Val Glu Trp Glu Ser Asn Gly Gln Pro Glu Asn Asn Tyr Lys Thr Thr
850                  855                  860

Pro Pro Val Leu Asp Ser Asp Gly Ser Phe Phe Leu Tyr Ser Arg Leu
865                  870                  875                  880

Thr Val Asp Lys Ser Arg Trp Gln Glu Gly Asn Val Phe Ser Cys Ser
                885                  890                  895

Val Met His Glu Ala Leu His Asn His Tyr Thr Gln Lys Ser Leu Ser
            900                  905                  910

Leu Ser Leu Gly Lys
        915

<210> SEQ ID NO 49
<211> LENGTH: 2754
<212> TYPE: DNA
<213> ORGANISM: Homo sapiens

<400> SEQUENCE: 49
atggtgcgct tgtacgtgtt ggtaatggga gtttctgcct tcaccttca gcctgcggca      60 cacacagggg ctgccagaag ctgccggttt cgtggagggc attacaagcg ggagttcagg    120
ctggaagggg agcctgtagc cctgaggtgc ccccaggtgc cctactggtt gtgggcctct    180
gtcagccccc gcatcaacct gacatggcat aaaaatgact ctgctaggac ggtcccagga    240
gaagaagaga cacggatgtg ggcccaggac ggtgctctgt ggcttctgcc agccttgcag    300
gaggactctg gcacctacgt ctgcactact agaaatgctt cttactgtga caaaatgtcc    360
attgagctca gagtttttga gaatacagat gctttcctgc cgttcatctc atacccgcaa    420
attttaacct tgtcaacctc tgggtatta gtatgccctg acctgagtga attcacccgt    480
gacaaaactg acgtgaagat tcaatggtac aaggattctc ttcttttgga taaagacaat    540
gagaaatttc taagtgtgag ggggaccact cacttactcg tacacgatgt ggccctggaa    600
gatgctggct attaccgctg tgtcctgaca tttgcccatg aaggccagca atacaacatc    660
```

-continued

| | |
|---|---|
| actaggagta ttgagctacg catcaagaaa aaaaaagaag agaccattcc tgtgatcatt | 720 |
| tcccccctca agaccatatc agcttctctg ggtcaagac tgacaatccc atgtaaggtg | 780 |
| tttctgggaa ccggcacacc cttaaccacc atgctgtggt ggacggccaa tgacacccac | 840 |
| atagagagcg cctacccggg aggccgcgtg accgagggc cacgccagga atattcagaa | 900 |
| aataatgaga actacattga agtgccattg attttttgatc ctgtcacaag agaggatttg | 960 |
| cacatggatt ttaaatgtgt tgtccataat accctgagtt ttcagacact acgcaccaca | 1020 |
| gtcaaggaag cctcctccac gttctcagaa cgctgcgatg actggggact agacaccatg | 1080 |
| aggcaaatcc aagtgtttga agatgagcca gctcgcatca agtgcccact ctttgaacac | 1140 |
| ttcttgaaat tcaactacag cacagcccat tcagctggcc ttactctgat ctggtattgg | 1200 |
| actaggcagg accgggacct tgaggagcca attaacttcc gcctccccga gaaccgcatt | 1260 |
| agtaaggaga aagatgtgct gtggttccgg cccactctcc tcaatgacac tggcaactat | 1320 |
| acctgcatgt taaggaacac tacatattgc agcaaagttg catttcccctt ggaagttgtt | 1380 |
| caaaaagaca gctgtttcaa ttcccccatg aaactcccag tgcataaact gtatatagaa | 1440 |
| tatggcattc agaggatcac ttgtccaaat gtagatggat attttccttc cagtgtcaaa | 1500 |
| ccgactatca cttggtatat gggctgttat aaaatacaga attttaataa tgtaataccc | 1560 |
| gaaggtatga acttgagttt cctcattgcc ttaatttcaa ataatggaaa ttacacatgt | 1620 |
| gttgttacat atccagaaaa tggacgtacg tttcatctca ccaggactct gactgtaaag | 1680 |
| gtagtaggct ctccaaaaaa tgcagtgccc cctgtgatcc attcacctaa tgatcatgtg | 1740 |
| gtctatgaga aagaaccagg agaggagcta ctcattccct gtacggtcta ttttagtttt | 1800 |
| ctgatggatt ctcgcaatga ggtttggtgg accattgatg gaaaaaaacc tgatgacatc | 1860 |
| actattgatg tcaccattaa cgaaagtata agtcatagta aacagaaga tgaaacaaga | 1920 |
| actcagattt tgagcatcaa gaaagttacc tctgaggatc tcaagcgcag ctatgtctgt | 1980 |
| catgctagaa gtgccaaagg cgaagttgcc aaagcagcca aggtgaagca gaaagtgcca | 2040 |
| gctccaagat acacagtgtc cggagagtcc aaatacggtc cgccatgccc accatgccca | 2100 |
| gcacctgagt tcctggggg accatcagtc ttcctgttcc ccccaaaacc caaggacact | 2160 |
| ctcatgatct cccggacccc tgaggtcacg tgcgtggtgg tggacgtgag ccaggaagac | 2220 |
| cccgaggtcc agttcaactg gtacgtggat ggcgtggagg tgcataatgc caagacaaag | 2280 |
| ccgcgggagg agcagttcaa cagcacgtac cgtgtggtca gcgtcctcac cgtcctgcac | 2340 |
| caggactggc tgaacggcaa ggagtacaag tgcaaggtct ccaacaaagg cctcccgtcc | 2400 |
| tccatcgaga aaaccatctc caaagccaaa gggcagcccc gagagccaca ggtgtacacc | 2460 |
| ctgcccccat cccaggagga gatgaccaag aaccaggtca gcctgacctg cctggtcaaa | 2520 |
| ggcttctacc ccagcgacat cgccgtggag tgggagagca tgggcagcc ggagaacaac | 2580 |
| tacaagacca cgcctcccgt gctggactcc gacggctcct tcttcctcta cagcaggcta | 2640 |
| accgtggaca agagcaggtg gcaggagggg aatgtcttct catgctccgt gatgcatgag | 2700 |
| gctctgcaca accactacac acagaagagc ctctccctgt ctctgggtaa atga | 2754 |

<210> SEQ ID NO 50
<211> LENGTH: 917
<212> TYPE: PRT
<213> ORGANISM: Homo sapiens

<400> SEQUENCE: 50

-continued

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
            35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
            115                 120                 125

Thr Asp Ala Phe Leu Pro Phe Ile Ser Tyr Pro Gln Ile Leu Thr Leu
            130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
            195                 200                 205

Leu Thr Phe Ala His Glu Gly Gln Gln Tyr Asn Ile Thr Arg Ser Ile
            210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
            275                 280                 285

Arg Val Thr Glu Gly Pro Arg Gln Glu Tyr Ser Glu Asn Asn Glu Asn
            290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
            355                 360                 365

Glu Pro Ala Arg Ile Lys Cys Pro Leu Phe Glu His Phe Leu Lys Phe
            370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
```

```
                420             425             430
Leu Leu Asn Asp Thr Gly Asn Tyr Thr Cys Met Leu Arg Asn Thr Thr
        435             440             445
Tyr Cys Ser Lys Val Ala Phe Pro Leu Glu Val Val Gln Lys Asp Ser
    450             455             460
Cys Phe Asn Ser Pro Met Lys Leu Pro Val His Lys Leu Tyr Ile Glu
465             470             475             480
Tyr Gly Ile Gln Arg Ile Thr Cys Pro Asn Val Asp Gly Tyr Phe Pro
                485             490             495
Ser Ser Val Lys Pro Thr Ile Thr Trp Tyr Met Gly Cys Tyr Lys Ile
            500             505             510
Gln Asn Phe Asn Asn Val Ile Pro Glu Gly Met Asn Leu Ser Phe Leu
        515             520             525
Ile Ala Leu Ile Ser Asn Asn Gly Asn Tyr Thr Cys Val Val Thr Tyr
    530             535             540
Pro Glu Asn Gly Arg Thr Phe His Leu Thr Arg Thr Leu Thr Val Lys
545             550             555             560
Val Val Gly Ser Pro Lys Asn Ala Val Pro Pro Val Ile His Ser Pro
                565             570             575
Asn Asp His Val Val Tyr Glu Lys Glu Pro Gly Glu Glu Leu Leu Ile
            580             585             590
Pro Cys Thr Val Tyr Phe Ser Phe Leu Met Asp Ser Arg Asn Glu Val
        595             600             605
Trp Trp Thr Ile Asp Gly Lys Lys Pro Asp Asp Ile Thr Ile Asp Val
    610             615             620
Thr Ile Asn Glu Ser Ile Ser His Ser Arg Thr Glu Asp Glu Thr Arg
625             630             635             640
Thr Gln Ile Leu Ser Ile Lys Lys Val Thr Ser Glu Asp Leu Lys Arg
                645             650             655
Ser Tyr Val Cys His Ala Arg Ser Ala Lys Gly Glu Val Ala Lys Ala
            660             665             670
Ala Lys Val Lys Gln Lys Val Pro Ala Pro Arg Tyr Thr Val Ser Gly
        675             680             685
Glu Ser Lys Tyr Gly Pro Pro Cys Pro Pro Cys Pro Ala Pro Glu Phe
    690             695             700
Leu Gly Gly Pro Ser Val Phe Leu Phe Pro Pro Lys Pro Lys Asp Thr
705             710             715             720
Leu Met Ile Ser Arg Thr Pro Glu Val Thr Cys Val Val Val Asp Val
                725             730             735
Ser Gln Glu Asp Pro Glu Val Gln Phe Asn Trp Tyr Val Asp Gly Val
            740             745             750
Glu Val His Asn Ala Lys Thr Lys Pro Arg Glu Glu Gln Phe Asn Ser
        755             760             765
Thr Tyr Arg Val Val Ser Val Leu Thr Val Leu His Gln Asp Trp Leu
    770             775             780
Asn Gly Lys Glu Tyr Lys Cys Lys Val Ser Asn Lys Gly Leu Pro Ser
785             790             795             800
Ser Ile Glu Lys Thr Ile Ser Lys Ala Lys Gly Gln Pro Arg Glu Pro
                805             810             815
Gln Val Tyr Thr Leu Pro Pro Ser Gln Glu Glu Met Thr Lys Asn Gln
            820             825             830
Val Ser Leu Thr Cys Leu Val Lys Gly Phe Tyr Pro Ser Asp Ile Ala
        835             840             845
```

```
Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
            885                 890                 895

Val Met His Glu Ala Leu His Asn His Tyr Thr Gln Lys Ser Leu Ser
        900                 905                 910

Leu Ser Leu Gly Lys
        915

<210> SEQ ID NO 51
<211> LENGTH: 2748
<212> TYPE: DNA
<213> ORGANISM: Homo sapiens

<400> SEQUENCE: 51
```

| | |
|---|---:|
| atggtgcttc tgtggtgtgt agtgagtctc tacttttatg gaatcctgca aagtgatgcc | 60 |
| tcagaacgct gcgatgactg gggactagac accatgaggc aaatccaagt gtttgaagat | 120 |
| gagccagctc gcatcaagtg cccactcttt gaacacttct gaaattcaa ctacagcaca | 180 |
| gcccattcag ctggccttac tctgatctgg tattggacta gcaggaccg ggaccttgag | 240 |
| gagccaatta acttccgcct ccccgagaac cgcattagta aggagaaaga tgtgctgtgg | 300 |
| ttccggccca ctctcctcaa tgacactggc aactataccct gcatgttaag gaacactaca | 360 |
| tattgcagca aagttgcatt tcccttggaa gttgttcaaa aagacagctg tttcaattcc | 420 |
| cccatgaaac tcccagtgca taaactgtat atagaatatg gcattcagag gatcacttgt | 480 |
| ccaaatgtag atggatattt tccttccagt gtcaaaccga ctatcacttg gtatatgggc | 540 |
| tgttataaaa tacagaattt taataatgta atacccgaag gtatgaactt gagtttcctc | 600 |
| attgccttaa tttcaaataa tggaaattac acatgtgttg ttacatatcc agaaaatgga | 660 |
| cgtacgtttc atctcaccag gactctgact gtaaaggtag taggctctcc aaaaaatgca | 720 |
| gtgccccctg tgatccattc acctaatgat catgtggtct atgagaaaga accaggagag | 780 |
| gagctactca ttccctgtac ggtctatttt agttttctga tggattctcg caatgaggtt | 840 |
| tggtggacca ttgatggaaa aaacctgat gacatcacta ttgatgtcac cattaacgaa | 900 |
| agtataagtc atagtagaac agaagatgaa acaagaactc agattttgag catcaagaaa | 960 |
| gttacctctg aggatctcaa gcgcagctat gtctgtcatg ctagaagtgc caaaggcgaa | 1020 |
| gttgccaaag cagccaaggt gaagcagaaa gtgccagctc caagatacac agtgcacaca | 1080 |
| ggggctgcca gaagctgccg gtttcgtggg aggcattaca gcgggagtt caggctggaa | 1140 |
| ggggagcctg tagccctgag gtgccccag gtgccctact ggttgtgggc ctctgtcagc | 1200 |
| ccccgcatca acctgacatg gcataaaaat gactctgcta gacggtccc aggagaagaa | 1260 |
| gagacacgga tgtgggccca ggacggtgct ctgtggcttc tgccagcctt gcaggaggac | 1320 |
| tctggcacct acgtctgcac tactagaaat gcttcttact gtgacaaaat gtccattgag | 1380 |
| ctcagagttt ttgagaatac agatgctttc ctgccgttca tctcataccc gcaaattta | 1440 |
| accttgtcaa cctctggggt attagtatgc cctgacctga gtgaattcac ccgtgacaaa | 1500 |
| actgacgtga agattcaatg gtacaaggat tctcttcttt tggataaaga caatgagaaa | 1560 |
| tttctaagtg tgaggggggac cactcactta ctcgtacacg atgtggccct ggaagatgct | 1620 |
| ggctattacc gctgtgtcct gacatttgcc catgaaggcc agcaatacaa catcactagg | 1680 |

-continued

```
agtattgagc tacgcatcaa gaaaaaaaaa gaagagacca ttcctgtgat catttccccc    1740
ctcaagacca tatcagcttc tctggggtca agactgacaa tcccatgtaa ggtgtttctg    1800
ggaaccggca caccccttaac caccatgctg tggtggacgg ccaatgacac ccacatagag   1860
agcgcctacc cgggaggccg cgtgaccgag gggccacgcc aggaatattc agaaaataat   1920
gagaactaca ttgaagtgcc attgattttt gatcctgtca agagagga  tttgcacatg    1980 gattttaaat gtgttgtcca taatacccctg agttttcaga cactacgcac cacagtcaag  2040
gaagcctcct ccacgttctc cggagacaaa actcacacat gcccaccgtg cccagcacct   2100
gaactcctgg ggggaccgtc agtcttcctc ttccccccaa aacccaagga caccctcatg   2160
atctcccgga cccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca aagccctccc agcccccatc   2400
gagaaaacca tctccaaagc caagggcag ccccgagaac cacaggtgta caccctgccc    2460
ccatcccggg atgagctgac caagaaccag gtcagcctga cctgcctggt caaaggcttc   2520
tatcccagcg acatcgccgt ggagtgggag agcaatgggc agccggagaa caactacaag   2580
accacgcctc ccgtgctgga ctccgacggc tccttcttcc tctatagcaa gctcaccgtg   2640
gacaagagca ggtggcagca ggggaacgtc ttctcatgct ccgtgatgca tgaggctctg   2700
cacaaccact acacgcagaa gagcctctcc ctgtctccgg gtaaatga               2748
```

<210> SEQ ID NO 52
<211> LENGTH: 915
<212> TYPE: PRT
<213> ORGANISM: Homo sapiens

<400> SEQUENCE: 52

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
```

-continued

```
                180                 185                 190
Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
        210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605
```

```
Met Leu Trp Trp Thr Ala Asn Asp Thr His Ile Glu Ser Ala Tyr Pro
    610                 615                 620
Gly Gly Arg Val Thr Glu Gly Pro Arg Gln Glu Tyr Ser Glu Asn Asn
625                 630                 635                 640
Glu Asn Tyr Ile Glu Val Pro Leu Ile Phe Asp Pro Val Thr Arg Glu
                645                 650                 655
Asp Leu His Met Asp Phe Lys Cys Val Val His Asn Thr Leu Ser Phe
            660                 665                 670
Gln Thr Leu Arg Thr Thr Val Lys Glu Ala Ser Ser Thr Phe Ser Gly
        675                 680                 685
Asp Lys Thr His Thr Cys Pro Pro Cys Pro Ala Pro Glu Leu Leu Gly
    690                 695                 700
Gly Pro Ser Val Phe Leu Phe Pro Pro Lys Pro Lys Asp Thr Leu Met
705                 710                 715                 720
Ile Ser Arg Thr Pro Glu Val Thr Cys Val Val Val Asp Val Ser His
                725                 730                 735
Glu Asp Pro Glu Val Lys Phe Asn Trp Tyr Val Asp Gly Val Glu Val
            740                 745                 750
His Asn Ala Lys Thr Lys Pro Arg Glu Glu Gln Tyr Asn Ser Thr Tyr
        755                 760                 765
Arg Val Val Ser Val Leu Thr Val Leu His Gln Asp Trp Leu Asn Gly
    770                 775                 780
Lys Glu Tyr Lys Cys Lys Val Ser Asn Lys Ala Leu Pro Ala Pro Ile
785                 790                 795                 800
Glu Lys Thr Ile Ser Lys Ala Lys Gly Gln Pro Arg Glu Pro Gln Val
                805                 810                 815
Tyr Thr Leu Pro Pro Ser Arg Asp Glu Leu Thr Lys Asn Gln Val Ser
            820                 825                 830
Leu Thr Cys Leu Val Lys Gly Phe Tyr Pro Ser Asp Ile Ala Val Glu
        835                 840                 845
Trp Glu Ser Asn Gly Gln Pro Glu Asn Asn Tyr Lys Thr Thr Pro Pro
    850                 855                 860
Val Leu Asp Ser Asp Gly Ser Phe Phe Leu Tyr Ser Lys Leu Thr Val
865                 870                 875                 880
Asp Lys Ser Arg Trp Gln Gln Gly Asn Val Phe Ser Cys Ser Val Met
                885                 890                 895
His Glu Ala Leu His Asn His Tyr Thr Gln Lys Ser Leu Ser Leu Ser
            900                 905                 910
Pro Gly Lys
        915

<210> SEQ ID NO 53
<211> LENGTH: 2754
<212> TYPE: DNA
<213> ORGANISM: Homo sapiens

<400> SEQUENCE: 53
atggtgcttc tgtggtgtgt agtgagtctc tactttatg gaatcctgca aagtgatgcc      60
tcagaacgct gcgatgactg gggactagac accatgaggc aaatccaagt gtttgaagat    120
gagccagctc gcatcaagtg cccactcttt gaacacttct tgaaattcaa ctacagcaca    180
gcccattcag ctggccttac tctgatctgg tattggacta ggcaggaccg ggaccttgag    240
gagccaatta acttccgcct ccccgagaac cgcattagta aggagaaaga tgtgctgtgg    300
```

-continued

```
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720 gtgcccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaggcgaa   1020 gttgccaaag cagccaaggt gaagcagaaa gtgccagctc caagatacac agtgcacaca   1080
ggggctgcca gaagctgccg gtttcgtggg aggcattaca agcgggagtt caggctggaa   1140
ggggagcctg tagccctgag gtgcccccag gtgccctact ggttgtgggc ctctgtcagc   1200
ccccgcatca acctgacatg gcataaaaat gactctgcta ggacggtccc aggagaagaa   1260
gagacacgga tgtgggccca ggacggtgct ctgtggcttc tgccagcctt gcaggaggac   1320 tctggcaccct acgtctgcac tactagaaat gcttcttact gtgacaaaat gtccattgag   1380
ctcagagttt ttgagaatac agatgctttc ctgccgttca tctcataccc gcaaaattta   1440
accttgtcaa cctctggggt attagtatgc cctgacctga gtgaattcac ccgtgacaaa   1500
actgacgtga agattcaatg gtacaaggat tctcttcttt tggataaaga caatgagaaa   1560
tttctaagtg tgaggggggac cactcactta ctcgtacacg atgtggccct ggaagatgct   1620
ggctattacc gctgtgtcct gacatttgcc catgaaggcc agcaatacaa catcactagg   1680
agtattgagc tacgcatcaa gaaaaaaaaa gaagagacca ttcctgtgat catttccccc   1740
ctcaagacca tatcagcttc tctggggtca agactgacaa tcccatgtaa ggtgtttctg   1800
ggaaccggca cacccttaac caccatgctg tggtggacgg ccaatgacac ccacatagag   1860
agcgcctacc cgggaggccg cgtgaccgag gggccacgcc aggaatattc agaaaataat   1920
gagaactaca ttgaagtgcc attgattttt gatcctgtca caagagagga tttgcacatg   1980
gattttaaat gtgttgtcca taatccctg agttttcaga cactacgcac cacagtcaag   2040
gaagcctcct ccacgttctc cggagagtcc aaatacggtc cgccatgccc atcatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460 ctgccccat cccaggagga gatgaccaag aaccaggtca gcctgacctg cctggtcaaa   2520
ggcttctacc ccagcgacat cgccgtggag tgggagagca atgggcagcc ggagaacaac   2580
tacaagacca cgcctcccgt gctggactcc gacggctcct tcttcctcta cagcaggcta   2640
accgtggaca agagcaggtg gcaggagggg aatgtcttct catgctccgt gatgcatgag   2700
```
gctctgcaca accactacac acagaagagc ctctccctgt ctctgggtaa atga      2754

<210> SEQ ID NO 54
<211> LENGTH: 917
<212> TYPE: PRT
<213> ORGANISM: Homo sapiens

<400> SEQUENCE: 54

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365
```

```
Arg Gly Arg His Tyr Lys Arg Glu Phe Arg Leu Glu Gly Pro Val
    370             375             380

Ala Leu Arg Cys Pro Gln Val Pro Tyr Trp Leu Trp Ala Ser Val Ser
385                 390             395                 400

Pro Arg Ile Asn Leu Thr Trp His Lys Asn Asp Ser Ala Arg Thr Val
                405             410             415

Pro Gly Glu Glu Glu Thr Arg Met Trp Ala Gln Asp Gly Ala Leu Trp
            420             425             430

Leu Leu Pro Ala Leu Gln Glu Asp Ser Gly Thr Tyr Val Cys Thr Thr
        435             440             445

Arg Asn Ala Ser Tyr Cys Asp Lys Met Ser Ile Glu Leu Arg Val Phe
    450             455             460

Glu Asn Thr Asp Ala Phe Leu Pro Phe Ile Ser Tyr Pro Gln Ile Leu
465             470             475                 480

Thr Leu Ser Thr Ser Gly Val Leu Val Cys Pro Asp Leu Ser Glu Phe
                485             490             495

Thr Arg Asp Lys Thr Asp Val Lys Ile Gln Trp Tyr Lys Asp Ser Leu
            500             505             510

Leu Leu Asp Lys Asp Asn Glu Lys Phe Leu Ser Val Arg Gly Thr Thr
        515             520             525

His Leu Leu Val His Asp Val Ala Leu Glu Asp Ala Gly Tyr Tyr Arg
    530             535             540

Cys Val Leu Thr Phe Ala His Glu Gly Gln Gln Tyr Asn Ile Thr Arg
545             550             555             560

Ser Ile Glu Leu Arg Ile Lys Lys Lys Glu Glu Thr Ile Pro Val
                565             570             575

Ile Ile Ser Pro Leu Lys Thr Ile Ser Ala Ser Leu Gly Ser Arg Leu
            580             585             590

Thr Ile Pro Cys Lys Val Phe Leu Gly Thr Gly Thr Pro Leu Thr Thr
        595             600             605

Met Leu Trp Trp Thr Ala Asn Asp Thr His Ile Glu Ser Ala Tyr Pro
    610             615             620

Gly Gly Arg Val Thr Glu Gly Pro Arg Gln Glu Tyr Ser Glu Asn Asn
625             630             635             640

Glu Asn Tyr Ile Glu Val Pro Leu Ile Phe Asp Pro Val Thr Arg Glu
                645             650             655

Asp Leu His Met Asp Phe Lys Cys Val Val His Asn Thr Leu Ser Phe
            660             665             670

Gln Thr Leu Arg Thr Thr Val Lys Glu Ala Ser Ser Thr Phe Ser Gly
        675             680             685

Glu Ser Lys Tyr Gly Pro Pro Cys Pro Ser Cys Pro Ala Pro Glu Phe
    690             695             700

Leu Gly Gly Pro Ser Val Phe Leu Phe Pro Pro Lys Pro Lys Asp Thr
705             710             715                 720

Leu Met Ile Ser Arg Thr Pro Glu Val Thr Cys Val Val Val Asp Val
                725             730             735

Ser Gln Glu Asp Pro Glu Val Gln Phe Asn Trp Tyr Val Asp Gly Val
            740             745             750

Glu Val His Asn Ala Lys Thr Lys Pro Arg Glu Glu Gln Phe Asn Ser
        755             760             765

Thr Tyr Arg Val Val Ser Val Leu Thr Val Leu His Gln Asp Trp Leu
    770             775             780
```

| | | | | | | | | | | | | |
|---|---|---|---|---|---|---|---|---|---|---|---|---|
|Asn|Gly|Lys|Glu|Tyr|Lys|Cys|Lys|Val|Ser|Asn|Lys|Gly|Leu|Pro|Ser|
|785| | | |790| | | |795| | | |800| | | |

| Ser | Ile | Glu | Lys | Thr | Ile | Ser | Lys | Ala | Lys | Gly | Gln | Pro | Arg | Glu | Pro |
|---|---|---|---|---|---|---|---|---|---|---|---|---|---|---|---|
| | | | | 805 | | | | | 810 | | | | | 815 | |

| Gln | Val | Tyr | Thr | Leu | Pro | Pro | Ser | Gln | Glu | Met | Thr | Lys | Asn | Gln |
|---|---|---|---|---|---|---|---|---|---|---|---|---|---|---|
| | | | 820 | | | | | 825 | | | | 830 | | |

| Val | Ser | Leu | Thr | Cys | Leu | Val | Lys | Gly | Phe | Tyr | Pro | Ser | Asp | Ile | Ala |
|---|---|---|---|---|---|---|---|---|---|---|---|---|---|---|---|
| | | | 835 | | | | | 840 | | | | | 845 | | |

| Val | Glu | Trp | Glu | Ser | Asn | Gly | Gln | Pro | Glu | Asn | Asn | Tyr | Lys | Thr | Thr |
|---|---|---|---|---|---|---|---|---|---|---|---|---|---|---|---|
| | 850 | | | | | 855 | | | | | 860 | | | | |

| Pro | Pro | Val | Leu | Asp | Ser | Asp | Gly | Ser | Phe | Phe | Leu | Tyr | Ser | Arg | Leu |
|---|---|---|---|---|---|---|---|---|---|---|---|---|---|---|---|
| 865 | | | | | 870 | | | | | 875 | | | | | 880 |

| Thr | Val | Asp | Lys | Ser | Arg | Trp | Gln | Glu | Gly | Asn | Val | Phe | Ser | Cys | Ser |
|---|---|---|---|---|---|---|---|---|---|---|---|---|---|---|---|
| | | | | 885 | | | | | 890 | | | | | 895 | |

| Val | Met | His | Glu | Ala | Leu | His | Asn | His | Tyr | Thr | Gln | Lys | Ser | Leu | Ser |
|---|---|---|---|---|---|---|---|---|---|---|---|---|---|---|---|
| | | | 900 | | | | | 905 | | | | | 910 | | |

| Leu | Ser | Leu | Gly | Lys |
|---|---|---|---|---|
| | | | | 915 |

<210> SEQ ID NO 55
<211> LENGTH: 2754
<212> TYPE: DNA
<213> ORGANISM: Homo sapiens

<400> SEQUENCE: 55

```
atggtgcttc tgtggtgtgt agtgagtctc tactttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta acttccgcct ccccgagaac cgcattagta aggagaaaga tgtgctgtgg     300
ttccggccca ctctcctcaa tgacactggc aactatacct gcatgttaag gaacactaca     360
tattgcagca aagttgcatt ccccttggaa gttgttcaaa aagacagctg tttcaattcc     420
cccatgaaac tcccagtgca taactgtat atagaatatg gcattcagag gatcacttgt     480
ccaaatgtag atgatatttt ccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgcccctg tgatccattc acctaatgat catgtggtct atgagaaaga accaggagag     780
gagctactca ttccctgtac ggtctatttt agttttctga tggattctcg caatgaggtt     840
tggtggacca ttgatggaaa aaacctgat gacatcacta ttgatgtcac cattaacgaa     900
agtataagtc atagtagaac agaagatgaa acaagaactc agattttgag catcaagaaa     960
gttacctctg aggatctcaa gcgcagctat gtctgtcatg ctagaagtgc aaaggcgaa    1020
gttgccaaag cagccaaggt gaagcagaaa gtgccagctc aagatacac agtgcacaca    1080
ggggctgcca gaagctgccg gtttcgtggg aggcattaca gcgggagtt caggctggaa    1140
ggggagcctg tagccctgag gtgccccag gtgcccctact ggttgtgggc ctctgtcagc    1200
ccccgcatca acctgacatg gcataaaaat gactctgcta ggacggtccc aggagaagaa    1260
gagacacgga tgtgggccca ggacggtgct ctgtggcttc tgccagcctt gcaggaggac    1320
```

-continued

```
tctggcacct acgtctgcac tactagaaat gcttcttact gtgacaaaat gtccattgag    1380
ctcagagttt ttgagaatac agatgctttc ctgccgttca tctcataccc gcaaatttta    1440
accttgtcaa cctctggggt attagtatgc cctgacctga gtgaattcac ccgtgacaaa    1500
actgacgtga agattcaatg gtacaaggat tctcttcttt tggataaaga caatgagaaa    1560
tttctaagtg tgaggggggac cactcactta ctcgtacacg atgtggccct ggaagatgct    1620
ggctattacc gctgtgtcct gacatttgcc catgaaggcc agcaatacaa catcactagg    1680
agtattgagc tacgcatcaa gaaaaaaaaa gaagagacca ttcctgtgat catttccccc    1740
ctcaagacca tatcagcttc tctggggtca agactgacaa tcccatgtaa ggtgtttctg    1800
ggaaccggca cacccttaac caccatgctg tggtggacgg ccaatgacac ccacatagag    1860
agcgcctacc cggaggccg cgtgaccgag gggccacgcc aggaatattc agaaaataat    1920
gagaactaca ttgaagtgcc attgattttt gatcctgtca aagagagga tttgcacatg    1980
gattttaaat gtgttgtcca taatccctg agttttcaga cactacgcac acagtcaag    2040
gaagcctcct ccacgttctc cggagagtcc aaatacggtc cgccatgccc accatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga gatgaccaag aaccaggtca gcctgacctg cctggtcaaa    2520
ggcttctacc ccagcgacat cgccgtggag tgggagagca tgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga          2754
```

<210> SEQ ID NO 56
<211> LENGTH: 917
<212> TYPE: PRT
<213> ORGANISM: Homo sapiens

<400> SEQUENCE: 56

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125
```

```
Leu Glu Val Val Gln Lys Asp Ser Cys Phe Asn Ser Pro Met Lys Leu
    130                 135                 140
Pro Val His Lys Leu Tyr Ile Glu Tyr Gly Ile Gln Arg Ile Thr Cys
145                 150                 155                 160
Pro Asn Val Asp Gly Tyr Phe Pro Ser Ser Val Lys Pro Thr Ile Thr
                165                 170                 175
Trp Tyr Met Gly Cys Tyr Lys Ile Gln Asn Phe Asn Asn Val Ile Pro
            180                 185                 190
Glu Gly Met Asn Leu Ser Phe Leu Ile Ala Leu Ile Ser Asn Asn Gly
        195                 200                 205
Asn Tyr Thr Cys Val Val Thr Tyr Pro Glu Asn Gly Arg Thr Phe His
    210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
            260                 265                 270
Leu Met Asp Ser Arg Asn Glu Val Trp Trp Thr Ile Asp Gly Lys Lys
        275                 280                 285
Pro Asp Asp Ile Thr Ile Asp Val Thr Ile Asn Glu Ser Ile Ser His
    290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
            340                 345                 350
Ala Pro Arg Tyr Thr Val His Thr Gly Ala Ala Arg Ser Cys Arg Phe
        355                 360                 365
Arg Gly Arg His Tyr Lys Arg Glu Phe Arg Leu Glu Gly Glu Pro Val
    370                 375                 380
Ala Leu Arg Cys Pro Gln Val Pro Tyr Trp Leu Trp Ala Ser Val Ser
385                 390                 395                 400
Pro Arg Ile Asn Leu Thr Trp His Lys Asn Asp Ser Ala Arg Thr Val
                405                 410                 415
Pro Gly Glu Glu Glu Thr Arg Met Trp Ala Gln Asp Gly Ala Leu Trp
            420                 425                 430
Leu Leu Pro Ala Leu Gln Glu Asp Ser Gly Thr Tyr Val Cys Thr Thr
        435                 440                 445
Arg Asn Ala Ser Tyr Cys Asp Lys Met Ser Ile Glu Leu Arg Val Phe
    450                 455                 460
Glu Asn Thr Asp Ala Phe Leu Pro Phe Ile Ser Tyr Pro Gln Ile Leu
465                 470                 475                 480
Thr Leu Ser Thr Ser Gly Val Leu Val Cys Pro Asp Leu Ser Glu Phe
                485                 490                 495
Thr Arg Asp Lys Thr Asp Val Lys Ile Gln Trp Tyr Lys Asp Ser Leu
            500                 505                 510
Leu Leu Asp Lys Asp Asn Glu Lys Phe Leu Ser Val Arg Gly Thr Thr
        515                 520                 525
His Leu Leu Val His Asp Val Ala Leu Glu Asp Ala Gly Tyr Tyr Arg
    530                 535                 540
```

-continued

```
Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
            565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
            595                 600                 605

Met Leu Trp Trp Thr Ala Asn Asp Thr His Ile Glu Ser Ala Tyr Pro
            610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
            645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
            675                 680                 685

Glu Ser Lys Tyr Gly Pro Pro Cys Pro Pro Cys Pro Ala Pro Glu Phe
690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
            725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
            755                 760                 765

Thr Tyr Arg Val Val Ser Val Leu Thr Val Leu His Gln Asp Trp Leu
            770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
            805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
            835                 840                 845

Val Glu Trp Glu Ser Asn Gly Gln Pro Glu Asn Asn Tyr Lys Thr Thr
            850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
            885                 890                 895

Val Met His Glu Ala Leu His Asn His Tyr Thr Gln Lys Ser Leu Ser
            900                 905                 910

Leu Ser Leu Gly Lys
            915
```

We claim:

1. A recombinant nucleic acid molecule encoding a fusion polypeptide which forms a multimer capable of binding interleukin-1 (IL-1) to form a nonfunctional complex, wherein the nucleic acid molecule comprises SEQ ID NO:33.

2. A fusion polypeptide encoded by the nucleic acid molecule of claim 1.

3. The nucleic acid molecule of claim 1, wherein the fusion polypeptide comprises the amino acid sequence of SEQ ID NO:34.

4. A recombinant nucleic acid molecule encoding a fusion polypeptide which forms a multimer capable of binding interleukin-1 (IL-1) to form a nonfunctional complex, wherein the nucleic acid molecule comprises SEQ ID NO:35.

5. A fusion polypeptide encoded by the nucleic acid molecule of claim 4.

6. A nucleic acid molecule encoding a fusion polypeptide comprising the amino acid sequence of SEQ ID NO:36.

7. A recombinant nucleic acid molecule encoding a fusion polypeptide which forms a multimer capable of binding interleukin-1 (IL-1) to form a nonfunctional complex, wherein the nucleic acid molecule comprises SEQ ID NO:37.

8. A fusion polypeptide encoded by the nucleic acid molecule of claim 7.

9. The A nucleic acid molecule encoding a fusion polypeptide comprising the amino acid sequence of SEQ ID NO:38.

10. The nucleic acid of claim 1, 4, or 7, wherein nucleotide 1979 is changed from A to C.

11. A fusion polypeptide encoded by the nucleic acid molecule of claim 10.

12. A recombinant nucleic acid molecule encoding a fusion polypeptide which forms a multimer capable of binding interleukin-1 (IL-1) to form a nonfunctional complex, wherein the nucleic acid molecule comprises SEQ ID NO:39.

13. A fusion polypeptide encoded by the nucleic acid molecule of claim 12.

14. A nucleic acid molecule encoding a fusion polypeptide comprising the amino acid sequence of SEQ ID NO:40.

15. A recombinant nucleic acid molecule encoding a fusion polypeptide which forms a multimer capable of binding interleukin-1 (IL-1) to form a nonfunctional complex, wherein the nucleic acid molecule comprises SEQ ID NO:41.

16. A fusion polypeptide encoded by the nucleic acid molecule of claim 15.

17. A nucleic acid molecule encoding a fusion polypeptide comprising the amino acid sequence of SEQ ID NO:42.

18. A recombinant nucleic acid molecule encoding a fusion polypeptide which forms a multimer capable of binding interleukin-1 (IL-1) to form a nonfunctional complex, wherein the nucleic acid molecule comprises SEQ ID NO:43.

19. A fusion polypeptide encoded by the nucleic acid molecule of claim 18.

20. A nucleic acid molecule encoding a fusion polypeptide comprising the amino acid sequence of SEQ ID NO:44.

21. The nucleic acid of claim 12, 15, or 18, wherein nucleotide 1043 is changed from A to C.

22. A fusion polypeptide encoded by the nucleic acid molecule of claim 21.

23. A composition capable of binding IL-1 to form a non-functional complex comprising a multimer of the fusion polypeptide of any of claims 2, 5, 8, 11, 13, 16, 19, or 22.

24. The composition of claim 23, wherein the multimer is a dimer.

25. A vector comprising the nucleic acid molecule of any of claims 1, 4, 7, 10, 12, 15, 18, and 21.

26. An expression vector comprising the nucleic acid molecule of any of claims 1, 4, 7, 10, 12, 15, 18, and 21 operatively linked to an expression control sequence.

27. A host-vector system for the production of a fusion polypeptide, comprising the expression vector of claim 26 in a suitable host cell.

28. The host-vector system of claim 27, wherein the suitable host cell is a bacterial cell, yeast cell, insect cell, or mammalian cell.

29. A method of producing a fusion polypeptide that comprises growing cells of the host-vector system of claim 27, under conditions permitting production of the fusion polypeptide and recovering the fusion polypeptide so produced.

30. The host-vector system of claim 28, wherein the suitable host cell is a CHO cell.

* * * * *